US009447387B2

(12) United States Patent
Jones et al.

(10) Patent No.: US 9,447,387 B2
(45) Date of Patent: Sep. 20, 2016

(54) **MODIFIED FORMS OF *PSEUDOMONAS* EXOTOXIN A**

(71) Applicant: Intrexon Corporation, Blacksburg, VA (US)

(72) Inventors: Timothy David Jones, Babraham (GB); Francis Joseph Carr, Balmedie (GB)

(73) Assignee: INTREXON CORPORATION, Blacksburg, VA (US)

( * ) Notice: Subject to any disclaimer, the term of this patent is extended or adjusted under 35 U.S.C. 154(b) by 0 days.

(21) Appl. No.: 14/984,006

(22) Filed: Dec. 30, 2015

(65) Prior Publication Data

US 2016/0108377 A1 Apr. 21, 2016

Related U.S. Application Data

(63) Continuation of application No. 14/561,707, filed on Dec. 5, 2014, which is a continuation of application No. 13/604,173, filed on Sep. 5, 2012, now Pat. No. 8,932,586.

(60) Provisional application No. 61/531,576, filed on Sep. 6, 2011.

(51) Int. Cl.

| | |
|---|---|
| ***C12N 9/10*** | (2006.01) |
| ***C07K 16/28*** | (2006.01) |
| ***C07K 14/21*** | (2006.01) |
| ***A61K 39/00*** | (2006.01) |
| ***A61K 39/02*** | (2006.01) |
| *A61K 38/00* | (2006.01) |

(52) U.S. Cl.

CPC ............. *C12N 9/1077* (2013.01); *A61K 39/00* (2013.01); *A61K 39/02* (2013.01); *C07K 14/21* (2013.01); *C07K 16/2803* (2013.01); *A61K 38/00* (2013.01); *C07K 2317/622* (2013.01); *C12Y 204/02036* (2013.01)

(58) Field of Classification Search

None

See application file for complete search history.

(56) References Cited

U.S. PATENT DOCUMENTS

| | | | |
|---|---|---|---|
| 4,545,985 | A | 10/1985 | Pastan et al. |
| 4,892,827 | A | 1/1990 | Pastan et al. |
| 5,458,878 | A | 10/1995 | Pastan et al. |
| 5,512,658 | A | 4/1996 | Pastan et al. |
| 5,602,095 | A | 2/1997 | Pastan et al. |
| 5,696,237 | A | 12/1997 | FitzGerald et al. |
| 5,705,156 | A | 1/1998 | Pastan et al. |
| 5,705,163 | A | 1/1998 | Pastan et al. |
| 5,821,238 | A | 10/1998 | Pastan et al. |
| 5,854,044 | A | 12/1998 | Pastan et al. |
| 5,863,745 | A | 1/1999 | Fitzgerald et al. |
| 5,980,895 | A | 11/1999 | Pastan et al. |
| 5,981,726 | A | 11/1999 | Pastan et al. |
| 6,051,405 | A | 4/2000 | FitzGerald et al. |
| 6,074,644 | A | 6/2000 | Pastan et al. |
| 6,426,075 | B1 | 7/2002 | Fitzgerald et al. |
| 7,314,632 | B1 | 1/2008 | Fitzgerald |
| 7,750,136 | B2 | 7/2010 | Baker et al. |
| 8,092,809 | B2 | 1/2012 | FitzGerald |
| 2006/0051359 | A1 | 3/2006 | Pastan et al. |
| 2008/0125363 | A1 | 5/2008 | Filpula et al. |
| 2008/0193976 | A1 | 8/2008 | Harding |
| 2009/0142341 | A1 | 6/2009 | Pastan et al. |
| 2009/0305411 | A1 | 12/2009 | FitzGerald et al. |
| 2010/0215656 | A1 | 8/2010 | Pastan et al. |
| 2012/0263674 | A1 | 10/2012 | Pastan et al. |

FOREIGN PATENT DOCUMENTS

| | | | |
|---|---|---|---|
| WO | WO 88/02401 | A1 | 4/1988 |
| WO | WO 89/10971 | A1 | 11/1989 |
| WO | WO 90/12592 | A1 | 11/1990 |
| WO | WO 91/09949 | A1 | 7/1991 |
| WO | WO 91/09965 | A1 | 7/1991 |
| WO | WO 91/18018 | A1 | 11/1991 |
| WO | WO 91/18099 | A1 | 11/1991 |
| WO | WO 91/18100 | A1 | 11/1991 |
| WO | WO 92/09613 | A1 | 6/1992 |
| WO | WO 93/07286 | A1 | 4/1993 |
| WO | WO 93/25690 | A1 | 12/1993 |
| WO | WO 94/04689 | A1 | 3/1994 |

(Continued)

OTHER PUBLICATIONS

Siegall et al., "Cell-Specific Toxicity of a Chimeric Protein Composed of Interleukin-6 and *Pseudomonas* Exotoxin (IL6-PE40) on Tumor Cells," *Mol. Cell. Biol.*, vol. 10, No. 6, pp. 2443-2447, American Society for Microbiology, Jun. 1990.

Pastan et al., "Recombinant Toxins for Cancer Treatment," *Science Mag.*, vol. 254, pp. 1173-1177, Nov. 22, 1991. Retrieved on Aug. 29, 2011 from www.sciencemag.org.

Siegall et al., "Analysis of Sequences in Domain II of *Pseudomonas* Exotoxin A Which Mediate Translocation," *Biochem.*, vol. 30, No. 29, pp. 7154-7159, American Chemical Society, 1991.

(Continued)

*Primary Examiner* — Amber D Steele
*Assistant Examiner* — Schuyler Milton
(74) *Attorney, Agent, or Firm* — Intrexon Corporation

(57) ABSTRACT

*Pseudomonas* exotoxin A or "PE" is a 66kD, highly potent, cytotoxic protein secreted by the bacterium *Pseudomonas aeruginosa*. Various forms of PE have been coupled to other proteins, such as antibodies, to generate therapeutically useful cytotoxin conjugates that selectively target cells of a desired phenotype (such as tumor cells). In the present invention, peptides spanning the sequence of an approximately 38kD form of *Pseudomonas* exotoxin A protein were analyzed for the presence of immunogenic CD4+ T cell epitopes. Six immunogenic T cell epitopes were identified. Residues were identified within each epitope for introduction of targeted amino acid substitutions to reduce or prevent immunogenic T-cell responses in PE molecules which may be administered to a heterologous host.

22 Claims, 12 Drawing Sheets

(56) References Cited

FOREIGN PATENT DOCUMENTS

| | | | |
|---|---|---|---|
| WO | WO 97/13529 | A1 | 4/1997 |
| WO | WO 98/20135 | A2 | 5/1998 |
| WO | WO 98/41641 | A1 | 9/1998 |
| WO | WO 99/28471 | A2 | 6/1999 |
| WO | WO 02/40545 | A2 | 5/2002 |
| WO | WO 2004/050849 | A2 | 6/2004 |
| WO | WO 2006/065867 | A2 | 6/2006 |
| WO | WO 2007/016150 | A2 | 2/2007 |
| WO | WO 2009/032954 | A1 | 3/2009 |
| WO | WO 2011/032022 | A1 | 3/2011 |
| WO | WO 2012/154530 | A1 | 11/2012 |
| WO | WO 2012/170617 | A1 | 12/2012 |
| WO | WO 2013/040141 | A1 | 3/2013 |

OTHER PUBLICATIONS

Theuer et al., "Immunotoxins Made with a Recombinant Form of *Pseudomonas* Exotoxin A That Do Not Require Proteolysis for Activity," *Cancer Res.*, vol. 53, pp. 340-347, American Assoc. for Cancer Research, Jan. 15, 1993. Retrieved on Jan. 9, 2014 from www.cancerres.aacjournals.org.

Benhar et al., "*Pseudomonas* Exotoxin A Mutants," *The Journal of Biol. Chem.*, vol. 269, No. 18, pp. 13398-13404, May 6, 1994.

Thomas et al., "Abrogation of Head and Neck Squamous Cell Carcinoma Growth by Epidermal Growth Factor Receptor Ligand Fused to *Pseudomonas* Exotoxin Transforming Growth Factor α-PE38," *Clin. Cancer Res.*, vol. 10, pp. 7079-7087, American Assoc. for Cancer Research, Oct. 15, 2004. Retrieved on Aug. 29, 2012 from www.clincancerres.aacjournals.org.

Bang et al., "HA22 (R490A) Is a Recombinant Immunotoxin with Increased Antitumor Activity without an Increase in Animal Toxicity," *Clin. Cancer Res.*, vol. 11, pp. 1545-1550, American Assoc. for Cancer Research, Feb. 15, 2005. Retrieved on Jan. 9, 2014 from www.clincancerres.aacjournals.org.

Onda et al., "An immunotoxin with greatly reduced immunogenicity by identification and removal of B cell epitopes," *PNAS*, vol. 105, No. 32, pp. 11311-11316. Aug. 12, 2008.

Weldon et al., "A protease-resistant immunotoxin against CD22 with greatly increased activity against CLL and diminished animal toxicity," *Blood*, vol. 113, No. 16, pp. 3792-3800, Apr. 16, 2009. Retrieved on Jan. 9, 2014 from www.bloodjournal.hematologylibrary.org.

Baker et al., "Pre-Clinical Considerations in the Assessment of Immunogenicity for Protein Therapeutics," *Current Drug Safety*, vol. 5, No. 4, pp. 1-6, Bentham Science Publishers Ltd., Feb. 19, 2010.

Kreitman et al., "Antibody Fusion Proteins: Anti-CD22 Recombinant Immunotoxin Moxetumomab Pasudotox," *Clin. Cancer Res.*, vol. 17, No. 20, pp. 6398-6405, American Assoc. for Cancer Research, Oct. 15, 2011.

Onda et al., "Recombinant immunotoxin against B-cell malignancies with no immunogenicity in mice by removal of B-cell epitopes," *PNAS*, vol. 108, No. 14, pp. 5742-5747, Apr. 5, 2011.

Pastan et al., "Immunotoxins with decreased immunogenicity and improved activity," *Leukemia & Lymphoma*, vol. 52, No. S2, pp. 87-90, Informa UK, Ltd., Jun. 2011. Retrieved on Jul. 11, 2011 from www.informahealthcare.com.

Weldon et al., "A guide to taming a toxin—recombinant immunotoxins constructed from *Pseudomonas* exotoxin A for the treatment of cancer," *The FEBS Journal*, vol. 278, pp. 4683-4700, FEBS, 2011.

Liu et al., "Recombinant immunotoxin engineered for low immunogenicity and antigenicity by identifying and silencing human B-cell epitopes," *PNAS*, vol. 109, No. 29, pp. 11782-11787, Jul. 17, 2012.

Hansen et al., "A Recombinant Immunotoxin Targeting CD22 With Low Immunogenicity, Low Nonspecific Toxicity, and High Antitumor Activity in Mice," *J Immunother*, vol. 33, No. 3, pp. 297-304, Lippincott Williams & Wilkins, Apr. 2010.

Hwang et al., "Functional Domains of Pseudomonas Exotoxin Identified by Deletion Analysis of the Gene Expressed in *E. Coli,*" *Cell*, vol. 48, pp. 129-136, Cell Press, Jan. 16, 1987.

Kreitman et al., "Recombinant immunotoxins and other therapies for relapsed/refractory hairy cell leukemia," *Leukemia & Lymphoma*, vol. 52, No. S2, pp. 82-86, Informa UK, Ltd., Jun. 2011.

Shapira et al., "An Immunoconjugate of Anti-CD24 and *Pseudomonas* Exotoxin Selectively Kills Human Colorectal Tumors in Mice," *Gastroenterology*, vol. 140, No. 3, pp. 935-946, Mar. 2011.

Chaudhary et al., "*Pseudomonas* exotoxin contains a specific sequence at the carboxyl terminus that is required for cytotoxicity," *Proc. Natl. Acad. Sci. USA*, vol. 87, pp. 308-312, Jan. 1990.

Hu et al., "Investigation of a plasmid containing a novel immunotoxin VEGF165-PE38 gene for antiangiogenic therapy in a malignant glioma model," *Int. J. Cancer*, vol. 127, pp. 2222-2229, 2010.

Itoi et al., "Targeting of Locus Ceruleus Noradrenergic Neurons Expressing Human Interleukin-2 Receptor α-Subunit in Transgenic Mice by a Recombinant Immunotoxin anti-Tac(Fv)-PE38: A Study for Exploring Noradrenergic Influence upon Anxiety-Like and Depression-Like Behaviors," *The Journal of Neuroscience*, vol. 31, No. 16, pp. 6132-6139, Society for Neuroscience, Apr. 20, 2011.

Kuan et al., "Affinity-matured anti-glycoprotein NMB recombinant immunotoxins targeting malignant gliomas and melanomas," *Int J Cancer*, vol. 129, No. 1, pp. 111-121, International Union Against Cancer, Jul. 1, 2011.

Mareeva et al., "A Novel Composite Immunotoxin That Suppresses Rabies Virus Production by the Infected Cells," *J Immunol Methods*, vol. 353, Nos. 1-2, pp. 1-18, Elsevier B.V., Feb. 28, 2010.

Nagata, S. and Pastan, I., "Removal of B cell epitopes as a practical approach for reducing the immunogenicity of foreign protein-based therapeutics," *Adv Drug Deliv Rev*, vol. 61, No. 11, pp. 977-985, Elsevier Science Publishers B.V., Sep. 30, 2009.

Seetharam et al., "Increased Cytotoxic Activity of *Pseudomonas* Exotoxin and Two Chimeric Toxins Ending in KDEL," *The Journal of Biological Chemistry*, vol. 266, No. 26, pp. 17376-17381, American Society for Biochemistry and Molecular Biology, Sep. 15, 1991.

Stish et al., "Design and modification of EGF4KDEL 7Mut, a novel bispecific ligand-directed toxin, with decreased immunogenicity and potent anti-mesothelioma activity," *British Journal of Cancer*, vol. 101, Cancer Research UK, Sep. 15, 2009.

Theuer et al., "A Recombinant Form of *Pseudomonas* Exotoxin Directed at the Epidermal Growth Factor Receptor That Is Cytotoxic without Requiring Proteolytic Processing," *The Journal of Biological Chemistry*, vol. 267, No. 24, pp. 16872-16877, American Society for Biochemistry and Molecular Biology, Aug. 25, 1992.

Zielinski et al.,"Affitoxin—A Novel Recombinant, HER2-Specific, Anti-Cancer Agent for Targeted Therapy of HER2-Positive Tumors," *J Immunother*, vol. 32, No. 8, pp. 817-825, Lippincott Williams & Wilkins, Oct. 2009.

Fontana et al., "Secreted Bacterial Effectors That Inhibit Host Protein Synthesis Are Critical for Induction of the Innate Immune Response to Virulent *Legionella pneumophila,*" *PLoS Pathog*, vol. 7, No. 2, Public Library of Science, Feb. 17, 2011.

International Search Report, mailed Jan. 28, 2013, for International Application No. PCT/US2012/53868, filed Sep. 6, 2012.

```
  1  AEEAFDLWNE CAKACVLDLK DGVRSSRMSV DPAIADTNGQ GVLHYSMVLE GGNDALKLAI
 61  DNALSITSDG LTIRLEGGVE PNKPVRYSYT RQARGSWSLN WLVPIGHEKP SNIKVFIHEL
121  NAGNQLSHMS PIYTIEMGDE LLAKLARDAT FFVRAHESNE MQPTLAISHA GVSVVMAQTQ
181  PRREKRWSEW ASGKVLCLLD PLDGVYNYLA QQRCNLDDTW EGKIYRVLAG NPAKHDLDIK
241  PTVISHRLHF PE GGSLAALT AHQACHLPLE TFTRHRQPRG WEQLEQCGYP VQRLVALYLA
301  ARLSWNQVDQ VIRNALASPG SGGDLGEAIR EQPEQARLAL TLAAAESERF VRQGTGNDEA
361  GAAN advvsl tcpvaageca GPADSGDALL ERNYPTGAE F LGDGGDVSFS TRGTQNWTVE
421  RLLQAHRQLE ERGYVFVGYH GTFLEAAQSI VFGGVRARSQ DLDAIWRGFY IAGDPALAYG
481  YAQDQEPDAR GRIRNGALLR VYVPRSSLPG FYRTSLTLAA PEAAGEVERL IGHPLPLRLD
541  AITGPEEEGG RLETILGWPL AERTVVIPSA IPTDPRNVGG DLDPSSIPDK EQAISALPDY
601  ASQPGKPPRE DLK  - 613          (SEQ ID NO:133)
```

Alternative carboxy-terminal tails:

```
609     REDLK - 613      (SEQ ID NO: 135)
609     REDL  - 612      (SEQ ID NO: 136)
609     KDEL  - 612      (SEQ ID NO: 137)
```

Amino Acids (AA):

1-252 = Domain IA (cell binding domain; underlined)

253-364 = Domain II (cytosolic translocation; *italics*)

365-399 = Domain IB (dashed underling; SEQ ID NO:139)

365-380 = optional deletion of 365- ADVVSLTCPVAAGECA -380

(SEQ ID NO:138)(lowercase letters; dashed underling)

400-613 = Domain III (cytotoxic portion; bold, double-underline)

609-613 or 609-612 = Alternative carboxy-terminal tails

FIG. 1

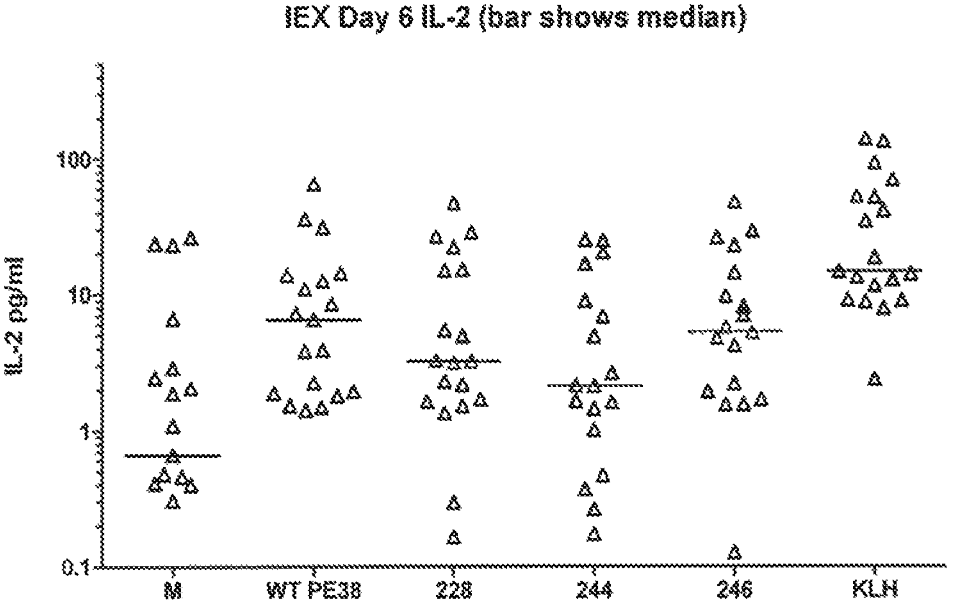
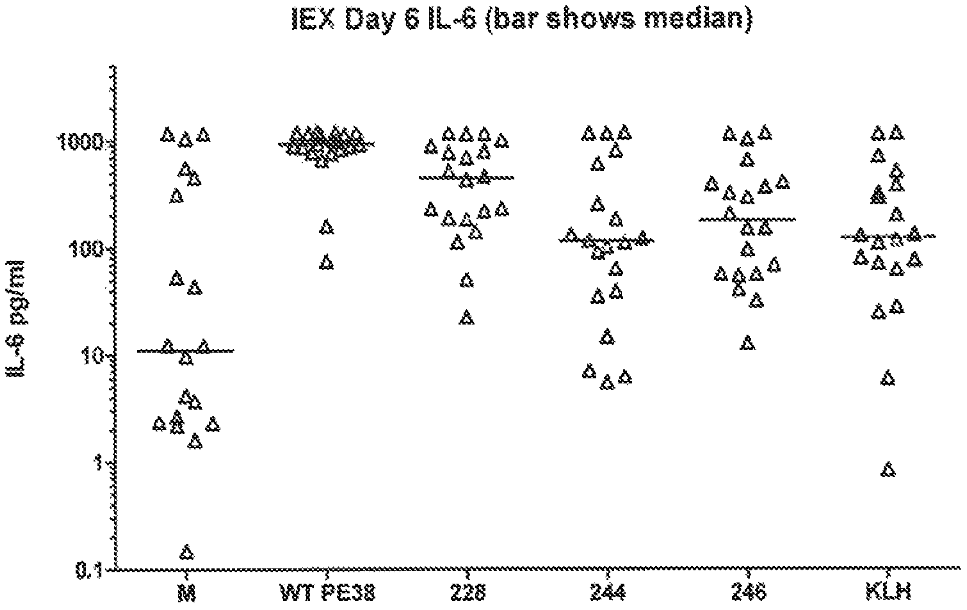
FIG. 11

SEQUENCE LISTING

```
<160> NUMBER OF SEQ ID NOS: 286

<210> SEQ ID NO 1
<211> LENGTH: 347
<212> TYPE: PRT
<213> ORGANISM: Pseudomonas aeruginosa
<220> FEATURE:
<221> NAME/KEY: MISC_FEATURE
<222> LOCATION: (1)..(347)
<223> OTHER INFORMATION: Pseudomonas aeruginosa PE38
<220> FEATURE:
<221> NAME/KEY: MISC_FEATURE
<222> LOCATION: (3)..(114)
<223> OTHER INFORMATION: Domain II (cytosolic translocation domain)
<220> FEATURE:
<221> NAME/KEY: MISC_FEATURE
<222> LOCATION: (115)..(133)
<223> OTHER INFORMATION: Partial Domain IB
<220> FEATURE:
<221> NAME/KEY: MISC_FEATURE
<222> LOCATION: (134)..(347)
<223> OTHER INFORMATION: Domain III (cytotoxic domain)
<220> FEATURE:
<221> NAME/KEY: MISC_FEATURE
<222> LOCATION: (343)..(347)
<223> OTHER INFORMATION: Alternative carboxy-terminal tail (amino
      acids..REDLK)

<400> SEQUENCE: 1

Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
    50                  55                  60

Ala Leu Ala Ser Pro Gly Ser Gly Gly Asp Leu Gly Glu Ala Ile Arg
65                  70                  75                  80

Glu Gln Pro Glu Gln Ala Arg Leu Ala Leu Thr Leu Ala Ala Ala Glu
                85                  90                  95
```

```
Ser Glu Arg Phe Val Arg Gln Gly Thr Gly Asn Asp Glu Ala Gly Ala
            100                 105                 110

Ala Ser Gly Pro Ala Asp Ser Gly Asp Ala Leu Leu Glu Arg Asn Tyr
        115                 120                 125

Pro Thr Gly Ala Glu Phe Leu Gly Asp Gly Gly Asp Ile Ser Phe Ser
    130                 135                 140

Thr Arg Gly Thr Gln Asn Trp Thr Val Glu Arg Leu Leu Gln Ala His
145                 150                 155                 160

Arg Gln Leu Glu Glu Arg Gly Tyr Val Phe Val Gly Tyr His Gly Thr
                165                 170                 175

Phe Leu Glu Ala Ala Gln Ser Ile Val Phe Gly Gly Val Arg Ala Arg
            180                 185                 190

Ser Gln Asp Leu Asp Ala Ile Trp Arg Gly Phe Tyr Ile Ala Gly Asp
        195                 200                 205

Pro Ala Leu Ala Tyr Gly Tyr Ala Gln Asp Gln Glu Pro Asp Ala Arg
    210                 215                 220

Gly Arg Ile Arg Asn Gly Ala Leu Leu Arg Val Tyr Val Pro Arg Ser
225                 230                 235                 240

Ser Leu Pro Gly Phe Tyr Arg Thr Gly Leu Thr Leu Ala Ala Pro Glu
                245                 250                 255

Ala Ala Gly Glu Val Glu Arg Leu Ile Gly His Pro Leu Pro Leu Arg
            260                 265                 270

Leu Asp Ala Ile Thr Gly Pro Glu Glu Glu Gly Gly Arg Leu Glu Thr
        275                 280                 285

Ile Leu Gly Trp Pro Leu Ala Glu Arg Thr Val Val Ile Pro Ser Ala
    290                 295                 300

Ile Pro Thr Asp Pro Arg Asn Val Gly Gly Asp Leu Asp Pro Ser Ser
305                 310                 315                 320

Ile Pro Asp Lys Glu Gln Ala Ile Ser Ala Leu Pro Asp Tyr Ala Ser
                325                 330                 335

Gln Pro Gly Lys Pro Pro Arg Glu Asp Leu Lys
            340                 345
```

<210> SEQ ID NO 2
<211> LENGTH: 359
<212> TYPE: PRT
<213> ORGANISM: Artificial Sequence
<220> FEATURE:
<223> OTHER INFORMATION: Gly-Ser-PE38 polypeptide
<220> FEATURE:
<221> NAME/KEY: MISC_FEATURE
<222> LOCATION: (1)..(12)
<223> OTHER INFORMATION: artificial linker sequence
<220> FEATURE:
<221> NAME/KEY: MISC_FEATURE
<222> LOCATION: (13)..(359)
<223> OTHER INFORMATION: Pseudomonas aeruginosa PE38
<220> FEATURE:
<221> NAME/KEY: MISC_FEATURE
<222> LOCATION: (15)..(126)
<223> OTHER INFORMATION: Domain II (cytosolic translocation domain)
<220> FEATURE:
<221> NAME/KEY: MISC_FEATURE
<222> LOCATION: (127)..(145)
<223> OTHER INFORMATION: Partial Domain IB
<220> FEATURE:
<221> NAME/KEY: MISC_FEATURE
<222> LOCATION: (146)..(359)
<223> OTHER INFORMATION: Domain III (cytotoxic domain)
<220> FEATURE:
<221> NAME/KEY: MISC_FEATURE
<222> LOCATION: (355)..(359)
<223> OTHER INFORMATION: Alternative carboxy-terminal tail (amino acids..REDLK)

<400> SEQUENCE: 2

```
Gly Gly Gly Gly Gly Ser Gly Gly Gly Gly Gly Ser Pro Glu Gly Gly
1               5                   10                  15

Ser Leu Ala Ala Leu Thr Ala His Gln Ala Cys His Leu Pro Leu Glu
            20                  25                  30

Thr Phe Thr Arg His Arg Gln Pro Arg Gly Trp Glu Gln Leu Glu Gln
        35                  40                  45

Cys Gly Tyr Pro Val Gln Arg Leu Val Ala Leu Tyr Leu Ala Ala Arg
    50                  55                  60

Leu Ser Trp Asn Gln Val Asp Gln Val Ile Arg Asn Ala Leu Ala Ser
65                  70                  75                  80

Pro Gly Ser Gly Gly Asp Leu Gly Glu Ala Ile Arg Glu Gln Pro Glu
                85                  90                  95

Gln Ala Arg Leu Ala Leu Thr Leu Ala Ala Ala Glu Ser Glu Arg Phe
            100                 105                 110

Val Arg Gln Gly Thr Gly Asn Asp Glu Ala Gly Ala Ala Ser Gly Pro
        115                 120                 125

Ala Asp Ser Gly Asp Ala Leu Leu Glu Arg Asn Tyr Pro Thr Gly Ala
    130                 135                 140

Glu Phe Leu Gly Asp Gly Gly Asp Ile Ser Phe Ser Thr Arg Gly Thr
145                 150                 155                 160

Gln Asn Trp Thr Val Glu Arg Leu Leu Gln Ala His Arg Gln Leu Glu
                165                 170                 175

Glu Arg Gly Tyr Val Phe Val Gly Tyr His Gly Thr Phe Leu Glu Ala
            180                 185                 190

Ala Gln Ser Ile Val Phe Gly Gly Val Arg Ala Arg Ser Gln Asp Leu
        195                 200                 205

Asp Ala Ile Trp Arg Gly Phe Tyr Ile Ala Gly Asp Pro Ala Leu Ala
    210                 215                 220

Tyr Gly Tyr Ala Gln Asp Gln Glu Pro Asp Ala Arg Gly Arg Ile Arg
225                 230                 235                 240

Asn Gly Ala Leu Leu Arg Val Tyr Val Pro Arg Ser Ser Leu Pro Gly
                245                 250                 255

Phe Tyr Arg Thr Gly Leu Thr Leu Ala Ala Pro Glu Ala Ala Gly Glu
            260                 265                 270

Val Glu Arg Leu Ile Gly His Pro Leu Pro Leu Arg Leu Asp Ala Ile
        275                 280                 285

Thr Gly Pro Glu Glu Glu Gly Gly Arg Leu Glu Thr Ile Leu Gly Trp
    290                 295                 300

Pro Leu Ala Glu Arg Thr Val Val Ile Pro Ser Ala Ile Pro Thr Asp
305                 310                 315                 320

Pro Arg Asn Val Gly Gly Asp Leu Asp Pro Ser Ser Ile Pro Asp Lys
                325                 330                 335

Glu Gln Ala Ile Ser Ala Leu Pro Asp Tyr Ala Ser Gln Pro Gly Lys
            340                 345                 350

Pro Pro Arg Glu Asp Leu Lys
        355
```

<210> SEQ ID NO 3
<211> LENGTH: 12
<212> TYPE: PRT
<213> ORGANISM: Artificial Sequence
<220> FEATURE:

-continued

<223> OTHER INFORMATION: 2x((Gx5)S) linker sequence
<220> FEATURE:
<221> NAME/KEY: MISC_FEATURE
<222> LOCATION: (1)..(12)
<223> OTHER INFORMATION: artificial linker sequence

<400> SEQUENCE: 3

```
Gly Gly Gly Gly Gly Ser Gly Gly Gly Gly Gly Ser
1               5                   10
```

<210> SEQ ID NO 4
<211> LENGTH: 347
<212> TYPE: PRT
<213> ORGANISM: Pseudomonas aeruginosa
<220> FEATURE:
<221> NAME/KEY: MISC_FEATURE
<222> LOCATION: (1)..(347)
<223> OTHER INFORMATION: Variant of Pseudomonas aeruginosa PE38 in SEQ ID NO:1
<220> FEATURE:
<221> NAME/KEY: MISC_FEATURE
<222> LOCATION: (114)..(114)
<223> OTHER INFORMATION: Ser-to-Asn change compared to SEQ ID NO:1
<220> FEATURE:
<221> NAME/KEY: MISC_FEATURE
<222> LOCATION: (141)..(141)
<223> OTHER INFORMATION: Ile-to-Val change compared to SEQ ID NO:1
<220> FEATURE:
<221> NAME/KEY: MISC_FEATURE
<222> LOCATION: (249)..(249)
<223> OTHER INFORMATION: Gly-to-Ser change compared to SEQ ID NO:1

<400> SEQUENCE: 4

```
Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
    50                  55                  60

Ala Leu Ala Ser Pro Gly Ser Gly Gly Asp Leu Gly Glu Ala Ile Arg
65                  70                  75                  80

Glu Gln Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Asn Gly Pro Ala Asp Ser Gly Asp Ala Leu Leu Glu Arg Asn Tyr
        115                 120                 125

Pro Thr Gly Ala Glu Phe Leu Gly Asp Gly Gly Asp Val Ser Phe Ser
    130                 135                 140

Thr Arg Gly Thr Gln Asn Trp Thr Val Glu Arg Leu Leu Gln Ala His
145                 150                 155                 160

Arg Gln Leu Glu Glu Arg Gly Tyr Val Phe Val Gly Tyr His Gly Thr
                165                 170                 175

Phe Leu Glu Ala Ala Gln Ser Ile Val Phe Gly Gly Val Arg Ala Arg
            180                 185                 190

Ser Gln Asp Leu Asp Ala Ile Trp Arg Gly Phe Tyr Ile Ala Gly Asp
        195                 200                 205

Pro Ala Leu Ala Tyr Gly Tyr Ala Gln Asp Gln Glu Pro Asp Ala Arg
    210                 215                 220

Gly Arg Ile Arg Asn Gly Ala Leu Leu Arg Val Tyr Val Pro Arg Ser
```

-continued

```
225                 230                 235                 240

Ser Leu Pro Gly Phe Tyr Arg Thr Ser Leu Thr Leu Ala Ala Pro Glu
                245                 250                 255

Ala Ala Gly Glu Val Glu Arg Leu Ile Gly His Pro Leu Pro Leu Arg
            260                 265                 270

Leu Asp Ala Ile Thr Gly Pro Glu Glu Glu Gly Gly Arg Leu Glu Thr
        275                 280                 285

Ile Leu Gly Trp Pro Leu Ala Glu Arg Thr Val Val Ile Pro Ser Ala
    290                 295                 300

Ile Pro Thr Asp Pro Arg Asn Val Gly Gly Asp Leu Asp Pro Ser Ser
305                 310                 315                 320

Ile Pro Asp Lys Glu Gln Ala Ile Ser Ala Leu Pro Asp Tyr Ala Ser
                325                 330                 335

Gln Pro Gly Lys Pro Pro Arg Glu Asp Leu Lys
            340                 345


<210> SEQ ID NO 5
<211> LENGTH: 9
<212> TYPE: PRT
<213> ORGANISM: Pseudomonas aeruginosa
<220> FEATURE:
<221> NAME/KEY: PEPTIDE
<222> LOCATION: (1)..(9)
<223> OTHER INFORMATION: Epitope 1

<400> SEQUENCE: 5

Ile Ser Phe Ser Thr Arg Gly Thr Gln
1               5


<210> SEQ ID NO 6
<211> LENGTH: 9
<212> TYPE: PRT
<213> ORGANISM: Pseudomonas aeruginosa
<220> FEATURE:
<221> NAME/KEY: PEPTIDE
<222> LOCATION: (1)..(9)
<223> OTHER INFORMATION: Epitope  2

<400> SEQUENCE: 6

Gly Thr Gln Asn Trp Thr Val Glu Arg
1               5


<210> SEQ ID NO 7
<211> LENGTH: 9
<212> TYPE: PRT
<213> ORGANISM: Pseudomonas aeruginosa
<220> FEATURE:
<221> NAME/KEY: PEPTIDE
<222> LOCATION: (1)..(9)
<223> OTHER INFORMATION: Epitope 3

<400> SEQUENCE: 7

Ile Val Phe Gly Gly Val Arg Ala Arg
1               5


<210> SEQ ID NO 8
<211> LENGTH: 9
<212> TYPE: PRT
<213> ORGANISM: Pseudomonas aeruginosa
<220> FEATURE:
<221> NAME/KEY: PEPTIDE
<222> LOCATION: (1)..(9)
<223> OTHER INFORMATION: Epitope 4

<400> SEQUENCE: 8
```

Ala Arg Ser Gln Asp Leu Asp Ala Ile
1               5

<210> SEQ ID NO 9
<211> LENGTH: 9
<212> TYPE: PRT
<213> ORGANISM: Pseudomonas aeruginosa
<220> FEATURE:
<221> NAME/KEY: PEPTIDE
<222> LOCATION: (1)..(9)
<223> OTHER INFORMATION: Epitope 5

<400> SEQUENCE: 9

Leu Arg Val Tyr Val Pro Arg Ser Ser
1               5

<210> SEQ ID NO 10
<211> LENGTH: 9
<212> TYPE: PRT
<213> ORGANISM: Pseudomonas aeruginosa
<220> FEATURE:
<221> NAME/KEY: PEPTIDE
<222> LOCATION: (1)..(9)
<223> OTHER INFORMATION: Epitope 6

<400> SEQUENCE: 10

Ile Pro Asp Lys Glu Gln Ala Ile Ser
1               5

<210> SEQ ID NO 11
<211> LENGTH: 15
<212> TYPE: PRT
<213> ORGANISM: Artificial Sequence
<220> FEATURE:
<223> OTHER INFORMATION: Gly-Ser linker plus PE38 sequence
<220> FEATURE:
<221> NAME/KEY: PEPTIDE
<222> LOCATION: (1)..(15)
<223> OTHER INFORMATION: Peptide 1

<400> SEQUENCE: 11

Gly Gly Gly Gly Gly Ser Gly Gly Gly Gly Gly Ser Pro Glu Gly
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Gly-Ser linker plus PE38 sequence
<220> FEATURE:
<221> NAME/KEY: PEPTIDE
<222> LOCATION: (1)..(15)
<223> OTHER INFORMATION: Peptide 2

<400> SEQUENCE: 12

Gly Gly Ser Gly Gly Gly Gly Gly Ser Pro Glu Gly Gly Ser Leu
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Gly-Ser linker plus PE38 sequence
<220> FEATURE:
<221> NAME/KEY: PEPTIDE
<222> LOCATION: (1)..(15)
<223> OTHER INFORMATION: Peptide 3

<400> SEQUENCE: 13

Gly Gly Gly Gly Gly Ser Pro Glu Gly Gly Ser Leu Ala Ala Leu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Gly-Ser linker plus PE38 sequence
<220> FEATURE:
<221> NAME/KEY: PEPTIDE
<222> LOCATION: (1)..(15)
<223> OTHER INFORMATION: Peptide 4

<400> SEQUENCE: 14

Gly Gly Ser Pro Glu Gly Gly Ser Leu Ala Ala Leu Thr Ala His
1               5                   10                  15

<210> SEQ ID NO 15
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 5

<400> SEQUENCE: 15

Pro Glu Gly Gly Ser Leu Ala Ala Leu Thr Ala His Gln Ala Cys
1               5                   10                  15

<210> SEQ ID NO 16
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 6

<400> SEQUENCE: 16

Gly Ser Leu Ala Ala Leu Thr Ala His Gln Ala Cys His Leu Pro
1               5                   10                  15

<210> SEQ ID NO 17
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 7

<400> SEQUENCE: 17

Ala Ala Leu Thr Ala His Gln Ala Cys His Leu Pro Leu Glu Thr
1               5                   10                  15

<210> SEQ ID NO 18
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 8

<400> SEQUENCE: 18

Thr Ala His Gln Ala Cys His Leu Pro Leu Glu Thr Phe Thr Arg
1 5 10 15

<210> SEQ ID NO 19
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 9

<400> SEQUENCE: 19

Gln Ala Cys His Leu Pro Leu Glu Thr Phe Thr Arg His Arg Gln
1 5 10 15

<210> SEQ ID NO 20
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 10

<400> SEQUENCE: 20

His Leu Pro Leu Glu Thr Phe Thr Arg His Arg Gln Pro Arg Gly
1 5 10 15

<210> SEQ ID NO 21
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 11

<400> SEQUENCE: 21

Leu Glu Thr Phe Thr Arg His Arg Gln Pro Arg Gly Trp Glu Gln
1 5 10 15

<210> SEQ ID NO 22
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 12

<400> SEQUENCE: 22

Phe Thr Arg His Arg Gln Pro Arg Gly Trp Glu Gln Leu Glu Gln
1 5 10 15

<210> SEQ ID NO 23
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 13

<400> SEQUENCE: 23

His Arg Gln Pro Arg Gly Trp Glu Gln Leu Glu Gln Cys Gly Tyr
1 5 10 15

<210> SEQ ID NO 24
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 14

<400> SEQUENCE: 24

Pro Arg Gly Trp Glu Gln Leu Glu Gln Cys Gly Tyr Pro Val Gln
1 5 10 15

<210> SEQ ID NO 25
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 15

<400> SEQUENCE: 25

Trp Glu Gln Leu Glu Gln Cys Gly Tyr Pro Val Gln Arg Leu Val
1 5 10 15

<210> SEQ ID NO 26
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 16

<400> SEQUENCE: 26

Leu Glu Gln Cys Gly Tyr Pro Val Gln Arg Leu Val Ala Leu Tyr
1 5 10 15

<210> SEQ ID NO 27
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 17

<400> SEQUENCE: 27

Cys Gly Tyr Pro Val Gln Arg Leu Val Ala Leu Tyr Leu Ala Ala
1 5 10 15

<210> SEQ ID NO 28
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 18

<400> SEQUENCE: 28

Pro Val Gln Arg Leu Val Ala Leu Tyr Leu Ala Ala Arg Leu Ser
1 5 10 15

<210> SEQ ID NO 29
<211> LENGTH: 15
<212> TYPE: PRT

<213> ORGANISM: Pseudomonas aeruginosa
<220> FEATURE:
<221> NAME/KEY: PEPTIDE
<222> LOCATION: (1)..(15)
<223> OTHER INFORMATION: Peptide 19

<400> SEQUENCE: 29

Arg Leu Val Ala Leu Tyr Leu Ala Ala Arg Leu Ser Trp Asn Gln
1               5                   10                  15

<210> SEQ ID NO 30
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 20

<400> SEQUENCE: 30

Ala Leu Tyr Leu Ala Ala Arg Leu Ser Trp Asn Gln Val Asp Gln
1               5                   10                  15

<210> SEQ ID NO 31
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 21

<400> SEQUENCE: 31

Leu Ala Ala Arg Leu Ser Trp Asn Gln Val Asp Gln Val Ile Arg
1               5                   10                  15

<210> SEQ ID NO 32
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 22

<400> SEQUENCE: 32

Arg Leu Ser Trp Asn Gln Val Asp Gln Val Ile Arg Asn Ala Leu
1               5                   10                  15

<210> SEQ ID NO 33
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 23

<400> SEQUENCE: 33

Trp Asn Gln Val Asp Gln Val Ile Arg Asn Ala Leu Ala Ser Pro
1               5                   10                  15

<210> SEQ ID NO 34
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)

<223> OTHER INFORMATION: Peptide 24

<400> SEQUENCE: 34

Val Asp Gln Val Ile Arg Asn Ala Leu Ala Ser Pro Gly Ser Gly
1 5 10 15

<210> SEQ ID NO 35
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 25

<400> SEQUENCE: 35

Val Ile Arg Asn Ala Leu Ala Ser Pro Gly Ser Gly Gly Asp Leu
1 5 10 15

<210> SEQ ID NO 36
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 26

<400> SEQUENCE: 36

Asn Ala Leu Ala Ser Pro Gly Ser Gly Gly Asp Leu Gly Glu Ala
1 5 10 15

<210> SEQ ID NO 37
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 27

<400> SEQUENCE: 37

Ala Ser Pro Gly Ser Gly Gly Asp Leu Gly Glu Ala Ile Arg Glu
1 5 10 15

<210> SEQ ID NO 38
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 28

<400> SEQUENCE: 38

Gly Ser Gly Gly Asp Leu Gly Glu Ala Ile Arg Glu Gln Pro Glu
1 5 10 15

<210> SEQ ID NO 39
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 29

<400> SEQUENCE: 39

```
Gly Asp Leu Gly Glu Ala Ile Arg Glu Gln Pro Glu Gln Ala Arg
1               5                   10                  15


<210> SEQ ID NO 40
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 30

<400> SEQUENCE: 40

Gly Glu Ala Ile Arg Glu Gln Pro Glu Gln Ala Arg Leu Ala Leu
1               5                   10                  15


<210> SEQ ID NO 41
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 31

<400> SEQUENCE: 41

Ile Arg Glu Gln Pro Glu Gln Ala Arg Leu Ala Leu Thr Leu Ala
1               5                   10                  15


<210> SEQ ID NO 42
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 32

<400> SEQUENCE: 42

Gln Pro Glu Gln Ala Arg Leu Ala Leu Thr Leu Ala Ala Ala Glu
1               5                   10                  15


<210> SEQ ID NO 43
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 33

<400> SEQUENCE: 43

Gln Ala Arg Leu Ala Leu Thr Leu Ala Ala Ala Glu Ser Glu Arg
1               5                   10                  15


<210> SEQ ID NO 44
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 34

<400> SEQUENCE: 44

Leu Ala Leu Thr Leu Ala Ala Ala Glu Ser Glu Arg Phe Val Arg
1               5                   10                  15
```

<210> SEQ ID NO 45
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 35

<400> SEQUENCE: 45

Thr Leu Ala Ala Ala Glu Ser Glu Arg Phe Val Arg Gln Gly Thr
1 5 10 15

<210> SEQ ID NO 46
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 36

<400> SEQUENCE: 46

Ala Ala Glu Ser Glu Arg Phe Val Arg Gln Gly Thr Gly Asn Asp
1 5 10 15

<210> SEQ ID NO 47
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 37

<400> SEQUENCE: 47

Ser Glu Arg Phe Val Arg Gln Gly Thr Gly Asn Asp Glu Ala Gly
1 5 10 15

<210> SEQ ID NO 48
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 38

<400> SEQUENCE: 48

Phe Val Arg Gln Gly Thr Gly Asn Asp Glu Ala Gly Ala Ala Ser
1 5 10 15

<210> SEQ ID NO 49
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 39

<400> SEQUENCE: 49

Gln Gly Thr Gly Asn Asp Glu Ala Gly Ala Ala Ser Gly Pro Ala
1 5 10 15

<210> SEQ ID NO 50
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 40

<400> SEQUENCE: 50

Gly Asn Asp Glu Ala Gly Ala Ala Ser Gly Pro Ala Asp Ser Gly
1 5 10 15

<210> SEQ ID NO 51
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 41

<400> SEQUENCE: 51

Glu Ala Gly Ala Ala Ser Gly Pro Ala Asp Ser Gly Asp Ala Leu
1 5 10 15

<210> SEQ ID NO 52
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 42

<400> SEQUENCE: 52

Ala Ala Ser Gly Pro Ala Asp Ser Gly Asp Ala Leu Leu Glu Arg
1 5 10 15

<210> SEQ ID NO 53
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 43

<400> SEQUENCE: 53

Gly Pro Ala Asp Ser Gly Asp Ala Leu Leu Glu Arg Asn Tyr Pro
1 5 10 15

<210> SEQ ID NO 54
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 44

<400> SEQUENCE: 54

Asp Ser Gly Asp Ala Leu Leu Glu Arg Asn Tyr Pro Thr Gly Ala
1 5 10 15

<210> SEQ ID NO 55
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 45

<400> SEQUENCE: 55

Asp Ala Leu Leu Glu Arg Asn Tyr Pro Thr Gly Ala Glu Phe Leu
1 5 10 15

<210> SEQ ID NO 56
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 46

<400> SEQUENCE: 56

Leu Glu Arg Asn Tyr Pro Thr Gly Ala Glu Phe Leu Gly Asp Gly
1 5 10 15

<210> SEQ ID NO 57
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 47

<400> SEQUENCE: 57

Asn Tyr Pro Thr Gly Ala Glu Phe Leu Gly Asp Gly Gly Asp Ile
1 5 10 15

<210> SEQ ID NO 58
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 48

<400> SEQUENCE: 58

Thr Gly Ala Glu Phe Leu Gly Asp Gly Gly Asp Ile Ser Phe Ser
1 5 10 15

<210> SEQ ID NO 59
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 49

<400> SEQUENCE: 59

Glu Phe Leu Gly Asp Gly Gly Asp Ile Ser Phe Ser Thr Arg Gly
1 5 10 15

<210> SEQ ID NO 60
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 50

<400> SEQUENCE: 60

Gly Asp Gly Gly Asp Ile Ser Phe Ser Thr Arg Gly Thr Gln Asn

```
1               5                   10                  15


<210> SEQ ID NO 61
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 51

<400> SEQUENCE: 61

Gly Asp Ile Ser Phe Ser Thr Arg Gly Thr Gln Asn Trp Thr Val
1               5                   10                  15


<210> SEQ ID NO 62
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 52

<400> SEQUENCE: 62

Ser Phe Ser Thr Arg Gly Thr Gln Asn Trp Thr Val Glu Arg Leu
1               5                   10                  15


<210> SEQ ID NO 63
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 53

<400> SEQUENCE: 63

Thr Arg Gly Thr Gln Asn Trp Thr Val Glu Arg Leu Leu Gln Ala
1               5                   10                  15


<210> SEQ ID NO 64
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 54

<400> SEQUENCE: 64

Thr Gln Asn Trp Thr Val Glu Arg Leu Leu Gln Ala His Arg Gln
1               5                   10                  15


<210> SEQ ID NO 65
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 55

<400> SEQUENCE: 65

Trp Thr Val Glu Arg Leu Leu Gln Ala His Arg Gln Leu Glu Glu
1               5                   10                  15


<210> SEQ ID NO 66
```

<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 56

<400> SEQUENCE: 66

Glu Arg Leu Leu Gln Ala His Arg Gln Leu Glu Glu Arg Gly Tyr
1 5 10 15

<210> SEQ ID NO 67
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 57

<400> SEQUENCE: 67

Leu Gln Ala His Arg Gln Leu Glu Glu Arg Gly Tyr Val Phe Val
1 5 10 15

<210> SEQ ID NO 68
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 58

<400> SEQUENCE: 68

His Arg Gln Leu Glu Glu Arg Gly Tyr Val Phe Val Gly Tyr His
1 5 10 15

<210> SEQ ID NO 69
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 59

<400> SEQUENCE: 69

Leu Glu Glu Arg Gly Tyr Val Phe Val Gly Tyr His Gly Thr Phe
1 5 10 15

<210> SEQ ID NO 70
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 60

<400> SEQUENCE: 70

Arg Gly Tyr Val Phe Val Gly Tyr His Gly Thr Phe Leu Glu Ala
1 5 10 15

<210> SEQ ID NO 71
<211> LENGTH: 15
<212> TYPE: PRT
<213> ORGANISM: Pseudomonas aeruginosa
<220> FEATURE:

<221> NAME/KEY: PEPTIDE
<222> LOCATION: (1)..(15)
<223> OTHER INFORMATION: Peptide 61

<400> SEQUENCE: 71

Val Phe Val Gly Tyr His Gly Thr Phe Leu Glu Ala Ala Gln Ser
1 5 10 15

<210> SEQ ID NO 72
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 62

<400> SEQUENCE: 72

Gly Tyr His Gly Thr Phe Leu Glu Ala Ala Gln Ser Ile Val Phe
1 5 10 15

<210> SEQ ID NO 73
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 63

<400> SEQUENCE: 73

Gly Thr Phe Leu Glu Ala Ala Gln Ser Ile Val Phe Gly Gly Val
1 5 10 15

<210> SEQ ID NO 74
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 64

<400> SEQUENCE: 74

Leu Glu Ala Ala Gln Ser Ile Val Phe Gly Gly Val Arg Ala Arg
1 5 10 15

<210> SEQ ID NO 75
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 65

<400> SEQUENCE: 75

Ala Gln Ser Ile Val Phe Gly Gly Val Arg Ala Arg Ser Gln Asp
1 5 10 15

<210> SEQ ID NO 76
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 66

<400> SEQUENCE: 76

Ile Val Phe Gly Gly Val Arg Ala Arg Ser Gln Asp Leu Asp Ala
1 5 10 15

<210> SEQ ID NO 77
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 67

<400> SEQUENCE: 77

Gly Gly Val Arg Ala Arg Ser Gln Asp Leu Asp Ala Ile Trp Arg
1 5 10 15

<210> SEQ ID NO 78
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 68

<400> SEQUENCE: 78

Arg Ala Arg Ser Gln Asp Leu Asp Ala Ile Trp Arg Gly Phe Tyr
1 5 10 15

<210> SEQ ID NO 79
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 69

<400> SEQUENCE: 79

Ser Gln Asp Leu Asp Ala Ile Trp Arg Gly Phe Tyr Ile Ala Gly
1 5 10 15

<210> SEQ ID NO 80
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 70

<400> SEQUENCE: 80

Leu Asp Ala Ile Trp Arg Gly Phe Tyr Ile Ala Gly Asp Pro Ala
1 5 10 15

<210> SEQ ID NO 81
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 71

<400> SEQUENCE: 81

Ile Trp Arg Gly Phe Tyr Ile Ala Gly Asp Pro Ala Leu Ala Tyr
1 5 10 15

<210> SEQ ID NO 82
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 72

<400> SEQUENCE: 82

Gly Phe Tyr Ile Ala Gly Asp Pro Ala Leu Ala Tyr Gly Tyr Ala
1 5 10 15

<210> SEQ ID NO 83
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 73

<400> SEQUENCE: 83

Ile Ala Gly Asp Pro Ala Leu Ala Tyr Gly Tyr Ala Gln Asp Gln
1 5 10 15

<210> SEQ ID NO 84
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 74

<400> SEQUENCE: 84

Asp Pro Ala Leu Ala Tyr Gly Tyr Ala Gln Asp Gln Glu Pro Asp
1 5 10 15

<210> SEQ ID NO 85
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 75

<400> SEQUENCE: 85

Leu Ala Tyr Gly Tyr Ala Gln Asp Gln Glu Pro Asp Ala Arg Gly
1 5 10 15

<210> SEQ ID NO 86
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 76

<400> SEQUENCE: 86

Gly Tyr Ala Gln Asp Gln Glu Pro Asp Ala Arg Gly Arg Ile Arg
1 5 10 15

<210> SEQ ID NO 87
<211> LENGTH: 15

<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 77

<400> SEQUENCE: 87

```
Gln Asp Gln Glu Pro Asp Ala Arg Gly Arg Ile Arg Asn Gly Ala
1               5                   10                  15
```

<210> SEQ ID NO 88
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 78

<400> SEQUENCE: 88

```
Glu Pro Asp Ala Arg Gly Arg Ile Arg Asn Gly Ala Leu Leu Arg
1               5                   10                  15
```

<210> SEQ ID NO 89
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 79

<400> SEQUENCE: 89

```
Ala Arg Gly Arg Ile Arg Asn Gly Ala Leu Leu Arg Val Tyr Val
1               5                   10                  15
```

<210> SEQ ID NO 90
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 80

<400> SEQUENCE: 90

```
Arg Ile Arg Asn Gly Ala Leu Leu Arg Val Tyr Val Pro Arg Ser
1               5                   10                  15
```

<210> SEQ ID NO 91
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 81

<400> SEQUENCE: 91

```
Asn Gly Ala Leu Leu Arg Val Tyr Val Pro Arg Ser Ser Leu Pro
1               5                   10                  15
```

<210> SEQ ID NO 92
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 82

<400> SEQUENCE: 92

Leu Leu Arg Val Tyr Val Pro Arg Ser Ser Leu Pro Gly Phe Tyr
1 5 10 15

<210> SEQ ID NO 93
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 83

<400> SEQUENCE: 93

Val Tyr Val Pro Arg Ser Ser Leu Pro Gly Phe Tyr Arg Thr Gly
1 5 10 15

<210> SEQ ID NO 94
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 84

<400> SEQUENCE: 94

Pro Arg Ser Ser Leu Pro Gly Phe Tyr Arg Thr Gly Leu Thr Leu
1 5 10 15

<210> SEQ ID NO 95
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 85

<400> SEQUENCE: 95

Ser Leu Pro Gly Phe Tyr Arg Thr Gly Leu Thr Leu Ala Ala Pro
1 5 10 15

<210> SEQ ID NO 96
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 86

<400> SEQUENCE: 96

Gly Phe Tyr Arg Thr Gly Leu Thr Leu Ala Ala Pro Glu Ala Ala
1 5 10 15

<210> SEQ ID NO 97
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 87

<400> SEQUENCE: 97

Arg Thr Gly Leu Thr Leu Ala Ala Pro Glu Ala Ala Gly Glu Val
1 5 10 15

<210> SEQ ID NO 98
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 88

<400> SEQUENCE: 98

Leu Thr Leu Ala Ala Pro Glu Ala Ala Gly Glu Val Glu Arg Leu
1 5 10 15

<210> SEQ ID NO 99
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 89

<400> SEQUENCE: 99

Ala Ala Pro Glu Ala Ala Gly Glu Val Glu Arg Leu Ile Gly His
1 5 10 15

<210> SEQ ID NO 100
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 90

<400> SEQUENCE: 100

Glu Ala Ala Gly Glu Val Glu Arg Leu Ile Gly His Pro Leu Pro
1 5 10 15

<210> SEQ ID NO 101
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 91

<400> SEQUENCE: 101

Gly Glu Val Glu Arg Leu Ile Gly His Pro Leu Pro Leu Arg Leu
1 5 10 15

<210> SEQ ID NO 102
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 92

<400> SEQUENCE: 102

Glu Arg Leu Ile Gly His Pro Leu Pro Leu Arg Leu Asp Ala Ile
1 5 10 15

<210> SEQ ID NO 103
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 93

<400> SEQUENCE: 103

Ile Gly His Pro Leu Pro Leu Arg Leu Asp Ala Ile Thr Gly Pro
1               5                   10                  15

<210> SEQ ID NO 104
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 94

<400> SEQUENCE: 104

Pro Leu Pro Leu Arg Leu Asp Ala Ile Thr Gly Pro Glu Glu Glu
1               5                   10                  15

<210> SEQ ID NO 105
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 95

<400> SEQUENCE: 105

Leu Arg Leu Asp Ala Ile Thr Gly Pro Glu Glu Glu Gly Gly Arg
1               5                   10                  15

<210> SEQ ID NO 106
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 96

<400> SEQUENCE: 106

Asp Ala Ile Thr Gly Pro Glu Glu Glu Gly Gly Arg Leu Glu Thr
1               5                   10                  15

<210> SEQ ID NO 107
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 97

<400> SEQUENCE: 107

Thr Gly Pro Glu Glu Glu Gly Gly Arg Leu Glu Thr Ile Leu Gly
1               5                   10                  15

<210> SEQ ID NO 108
<211> LENGTH: 15
<212> TYPE: PRT

<213> ORGANISM: Pseudomonas aeruginosa
<220> FEATURE:
<221> NAME/KEY: PEPTIDE
<222> LOCATION: (1)..(15)
<223> OTHER INFORMATION: Peptide 98

<400> SEQUENCE: 108

Glu Glu Glu Gly Gly Arg Leu Glu Thr Ile Leu Gly Trp Pro Leu
1 5 10 15

<210> SEQ ID NO 109
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 99

<400> SEQUENCE: 109

Gly Gly Arg Leu Glu Thr Ile Leu Gly Trp Pro Leu Ala Glu Arg
1 5 10 15

<210> SEQ ID NO 110
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 100

<400> SEQUENCE: 110

Leu Glu Thr Ile Leu Gly Trp Pro Leu Ala Glu Arg Thr Val Val
1 5 10 15

<210> SEQ ID NO 111
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 101

<400> SEQUENCE: 111

Ile Leu Gly Trp Pro Leu Ala Glu Arg Thr Val Val Ile Pro Ser
1 5 10 15

<210> SEQ ID NO 112
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 102

<400> SEQUENCE: 112

Trp Pro Leu Ala Glu Arg Thr Val Val Ile Pro Ser Ala Ile Pro
1 5 10 15

<210> SEQ ID NO 113
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)

-continued

<223> OTHER INFORMATION: Peptide 103

<400> SEQUENCE: 113

Ala Glu Arg Thr Val Val Ile Pro Ser Ala Ile Pro Thr Asp Pro
1 5 10 15

<210> SEQ ID NO 114
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 104

<400> SEQUENCE: 114

Thr Val Val Ile Pro Ser Ala Ile Pro Thr Asp Pro Arg Asn Val
1 5 10 15

<210> SEQ ID NO 115
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 105

<400> SEQUENCE: 115

Ile Pro Ser Ala Ile Pro Thr Asp Pro Arg Asn Val Gly Gly Asp
1 5 10 15

<210> SEQ ID NO 116
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 106

<400> SEQUENCE: 116

Ala Ile Pro Thr Asp Pro Arg Asn Val Gly Gly Asp Leu Asp Pro
1 5 10 15

<210> SEQ ID NO 117
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 107

<400> SEQUENCE: 117

Thr Asp Pro Arg Asn Val Gly Gly Asp Leu Asp Pro Ser Ser Ile
1 5 10 15

<210> SEQ ID NO 118
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 108

<400> SEQUENCE: 118

```
Arg Asn Val Gly Gly Asp Leu Asp Pro Ser Ser Ile Pro Asp Lys
1               5                   10                  15


<210> SEQ ID NO 119
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 109

<400> SEQUENCE: 119

Gly Gly Asp Leu Asp Pro Ser Ser Ile Pro Asp Lys Glu Gln Ala
1               5                   10                  15


<210> SEQ ID NO 120
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 110

<400> SEQUENCE: 120

Leu Asp Pro Ser Ser Ile Pro Asp Lys Glu Gln Ala Ile Ser Ala
1               5                   10                  15


<210> SEQ ID NO 121
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 111

<400> SEQUENCE: 121

Ser Ser Ile Pro Asp Lys Glu Gln Ala Ile Ser Ala Leu Pro Asp
1               5                   10                  15


<210> SEQ ID NO 122
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 112

<400> SEQUENCE: 122

Pro Asp Lys Glu Gln Ala Ile Ser Ala Leu Pro Asp Tyr Ala Ser
1               5                   10                  15


<210> SEQ ID NO 123
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 113

<400> SEQUENCE: 123

Glu Gln Ala Ile Ser Ala Leu Pro Asp Tyr Ala Ser Gln Pro Gly
1               5                   10                  15
```

-continued

<210> SEQ ID NO 124
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 114

<400> SEQUENCE: 124

Ile Ser Ala Leu Pro Asp Tyr Ala Ser Gln Pro Gly Lys Pro Pro
1 5 10 15

<210> SEQ ID NO 125
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 115

<400> SEQUENCE: 125

Leu Pro Asp Tyr Ala Ser Gln Pro Gly Lys Pro Pro Arg Glu Asp
1 5 10 15

<210> SEQ ID NO 126
<211> LENGTH: 14
<212> TYPE: PRT
<213> ORGANISM: Pseudomonas aeruginosa
<220> FEATURE:
<221> NAME/KEY: PEPTIDE
<222> LOCATION: (1)..(14)
<223> OTHER INFORMATION: Peptide 116

<400> SEQUENCE: 126

Tyr Ala Ser Gln Pro Gly Lys Pro Pro Arg Glu Asp Leu Lys
1 5 10

<210> SEQ ID NO 127
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 117

<400> SEQUENCE: 127

Ile Thr Gly Pro Glu Glu Glu Gly Gly Arg Leu Asp Thr Ile Leu
1 5 10 15

<210> SEQ ID NO 128
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 118

<400> SEQUENCE: 128

Pro Glu Glu Glu Gly Gly Arg Leu Asp Thr Ile Leu Gly Trp Pro
1 5 10 15

<210> SEQ ID NO 129
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 119

<400> SEQUENCE: 129

Glu Gly Gly Arg Leu Asp Thr Ile Leu Gly Trp Pro Leu Ala Glu
1 5 10 15

<210> SEQ ID NO 130
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Peptide 120

<400> SEQUENCE: 130

Arg Leu Asp Thr Ile Leu Gly Trp Pro Leu Ala Glu Arg Thr Val
1 5 10 15

<210> SEQ ID NO 131
<211> LENGTH: 15
<212> TYPE: PRT
<213> ORGANISM: Pseudomonas aeruginosa
<220> FEATURE:
<221> NAME/KEY: PEPTIDE
<222> LOCATION: (1)..(15)
<223> OTHER INFORMATION: Hypothetical Peptide 121

<400> SEQUENCE: 131

Ile Ser Phe Ser Thr Arg Gly Thr Gln Asn Trp Thr Val Glu Arg
1 5 10 15

<210> SEQ ID NO 132
<211> LENGTH: 16
<212> TYPE: PRT
<213> ORGANISM: Pseudomonas aeruginosa
<220> FEATURE:
<221> NAME/KEY: PEPTIDE
<222> LOCATION: (1)..(16)
<223> OTHER INFORMATION: Hypothetical Peptide 122

<400> SEQUENCE: 132

Ile Val Phe Gly Gly Val Arg Ala Arg Ser Gln Asp Leu Asp Ala Ile
1 5 10 15

<210> SEQ ID NO 133
<211> LENGTH: 613
<212> TYPE: PRT
<213> ORGANISM: Pseudomonas aeruginosa
<220> FEATURE:
<221> NAME/KEY: VARIANT
<222> LOCATION: (1)..(613)
<223> OTHER INFORMATION: Pseudomonas Exotoxin A variant

<400> SEQUENCE: 133

Ala Glu Glu Ala Phe Asp Leu Trp Asn Glu Cys Ala Lys Ala Cys Val
1 5 10 15

Leu Asp Leu Lys Asp Gly Val Arg Ser Ser Arg Met Ser Val Asp Pro
20 25 30

Ala Ile Ala Asp Thr Asn Gly Gln Gly Val Leu His Tyr Ser Met Val
35 40 45

Leu Glu Gly Gly Asn Asp Ala Leu Lys Leu Ala Ile Asp Asn Ala Leu
50 55 60

-continued

Ser Ile Thr Ser Asp Gly Leu Thr Ile Arg Leu Glu Gly Gly Val Glu
65 70 75 80

Pro Asn Lys Pro Val Arg Tyr Ser Tyr Thr Arg Gln Ala Arg Gly Ser
85 90 95

Trp Ser Leu Asn Trp Leu Val Pro Ile Gly His Glu Lys Pro Ser Asn
100 105 110

Ile Lys Val Phe Ile His Glu Leu Asn Ala Gly Asn Gln Leu Ser His
115 120 125

Met Ser Pro Ile Tyr Thr Ile Glu Met Gly Asp Glu Leu Leu Ala Lys
130 135 140

Leu Ala Arg Asp Ala Thr Phe Phe Val Arg Ala His Glu Ser Asn Glu
145 150 155 160

Met Gln Pro Thr Leu Ala Ile Ser His Ala Gly Val Ser Val Val Met
165 170 175

Ala Gln Thr Gln Pro Arg Arg Glu Lys Arg Trp Ser Glu Trp Ala Ser
180 185 190

Gly Lys Val Leu Cys Leu Leu Asp Pro Leu Asp Gly Val Tyr Asn Tyr
195 200 205

Leu Ala Gln Gln Arg Cys Asn Leu Asp Asp Thr Trp Glu Gly Lys Ile
210 215 220

Tyr Arg Val Leu Ala Gly Asn Pro Ala Lys His Asp Leu Asp Ile Lys
225 230 235 240

Pro Thr Val Ile Ser His Arg Leu His Phe Pro Glu Gly Gly Ser Leu
245 250 255

Ala Ala Leu Thr Ala His Gln Ala Cys His Leu Pro Leu Glu Thr Phe
260 265 270

Thr Arg His Arg Gln Pro Arg Gly Trp Glu Gln Leu Glu Gln Cys Gly
275 280 285

Tyr Pro Val Gln Arg Leu Val Ala Leu Tyr Leu Ala Ala Arg Leu Ser
290 295 300

Trp Asn Gln Val Asp Gln Val Ile Arg Asn Ala Leu Ala Ser Pro Gly
305 310 315 320

Ser Gly Gly Asp Leu Gly Glu Ala Ile Arg Glu Gln Pro Glu Gln Ala
325 330 335

Arg Leu Ala Leu Thr Leu Ala Ala Ala Glu Ser Glu Arg Phe Val Arg
340 345 350

Gln Gly Thr Gly Asn Asp Glu Ala Gly Ala Ala Asn Ala Asp Val Val
355 360 365

Ser Leu Thr Cys Pro Val Ala Ala Gly Glu Cys Ala Gly Pro Ala Asp
370 375 380

Ser Gly Asp Ala Leu Leu Glu Arg Asn Tyr Pro Thr Gly Ala Glu Phe
385 390 395 400

Leu Gly Asp Gly Gly Asp Val Ser Phe Ser Thr Arg Gly Thr Gln Asn
405 410 415

Trp Thr Val Glu Arg Leu Leu Gln Ala His Arg Gln Leu Glu Glu Arg
420 425 430

Gly Tyr Val Phe Val Gly Tyr His Gly Thr Phe Leu Glu Ala Ala Gln
435 440 445

Ser Ile Val Phe Gly Gly Val Arg Ala Arg Ser Gln Asp Leu Asp Ala
450 455 460

Ile Trp Arg Gly Phe Tyr Ile Ala Gly Asp Pro Ala Leu Ala Tyr Gly
465 470 475 480

Tyr Ala Gln Asp Gln Glu Pro Asp Ala Arg Gly Arg Ile Arg Asn Gly

```
            485                 490                 495

Ala Leu Leu Arg Val Tyr Val Pro Arg Ser Ser Leu Pro Gly Phe Tyr
        500                 505                 510

Arg Thr Ser Leu Thr Leu Ala Ala Pro Glu Ala Ala Gly Glu Val Glu
    515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610


<210> SEQ ID NO 134
<211> LENGTH: 649
<212> TYPE: PRT
<213> ORGANISM: Pseudomonas aeruginosa
<220> FEATURE:
<221> NAME/KEY: VARIANT
<222> LOCATION: (1)..(649)
<223> OTHER INFORMATION: Pseudomonas Exotoxin A variant

<400> SEQUENCE: 134

Asn Ala Asp Val Val Ser Leu Thr Cys Pro Val Ala Ala Gly Glu Cys
1               5                   10                  15

Ala Gly Pro Ala Asp Ser Gly Asp Ala Leu Leu Glu Arg Asn Tyr Pro
            20                  25                  30

Thr Gly Ala Glu Ala Glu Glu Ala Phe Asp Leu Trp Asn Glu Cys Ala
        35                  40                  45

Lys Ala Cys Val Leu Asp Leu Lys Asp Gly Val Arg Ser Ser Arg Met
    50                  55                  60

Ser Val Asp Pro Ala Ile Ala Asp Thr Asn Gly Gln Gly Val Leu His
65                  70                  75                  80

Tyr Ser Met Val Leu Glu Gly Gly Asn Asp Ala Leu Lys Leu Ala Ile
                85                  90                  95

Asp Asn Ala Leu Ser Ile Thr Ser Asp Gly Leu Thr Ile Arg Leu Glu
            100                 105                 110

Gly Gly Val Glu Pro Asn Lys Pro Val Arg Tyr Ser Tyr Thr Arg Gln
        115                 120                 125

Ala Arg Gly Ser Trp Ser Leu Asn Trp Leu Val Pro Ile Gly His Glu
    130                 135                 140

Lys Pro Ser Asn Ile Lys Val Phe Ile His Glu Leu Asn Ala Gly Asn
145                 150                 155                 160

Gln Leu Ser His Met Ser Pro Ile Tyr Thr Ile Glu Met Gly Asp Glu
                165                 170                 175

Leu Leu Ala Lys Leu Ala Arg Asp Ala Thr Phe Phe Val Arg Ala His
            180                 185                 190

Glu Ser Asn Glu Met Gln Pro Thr Leu Ala Ile Ser His Ala Gly Val
        195                 200                 205

Ser Val Val Met Ala Gln Thr Gln Pro Arg Arg Glu Lys Arg Trp Ser
    210                 215                 220
```

-continued

```
Glu Trp Ala Ser Gly Lys Val Leu Cys Leu Leu Asp Pro Leu Asp Gly
225                 230                 235                 240

Val Tyr Asn Tyr Leu Ala Gln Gln Arg Cys Asn Leu Asp Asp Thr Trp
                245                 250                 255

Glu Gly Lys Ile Tyr Arg Val Leu Ala Gly Asn Pro Ala Lys His Asp
            260                 265                 270

Leu Asp Ile Lys Pro Thr Val Ile Ser His Arg Leu His Phe Pro Glu
        275                 280                 285

Gly Gly Ser Leu Ala Ala Leu Thr Ala His Gln Ala Cys His Leu Pro
    290                 295                 300

Leu Glu Thr Phe Thr Arg His Arg Gln Pro Arg Gly Trp Glu Gln Leu
305                 310                 315                 320

Glu Gln Cys Gly Tyr Pro Val Gln Arg Leu Val Ala Leu Tyr Leu Ala
                325                 330                 335

Ala Arg Leu Ser Trp Asn Gln Val Asp Gln Val Ile Arg Asn Ala Leu
            340                 345                 350

Ala Ser Pro Gly Ser Gly Gly Asp Leu Gly Glu Ala Ile Arg Glu Gln
        355                 360                 365

Pro Glu Gln Ala Arg Leu Ala Leu Thr Leu Ala Ala Ala Glu Ser Glu
    370                 375                 380

Arg Phe Val Arg Gln Gly Thr Gly Asn Asp Glu Ala Gly Ala Ala Ser
385                 390                 395                 400

Ala Asp Val Val Ser Leu Thr Cys Pro Val Ala Ala Gly Glu Cys Ala
                405                 410                 415

Gly Pro Ala Asp Asn Gly Asp Ala Leu Leu Glu Arg Asn Tyr Pro Thr
            420                 425                 430

Gly Ala Glu Phe Leu Gly Asp Gly Gly Asp Ile Ser Phe Ser Thr Arg
        435                 440                 445

Gly Thr Gln Asn Trp Thr Val Glu Arg Leu Leu Gln Ala His Arg Gln
    450                 455                 460

Leu Glu Glu Arg Gly Tyr Val Phe Val Gly Tyr His Gly Thr Phe Leu
465                 470                 475                 480

Glu Ala Ala Gln Ser Ile Val Phe Gly Gly Val Arg Ala Arg Ser Gln
                485                 490                 495

Asp Leu Asp Ala Ile Trp Arg Gly Phe Tyr Ile Ala Gly Asp Pro Ala
            500                 505                 510

Leu Ala Tyr Gly Tyr Ala Gln Asp Gln Glu Pro Asp Ala Arg Gly Arg
        515                 520                 525

Ile Arg Asn Gly Ala Leu Leu Arg Val Tyr Val Pro Arg Ser Ser Leu
    530                 535                 540

Pro Gly Phe Tyr Arg Thr Gly Leu Thr Leu Ala Ala Pro Glu Ala Ala
545                 550                 555                 560

Gly Glu Val Glu Arg Leu Ile Gly His Pro Leu Pro Leu Arg Leu Asp
                565                 570                 575

Ala Ile Thr Gly Pro Glu Glu Glu Gly Gly Arg Leu Glu Thr Ile Leu
            580                 585                 590

Gly Trp Pro Leu Ala Glu Arg Thr Val Val Ile Pro Ser Ala Ile Pro
        595                 600                 605

Thr Asp Pro Arg Asn Val Gly Gly Asp Leu Asp Pro Ser Ser Ile Pro
    610                 615                 620

Asp Lys Glu Gln Ala Ile Ser Ala Leu Pro Asp Tyr Ala Ser Gln Pro
625                 630                 635                 640
```

Gly Lys Pro Pro Arg Glu Asp Leu Lys
645

<210> SEQ ID NO 135
<211> LENGTH: 5
<212> TYPE: PRT
<213> ORGANISM: Pseudomonas aeruginosa
<220> FEATURE:
<221> NAME/KEY: VARIANT
<222> LOCATION: (1)..(5)
<223> OTHER INFORMATION: Alternative carboxy terminal tail

<400> SEQUENCE: 135

Arg Glu Asp Leu Lys
1 5

<210> SEQ ID NO 136
<211> LENGTH: 4
<212> TYPE: PRT
<213> ORGANISM: Pseudomonas aeruginosa
<220> FEATURE:
<221> NAME/KEY: VARIANT
<222> LOCATION: (1)..(4)
<223> OTHER INFORMATION: Alternative carboxy terminal tail

<400> SEQUENCE: 136

Arg Glu Asp Leu
1

<210> SEQ ID NO 137
<211> LENGTH: 4
<212> TYPE: PRT
<213> ORGANISM: Pseudomonas aeruginosa
<220> FEATURE:
<221> NAME/KEY: VARIANT
<222> LOCATION: (1)..(4)
<223> OTHER INFORMATION: Alternative carboxy terminal tail

<400> SEQUENCE: 137

Lys Asp Glu Leu
1

<210> SEQ ID NO 138
<211> LENGTH: 16
<212> TYPE: PRT
<213> ORGANISM: Pseudomonas aeruginosa
<220> FEATURE:
<221> NAME/KEY: VARIANT
<222> LOCATION: (1)..(16)
<223> OTHER INFORMATION: alternative amino terminal portion of Domain IB

<400> SEQUENCE: 138

Ala Asp Val Val Ser Leu Thr Cys Pro Val Ala Ala Gly Glu Cys Ala
1 5 10 15

<210> SEQ ID NO 139
<211> LENGTH: 35
<212> TYPE: PRT
<213> ORGANISM: Pseudomonas aeruginosa
<220> FEATURE:
<221> NAME/KEY: VARIANT
<222> LOCATION: (1)..(35)
<223> OTHER INFORMATION: Domain IB

<400> SEQUENCE: 139

Ala Asp Val Val Ser Leu Thr Cys Pro Val Ala Ala Gly Glu Cys Ala
1 5 10 15

Gly Pro Ala Asp Ser Gly Asp Ala Leu Leu Glu Arg Asn Tyr Pro Thr

```
            20                  25                  30

Gly Ala Glu
        35


<210> SEQ ID NO 140
<211> LENGTH: 17
<212> TYPE: DNA
<213> ORGANISM: Artificial Sequence
<220> FEATURE:
<223> OTHER INFORMATION: Response element for ecdysone receptor
<220> FEATURE:
<221> NAME/KEY: misc_feature
<222> LOCATION: (9)..(9)
<223> OTHER INFORMATION: n is a, c, g, or t

<400> SEQUENCE: 140

rrggttcant gacacyy                                                      17


<210> SEQ ID NO 141
<211> LENGTH: 14
<212> TYPE: DNA
<213> ORGANISM: Artificial Sequence
<220> FEATURE:
<223> OTHER INFORMATION: Ecdysone receptor response element
<220> FEATURE:
<221> NAME/KEY: misc_feature
<222> LOCATION: (7)..(8)
<223> OTHER INFORMATION: nn at positions 7-8 is to indicate any number
      of spacer nucleotides

<400> SEQUENCE: 141

aggtcannag gtca                                                         14


<210> SEQ ID NO 142
<211> LENGTH: 15
<212> TYPE: DNA
<213> ORGANISM: Unknown
<220> FEATURE:
<223> OTHER INFORMATION: ecdysone receptor response element
<220> FEATURE:
<221> NAME/KEY: misc_feature
<222> LOCATION: (1)..(15)
<223> OTHER INFORMATION: ecdysone receptor response element

<400> SEQUENCE: 142

gggttgaatg aattt                                                        15


<210> SEQ ID NO 143
<211> LENGTH: 638
<212> TYPE: PRT
<213> ORGANISM: Pseudomonas aeruginosa
<220> FEATURE:
<221> NAME/KEY: VARIANT
<222> LOCATION: (1)..(638)
<223> OTHER INFORMATION: Pseudomonas Exotoxin A variant

<400> SEQUENCE: 143

Met His Leu Ile Pro His Trp Ile Pro Leu Val Ala Ser Leu Gly Leu
1               5                   10                  15

Leu Ala Gly Gly Ser Ser Ala Ser Ala Ala Glu Glu Ala Phe Asp Leu
            20                  25                  30

Trp Asn Glu Cys Ala Lys Ala Cys Val Leu Asp Leu Lys Asp Gly Val
        35                  40                  45

Arg Ser Ser Arg Met Ser Val Asp Pro Ala Ile Ala Asp Thr Asn Gly
    50                  55                  60

Gln Gly Val Leu His Tyr Ser Met Val Leu Glu Gly Gly Asn Asp Ala
```

-continued

```
65                  70                  75                  80

Leu Lys Leu Ala Ile Asp Asn Ala Leu Ser Ile Thr Ser Asn Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
        115                 120                 125

Pro Ile Gly His Glu Lys Pro Ser Asn Ile Lys Val Phe Ile His Glu
    130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Val Met Ala Gln Ala Gln Pro Arg Arg
        195                 200                 205

Glu Lys Arg Trp Ser Glu Trp Ala Ser Gly Lys Val Leu Cys Leu Leu
    210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
            260                 265                 270

Leu His Phe Pro Glu Gly Gly Ser Leu Ala Ala Leu Thr Ala His Gln
        275                 280                 285

Ala Cys His Leu Pro Leu Glu Thr Phe Thr Arg His Arg Gln Pro Arg
    290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Gly Asp Leu Gly Glu
            340                 345                 350

Ala Ile Arg Glu Gln Pro Glu Gln Ala Arg Leu Ala Leu Thr Leu Ala
        355                 360                 365

Ala Ala Glu Ser Glu Arg Phe Val Arg Gln Gly Thr Gly Asn Asp Glu
    370                 375                 380

Ala Gly Ala Ala Ser Ala Asp Val Val Ser Leu Thr Cys Pro Val Ala
385                 390                 395                 400

Ala Gly Glu Cys Ala Gly Pro Ala Asp Ser Gly Asp Ala Leu Leu Glu
                405                 410                 415

Arg Asn Tyr Pro Thr Gly Ala Glu Phe Leu Gly Asp Gly Gly Asp Ile
            420                 425                 430

Ser Phe Ser Thr Arg Gly Thr Gln Asn Trp Thr Val Glu Arg Leu Leu
        435                 440                 445

Gln Ala His Arg Gln Leu Glu Glu Arg Gly Tyr Val Phe Val Gly Tyr
    450                 455                 460

His Gly Thr Phe Leu Glu Ala Ala Gln Ser Ile Val Phe Gly Gly Val
465                 470                 475                 480

Arg Ala Arg Ser Gln Asp Leu Asp Ala Ile Trp Arg Gly Phe Tyr Ile
                485                 490                 495
```

```
Ala Gly Asp Pro Ala Leu Ala Tyr Gly Tyr Ala Gln Asp Gln Glu Pro
            500                 505                 510

Asp Ala Arg Gly Arg Ile Arg Asn Gly Ala Leu Leu Arg Val Tyr Val
        515                 520                 525

Pro Arg Ser Ser Leu Pro Gly Phe Tyr Arg Thr Gly Leu Thr Leu Ala
    530                 535                 540

Ala Pro Glu Ala Ala Gly Glu Val Glu Arg Leu Ile Gly His Pro Leu
545                 550                 555                 560

Pro Leu Arg Leu Asp Ala Ile Thr Gly Pro Glu Glu Glu Gly Gly Arg
                565                 570                 575

Leu Glu Thr Ile Leu Gly Trp Pro Leu Ala Glu Arg Thr Val Val Ile
            580                 585                 590

Pro Ser Ala Ile Pro Thr Asp Pro Arg Asn Val Gly Gly Asp Leu Asp
        595                 600                 605

Pro Ser Ser Ile Pro Asp Lys Glu Gln Ala Ile Ser Ala Leu Pro Asp
    610                 615                 620

Tyr Ala Ser Gln Pro Gly Lys Pro Pro Arg Glu Asp Leu Lys
625                 630                 635


<210> SEQ ID NO 144
<211> LENGTH: 613
<212> TYPE: PRT
<213> ORGANISM: Pseudomonas aeruginosa
<220> FEATURE:
<221> NAME/KEY: VARIANT
<222> LOCATION: (1)..(613)
<223> OTHER INFORMATION: PE variant

<400> SEQUENCE: 144

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205
```

-continued

```
Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Ser Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Ile Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Gly Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610
```

<210> SEQ ID NO 145
<211> LENGTH: 318
<212> TYPE: PRT
<213> ORGANISM: Pseudomonas aeruginosa
<220> FEATURE:
<221> NAME/KEY: VARIANT
<222> LOCATION: (1)..(318)
<223> OTHER INFORMATION: PE variant

<400> SEQUENCE: 145

Met Trp Glu Gln Leu Glu Gln Ser Gly Tyr Pro Val Gln Arg Leu Val
1               5                   10                  15

Ala Leu Tyr Leu Ala Ala Arg Leu Ser Trp Asn Gln Val Asp Gln Val
            20                  25                  30

Ile Arg Asn Ala Leu Ala Ser Pro Gly Ser Gly Gly Asp Leu Gly Glu
        35                  40                  45

Ala Ile Arg Glu Gln Pro Glu Gln Ala Arg Leu Ala Leu Thr Leu Ala
    50                  55                  60

Ala Ala Glu Ser Glu Arg Phe Val Arg Gln Gly Thr Gly Asn Asp Glu
65                  70                  75                  80

Ala Gly Ala Ala Ser Gly Pro Ala Asp Ser Gly Asp Ala Leu Leu Glu
                85                  90                  95

Arg Asn Tyr Pro Thr Gly Ala Glu Phe Leu Gly Asp Gly Gly Asp Ile
            100                 105                 110

Ser Phe Ser Thr Arg Gly Thr Gln Asn Trp Thr Val Glu Arg Leu Leu
        115                 120                 125

Gln Ala His Arg Gln Leu Glu Glu Arg Gly Tyr Val Phe Val Gly Tyr
    130                 135                 140

His Gly Thr Phe Leu Glu Ala Ala Gln Ser Ile Val Phe Gly Gly Val
145                 150                 155                 160

Arg Ala Arg Ser Gln Asp Leu Asp Ala Ile Trp Arg Gly Phe Tyr Ile
                165                 170                 175

Ala Gly Asp Pro Ala Leu Ala Tyr Gly Tyr Ala Gln Asp Gln Glu Pro
            180                 185                 190

Asp Ala Arg Gly Arg Ile Arg Asn Gly Ala Leu Leu Arg Val Tyr Val
        195                 200                 205

Pro Arg Ser Ser Leu Pro Gly Phe Tyr Arg Thr Gly Leu Thr Leu Ala
    210                 215                 220

Ala Pro Glu Ala Ala Gly Glu Val Glu Arg Leu Ile Gly His Pro Leu
225                 230                 235                 240

Pro Leu Arg Leu Asp Ala Ile Thr Gly Pro Glu Glu Glu Gly Gly Arg
                245                 250                 255

Leu Glu Thr Ile Leu Gly Trp Pro Leu Ala Glu Arg Thr Val Val Ile
            260                 265                 270

Pro Ser Ala Ile Pro Thr Asp Pro Arg Asn Val Gly Gly Asp Leu Asp
        275                 280                 285

Pro Ser Ser Ile Pro Asp Lys Glu Gln Ala Ile Ser Ala Leu Pro Asp
    290                 295                 300

Tyr Ala Ser Gln Pro Gly Lys Pro Pro Arg Glu Asp Leu Lys
305                 310                 315

<210> SEQ ID NO 146
<211> LENGTH: 613
<212> TYPE: PRT
<213> ORGANISM: Pseudomonas aeruginosa
<220> FEATURE:
<221> NAME/KEY: VARIANT
<222> LOCATION: (1)..(613)

<223> OTHER INFORMATION: PE variant

<400> SEQUENCE: 146

```
Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Ser Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400
```

```
Leu Gly Asp Gly Gly Asp Ile Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Gly Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610


<210> SEQ ID NO 147
<211> LENGTH: 613
<212> TYPE: PRT
<213> ORGANISM: Pseudomonas aeruginosa
<220> FEATURE:
<221> NAME/KEY: VARIANT
<222> LOCATION: (1)..(613)

<400> SEQUENCE: 147

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140
```

-continued

```
Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Ser Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Ile Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Gly Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560
```

```
Ala Glu Arg Thr Val Val Ile Pro Ser Ala Ile Pro Thr Asp Pro Arg
            565                 570                 575

Asn Val Gly Gly Asp Leu Asp Pro Ser Ser Ile Pro Asp Gln Glu Gln
            580                 585                 590

Ala Ile Ser Ala Leu Pro Asp Tyr Ala Ser Gln Pro Gly Gln Pro Pro
        595                 600                 605

Arg Glu Asp Leu Arg
    610


<210> SEQ ID NO 148
<211> LENGTH: 346
<212> TYPE: PRT
<213> ORGANISM: Pseudomonas aeruginosa
<220> FEATURE:
<221> NAME/KEY: VARIANT
<222> LOCATION: (1)..(346)
<223> OTHER INFORMATION: PE variant

<400> SEQUENCE: 148

Met Gly Gly Ser Leu Ala Ala Leu Thr Ala His Gln Ala Cys His Leu
1               5                   10                  15

Pro Leu Glu Thr Phe Thr Arg His Arg Gln Pro Arg Gly Trp Glu Gln
            20                  25                  30

Leu Glu Gln Cys Gly Tyr Pro Val Gln Arg Leu Val Ala Leu Tyr Leu
        35                  40                  45

Ala Ala Arg Leu Ser Trp Asn Gln Val Asp Gln Val Ile Arg Asn Ala
    50                  55                  60

Leu Ala Ser Pro Gly Ser Gly Gly Asp Leu Gly Glu Ala Ile Arg Glu
65                  70                  75                  80

Gln Pro Glu Gln Ala Arg Leu Ala Leu Thr Leu Ala Ala Ala Glu Ser
                85                  90                  95

Glu Arg Phe Val Arg Gln Gly Thr Gly Asn Asp Glu Ala Gly Ala Ala
            100                 105                 110

Ser Gly Pro Ala Asp Ser Gly Asp Ala Leu Leu Glu Arg Asn Tyr Pro
        115                 120                 125

Thr Gly Ala Glu Phe Leu Gly Asp Gly Gly Asp Ile Ser Phe Ser Thr
    130                 135                 140

Arg Gly Thr Gln Asn Trp Thr Val Glu Arg Leu Leu Gln Ala His Arg
145                 150                 155                 160

Gln Leu Glu Glu Arg Gly Tyr Val Phe Val Gly Tyr His Gly Thr Phe
                165                 170                 175

Leu Glu Ala Ala Gln Ser Ile Val Phe Gly Gly Val Arg Ala Arg Ser
            180                 185                 190

Gln Asp Leu Asp Ala Ile Trp Arg Gly Phe Tyr Ile Ala Gly Asp Pro
        195                 200                 205

Ala Leu Ala Tyr Gly Tyr Ala Gln Asp Gln Glu Pro Asp Ala Arg Gly
    210                 215                 220

Arg Ile Arg Asn Gly Ala Leu Leu Arg Val Tyr Val Pro Arg Ser Ser
225                 230                 235                 240

Leu Pro Gly Phe Tyr Arg Thr Gly Leu Thr Leu Ala Ala Pro Glu Ala
                245                 250                 255

Ala Gly Glu Val Glu Arg Leu Ile Gly His Pro Leu Pro Leu Arg Leu
            260                 265                 270

Asp Ala Ile Thr Gly Pro Glu Glu Glu Gly Gly Arg Leu Glu Thr Ile
        275                 280                 285

Leu Gly Trp Pro Leu Ala Glu Arg Thr Val Val Ile Pro Ser Ala Ile
```

```
    290                 295                 300

Pro Thr Asp Pro Arg Asn Val Gly Gly Asp Leu Asp Pro Ser Ser Ile
305                 310                 315                 320

Pro Asp Gln Glu Gln Ala Ile Ser Ala Leu Pro Asp Tyr Ala Ser Gln
                325                 330                 335

Pro Gly Gln Pro Pro Arg Glu Asp Leu Arg
            340                 345


<210> SEQ ID NO 149
<211> LENGTH: 613
<212> TYPE: PRT
<213> ORGANISM: Pseudomonas aeruginosa
<220> FEATURE:
<221> NAME/KEY: VARIANT
<222> LOCATION: (1)..(613)
<223> OTHER INFORMATION: PE variant
<220> FEATURE:
<221> NAME/KEY: VARIANT
<222> LOCATION: (1)..(613)
<223> OTHER INFORMATION: To use for fusion to ligand at c-terminus,
      delete AA 1-252 and 365-380; all of domain IB and portion of
      domain II (AA 350-394 can be deleted and replaced with GGGGS
      linker sequence.

<400> SEQUENCE: 149

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
```

```
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Ser Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Ile Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Gly Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610


<210> SEQ ID NO 150
<211> LENGTH: 321
<212> TYPE: PRT
<213> ORGANISM: Pseudomonas aeruginosa
<220> FEATURE:
<221> NAME/KEY: VARIANT
<222> LOCATION: (1)..(321)
<223> OTHER INFORMATION: PE variant with deletions for use as fusion
      protein to ligand C-terminus
```

<400> SEQUENCE: 150

Gly Gly Gly Gly Ser Gly Gly Ser Leu Ala Ala Leu Thr Ala His Gln
1               5                   10                  15

Ala Cys His Leu Pro Leu Glu Thr Phe Thr Arg His Arg Gln Pro Arg
            20                  25                  30

Gly Trp Glu Gln Leu Glu Gln Cys Gly Tyr Pro Val Gln Arg Leu Val
        35                  40                  45

Ala Leu Tyr Leu Ala Ala Arg Leu Ser Trp Asn Gln Val Asp Gln Val
    50                  55                  60

Ile Arg Asn Ala Leu Ala Ser Pro Gly Ser Gly Gly Asp Leu Gly Glu
65                  70                  75                  80

Ala Ile Arg Glu Gln Pro Glu Gln Ala Arg Leu Ala Leu Thr Leu Ala
                85                  90                  95

Ala Ala Glu Ser Glu Arg Pro Thr Gly Ala Glu Phe Leu Gly Asp Gly
            100                 105                 110

Gly Asp Ile Ser Phe Ser Thr Arg Gly Thr Gln Asn Trp Thr Val Glu
        115                 120                 125

Arg Leu Leu Gln Ala His Arg Gln Leu Glu Glu Arg Gly Tyr Val Phe
    130                 135                 140

Val Gly Tyr His Gly Thr Phe Leu Glu Ala Ala Gln Ser Ile Val Phe
145                 150                 155                 160

Gly Gly Val Arg Ala Arg Ser Gln Asp Leu Asp Ala Ile Trp Arg Gly
                165                 170                 175

Phe Tyr Ile Ala Gly Asp Pro Ala Leu Ala Tyr Gly Tyr Ala Gln Asp
            180                 185                 190

Gln Glu Pro Asp Ala Arg Gly Arg Ile Arg Asn Gly Ala Leu Leu Arg
        195                 200                 205

Val Tyr Val Pro Arg Ser Ser Leu Pro Gly Phe Tyr Arg Thr Gly Leu
    210                 215                 220

Thr Leu Ala Ala Pro Glu Ala Ala Gly Glu Val Glu Arg Leu Ile Gly
225                 230                 235                 240

His Pro Leu Pro Leu Arg Leu Asp Ala Ile Thr Gly Pro Glu Glu Glu
                245                 250                 255

Gly Gly Arg Leu Glu Thr Ile Leu Gly Trp Pro Leu Ala Glu Arg Thr
            260                 265                 270

Val Val Ile Pro Ser Ala Ile Pro Thr Asp Pro Arg Asn Val Gly Gly
        275                 280                 285

Asp Leu Asp Pro Ser Ser Ile Pro Asp Lys Glu Gln Ala Ile Ser Ala
    290                 295                 300

Leu Pro Asp Tyr Ala Ser Gln Pro Gly Lys Pro Pro Arg Glu Asp Leu
305                 310                 315                 320

Lys

<210> SEQ ID NO 151
<211> LENGTH: 321
<212> TYPE: PRT
<213> ORGANISM: Pseudomonas aeruginosa
<220> FEATURE:
<221> NAME/KEY: VARIANT
<222> LOCATION: (1)..(321)
<223> OTHER INFORMATION: PE variant

<400> SEQUENCE: 151

Gly Gly Gly Gly Ser Gly Gly Ser Leu Ala Ala Leu Thr Ala His Gln
1               5                   10                  15

```
Ala Cys His Leu Pro Leu Glu Thr Phe Thr Arg His Arg Gln Pro Arg
            20                  25                  30

Gly Trp Glu Gln Leu Glu Gln Cys Gly Tyr Pro Val Gln Arg Leu Val
        35                  40                  45

Ala Leu Tyr Leu Ala Ala Arg Leu Ser Trp Asn Gln Val Asp Gln Val
    50                  55                  60

Ile Arg Asn Ala Leu Ala Ser Pro Gly Ser Gly Gly Asp Leu Gly Glu
65                  70                  75                  80

Ala Ile Arg Glu Gln Pro Glu Gln Ala Arg Leu Ala Leu Thr Leu Ala
                85                  90                  95

Ala Ala Glu Ser Glu Arg Pro Thr Gly Ala Glu Phe Leu Gly Asp Gly
            100                 105                 110

Gly Asp Ile Ser Phe Ser Thr Arg Gly Thr Gln Asn Trp Thr Val Glu
        115                 120                 125

Arg Leu Leu Gln Ala His Arg Gln Leu Glu Glu Arg Gly Tyr Val Phe
    130                 135                 140

Val Gly Tyr His Gly Thr Phe Leu Glu Ala Ala Gln Ser Ile Val Phe
145                 150                 155                 160

Gly Gly Val Arg Ala Arg Ser Gln Asp Leu Asp Ala Ile Trp Arg Gly
                165                 170                 175

Phe Tyr Ile Ala Gly Asp Pro Ala Leu Ala Tyr Gly Tyr Ala Gln Asp
            180                 185                 190

Gln Glu Pro Asp Ala Arg Gly Arg Ile Arg Asn Gly Ala Leu Leu Arg
        195                 200                 205

Val Tyr Val Pro Arg Ser Ser Leu Pro Gly Phe Tyr Arg Thr Gly Leu
    210                 215                 220

Thr Leu Ala Ala Pro Glu Ala Ala Gly Glu Val Glu Arg Leu Ile Gly
225                 230                 235                 240

His Pro Leu Pro Leu Arg Leu Asp Ala Ile Thr Gly Pro Glu Glu Glu
                245                 250                 255

Gly Gly Arg Leu Glu Thr Ile Leu Gly Trp Pro Leu Ala Glu Arg Thr
            260                 265                 270

Val Val Ile Pro Ser Ala Ile Pro Thr Asp Pro Arg Asn Val Gly Gly
        275                 280                 285

Asp Leu Asp Pro Ser Ser Ile Pro Asp Gln Glu Gln Ala Ile Ser Ala
    290                 295                 300

Leu Pro Asp Tyr Ala Ser Gln Pro Gly Gln Pro Pro Arg Glu Asp Leu
305                 310                 315                 320

Arg


<210> SEQ ID NO 152
<211> LENGTH: 613
<212> TYPE: PRT
<213> ORGANISM: Pseudomonas aeruginosa
<220> FEATURE:
<221> NAME/KEY: VARIANT
<222> LOCATION: (1)..(613)
<223> OTHER INFORMATION: PE variant

<400> SEQUENCE: 152

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45
```

-continued

```
Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Ser Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Ile Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460
```

```
Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Gly Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610


<210> SEQ ID NO 153
<211> LENGTH: 363
<212> TYPE: PRT
<213> ORGANISM: Pseudomonas aeruginosa
<220> FEATURE:
<221> NAME/KEY: VARIANT
<222> LOCATION: (1)..(363)
<223> OTHER INFORMATION: PE variant

<400> SEQUENCE: 153

Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
    50                  55                  60

Ala Leu Ala Ser Pro Gly Ser Gly Gly Asp Leu Gly Glu Ala Ile Arg
65                  70                  75                  80

Glu Gln Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Ser Ala Asp Val Val Ser Leu Thr Cys Pro Val Ala Ala Gly Glu
        115                 120                 125

Cys Ala Gly Pro Ala Asp Ser Gly Asp Ala Leu Leu Glu Arg Asn Tyr
    130                 135                 140

Pro Thr Gly Ala Glu Phe Leu Gly Asp Gly Gly Asp Ile Ser Phe Ser
145                 150                 155                 160

Thr Arg Gly Thr Gln Asn Trp Thr Val Glu Arg Leu Leu Gln Ala His
                165                 170                 175

Arg Gln Leu Glu Glu Arg Gly Tyr Val Phe Val Gly Tyr His Gly Thr
            180                 185                 190

Phe Leu Glu Ala Ala Gln Ser Ile Val Phe Gly Gly Val Arg Ala Arg
```

```
        195                 200                 205

Ser Gln Asp Leu Asp Ala Ile Trp Arg Gly Phe Tyr Ile Ala Gly Asp
    210                 215                 220

Pro Ala Leu Ala Tyr Gly Tyr Ala Gln Asp Gln Glu Pro Asp Ala Arg
225                 230                 235                 240

Gly Arg Ile Arg Asn Gly Ala Leu Leu Arg Val Tyr Val Pro Arg Ser
                245                 250                 255

Ser Leu Pro Gly Phe Tyr Arg Thr Gly Leu Thr Leu Ala Ala Pro Glu
            260                 265                 270

Ala Ala Gly Glu Val Glu Arg Leu Ile Gly His Pro Leu Pro Leu Arg
        275                 280                 285

Leu Asp Ala Ile Thr Gly Pro Glu Glu Glu Gly Gly Arg Leu Glu Thr
    290                 295                 300

Ile Leu Gly Trp Pro Leu Ala Glu Arg Thr Val Val Ile Pro Ser Ala
305                 310                 315                 320

Ile Pro Thr Asp Pro Arg Asn Val Gly Gly Asp Leu Asp Pro Ser Ser
                325                 330                 335

Ile Pro Asp Lys Glu Gln Ala Ile Ser Ala Leu Pro Asp Tyr Ala Ser
            340                 345                 350

Gln Pro Gly Lys Pro Pro Arg Glu Asp Leu Lys
        355                 360


<210> SEQ ID NO 154
<211> LENGTH: 318
<212> TYPE: PRT
<213> ORGANISM: Pseudomonas aeruginosa
<220> FEATURE:
<221> NAME/KEY: VARIANT
<222> LOCATION: (1)..(318)
<223> OTHER INFORMATION: PE37 variant begining with initiation
      methionine

<400> SEQUENCE: 154

Met Trp Glu Gln Leu Glu Gln Cys Gly Tyr Pro Val Gln Arg Leu Val
1               5                   10                  15

Ala Leu Tyr Leu Ala Ala Arg Leu Ser Trp Asn Gln Val Asp Gln Val
            20                  25                  30

Ile Arg Asn Ala Leu Ala Ser Pro Gly Ser Gly Gly Asp Leu Gly Glu
        35                  40                  45

Ala Ile Arg Glu Gln Pro Glu Gln Ala Arg Leu Ala Leu Thr Leu Ala
    50                  55                  60

Ala Ala Glu Ser Glu Arg Phe Val Arg Gln Gly Thr Gly Asn Asp Glu
65                  70                  75                  80

Ala Gly Ala Ala Asn Gly Pro Ala Asp Ser Gly Asp Ala Leu Leu Glu
                85                  90                  95

Arg Asn Tyr Pro Thr Gly Ala Glu Phe Leu Gly Asp Gly Gly Asp Val
            100                 105                 110

Ser Phe Ser Thr Arg Gly Thr Gln Asn Trp Thr Val Glu Arg Leu Leu
        115                 120                 125

Gln Ala His Arg Gln Leu Glu Glu Arg Gly Tyr Val Phe Val Gly Tyr
    130                 135                 140

His Gly Thr Phe Leu Glu Ala Ala Gln Ser Ile Val Phe Gly Gly Val
145                 150                 155                 160

Arg Ala Arg Ser Gln Asp Leu Asp Ala Ile Trp Arg Gly Phe Tyr Ile
                165                 170                 175

Ala Gly Asp Pro Ala Leu Ala Tyr Gly Tyr Ala Gln Asp Gln Glu Pro
```

```
            180                 185                 190

Asp Ala Arg Gly Arg Ile Arg Asn Gly Ala Leu Leu Arg Val Tyr Val
        195                 200                 205

Pro Arg Ser Ser Leu Pro Gly Phe Tyr Arg Thr Ser Leu Thr Leu Ala
    210                 215                 220

Ala Pro Glu Ala Ala Gly Glu Val Glu Arg Leu Ile Gly His Pro Leu
225                 230                 235                 240

Pro Leu Arg Leu Asp Ala Ile Thr Gly Pro Glu Glu Glu Gly Gly Arg
                245                 250                 255

Leu Glu Thr Ile Leu Gly Trp Pro Leu Ala Glu Arg Thr Val Val Ile
            260                 265                 270

Pro Ser Ala Ile Pro Thr Asp Pro Arg Asn Val Gly Gly Asp Leu Asp
        275                 280                 285

Pro Ser Ser Ile Pro Asp Lys Glu Gln Ala Ile Ser Ala Leu Pro Asp
    290                 295                 300

Tyr Ala Ser Gln Pro Gly Lys Pro Pro Arg Glu Asp Leu Lys
305                 310                 315


<210> SEQ ID NO 155
<211> LENGTH: 346
<212> TYPE: PRT
<213> ORGANISM: Pseudomonas aeruginosa
<220> FEATURE:
<221> NAME/KEY: VARIANT
<222> LOCATION: (1)..(346)
<223> OTHER INFORMATION: PE variant begining with methionine

<400> SEQUENCE: 155

Met Gly Gly Ser Leu Ala Ala Leu Thr Ala His Gln Ala Cys His Leu
1               5                   10                  15

Pro Leu Glu Thr Phe Thr Arg His Arg Gln Pro Arg Gly Trp Glu Gln
            20                  25                  30

Leu Glu Gln Cys Gly Tyr Pro Val Gln Arg Leu Val Ala Leu Tyr Leu
        35                  40                  45

Ala Ala Arg Leu Ser Trp Asn Gln Val Asp Gln Val Ile Arg Asn Ala
    50                  55                  60

Leu Ala Ser Pro Gly Ser Gly Gly Asp Leu Gly Glu Ala Ile Arg Glu
65                  70                  75                  80

Gln Pro Glu Gln Ala Arg Leu Ala Leu Thr Leu Ala Ala Ala Glu Ser
                85                  90                  95

Glu Arg Phe Val Arg Gln Gly Thr Gly Asn Asp Glu Ala Gly Ala Ala
            100                 105                 110

Asn Gly Pro Ala Asp Ser Gly Asp Ala Leu Leu Glu Arg Asn Tyr Pro
        115                 120                 125

Thr Gly Ala Glu Phe Leu Gly Asp Gly Gly Asp Val Ser Phe Ser Thr
    130                 135                 140

Arg Gly Thr Gln Asn Trp Thr Val Glu Arg Leu Leu Gln Ala His Arg
145                 150                 155                 160

Gln Leu Glu Glu Arg Gly Tyr Val Phe Val Gly Tyr His Gly Thr Phe
                165                 170                 175

Leu Glu Ala Ala Gln Ser Ile Val Phe Gly Gly Val Arg Ala Arg Ser
            180                 185                 190

Gln Asp Leu Asp Ala Ile Trp Arg Gly Phe Tyr Ile Ala Gly Asp Pro
        195                 200                 205

Ala Leu Ala Tyr Gly Tyr Ala Gln Asp Gln Glu Pro Asp Ala Arg Gly
    210                 215                 220
```

```
Arg Ile Arg Asn Gly Ala Leu Leu Arg Val Tyr Val Pro Arg Ser Ser
225                 230                 235                 240

Leu Pro Gly Phe Tyr Arg Thr Ser Leu Thr Leu Ala Ala Pro Glu Ala
                245                 250                 255

Ala Gly Glu Val Glu Arg Leu Ile Gly His Pro Leu Pro Leu Arg Leu
            260                 265                 270

Asp Ala Ile Thr Gly Pro Glu Glu Glu Gly Gly Arg Leu Glu Thr Ile
        275                 280                 285

Leu Gly Trp Pro Leu Ala Glu Arg Thr Val Val Ile Pro Ser Ala Ile
    290                 295                 300

Pro Thr Asp Pro Arg Asn Val Gly Gly Asp Leu Asp Pro Ser Ser Ile
305                 310                 315                 320

Pro Asp Gln Glu Gln Ala Ile Ser Ala Leu Pro Asp Tyr Ala Ser Gln
                325                 330                 335

Pro Gly Gln Pro Pro Arg Glu Asp Leu Arg
            340                 345


<210> SEQ ID NO 156
<211> LENGTH: 613
<212> TYPE: PRT
<213> ORGANISM: Pseudomonas aeruginosa

<400> SEQUENCE: 156

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
```

```
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Gln Glu Gln
            580                 585                 590

Ala Ile Ser Ala Leu Pro Asp Tyr Ala Ser Gln Pro Gly Gln Pro Pro
        595                 600                 605

Arg Glu Asp Leu Arg
    610


<210> SEQ ID NO 157
<211> LENGTH: 224
<212> TYPE: PRT
<213> ORGANISM: Pseudomonas aeruginosa
<220> FEATURE:
<221> NAME/KEY: VARIANT
<222> LOCATION: (1)..(224)
```

<223> OTHER INFORMATION: PE variant fusion-ready seqeunce with Gly-Ser linker at amino terminus for joining to C-terminal end of heterologous protein
<220> FEATURE:
<221> NAME/KEY: VARIANT
<222> LOCATION: (1)..(5)
<223> OTHER INFORMATION: Gly-Ser linker

<400> SEQUENCE: 157

```
Gly Gly Gly Gly Ser Pro Thr Gly Ala Glu Phe Leu Gly Asp Gly Gly
1               5                   10                  15

Asp Val Ser Phe Ser Thr Arg Gly Thr Gln Asn Trp Thr Val Glu Arg
            20                  25                  30

Leu Leu Gln Ala His Arg Gln Leu Glu Glu Arg Gly Tyr Val Phe Val
        35                  40                  45

Gly Tyr His Gly Thr Phe Leu Glu Ala Ala Gln Ser Ile Val Phe Gly
    50                  55                  60

Gly Val Arg Ala Arg Ser Gln Asp Leu Asp Ala Ile Trp Arg Gly Phe
65                  70                  75                  80

Tyr Ile Ala Gly Asp Pro Ala Leu Ala Tyr Gly Tyr Ala Gln Asp Gln
                85                  90                  95

Glu Pro Asp Ala Arg Gly Arg Ile Arg Asn Gly Ala Leu Leu Arg Val
            100                 105                 110

Tyr Val Pro Arg Ser Ser Leu Pro Gly Phe Tyr Arg Thr Ser Leu Thr
        115                 120                 125

Leu Ala Ala Pro Glu Ala Ala Gly Glu Val Glu Arg Leu Ile Gly His
    130                 135                 140

Pro Leu Pro Leu Arg Leu Asp Ala Ile Thr Gly Pro Glu Glu Glu Gly
145                 150                 155                 160

Gly Arg Leu Glu Thr Ile Leu Gly Trp Pro Leu Ala Glu Arg Thr Val
                165                 170                 175

Val Ile Pro Ser Ala Ile Pro Thr Asp Pro Arg Asn Val Gly Gly Asp
            180                 185                 190

Leu Asp Pro Ser Ser Ile Pro Asp Gln Glu Gln Ala Ile Ser Ala Leu
        195                 200                 205

Pro Asp Tyr Ala Ser Gln Pro Gly Gln Pro Pro Arg Glu Asp Leu Arg
    210                 215                 220
```

<210> SEQ ID NO 158
<211> LENGTH: 334
<212> TYPE: PRT
<213> ORGANISM: Pseudomonas aeruginosa
<220> FEATURE:
<221> NAME/KEY: VARIANT
<222> LOCATION: (1)..(334)
<223> OTHER INFORMATION: PE variant

<400> SEQUENCE: 158

```
Met Trp Glu Gln Leu Glu Gln Ser Gly Tyr Pro Val Gln Arg Leu Val
1               5                   10                  15

Ala Leu Tyr Leu Ala Ala Arg Leu Ser Trp Asn Gln Val Asp Gln Val
            20                  25                  30

Ile Arg Asn Ala Leu Ala Ser Pro Gly Ser Gly Gly Asp Leu Gly Glu
        35                  40                  45

Ala Ile Arg Glu Gln Pro Glu Gln Ala Arg Leu Ala Leu Thr Leu Ala
    50                  55                  60

Ala Ala Glu Ser Glu Arg Phe Val Arg Gln Gly Thr Gly Asn Asp Glu
65                  70                  75                  80
```

```
Ala Gly Ala Ala Asn Ala Asp Val Val Ser Leu Thr Cys Pro Val Ala
                85                  90                  95

Ala Gly Glu Cys Ala Gly Pro Ala Asp Ser Gly Asp Ala Leu Leu Glu
            100                 105                 110

Arg Asn Tyr Pro Thr Gly Ala Glu Phe Leu Gly Asp Gly Gly Asp Val
        115                 120                 125

Ser Phe Ser Thr Arg Gly Thr Gln Asn Trp Thr Val Glu Arg Leu Leu
    130                 135                 140

Gln Ala His Arg Gln Leu Glu Glu Arg Gly Tyr Val Phe Val Gly Tyr
145                 150                 155                 160

His Gly Thr Phe Leu Glu Ala Ala Gln Ser Ile Val Phe Gly Gly Val
                165                 170                 175

Arg Ala Arg Ser Gln Asp Leu Asp Ala Ile Trp Arg Gly Phe Tyr Ile
            180                 185                 190

Ala Gly Asp Pro Ala Leu Ala Tyr Gly Tyr Ala Gln Asp Gln Glu Pro
        195                 200                 205

Asp Ala Arg Gly Arg Ile Arg Asn Gly Ala Leu Leu Arg Val Tyr Val
    210                 215                 220

Pro Arg Ser Ser Leu Pro Gly Phe Tyr Arg Thr Ser Leu Thr Leu Ala
225                 230                 235                 240

Ala Pro Glu Ala Ala Gly Glu Val Glu Arg Leu Ile Gly His Pro Leu
                245                 250                 255

Pro Leu Arg Leu Asp Ala Ile Thr Gly Pro Glu Glu Glu Gly Gly Arg
            260                 265                 270

Leu Glu Thr Ile Leu Gly Trp Pro Leu Ala Glu Arg Thr Val Val Ile
        275                 280                 285

Pro Ser Ala Ile Pro Thr Asp Pro Arg Asn Val Gly Gly Asp Leu Asp
    290                 295                 300

Pro Ser Ser Ile Pro Asp Lys Glu Gln Ala Ile Ser Ala Leu Pro Asp
305                 310                 315                 320

Tyr Ala Ser Gln Pro Gly Lys Pro Pro Arg Glu Asp Leu Lys
                325                 330


<210> SEQ ID NO 159
<211> LENGTH: 318
<212> TYPE: PRT
<213> ORGANISM: Pseudomonas aeruginosa
<220> FEATURE:
<221> NAME/KEY: VARIANT
<222> LOCATION: (1)..(318)
<223> OTHER INFORMATION: PE variant

<400> SEQUENCE: 159

Met Trp Glu Gln Leu Glu Gln Ser Gly Tyr Pro Val Gln Arg Leu Val
1               5                   10                  15

Ala Leu Tyr Leu Ala Ala Arg Leu Ser Trp Asn Gln Val Asp Gln Val
            20                  25                  30

Ile Arg Asn Ala Leu Ala Ser Pro Gly Ser Gly Gly Asp Leu Gly Glu
        35                  40                  45

Ala Ile Arg Glu Gln Pro Glu Gln Ala Arg Leu Ala Leu Thr Leu Ala
    50                  55                  60

Ala Ala Glu Ser Glu Arg Phe Val Arg Gln Gly Thr Gly Asn Asp Glu
65                  70                  75                  80

Ala Gly Ala Ala Asn Gly Pro Ala Asp Ser Gly Asp Ala Leu Leu Glu
                85                  90                  95

Arg Asn Tyr Pro Thr Gly Ala Glu Phe Leu Gly Asp Gly Gly Asp Val
```

```
            100                 105                 110

Ser Phe Ser Thr Arg Gly Thr Gln Asn Trp Thr Val Glu Arg Leu Leu
        115                 120                 125

Gln Ala His Arg Gln Leu Glu Glu Arg Gly Tyr Val Phe Val Gly Tyr
    130                 135                 140

His Gly Thr Phe Leu Glu Ala Ala Gln Ser Ile Val Phe Gly Gly Val
145                 150                 155                 160

Arg Ala Arg Ser Gln Asp Leu Asp Ala Ile Trp Arg Gly Phe Tyr Ile
                165                 170                 175

Ala Gly Asp Pro Ala Leu Ala Tyr Gly Tyr Ala Gln Asp Gln Glu Pro
            180                 185                 190

Asp Ala Arg Gly Arg Ile Arg Asn Gly Ala Leu Leu Arg Val Tyr Val
        195                 200                 205

Pro Arg Ser Ser Leu Pro Gly Phe Tyr Arg Thr Ser Leu Thr Leu Ala
    210                 215                 220

Ala Pro Glu Ala Ala Gly Glu Val Glu Arg Leu Ile Gly His Pro Leu
225                 230                 235                 240

Pro Leu Arg Leu Asp Ala Ile Thr Gly Pro Glu Glu Glu Gly Gly Arg
                245                 250                 255

Leu Glu Thr Ile Leu Gly Trp Pro Leu Ala Glu Arg Thr Val Val Ile
            260                 265                 270

Pro Ser Ala Ile Pro Thr Asp Pro Arg Asn Val Gly Gly Asp Leu Asp
        275                 280                 285

Pro Ser Ser Ile Pro Asp Lys Glu Gln Ala Ile Ser Ala Leu Pro Asp
    290                 295                 300

Tyr Ala Ser Gln Pro Gly Lys Pro Pro Arg Glu Asp Leu Lys
305                 310                 315


<210> SEQ ID NO 160
<211> LENGTH: 363
<212> TYPE: PRT
<213> ORGANISM: Pseudomonas aeruginosa
<220> FEATURE:
<221> NAME/KEY: VARIANT
<222> LOCATION: (1)..(363)
<223> OTHER INFORMATION: PE variant

<400> SEQUENCE: 160

Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
    50                  55                  60

Ala Leu Ala Ser Pro Gly Ser Gly Gly Asp Leu Gly Glu Ala Ile Arg
65                  70                  75                  80

Glu Gln Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Asn Ala Asp Val Val Ser Leu Thr Cys Pro Val Ala Ala Gly Glu
        115                 120                 125

Cys Ala Gly Pro Ala Asp Ser Gly Asp Ala Leu Leu Glu Arg Asn Tyr
    130                 135                 140
```

```
Pro Thr Gly Ala Glu Phe Leu Gly Asp Gly Gly Asp Val Ser Phe Ser
145                 150                 155                 160

Thr Arg Gly Thr Gln Asn Trp Thr Val Glu Arg Leu Leu Gln Ala His
                165                 170                 175

Arg Gln Leu Glu Glu Arg Gly Tyr Val Phe Val Gly Tyr His Gly Thr
            180                 185                 190

Phe Leu Glu Ala Ala Gln Ser Ile Val Phe Gly Gly Val Arg Ala Arg
        195                 200                 205

Ser Gln Asp Leu Asp Ala Ile Trp Arg Gly Phe Tyr Ile Ala Gly Asp
    210                 215                 220

Pro Ala Leu Ala Tyr Gly Tyr Ala Gln Asp Gln Glu Pro Asp Ala Arg
225                 230                 235                 240

Gly Arg Ile Arg Asn Gly Ala Leu Leu Arg Val Tyr Val Pro Arg Ser
                245                 250                 255

Ser Leu Pro Gly Phe Tyr Arg Thr Ser Leu Thr Leu Ala Ala Pro Glu
            260                 265                 270

Ala Ala Gly Glu Val Glu Arg Leu Ile Gly His Pro Leu Pro Leu Arg
        275                 280                 285

Leu Asp Ala Ile Thr Gly Pro Glu Glu Glu Gly Gly Arg Leu Glu Thr
    290                 295                 300

Ile Leu Gly Trp Pro Leu Ala Glu Arg Thr Val Val Ile Pro Ser Ala
305                 310                 315                 320

Ile Pro Thr Asp Pro Arg Asn Val Gly Gly Asp Leu Asp Pro Ser Ser
                325                 330                 335

Ile Pro Asp Lys Glu Gln Ala Ile Ser Ala Leu Pro Asp Tyr Ala Ser
            340                 345                 350

Gln Pro Gly Lys Pro Pro Arg Glu Asp Leu Lys
        355                 360
```

<210> SEQ ID NO 161
<211> LENGTH: 635
<212> TYPE: PRT
<213> ORGANISM: Pseudomonas aeruginosa
<220> FEATURE:
<221> NAME/KEY: VARIANT
<222> LOCATION: (1)..(635)
<223> OTHER INFORMATION: PE variant from GenBank Accession Number YP_792118

<400> SEQUENCE: 161

```
Met His Leu Ile Pro His Trp Ile Pro Leu Val Ala Ser Leu Gly Leu
1               5                   10                  15

Leu Ala Gly Gly Ser Phe Ala Ser Ala Ala Glu Glu Ala Phe Asp Leu
            20                  25                  30

Trp Asn Glu Cys Ala Lys Ala Cys Val Leu Asp Leu Lys Asp Gly Val
        35                  40                  45

Arg Ser Ser Arg Met Ser Val Asp Pro Ala Ile Ala Asp Thr Asn Gly
    50                  55                  60

Gln Gly Val Leu His Tyr Ser Met Val Leu Glu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
        115                 120                 125
```

```
Pro Ile Gly His Glu Lys Pro Ser Asn Ile Lys Val Phe Ile His Glu
    130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Val Met Ala Gln Thr Gln Pro Arg Arg
        195                 200                 205

Glu Lys Arg Trp Ser Glu Trp Ala Ser Gly Lys Val Leu Cys Leu Leu
    210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
            260                 265                 270

Leu His Phe Pro Glu Gly Gly Ser Leu Ala Ala Leu Thr Ala His Gln
        275                 280                 285

Ala Cys His Leu Pro Leu Glu Thr Phe Thr Arg His Arg Gln Pro Arg
    290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Gly Asp Leu Gly Glu
            340                 345                 350

Ala Ile Arg Glu Gln Pro Glu Gln Ala Arg Leu Ala Leu Thr Leu Ala
        355                 360                 365

Ala Ala Glu Ser Glu Arg Phe Val Arg Gln Gly Thr Gly Asn Asp Glu
    370                 375                 380

Ala Ser Ala Asp Val Val Ser Leu Thr Cys Pro Val Ala Ala Gly Glu
385                 390                 395                 400

Cys Ala Gly Pro Ala Asp Ser Gly Asp Ala Leu Leu Glu Arg Asn Tyr
                405                 410                 415

Pro Thr Gly Ala Glu Phe Leu Gly Asp Gly Gly Asp Val Ser Phe Ser
            420                 425                 430

Thr Arg Gly Thr Gln Asn Trp Thr Val Glu Arg Leu Leu Gln Ala His
        435                 440                 445

Arg Gln Leu Glu Glu Arg Gly Tyr Val Phe Val Gly Tyr His Gly Thr
    450                 455                 460

Phe Leu Glu Ala Ala Gln Ser Ile Val Phe Gly Gly Val Arg Ala Arg
465                 470                 475                 480

Ser Gln Asp Leu Asp Ala Ile Trp Arg Gly Phe Tyr Ile Ala Gly Asp
                485                 490                 495

Pro Ala Leu Ala Tyr Gly Tyr Ala Gln Asp Gln Glu Pro Asp Ala Arg
            500                 505                 510

Gly Arg Ile Arg Asn Gly Ala Leu Leu Arg Val Tyr Val Pro Arg Ser
        515                 520                 525

Ser Leu Pro Gly Phe Tyr Arg Thr Gly Leu Thr Leu Ala Ala Pro Glu
    530                 535                 540
```

```
Ala Ala Gly Glu Val Glu Arg Leu Ile Gly His Pro Leu Pro Leu Arg
545                 550                 555                 560

Leu Asp Ala Ile Thr Gly Pro Glu Glu Glu Gly Gly Arg Leu Glu Thr
                565                 570                 575

Ile Leu Gly Trp Pro Leu Ala Glu Arg Thr Val Val Ile Pro Ser Ala
            580                 585                 590

Ile Pro Thr Asp Pro Arg Asn Val Gly Gly Asp Leu Asp Pro Ser Ser
        595                 600                 605

Ile Pro Asp Gln Glu Gln Ala Ile Ser Ala Leu Pro Asp Tyr Ala Ser
    610                 615                 620

Gln Pro Gly Lys Pro Ser Arg Glu Asp Leu Lys
625                 630                 635


<210> SEQ ID NO 162
<211> LENGTH: 613
<212> TYPE: PRT
<213> ORGANISM: Pseudomonas aeruginosa
<220> FEATURE:
<221> NAME/KEY: VARIANT
<222> LOCATION: (1)..(613)
<223> OTHER INFORMATION: PE variant from Genbank Accession number 1IKQ_A

<400> SEQUENCE: 162

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
```

```
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610
```

<210> SEQ ID NO 163
<211> LENGTH: 613
<212> TYPE: PRT
<213> ORGANISM: Pseudomonas aeruginosa
<220> FEATURE:
<221> NAME/KEY: VARIANT
<222> LOCATION: (1)..(613)
<223> OTHER INFORMATION: PE variant from Genbank Accession number 1IKP_A

<400> SEQUENCE: 163

-continued

```
Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Gln Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Ala Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415
```

Trp Thr Val Glu Arg Leu Leu Gln Ala His Arg Gln Leu Glu Glu Arg
420 425 430

Gly Tyr Val Phe Val Gly Tyr His Gly Thr Phe Leu Glu Ala Ala Gln
435 440 445

Ser Ile Val Phe Gly Gly Val Arg Ala Arg Ser Gln Asp Leu Asp Ala
450 455 460

Ile Trp Arg Gly Phe Tyr Ile Ala Gly Asp Pro Ala Leu Ala Tyr Gly
465 470 475 480

Tyr Ala Gln Asp Gln Glu Pro Asp Ala Arg Gly Arg Ile Arg Asn Gly
485 490 495

Ala Leu Leu Arg Val Tyr Val Pro Arg Ser Ser Leu Pro Gly Phe Tyr
500 505 510

Arg Thr Ser Leu Thr Leu Ala Ala Pro Glu Ala Ala Gly Glu Val Glu
515 520 525

Arg Leu Ile Gly His Pro Leu Pro Leu Arg Leu Asp Ala Ile Thr Gly
530 535 540

Pro Glu Glu Glu Gly Gly Arg Leu Glu Thr Ile Leu Gly Trp Pro Leu
545 550 555 560

Ala Glu Arg Thr Val Val Ile Pro Ser Ala Ile Pro Thr Asp Pro Arg
565 570 575

Asn Val Gly Gly Asp Leu Asp Pro Ser Ser Ile Pro Asp Lys Glu Gln
580 585 590

Ala Ile Ser Ala Leu Pro Asp Tyr Ala Ser Gln Pro Gly Lys Pro Pro
595 600 605

Arg Glu Asp Leu Lys
610

<210> SEQ ID NO 164
<211> LENGTH: 517
<212> TYPE: PRT
<213> ORGANISM: Artificial Sequence
<220> FEATURE:
<223> OTHER INFORMATION: IL2-PE fusion protein
<220> FEATURE:
<221> NAME/KEY: SIGNAL
<222> LOCATION: (1)..(20)
<223> OTHER INFORMATION: Predicted signal peptide sequence

<400> SEQUENCE: 164

Met Tyr Arg Met Gln Leu Leu Ser Cys Ile Ala Leu Ser Leu Ala Leu
1 5 10 15

Val Thr Asn Ser Ala Pro Thr Ser Ser Ser Thr Lys Lys Thr Gln Leu
20 25 30

Gln Leu Glu His Leu Leu Leu Asp Leu Gln Met Ile Leu Asn Gly Ile
35 40 45

Asn Asn Tyr Lys Asn Pro Lys Leu Thr Arg Met Leu Thr Phe Lys Phe
50 55 60

Tyr Met Pro Lys Lys Ala Thr Glu Leu Lys His Leu Gln Cys Leu Glu
65 70 75 80

Glu Glu Leu Lys Pro Leu Glu Glu Val Leu Asn Leu Ala Gln Ser Lys
85 90 95

Asn Phe His Leu Arg Pro Arg Asp Leu Ile Ser Asn Ile Asn Val Ile
100 105 110

Val Leu Glu Leu Lys Gly Ser Glu Thr Thr Phe Met Cys Glu Tyr Ala
115 120 125

Asp Glu Thr Ala Thr Ile Val Glu Phe Leu Asn Arg Trp Ile Thr Phe
130 135 140

-continued

```
Cys Gln Ser Ile Ile Ser Thr Leu Thr Ile Pro Glu Gly Gly Ser Leu
145                 150                 155                 160

Ala Ala Leu Thr Ala His Gln Ala Cys His Leu Pro Leu Glu Thr Phe
                165                 170                 175

Thr Arg His Arg Gln Pro Arg Gly Trp Glu Gln Leu Glu Gln Cys Gly
            180                 185                 190

Tyr Pro Val Gln Arg Leu Val Ala Leu Tyr Leu Ala Ala Arg Leu Ser
        195                 200                 205

Trp Asn Gln Val Asp Gln Val Ile Arg Asn Ala Leu Ala Ser Pro Gly
    210                 215                 220

Ser Gly Gly Asp Leu Gly Glu Ala Ile Arg Glu Gln Pro Glu Gln Ala
225                 230                 235                 240

Arg Leu Ala Leu Thr Leu Ala Ala Ala Glu Ser Glu Arg Phe Val Arg
                245                 250                 255

Gln Gly Thr Gly Asn Asp Glu Ala Gly Ala Ala Ser Ala Asp Val Val
            260                 265                 270

Ser Leu Thr Cys Pro Val Ala Ala Gly Glu Cys Ala Gly Pro Ala Asp
        275                 280                 285

Ser Gly Asp Ala Leu Leu Glu Arg Asn Tyr Pro Thr Gly Ala Glu Phe
    290                 295                 300

Leu Gly Asp Gly Gly Asp Ile Ser Phe Ser Thr Arg Gly Thr Gln Asn
305                 310                 315                 320

Trp Thr Val Glu Arg Leu Leu Gln Ala His Arg Gln Leu Glu Glu Arg
                325                 330                 335

Gly Tyr Val Phe Val Gly Tyr His Gly Thr Phe Leu Glu Ala Ala Gln
            340                 345                 350

Ser Ile Val Phe Gly Gly Val Arg Ala Arg Ser Gln Asp Leu Asp Ala
        355                 360                 365

Ile Trp Arg Gly Phe Tyr Ile Ala Gly Asp Pro Ala Leu Ala Tyr Gly
    370                 375                 380

Tyr Ala Gln Asp Gln Glu Pro Asp Ala Arg Gly Arg Ile Arg Asn Gly
385                 390                 395                 400

Ala Leu Leu Arg Val Tyr Val Pro Arg Ser Ser Leu Pro Gly Phe Tyr
                405                 410                 415

Arg Thr Gly Leu Thr Leu Ala Ala Pro Glu Ala Ala Gly Glu Val Glu
            420                 425                 430

Arg Leu Ile Gly His Pro Leu Pro Leu Arg Leu Asp Ala Ile Thr Gly
        435                 440                 445

Pro Glu Glu Glu Gly Gly Arg Leu Glu Thr Ile Leu Gly Trp Pro Leu
    450                 455                 460

Ala Glu Arg Thr Val Val Ile Pro Ser Ala Ile Pro Thr Asp Pro Arg
465                 470                 475                 480

Asn Val Gly Gly Asp Leu Asp Pro Ser Ser Ile Pro Asp Lys Glu Gln
                485                 490                 495

Ala Ile Ser Ala Leu Pro Asp Tyr Ala Ser Gln Pro Gly Lys Pro Pro
            500                 505                 510

Arg Glu Asp Leu Lys
        515
```

<210> SEQ ID NO 165
<211> LENGTH: 506
<212> TYPE: PRT
<213> ORGANISM: Artificial Sequence
<220> FEATURE:

-continued

```
<223> OTHER INFORMATION: IL2-PE fusion protein with Gly-Ser linker
<220> FEATURE:
<221> NAME/KEY: MISC_FEATURE
<222> LOCATION: (1)..(506)
<223> OTHER INFORMATION: IL2-PE fusion protein with Gly-Ser linker
<220> FEATURE:
<221> NAME/KEY: MISC_FEATURE
<222> LOCATION: (154)..(159)
<223> OTHER INFORMATION: Gly-Ser linker

<400> SEQUENCE: 165

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Gly Gly Gly Gly Ser Pro
145                 150                 155                 160

Glu Gly Gly Ser Leu Ala Ala Leu Thr Ala His Gln Ala Cys His Leu
                165                 170                 175

Pro Leu Glu Thr Phe Thr Arg His Arg Gln Pro Arg Gly Trp Glu Gln
            180                 185                 190

Leu Glu Gln Cys Gly Tyr Pro Val Gln Arg Leu Val Ala Leu Tyr Leu
        195                 200                 205

Ala Ala Arg Leu Ser Trp Asn Gln Val Asp Gln Val Ile Arg Asn Ala
    210                 215                 220

Leu Ala Ser Pro Gly Ser Gly Gly Asp Leu Gly Glu Ala Ile Arg Glu
225                 230                 235                 240

Gln Pro Glu Gln Ala Arg Leu Ala Leu Thr Leu Ala Ala Ala Glu Ser
                245                 250                 255

Glu Arg Phe Val Arg Gln Gly Thr Gly Asn Asp Glu Ala Gly Ala Ala
            260                 265                 270

Ser Gly Pro Ala Asp Ser Gly Asp Ala Leu Leu Glu Arg Asn Tyr Pro
        275                 280                 285

Thr Gly Ala Glu Phe Leu Gly Asp Gly Gly Asp Ile Ser Phe Ser Thr
    290                 295                 300

Arg Gly Thr Gln Asn Trp Thr Val Glu Arg Leu Leu Gln Ala His Arg
305                 310                 315                 320

Gln Leu Glu Glu Arg Gly Tyr Val Phe Val Gly Tyr His Gly Thr Phe
                325                 330                 335

Leu Glu Ala Ala Gln Ser Ile Val Phe Gly Gly Val Arg Ala Arg Ser
            340                 345                 350

Gln Asp Leu Asp Ala Ile Trp Arg Gly Phe Tyr Ile Ala Gly Asp Pro
```

355 360 365

Ala Leu Ala Tyr Gly Tyr Ala Gln Asp Gln Glu Pro Asp Ala Arg Gly
370 375 380

Arg Ile Arg Asn Gly Ala Leu Leu Arg Val Tyr Val Pro Arg Ser Ser
385 390 395 400

Leu Pro Gly Phe Tyr Arg Thr Gly Leu Thr Leu Ala Ala Pro Glu Ala
405 410 415

Ala Gly Glu Val Glu Arg Leu Ile Gly His Pro Leu Pro Leu Arg Leu
420 425 430

Asp Ala Ile Thr Gly Pro Glu Glu Glu Gly Gly Arg Leu Glu Thr Ile
435 440 445

Leu Gly Trp Pro Leu Ala Glu Arg Thr Val Val Ile Pro Ser Ala Ile
450 455 460

Pro Thr Asp Pro Arg Asn Val Gly Gly Asp Leu Asp Pro Ser Ser Ile
465 470 475 480

Pro Asp Lys Glu Gln Ala Ile Ser Ala Leu Pro Asp Tyr Ala Ser Gln
485 490 495

Pro Gly Lys Pro Pro Arg Glu Asp Leu Lys
500 505

<210> SEQ ID NO 166
<211> LENGTH: 517
<212> TYPE: PRT
<213> ORGANISM: Artificial Sequence
<220> FEATURE:
<223> OTHER INFORMATION: IL2-PE fusion sequence
<220> FEATURE:
<221> NAME/KEY: VARIANT
<222> LOCATION: (1)..(517)
<223> OTHER INFORMATION: IL2-PE fusion protein
<220> FEATURE:
<221> NAME/KEY: VARIANT
<222> LOCATION: (1)..(20)
<223> OTHER INFORMATION: predicted signal peptide sequence
<220> FEATURE:
<221> NAME/KEY: VARIANT
<222> LOCATION: (21)..(153)
<223> OTHER INFORMATION: IL2 sequence
<220> FEATURE:
<221> NAME/KEY: VARIANT
<222> LOCATION: (21)..(153)
<223> OTHER INFORMATION: IL2 sequence
<220> FEATURE:
<221> NAME/KEY: VARIANT
<222> LOCATION: (154)..(154)
<223> OTHER INFORMATION: Linking isoleucine amino acid
<220> FEATURE:
<221> NAME/KEY: VARIANT
<222> LOCATION: (154)..(154)
<223> OTHER INFORMATION: Linking isoleucine amino acid
<220> FEATURE:
<221> NAME/KEY: VARIANT
<222> LOCATION: (155)..(517)
<223> OTHER INFORMATION: PE variant sequence

<400> SEQUENCE: 166

Met Tyr Arg Met Gln Leu Leu Ser Cys Ile Ala Leu Ser Leu Ala Leu
1 5 10 15

Val Thr Asn Ser Ala Pro Thr Ser Ser Ser Thr Lys Lys Thr Gln Leu
20 25 30

Gln Leu Glu His Leu Leu Leu Asp Leu Gln Met Ile Leu Asn Gly Ile
35 40 45

Asn Asn Tyr Lys Asn Pro Lys Leu Thr Arg Met Leu Thr Phe Lys Phe
50 55 60

-continued

```
Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Ile Pro Glu Gly Gly Ser Leu
145                 150                 155                 160

Ala Ala Leu Thr Ala His Gln Ala Cys His Leu Pro Leu Glu Thr Phe
                165                 170                 175

Thr Arg His Arg Gln Pro Arg Gly Trp Glu Gln Leu Glu Gln Cys Gly
            180                 185                 190

Tyr Pro Val Gln Arg Leu Val Ala Leu Tyr Leu Ala Ala Arg Leu Ser
        195                 200                 205

Trp Asn Gln Val Asp Gln Val Ile Arg Asn Ala Leu Ala Ser Pro Gly
    210                 215                 220

Ser Gly Gly Asp Leu Gly Glu Ala Ile Arg Glu Gln Pro Glu Gln Ala
225                 230                 235                 240

Arg Leu Ala Leu Thr Leu Ala Ala Ala Glu Ser Glu Arg Phe Val Arg
                245                 250                 255

Gln Gly Thr Gly Asn Asp Glu Ala Gly Ala Ala Asn Ala Asp Val Val
            260                 265                 270

Ser Leu Thr Cys Pro Val Ala Ala Gly Glu Cys Ala Gly Pro Ala Asp
        275                 280                 285

Ser Gly Asp Ala Leu Leu Glu Arg Asn Tyr Pro Thr Gly Ala Glu Phe
    290                 295                 300

Leu Gly Asp Gly Gly Asp Val Ser Phe Ser Thr Arg Gly Thr Gln Asn
305                 310                 315                 320

Trp Thr Val Glu Arg Leu Leu Gln Ala His Arg Gln Leu Glu Glu Arg
                325                 330                 335

Gly Tyr Val Phe Val Gly Tyr His Gly Thr Phe Leu Glu Ala Ala Gln
            340                 345                 350

Ser Ile Val Phe Gly Gly Val Arg Ala Arg Ser Gln Asp Leu Asp Ala
        355                 360                 365

Ile Trp Arg Gly Phe Tyr Ile Ala Gly Asp Pro Ala Leu Ala Tyr Gly
    370                 375                 380

Tyr Ala Gln Asp Gln Glu Pro Asp Ala Arg Gly Arg Ile Arg Asn Gly
385                 390                 395                 400

Ala Leu Leu Arg Val Tyr Val Pro Arg Ser Ser Leu Pro Gly Phe Tyr
                405                 410                 415

Arg Thr Ser Leu Thr Leu Ala Ala Pro Glu Ala Ala Gly Glu Val Glu
            420                 425                 430

Arg Leu Ile Gly His Pro Leu Pro Leu Arg Leu Asp Ala Ile Thr Gly
        435                 440                 445

Pro Glu Glu Glu Gly Gly Arg Leu Glu Thr Ile Leu Gly Trp Pro Leu
    450                 455                 460

Ala Glu Arg Thr Val Val Ile Pro Ser Ala Ile Pro Thr Asp Pro Arg
465                 470                 475                 480

Asn Val Gly Gly Asp Leu Asp Pro Ser Ser Ile Pro Asp Lys Glu Gln
```

```
                485                 490                 495

Ala Ile Ser Ala Leu Pro Asp Tyr Ala Ser Gln Pro Gly Lys Pro Pro
            500                 505                 510

Arg Glu Asp Leu Lys
        515


<210> SEQ ID NO 167
<211> LENGTH: 630
<212> TYPE: PRT
<213> ORGANISM: Homo sapiens
<220> FEATURE:
<221> NAME/KEY: MISC_FEATURE
<222> LOCATION: (1)..(630)
<223> OTHER INFORMATION: Mesothelin sequence from GenBank accession
      NP_037536

<400> SEQUENCE: 167

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
```

```
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
        435                 440                 445

Leu Cys Ser Leu Ser Pro Glu Glu Leu Ser Ser Val Pro Pro Ser Ser
    450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
            500                 505                 510

Thr Glu Asp Leu Lys Ala Leu Ser Gln Gln Asn Val Ser Met Asp Leu
        515                 520                 525

Ala Thr Phe Met Lys Leu Arg Thr Asp Ala Val Leu Pro Leu Thr Val
    530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
        595                 600                 605

Pro Cys Leu Leu Gly Pro Gly Pro Val Leu Thr Val Leu Ala Leu Leu
    610                 615                 620

Leu Ala Ser Thr Leu Ala
625                 630
```

<210> SEQ ID NO 168
<211> LENGTH: 80
<212> TYPE: PRT
<213> ORGANISM: Homo sapiens
<220> FEATURE:
<221> NAME/KEY: MISC_FEATURE
<222> LOCATION: (1)..(80)
<223> OTHER INFORMATION: CD24 sequence from Genbank accession number AAH64619

<400> SEQUENCE: 168

```
Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
```

```
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Ala Ala Gly Gly Ala Leu Gln Ser
    50                  55                  60

Thr Ala Ser Leu Phe Val Val Ser Leu Ser Leu Leu His Leu Tyr Ser
65                  70                  75                  80


<210> SEQ ID NO 169
<211> LENGTH: 40
<212> TYPE: PRT
<213> ORGANISM: Homo sapiens
<220> FEATURE:
<221> NAME/KEY: MISC_FEATURE
<222> LOCATION: (1)..(40)
<223> OTHER INFORMATION: CD22 sequence from Genbank accession number
      BAA36576

<400> SEQUENCE: 169

Val Arg Arg Ala Pro Leu Ser Glu Gly Pro His Ser Leu Gly Cys Tyr
1               5                   10                  15

Asn Pro Met Met Glu Asp Gly Ile Ser Tyr Thr Thr Leu Arg Phe Pro
            20                  25                  30

Glu Met Asn Ile Pro Arg Thr Gly
        35                  40


<210> SEQ ID NO 170
<211> LENGTH: 272
<212> TYPE: PRT
<213> ORGANISM: Homo sapiens
<220> FEATURE:
<221> NAME/KEY: MISC_FEATURE
<222> LOCATION: (1)..(272)
<223> OTHER INFORMATION: CD25 sequence from Genbank accession number
      NP_000408

<400> SEQUENCE: 170

Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
            20                  25                  30

His Ala Thr Phe Lys Ala Met Ala Tyr Lys Glu Gly Thr Met Leu Asn
        35                  40                  45

Cys Glu Cys Lys Arg Gly Phe Arg Arg Ile Lys Ser Gly Ser Leu Tyr
    50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125

Pro Pro Trp Glu Asn Glu Ala Thr Glu Arg Ile Tyr His Phe Val Val
    130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175
```

-continued

```
Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
        195                 200                 205

Ser Glu Thr Ser Cys Leu Val Thr Thr Thr Asp Phe Gln Ile Gln Thr
    210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270


<210> SEQ ID NO 171
<211> LENGTH: 361
<212> TYPE: PRT
<213> ORGANISM: Homo sapiens
<220> FEATURE:
<221> NAME/KEY: MISC_FEATURE
<222> LOCATION: (1)..(361)
<223> OTHER INFORMATION: CD174 sequence from Genbank accession number
      NP_000140

<400> SEQUENCE: 171

Met Asp Pro Leu Gly Ala Ala Lys Pro Gln Trp Pro Trp Arg Arg Cys
1               5                   10                  15

Leu Ala Ala Leu Leu Phe Gln Leu Leu Val Ala Val Cys Phe Phe Ser
            20                  25                  30

Tyr Leu Arg Val Ser Arg Asp Asp Ala Thr Gly Ser Pro Arg Ala Pro
        35                  40                  45

Ser Gly Ser Ser Arg Gln Asp Thr Thr Pro Thr Arg Pro Thr Leu Leu
    50                  55                  60

Ile Leu Leu Trp Thr Trp Pro Phe His Ile Pro Val Ala Leu Ser Arg
65                  70                  75                  80

Cys Ser Glu Met Val Pro Gly Thr Ala Asp Cys His Ile Thr Ala Asp
                85                  90                  95

Arg Lys Val Tyr Pro Gln Ala Asp Thr Val Ile Val His His Trp Asp
            100                 105                 110

Ile Met Ser Asn Pro Lys Ser Arg Leu Pro Pro Ser Pro Arg Pro Gln
        115                 120                 125

Gly Gln Arg Trp Ile Trp Phe Asn Leu Glu Pro Pro Pro Asn Cys Gln
    130                 135                 140

His Leu Glu Ala Leu Asp Arg Tyr Phe Asn Leu Thr Met Ser Tyr Arg
145                 150                 155                 160

Ser Asp Ser Asp Ile Phe Thr Pro Tyr Gly Trp Leu Glu Pro Trp Ser
                165                 170                 175

Gly Gln Pro Ala His Pro Pro Leu Asn Leu Ser Ala Lys Thr Glu Leu
            180                 185                 190

Val Ala Trp Ala Val Ser Asn Trp Lys Pro Asp Ser Ala Arg Val Arg
        195                 200                 205

Tyr Tyr Gln Ser Leu Gln Ala His Leu Lys Val Asp Val Tyr Gly Arg
    210                 215                 220

Ser His Lys Pro Leu Pro Lys Gly Thr Met Met Glu Thr Leu Ser Arg
225                 230                 235                 240

Tyr Lys Phe Tyr Leu Ala Phe Glu Asn Ser Leu His Pro Asp Tyr Ile
                245                 250                 255
```

```
Thr Glu Lys Leu Trp Arg Asn Ala Leu Glu Ala Trp Ala Val Pro Val
            260                 265                 270

Val Leu Gly Pro Ser Arg Ser Asn Tyr Glu Arg Phe Leu Pro Pro Asp
        275                 280                 285

Ala Phe Ile His Val Asp Asp Phe Gln Ser Pro Lys Asp Leu Ala Arg
    290                 295                 300

Tyr Leu Gln Glu Leu Asp Lys Asp His Ala Arg Tyr Leu Ser Tyr Phe
305                 310                 315                 320

Arg Trp Arg Glu Thr Leu Arg Pro Arg Ser Phe Ser Trp Ala Leu Asp
                325                 330                 335

Phe Cys Lys Ala Cys Trp Lys Leu Gln Gln Glu Ser Arg Tyr Gln Thr
            340                 345                 350

Val Arg Ser Ile Ala Ala Trp Phe Thr
        355                 360


<210> SEQ ID NO 172
<211> LENGTH: 420
<212> TYPE: PRT
<213> ORGANISM: Homo sapiens
<220> FEATURE:
<221> NAME/KEY: MISC_FEATURE
<222> LOCATION: (1)..(420)
<223> OTHER INFORMATION: TPBG sequence from Genbank accession number
      CAA09930

<400> SEQUENCE: 172

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
            20                  25                  30

Ser Pro Thr Ser Ser Ala Ser Ser Phe Ser Ser Ser Ala Pro Phe Leu
        35                  40                  45

Ala Ser Ala Val Ser Ala Gln Pro Pro Leu Pro Asp Gln Cys Pro Ala
    50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
                85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
    130                 135                 140

Arg Gln Leu Asp Leu Ser His Asn Pro Leu Ala Asp Leu Ser Pro Phe
145                 150                 155                 160

Ala Phe Ser Gly Ser Asn Ala Ser Val Ser Ala Pro Ser Pro Leu Val
                165                 170                 175

Glu Leu Ile Leu Asn His Ile Val Pro Pro Glu Asp Glu Arg Gln Asn
            180                 185                 190

Arg Ser Phe Glu Gly Met Val Val Ala Ala Leu Leu Ala Gly Arg Ala
        195                 200                 205

Leu Gln Gly Leu Arg Arg Leu Glu Leu Ala Ser Asn His Phe Leu Tyr
    210                 215                 220

Leu Pro Arg Asp Val Leu Ala Gln Leu Pro Ser Leu Arg His Leu Asp
225                 230                 235                 240
```

```
Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Ile Arg
        275                 280                 285

Val Phe Leu Asp Asn Asn Pro Trp Val Cys Asp Cys His Met Ala Asp
    290                 295                 300

Met Val Thr Trp Leu Lys Glu Thr Glu Val Val Gln Gly Lys Asp Arg
305                 310                 315                 320

Leu Thr Cys Ala Tyr Pro Glu Lys Met Arg Asn Arg Val Leu Leu Glu
                325                 330                 335

Leu Asn Ser Ala Asp Leu Asp Cys Asp Pro Ile Leu Pro Pro Ser Leu
            340                 345                 350

Gln Thr Ser Tyr Val Phe Leu Gly Ile Val Leu Ala Leu Ile Gly Ala
        355                 360                 365

Ile Phe Leu Leu Val Leu Tyr Leu Asn Arg Lys Gly Ile Lys Lys Trp
    370                 375                 380

Met His Asn Ile Arg Asp Ala Cys Arg Asp His Met Glu Gly Tyr His
385                 390                 395                 400

Tyr Arg Tyr Glu Ile Asn Ala Asp Pro Arg Leu Thr Asn Leu Ser Ser
                405                 410                 415

Asn Ser Asp Val
            420


<210> SEQ ID NO 173
<211> LENGTH: 848
<212> TYPE: PRT
<213> ORGANISM: Homo sapiens
<220> FEATURE:
<221> NAME/KEY: MISC_FEATURE
<222> LOCATION: (1)..(848)
<223> OTHER INFORMATION: CD56 sequence from Genbank accession number
      NP_000606

<400> SEQUENCE: 173

Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
    50                  55                  60

Asn Gln Gln Arg Ile Ser Val Val Trp Asn Asp Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
    130                 135                 140

Leu Pro Pro Thr Ile Ile Trp Lys His Lys Gly Arg Asp Val Ile Leu
145                 150                 155                 160
```

-continued

```
Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Gln Ala Arg Gln Asn Ile Val Asn Ala Thr
    210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
                245                 250                 255

Glu Glu Asp Asp Glu Lys Tyr Ile Phe Ser Asp Asp Ser Ser Gln Leu
            260                 265                 270

Thr Ile Lys Lys Val Asp Lys Asn Asp Glu Ala Glu Tyr Ile Cys Ile
        275                 280                 285

Ala Glu Asn Lys Ala Gly Glu Gln Asp Ala Thr Ile His Leu Lys Val
    290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                325                 330                 335

Pro Ser Ile Thr Trp Arg Thr Ser Thr Arg Asn Ile Ser Ser Glu Glu
            340                 345                 350

Lys Thr Leu Asp Gly His Met Val Val Arg Ser His Ala Arg Val Ser
        355                 360                 365

Ser Leu Thr Leu Lys Ser Ile Gln Tyr Thr Asp Ala Gly Glu Tyr Ile
    370                 375                 380

Cys Thr Ala Ser Asn Thr Ile Gly Gln Asp Ser Gln Ser Met Tyr Leu
385                 390                 395                 400

Glu Val Gln Tyr Ala Pro Lys Leu Gln Gly Pro Val Ala Val Tyr Thr
                405                 410                 415

Trp Glu Gly Asn Gln Val Asn Ile Thr Cys Glu Val Phe Ala Tyr Pro
            420                 425                 430

Ser Ala Thr Ile Ser Trp Phe Arg Asp Gly Gln Leu Leu Pro Ser Ser
        435                 440                 445

Asn Tyr Ser Asn Ile Lys Ile Tyr Asn Thr Pro Ser Ala Ser Tyr Leu
    450                 455                 460

Glu Val Thr Pro Asp Ser Glu Asn Asp Phe Gly Asn Tyr Asn Cys Thr
465                 470                 475                 480

Ala Val Asn Arg Ile Gly Gln Glu Ser Leu Glu Phe Ile Leu Val Gln
                485                 490                 495

Ala Asp Thr Pro Ser Ser Pro Ser Ile Asp Gln Val Glu Pro Tyr Ser
            500                 505                 510

Ser Thr Ala Gln Val Gln Phe Asp Glu Pro Glu Ala Thr Gly Gly Val
        515                 520                 525

Pro Ile Leu Lys Tyr Lys Ala Glu Trp Arg Ala Val Gly Glu Glu Val
    530                 535                 540

Trp His Ser Lys Trp Tyr Asp Ala Lys Glu Ala Ser Met Glu Gly Ile
545                 550                 555                 560

Val Thr Ile Val Gly Leu Lys Pro Glu Thr Thr Tyr Ala Val Arg Leu
                565                 570                 575

Ala Ala Leu Asn Gly Lys Gly Leu Gly Glu Ile Ser Ala Ala Ser Glu
```

-continued

```
            580                 585                 590

Phe Lys Thr Gln Pro Val Gln Gly Glu Pro Ser Ala Pro Lys Leu Glu
        595                 600                 605

Gly Gln Met Gly Glu Asp Gly Asn Ser Ile Lys Val Asn Leu Ile Lys
    610                 615                 620

Gln Asp Asp Gly Gly Ser Pro Ile Arg His Tyr Leu Val Arg Tyr Arg
625                 630                 635                 640

Ala Leu Ser Ser Glu Trp Lys Pro Glu Ile Arg Leu Pro Ser Gly Ser
                645                 650                 655

Asp His Val Met Leu Lys Ser Leu Asp Trp Asn Ala Glu Tyr Glu Val
            660                 665                 670

Tyr Val Val Ala Glu Asn Gln Gln Gly Lys Ser Lys Ala Ala His Phe
        675                 680                 685

Val Phe Arg Thr Ser Ala Gln Pro Thr Ala Ile Pro Ala Asn Gly Ser
    690                 695                 700

Pro Thr Ser Gly Leu Ser Thr Gly Ala Ile Val Gly Ile Leu Ile Val
705                 710                 715                 720

Ile Phe Val Leu Leu Leu Val Val Val Asp Ile Thr Cys Tyr Phe Leu
                725                 730                 735

Asn Lys Cys Gly Leu Phe Met Cys Ile Ala Val Asn Leu Cys Gly Lys
            740                 745                 750

Ala Gly Pro Gly Ala Lys Gly Lys Asp Met Glu Glu Gly Lys Ala Ala
        755                 760                 765

Phe Ser Lys Asp Glu Ser Lys Glu Pro Ile Val Glu Val Arg Thr Glu
    770                 775                 780

Glu Glu Arg Thr Pro Asn His Asp Gly Gly Lys His Thr Glu Pro Asn
785                 790                 795                 800

Glu Thr Thr Pro Leu Thr Glu Pro Glu Lys Gly Pro Val Glu Ala Lys
                805                 810                 815

Pro Glu Cys Gln Glu Thr Glu Thr Lys Pro Ala Pro Ala Glu Val Lys
            820                 825                 830

Thr Val Pro Asn Asp Ala Thr Gln Thr Lys Glu Asn Glu Ser Lys Ala
        835                 840                 845


<210> SEQ ID NO 174
<211> LENGTH: 275
<212> TYPE: PRT
<213> ORGANISM: Homo sapiens
<220> FEATURE:
<221> NAME/KEY: MISC_FEATURE
<222> LOCATION: (1)..(275)
<223> OTHER INFORMATION: C-type lectin-like molecule-1 from Genbank
      accession number AAT11783

<400> SEQUENCE: 174

Met Trp Ile Asp Phe Phe Thr Tyr Ser Ser Met Ser Glu Glu Val Thr
1               5                   10                  15

Tyr Ala Asp Leu Gln Phe Gln Asn Ser Ser Glu Met Glu Lys Ile Pro
            20                  25                  30

Glu Ile Gly Lys Phe Gly Glu Lys Ala Pro Pro Ala Pro Ser His Val
        35                  40                  45

Trp Arg Pro Ala Ala Leu Phe Leu Thr Leu Leu Cys Leu Leu Leu Leu
    50                  55                  60

Ile Gly Leu Gly Val Leu Ala Ser Met Phe His Val Thr Leu Lys Ile
65                  70                  75                  80

Glu Met Lys Lys Met Asn Lys Leu Gln Asn Ile Ser Glu Glu Leu Gln
```

```
                85                  90                  95

Arg Asn Ile Ser Leu Gln Leu Met Ser Asn Met Asn Ile Ser Asn Lys
            100                 105                 110

Ile Arg Asn Leu Ser Thr Thr Leu Gln Thr Ile Ala Thr Lys Leu Cys
        115                 120                 125

Arg Glu Leu Tyr Ser Lys Glu Gln Glu His Lys Cys Lys Pro Cys Pro
    130                 135                 140

Arg Arg Trp Ile Trp His Lys Asp Ser Cys Tyr Phe Leu Ser Asp Asp
145                 150                 155                 160

Val Gln Thr Trp Gln Glu Ser Lys Met Ala Cys Ala Ala Gln Asn Ala
                165                 170                 175

Ser Leu Leu Lys Ile Asn Asn Lys Asn Ala Leu Glu Phe Ile Lys Ser
            180                 185                 190

Gln Ser Arg Ser Tyr Asp Tyr Trp Leu Gly Leu Ser Pro Glu Glu Asp
        195                 200                 205

Ser Thr Arg Gly Met Arg Val Asp Asn Ile Ile Asn Ser Ser Ala Trp
    210                 215                 220

Val Ile Arg Asn Ala Pro Asp Leu Asn Asn Met Tyr Cys Gly Tyr Ile
225                 230                 235                 240

Asn Arg Leu Tyr Val Gln Tyr Tyr His Cys Thr Tyr Lys Gln Arg Met
                245                 250                 255

Ile Cys Glu Lys Met Ala Asn Pro Val Gln Leu Gly Ser Thr Tyr Phe
            260                 265                 270

Arg Glu Ala
        275


<210> SEQ ID NO 175
<211> LENGTH: 613
<212> TYPE: PRT
<213> ORGANISM: Pseudomonas aeruginosa
<220> FEATURE:
<221> NAME/KEY: VARIANT
<222> LOCATION: (1)..(613)
<223> OTHER INFORMATION: PE variant from Genbank Accession number GI
      17943391, version 1IKQ_A

<400> SEQUENCE: 175

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
```

```
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575
```

```
Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610


<210> SEQ ID NO 176
<211> LENGTH: 10
<212> TYPE: DNA
<213> ORGANISM: Artificial Sequence
<220> FEATURE:
<223> OTHER INFORMATION: Modified Kozak consensus sequence
<220> FEATURE:
<221> NAME/KEY: misc_feature
<222> LOCATION: (1)..(10)
<223> OTHER INFORMATION: consensus sequence

<400> SEQUENCE: 176

gccaccatgg                                                            10


<210> SEQ ID NO 177
<211> LENGTH: 347
<212> TYPE: PRT
<213> ORGANISM: Artificial Sequence
<220> FEATURE:
<223> OTHER INFORMATION: pIEX02-228 PE-A amino acid substitution mutant
<220> FEATURE:
<221> NAME/KEY: MISC_FEATURE
<222> LOCATION: (141)..(141)
<223> OTHER INFORMATION: Amino acid change Ile-141 to Ala-141
<220> FEATURE:
<221> NAME/KEY: MISC_FEATURE
<222> LOCATION: (152)..(152)
<223> OTHER INFORMATION: Amino acid change Thr-152 to Arg-152
<220> FEATURE:
<221> NAME/KEY: MISC_FEATURE
<222> LOCATION: (197)..(197)
<223> OTHER INFORMATION: Amino acid change Asp-197 to Lys-197
<220> FEATURE:
<221> NAME/KEY: MISC_FEATURE
<222> LOCATION: (241)..(241)
<223> OTHER INFORMATION: Amino acid change Ser-241 to Thr-241
<220> FEATURE:
<221> NAME/KEY: MISC_FEATURE
<222> LOCATION: (326)..(326)
<223> OTHER INFORMATION: Amino acid change Gln-326 to Glu-326

<400> SEQUENCE: 177

Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
    50                  55                  60

Ala Leu Ala Ser Pro Gly Ser Gly Gly Asp Leu Gly Glu Ala Ile Arg
65                  70                  75                  80

Glu Gln Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Ser Gly Pro Ala Asp Ser Gly Asp Ala Leu Leu Glu Arg Asn Tyr
        115                 120                 125
```

```
Pro Thr Gly Ala Glu Phe Leu Gly Asp Gly Gly Asp Ala Ser Phe Ser
    130                 135                 140

Thr Arg Gly Thr Gln Asn Trp Arg Val Glu Arg Leu Leu Gln Ala His
145                 150                 155                 160

Arg Gln Leu Glu Glu Arg Gly Tyr Val Phe Val Gly Tyr His Gly Thr
                165                 170                 175

Phe Leu Glu Ala Ala Gln Ser Ile Val Phe Gly Gly Val Arg Ala Arg
            180                 185                 190

Ser Gln Asp Leu Lys Ala Ile Trp Arg Gly Phe Tyr Ile Ala Gly Asp
        195                 200                 205

Pro Ala Leu Ala Tyr Gly Tyr Ala Gln Asp Gln Glu Pro Asp Ala Arg
    210                 215                 220

Gly Arg Ile Arg Asn Gly Ala Leu Leu Arg Val Tyr Val Pro Arg Ser
225                 230                 235                 240

Thr Leu Pro Gly Phe Tyr Arg Thr Gly Leu Thr Leu Ala Ala Pro Glu
                245                 250                 255

Ala Ala Gly Glu Val Glu Arg Leu Ile Gly His Pro Leu Pro Leu Arg
            260                 265                 270

Leu Asp Ala Ile Thr Gly Pro Glu Glu Glu Gly Gly Arg Leu Glu Thr
        275                 280                 285

Ile Leu Gly Trp Pro Leu Ala Glu Arg Thr Val Val Ile Pro Ser Ala
    290                 295                 300

Ile Pro Thr Asp Pro Arg Asn Val Gly Gly Asp Leu Asp Pro Ser Ser
305                 310                 315                 320

Ile Pro Asp Lys Glu Glu Ala Ile Ser Ala Leu Pro Asp Tyr Ala Ser
                325                 330                 335

Gln Pro Gly Lys Pro Pro Arg Glu Asp Leu Lys
            340                 345
```

<210> SEQ ID NO 178
<211> LENGTH: 347
<212> TYPE: PRT
<213> ORGANISM: Artificial Sequence
<220> FEATURE:
<223> OTHER INFORMATION: pIEX02-244 PE-A amino acid substitution mutant
<220> FEATURE:
<221> NAME/KEY: MISC_FEATURE
<222> LOCATION: (141)..(141)
<223> OTHER INFORMATION: Amino acid change Ile-141 to Thr-141
<220> FEATURE:
<221> NAME/KEY: MISC_FEATURE
<222> LOCATION: (152)..(152)
<223> OTHER INFORMATION: Amino acid change Thr-152 to Ala-152
<220> FEATURE:
<221> NAME/KEY: MISC_FEATURE
<222> LOCATION: (192)..(192)
<223> OTHER INFORMATION: Amino acid change Arg-192 to Ala-192
<220> FEATURE:
<221> NAME/KEY: MISC_FEATURE
<222> LOCATION: (197)..(197)
<223> OTHER INFORMATION: Amino acid change Asp-197 to Lys-197
<220> FEATURE:
<221> NAME/KEY: MISC_FEATURE
<222> LOCATION: (241)..(241)
<223> OTHER INFORMATION: Amino acid change Ser-241 to Thr-241
<220> FEATURE:
<221> NAME/KEY: MISC_FEATURE
<222> LOCATION: (326)..(326)
<223> OTHER INFORMATION: Amino acid change Gln-326 to Glu-326

<400> SEQUENCE: 178

```
Pro Glu Gly Gly Ser Leu Ala Ala Leu Thr Ala His Gln Ala Cys His
1               5                   10                  15
```

```
Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
    50                  55                  60

Ala Leu Ala Ser Pro Gly Ser Gly Gly Asp Leu Gly Glu Ala Ile Arg
65                  70                  75                  80

Glu Gln Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Ser Gly Pro Ala Asp Ser Gly Asp Ala Leu Leu Glu Arg Asn Tyr
        115                 120                 125

Pro Thr Gly Ala Glu Phe Leu Gly Asp Gly Gly Asp Thr Ser Phe Ser
    130                 135                 140

Thr Arg Gly Thr Gln Asn Trp Ala Val Glu Arg Leu Leu Gln Ala His
145                 150                 155                 160

Arg Gln Leu Glu Glu Arg Gly Tyr Val Phe Val Gly Tyr His Gly Thr
                165                 170                 175

Phe Leu Glu Ala Ala Gln Ser Ile Val Phe Gly Gly Val Arg Ala Ala
            180                 185                 190

Ser Gln Asp Leu Lys Ala Ile Trp Arg Gly Phe Tyr Ile Ala Gly Asp
        195                 200                 205

Pro Ala Leu Ala Tyr Gly Tyr Ala Gln Asp Gln Glu Pro Asp Ala Arg
    210                 215                 220

Gly Arg Ile Arg Asn Gly Ala Leu Leu Arg Val Tyr Val Pro Arg Ser
225                 230                 235                 240

Thr Leu Pro Gly Phe Tyr Arg Thr Gly Leu Thr Leu Ala Ala Pro Glu
                245                 250                 255

Ala Ala Gly Glu Val Glu Arg Leu Ile Gly His Pro Leu Pro Leu Arg
            260                 265                 270

Leu Asp Ala Ile Thr Gly Pro Glu Glu Glu Gly Gly Arg Leu Glu Thr
        275                 280                 285

Ile Leu Gly Trp Pro Leu Ala Glu Arg Thr Val Val Ile Pro Ser Ala
    290                 295                 300

Ile Pro Thr Asp Pro Arg Asn Val Gly Gly Asp Leu Asp Pro Ser Ser
305                 310                 315                 320

Ile Pro Asp Lys Glu Glu Ala Ile Ser Ala Leu Pro Asp Tyr Ala Ser
                325                 330                 335

Gln Pro Gly Lys Pro Pro Arg Glu Asp Leu Lys
            340                 345
```

<210> SEQ ID NO 179
<211> LENGTH: 347
<212> TYPE: PRT
<213> ORGANISM: Artificial Sequence
<220> FEATURE:
<223> OTHER INFORMATION: pIEX02-246 PE-A amino acid substitution mutant
<220> FEATURE:
<221> NAME/KEY: MISC_FEATURE
<222> LOCATION: (141)..(141)
<223> OTHER INFORMATION: Amino acid change Ile-141 to Ala-141
<220> FEATURE:
<221> NAME/KEY: MISC_FEATURE
<222> LOCATION: (152)..(152)
<223> OTHER INFORMATION: Amino acid change Thr-152 to Ala-152

```
<220> FEATURE:
<221> NAME/KEY: MISC_FEATURE
<222> LOCATION: (192)..(192)
<223> OTHER INFORMATION: Amino acid change Arg-192 to Ala-192
<220> FEATURE:
<221> NAME/KEY: MISC_FEATURE
<222> LOCATION: (197)..(197)
<223> OTHER INFORMATION: Amino acid change Asp-197 to Lys-197
<220> FEATURE:
<221> NAME/KEY: MISC_FEATURE
<222> LOCATION: (241)..(241)
<223> OTHER INFORMATION: Amino acid change Ser-241 to Thr-241
<220> FEATURE:
<221> NAME/KEY: MISC_FEATURE
<222> LOCATION: (326)..(326)
<223> OTHER INFORMATION: Amino acid change Gln-326 to Glu-326

<400> SEQUENCE: 179

Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
    50                  55                  60

Ala Leu Ala Ser Pro Gly Ser Gly Gly Asp Leu Gly Glu Ala Ile Arg
65                  70                  75                  80

Glu Gln Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Ser Gly Pro Ala Asp Ser Gly Asp Ala Leu Leu Glu Arg Asn Tyr
        115                 120                 125

Pro Thr Gly Ala Glu Phe Leu Gly Asp Gly Gly Asp Ala Ser Phe Ser
    130                 135                 140

Thr Arg Gly Thr Gln Asn Trp Ala Val Glu Arg Leu Leu Gln Ala His
145                 150                 155                 160

Arg Gln Leu Glu Glu Arg Gly Tyr Val Phe Val Gly Tyr His Gly Thr
                165                 170                 175

Phe Leu Glu Ala Ala Gln Ser Ile Val Phe Gly Gly Val Arg Ala Ala
            180                 185                 190

Ser Gln Asp Leu Lys Ala Ile Trp Arg Gly Phe Tyr Ile Ala Gly Asp
        195                 200                 205

Pro Ala Leu Ala Tyr Gly Tyr Ala Gln Asp Gln Glu Pro Asp Ala Arg
    210                 215                 220

Gly Arg Ile Arg Asn Gly Ala Leu Leu Arg Val Tyr Val Pro Arg Ser
225                 230                 235                 240

Thr Leu Pro Gly Phe Tyr Arg Thr Gly Leu Thr Leu Ala Ala Pro Glu
                245                 250                 255

Ala Ala Gly Glu Val Glu Arg Leu Ile Gly His Pro Leu Pro Leu Arg
            260                 265                 270

Leu Asp Ala Ile Thr Gly Pro Glu Glu Glu Gly Gly Arg Leu Glu Thr
        275                 280                 285

Ile Leu Gly Trp Pro Leu Ala Glu Arg Thr Val Val Ile Pro Ser Ala
    290                 295                 300

Ile Pro Thr Asp Pro Arg Asn Val Gly Gly Asp Leu Asp Pro Ser Ser
305                 310                 315                 320
```

```
Ile Pro Asp Lys Glu Glu Ala Ile Ser Ala Leu Pro Asp Tyr Ala Ser
                325                 330                 335

Gln Pro Gly Lys Pro Pro Arg Glu Asp Leu Lys
            340                 345


<210> SEQ ID NO 180
<211> LENGTH: 347
<212> TYPE: PRT
<213> ORGANISM: Artificial Sequence
<220> FEATURE:
<223> OTHER INFORMATION: PE38 NULL MUTANT (E287D)
<220> FEATURE:
<221> NAME/KEY: MISC_FEATURE
<222> LOCATION: (287)..(287)
<223> OTHER INFORMATION: Amino acid change Glu-287 to Asp-287

<400> SEQUENCE: 180

Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
    50                  55                  60

Ala Leu Ala Ser Pro Gly Ser Gly Gly Asp Leu Gly Glu Ala Ile Arg
65                  70                  75                  80

Glu Gln Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Ser Gly Pro Ala Asp Ser Gly Asp Ala Leu Leu Glu Arg Asn Tyr
        115                 120                 125

Pro Thr Gly Ala Glu Phe Leu Gly Asp Gly Gly Asp Ile Ser Phe Ser
    130                 135                 140

Thr Arg Gly Thr Gln Asn Trp Thr Val Glu Arg Leu Leu Gln Ala His
145                 150                 155                 160

Arg Gln Leu Glu Glu Arg Gly Tyr Val Phe Val Gly Tyr His Gly Thr
                165                 170                 175

Phe Leu Glu Ala Ala Gln Ser Ile Val Phe Gly Gly Val Arg Ala Arg
            180                 185                 190

Ser Gln Asp Leu Asp Ala Ile Trp Arg Gly Phe Tyr Ile Ala Gly Asp
        195                 200                 205

Pro Ala Leu Ala Tyr Gly Tyr Ala Gln Asp Gln Glu Pro Asp Ala Arg
    210                 215                 220

Gly Arg Ile Arg Asn Gly Ala Leu Leu Arg Val Tyr Val Pro Arg Ser
225                 230                 235                 240

Ser Leu Pro Gly Phe Tyr Arg Thr Gly Leu Thr Leu Ala Ala Pro Glu
                245                 250                 255

Ala Ala Gly Glu Val Glu Arg Leu Ile Gly His Pro Leu Pro Leu Arg
            260                 265                 270

Leu Asp Ala Ile Thr Gly Pro Glu Glu Glu Gly Gly Arg Leu Asp Thr
        275                 280                 285

Ile Leu Gly Trp Pro Leu Ala Glu Arg Thr Val Val Ile Pro Ser Ala
    290                 295                 300

Ile Pro Thr Asp Pro Arg Asn Val Gly Gly Asp Leu Asp Pro Ser Ser
305                 310                 315                 320
```

```
Ile Pro Asp Lys Glu Gln Ala Ile Ser Ala Leu Pro Asp Tyr Ala Ser
                325                 330                 335

Gln Pro Gly Lys Pro Pro Arg Glu Asp Leu Lys
            340                 345


<210> SEQ ID NO 181
<211> LENGTH: 347
<212> TYPE: PRT
<213> ORGANISM: Artificial Sequence
<220> FEATURE:
<223> OTHER INFORMATION: PE VARIANT 238 (pIEX02-228 with E287D)
<220> FEATURE:
<221> NAME/KEY: MISC_FEATURE
<222> LOCATION: (141)..(141)
<223> OTHER INFORMATION: Amino acid change Ile-141 to Ala-141
<220> FEATURE:
<221> NAME/KEY: MISC_FEATURE
<222> LOCATION: (152)..(152)
<223> OTHER INFORMATION: Amino acid change Thr-152 to Arg-152
<220> FEATURE:
<221> NAME/KEY: MISC_FEATURE
<222> LOCATION: (197)..(197)
<223> OTHER INFORMATION: Amino acid change Asp-197 to Lys-197
<220> FEATURE:
<221> NAME/KEY: MISC_FEATURE
<222> LOCATION: (241)..(241)
<223> OTHER INFORMATION: Amino acid change Ser-241 to Thr-241
<220> FEATURE:
<221> NAME/KEY: MISC_FEATURE
<222> LOCATION: (287)..(287)
<223> OTHER INFORMATION: Amino acid change Glu-287 to Asp-287
<220> FEATURE:
<221> NAME/KEY: MISC_FEATURE
<222> LOCATION: (326)..(326)
<223> OTHER INFORMATION: Amino acid change Gln-326 to Glu-326

<400> SEQUENCE: 181

Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
    50                  55                  60

Ala Leu Ala Ser Pro Gly Ser Gly Gly Asp Leu Gly Glu Ala Ile Arg
65                  70                  75                  80

Glu Gln Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Ser Gly Pro Ala Asp Ser Gly Asp Ala Leu Leu Glu Arg Asn Tyr
        115                 120                 125

Pro Thr Gly Ala Glu Phe Leu Gly Asp Gly Gly Asp Ala Ser Phe Ser
    130                 135                 140

Thr Arg Gly Thr Gln Asn Trp Arg Val Glu Arg Leu Leu Gln Ala His
145                 150                 155                 160

Arg Gln Leu Glu Glu Arg Gly Tyr Val Phe Val Gly Tyr His Gly Thr
                165                 170                 175

Phe Leu Glu Ala Ala Gln Ser Ile Val Phe Gly Gly Val Arg Ala Arg
            180                 185                 190

Ser Gln Asp Leu Lys Ala Ile Trp Arg Gly Phe Tyr Ile Ala Gly Asp
        195                 200                 205
```

```
Pro Ala Leu Ala Tyr Gly Tyr Ala Gln Asp Gln Glu Pro Asp Ala Arg
    210                 215                 220

Gly Arg Ile Arg Asn Gly Ala Leu Leu Arg Val Tyr Val Pro Arg Ser
225                 230                 235                 240

Thr Leu Pro Gly Phe Tyr Arg Thr Gly Leu Thr Leu Ala Ala Pro Glu
                245                 250                 255

Ala Ala Gly Glu Val Glu Arg Leu Ile Gly His Pro Leu Pro Leu Arg
            260                 265                 270

Leu Asp Ala Ile Thr Gly Pro Glu Glu Glu Gly Gly Arg Leu Asp Thr
        275                 280                 285

Ile Leu Gly Trp Pro Leu Ala Glu Arg Thr Val Val Ile Pro Ser Ala
    290                 295                 300

Ile Pro Thr Asp Pro Arg Asn Val Gly Gly Asp Leu Asp Pro Ser Ser
305                 310                 315                 320

Ile Pro Asp Lys Glu Glu Ala Ile Ser Ala Leu Pro Asp Tyr Ala Ser
                325                 330                 335

Gln Pro Gly Lys Pro Pro Arg Glu Asp Leu Lys
            340                 345


<210> SEQ ID NO 182
<211> LENGTH: 347
<212> TYPE: PRT
<213> ORGANISM: Artificial Sequence
<220> FEATURE:
<223> OTHER INFORMATION: PE VARIANT 245 (pIEX02-244 with E287D)
<220> FEATURE:
<221> NAME/KEY: MISC_FEATURE
<222> LOCATION: (141)..(141)
<223> OTHER INFORMATION: Amino acid change Ile-141 to Thr-141
<220> FEATURE:
<221> NAME/KEY: MISC_FEATURE
<222> LOCATION: (152)..(152)
<223> OTHER INFORMATION: Amino acid change Thr-152 to Ala-152
<220> FEATURE:
<221> NAME/KEY: MISC_FEATURE
<222> LOCATION: (192)..(192)
<223> OTHER INFORMATION: Amino acid change Arg-192 to Ala-192
<220> FEATURE:
<221> NAME/KEY: MISC_FEATURE
<222> LOCATION: (197)..(197)
<223> OTHER INFORMATION: Amino acid change Asp-197 to Lys-197
<220> FEATURE:
<221> NAME/KEY: MISC_FEATURE
<222> LOCATION: (241)..(241)
<223> OTHER INFORMATION: Amino acid change Ser-241 to Thr-241
<220> FEATURE:
<221> NAME/KEY: MISC_FEATURE
<222> LOCATION: (287)..(287)
<223> OTHER INFORMATION: Amino acid change Glu-287 to Asp-287
<220> FEATURE:
<221> NAME/KEY: MISC_FEATURE
<222> LOCATION: (326)..(326)
<223> OTHER INFORMATION: Amino acid change Gln-326 to Glu-326

<400> SEQUENCE: 182

Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
    50                  55                  60

Ala Leu Ala Ser Pro Gly Ser Gly Gly Asp Leu Gly Glu Ala Ile Arg
```

```
65                  70                  75                  80

Glu Gln Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Ser Gly Pro Ala Asp Ser Gly Asp Ala Leu Leu Glu Arg Asn Tyr
        115                 120                 125

Pro Thr Gly Ala Glu Phe Leu Gly Asp Gly Gly Asp Thr Ser Phe Ser
    130                 135                 140

Thr Arg Gly Thr Gln Asn Trp Ala Val Glu Arg Leu Leu Gln Ala His
145                 150                 155                 160

Arg Gln Leu Glu Glu Arg Gly Tyr Val Phe Val Gly Tyr His Gly Thr
                165                 170                 175

Phe Leu Glu Ala Ala Gln Ser Ile Val Phe Gly Gly Val Arg Ala Ala
            180                 185                 190

Ser Gln Asp Leu Lys Ala Ile Trp Arg Gly Phe Tyr Ile Ala Gly Asp
        195                 200                 205

Pro Ala Leu Ala Tyr Gly Tyr Ala Gln Asp Gln Glu Pro Asp Ala Arg
    210                 215                 220

Gly Arg Ile Arg Asn Gly Ala Leu Leu Arg Val Tyr Val Pro Arg Ser
225                 230                 235                 240

Thr Leu Pro Gly Phe Tyr Arg Thr Gly Leu Thr Leu Ala Ala Pro Glu
                245                 250                 255

Ala Ala Gly Glu Val Glu Arg Leu Ile Gly His Pro Leu Pro Leu Arg
            260                 265                 270

Leu Asp Ala Ile Thr Gly Pro Glu Glu Glu Gly Gly Arg Leu Asp Thr
        275                 280                 285

Ile Leu Gly Trp Pro Leu Ala Glu Arg Thr Val Val Ile Pro Ser Ala
    290                 295                 300

Ile Pro Thr Asp Pro Arg Asn Val Gly Gly Asp Leu Asp Pro Ser Ser
305                 310                 315                 320

Ile Pro Asp Lys Glu Glu Ala Ile Ser Ala Leu Pro Asp Tyr Ala Ser
                325                 330                 335

Gln Pro Gly Lys Pro Pro Arg Glu Asp Leu Lys
            340                 345


<210> SEQ ID NO 183
<211> LENGTH: 347
<212> TYPE: PRT
<213> ORGANISM: Artificial Sequence
<220> FEATURE:
<223> OTHER INFORMATION: PE VARIANT 247(pIEX02-246 with E287D)
<220> FEATURE:
<221> NAME/KEY: MISC_FEATURE
<222> LOCATION: (141)..(141)
<223> OTHER INFORMATION: Amino acid change Ile-141 to Ala-141
<220> FEATURE:
<221> NAME/KEY: MISC_FEATURE
<222> LOCATION: (152)..(152)
<223> OTHER INFORMATION: Amino acid change Thr-152 to Ala-152
<220> FEATURE:
<221> NAME/KEY: MISC_FEATURE
<222> LOCATION: (192)..(192)
<223> OTHER INFORMATION: Amino acid change Arg-192 to Ala-192
<220> FEATURE:
<221> NAME/KEY: MISC_FEATURE
<222> LOCATION: (197)..(197)
<223> OTHER INFORMATION: Amino acid change Asp-197 to Lys-197
<220> FEATURE:
<221> NAME/KEY: MISC_FEATURE
<222> LOCATION: (241)..(241)
```

```
<223> OTHER INFORMATION: Amino acid change Ser-241 to Thr-241
<220> FEATURE:
<221> NAME/KEY: MISC_FEATURE
<222> LOCATION: (287)..(287)
<223> OTHER INFORMATION: Amino acid change Glu-287 to Asp-287
<220> FEATURE:
<221> NAME/KEY: MISC_FEATURE
<222> LOCATION: (326)..(326)
<223> OTHER INFORMATION: Amino acid change Gln-326 to Glu-326

<400> SEQUENCE: 183

Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
    50                  55                  60

Ala Leu Ala Ser Pro Gly Ser Gly Gly Asp Leu Gly Glu Ala Ile Arg
65                  70                  75                  80

Glu Gln Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Ser Gly Pro Ala Asp Ser Gly Asp Ala Leu Leu Glu Arg Asn Tyr
        115                 120                 125

Pro Thr Gly Ala Glu Phe Leu Gly Asp Gly Gly Asp Ala Ser Phe Ser
    130                 135                 140

Thr Arg Gly Thr Gln Asn Trp Ala Val Glu Arg Leu Leu Gln Ala His
145                 150                 155                 160

Arg Gln Leu Glu Glu Arg Gly Tyr Val Phe Val Gly Tyr His Gly Thr
                165                 170                 175

Phe Leu Glu Ala Ala Gln Ser Ile Val Phe Gly Gly Val Arg Ala Ala
            180                 185                 190

Ser Gln Asp Leu Lys Ala Ile Trp Arg Gly Phe Tyr Ile Ala Gly Asp
        195                 200                 205

Pro Ala Leu Ala Tyr Gly Tyr Ala Gln Asp Gln Glu Pro Asp Ala Arg
    210                 215                 220

Gly Arg Ile Arg Asn Gly Ala Leu Leu Arg Val Tyr Val Pro Arg Ser
225                 230                 235                 240

Thr Leu Pro Gly Phe Tyr Arg Thr Gly Leu Thr Leu Ala Ala Pro Glu
                245                 250                 255

Ala Ala Gly Glu Val Glu Arg Leu Ile Gly His Pro Leu Pro Leu Arg
            260                 265                 270

Leu Asp Ala Ile Thr Gly Pro Glu Glu Glu Gly Gly Arg Leu Asp Thr
        275                 280                 285

Ile Leu Gly Trp Pro Leu Ala Glu Arg Thr Val Val Ile Pro Ser Ala
    290                 295                 300

Ile Pro Thr Asp Pro Arg Asn Val Gly Gly Asp Leu Asp Pro Ser Ser
305                 310                 315                 320

Ile Pro Asp Lys Glu Glu Ala Ile Ser Ala Leu Pro Asp Tyr Ala Ser
                325                 330                 335

Gln Pro Gly Lys Pro Pro Arg Glu Asp Leu Lys
            340                 345
```

<210> SEQ ID NO 184
<211> LENGTH: 611
<212> TYPE: PRT
<213> ORGANISM: Artificial Sequence
<220> FEATURE:
<223> OTHER INFORMATION: FUSION RFB4-WT PE38-HIS8-EDLK

<400> SEQUENCE: 184

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Asp Ile Gln Met Thr Gln
    130                 135                 140

Thr Thr Ser Ser Leu Ser Ala Ser Leu Gly Asp Arg Val Thr Ile Ser
145                 150                 155                 160

Cys Arg Ala Ser Gln Asp Ile Ser Asn Tyr Leu Asn Trp Tyr Gln Gln
                165                 170                 175

Lys Pro Asp Gly Thr Val Lys Leu Leu Ile Tyr Tyr Thr Ser Ile Leu
            180                 185                 190

His Ser Gly Val Pro Ser Arg Phe Ser Gly Ser Gly Ser Gly Thr Asp
        195                 200                 205

Tyr Ser Leu Thr Ile Ser Asn Leu Glu Gln Glu Asp Phe Ala Thr Tyr
    210                 215                 220

Phe Cys Gln Gln Gly Asn Thr Leu Pro Trp Thr Phe Gly Gly Gly Thr
225                 230                 235                 240

Lys Leu Glu Ile Lys Ser Ser Gly Leu Val Pro Arg Gly Ser His Met
                245                 250                 255

Pro Glu Gly Gly Ser Leu Ala Ala Leu Thr Ala His Gln Ala Cys His
            260                 265                 270

Leu Pro Leu Glu Thr Phe Thr Arg His Arg Gln Pro Arg Gly Trp Glu
        275                 280                 285

Gln Leu Glu Gln Cys Gly Tyr Pro Val Gln Arg Leu Val Ala Leu Tyr
    290                 295                 300

Leu Ala Ala Arg Leu Ser Trp Asn Gln Val Asp Gln Val Ile Arg Asn
305                 310                 315                 320

Ala Leu Ala Ser Pro Gly Ser Gly Gly Asp Leu Gly Glu Ala Ile Arg
                325                 330                 335

Glu Gln Pro Glu Gln Ala Arg Leu Ala Leu Thr Leu Ala Ala Ala Glu
            340                 345                 350

Ser Glu Arg Phe Val Arg Gln Gly Thr Gly Asn Asp Glu Ala Gly Ala
        355                 360                 365

Ala Ser Gly Pro Ala Asp Ser Gly Asp Ala Leu Leu Glu Arg Asn Tyr
```

```
    370                 375                 380

Pro Thr Gly Ala Glu Phe Leu Gly Asp Gly Gly Asp Ile Ser Phe Ser
385                 390                 395                 400

Thr Arg Gly Thr Gln Asn Trp Thr Val Glu Arg Leu Leu Gln Ala His
                405                 410                 415

Arg Gln Leu Glu Glu Arg Gly Tyr Val Phe Val Gly Tyr His Gly Thr
            420                 425                 430

Phe Leu Glu Ala Ala Gln Ser Ile Val Phe Gly Gly Val Arg Ala Arg
        435                 440                 445

Ser Gln Asp Leu Asp Ala Ile Trp Arg Gly Phe Tyr Ile Ala Gly Asp
    450                 455                 460

Pro Ala Leu Ala Tyr Gly Tyr Ala Gln Asp Gln Glu Pro Asp Ala Arg
465                 470                 475                 480

Gly Arg Ile Arg Asn Gly Ala Leu Leu Arg Val Tyr Val Pro Arg Ser
                485                 490                 495

Ser Leu Pro Gly Phe Tyr Arg Thr Gly Leu Thr Leu Ala Ala Pro Glu
            500                 505                 510

Ala Ala Gly Glu Val Glu Arg Leu Ile Gly His Pro Leu Pro Leu Arg
        515                 520                 525

Leu Asp Ala Ile Thr Gly Pro Glu Glu Glu Gly Gly Arg Leu Glu Thr
    530                 535                 540

Ile Leu Gly Trp Pro Leu Ala Glu Arg Thr Val Val Ile Pro Ser Ala
545                 550                 555                 560

Ile Pro Thr Asp Pro Arg Asn Val Gly Gly Asp Leu Asp Pro Ser Ser
                565                 570                 575

Ile Pro Asp Lys Glu Gln Ala Ile Ser Ala Leu Pro Asp Tyr Ala Ser
            580                 585                 590

Gln Pro Gly Lys Pro Pro Arg His His His His His His His His Glu
        595                 600                 605

Asp Leu Lys
    610


<210> SEQ ID NO 185
<211> LENGTH: 614
<212> TYPE: PRT
<213> ORGANISM: Artificial Sequence
<220> FEATURE:
<223> OTHER INFORMATION: FUSION RFB4-HIS6-WT PE38-EDLK

<400> SEQUENCE: 185

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser Gly Gly Gly Gly Ser
```

-continued

```
        115                 120                 125

Gly Gly Gly Gly Ser Gly Gly Gly Gly Ser Asp Ile Gln Met Thr Gln
    130                 135                 140

Thr Thr Ser Ser Leu Ser Ala Ser Leu Gly Asp Arg Val Thr Ile Ser
145                 150                 155                 160

Cys Arg Ala Ser Gln Asp Ile Ser Asn Tyr Leu Asn Trp Tyr Gln Gln
                165                 170                 175

Lys Pro Asp Gly Thr Val Lys Leu Leu Ile Tyr Tyr Thr Ser Ile Leu
            180                 185                 190

His Ser Gly Val Pro Ser Arg Phe Ser Gly Ser Gly Ser Gly Thr Asp
        195                 200                 205

Tyr Ser Leu Thr Ile Ser Asn Leu Glu Gln Glu Asp Phe Ala Thr Tyr
    210                 215                 220

Phe Cys Gln Gln Gly Asn Thr Leu Pro Trp Thr Phe Gly Gly Gly Thr
225                 230                 235                 240

Lys Leu Glu Ile Lys Ala His Gly Gly Ser His His His His His His
                245                 250                 255

Ser Ser Gly Leu Val Pro Arg Gly Ser His Met Pro Glu Gly Gly Ser
            260                 265                 270

Leu Ala Ala Leu Thr Ala His Gln Ala Cys His Leu Pro Leu Glu Thr
        275                 280                 285

Phe Thr Arg His Arg Gln Pro Arg Gly Trp Glu Gln Leu Glu Gln Cys
    290                 295                 300

Gly Tyr Pro Val Gln Arg Leu Val Ala Leu Tyr Leu Ala Ala Arg Leu
305                 310                 315                 320

Ser Trp Asn Gln Val Asp Gln Val Ile Arg Asn Ala Leu Ala Ser Pro
                325                 330                 335

Gly Ser Gly Gly Asp Leu Gly Glu Ala Ile Arg Glu Gln Pro Glu Gln
            340                 345                 350

Ala Arg Leu Ala Leu Thr Leu Ala Ala Ala Glu Ser Glu Arg Phe Val
        355                 360                 365

Arg Gln Gly Thr Gly Asn Asp Glu Ala Gly Ala Ala Ser Gly Pro Ala
    370                 375                 380

Asp Ser Gly Asp Ala Leu Leu Glu Arg Asn Tyr Pro Thr Gly Ala Glu
385                 390                 395                 400

Phe Leu Gly Asp Gly Gly Asp Ile Ser Phe Ser Thr Arg Gly Thr Gln
                405                 410                 415

Asn Trp Thr Val Glu Arg Leu Leu Gln Ala His Arg Gln Leu Glu Glu
            420                 425                 430

Arg Gly Tyr Val Phe Val Gly Tyr His Gly Thr Phe Leu Glu Ala Ala
        435                 440                 445

Gln Ser Ile Val Phe Gly Gly Val Arg Ala Arg Ser Gln Asp Leu Asp
    450                 455                 460

Ala Ile Trp Arg Gly Phe Tyr Ile Ala Gly Asp Pro Ala Leu Ala Tyr
465                 470                 475                 480

Gly Tyr Ala Gln Asp Gln Glu Pro Asp Ala Arg Gly Arg Ile Arg Asn
                485                 490                 495

Gly Ala Leu Leu Arg Val Tyr Val Pro Arg Ser Ser Leu Pro Gly Phe
            500                 505                 510

Tyr Arg Thr Gly Leu Thr Leu Ala Ala Pro Glu Ala Ala Gly Glu Val
        515                 520                 525

Glu Arg Leu Ile Gly His Pro Leu Pro Leu Arg Leu Asp Ala Ile Thr
    530                 535                 540
```

```
Gly Pro Glu Glu Glu Gly Gly Arg Leu Glu Thr Ile Leu Gly Trp Pro
545                 550                 555                 560

Leu Ala Glu Arg Thr Val Val Ile Pro Ser Ala Ile Pro Thr Asp Pro
                565                 570                 575

Arg Asn Val Gly Gly Asp Leu Asp Pro Ser Ser Ile Pro Asp Lys Glu
            580                 585                 590

Gln Ala Ile Ser Ala Leu Pro Asp Tyr Ala Ser Gln Pro Gly Lys Pro
        595                 600                 605

Pro Arg Glu Asp Leu Lys
    610


<210> SEQ ID NO 186
<211> LENGTH: 611
<212> TYPE: PRT
<213> ORGANISM: Artificial Sequence
<220> FEATURE:
<223> OTHER INFORMATION: FUSION RFB4-VARIANT 244-HIS8-EDLK

<400> SEQUENCE: 186

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Asp Ile Gln Met Thr Gln
    130                 135                 140

Thr Thr Ser Ser Leu Ser Ala Ser Leu Gly Asp Arg Val Thr Ile Ser
145                 150                 155                 160

Cys Arg Ala Ser Gln Asp Ile Ser Asn Tyr Leu Asn Trp Tyr Gln Gln
                165                 170                 175

Lys Pro Asp Gly Thr Val Lys Leu Leu Ile Tyr Tyr Thr Ser Ile Leu
            180                 185                 190

His Ser Gly Val Pro Ser Arg Phe Ser Gly Ser Gly Ser Gly Thr Asp
        195                 200                 205

Tyr Ser Leu Thr Ile Ser Asn Leu Glu Gln Glu Asp Phe Ala Thr Tyr
    210                 215                 220

Phe Cys Gln Gln Gly Asn Thr Leu Pro Trp Thr Phe Gly Gly Gly Thr
225                 230                 235                 240

Lys Leu Glu Ile Lys Ser Ser Gly Leu Val Pro Arg Gly Ser His Met
                245                 250                 255

Pro Glu Gly Gly Ser Leu Ala Ala Leu Thr Ala His Gln Ala Cys His
            260                 265                 270

Leu Pro Leu Glu Thr Phe Thr Arg His Arg Gln Pro Arg Gly Trp Glu
        275                 280                 285
```

```
Gln Leu Glu Gln Cys Gly Tyr Pro Val Gln Arg Leu Val Ala Leu Tyr
    290                 295                 300

Leu Ala Ala Arg Leu Ser Trp Asn Gln Val Asp Gln Val Ile Arg Asn
305                 310                 315                 320

Ala Leu Ala Ser Pro Gly Ser Gly Gly Asp Leu Gly Glu Ala Ile Arg
                325                 330                 335

Glu Gln Pro Glu Gln Ala Arg Leu Ala Leu Thr Leu Ala Ala Ala Glu
            340                 345                 350

Ser Glu Arg Phe Val Arg Gln Gly Thr Gly Asn Asp Glu Ala Gly Ala
        355                 360                 365

Ala Ser Gly Pro Ala Asp Ser Gly Asp Ala Leu Leu Glu Arg Asn Tyr
    370                 375                 380

Pro Thr Gly Ala Glu Phe Leu Gly Asp Gly Gly Asp Thr Ser Phe Ser
385                 390                 395                 400

Thr Arg Gly Thr Gln Asn Trp Ala Val Glu Arg Leu Leu Gln Ala His
                405                 410                 415

Arg Gln Leu Glu Glu Arg Gly Tyr Val Phe Val Gly Tyr His Gly Thr
            420                 425                 430

Phe Leu Glu Ala Ala Gln Ser Ile Val Phe Gly Gly Val Arg Ala Ala
        435                 440                 445

Ser Gln Asp Leu Lys Ala Ile Trp Arg Gly Phe Tyr Ile Ala Gly Asp
    450                 455                 460

Pro Ala Leu Ala Tyr Gly Tyr Ala Gln Asp Gln Glu Pro Asp Ala Arg
465                 470                 475                 480

Gly Arg Ile Arg Asn Gly Ala Leu Leu Arg Val Tyr Val Pro Arg Ser
                485                 490                 495

Thr Leu Pro Gly Phe Tyr Arg Thr Gly Leu Thr Leu Ala Ala Pro Glu
            500                 505                 510

Ala Ala Gly Glu Val Glu Arg Leu Ile Gly His Pro Leu Pro Leu Arg
        515                 520                 525

Leu Asp Ala Ile Thr Gly Pro Glu Glu Glu Gly Gly Arg Leu Glu Thr
    530                 535                 540

Ile Leu Gly Trp Pro Leu Ala Glu Arg Thr Val Val Ile Pro Ser Ala
545                 550                 555                 560

Ile Pro Thr Asp Pro Arg Asn Val Gly Gly Asp Leu Asp Pro Ser Ser
                565                 570                 575

Ile Pro Asp Lys Glu Glu Ala Ile Ser Ala Leu Pro Asp Tyr Ala Ser
            580                 585                 590

Gln Pro Gly Lys Pro Pro Arg His His His His His His His His Glu
        595                 600                 605

Asp Leu Lys
    610
```

<210> SEQ ID NO 187
<211> LENGTH: 614
<212> TYPE: PRT
<213> ORGANISM: Artificial Sequence
<220> FEATURE:
<223> OTHER INFORMATION: FUSION RFB4-HIS6-WT PE38-EDLK

<400> SEQUENCE: 187

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30
```

-continued

```
Asp Met Ser Trp Val Arg Gln Thr Pro Glu Lys Arg Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Asp Ile Gln Met Thr Gln
    130                 135                 140

Thr Thr Ser Ser Leu Ser Ala Ser Leu Gly Asp Arg Val Thr Ile Ser
145                 150                 155                 160

Cys Arg Ala Ser Gln Asp Ile Ser Asn Tyr Leu Asn Trp Tyr Gln Gln
                165                 170                 175

Lys Pro Asp Gly Thr Val Lys Leu Leu Ile Tyr Tyr Thr Ser Ile Leu
            180                 185                 190

His Ser Gly Val Pro Ser Arg Phe Ser Gly Ser Gly Ser Gly Thr Asp
        195                 200                 205

Tyr Ser Leu Thr Ile Ser Asn Leu Glu Gln Glu Asp Phe Ala Thr Tyr
    210                 215                 220

Phe Cys Gln Gln Gly Asn Thr Leu Pro Trp Thr Phe Gly Gly Gly Thr
225                 230                 235                 240

Lys Leu Glu Ile Lys Ala His Gly Gly Ser His His His His His His
                245                 250                 255

Ser Ser Gly Leu Val Pro Arg Gly Ser His Met Pro Glu Gly Gly Ser
            260                 265                 270

Leu Ala Ala Leu Thr Ala His Gln Ala Cys His Leu Pro Leu Glu Thr
        275                 280                 285

Phe Thr Arg His Arg Gln Pro Arg Gly Trp Glu Gln Leu Glu Gln Cys
    290                 295                 300

Gly Tyr Pro Val Gln Arg Leu Val Ala Leu Tyr Leu Ala Ala Arg Leu
305                 310                 315                 320

Ser Trp Asn Gln Val Asp Gln Val Ile Arg Asn Ala Leu Ala Ser Pro
                325                 330                 335

Gly Ser Gly Gly Asp Leu Gly Glu Ala Ile Arg Glu Gln Pro Glu Gln
            340                 345                 350

Ala Arg Leu Ala Leu Thr Leu Ala Ala Ala Glu Ser Glu Arg Phe Val
        355                 360                 365

Arg Gln Gly Thr Gly Asn Asp Glu Ala Gly Ala Ala Ser Gly Pro Ala
    370                 375                 380

Asp Ser Gly Asp Ala Leu Leu Glu Arg Asn Tyr Pro Thr Gly Ala Glu
385                 390                 395                 400

Phe Leu Gly Asp Gly Gly Asp Thr Ser Phe Ser Thr Arg Gly Thr Gln
                405                 410                 415

Asn Trp Ala Val Glu Arg Leu Leu Gln Ala His Arg Gln Leu Glu Glu
            420                 425                 430

Arg Gly Tyr Val Phe Val Gly Tyr His Gly Thr Phe Leu Glu Ala Ala
        435                 440                 445
```

-continued

```
Gln Ser Ile Val Phe Gly Gly Val Arg Ala Ala Ser Gln Asp Leu Lys
    450                 455                 460

Ala Ile Trp Arg Gly Phe Tyr Ile Ala Gly Asp Pro Ala Leu Ala Tyr
465                 470                 475                 480

Gly Tyr Ala Gln Asp Gln Glu Pro Asp Ala Arg Gly Arg Ile Arg Asn
                485                 490                 495

Gly Ala Leu Leu Arg Val Tyr Val Pro Arg Ser Thr Leu Pro Gly Phe
            500                 505                 510

Tyr Arg Thr Gly Leu Thr Leu Ala Ala Pro Glu Ala Ala Gly Glu Val
        515                 520                 525

Glu Arg Leu Ile Gly His Pro Leu Pro Leu Arg Leu Asp Ala Ile Thr
    530                 535                 540

Gly Pro Glu Glu Glu Gly Gly Arg Leu Glu Thr Ile Leu Gly Trp Pro
545                 550                 555                 560

Leu Ala Glu Arg Thr Val Val Ile Pro Ser Ala Ile Pro Thr Asp Pro
                565                 570                 575

Arg Asn Val Gly Gly Asp Leu Asp Pro Ser Ser Ile Pro Asp Lys Glu
            580                 585                 590

Glu Ala Ile Ser Ala Leu Pro Asp Tyr Ala Ser Gln Pro Gly Lys Pro
        595                 600                 605

Pro Arg Glu Asp Leu Lys
    610
```

<210> SEQ ID NO 188
<211> LENGTH: 245
<212> TYPE: PRT
<213> ORGANISM: Artificial Sequence
<220> FEATURE:
<223> OTHER INFORMATION: RFB4 SCFV

<400> SEQUENCE: 188

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Asp Ile Gln Met Thr Gln
    130                 135                 140

Thr Thr Ser Ser Leu Ser Ala Ser Leu Gly Asp Arg Val Thr Ile Ser
145                 150                 155                 160

Cys Arg Ala Ser Gln Asp Ile Ser Asn Tyr Leu Asn Trp Tyr Gln Gln
                165                 170                 175

Lys Pro Asp Gly Thr Val Lys Leu Leu Ile Tyr Tyr Thr Ser Ile Leu
            180                 185                 190
```

```
His Ser Gly Val Pro Ser Arg Phe Ser Gly Ser Gly Ser Gly Thr Asp
        195                 200                 205

Tyr Ser Leu Thr Ile Ser Asn Leu Glu Gln Glu Asp Phe Ala Thr Tyr
    210                 215                 220

Phe Cys Gln Gln Gly Asn Thr Leu Pro Trp Thr Phe Gly Gly Gly Thr
225                 230                 235                 240

Lys Leu Glu Ile Lys
                245


<210> SEQ ID NO 189
<211> LENGTH: 1107
<212> TYPE: DNA
<213> ORGANISM: Artificial Sequence
<220> FEATURE:
<223> OTHER INFORMATION: PE38 WT as expressed by pIEX02-001 (pET14b-K
      PE38)

<400> SEQUENCE: 189

atgggcagca gccatcatca tcatcatcac agcagcggcc tggtgccgcg cggcagccat     60

atgccagaag gcggtagcct ggccgctctg accgcacatc aggcctgtca cctgccgctg    120

gaaaccttca cccgtcaccg tcagccgcgt ggttgggaac aactggaaca atgtggctat    180

ccggtacagc gtctggtggc gctgtacctg gctgctcgtc tgtcttggaa ccaagtagat    240

caggtcatcc gtaacgcgct ggcaagcccg ggttccggtg gtgatctggg tgaagctatc    300

cgtgaacaac cggaacaggc tcgtctggcg ctgaccctgg cggcagcgga atctgaacgt    360

tttgtgcgcc agggtacggg taacgacgaa gctggcgctg cgagcggtcc tgccgactcc    420

ggtgacgctc tgctggaacg taactacccg accggtgcag aatttctggg tgatggcggc    480

gatatctctt tttctacccg cggcacccag aactggaccg ttgaacgtct gctgcaggcg    540

caccgtcaac tggaagaacg cggttacgtc ttcgtaggtt accacggtac cttcctggaa    600

gctgctcagt ctatcgtgtt cggtggcgta cgtgctcgta gccaggacct ggatgccatc    660

tggcgtggct tctacattgc gggtgatccg gccctggcct atggttatgc acaggatcag    720

gagccagacg ctcgtggtcg tatccgtaac ggcgctctgc tgcgcgtgta cgtaccgcgc    780

agctccctgc cgggtttcta tcgtactggc ctgaccctgg ctgcgccgga agcagccggt    840

gaagtggaac gcctgatcgg ccatccgctg ccactgcgtc tggacgctat cactggtcct    900

gaagaagagg gtggtcgcct ggagactatc ctgggttggc cgctggctga acgcactgta    960

gtaatcccgt ccgcgatccc aacggatccg cgcaatgttg gtggcgatct ggacccaagc   1020

tctatcccgg ataaagaaca ggctatttct gccctgccgg actacgcctc ccagccgggt   1080

aaaccgccgc gtgaggacct gaagtaa                                       1107


<210> SEQ ID NO 190
<211> LENGTH: 368
<212> TYPE: PRT
<213> ORGANISM: Artificial Sequence
<220> FEATURE:
<223> OTHER INFORMATION: PE38 WT as expressed by pIEX02-001 (pET14b-K
      PE38)

<400> SEQUENCE: 190

Met Gly Ser Ser His His His His His His Ser Ser Gly Leu Val Pro
1               5                   10                  15

Arg Gly Ser His Met Pro Glu Gly Gly Ser Leu Ala Ala Leu Thr Ala
            20                  25                  30

His Gln Ala Cys His Leu Pro Leu Glu Thr Phe Thr Arg His Arg Gln
```

```
        35                  40                  45

Pro Arg Gly Trp Glu Gln Leu Glu Gln Cys Gly Tyr Pro Val Gln Arg
    50                  55                  60

Leu Val Ala Leu Tyr Leu Ala Ala Arg Leu Ser Trp Asn Gln Val Asp
65                  70                  75                  80

Gln Val Ile Arg Asn Ala Leu Ala Ser Pro Gly Ser Gly Gly Asp Leu
                85                  90                  95

Gly Glu Ala Ile Arg Glu Gln Pro Glu Gln Ala Arg Leu Ala Leu Thr
            100                 105                 110

Leu Ala Ala Ala Glu Ser Glu Arg Phe Val Arg Gln Gly Thr Gly Asn
        115                 120                 125

Asp Glu Ala Gly Ala Ala Ser Gly Pro Ala Asp Ser Gly Asp Ala Leu
    130                 135                 140

Leu Glu Arg Asn Tyr Pro Thr Gly Ala Glu Phe Leu Gly Asp Gly Gly
145                 150                 155                 160

Asp Ile Ser Phe Ser Thr Arg Gly Thr Gln Asn Trp Thr Val Glu Arg
                165                 170                 175

Leu Leu Gln Ala His Arg Gln Leu Glu Glu Arg Gly Tyr Val Phe Val
            180                 185                 190

Gly Tyr His Gly Thr Phe Leu Glu Ala Ala Gln Ser Ile Val Phe Gly
        195                 200                 205

Gly Val Arg Ala Arg Ser Gln Asp Leu Asp Ala Ile Trp Arg Gly Phe
    210                 215                 220

Tyr Ile Ala Gly Asp Pro Ala Leu Ala Tyr Gly Tyr Ala Gln Asp Gln
225                 230                 235                 240

Glu Pro Asp Ala Arg Gly Arg Ile Arg Asn Gly Ala Leu Leu Arg Val
                245                 250                 255

Tyr Val Pro Arg Ser Ser Leu Pro Gly Phe Tyr Arg Thr Gly Leu Thr
            260                 265                 270

Leu Ala Ala Pro Glu Ala Ala Gly Glu Val Glu Arg Leu Ile Gly His
        275                 280                 285

Pro Leu Pro Leu Arg Leu Asp Ala Ile Thr Gly Pro Glu Glu Glu Gly
    290                 295                 300

Gly Arg Leu Glu Thr Ile Leu Gly Trp Pro Leu Ala Glu Arg Thr Val
305                 310                 315                 320

Val Ile Pro Ser Ala Ile Pro Thr Asp Pro Arg Asn Val Gly Gly Asp
                325                 330                 335

Leu Asp Pro Ser Ser Ile Pro Asp Lys Glu Gln Ala Ile Ser Ala Leu
            340                 345                 350

Pro Asp Tyr Ala Ser Gln Pro Gly Lys Pro Pro Arg Glu Asp Leu Lys
        355                 360                 365
```

<210> SEQ ID NO 191
<211> LENGTH: 1107
<212> TYPE: DNA
<213> ORGANISM: Artificial Sequence
<220> FEATURE:
<223> OTHER INFORMATION: pIEX02-001 E229D (pET14b-K PE38 E299D)

<400> SEQUENCE: 191

```
atgggcagca gccatcatca tcatcatcac agcagcggcc tggtgccgcg cggcagccat      60

atgccagaag gcggtagcct ggccgctctg accgcacatc aggcctgtca cctgccgctg     120

gaaaccttca cccgtcaccg tcagccgcgt ggttgggaac aactggaaca atgtggctat     180

ccggtacagc gtctggtggc gctgtacctg gctgctcgtc tgtcttggaa ccaagtagat     240
```

```
caggtcatcc gtaacgcgct ggcaagcccg ggttccggtg gtgatctggg tgaagctatc    300

cgtgaacaac cggaacaggc tcgtctggcg ctgaccctgg cggcagcgga atctgaacgt    360

tttgtgcgcc agggtacggg taacgacgaa gctggcgctg cgagcggtcc tgccgactcc    420

ggtgacgctc tgctggaacg taactacccg accggtgcag aatttctggg tgatggcggc    480

gatatctctt tttctacccg cggcacccag aactggaccg ttgaacgtct gctgcaggcg    540

caccgtcaac tggaagaacg cggttacgtc ttcgtaggtt accacggtac cttcctggaa    600

gctgctcagt ctatcgtgtt cggtggcgta cgtgctcgta gccaggacct ggatgccatc    660

tggcgtggct tctacattgc gggtgatccg gccctggcct atggttatgc acaggatcag    720

gagccagacg ctcgtggtcg tatccgtaac ggcgctctgc tgcgcgtgta cgtaccgcgc    780

agctccctgc cgggtttcta tcgtactggc ctgaccctgg ctgcgccgga agcagccggt    840

gaagtggaac gcctgatcgg ccatccgctg ccactgcgtc tggacgctat cactggtcct    900

gaagaagagg gtggtcgcct ggacactatc ctgggttggc cgctggctga acgcactgta    960

gtaatcccgt ccgcgatccc aacggatccg cgcaatgttg gtggcgatct ggacccaagc   1020

tctatcccgg ataaagaaca ggctatttct gccctgccgg actacgcctc ccagccgggt   1080

aaaccgccgc gtgaggacct gaagtaa                                       1107
```

```
<210> SEQ ID NO 192
<211> LENGTH: 368
<212> TYPE: PRT
<213> ORGANISM: Artificial Sequence
<220> FEATURE:
<223> OTHER INFORMATION: pIEX02-001 E229D (pET14b-K PE38 E299D)

<400> SEQUENCE: 192

Met Gly Ser Ser His His His His His His Ser Ser Gly Leu Val Pro
1               5                   10                  15

Arg Gly Ser His Met Pro Glu Gly Gly Ser Leu Ala Ala Leu Thr Ala
            20                  25                  30

His Gln Ala Cys His Leu Pro Leu Glu Thr Phe Thr Arg His Arg Gln
        35                  40                  45

Pro Arg Gly Trp Glu Gln Leu Glu Gln Cys Gly Tyr Pro Val Gln Arg
    50                  55                  60

Leu Val Ala Leu Tyr Leu Ala Ala Arg Leu Ser Trp Asn Gln Val Asp
65                  70                  75                  80

Gln Val Ile Arg Asn Ala Leu Ala Ser Pro Gly Ser Gly Gly Asp Leu
                85                  90                  95

Gly Glu Ala Ile Arg Glu Gln Pro Glu Gln Ala Arg Leu Ala Leu Thr
            100                 105                 110

Leu Ala Ala Ala Glu Ser Glu Arg Phe Val Arg Gln Gly Thr Gly Asn
        115                 120                 125

Asp Glu Ala Gly Ala Ala Ser Gly Pro Ala Asp Ser Gly Asp Ala Leu
    130                 135                 140

Leu Glu Arg Asn Tyr Pro Thr Gly Ala Glu Phe Leu Gly Asp Gly Gly
145                 150                 155                 160

Asp Ile Ser Phe Ser Thr Arg Gly Thr Gln Asn Trp Thr Val Glu Arg
                165                 170                 175

Leu Leu Gln Ala His Arg Gln Leu Glu Glu Arg Gly Tyr Val Phe Val
            180                 185                 190

Gly Tyr His Gly Thr Phe Leu Glu Ala Ala Gln Ser Ile Val Phe Gly
        195                 200                 205
```

```
Gly Val Arg Ala Arg Ser Gln Asp Leu Asp Ala Ile Trp Arg Gly Phe
    210                 215                 220

Tyr Ile Ala Gly Asp Pro Ala Leu Ala Tyr Gly Tyr Ala Gln Asp Gln
225                 230                 235                 240

Glu Pro Asp Ala Arg Gly Arg Ile Arg Asn Gly Ala Leu Leu Arg Val
                245                 250                 255

Tyr Val Pro Arg Ser Ser Leu Pro Gly Phe Tyr Arg Thr Gly Leu Thr
            260                 265                 270

Leu Ala Ala Pro Glu Ala Ala Gly Glu Val Glu Arg Leu Ile Gly His
        275                 280                 285

Pro Leu Pro Leu Arg Leu Asp Ala Ile Thr Gly Pro Glu Glu Glu Gly
    290                 295                 300

Gly Arg Leu Asp Thr Ile Leu Gly Trp Pro Leu Ala Glu Arg Thr Val
305                 310                 315                 320

Val Ile Pro Ser Ala Ile Pro Thr Asp Pro Arg Asn Val Gly Gly Asp
                325                 330                 335

Leu Asp Pro Ser Ser Ile Pro Asp Lys Glu Gln Ala Ile Ser Ala Leu
            340                 345                 350

Pro Asp Tyr Ala Ser Gln Pro Gly Lys Pro Pro Arg Glu Asp Leu Lys
        355                 360                 365
```

```
<210> SEQ ID NO 193
<211> LENGTH: 1107
<212> TYPE: DNA
<213> ORGANISM: Artificial Sequence
<220> FEATURE:
<223> OTHER INFORMATION: PE38 mut228 as expressed by pIEX02-228
      (pET14b-K PE38 S253T D209K I153A T164R Q338E)

<400> SEQUENCE: 193

atgggcagca gccatcatca tcatcatcac agcagcggcc tggtgccgcg cggcagccat     60

atgccagaag gcggtagcct ggccgctctg accgcacatc aggcctgtca cctgccgctg    120

gaaaccttca cccgtcaccg tcagccgcgt ggttgggaac aactggaaca atgtggctat    180

ccggtacagc gtctggtggc gctgtacctg gctgctcgtc tgtcttggaa ccaagtagat    240

caggtcatcc gtaacgcgct ggcaagcccg ggttccggtg gtgatctggg tgaagctatc    300

cgtgaacaac cggaacaggc tcgtctggcg ctgaccctgg cggcagcgga atctgaacgt    360

tttgtgcgcc agggtacggg taacgacgaa gctggcgctg cgagcggtcc tgccgactcc    420

ggtgacgctc tgctggaacg taactacccg accggtgcag aatttctggg tgatggcggc    480

gatgcctctt tttctacccg cggcacccag aactggagag ttgaacgtct gctgcaggcg    540

caccgtcaac tggaagaacg cggttacgtc ttcgtaggtt accacggtac cttcctggaa    600

gctgctcagt ctatcgtgtt cggtggcgta cgtgctcgta gccaggacct gaaggccatc    660

tggcgtggct tctacattgc gggtgatccg gccctggcct atggttatgc acaggatcag    720

gagccagacg ctcgtggtcg tatccgtaac ggcgctctgc tgcgcgtgta cgtaccgcgc    780

agcaccctgc cgggtttcta tcgtactggc ctgaccctgg ctgcgccgga agcagccggt    840

gaagtggaac gcctgatcgg ccatccgctg ccactgcgtc tggacgctat cactggtcct    900

gaagaagagg gtggtcgcct ggagactatc ctgggttggc cgctggctga acgcactgta    960

gtaatcccgt ccgcgatccc aacggatccg cgcaatgttg gtggcgatct ggacccaagc   1020

tctatcccgg ataaagaaga ggctatttct gccctgccgg actacgcctc ccagccgggt   1080

aaaccgccgc gtgaggacct gaagtaa                                       1107
```

<210> SEQ ID NO 194
<211> LENGTH: 368
<212> TYPE: PRT
<213> ORGANISM: Artificial Sequence
<220> FEATURE:
<223> OTHER INFORMATION: PE38 mut228 as expressed by pIEX02-228
(pET14b-K PE38 S253T D209K I153A T164R Q338E)

<400> SEQUENCE: 194

```
Met Gly Ser Ser His His His His His His Ser Ser Gly Leu Val Pro
1               5                   10                  15

Arg Gly Ser His Met Pro Glu Gly Gly Ser Leu Ala Ala Leu Thr Ala
            20                  25                  30

His Gln Ala Cys His Leu Pro Leu Glu Thr Phe Thr Arg His Arg Gln
        35                  40                  45

Pro Arg Gly Trp Glu Gln Leu Glu Gln Cys Gly Tyr Pro Val Gln Arg
    50                  55                  60

Leu Val Ala Leu Tyr Leu Ala Ala Arg Leu Ser Trp Asn Gln Val Asp
65                  70                  75                  80

Gln Val Ile Arg Asn Ala Leu Ala Ser Pro Gly Ser Gly Gly Asp Leu
                85                  90                  95

Gly Glu Ala Ile Arg Glu Gln Pro Glu Gln Ala Arg Leu Ala Leu Thr
            100                 105                 110

Leu Ala Ala Ala Glu Ser Glu Arg Phe Val Arg Gln Gly Thr Gly Asn
        115                 120                 125

Asp Glu Ala Gly Ala Ala Ser Gly Pro Ala Asp Ser Gly Asp Ala Leu
    130                 135                 140

Leu Glu Arg Asn Tyr Pro Thr Gly Ala Glu Phe Leu Gly Asp Gly Gly
145                 150                 155                 160

Asp Ala Ser Phe Ser Thr Arg Gly Thr Gln Asn Trp Arg Val Glu Arg
                165                 170                 175

Leu Leu Gln Ala His Arg Gln Leu Glu Glu Arg Gly Tyr Val Phe Val
            180                 185                 190

Gly Tyr His Gly Thr Phe Leu Glu Ala Ala Gln Ser Ile Val Phe Gly
        195                 200                 205

Gly Val Arg Ala Arg Ser Gln Asp Leu Lys Ala Ile Trp Arg Gly Phe
    210                 215                 220

Tyr Ile Ala Gly Asp Pro Ala Leu Ala Tyr Gly Tyr Ala Gln Asp Gln
225                 230                 235                 240

Glu Pro Asp Ala Arg Gly Arg Ile Arg Asn Gly Ala Leu Leu Arg Val
                245                 250                 255

Tyr Val Pro Arg Ser Thr Leu Pro Gly Phe Tyr Arg Thr Gly Leu Thr
            260                 265                 270

Leu Ala Ala Pro Glu Ala Ala Gly Glu Val Glu Arg Leu Ile Gly His
        275                 280                 285

Pro Leu Pro Leu Arg Leu Asp Ala Ile Thr Gly Pro Glu Glu Glu Gly
    290                 295                 300

Gly Arg Leu Glu Thr Ile Leu Gly Trp Pro Leu Ala Glu Arg Thr Val
305                 310                 315                 320

Val Ile Pro Ser Ala Ile Pro Thr Asp Pro Arg Asn Val Gly Gly Asp
                325                 330                 335

Leu Asp Pro Ser Ser Ile Pro Asp Lys Glu Glu Ala Ile Ser Ala Leu
            340                 345                 350

Pro Asp Tyr Ala Ser Gln Pro Gly Lys Pro Pro Arg Glu Asp Leu Lys
```

355 360 365

<210> SEQ ID NO 195
<211> LENGTH: 1107
<212> TYPE: DNA
<213> ORGANISM: Artificial Sequence
<220> FEATURE:
<223> OTHER INFORMATION: pIEX02-228 E299D (pET14b-K PE38 S253T D209K I153A T164R Q338E E299D)

<400> SEQUENCE: 195
atgggcagca gccatcatca tcatcatcac agcagcggcc tggtgccgcg cggcagccat 60
atgccagaag gcggtagcct ggccgctctg accgcacatc aggcctgtca cctgccgctg 120
gaaaccttca cccgtcaccg tcagccgcgt ggttgggaac aactggaaca atgtggctat 180
ccggtacagc gtctggtggc gctgtacctg gctgctcgtc tgtcttggaa ccaagtagat 240
caggtcatcc gtaacgcgct ggcaagcccg ggttccggtg gtgatctggg tgaagctatc 300
cgtgaacaac cggaacaggc tcgtctggcg ctgaccctgg cggcagcgga atctgaacgt 360
tttgtgcgcc agggtacggg taacgacgaa gctggcgctg cgagcggtcc tgccgactcc 420
ggtgacgctc tgctggaacg taactacccg accggtgcag aatttctggg tgatggcggc 480
gatgcctctt tttctacccg cggcacccag aactggagag ttgaacgtct gctgcaggcg 540
caccgtcaac tggaagaacg cggttacgtc ttcgtaggtt accacggtac cttcctggaa 600
gctgctcagt ctatcgtgtt cggtggcgta cgtgctcgta gccaggacct gaaggccatc 660
tggcgtggct tctacattgc gggtgatccg gccctggcct atggttatgc acaggatcag 720
gagccagacg ctcgtggtcg tatccgtaac ggcgctctgc tgcgcgtgta cgtaccgcgc 780
agcaccctgc cgggtttcta tcgtactggc ctgaccctgg ctgcgccgga agcagccggt 840
gaagtggaac gcctgatcgg ccatccgctg ccactgcgtc tggacgctat cactggtcct 900
gaagaagagg gtggtcgcct ggacactatc ctgggttggc cgctggctga acgcactgta 960
gtaatcccgt ccgcgatccc aacggatccg cgcaatgttg gtggcgatct ggacccaagc 1020
tctatcccgg ataaagaaga ggctatttct gccctgccgg actacgcctc ccagccgggt 1080
aaaccgccgc gtgaggacct gaagtaa 1107

<210> SEQ ID NO 196
<211> LENGTH: 368
<212> TYPE: PRT
<213> ORGANISM: Artificial Sequence
<220> FEATURE:
<223> OTHER INFORMATION: pIEX02-228 E299D (pET14b-K PE38 S253T D209K I153A T164R Q338E E299D)

<400> SEQUENCE: 196

Met Gly Ser Ser His His His His His His Ser Ser Gly Leu Val Pro
1 5 10 15

Arg Gly Ser His Met Pro Glu Gly Gly Ser Leu Ala Ala Leu Thr Ala
20 25 30

His Gln Ala Cys His Leu Pro Leu Glu Thr Phe Thr Arg His Arg Gln
35 40 45

Pro Arg Gly Trp Glu Gln Leu Glu Gln Cys Gly Tyr Pro Val Gln Arg
50 55 60

Leu Val Ala Leu Tyr Leu Ala Ala Arg Leu Ser Trp Asn Gln Val Asp
65 70 75 80

Gln Val Ile Arg Asn Ala Leu Ala Ser Pro Gly Ser Gly Gly Asp Leu
85 90 95

-continued

```
Gly Glu Ala Ile Arg Glu Gln Pro Glu Gln Ala Arg Leu Ala Leu Thr
            100                 105                 110

Leu Ala Ala Ala Glu Ser Glu Arg Phe Val Arg Gln Gly Thr Gly Asn
        115                 120                 125

Asp Glu Ala Gly Ala Ala Ser Gly Pro Ala Asp Ser Gly Asp Ala Leu
    130                 135                 140

Leu Glu Arg Asn Tyr Pro Thr Gly Ala Glu Phe Leu Gly Asp Gly Gly
145                 150                 155                 160

Asp Ala Ser Phe Ser Thr Arg Gly Thr Gln Asn Trp Arg Val Glu Arg
                165                 170                 175

Leu Leu Gln Ala His Arg Gln Leu Glu Glu Arg Gly Tyr Val Phe Val
            180                 185                 190

Gly Tyr His Gly Thr Phe Leu Glu Ala Ala Gln Ser Ile Val Phe Gly
        195                 200                 205

Gly Val Arg Ala Arg Ser Gln Asp Leu Lys Ala Ile Trp Arg Gly Phe
    210                 215                 220

Tyr Ile Ala Gly Asp Pro Ala Leu Ala Tyr Gly Tyr Ala Gln Asp Gln
225                 230                 235                 240

Glu Pro Asp Ala Arg Gly Arg Ile Arg Asn Gly Ala Leu Leu Arg Val
                245                 250                 255

Tyr Val Pro Arg Ser Thr Leu Pro Gly Phe Tyr Arg Thr Gly Leu Thr
            260                 265                 270

Leu Ala Ala Pro Glu Ala Ala Gly Glu Val Glu Arg Leu Ile Gly His
        275                 280                 285

Pro Leu Pro Leu Arg Leu Asp Ala Ile Thr Gly Pro Glu Glu Glu Gly
    290                 295                 300

Gly Arg Leu Asp Thr Ile Leu Gly Trp Pro Leu Ala Glu Arg Thr Val
305                 310                 315                 320

Val Ile Pro Ser Ala Ile Pro Thr Asp Pro Arg Asn Val Gly Gly Asp
                325                 330                 335

Leu Asp Pro Ser Ser Ile Pro Asp Lys Glu Glu Ala Ile Ser Ala Leu
            340                 345                 350

Pro Asp Tyr Ala Ser Gln Pro Gly Lys Pro Pro Arg Glu Asp Leu Lys
        355                 360                 365
```

<210> SEQ ID NO 197
<211> LENGTH: 1107
<212> TYPE: DNA
<213> ORGANISM: Artificial Sequence
<220> FEATURE:
<223> OTHER INFORMATION: pIEX02-244 (pET14b-K PE38 S253T D209K R204A I153T T164A Q338E)

<400> SEQUENCE: 197

```
atgggcagca gccatcatca tcatcatcac agcagcggcc tggtgccgcg cggcagccat      60

atgccagaag gcggtagcct ggccgctctg accgcacatc aggcctgtca cctgccgctg     120

gaaaccttca cccgtcaccg tcagccgcgt ggttgggaac aactggaaca atgtggctat     180

ccggtacagc gtctggtggc gctgtacctg gctgctcgtc tgtcttggaa ccaagtagat     240

caggtcatcc gtaacgcgct ggcaagcccg ggttccggtg gtgatctggg tgaagctatc     300

cgtgaacaac cggaacaggc tcgtctggcg ctgaccctgg cggcagcgga atctgaacgt     360

tttgtgcgcc agggtacggg taacgacgaa gctggcgctg cgagcggtcc tgccgactcc     420

ggtgacgctc tgctggaacg taactacccg accggtgcag aatttctggg tgatggcggc     480
```

```
gatacctctt tttctacccg cggcacccag aactgggccg ttgaacgtct gctgcaggcg    540

caccgtcaac tggaagaacg cggttacgtc ttcgtaggtt accacggtac cttcctggaa    600

gctgctcagt ctatcgtgtt cggtggcgta cgtgctgcca gccaggacct gaaggccatc    660

tggcgtggct tctacattgc gggtgatccg gccctggcct atggttatgc acaggatcag    720

gagccagacg ctcgtggtcg tatccgtaac ggcgctctgc tgcgcgtgta cgtaccgcgc    780

agcaccctgc cgggtttcta tcgtactggc ctgaccctgg ctgcgccgga agcagccggt    840

gaagtggaac gcctgatcgg ccatccgctg ccactgcgtc tggacgctat cactggtcct    900

gaagaagagg gtggtcgcct ggagactatc ctgggttggc cgctggctga acgcactgta    960

gtaatcccgt ccgcgatccc aacggatccg cgcaatgttg gtggcgatct ggacccaagc   1020

tctatcccgg ataaagaaga ggctatttct gccctgccgg actacgcctc ccagccgggt   1080

aaaccgccgc gtgaggacct gaagtaa                                       1107


<210> SEQ ID NO 198
<211> LENGTH: 368
<212> TYPE: PRT
<213> ORGANISM: Artificial Sequence
<220> FEATURE:
<223> OTHER INFORMATION: pIEX02-244 (pET14b-K PE38 S253T D209K R204A
      I153T T164A Q338E)

<400> SEQUENCE: 198

Met Gly Ser Ser His His His His His His Ser Ser Gly Leu Val Pro
1               5                   10                  15

Arg Gly Ser His Met Pro Glu Gly Gly Ser Leu Ala Ala Leu Thr Ala
            20                  25                  30

His Gln Ala Cys His Leu Pro Leu Glu Thr Phe Thr Arg His Arg Gln
        35                  40                  45

Pro Arg Gly Trp Glu Gln Leu Glu Gln Cys Gly Tyr Pro Val Gln Arg
    50                  55                  60

Leu Val Ala Leu Tyr Leu Ala Ala Arg Leu Ser Trp Asn Gln Val Asp
65                  70                  75                  80

Gln Val Ile Arg Asn Ala Leu Ala Ser Pro Gly Ser Gly Gly Asp Leu
                85                  90                  95

Gly Glu Ala Ile Arg Glu Gln Pro Glu Gln Ala Arg Leu Ala Leu Thr
            100                 105                 110

Leu Ala Ala Ala Glu Ser Glu Arg Phe Val Arg Gln Gly Thr Gly Asn
        115                 120                 125

Asp Glu Ala Gly Ala Ala Ser Gly Pro Ala Asp Ser Gly Asp Ala Leu
    130                 135                 140

Leu Glu Arg Asn Tyr Pro Thr Gly Ala Glu Phe Leu Gly Asp Gly Gly
145                 150                 155                 160

Asp Thr Ser Phe Ser Thr Arg Gly Thr Gln Asn Trp Ala Val Glu Arg
                165                 170                 175

Leu Leu Gln Ala His Arg Gln Leu Glu Glu Arg Gly Tyr Val Phe Val
            180                 185                 190

Gly Tyr His Gly Thr Phe Leu Glu Ala Ala Gln Ser Ile Val Phe Gly
        195                 200                 205

Gly Val Arg Ala Ala Ser Gln Asp Leu Lys Ala Ile Trp Arg Gly Phe
    210                 215                 220

Tyr Ile Ala Gly Asp Pro Ala Leu Ala Tyr Gly Tyr Ala Gln Asp Gln
225                 230                 235                 240

Glu Pro Asp Ala Arg Gly Arg Ile Arg Asn Gly Ala Leu Leu Arg Val
```

245 250 255

Tyr Val Pro Arg Ser Thr Leu Pro Gly Phe Tyr Arg Thr Gly Leu Thr
260 265 270

Leu Ala Ala Pro Glu Ala Ala Gly Glu Val Glu Arg Leu Ile Gly His
275 280 285

Pro Leu Pro Leu Arg Leu Asp Ala Ile Thr Gly Pro Glu Glu Glu Gly
290 295 300

Gly Arg Leu Glu Thr Ile Leu Gly Trp Pro Leu Ala Glu Arg Thr Val
305 310 315 320

Val Ile Pro Ser Ala Ile Pro Thr Asp Pro Arg Asn Val Gly Gly Asp
325 330 335

Leu Asp Pro Ser Ser Ile Pro Asp Lys Glu Glu Ala Ile Ser Ala Leu
340 345 350

Pro Asp Tyr Ala Ser Gln Pro Gly Lys Pro Pro Arg Glu Asp Leu Lys
355 360 365

<210> SEQ ID NO 199
<211> LENGTH: 1107
<212> TYPE: DNA
<213> ORGANISM: Artificial Sequence
<220> FEATURE:
<223> OTHER INFORMATION: pIEX02-244 E299D (pET14b-K PE38 S253T D209K R204A I153T T164A Q338E E299D)

<400> SEQUENCE: 199
atgggcagca gccatcatca tcatcatcac agcagcggcc tggtgccgcg cggcagccat 60
atgccagaag gcggtagcct ggccgctctg accgcacatc aggcctgtca cctgccgctg 120
gaaaccttca cccgtcaccg tcagccgcgt ggttgggaac aactggaaca atgtggctat 180
ccggtacagc gtctggtggc gctgtacctg gctgctcgtc tgtcttggaa ccaagtagat 240
caggtcatcc gtaacgcgct ggcaagcccg ggttccggtg gtgatctggg tgaagctatc 300
cgtgaacaac cggaacaggc tcgtctggcg ctgaccctgg cggcagcgga atctgaacgt 360
tttgtgcgcc agggtacggg taacgacgaa gctggcgctg cgagcggtcc tgccgactcc 420
ggtgacgctc tgctggaacg taactacccg accggtgcag aatttctggg tgatggcggc 480
gatacctctt tttctacccg cggcacccag aactgggccg ttgaacgtct gctgcaggcg 540
caccgtcaac tggaagaacg cggttacgtc ttcgtaggtt accacggtac cttcctggaa 600
gctgctcagt ctatcgtgtt cggtggcgta cgtgctgcca gccaggacct gaaggccatc 660
tggcgtggct tctacattgc gggtgatccg gccctggcct atggttatgc acaggatcag 720
gagccagacg ctcgtggtcg tatccgtaac ggcgctctgc tgcgcgtgta cgtaccgcgc 780
agcaccctgc cgggtttcta tcgtactggc ctgaccctgg ctgcgccgga agcagccggt 840
gaagtggaac gcctgatcgg ccatccgctg ccactgcgtc tggacgctat cactggtcct 900
gaagaagagg gtggtcgcct ggacactatc ctgggttggc cgctggctga acgcactgta 960
gtaatcccgt ccgcgatccc aacggatccg cgcaatgttg gtggcgatct ggacccaagc 1020
tctatcccgg ataaagaaga ggctatttct gccctgccgg actacgcctc ccagccgggt 1080
aaaccgccgc gtgaggacct gaagtaa 1107

<210> SEQ ID NO 200
<211> LENGTH: 368
<212> TYPE: PRT
<213> ORGANISM: Artificial Sequence
<220> FEATURE:
<223> OTHER INFORMATION: pIEX02-244 E299D (pET14b-K PE38 S253T D209K

R204A I153T T164A Q338E E299D)

<400> SEQUENCE: 200

```
Met Gly Ser Ser His His His His His His Ser Ser Gly Leu Val Pro
1               5                   10                  15

Arg Gly Ser His Met Pro Glu Gly Gly Ser Leu Ala Ala Leu Thr Ala
            20                  25                  30

His Gln Ala Cys His Leu Pro Leu Glu Thr Phe Thr Arg His Arg Gln
        35                  40                  45

Pro Arg Gly Trp Glu Gln Leu Glu Gln Cys Gly Tyr Pro Val Gln Arg
    50                  55                  60

Leu Val Ala Leu Tyr Leu Ala Ala Arg Leu Ser Trp Asn Gln Val Asp
65                  70                  75                  80

Gln Val Ile Arg Asn Ala Leu Ala Ser Pro Gly Ser Gly Gly Asp Leu
                85                  90                  95

Gly Glu Ala Ile Arg Glu Gln Pro Glu Gln Ala Arg Leu Ala Leu Thr
            100                 105                 110

Leu Ala Ala Ala Glu Ser Glu Arg Phe Val Arg Gln Gly Thr Gly Asn
        115                 120                 125

Asp Glu Ala Gly Ala Ala Ser Gly Pro Ala Asp Ser Gly Asp Ala Leu
    130                 135                 140

Leu Glu Arg Asn Tyr Pro Thr Gly Ala Glu Phe Leu Gly Asp Gly Gly
145                 150                 155                 160

Asp Thr Ser Phe Ser Thr Arg Gly Thr Gln Asn Trp Ala Val Glu Arg
                165                 170                 175

Leu Leu Gln Ala His Arg Gln Leu Glu Glu Arg Gly Tyr Val Phe Val
            180                 185                 190

Gly Tyr His Gly Thr Phe Leu Glu Ala Ala Gln Ser Ile Val Phe Gly
        195                 200                 205

Gly Val Arg Ala Ala Ser Gln Asp Leu Lys Ala Ile Trp Arg Gly Phe
    210                 215                 220

Tyr Ile Ala Gly Asp Pro Ala Leu Ala Tyr Gly Tyr Ala Gln Asp Gln
225                 230                 235                 240

Glu Pro Asp Ala Arg Gly Arg Ile Arg Asn Gly Ala Leu Leu Arg Val
                245                 250                 255

Tyr Val Pro Arg Ser Thr Leu Pro Gly Phe Tyr Arg Thr Gly Leu Thr
            260                 265                 270

Leu Ala Ala Pro Glu Ala Ala Gly Glu Val Glu Arg Leu Ile Gly His
        275                 280                 285

Pro Leu Pro Leu Arg Leu Asp Ala Ile Thr Gly Pro Glu Glu Glu Gly
    290                 295                 300

Gly Arg Leu Asp Thr Ile Leu Gly Trp Pro Leu Ala Glu Arg Thr Val
305                 310                 315                 320

Val Ile Pro Ser Ala Ile Pro Thr Asp Pro Arg Asn Val Gly Gly Asp
                325                 330                 335

Leu Asp Pro Ser Ser Ile Pro Asp Lys Glu Glu Ala Ile Ser Ala Leu
            340                 345                 350

Pro Asp Tyr Ala Ser Gln Pro Gly Lys Pro Pro Arg Glu Asp Leu Lys
        355                 360                 365
```

<210> SEQ ID NO 201
<211> LENGTH: 1107
<212> TYPE: DNA
<213> ORGANISM: Artificial Sequence
<220> FEATURE:

<223> OTHER INFORMATION: pIEX02-246 (pET14b-K PE38 S253T D209K R204 I153A Q338E T164A)

<400> SEQUENCE: 201

```
atgggcagca gccatcatca tcatcatcac agcagcggcc tggtgccgcg cggcagccat      60
atgccagaag gcggtagcct ggccgctctg accgcacatc aggcctgtca cctgccgctg     120
gaaaccttca cccgtcaccg tcagccgcgt ggttgggaac aactggaaca atgtggctat     180
ccggtacagc gtctggtggc gctgtacctg gctgctcgtc tgtcttggaa ccaagtagat     240
caggtcatcc gtaacgcgct ggcaagcccg ggttccggtg gtgatctggg tgaagctatc     300
cgtgaacaac cggaacaggc tcgtctggcg ctgaccctgg cggcagcgga atctgaacgt     360
tttgtgcgcc agggtacggg taacgacgaa gctggcgctg cgagcggtcc tgccgactcc     420
ggtgacgctc tgctggaacg taactacccg accggtgcag aatttctggg tgatggcggc     480
gatgcctctt tttctacccg cggcacccag aactgggccg ttgaacgtct gctgcaggcg     540
caccgtcaac tggaagaacg cggttacgtc ttcgtaggtt accacggtac cttcctggaa     600
gctgctcagt ctatcgtgtt cggtggcgta cgtgctgcca gccaggacct gaaggccatc     660
tggcgtggct tctacattgc gggtgatccg gccctggcct atggttatgc acaggatcag     720
gagccagacg ctcgtggtcg tatccgtaac ggcgctctgc tgcgcgtgta cgtaccgcgc     780
agcaccctgc cgggtttcta tcgtactggc ctgaccctgg ctgcgccgga agcagccggt     840
gaagtggaac gcctgatcgg ccatccgctg ccactgcgtc tggacgctat cactggtcct     900
gaagaagagg gtggtcgcct ggagactatc ctgggttggc cgctggctga acgcactgta     960
gtaatcccgt ccgcgatccc aacggatccg cgcaatgttg gtggcgatct ggacccaagc    1020
tctatcccgg ataaagaaga ggctatttct gccctgccgg actacgcctc ccagccgggt    1080
aaaccgccgc gtgaggacct gaagtaa                                        1107
```

<210> SEQ ID NO 202
<211> LENGTH: 368
<212> TYPE: PRT
<213> ORGANISM: Artificial Sequence
<220> FEATURE:
<223> OTHER INFORMATION: pIEX02-246 (pET14b-K PE38 S253T D209K R204 I153A Q338E T164A)

<400> SEQUENCE: 202

```
Met Gly Ser Ser His His His His His His Ser Ser Gly Leu Val Pro
1               5                   10                  15

Arg Gly Ser His Met Pro Glu Gly Gly Ser Leu Ala Ala Leu Thr Ala
            20                  25                  30

His Gln Ala Cys His Leu Pro Leu Glu Thr Phe Thr Arg His Arg Gln
        35                  40                  45

Pro Arg Gly Trp Glu Gln Leu Glu Gln Cys Gly Tyr Pro Val Gln Arg
    50                  55                  60

Leu Val Ala Leu Tyr Leu Ala Ala Arg Leu Ser Trp Asn Gln Val Asp
65                  70                  75                  80

Gln Val Ile Arg Asn Ala Leu Ala Ser Pro Gly Ser Gly Gly Asp Leu
                85                  90                  95

Gly Glu Ala Ile Arg Glu Gln Pro Glu Gln Ala Arg Leu Ala Leu Thr
            100                 105                 110

Leu Ala Ala Ala Glu Ser Glu Arg Phe Val Arg Gln Gly Thr Gly Asn
        115                 120                 125

Asp Glu Ala Gly Ala Ala Ser Gly Pro Ala Asp Ser Gly Asp Ala Leu
```

```
    130                 135                 140

Leu Glu Arg Asn Tyr Pro Thr Gly Ala Glu Phe Leu Gly Asp Gly Gly
145                 150                 155                 160

Asp Ala Ser Phe Ser Thr Arg Gly Thr Gln Asn Trp Ala Val Glu Arg
                165                 170                 175

Leu Leu Gln Ala His Arg Gln Leu Glu Glu Arg Gly Tyr Val Phe Val
            180                 185                 190

Gly Tyr His Gly Thr Phe Leu Glu Ala Ala Gln Ser Ile Val Phe Gly
        195                 200                 205

Gly Val Arg Ala Ala Ser Gln Asp Leu Lys Ala Ile Trp Arg Gly Phe
    210                 215                 220

Tyr Ile Ala Gly Asp Pro Ala Leu Ala Tyr Gly Tyr Ala Gln Asp Gln
225                 230                 235                 240

Glu Pro Asp Ala Arg Gly Arg Ile Arg Asn Gly Ala Leu Leu Arg Val
                245                 250                 255

Tyr Val Pro Arg Ser Thr Leu Pro Gly Phe Tyr Arg Thr Gly Leu Thr
            260                 265                 270

Leu Ala Ala Pro Glu Ala Ala Gly Glu Val Glu Arg Leu Ile Gly His
        275                 280                 285

Pro Leu Pro Leu Arg Leu Asp Ala Ile Thr Gly Pro Glu Glu Glu Gly
    290                 295                 300

Gly Arg Leu Glu Thr Ile Leu Gly Trp Pro Leu Ala Glu Arg Thr Val
305                 310                 315                 320

Val Ile Pro Ser Ala Ile Pro Thr Asp Pro Arg Asn Val Gly Gly Asp
                325                 330                 335

Leu Asp Pro Ser Ser Ile Pro Asp Lys Glu Glu Ala Ile Ser Ala Leu
            340                 345                 350

Pro Asp Tyr Ala Ser Gln Pro Gly Lys Pro Pro Arg Glu Asp Leu Lys
        355                 360                 365


<210> SEQ ID NO 203
<211> LENGTH: 1107
<212> TYPE: DNA
<213> ORGANISM: Artificial Sequence
<220> FEATURE:
<223> OTHER INFORMATION: pIEX02-246 E299D (pET14b-K PE38 S253T D209K
      R204 I153A Q338E T164A E299D)

<400> SEQUENCE: 203

atgggcagca gccatcatca tcatcatcac agcagcggcc tggtgccgcg cggcagccat      60

atgccagaag gcggtagcct ggccgctctg accgcacatc aggcctgtca cctgccgctg     120

gaaaccttca cccgtcaccg tcagccgcgt ggttgggaac aactggaaca atgtggctat     180

ccggtacagc gtctggtggc gctgtacctg gctgctcgtc tgtcttggaa ccaagtagat     240

caggtcatcc gtaacgcgct ggcaagcccg ggttccggtg gtgatctggg tgaagctatc     300

cgtgaacaac cggaacaggc tcgtctggcg ctgaccctgg cggcagcgga atctgaacgt     360

tttgtgcgcc agggtacggg taacgacgaa gctggcgctg cgagcggtcc tgccgactcc     420

ggtgacgctc tgctggaacg taactacccg accggtgcag aatttctggg tgatggcggc     480

gatgcctctt tttctacccg cggcacccag aactgggccg ttgaacgtct gctgcaggcg     540

caccgtcaac tggaagaacg cggttacgtc ttcgtaggtt accacggtac cttcctggaa     600

gctgctcagt ctatcgtgtt cggtggcgta cgtgctgcca gccaggacct gaaggccatc     660

tggcgtggct tctacattgc gggtgatccg gccctggcct atggttatgc acaggatcag     720
```

gagccagacg ctcgtggtcg tatccgtaac ggcgctctgc tgcgcgtgta cgtaccgcgc 780
agcaccctgc cgggtttcta tcgtactggc ctgaccctgg ctgcgccgga agcagccggt 840
gaagtggaac gcctgatcgg ccatccgctg ccactgcgtc tggacgctat cactggtcct 900
gaagaagagg gtggtcgcct ggacactatc ctgggttggc cgctggctga acgcactgta 960
gtaatcccgt ccgcgatccc aacggatccg cgcaatgttg gtggcgatct ggacccaagc 1020
tctatcccgg ataaagaaga ggctatttct gccctgccgg actacgcctc ccagccgggt 1080
aaaccgccgc gtgaggacct gaagtaa 1107

<210> SEQ ID NO 204
<211> LENGTH: 368
<212> TYPE: PRT
<213> ORGANISM: Artificial Sequence
<220> FEATURE:
<223> OTHER INFORMATION: pIEX02-246 E299D (pET14b-K PE38 S253T D209K R204 I153A Q338E T164A E299D)

<400> SEQUENCE: 204

Met Gly Ser Ser His His His His His His Ser Ser Gly Leu Val Pro
1 5 10 15

Arg Gly Ser His Met Pro Glu Gly Gly Ser Leu Ala Ala Leu Thr Ala
20 25 30

His Gln Ala Cys His Leu Pro Leu Glu Thr Phe Thr Arg His Arg Gln
35 40 45

Pro Arg Gly Trp Glu Gln Leu Glu Gln Cys Gly Tyr Pro Val Gln Arg
50 55 60

Leu Val Ala Leu Tyr Leu Ala Ala Arg Leu Ser Trp Asn Gln Val Asp
65 70 75 80

Gln Val Ile Arg Asn Ala Leu Ala Ser Pro Gly Ser Gly Gly Asp Leu
85 90 95

Gly Glu Ala Ile Arg Glu Gln Pro Glu Gln Ala Arg Leu Ala Leu Thr
100 105 110

Leu Ala Ala Ala Glu Ser Glu Arg Phe Val Arg Gln Gly Thr Gly Asn
115 120 125

Asp Glu Ala Gly Ala Ala Ser Gly Pro Ala Asp Ser Gly Asp Ala Leu
130 135 140

Leu Glu Arg Asn Tyr Pro Thr Gly Ala Glu Phe Leu Gly Asp Gly Gly
145 150 155 160

Asp Ala Ser Phe Ser Thr Arg Gly Thr Gln Asn Trp Ala Val Glu Arg
165 170 175

Leu Leu Gln Ala His Arg Gln Leu Glu Glu Arg Gly Tyr Val Phe Val
180 185 190

Gly Tyr His Gly Thr Phe Leu Glu Ala Ala Gln Ser Ile Val Phe Gly
195 200 205

Gly Val Arg Ala Ala Ser Gln Asp Leu Lys Ala Ile Trp Arg Gly Phe
210 215 220

Tyr Ile Ala Gly Asp Pro Ala Leu Ala Tyr Gly Tyr Ala Gln Asp Gln
225 230 235 240

Glu Pro Asp Ala Arg Gly Arg Ile Arg Asn Gly Ala Leu Leu Arg Val
245 250 255

Tyr Val Pro Arg Ser Thr Leu Pro Gly Phe Tyr Arg Thr Gly Leu Thr
260 265 270

Leu Ala Ala Pro Glu Ala Ala Gly Glu Val Glu Arg Leu Ile Gly His
275 280 285

```
Pro Leu Pro Leu Arg Leu Asp Ala Ile Thr Gly Pro Glu Glu Glu Gly
    290                 295                 300

Gly Arg Leu Asp Thr Ile Leu Gly Trp Pro Leu Ala Glu Arg Thr Val
305                 310                 315                 320

Val Ile Pro Ser Ala Ile Pro Thr Asp Pro Arg Asn Val Gly Gly Asp
                325                 330                 335

Leu Asp Pro Ser Ser Ile Pro Asp Lys Glu Glu Ala Ile Ser Ala Leu
            340                 345                 350

Pro Asp Tyr Ala Ser Gln Pro Gly Lys Pro Pro Arg Glu Asp Leu Lys
        355                 360                 365


<210> SEQ ID NO 205
<211> LENGTH: 24
<212> TYPE: DNA
<213> ORGANISM: Artificial Sequence
<220> FEATURE:
<223> OTHER INFORMATION: OL 001 M13 FOR

<400> SEQUENCE: 205

cgccagggtt ttcccagtca cgac                                            24


<210> SEQ ID NO 206
<211> LENGTH: 24
<212> TYPE: DNA
<213> ORGANISM: Artificial Sequence
<220> FEATURE:
<223> OTHER INFORMATION: OL 002 M13 REV

<400> SEQUENCE: 206

agcggataac aatttcacac agga                                            24


<210> SEQ ID NO 207
<211> LENGTH: 18
<212> TYPE: DNA
<213> ORGANISM: Artificial Sequence
<220> FEATURE:
<223> OTHER INFORMATION: OL 2043 RFB4 VH5' PCR primer sequence

<400> SEQUENCE: 207

gaagtgcagc tggtggag                                                   18


<210> SEQ ID NO 208
<211> LENGTH: 49
<212> TYPE: DNA
<213> ORGANISM: Artificial Sequence
<220> FEATURE:
<223> OTHER INFORMATION: OL 2044 RFB4 VH3' PCR primer sequence

<400> SEQUENCE: 208

cagagccacc tccgcctgaa ccgcctccac ctgaggagac agtgaccag                 49


<210> SEQ ID NO 209
<211> LENGTH: 50
<212> TYPE: DNA
<213> ORGANISM: Artificial Sequence
<220> FEATURE:
<223> OTHER INFORMATION: OL 2045 RFB4 VK 5' PCR Primer Sequence

<400> SEQUENCE: 209

caggcggagg tggctctggc ggtggcggat cggatatcca gatgacccag                50


<210> SEQ ID NO 210
<211> LENGTH: 19
<212> TYPE: DNA
```

<213> ORGANISM: Artificial Sequence
<220> FEATURE:
<223> OTHER INFORMATION: OL 2046 RFB4 VK 3' PCR Primer sequence

<400> SEQUENCE: 210
tttgatctcc agcttggtg 19

<210> SEQ ID NO 211
<211> LENGTH: 35
<212> TYPE: DNA
<213> ORGANISM: Artificial Sequence
<220> FEATURE:
<223> OTHER INFORMATION: OL 2047 RFB4 Pull through Primer (FOR))

<400> SEQUENCE: 211
cccagccggc catggcggaa gtgcagctgg tggag 35

<210> SEQ ID NO 212
<211> LENGTH: 41
<212> TYPE: DNA
<213> ORGANISM: Artificial Sequence
<220> FEATURE:
<223> OTHER INFORMATION: OL 2048 RFB4 Pull through Primer (REV)

<400> SEQUENCE: 212
ggtgctcgag tgcggccgcc cgtttgatct ccagcttggt g 41

<210> SEQ ID NO 213
<211> LENGTH: 39
<212> TYPE: DNA
<213> ORGANISM: Artificial Sequence
<220> FEATURE:
<223> OTHER INFORMATION: OL 2097 IEX02 GroEL/ES REV

<400> SEQUENCE: 213
aaccgcccgg ccgttcttct ccgtgttgcc cggaaagcc 39

<210> SEQ ID NO 214
<211> LENGTH: 36
<212> TYPE: DNA
<213> ORGANISM: Artificial Sequence
<220> FEATURE:
<223> OTHER INFORMATION: OL 2098 IEX02 GroEL/ES FOR

<400> SEQUENCE: 214
gggccaaagc ttgttcttgt ttgagtccac tcatgg 36

<210> SEQ ID NO 215
<211> LENGTH: 32
<212> TYPE: DNA
<213> ORGANISM: Artificial Sequence
<220> FEATURE:
<223> OTHER INFORMATION: OL 2154 IEX02 PE38 FOR, introducing NdeI

<400> SEQUENCE: 215
attgtccata tgccagaagg cggtagcctg gc 32

<210> SEQ ID NO 216
<211> LENGTH: 32
<212> TYPE: DNA
<213> ORGANISM: Artificial Sequence
<220> FEATURE:
<223> OTHER INFORMATION: OL 2161 IEX02 PE38 REV, introducing XhoI

<400> SEQUENCE: 216
atcctcgagt tacttcaggt cctcacgcgg cg 32

<210> SEQ ID NO 217
<211> LENGTH: 30
<212> TYPE: DNA
<213> ORGANISM: Artificial Sequence
<220> FEATURE:
<223> OTHER INFORMATION: OL 2162 IEX02 PE38 NM E229D FOR

<400> SEQUENCE: 217
gggtggtcgc ctggacacta tcctgggttg 30

<210> SEQ ID NO 218
<211> LENGTH: 30
<212> TYPE: DNA
<213> ORGANISM: Artificial Sequence
<220> FEATURE:
<223> OTHER INFORMATION: OL 2163 IEX02 PE38 NM E229D REV

<400> SEQUENCE: 218
caacccagga tagtgtccag gcgaccaccc 30

<210> SEQ ID NO 219
<211> LENGTH: 40
<212> TYPE: DNA
<213> ORGANISM: Artificial Sequence
<220> FEATURE:
<223> OTHER INFORMATION: OL 2164 IEX02 PE38 S253N

<400> SEQUENCE: 219
cagtacgata gaaacccggc agattgctgc gcggtacgta 40

<210> SEQ ID NO 220
<211> LENGTH: 40
<212> TYPE: DNA
<213> ORGANISM: Artificial Sequence
<220> FEATURE:
<223> OTHER INFORMATION: OL 2165 IEX02 PE38 S253K

<400> SEQUENCE: 220
cagtacgata gaaacccggc agcttgctgc gcggtacgta 40

<210> SEQ ID NO 221
<211> LENGTH: 40
<212> TYPE: DNA
<213> ORGANISM: Artificial Sequence
<220> FEATURE:
<223> OTHER INFORMATION: OL 2166 IEX02 PE38 S253P

<400> SEQUENCE: 221
cagtacgata gaaacccggc agagggctgc gcggtacgta 40

<210> SEQ ID NO 222
<211> LENGTH: 40
<212> TYPE: DNA
<213> ORGANISM: Artificial Sequence
<220> FEATURE:
<223> OTHER INFORMATION: OL 2167 IEX02 PE38 S253T

<400> SEQUENCE: 222
cagtacgata gaaacccggc agggtgctgc gcggtacgta 40

<210> SEQ ID NO 223
<211> LENGTH: 33
<212> TYPE: DNA
<213> ORGANISM: Artificial Sequence
<220> FEATURE:

<223> OTHER INFORMATION: OL 2168 IEX02 PE38 Q206R

<400> SEQUENCE: 223
gtacgtgctc gtagcagaga cctggatgcc atc 33

<210> SEQ ID NO 224
<211> LENGTH: 33
<212> TYPE: DNA
<213> ORGANISM: Artificial Sequence
<220> FEATURE:
<223> OTHER INFORMATION: OL 2169 IEX02 PE38 Q206R

<400> SEQUENCE: 224
gatggcatcc aggtctctgc tacgagcacg tac 33

<210> SEQ ID NO 225
<211> LENGTH: 33
<212> TYPE: DNA
<213> ORGANISM: Artificial Sequence
<220> FEATURE:
<223> OTHER INFORMATION: OL 2170 IEX02 PE38 D209K

<400> SEQUENCE: 225
cgtagccagg acctgaaggc catctggcgt ggc 33

<210> SEQ ID NO 226
<211> LENGTH: 33
<212> TYPE: DNA
<213> ORGANISM: Artificial Sequence
<220> FEATURE:
<223> OTHER INFORMATION: OL 2171 IEX02 PE38 D209K

<400> SEQUENCE: 226
gccacgccag atggccttca ggtcctggct acg 33

<210> SEQ ID NO 227
<211> LENGTH: 32
<212> TYPE: DNA
<213> ORGANISM: Artificial Sequence
<220> FEATURE:
<223> OTHER INFORMATION: OL 2183 IEX02 PE38 I196A FOR, to pair with
OL2161

<400> SEQUENCE: 227
gaagctgctc agtctgccgt gttcggtggc gt 32

<210> SEQ ID NO 228
<211> LENGTH: 32
<212> TYPE: DNA
<213> ORGANISM: Artificial Sequence
<220> FEATURE:
<223> OTHER INFORMATION: OL 2184 IEX02 PE38 I196A REV, to pair with
OL2268

<400> SEQUENCE: 228
acgccaccga acacggcaga ctgagcagct tc 32

<210> SEQ ID NO 229
<211> LENGTH: 32
<212> TYPE: DNA
<213> ORGANISM: Artificial Sequence
<220> FEATURE:
<223> OTHER INFORMATION: OL 2185 IEX02 PE38 I196N FOR, to pair with
OL2161

<400> SEQUENCE: 229
gaagctgctc agtctaacgt gttcggtggc gt 32

<210> SEQ ID NO 230
<211> LENGTH: 32
<212> TYPE: DNA
<213> ORGANISM: Artificial Sequence
<220> FEATURE:
<223> OTHER INFORMATION: OL 2186 IEX02 PE38 I196N REV, to pair with OL2268

<400> SEQUENCE: 230
acgccaccga acacgttaga ctgagcagct tc 32

<210> SEQ ID NO 231
<211> LENGTH: 33
<212> TYPE: DNA
<213> ORGANISM: Artificial Sequence
<220> FEATURE:
<223> OTHER INFORMATION: OL 2187 IEX02 to introduce I153A FOR

<400> SEQUENCE: 231
ggtgatggcg gcgatgcctc tttttctacc cgc 33

<210> SEQ ID NO 232
<211> LENGTH: 33
<212> TYPE: DNA
<213> ORGANISM: Artificial Sequence
<220> FEATURE:
<223> OTHER INFORMATION: OL 2188 IEX02 to introduce I153A REV

<400> SEQUENCE: 232
gcgggtagaa aaagaggcat cgccgccatc acc 33

<210> SEQ ID NO 233
<211> LENGTH: 33
<212> TYPE: DNA
<213> ORGANISM: Artificial Sequence
<220> FEATURE:
<223> OTHER INFORMATION: OL 2189 IEX02 to introduce I153T FOR

<400> SEQUENCE: 233
ggtgatggcg gcgatacctc tttttctacc cgc 33

<210> SEQ ID NO 234
<211> LENGTH: 33
<212> TYPE: DNA
<213> ORGANISM: Artificial Sequence
<220> FEATURE:
<223> OTHER INFORMATION: OL 2190 IEX02 to introduce I153T REV

<400> SEQUENCE: 234
gcgggtagaa aaagaggtat cgccgccatc acc 33

<210> SEQ ID NO 235
<211> LENGTH: 33
<212> TYPE: DNA
<213> ORGANISM: Artificial Sequence
<220> FEATURE:
<223> OTHER INFORMATION: OL 2191 IEX02 to introduce I153H FOR

<400> SEQUENCE: 235
ggtgatggcg gcgatcactc tttttctacc cgc 33

<210> SEQ ID NO 236
<211> LENGTH: 33
<212> TYPE: DNA

<213> ORGANISM: Artificial Sequence
<220> FEATURE:
<223> OTHER INFORMATION: OL 2192 IEX02 to introduce I153H REV

<400> SEQUENCE: 236
gcgggtagaa aaagagtgat cgccgccatc acc 33

<210> SEQ ID NO 237
<211> LENGTH: 32
<212> TYPE: DNA
<213> ORGANISM: Artificial Sequence
<220> FEATURE:
<223> OTHER INFORMATION: OL 2193 IEX02 to introduce T164R FOR

<400> SEQUENCE: 237
gcacccagaa ctggagagtt gaacgtctgc tg 32

<210> SEQ ID NO 238
<211> LENGTH: 32
<212> TYPE: DNA
<213> ORGANISM: Artificial Sequence
<220> FEATURE:
<223> OTHER INFORMATION: OL 2194 IEX02 to introduce T164R REV

<400> SEQUENCE: 238
cagcagacgt tcaactctcc agttctgggt gc 32

<210> SEQ ID NO 239
<211> LENGTH: 39
<212> TYPE: DNA
<213> ORGANISM: Artificial Sequence
<220> FEATURE:
<223> OTHER INFORMATION: OL 2216 IEX02 Linker to optimize Kozak in pET14b, to anneal with OL2217

<400> SEQUENCE: 239
catggtggct ctccttctta aagttaaaca aaattattt 39

<210> SEQ ID NO 240
<211> LENGTH: 39
<212> TYPE: DNA
<213> ORGANISM: Artificial Sequence
<220> FEATURE:
<223> OTHER INFORMATION: OL 2217 IEX02 Linker to optimize Kozak in pET14b, to anneal with OL2216

<400> SEQUENCE: 240
ctagaaataa ttttgtttaa ctttaagaag gagagccac 39

<210> SEQ ID NO 241
<211> LENGTH: 38
<212> TYPE: DNA
<213> ORGANISM: Artificial Sequence
<220> FEATURE:
<223> OTHER INFORMATION: OL 2268 IEX02 outside FOR spanns over XbaI site (pET14b) - to be paired with OL2161

<400> SEQUENCE: 241
atctccctct agaaataatt ttgtttaact ttaagaag 38

<210> SEQ ID NO 242
<211> LENGTH: 32
<212> TYPE: DNA
<213> ORGANISM: Artificial Sequence
<220> FEATURE:
<223> OTHER INFORMATION: OL 2279 IEX02 FOR oligo to remove TM to be paired with OL2161

<400> SEQUENCE: 242
gaagctgctc agtctatcgt gttcggtggc gt 32

<210> SEQ ID NO 243
<211> LENGTH: 32
<212> TYPE: DNA
<213> ORGANISM: Artificial Sequence
<220> FEATURE:
<223> OTHER INFORMATION: OL 2280 IEX02 REV oligo to remove TM to be paired with OL2268

<400> SEQUENCE: 243
acgccaccga acacgataga ctgagcagct tc 32

<210> SEQ ID NO 244
<211> LENGTH: 32
<212> TYPE: DNA
<213> ORGANISM: Artificial Sequence
<220> FEATURE:
<223> OTHER INFORMATION: OL 2281 IEX02 A201 REV, ONLY for templates having Q206

<400> SEQUENCE: 244
ctctgctacg agcacgggcg ccaccgaaca cg 32

<210> SEQ ID NO 245
<211> LENGTH: 32
<212> TYPE: DNA
<213> ORGANISM: Artificial Sequence
<220> FEATURE:
<223> OTHER INFORMATION: OL 2282 IEX02 A201 FOR, ONLY for templates having Q206

<400> SEQUENCE: 245
cgtgttcggt ggcgcccgtg ctcgtagcag ag 32

<210> SEQ ID NO 246
<211> LENGTH: 33
<212> TYPE: DNA
<213> ORGANISM: Artificial Sequence
<220> FEATURE:
<223> OTHER INFORMATION: OL 2283 IEX02 A204 REV, ONLY for templates having Q206

<400> SEQUENCE: 246
catccaggtc tctgctggca gcacgtacgc cac 33

<210> SEQ ID NO 247
<211> LENGTH: 33
<212> TYPE: DNA
<213> ORGANISM: Artificial Sequence
<220> FEATURE:
<223> OTHER INFORMATION: OL 2284 IEX02 A204 FOR, ONLY for templates having Q206

<400> SEQUENCE: 247
gtggcgtacg tgctgccagc agagacctgg atg 33

<210> SEQ ID NO 248
<211> LENGTH: 33
<212> TYPE: DNA
<213> ORGANISM: Artificial Sequence
<220> FEATURE:
<223> OTHER INFORMATION: OL 2285 IEX02 Q204 REV, ONLY for templates having Q206

<400> SEQUENCE: 248
catccaggtc tctgctctga gcacgtacgc cac 33

<210> SEQ ID NO 249
<211> LENGTH: 33
<212> TYPE: DNA
<213> ORGANISM: Artificial Sequence
<220> FEATURE:
<223> OTHER INFORMATION: OL 2286 IEX02 Q204 FOR, ONLY for templates
having Q206

<400> SEQUENCE: 249
gtggcgtacg tgctcagagc agagacctgg atg 33

<210> SEQ ID NO 250
<211> LENGTH: 31
<212> TYPE: DNA
<213> ORGANISM: Artificial Sequence
<220> FEATURE:
<223> OTHER INFORMATION: OL 2287 IEX02 A158 REV

<400> SEQUENCE: 250
ccagttctgg gtgccggcgg tagaaaaaga g 31

<210> SEQ ID NO 251
<211> LENGTH: 31
<212> TYPE: DNA
<213> ORGANISM: Artificial Sequence
<220> FEATURE:
<223> OTHER INFORMATION: OL 2288 IEX02 A158 FOR

<400> SEQUENCE: 251
ctctttttct accgccggca cccagaactg g 31

<210> SEQ ID NO 252
<211> LENGTH: 36
<212> TYPE: DNA
<213> ORGANISM: Artificial Sequence
<220> FEATURE:
<223> OTHER INFORMATION: OL 2289 IEX02 Q158 REV

<400> SEQUENCE: 252
ccagttctgg gtgccctggg tagaaaaaga gatatc 36

<210> SEQ ID NO 253
<211> LENGTH: 36
<212> TYPE: DNA
<213> ORGANISM: Artificial Sequence
<220> FEATURE:
<223> OTHER INFORMATION: OL 2290 IEX02 Q158 FOR

<400> SEQUENCE: 253
gatatctctt tttctaccca gggcacccag aactgg 36

<210> SEQ ID NO 254
<211> LENGTH: 38
<212> TYPE: DNA
<213> ORGANISM: Artificial Sequence
<220> FEATURE:
<223> OTHER INFORMATION: OL 2291 IEX02 S159 REV

<400> SEQUENCE: 254
gtccagttct gggtggagcg ggtagaaaaa gagatatc 38

<210> SEQ ID NO 255

<211> LENGTH: 38
<212> TYPE: DNA
<213> ORGANISM: Artificial Sequence
<220> FEATURE:
<223> OTHER INFORMATION: OL 2292 IEX02 S159 FOR

<400> SEQUENCE: 255
gatatctctt tttctacccg ctccacccag aactggac 38

<210> SEQ ID NO 256
<211> LENGTH: 25
<212> TYPE: DNA
<213> ORGANISM: Artificial Sequence
<220> FEATURE:
<223> OTHER INFORMATION: OL 2293 IEX02 T159 REV

<400> SEQUENCE: 256
accacccaga actggaccgt tgaac 25

<210> SEQ ID NO 257
<211> LENGTH: 31
<212> TYPE: DNA
<213> ORGANISM: Artificial Sequence
<220> FEATURE:
<223> OTHER INFORMATION: OL 2294 IEX02 T159 FOR

<400> SEQUENCE: 257
ccagttctgg gtggtgcggg tagaaaaaga g 31

<210> SEQ ID NO 258
<211> LENGTH: 23
<212> TYPE: DNA
<213> ORGANISM: Artificial Sequence
<220> FEATURE:
<223> OTHER INFORMATION: OL 2295 IEX02 generic REV oligo for mutations
at 333

<400> SEQUENCE: 258
gagcttgggt ccagatcgcc acc 23

<210> SEQ ID NO 259
<211> LENGTH: 31
<212> TYPE: DNA
<213> ORGANISM: Artificial Sequence
<220> FEATURE:
<223> OTHER INFORMATION: OL 2296 IEX02 A333 FOR

<400> SEQUENCE: 259
ctggacccaa gctctgcccc ggataaagaa c 31

<210> SEQ ID NO 260
<211> LENGTH: 28
<212> TYPE: DNA
<213> ORGANISM: Artificial Sequence
<220> FEATURE:
<223> OTHER INFORMATION: OL 2297 IEX02 N333 FOR

<400> SEQUENCE: 260
ctggacccaa gctctaaccc ggataaag 28

<210> SEQ ID NO 261
<211> LENGTH: 28
<212> TYPE: DNA
<213> ORGANISM: Artificial Sequence
<220> FEATURE:
<223> OTHER INFORMATION: OL 2298 IEX02 T333 FOR

<400> SEQUENCE: 261
ctggacccaa gctctacccc ggataaag 28

<210> SEQ ID NO 262
<211> LENGTH: 31
<212> TYPE: DNA
<213> ORGANISM: Artificial Sequence
<220> FEATURE:
<223> OTHER INFORMATION: OL 2299 IEX02 Q333 FOR

<400> SEQUENCE: 262
ctggacccaa gctctcagcc ggataaagaa c 31

<210> SEQ ID NO 263
<211> LENGTH: 28
<212> TYPE: DNA
<213> ORGANISM: Artificial Sequence
<220> FEATURE:
<223> OTHER INFORMATION: OL 2300 IEX02 H333 FOR

<400> SEQUENCE: 263
ctggacccaa gctctcaccc ggataaag 28

<210> SEQ ID NO 264
<211> LENGTH: 48
<212> TYPE: DNA
<213> ORGANISM: Artificial Sequence
<220> FEATURE:
<223> OTHER INFORMATION: OL 2301 IEX02 N338 FOR

<400> SEQUENCE: 264
ctggacccaa gctctatccc ggataaagaa aacgctattt ctgccctg 48

<210> SEQ ID NO 265
<211> LENGTH: 46
<212> TYPE: DNA
<213> ORGANISM: Artificial Sequence
<220> FEATURE:
<223> OTHER INFORMATION: OL 2302 IEX02 E338 FOR

<400> SEQUENCE: 265
ctggacccaa gctctatccc ggataaagaa gaggctattt ctgccc 46

<210> SEQ ID NO 266
<211> LENGTH: 28
<212> TYPE: DNA
<213> ORGANISM: Artificial Sequence
<220> FEATURE:
<223> OTHER INFORMATION: OL 2303 IEX02 V201A REV

<400> SEQUENCE: 266
ctggctacga gcacgggcgc caccgaac 28

<210> SEQ ID NO 267
<211> LENGTH: 28
<212> TYPE: DNA
<213> ORGANISM: Artificial Sequence
<220> FEATURE:
<223> OTHER INFORMATION: OL 2304 IEX02 V201A FOR

<400> SEQUENCE: 267
gttcggtggc gcccgtgctc gtagccag 28

<210> SEQ ID NO 268
<211> LENGTH: 30

<212> TYPE: DNA
<213> ORGANISM: Artificial Sequence
<220> FEATURE:
<223> OTHER INFORMATION: OL 2305 IEX02 R204A REV, ONLY for templates
having D209K

<400> SEQUENCE: 268
cttcaggtcc tggctggcag cacgtacgcc 30

<210> SEQ ID NO 269
<211> LENGTH: 30
<212> TYPE: DNA
<213> ORGANISM: Artificial Sequence
<220> FEATURE:
<223> OTHER INFORMATION: OL 2306 IEX02 R204A FOR, ONLY for templates
having D209K

<400> SEQUENCE: 269
ggcgtacgtg ctgccagcca ggacctgaag 30

<210> SEQ ID NO 270
<211> LENGTH: 29
<212> TYPE: DNA
<213> ORGANISM: Artificial Sequence
<220> FEATURE:
<223> OTHER INFORMATION: OL 2307 IEX02 R204Q REV, ONLY for templates
having D209K

<400> SEQUENCE: 270
cttcaggtcc tggctctgag cacgtacgc 29

<210> SEQ ID NO 271
<211> LENGTH: 29
<212> TYPE: DNA
<213> ORGANISM: Artificial Sequence
<220> FEATURE:
<223> OTHER INFORMATION: OL 2308 IEX02 R204Q FOR, ONLY for templates
having D209K

<400> SEQUENCE: 271
gcgtacgtgc tcagagccag gacctgaag 29

<210> SEQ ID NO 272
<211> LENGTH: 33
<212> TYPE: DNA
<213> ORGANISM: Artificial Sequence
<220> FEATURE:
<223> OTHER INFORMATION: OL 2309 IEX02 Q161N REV

<400> SEQUENCE: 272
gttcaacggt ccagttgttg gtgccgcggg tag 33

<210> SEQ ID NO 273
<211> LENGTH: 33
<212> TYPE: DNA
<213> ORGANISM: Artificial Sequence
<220> FEATURE:
<223> OTHER INFORMATION: OL 2310 IEX02 Q161N FOR

<400> SEQUENCE: 273
ctacccgcgg caccaacaac tggaccgttg aac 33

<210> SEQ ID NO 274
<211> LENGTH: 33
<212> TYPE: DNA
<213> ORGANISM: Artificial Sequence
<220> FEATURE:

<223> OTHER INFORMATION: OL 2311 IEX02 Q161T REV

<400> SEQUENCE: 274
gttcaacggt ccagttggtg gtgccgcggg tag 33

<210> SEQ ID NO 275
<211> LENGTH: 33
<212> TYPE: DNA
<213> ORGANISM: Artificial Sequence
<220> FEATURE:
<223> OTHER INFORMATION: OL 2312 IEX02 Q161T FOR

<400> SEQUENCE: 275
ctacccgcgg caccaccaac tggaccgttg aac 33

<210> SEQ ID NO 276
<211> LENGTH: 31
<212> TYPE: DNA
<213> ORGANISM: Artificial Sequence
<220> FEATURE:
<223> OTHER INFORMATION: OL 2313 IEX02 T164A REV

<400> SEQUENCE: 276
cagcagacgt tcaacggccc agttctgggt g 31

<210> SEQ ID NO 277
<211> LENGTH: 31
<212> TYPE: DNA
<213> ORGANISM: Artificial Sequence
<220> FEATURE:
<223> OTHER INFORMATION: OL 2314 IEX02 T164A FOR

<400> SEQUENCE: 277
cacccagaac tgggccgttg aacgtctgct g 31

<210> SEQ ID NO 278
<211> LENGTH: 33
<212> TYPE: DNA
<213> ORGANISM: Artificial Sequence
<220> FEATURE:
<223> OTHER INFORMATION: OL 2315 IEX02 N162A REV

<400> SEQUENCE: 278
gacgttcaac ggtccaggcc tgggtgccgc ggg 33

<210> SEQ ID NO 279
<211> LENGTH: 33
<212> TYPE: DNA
<213> ORGANISM: Artificial Sequence
<220> FEATURE:
<223> OTHER INFORMATION: OL 2316 IEX02 N162A FOR

<400> SEQUENCE: 279
cccgcggcac ccaggcctgg accgttgaac gtc 33

<210> SEQ ID NO 280
<211> LENGTH: 22
<212> TYPE: DNA
<213> ORGANISM: Artificial Sequence
<220> FEATURE:
<223> OTHER INFORMATION: OL 2318 IEX02 FOR RFB4 (NcoI)

<400> SEQUENCE: 280
attgccacca tggcggaagt gc 22

<210> SEQ ID NO 281
<211> LENGTH: 31
<212> TYPE: DNA
<213> ORGANISM: Artificial Sequence
<220> FEATURE:
<223> OTHER INFORMATION: OL 2320 IEX02 REV to create RBF4 for
RFB4-PE38-8xHis to pair with OL2318

<400> SEQUENCE: 281
caccaggccg ctgcttttga tctccagctt g 31

<210> SEQ ID NO 282
<211> LENGTH: 31
<212> TYPE: DNA
<213> ORGANISM: Artificial Sequence
<220> FEATURE:
<223> OTHER INFORMATION: OL 2321 IEX02 FOR to create RFB4-PE38-8xHis to
pair with OL2322

<400> SEQUENCE: 282
caagctggag atcaaaagca gcggcctggt g 31

<210> SEQ ID NO 283
<211> LENGTH: 66
<212> TYPE: DNA
<213> ORGANISM: Artificial Sequence
<220> FEATURE:
<223> OTHER INFORMATION: OL 2322 IEX02 REV introducing 8xHis C-terminus
of PE, introducing XhoI

<400> SEQUENCE: 283
cgattctcga gttacttcag gtcctcgtgg tggtggtgat gatgatgatg acgcggcggt 60
ttaccc 66

<210> SEQ ID NO 284
<211> LENGTH: 44
<212> TYPE: DNA
<213> ORGANISM: Artificial Sequence
<220> FEATURE:
<223> OTHER INFORMATION: OL 2323 IEX02 FOR to create RFB4-6xHis PE38
fusions (pIEX02-302 and pIEX02-304) to pair with OL2161

<400> SEQUENCE: 284
caagctggag atcaaagctc atgggggcag ccatcatcat catc 44

<210> SEQ ID NO 285
<211> LENGTH: 44
<212> TYPE: DNA
<213> ORGANISM: Artificial Sequence
<220> FEATURE:
<223> OTHER INFORMATION: OL 2324 IEX02 REV to create RFB4-6xHis PE38
fusions (pIEX02-302 and pIEX02-304) to pair with OL2318

<400> SEQUENCE: 285
gatgatgatg atggctgccc ccatgagctt tgatctccag cttg 44

<210> SEQ ID NO 286
<211> LENGTH: 13
<212> TYPE: DNA
<213> ORGANISM: Artificial Sequence
<220> FEATURE:
<223> OTHER INFORMATION: Modified Kozak sequence
<220> FEATURE:
<221> NAME/KEY: misc_feature -continued

```
<222> LOCATION: (7)..(7)
<223> OTHER INFORMATION: r at position 7 is a purine (adenine or
      guanine)

<400> SEQUENCE: 286

gccgccrcca ugg                                                          13
```

MODIFIED FORMS OF *PSEUDOMONAS* EXOTOXIN A

CROSS-REFERENCE TO RELATED APPLICATIONS

This application is a continuation of U.S. application Ser. No. 14/561,707 filed Dec. 5, 2014, which is a continuation of U.S. application Ser. No. 13/604,173 filed Sep. 5, 2012 (now U.S. Pat. No. 8,932,586), which claims priority benefit of U.S. Application No. 61/531,576 filed Sep. 6, 2011.

REFERENCE TO RELATED APPLICATION

This application claims benefit of and priority based on U.S. Provisional Patent Application Ser. No. 61/531,576, filed Sep. 6, 2011, the contents of which are herein incorporated by reference in their entirety.

NAMES OF THE PARTIES IN A JOINT RESEARCH AGREEMENT

The claimed invention was made pursuant to a joint research agreement, as defined in 35 U.S.C. §103 (c)(3), that was in effect on or before the date the claimed invention was made, and as a result of activities undertaken within the scope of the joint research agreement, by or on behalf of the Intrexon Corp. (Foster City, Calif., U.S.A.) and Antitope Ltd. (Cambridge, UK).

REFERENCE TO SEQUENCE LISTING SUBMITTED ELECTRONICALLY

A Sequence Listing is submitted electronically via EFS-Web as an ASCII formatted sequence listing in a file named "OT050-PCT_SEQLIST.txt", created on Sep. 4, 2012, and having a file size of 295,678 bytes which is filed concurrently with the present specification, claims, abstract and figures provided herewith. The sequence listing contained in this ASCII formatted document is part of the specification and is herein incorporated by reference in its entirety.

BACKGROUND OF THE INVENTION

Immune System and T Cell Epitopes

Immune responses to biological therapeutic agents are wide ranging, and can be directed against agents that are both non-human and human in origin. These responses include those that elicit a weak clinical effect and those that limit efficacy which can occasionally result in morbidity or even mortality in patients. In particular, serious complications can arise with the production of neutralizing antibodies, especially when they target recombinant self proteins and therefore have the potential to cross react with the patient's own endogenous protein (Lim, 2005). Problems associated with immunogenicity to biologics (i.e., therapeutic medical products; such as, antibodies and recombinant proteins/polypeptides) have been reduced largely due to advances in molecular biology. There are, however, many recombinant protein biologics that are identical to endogenously expressed human sequences that still elicit potent neutralizing immune responses in patients (Hochuli, 1997; Schellekens et al, 1997; Namaka et al, 2006). The mechanism by which immunogenicity is triggered remains unclear although the tolerance to self proteins may be broken by a number of factors linked to both the product and the patient (reviewed in Chester et a, 2006; Baker and Jones, 2007). For the product, these include dose, frequency of administration, route, immunomodulatory capacity of the protein therapeutic, and the formulation (Jaber and Baker, 2007). For the patient, factors such as immune competence (i.e. whether the patient is receiving immunosuppressive treatment), patient's MHC haplotype and intrinsic tolerance to the protein therapeutic will influence immunogenicity. Regardless of how immunogenicity is triggered, one of the single most important factors in the development of an ensuing immune response is the presence of epitopes that are able to effectively stimulate a potent CD4+ T cell response (reviewed Baker and Jones, 2007).

T cells or T lymphocytes are a subset of white blood cells known as lymphocytes. (The abbreviation "T" in T cell is for "thymus" since this is the primary organ responsible for T cell maturation.) T cells play a central role in cell-mediated immunity. They can be distinguished from other types of lymphocytes (such as B cells and natural killer cells (NK cells)), by the presence of cell-surface proteins called T cell receptors (TCRs). Different types of T cells have also been identified; these can be distinguished based on the differing functions they serve (e.g., CD4+ T cells (a.k.a., $T_H$ or T helper cells), CD8+ cytotoxic T cells (CTLs), memory T cells, regulatory T cells ($T_{reg}$ cells), natural killer cells (NK cells), and gamma delta T cells (γδ T cells)).

T helper ($T_H$) cells are so named because they aid other white blood cells in immunologic processes including, inter alia, assisting the maturation of B cells into plasma and B memory cells, and activation of cytotoxic T cells and macrophages. $T_H$ cells are also known as CD4+ T cells because they express CD4 protein on the cell-surface. CD4+ T cells are activated when peptide antigens are presented by MHC class II molecules expressed on the surface of Antigen Presenting Cells (APCs). Once activated, CD4+ T cells divide rapidly and secrete chemokines that further assist in activating or regulating immune responses.

T cell epitope analysis is becoming increasingly important particularly in the pre-clinical analysis of biologics and may, in time, become a requirement for regulatory approval for clinical trials. To this end, a pre-clinical ex vivo T cell assay (EPISCREEN™) has been used to provide an effective technology for predicting T cell immunogenicity by identifying linear T cell epitopes present in protein sequences. Synthetic overlapping peptides typically of about 15 amino acids in length are tested against a cohort of community blood donors carefully selected based on MHC class II haplotypes to provide a quantitative analysis of T cell epitopes present in protein sequences. This technology has been used successfully to compare protein variants for the potential to induce an immune response in vivo. By providing a high degree of sensitivity along with high reproducibility, the EPISCREEN™ assay allows an accurate pre-clinical assessment of the potential for immunogenicity of biologics. See, Baker & Carr, "Preclinical Considerations in the Assessment of Immunogenicity for Protein Therapeutics," *Current Drug Safety* 5(4):1-6 (2010); Bryson et al., "Prediction of Immunogenicity of Therapeutic Proteins: Validity of Computational Tools," *Biodrugs* 24(1)1-8 (2010); Holgate & Baker, "Circumventing Immunogenicity in the Development of Therapeutic Antibodies," *IDrugs* 12(4):233-237 (2009); Perry et al., "New Approaches to Prediction of Immune Responses to Therapeutic Proteins during Preclinical Development," *Drugs R D* 9(6):385-396 (2008); and, Baker & Jones, "Identification and removal of immunogenicity in therapeutic proteins," *Current Opinion in Drug Discovery & Development* 10(2):219-227 (2007).

*Pseudomonas* Exotoxin A

*Pseudomonas* exotoxin A (PE-A) is a highly potent, 66 kD, cytotoxic protein secreted by the bacterium *Pseudomonas aeruginosa*. PE-A causes cell death by inhibiting protein synthesis in eukaryotic cells via inactivation of translation elongation factor 2 (EF-2), which is mediated by PE-A catalyzing ADP-ribosylation of EF-2 (i.e., transfer of an ADP ribosyl moiety onto EF-2). PE-A typically produces death by causing liver failure.

PE-A has at least three different structural domains responsible for various biological activities (FIG. 1). See e.g., Siegall et al., *Biochemistry*, vol. 30, pp. 7154-7159 (1991); Theuer et al., *Jour. Biol. Chem*., vol. 267, no. 24, pp. 16872-16877 (1992); and, U.S. Pat. No. 5,821,238. PE-A domain IA (amino acids 1-252 (see e.g., SEQ ID NO:133)) is responsible for cell binding. Domain II (amino acids 253-364 (see e.g., SEQ ID NO:133)) is responsible for translocation of PE-A into the cell cytosol. Domain III, the cytotoxic domain (amino acids 400-613 (see e.g., SEQ ID NO:133)), is responsible for ADP ribosylation of Elongation Factor 2 (EF2); which thereby inactivates EF2, subsequently causing cell death. Additionally, a function for domain IB (amino acids 365-399 (SEQ ID NO:139)) has not been established. Indeed, it has been reported that amino acids 365-380 (SEQ ID NO:138) within domain IB can be deleted without producing an identifiable a loss of function. See, Siegall et al., *Biochemistry*, vol. 30, pp. 7154-7159 (1991).

It has also been reported that PE-A may comprise any one of at least three different carboxy-terminal tails (FIG. 1); these appear to be essential for maintaining or recycling proteins into the endoplasmic reticulum. See, Theuer et al., *J. Biol. Chem*., vol. 267, no. 24, pp. 16872-16877 (1992); Chaudhary et al., *Proc. Natl. Acad. Sci. USA*, vol. 87, pp. 308-312 (1990); and, Seetharam et al., *Jour. Biol. Chem*., vol. 266, 17376-17381 (1991). In particular, in correspondence with the exemplary sequence shown in FIG. 1 (SEQ ID NO: 133) these alternative carboxy-terminal tails comprise amino acid sequences:

```
609-REDLK-613 (SEQ ID NO: 135);

609-REDL-612 (SEQ ID NO: 136);
and

609-KDEL-612 (SEQ ID NO: 137).
```

Variants of PE-A, modified to lack the cell binding domain but coupled to heterologous cell-specific targeting molecules (e.g., antibodies), have been shown to have reduced levels of non-specific toxicity. See e.g., U.S. Pat. No. 4,892,827.

Various forms of PE-A (e.g., truncated/deletion forms with molecular weights of ~37 kD, 38 kD, 40 kD, et cetera) have been combined with a number of growth factors, antibodies, and other proteins to generate cytotoxins which selectively target cells of a desired phenotype. See, for example:

- Kreitman et al., "Recombinant immunotoxins and other therapies for relapsed/refractory hairy cell leukemia," *Leuk. Lymphoma*, Suppl. 2:82-86 (June-2011);
- Itoi et al., "Targeting of locus ceruleus noradrenergic neurons expressing human interleukin-2 receptor α-subunit in transgenic mice by a recombinant immunotoxin anti-Tac(Fv)-PE38," *J. Neurosci*., 31(16): 6132-6139 (April-2011);
- Shapira et al., "An immunoconjugate of anti-CD24 and *Pseudomonas* exotoxin selectively kills human colorectal tumors in mice," *Gastroenterology*, 140(3):935-946 (March-2011);
- Kuan et al., "Affinity-matured anti-glycoprotein NMB recombinant immunotoxins targeting malignant gliomas and melanomas," Int. J. Cancer, 129(1):111-21 (July-2011);
- Hu et al., "Investigation of a plasmid containing a novel immunotoxin VEGF165-PE38 gene for antiangiogenic therapy in a malignant glioma model," *Int. J. Cancer,* 127(9):2222-2229 (November-2010);
- Mareeva et al., "A novel composite immunotoxin that suppresses rabies virus production by the infected cells," *J. Immunol. Methods,* 353(1-2):78-86 (February-2010);
- Zielinski et al., "Affitoxin—a novel recombinant, HER2-specific, anticancer agent for targeted therapy of HER2-positive tumors," J. Immunother. 32(8):817-825 (October-2009);
- Theuer et al., *J. Biol. Chem.,* 267(24):16872-16877 (1992);
- Pastan et al., "Recombinant toxins for cancer treatment," Science, 254:1173-1177 (1991);
- U.S. Pat. No. 5,821,238 ("Recombinant *Pseudomonas* Exotoxins with Increased Activity"); and
- U.S. Pat. No. 4,892,827 ("Recombinant *Pseudomonas* Exotoxins: Construction of an Active Immunotoxin with Low Side Effects").

A significant disadvantage in using PE-A for treatment of disease, however, is that it is a foreign (non-self) protein being introduced into a heterologous host (e.g., a human). Introduction of non-self proteins into heterologous hosts commonly elicits host immune reactions, such as the generation of antibodies ("neutralizing antibodies") or immune cell reactions (e.g., cytotoxic T cell responses) which are directed at eliminating the non-self protein (i.e., PE-A). Accordingly, it would be advantageous if elements of PE-A (PE-A epitopes) which are recognized and targeted as "non-self" could be removed prior to use of this molecule as a therapeutic agent.

Deimmunization of PE

Some investigators have previously attempted to identify and remove immunogenic determinants from PE-A (i.e., to "deimmunize" PE-A). See, for example:

- Pastan et al., "Immunotoxins with decreased immunogenicity and improved activity," Leukemia and Lymphoma, 52(S2):87-90 (June-2011);
- Onda et al., "Recombinant immunotoxin against B-cell malignancies with no immunogenicity in mice by removal of B-cell epitopes," *Proc. Natl. Acad. Sci. USA*, 108(14):5742-5747 (April-2011);
- Hansen et al., "A recombinant immunotoxin targeting CD22 with low immunogenicity, low nonspecific toxicity, and high antitumor activity in mice," *J. Immunother.* 33(3):297-304 (April-2011);
- Stish et al., "Design and modification of EGF4KDEL 7Mut, a novel bispecific ligand-directed toxin, with decreased immunogenicity and potent anti-mesothelioma activity," *Br. J. Cancer,* 101(7):1114-1123 (October-2009);
- Nagata et al., "Removal of B cell epitopes as a practical approach for reducing the immunogenicity of foreign protein-based therapeutics," *Adv. Drug Deliv. Rev.,* 61(11):977-985 (September-2009);
- Onda et al., "An immunotoxin with greatly reduced immunogenicity by identification and removal of B cell epitopes," *Proc. Natl. Acad. Sci. USA*, 105(32):11311-11316 (August-2008); and Pastan et al, "Mutated *Pseudomonas* Exotoxins with Reduced Antigenicity," U.S. Patent Application No. 2009/0142341.

Despite progress in the area of deimmunization of PE-A, there remains a need for the development of optimized, less immunogenic or non-immunogenic, biologically active forms of this useful cytotoxin. The invention described herein addresses this need.

BRIEF SUMMARY OF THE INVENTION

Peptides spanning the sequence of an approximately 38 kD (predicted molecular weight) form of *Pseudomonas* exotoxin A protein (SEQ ID NO:1) were analyzed for the presence of immunogenic CD4+ T cell epitopes. A total of 120 overlapping 15mer peptides spanning this sequence (SEQ ID NO: 1), but also including an amino terminal $(Gly_{x5}\text{-}Ser)_{x2}$ linker sequence (SEQ ID NO:3) to produce a 359 amino acid Gly-Ser-PE38 polypeptide sequence (SEQ ID NO:2), were tested against a cohort of healthy human donors. CD4+ T cell responses against individual peptides were measured via proliferation assays. Assay data was used to compile a T cell epitope map of the PE38 sequence. Six immunogenic T cell epitopes were identified. Residues were then identified within each of these epitopes for use in targeted amino acid substitutions to reduce or prevent PE38-induced immunogenicity. Reduction or prevention of PE immunogenicity should allow for multiple therapeutic administrations of cytotoxic PE for use, for example, in the targeted destruction of cancer cells in vivo (such as when administered as an immunoconjugate or cell-surface targeted fusion protein).

BRIEF DESCRIPTION OF THE DRAWINGS

FIG. 1. Example of a *Pseudomonas* exotoxin A protein and domains which may be contained therein.

FIG. 11. Analysis of production of cytokines IL-2 and IL-6 stimulated in response to expression of genes encoding either Wild-Type (WT) PE or encoding amino acid substituted PE.

DETAILED DESCRIPTION OF THE INVENTION

I. Definitions and Descriptions

Figure 2:
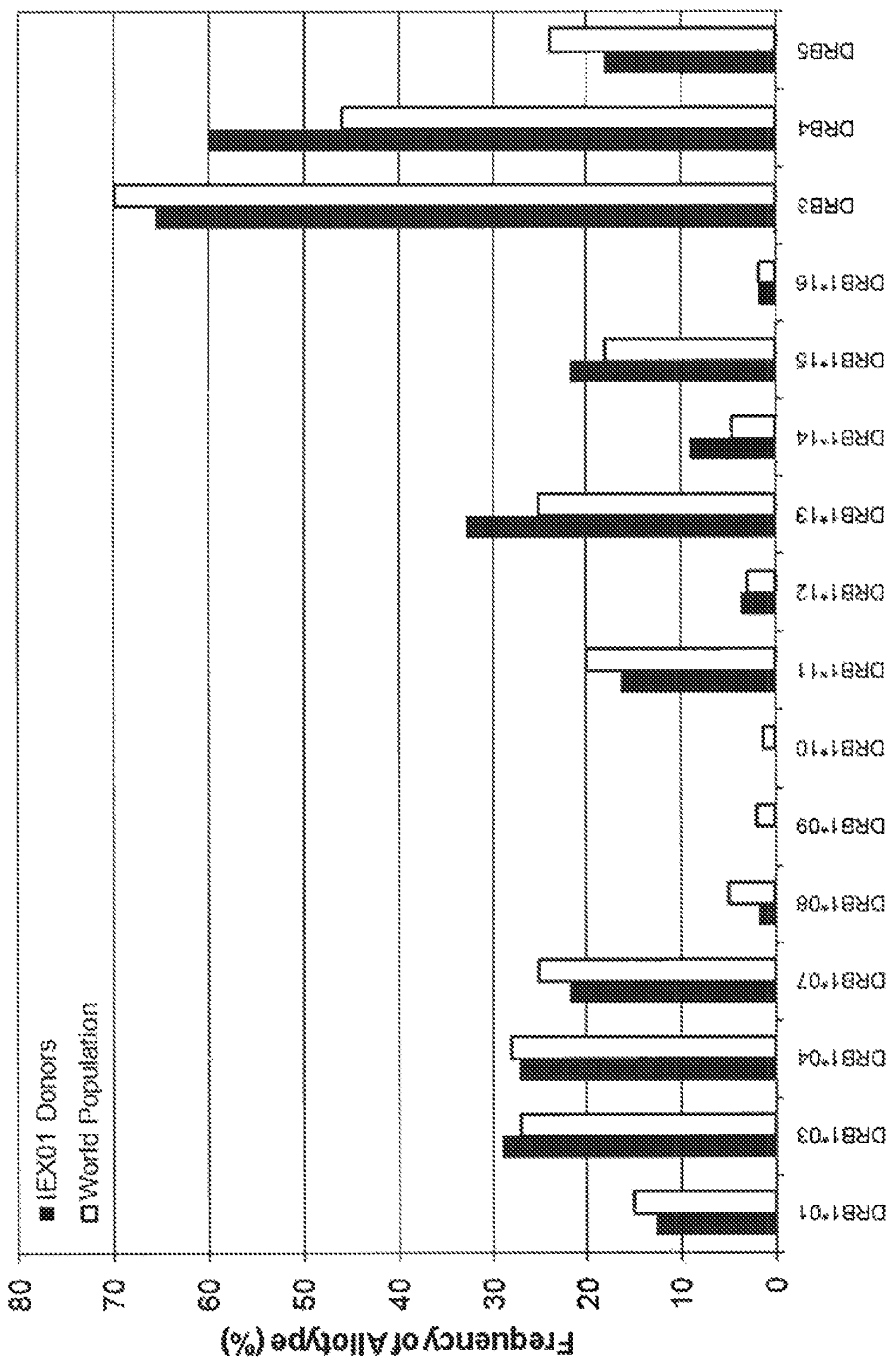
FIG. 2. Comparison of the frequency of donor allotypes expressed in the IEX01 study cohort (n=52) and the world population.

Unless specifically indicated otherwise, as used herein the term "PE" or "PE-A" is intended to indicate a polypeptide comprising a cytotoxic polypeptide sequence derived from a wild-type or naturally occurring form of *Pseudomonas aeruginosa* exotoxin A protein. In addition to cytotoxic polypeptide sequences, PE polypeptides may comprise additional naturally occurring or heterologous polypeptide sequences. Additional naturally occurring polypeptide sequences may include sequences such as are found in full-length *Pseudomonas* exotoxin A protein, for example, amino acid sequences responsible for cytosolic translocation and cell-specific targeting (as discussed further herein)). Additional heterologous polypeptide sequences may include sequences with which at least a PE cytotoxic polypeptide is fused to impart additional functions or properties. (For example, a PE cytotoxic polypeptide may be fused to antigen binding polypeptide sequences such as an scFv antibody.) Examples of sequences comprising a cytotoxic portion of PE can be found in SEQ ID NO:1 and SEQ ID NO:4 spanning amino acid residues Phe-134 to Lys-347. Examples of sequences comprising a cytotoxic portion of PE can also be found in SEQ ID NO:133 and SEQ ID NO:134 spanning amino acid residues Phe-400 to Lys-613.

As used herein in reference to PE, unless indicated otherwise, a "cytotoxic polypeptide" or "cytotoxic polypeptide sequence" is intended to indicate a polypeptide (or portion thereof) which is capable of inactivating translation elongation factor 2 (EF-2), mediating ADP-ribosylation of EF-2, inhibiting protein synthesis, or inducing cell death. For example, it has been demonstrated that PE domain III, comprised of amino acid residues 400-613 of SEQ ID NO:133, is sufficient to mediate ADP-ribosylation of EF-2 and thereby cause cell death. See, Theuer et al., *J. Biol. Chem*., vol. 267, no. 24, pp. 16872-16877 (1992) and Hwang et al., *Cell, vol.* 48, pp. 129-136 (1987).

Cytotoxic polypeptide sequences in the present invention may also comprise alternative carboxy-terminal sequences. See, Theuer et al., Chaudhary et al. and, Seetharam et al. In particular embodiments, examples of carboxy-terminal tails of PE38 in the present invention may comprise sequences as shown in FIG. 1 (SEQ ID NO:133). Hence, exemplary alternative carboxy-terminal tails may comprise amino acid sequences:

```
609-REDLK-613
(SEQ ID NO: 135; numbers 609-613 correspond
to SEQ ID NO: 133)

609-REDL-612
(SEQ ID NO: 136; numbers 609-612 correspond
to SEQ ID NO: 133);
and

609-KDEL-612
(SEQ ID NO: 137; numbers 609-612 correspond
to SEQ ID NO: 133).
```

Unless specifically indicated otherwise, as used herein the term "PE38" is intended to indicate a *Pseudomonas aeruginosa* exotoxin A (PE (or PE-A)) molecule comprising an amino acid sequence as shown in SEQ ID NO: 1. The amino acid sequence used to generate peptide sequences referenced in the Examples is shown in SEQ ID NO:2. SEQ ID NO:2 comprises an amino terminal GGGGGSGGGGGS linker sequence (SEQ ID NO:3) fused to the PE38 amino acid sequence of SEQ ID NO:1. A variant form of PE38 is shown in SEQ ID NO:4. SEQ ID NO:4 differs from SEQ ID NO:1 by comprising a Ser-to-Asn change at position 114, a Ile-to-Val change at position 141, and a Gly-to-Ser change at position 249.

As used herein, unless specifically stated otherwise, "biological activity" in reference to *Pseudomonas* exotoxin A (PE-A), PE or PE38 is intended to indicate at least one of the biological activities exhibited by naturally occurring forms of the *Pseudomonas aeruginosa* exotoxin A molecule. These activities include, for example, cell killing or cell cytotoxic activity (a.k.a., cell cytotoxicity), inactivation of translation elongation factor EF-2, ADP-ribosylation of EF-2, and inhibition of protein synthesis. The biological activity of PE and PE38 polypeptides (and modified forms thereof; e.g., PE and PE38 amino acid substituted variants and fusion proteins) can be measured using assays and experiments which are well-known and routinely used by those skilled in the art. Examples of some of these assays and experiments are further described and referenced herein, without limitation, in the Examples sections included herein.

As used herein, the term "having *Pseudomonas* exotoxin A (PE-A) biological activity" (or "PE biological activity") is intended to indicate molecules exhibiting about 5% or more of at least one biological activity compared to a corresponding wild-type, naturally occurring, or non-amino acid substituted form of PE or PE-A. In some embodiments, molecules "having *Pseudomonas* exotoxin A biological activity" (or "PE biological activity") exhibit 5% or more, about 10% or more, 10% or more, about 15% or more, 15% or more, about 20% or more, 20% or more, about 25% or more, 25% or more, about 30% or more, 30% or more, about 35% or more, 35% or more, about 40% or more, 40% or more, about 45% or more, 45% or more, about 50% or more, 50% or more, about 60% or more, 60% or more, about 70% or more, 70% or more, about 75% or more, 75% or more, about 80% or more, 80% or more, about 85% or more, 85% or more, about 90% or more, 90% or more, about 95% or more, 95% or more, about 100%, or 100% of at least one biological activity compared to a corresponding wild-type, naturally occurring, or non-amino acid substituted forms of PE or PE-A.

As used herein, the term "wild-type" *Pseudomonas* exotoxin A (PE-A) (or "wild-type" PE) biological activity is intended to indicate at least one or more biological activities exhibited by naturally occurring forms of the *Pseudomonas* exotoxin A (PE-A) or PE polypeptides. These include, for example, without limitation, activities such as cell killing or cell cytotoxic activity (a.k.a., cell cytotoxicity), inactivation of translation elongation factor EF-2, ADP-ribosylation of EF-2, and inhibition of protein synthesis. Two examples, without limitation, of polypeptide sequences representing "wild-type" or non-amino acid substituted forms of PE-A are shown in SEQ ID NO:133 and SEQ ID NO:134. Two examples, without limitation, of polypeptide sequences representing "wild-type" or non-amino acid substituted forms of PE are shown in SEQ ID NO:1 (PE38) and SEQ ID NO:4 (variant of PE38).

As used or claimed herein the term "a" or "an" in reference to the subsequent recited entity refers to one or more of that entity; for example, "a PE38 antibody" or "a polynucleotide encoding PE38" is understood to indicate one or more PE38 antibody molecules and one or more polynucleotides encoding PE38, not a single PE38 antibody molecule nor a single polynucleotide molecule encoding PE38, respectively. As such, the terms "a" (or "an"), "one or more," and "at least one" can be used interchangeably herein.

Likewise, as used herein, the term "polypeptide" is intended to encompass a singular "polypeptide" as well as plural "polypeptides," and refers to a molecule composed of monomers (amino acids) linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, such as, but without limitation glycosylation, acetylation, phosphorylation, amidation, et cetera. A "polypeptide" unless specifically described otherwise herein, may be derived from a natural biological source or produced by recombinant technology, but is not necessarily translated from a designated nucleic acid sequence. It may be generated in any manner, including by chemical synthesis.

Polypeptides may have a defined three-dimensional structure, although they do not necessarily have such structure. Polypeptides with a defined three-dimensional structure may be referred to as "folded" or having a "tertiary" structure.

Polypeptides not configured into a three-dimensional structure, are referred to as unfolded. As used herein, the term glycoprotein refers to a protein coupled to at least one carbohydrate moiety attached to the protein via a covalent bond.

The term "isolated" is intended to indicate a biological component no longer in its naturally occurring milieu. For example, an "isolated polypeptide" or "isolated polynucleotide" is intended to indicate a polypeptide or polynucleotide, respectively, which has been removed from its naturally occurring milieu and which may have been inserted within a non-naturally occurring milieu. By way of example, this would include, without limitation, a polynucleotide which has been removed from a naturally occurring location within a host genome, and subsequently inserted, for example, into an expression vector or inserted into a new host genome location or into the genome of a heterologous host organism. The "isolation" of a polypeptide or polynucleotide, as used herein, requires no particular level of purification. For example, recombinantly produced polypeptides expressed in host cells are considered isolated for purposes of the invention, as are native or recombinant polypeptides which have been separated, fractionated, or partially or substantially purified by any suitable technique.

Polypeptide embodiments also include fragments, derivatives, analogs, variants and fusion proteins; preferably but not necessarily wherein such embodiments retain one or more biological activities associated with a corresponding full-length or naturally occurring polypeptide. Fragments include proteolytic fragments, deletion fragments, and fragments encoded by synthetically or recombinantly produced polynucleotides. Variants may occur naturally or be non-naturally occurring. Non-naturally occurring variants may be produced using art-known mutagenesis techniques. Variant polypeptides may comprise conservative or non-conservative amino acid substitutions, deletions, or additions. Derivatives include, but are not limited to, polypeptides which contain one or more non-naturally occurring amino acids, non-standard amino acids, and amino acid analogs. Polypeptide embodiments may comprise amino acid sequences which are at least 60% identical, at least 70% identical, at least 80% identical, at least 85% identical, at least 90% identical, at least 95% identical, at least 97% identical, at least 98% identical, or at least 99% identical to SEQ ID NO: 1.

Unless specifically defined otherwise, the term "polynucleotide" is intended to indicate nucleic acid molecules or constructs as routinely used and understood by those of skill in the art. For example, nucleic acids include, but are not limited to, molecules such as messenger RNA (mRNA), plasmid DNA (pDNA), complementary DNA (cDNA), and genomic DNA (gDNA). A polynucleotide may comprise a conventional phosphodiester bond or a non-conventional bond (e.g., an amide bond, such as found in peptide nucleic acids (PNA)). The terms "polynucleotide" and "nucleic acid" are intended to include embodiments wherein any one or more sequences of polynucleotide or nucleic acid segments are contained, or comprised within, a larger polynucleotide or nucleic acid sequence. For example, but without limitation, and unless stated otherwise to the contrary herein, reference to a nucleic acid such as "a polynucleotide encoding PE38" is intended to include nucleic acids comprising "a polynucleotide encoding PE38" wherein such polynucleotide may also be part of a larger nucleic acid or polynucleotide, such as an expression vector or a polynucleotide/nucleic acid encoding an PE fusion protein.

An "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro synthesized RNA molecules; including synthetically produced molecules.

As used herein, a "coding region" is a portion of nucleic acid containing codons which may be translated into amino acids, although "stop codons" (TAG, TGA, or TAA) are not translated into an amino acids, but may also be considered to be part of a coding region. Unless stated otherwise herein, promoters, ribosome binding sites, transcriptional terminators, introns, and the like, are not considered part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid embodiments may encode heterologous coding regions, either fused or unfused to a nucleic acid encoding a different heterologous polypeptide. Heterologous coding regions include without limitation specialized elements or motifs, such as a secretory signal peptide or a heterologous functional domains.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product. Thus, a promoter region would be operably associated with a nucleic acid encoding a polypeptide if the promoter was capable of effecting transcription of that nucleic acid. Other transcription control elements, besides a promoter, include for example, but without limitation, enhancers, operators, repressors, and transcription termination signals, can be operably associated with the polynucleotide to direct cell-specific transcription. Suitable promoters and other transcription control regions are disclosed herein.

The terms "antibody" and "immunoglobulin" may be used interchangeably herein. An antibody or immunoglobulin comprises at least the antigen-binding elements (e.g., complementarity determining regions or CDRs) of the variable domain of a heavy chain and/or of the variable domain of a light chain. Basic immunoglobulin structures in vertebrate systems are well understood by those of skill in the art. See, e.g., Harlow & Lane, Using Antibodies: A Laboratory Manual, (Cold Spring Harbor Laboratory Press, 1999 (ISBN 0879695447)); see also, Harlow & Lane, Antibodies: A Laboratory Manual, (Cold Spring Harbor Laboratory Press, 2nd ed. 1988). The term "immunoglobulin" or "antibody"

comprises various broad classes of antibody molecules, such as, but without limitation, IgG, IgM, IgA IgG, and IgE classes of antibodies; as well as antibody subclasses (isotypes), such as, IgG1, IgG2, IgG3, IgG4, IgA1, et cetera.

Antibodies or antigen-binding fragments, variants, or derivatives thereof of the invention include, but are not limited to, polyclonal, monoclonal, multispecific, human, humanized, primatized, or chimeric antibodies, single chain antibodies, epitope-binding fragments, e.g., Fab, Fab' and $F(ab')_2$, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies.

As used herein, an “epitope” or “antigenic determinant” is the part of a polypeptide, antigen, or molecule that is recognized by the immune system, specifically by antibodies, B cells, or T cells. Epitopes of polypeptide antigens may function as conformational epitopes or linear epitopes. A conformational epitope is comprised of non-linear sections of a target molecule (such as that formed via the tertiary structure of a folded polypeptide). In contrast, amino acids that make up a linear epitope may be comprised of a continuous sequence of amino acids or may be comprised only of particular amino acid residues critical to antibody/B cell/T cell binding.

By “specifically binds,” it is generally meant that an antibody binds to an epitope via its antigen binding domain, and that the binding entails some complementarity between the antigen binding domain and the epitope. According to this definition, an antibody is said to “specifically bind” to an epitope when it binds to that epitope, via its antigen binding domain more readily than it would bind to a random, unrelated epitope. The term “specificity” may be used herein to qualify the relative affinity by which a certain antibody binds to a certain epitope. For example, antibody “A” may be deemed to have a higher specificity for a given epitope than antibody “B,” or antibody “A” may be said to bind to epitope “C” with a higher specificity than it has for related epitope “D.”

By “preferentially binds,” it is meant that the antibody specifically binds to an epitope more readily than it would bind to a related, similar, homologous, or analogous epitope. Thus, an antibody which “preferentially binds” to a given epitope would more likely bind to that epitope than to a related epitope, even though such an antibody may cross-react with the related epitope.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term “affinity” refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term “avidity” refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

The term “cross-reactivity” refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

As used herein, the terms “linked,” “fused” or “fusion” may be used interchangeably. These terms refer to the joining together of two more elements or components, by whatever means including chemical conjugation or recombinant means. An “in-frame fusion” refers to the joining of two or more polynucleotide open reading frames (ORFs) to form a continuous longer ORF, in a manner that maintains the correct translational reading frame of the original ORFs. Thus, a recombinant fusion protein is a single protein containing two ore more segments that correspond to polypeptides encoded by the original ORFs (which segments are not normally so joined in nature.) Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the “fused” CDRs are co-translated as part of a continuous polypeptide.

In the context of polypeptides, a “linear sequence” or a “sequence” is an order of amino acids in a polypeptide in an amino to carboxyl terminal direction in which residues that neighbor each other in the sequence are contiguous in the primary structure of the polypeptide.

A “variant” of a polypeptide or protein refers to any analogue, fragment, derivative, or mutant which is derived from a polypeptide or protein and which retains at least one biological property of the polypeptide or protein. Different variants of the polypeptide or protein may exist in nature or may be generated artificially (e.g., via synthetic or genetic engineering). Variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. Variants may include, inter alia: (a) variants in which one or more amino acid residues are substituted with, for example, conservative amino acids, non-conservative amino acids, or amino acid analogs (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to those of skill in the art.

The term “expression” as used herein refers to a process by which a gene produces a biochemical, for example, an RNA or polypeptide. It includes without limitation transcription of the gene into RNA molecules such as, for example, messenger RNA (mRNA), transfer RNA (tRNA) or any other RNA product, and the translation of mRNA into polypeptide(s).

Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, et cetera.

As used herein, the term "gene" refers to a polynucleotide comprising nucleotides that encode a functional molecule, including functional molecules produced by transcription only (e.g., a bioactive RNA species) or by transcription and translation (e.g. a polypeptide). The term "gene" encompasses cDNA and genomic DNA nucleic acids. "Gene" also refers to a nucleic acid fragment that expresses a specific RNA, protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence.

A "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" includes both viral and nonviral vehicles for introducing the nucleic acid into a cell in vitro, ex vivo or in vivo. A large number of vectors known in the art may be used to manipulate nucleic acids, incorporate coding sequences into genes, et cetera. Possible vectors include, for example, plasmids or modified viruses including, for example bacteriophages such as lambda derivatives, or plasmids such as pBR322 or pUC plasmid derivatives, or the Bluescript vector. Another example of vectors that are useful in the present invention is the Ultra Vector™ Production System (Intrexon Corp., Blacksburg, Va.) as described in WO 2007/038276, incorporated by reference herein. For example, the insertion of the DNA fragments corresponding to response elements and promoters into a suitable vector for in vitro and/or in vivo expression of modified forms of PE (and fragments thereof) as described herein (including fusion proteins, conjugates, and otherwise linked forms) can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used to express embodiments of the invention described herein include, but are not limited to, retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (e.g., monitoring transfer to target or non-target tissues, duration of expression, et cetera).

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" refers to a "replicon," which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector"). Cloning vectors may comprise one or more sequences that can be used for selection of cells comprising the vector and/or one or more multiple cloning sites for insertion of sequences of interest. The term "expression vector" refers to a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving expression of these genes can be used in an expression vector, including but not limited to, viral promoters, bacterial promoters, animal promoters, mammalian promoters, synthetic promoters, constitutive promoters, tissue specific promoters, pathogenesis or disease related promoters, developmental specific promoters, inducible promoters, light regulated promoters; CYCl, HIS3, GALl, GAL4, GALlO, ADHl, PGK, PH05, GAPDH, ADCl, TRPl, URA3, LEU2, ENO, TPI, alkaline phosphatase promoters (useful for expression in *Saccharomyces*); AOXl promoter (useful for expression in *Pichia*); β3-lactamase, lac, ara, tet, trp, $IP_L$, $IP_R$, T7, tac, and trc promoters (useful for expression in *Escherichia coli*); light regulated-, seed specific-, pollen specific-, ovary specific-, cauliflower mosaic virus 35S, CMV 35S minimal, cassava vein mosaic virus (CsVMV), chlorophyll a/b binding protein, ribulose 1,5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art including, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo All control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Vectors comprising polynucleotides of the invention may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al, *J. Biol. Chem*. 267:963 (1992); Wu et al, *J. Biol. Chem*. 263:14621 (1988); and Hartmut et al, Canadian Patent No. 2,012,311).

Vectors and polynucleotides of the invention may be introduced in vivo by lipofection. For example, via use of liposomes for encapsulation and transfection of nucleic acids in vitro. Synthetic cationic lipids designed to limit the difficulties encountered with liposome-mediated transfection can be used to prepare liposomes for in vivo transfection of a gene encoding a marker (Feigner et al, *Proc. Natl. Acad. Sci* USA. 84:7413 (1987); Mackey et al, *Proc. Natl. Acad. Sci* USA 85:8027 (1988); and Ulmer et al, *Science* 259:1745 (1993)). Use of cationic lipids may promote encapsulation of negatively charged nucleic acids, and also promote fusion with negatively charged cell membranes (Feigner et al, *Science* 337:387 (1989)). Particularly useful lipid compounds and compositions for transfer of nucleic acids are described in WO95/18863, WO96/17823 and U.S. Pat. No. 5,459,127.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., Hum. Gene Ther. 3:147 (1992); and Wu et al., *J. Biol. Chem.* 262:4429 (1987)).

The term "transfection" refers to the uptake of exogenous or heterologous RNA or DNA by a cell. A cell has been "transfected" by exogenous or heterologous RNA or DNA when such RNA or DNA has been introduced inside the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

In addition, recombinant vector comprising polynucleotides of the invention may include one or more origins for replication in the cellular hosts in which their amplification or their expression is sought, markers or selectable markers.

The term "selectable marker" refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter and "promoter sequence" are used interchangeably and refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths may have identical promoter activity.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease Sl), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains nitrons) and translated into the protein encoded by the coding sequence.

"Transcriptional and translational control sequences" refer to DNA regulatory sequences, such as promoters, enhancers, terminators, and the like, that provide for the expression of a coding sequence in a host cell. In eukaryotic cells, polyadenylation signals are control sequences.

The term "response element" ("RE") refers to one or more cis-acting DNA elements which confer responsiveness on a promoter mediated through interaction with the DNA-binding domains of a transcription factor. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the transcription factor binds, in the presence or absence of a ligand, to the DNA sequence of a response element to initiate or suppress transcription of downstream gene(s) under the regulation of this response element.

Examples of DNA sequences for response elements of the natural ecdysone receptor include: RRGG/TTCANTGAC/ACYY (SEQ ID NO:140) (see Cherbas et. al., Genes Dev. 5:120-131 (1991)); AGGTCAN(n)AGGTCA (SEQ ID NO:141), where N(n) can be one or more spacer nucleotides (see D'Avino et al., Mol. Cell. Endocrinol. 113:1 (1995)); and GGGTTGAATGAATTT (SEQ ID NO:142) (see Antoniewski et al., Mol. Cell Biol. 14:4465 (1994)).

The terms "operably linked," "operably associated," "through operable association," and the like refer to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "cassette," "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of expressing polynucleotides and polypeptides under control of a gene switch mechanism, the term "gene switch" refers to the combination of a response element associated with a promoter, and a ligand-dependent transcription factor-based system which, in the presence of one or more ligands, modulates the expression of a gene into which the response element and promoter are incorporated. Stated otherwise, a "gene switch" refers to a peptide, protein or polypeptide complex that functions to (a) bind an activating ligand, and (b) regulate the transcription of a gene of interest in a ligand-dependent fashion.

As used herein with respect to gene switch regulation systems, the term "dimerizes with the ligand binding domain that binds an activating ligand" refers to a selective protein-protein interaction that is induced by the presence of activating ligand.

As used herein, the term "ligand binding domain that binds an activating ligand" refers to an amino acid sequence that selectively binds an activating ligand. In the methods disclosed herein, an activating ligand binds to a ligand binding domain, e.g., an ecdysone receptor ligand binding domain, that is part of a ligand-dependent transcriptional activation complex that regulates the expression of a polynucleotide sequence that encodes a gene of interest. Hence, the expression of the gene of interest is regulated in a ligand-dependent fashion.

The term “ecdysone receptor-based,” with respect to a gene switch, refers to a gene switch comprising at least a functional part of a naturally occurring or synthetic ecdysone receptor ligand binding domain and which regulates gene expression in response to a ligand that binds to the ecdysone receptor ligand binding domain.

The terms “modulate” and “modulates” mean to induce, reduce or inhibit nucleic acid or gene expression, resulting in the respective induction, reduction or inhibition of protein or polypeptide production.

Polynucleotides or vectors comprising sequences encoding polypeptides of the present invention may further comprise at least one promoter suitable for driving expression of a gene in a modified cell.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, et cetera.

“Regulatory region” refers to a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

The term “exogenous gene” or “heterologous gene” means a gene foreign to the subject or organism, that is, a gene which is introduced into the subject through a transformation process, an unmutated version of an endogenous mutated gene or a mutated version of an endogenous unmutated gene. The method of transformation is not critical to this invention and may be any method suitable for the subject known to those in the art. Exogenous genes can be either natural or synthetic genes which are introduced into the subject in the form of DNA or RNA which may function through a DNA intermediate such as by reverse transcriptase. Such genes can be introduced into target cells, directly introduced into the subject, or indirectly introduced by the transfer of transformed cells into the subject.

Polynucleotides and polypeptides of the invention may be expressed in vivo under control of a “gene switch” control mechanism, such as those described in, for example, but not limited to:

WO 2009/045370 (PCT/US2008/011270);
WO 2009/025866 (PCT/US2008/010040);
WO 2008/073154 (PCT/US2007/016747);
WO 2005/108617 (PCT/US2005/015089);
WO 2003/0/27289 (PCT/US2002/005026);
WO 2002/066615 (PCT/US2002/005708);
WO 2003/027266 (PCT/US/2002/05234);
WO 2002/066612 (PCT/US2002/005090);
WO 2002/066614 (PCT/US/2002/005706);
WO 2002/066613 (PCT/US2002/005090);
WO 2002/029075 (PCT/US2001/030608); and
WO 2001/070816 (PCT/US2001/090500), each of which are incorporated by reference herein.

The term “ligand-dependent transcription factor complex” or “LDTFC” refers to a transcription factor comprising one or more protein subunits, which complex can regulate gene expression driven by a “factor-regulated promoter” as defined herein. A model LDTFC is an “ecdysone receptor complex” generally refers to a heterodimeric protein complex having at least two members of the nuclear receptor family, ecdysone receptor (“EcR”) and ultraspiracle (“USP”) proteins (see Yao et al., *Nature* 366:476 (1993)); Yao et al., *Cell* 71:63 (1992)). A functional LDTFC such as an EcR complex may also include additional protein(s) such as immunophilins. Additional members of the nuclear receptor family of proteins, known as transcriptional factors (such as DHR38, betaFTZ-1 or other insect homologs), may also be ligand dependent or independent partners for EcR and/or USP. A LDTFC such as an EcR complex can also be a heterodimer of EcR protein and the vertebrate homolog of ultraspiracle protein, retinoic acid-X-receptor (“RXR”) protein or a chimera of USP and RXR. The terms “LDTFC” and “EcR complex” also encompass homodimer complexes of the EcR protein or USP, as well as single polypeptides or trimers, tetramer, and other multimers serving the same function.

A LDTFC such as an EcR complex can be activated by an active ecdysteroid or non-steroidal ligand bound to one of the proteins of the complex, inclusive of EcR, but not excluding other proteins of the complex. As used herein, the term “ligand,” as applied to LDTFC-based gene switches e.g., EcD complex based gene switches, describes small and soluble molecules having the capability of activating a gene switch to stimulate expression of a polypeptide encoded therein. Examples of ligands include, without limitation, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; 5,378,726; and 7,304,161 and U.S. Pat. No. 7,456,315; oxadiazolines as described in U.S. Pat. No. 7,304,162; dibenzoylalkyl cyanohydrazines such as those disclosed in European Patent No. 461,809B1; N-alkyl-N,N'-diaroylhydrazines such as those disclosed in U.S. Pat. No. 5,225,443; N-acyl-N-alkylcarbonylhydrazines such as those disclosed in European Patent No. 234,994B1; N-aroyl-N-alkyl-N'-aroylhydrazines such as those described in U.S. Pat. No. 4,985,461; amidoketones such as those described in U.S. Pat. No. 7,375,093; each of which is incorporated herein by reference and other similar materials including 3,5-di-tert-butyl-4-hydroxy-N-isobutyl-benzamide, 8-O-acetylharpagide, oxysterol s, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, famesol, bile acids, 1,1-biphosphonate esters, juvenile hormone III, and the like. Examples of diacylhydrazine ligands useful in the present invention include RG-115819 (3,5-Dimethyl-benzoic acid N-(1-ethyl-2,2-dimethyl-propyl)-N'-(2-methyl-3-methoxy-benzoyl)-hydrazide), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See, e.g., U.S. Pat. No. 8,076,517 (Publication No. 2009/0163592), and PCT Appl. No. PCT/US2008/006757 (WO 2008/153801), both of which are incorporated herein by reference in their entireties.

A LDTFC such as an EcR complex includes proteins which are members of the nuclear receptor superfamily wherein all members are characterized by the presence of one or more polypeptide subunits comprising an amino-terminal transactivation domain ("AD," "TD," or "TA," used interchangeably herein), a DNA binding domain ("DBD"), and a ligand binding domain ("LBD"). The AD may be present as a fusion with a "heterodimerization partner" or "HP." A fusion protein comprising an AD and HP of the invention is referred to herein as a "coactivation protein" or "CAP." The DBD and LBD may be expressed as a fusion protein, referred to herein as a "ligand-inducible transcription factor ("LTF"). The fusion partners may be separated by a linker, e.g., a hinge region. Some members of the LTF family may also have another transactivation domain on the carboxy-terminal side of the LBD. The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins.

EcR ligands, when used with a LDTFC, e.g., an EcR complex, which in turn is bound to the response element linked to an exogenous gene (e.g., a reporter gene), provide the means for external temporal regulation of expression of the exogenous gene. The order in which the various components bind to each other, that is, ligand to receptor complex and receptor complex to response element, is not critical. Typically, modulation of expression of the exogenous gene is in response to the binding of a LDTFC, e.g., an EcR complex, to a specific control, or regulatory, DNA element. The EcR protein, like other members of the nuclear receptor family, possesses at least three domains, an AD, a DBD, and a LBD. This receptor, like a subset of the nuclear receptor family, also possesses less well-defined regions responsible for heterodimerization properties (referred to herein as a "heterodimerization partner" or "HP"). Binding of the ligand to the ligand binding domain of a LTF, e.g., an EcR protein, after heterodimerization with a CAP including, e.g., an AD and/or an HP, e.g., a USP or RXR protein, enables the DNA binding domains of the heterodimeric proteins to bind to the response element in an activated form, thus resulting in expression or suppression of the exogenous gene. This mechanism does not exclude the potential for ligand binding to individual subunits, e.g., LTF or CAP, e.g., an EcR or USP, and the resulting formation of active homodimer complexes (e.g. EcR+EcR or USP+USP). In one embodiment, one or more of the receptor domains can be varied producing a chimeric gene switch. Typically, one or more of the three domains may be chosen from a source different than the source of the other domains so that the chimeric receptor is optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988) or LexA protein from *E. coli* (see Brent et al., *Cell* 43:729-736 (1985)) to accommodate chimeric LDTFCs, e.g., EcR complexes. Another advantage of chimeric systems is that they allow choice of a promoter used to drive the exogenous gene according to a desired end result. Such double control can be particularly important in areas of gene therapy, especially when cytotoxic proteins are produced, because both the timing of expression as well as the cells wherein expression occurs can be controlled. When exogenous genes, operatively linked to a suitable promoter, are introduced into the cells of the subject, expression of the exogenous genes is controlled by the presence of the ligand of this invention. Promoters may be constitutively or inducibly regulated or may be tissue-specific (that is, expressed only in a particular type of cell) or specific to certain developmental stages of the organism.

For in vivo use, the ligands described herein may be taken up in pharmaceutically acceptable carriers, such as, for example, solutions, suspensions, tablets, capsules, ointments, elixirs, and injectable compositions. Pharmaceutical compositions may contain from 0.01% to 99% by weight of the ligand. Compositions may be either in single or multiple dose forms. The amount of ligand in any particular pharmaceutical composition will depend upon the effective dose, that is, the dose required to elicit the desired gene expression or suppression.

Suitable routes of administering the pharmaceutical preparations include oral, rectal, topical (including dermal, buccal and sublingual), vaginal, parenteral (including subcutaneous, intramuscular, intravenous, intradermal, intrathecal and epidural) and by naso-gastric tube. It will be understood by those skilled in the art that the preferred route of administration will depend upon the condition being treated and may vary with factors such as the condition of the recipient.

As used herein, the terms "treat" or "treatment" refer to both therapeutic treatment and prophylactic or preventative measures, wherein the object is to prevent or slow down (lessen) an undesired physiological change or disorder, such as the development, progression or spread (i.e., metastasis) of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total). "Treatment" can also mean prolonging survival as compared to expected survival if not receiving treatment. Those in need of treatment include those already with the condition or disorder as well as those prone to have the condition or disorder or those in which the condition or disorder is to be prevented.

The terms "subject," "individual," "animal," "patient," or "mammal," is meant any subject, particularly a mammalian subject, for whom diagnosis, prognosis, or therapy is desired. Mammalian subjects include, without limitation, humans, domestic animals, farm animals, and zoo, sports, or pet animals such as dogs, cats, guinea pigs, rabbits, rats, mice, horses, cattle, cows, et cetera.

The terms "hyperproliferative disease or disorder" is intended to encompass all neoplastic cell growth and proliferation, whether malignant or benign, including all transformed cells and tissues and all cancerous cells and tissues. Hyperproliferative diseases or disorders include, but are not limited to, precancerous lesions, abnormal cell growths, tumors (whether benign or malignant), "cancer" and other hyperplasias.

The term "cancer" includes, but is not limited to, primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

A tumor or tumor tissue may also comprise "tumor-associated non-tumor cells", e.g., vascular cells which form blood vessels to supply the tumor or tumor tissue. Non-tumor cells may be induced to replicate and develop by tumor cells, for example, the induction of angiogenesis in a tumor or tumor tissue.

Some examples of cancer include, but are not limited to, carcinoma, lymphoma, blastoma, sarcoma, and leukemia or lymphoid malignancies. More particular examples of such cancers are noted below and include: squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, as well as head (e.g., brain) and neck cancer.

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

Naturally Occurring Amino Acid Substitutions

List of naturally occurring amino acids and some of their biochemical properties.

| Amino Acid | 3-Letter Code | 1-Letter Code | Side-chain polarity* | Side-chain charge (pH 7.4)* | Hydropathy index** |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | polar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive(10%) neutral(90%) | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

*Hausman & Cooper, (2004), *The Cell: A Molecular Approach*, Washington, D.C: ASM Press. p. 51 (2004)(ISBN 0-87893-214-3).

**Kyte & Doolittle, "A simple method for displaying the hydropathic character of a protein," *Journal of Molecular Biology*, 157(1): 105-132 (May 1982).

Conservative Amino Acid Substitutions

Polypeptides may be made to differ by introduction of conservative or non-conservative amino acid changes. Conservative amino acid substitutions refer to the interchangeability of residues having similar amino acid side chains. "Conservative amino acid substitutions" refer to substitutions of one or more amino acids in a native amino acid sequence (e.g., wild-type or naturally occurring form of PE) with other amino acid(s) having similar side chains (e.g., side chains similar in terms of size, charge, element composition, and/or hydrophobicity/hydrophilicity).

Conserved substitutes for an amino acid within a native amino acid sequence can be selected from other members of the group to which the naturally occurring amino acid belongs. For example, conservative amino acid residue substitution groups include:

(1) Alanine (A)-Glycine (G)-Serine (S)-Threonine;
(2) Aspartic acid (D)-Glutamic acid (E);
(3) Asparagine (N)-Glutamine (Q);
(4) Arginine (R)-Lysine (K)-Histidine (H);
(5) Isoleucine (I)-Leucine (L)-Methionine (M)-Valine (V); and
(6) Phenylalanine (F)-Tyrosine (Y)-Tryptophan (W).

Other substitution groups of amino acids can be envisioned. For example, amino acids can be grouped by similar function or chemical structure or composition (e.g., acidic, basic, aliphatic, aromatic, sulfur-containing). For example, an Aliphatic grouping may comprise: Glycine (G), Alanine (A), Valine (V), Leucine (L), Isoleucine (I). Other groups containing amino acids that are considered conservative substitutions for one another include:

Aromatic: Phenylalanine (F)-Tyrosine (Y)-Tryptophan (W);
Sulfur-containing: Methionine (M)-Cysteine (C);
Basic: Arginine (R)-Lysine (K)-Histidine (H);
Acidic: Aspartic acid (D)-Glutamic acid (E);
Non-polar uncharged residues: Cysteine (C)-Methionine (M)-Proline (P); and
Hydrophilic Uncharged Residues: Serine (S)-Threonine (T)-Asparagine (N)-Glutamine (Q).

Exemplary embodiments of conservative amino acid substitutions include the interchangeability of: valine-leucine, valine-isoleucine-leucine, phenylalanine-tyrosine, lysine-arginine, alanine-valine, aspartic acid-glutamic acid, and asparagine-glutamine.

Examples of Amino Acid Analogs and Non-Standard Amino Acid Residues

Examples of a few of the many possible amino acid analogs routinely known to those of skill in the art include, for example, but without limitation, analogs such as: 4-hydroxyproline which may be substituted for proline; 5-hydroxylysine which may be substituted for lysine; 3-methylhistidine which may be substituted for histidine; homoserine which may be substituted for serine; and ornithine which may be substituted for lysine.

Examples of a few of the many possible non-standard amino acids routinely known to those of skill in the art include, for example, but without limitation, molecules such as: ornithine, citrulline, lanthionine, 2-aminoisobutyric acid, dehydroalanine, γ-aminobutyric acid, β-alanine (3-aminopropanoic acid), selenocysteine and pyrrolysine.

Substitution mutations may be made by any technique for mutagenesis known in the art including, for example, but not limited to, in vitro site-directed mutagenesis (Hutchinson et al, *J. Biol. Chem.* 255:6551 (1978); Zoller et al, *DNA* 3:479 (1984); Oliphant et al, *Gene* 44:177 (1986); Hutchinson et al, *Proc. Natl. Acad. Sci. USA* 83:710 (1986)), use of TAB® linkers (Pharmacia), restriction endonuclease digestion/fragment deletion and substitution, PCR-mediated/oligonucleotide-directed mutagenesis, et cetera. PCR-based techniques are preferred for site-directed mutagenesis (see Higuchi, 1989, "Using PCR to Engineer DNA", in PCR Technology: Principles and Applications for DNA Amplification, H. Erlich, ed., Stockton Press, Chapter 6, pp. 61-70).

Embodiments of the Invention

Embodiments of the invention include isolated polypeptides (proteins) comprising or consisting of a modified form of *Pseudomonas* exotoxin A, or a fragment thereof, wherein said modified form, or fragment thereof, comprises an epitope selected from the group consisting of:

ISFSTRGTQ (epitope 1; SEQ ID NO: 5);
GTQNWTVER (epitope 2; SEQ ID NO: 6);
IVFGGVRAR (epitope 3; SEQ ID NO: 7);
ARSQDLDAI (epitope 4; SEQ ID NO: 8);
LRVYVPRSS (epitope 5; SEQ ID NO: 9);
and
IPDKEQAIS (epitope 6; SEQ ID NO: 10)

wherein one or more amino acid residues in any one or more of these epitopes are substituted with a different amino acid residue.

Embodiments of the invention include isolated polypeptides (proteins) comprising or consisting of a modified form of *Pseudomonas* exotoxin A, or a fragment thereof, wherein said modified form, or fragment thereof, comprises an epitope selected from the group consisting of:

GDGGDISFSTRGTQN
(peptide 50 (epitope 1); SEQ ID NO: 60);

SFSTRGTQNWTVERL
(peptide 52 (epitope 2); SEQ ID NO: 62);

TRGTQNWTVERLLQA
(peptide 53 (epitope 2); SEQ ID NO: 63);

AQSIVFGGVRARSQD
(peptide 65 (epitope 3); SEQ ID NO: 75);

GGVRARSQDLDAIWR
(peptide 67 (epitope 4); SEQ ID NO: 77);

RARSQDLDAIWRGFY
(peptide 68 (epitope 4); SEQ ID NO: 78);

NGALLRVYVPRSSLP
(peptide 81 (epitope 5); SEQ ID NO: 91);

LLRVYVPRSSLPGFY
(peptide 82 (epitope 5); SEQ ID NO: 92);

LDPSSIPDKEQAISA
(peptide 110 (epitope 6); SEQ ID NO: 120);

SSIPDKEQAISALPD
(peptide 111 (epitope 6); SEQ ID NO: 121);

ISFSTRGTQNWTVER
(overlapping epitopes 1 and 2; SEQ ID NO: 131);

IVFGGVRARSQDLDAI
(overlapping epitopes 3 and 4; SEQ ID NO: 132)

wherein one or more amino acid residues in any one or more of these epitopes are substituted with a different amino acid residue.

Embodiments of the invention include isolated polypeptides (proteins) comprising or consisting of a modified form of *Pseudomonas* exotoxin A, or a fragment thereof, wherein said modified form, or fragment thereof, comprises an epitope selected from the group consisting of:

a) ISFSTRGTQ (SEQ ID NO:5), wherein amino acid residues at one or more of positions 1, 6 and 9 are substituted with a different amino acid residue;
b) GTQNWTVER (SEQ ID NO:6), wherein amino acid residues at one or more of positions 3, 4 and 6 are substituted with a different amino acid residue;
c) IVFGGVRAR (SEQ ID NO:7), wherein amino acid residues at one or more of positions 1 and 6 are substituted with a different amino acid residue;
d) ARSQDLDAI (SEQ ID NO:8), wherein amino acid residues at one or more of positions 4 and 7 are substituted with a different amino acid residue;
e) LRVYVPRSS (SEQ ID NO:9), wherein amino acid residues at one or more of positions 1, 2 and 9 are substituted with a different amino acid residue;
f) IPDKEQAIS (SEQ ID NO:10), wherein amino acid residues at one or more of positions 1, 4, 6 and 7 are substituted with a different amino acid residue;
g) ISFSTRGTQNWTVER (SEQ ID NO:131), wherein amino acid residues at one or more of positions 1, 6, 9, 10 and 12 are substituted with a different amino acid residue; and
h) IVFGGVRARSQDLDAI (SEQ ID NO: 132), wherein amino acid residues at one or more of positions 1, 6, 11, and 14 are substituted with a different amino acid residue.

Embodiments of the invention include isolated polypeptides (proteins) comprising or consisting of a modified form of *Pseudomonas* exotoxin A, or a fragment thereof, wherein said modified form, or fragment thereof, comprises an epitope selected from the group consisting of:

a) ISFSTRGTQ (SEQ ID NO:5), wherein amino acid residues at one or more of positions 1, 6 and 9 are substituted with a conservative amino acid substitution;
b) GTQNWTVER (SEQ ID NO:6), wherein amino acid residues at one or more of positions 3, 4 and 6 are substituted with a conservative amino acid substitution;
c) IVFGGVRAR (SEQ ID NO:7), wherein amino acid residues at one or more of positions 1 and 6 are substituted with a conservative amino acid substitution;
d) ARSQDLDAI (SEQ ID NO:8), wherein amino acid residues at one or more of positions 4 and 7 are substituted with a conservative amino acid substitution;
e) LRVYVPRSS (SEQ ID NO:9), wherein amino acid residues at one or more of positions 1, 2 and 9 are substituted with a conservative amino acid substitution;
f) IPDKEQAIS (SEQ ID NO:10), wherein amino acid residues at one or more of positions 1, 4, 6 and 7 are substituted with a conservative amino acid substitution;
g) ISFSTRGTQNWTVER (SEQ ID NO:131), wherein amino acid residues at one or more of positions 1, 6, 9, 10 and 12 are substituted with a conservative amino acid substitution; and
h) IVFGGVRARSQDLDAI (SEQ ID NO: 132), wherein amino acid residues at one or more of positions 1, 6, 11, and 14 are substituted with a conservative amino acid substitution.

Embodiments of the invention include isolated polypeptides (proteins) comprising or consisting of a modified form of *Pseudomonas* exotoxin A, or a fragment thereof, wherein said modified form, or fragment thereof, comprises an epitope selected from the group consisting of:

a) ISFSTRGTQ (SEQ ID NO:5), wherein amino acid residues at one or more of positions 1, 6 and 9 are substituted with a conservative amino acid substitution;
b) GTQNWTVER (SEQ ID NO:6), wherein amino acid residues at one or more of positions 3, 4 and 6 are substituted with a conservative amino acid substitution;
c) IVFGGVRAR (SEQ ID NO:7), wherein amino acid residues at one or more of positions 1 and 6 are substituted with a conservative amino acid substitution;
d) ARSQDLDAI (SEQ ID NO:8), wherein amino acid residues at one or more of positions 4 and 7 are substituted with a conservative amino acid substitution;
e) LRVYVPRSS (SEQ ID NO:9), wherein amino acid residues at one or more of positions 1, 2 and 9 are substituted with a conservative amino acid substitution;
f) IPDKEQAIS (SEQ ID NO:10), wherein amino acid residues at one or more of positions 1, 4, 6 and 7 are substituted with a conservative amino acid substitution;
g) ISFSTRGTQNWTVER (SEQ ID NO:131), wherein amino acid residues at one or more of positions 1, 6, 9, 10 and 12 are substituted with a conservative amino acid substitution; and
h) IVFGGVRARSQDLDAI (SEQ ID NO: 132), wherein amino acid residues at one or more of positions 1, 6, 11, and 14 are substituted with a conservative amino acid substitution, wherein the conservative amino acid substitution at one or more of said positions in a) through f) is selected from the group consisting of:

1) A is substituted with any one of G, I, L, S, T or V;
2) D is substituted with E;
3) I is substituted with any one of L, M or V;
4) K is substituted with any one of H or R;
5) L is substituted with any one of A, G, I, M or V;
6) N is substituted with any one of S, T or Q;
7) Q is substituted with any one of S, T or N;
8) R is substituted with any one of K or H;
9) S is substituted with any one of A, G, N, T or Q;
10) T is substituted with any one of A, G, N, Q or S; and
11) V is substituted with any one of A, G, I, L or M.

Embodiments of the invention also comprise or consist of isolated polypeptides and peptides comprising or consisting of the above-referenced amino acids sequences, except wherein one or more amino acids have been substituted with conservative amino acids substitutions. Embodiments of the invention further comprise or consist of isolated polypeptides (proteins) and peptides comprising or consisting of the above-referenced amino acids sequences, except wherein one or more amino acids have been substituted with amino acids which are naturally occurring, non-naturally occurring, non-standard amino acids, or amino acid analogs.

Embodiments of the invention include isolated polypeptides (proteins) comprising or consisting of a modified form of *Pseudomonas* exotoxin A, or a fragment thereof, wherein said modified form, or fragment thereof, comprises an epitope selected from the group consisting of:

a) ISFSTRGTQ (SEQ ID NO:5), wherein amino the acid residue at position 1 (I) is substituted with A, N, T, Q or H, or wherein the amino acid residue at position 6 (R) is substituted with Q, or wherein the amino acid residue at position 9 (Q) is substituted with N or T, or wherein the amino acid sequence ISFSTRGTQ (SEQ ID NO:5) comprises two or more of said substitutions in any combination;

b) GTQNWTVER (SEQ ID NO:6), wherein the amino acid residue at position 3 (Q) is substituted with N or T, wherein amino the acid residue at position 4 (N) is substituted with K or R, or wherein the amino acid residue at position 6 (T) is substituted with K or R, or wherein the amino acid sequence GTQNWTVER (SEQ ID NO:6) comprises two or more of said substitutions in any combination;

c) IVFGGVRAR (SEQ ID NO:7), wherein amino the acid residue at position 1 (I) is substituted with A or N, or wherein the amino acid residue at position 6 (V) is substituted with D, M, or N, or wherein the amino acid sequence IVFGGVRAR (SEQ ID NO:7) comprises substitutions at both positions in any combination of amino acid residues A or N at position 1 (I) and D, M, or N at position 6 (V);

d) ARSQDLDAI (SEQ ID NO:8), wherein amino the acid residue at position 4 (Q) is substituted with K or R, or wherein the amino acid residue at position 7 (D) is substituted with K or R, or wherein the amino acid sequence ARSQDLDAI (SEQ ID NO:8) comprises substitutions with K or R in any combination at both positions 4 (Q) and 7 (D);

e) LRVYVPRSS (SEQ ID NO:9), wherein amino the acid residue at position 1 (L) is substituted with A, or wherein the amino acid residue at position 2 (R) is substituted with D, S or A, or wherein the amino acid residue at position 9 (S) is substituted with D, E, N, K, P or T, or wherein the amino acid sequence LRVYVPRSS (SEQ ID NO:9) comprises two or more of said substitutions in any combination;

f) IPDKEQAIS (SEQ ID NO:10), wherein amino acid residues at one or more of positions 1, 4, 6 and 7 are substituted with a different amino acid residue. wherein amino the acid residue at position 1 (I) is substituted with A, N, T, Q or H, or wherein the amino acid residue at position 4 (K) is substituted with T, or wherein the amino acid residue at position 6 (Q) is substituted with D, or wherein the amino acid residue at position 7 (A) is substituted with D, or wherein the amino acid sequence IPDKEQAIS (SEQ ID NO:10) comprises two or more of said substitutions in any combination;

g) ISFSTRGTQNWTVER (SEQ ID NO:131), wherein amino acid residues at one or more of positions 1, 6, 9, 10 and 12 are substituted with a different amino acid residues wherein amino the acid residue at position 1 (I) is substituted with A, N, T, Q or H, or wherein the amino acid residue at position 6 (R) is substituted with Q, or wherein the amino acid residue at position 9 (Q) is substituted with N or T, or wherein amino the acid residue at position 10 (N) is substituted with K or R, or wherein the amino acid residue at position 12 (T) is substituted with K or R, or wherein the amino acid sequence ISFSTRGTQNWTVER (SEQ ID NO: 131) comprises two or more of said substitutions in any combination; and h) IVFGGVRARSQDLDAI (SEQ ID NO:132), wherein amino the acid residue at position 1 (I) is substituted with A or N, or wherein the amino acid residue at position 6 (V) is substituted with D, M, or N, wherein amino the acid residue at position 11 (Q) is substituted with K or R, or wherein the amino acid residue at position 14 (D) is substituted with K or R, or wherein the amino acid sequence IVFGGVRARSQDLDAI (SEQ ID NO: 132) comprises two or more of said substitutions in any combination.

Embodiments of the invention include an isolated polypeptide comprising a modified form of *Pseudomonas* exotoxin A, or a fragment thereof, wherein said modified form, or fragment thereof, comprises one or more amino acid substitutions selected from the group consisting of:

a) I at position 141 changed to any amino acid residue; (epitope 1)

b) R at position 146 changed to any amino acid residue; (epitope 1)

c) Q at position 149 changed to any amino acid residue; (epitope 1)

d) N at position 150 changed to any amino acid residue; (epitope 2)

e) T at position 152 changed to any amino acid residue; (epitope 2)

f) I at position 184 changed to any amino acid residue; (epitope 3)

g) V at position 189 changed to any amino acid residue; (epitope 3)

h) Q at position 194 changed to any amino acid residue; (epitope 4)

i) D at position 197 changed to any amino acid residue; (epitope 4)

j) L at position 233 changed to any amino acid residue; (epitope 5)

k) R at position 234 changed to any amino acid residue; (epitope 5)

l) S at position 241 changed to any amino acid residue; (epitope 5)

m) I at position 321 changed to any amino acid residue; (epitope 6)

n) K at position 324 changed to any amino acid residue; (epitope 6)

o) Q at position 326 changed to any amino acid residue; (epitope 6)

p) A at position 327 changed to any amino acid residue; (epitope 6)

q) any combination of one or more of a) through ao), wherein the amino acid numbering corresponds to SEQ ID NO: 1.

Embodiments of the invention include an isolated polypeptide comprising a modified form of *Pseudomonas* exotoxin A, or a fragment thereof, wherein said modified form, or fragment thereof, comprises one or more amino acid substitutions selected from the group consisting of:

a) I at position 141 changed to A; (epitope 1)
b) I at position 141 changed to N; (epitope 1)
c) I at position 141 changed to T; (epitope 1)
d) I at position 141 changed to Q; (epitope 1)
e) I at position 141 changed to H; (epitope 1)
f) R at position 146 changed to Q; (epitope 1)
g) Q at position 149 changed to N; (epitope 1)
h) Q at position 149 changed to T; (epitope 1)
i) N at position 150 changed to R; (epitope 2)
j) N at position 150 changed to K; (epitope 2)
k) T at position 152 changed to R; (epitope 2)
l) T at position 152 changed to K; (epitope 2)
m) I at position 184 changed to A; (epitope 3)
n) I at position 184 changed to N; (epitope 3)
o) V at position 189 changed to D; (epitope 3)
p) V at position 189 changed to M; (epitope 3)
q) V at position 189 changed to N; (epitope 3)
r) Q at position 194 changed to R; (epitope 4)
s) Q at position 194 changed to K; (epitope 4)
t) D at position 197 changed to R; (epitope 4)
u) D at position 197 changed to K; (epitope 4)
v) L at position 233 changed to A; (epitope 5)

w) R at position 234 changed to D; (epitope 5)
x) R at position 234 changed to S; (epitope 5)
y) R at position 234 changed to A; (epitope 5)
z) S at position 241 changed to D; (epitope 5)
ab) S at position 241 changed to E; (epitope 5)
ac) S at position 241 changed to N; (epitope 5)
ad) S at position 241 changed to K; (epitope 5)
ae) S at position 241 changed to P; (epitope 5)
af) S at position 241 changed to T; (epitope 5)
ag) I at position 321 changed to A; (epitope 6)
ah) I at position 321 changed to N; (epitope 6)
ai) I at position 321 changed to T; (epitope 6)
ak) I at position 321 changed to Q; (epitope 6)
al) I at position 321 changed to H; (epitope 6)
am) K at position 324 changed to T; (epitope 6)
an) Q at position 326 changed to D; (epitope 6)
ao) A at position 327 changed to D; (epitope 6)
ap) any combination of one or more of a) through ao),
wherein the amino acid numbering corresponds to SEQ ID NO: 1.

Embodiments of the invention comprise isolated polypeptides as described above, including polypeptides comprising amino acid substitutions introduced at each of amino acid positions 141, 146, 149, 150, 152, 184, 189, 194, 197, 233, 234, 241, 321, 324, 326 and 327 (in comparison to the amino acid sequence of SEQ ID NO: 1).

Embodiments of the invention include isolated polypeptides (proteins) and peptides comprising, or consisting of, the following amino acid sequences:

GGGGGSGGGGGSPEG (peptide 1; SEQ ID NO: 11);
GGSGGGGGSPEGGSL (peptide 2; SEQ ID NO: 12);
GGGGGSPEGGSLAAL (peptide 3; SEQ ID NO: 13);
GGSPEGGSLAALTAH (peptide 4; SEQ ID NO: 14);
PEGGSLAALTAHQAC (peptide 5; SEQ ID NO: 15);
GSLAALTAHQACHLP (peptide 6; SEQ ID NO: 16);
AALTAHQACHLPLET (peptide 7; SEQ ID NO: 17);
TAHQACHLPLETFTR (peptide 8; SEQ ID NO: 18);
HLPLETFTRHRQPRG (peptide 10; SEQ ID NO: 20);
LETFTRHRQPRGWEQ (peptide 11; SEQ ID NO: 21);
FTRHRQPRGWEQLEQ (peptide 12; SEQ ID NO: 22);
HRQPRGWEQLEQCGY (peptide 13; SEQ ID NO: 23);
PRGWEGLEQCGYPVQ (peptide 14; SEQ ID NO: 24);
WEQLEQCGYPVQRLV (peptide 15; SEQ ID NO: 25);
LEQCGYPVQRLVALY (peptide 16; SEQ ID NO: 26);
CGYPVQRLVALYLAA (peptide 17; SEQ ID NO: 27);
PVQRLVALYLAARLS (peptide 18; SEQ ID NO: 28);
RLVALYLAARLSWNQ (peptide 19; SEQ ID NO: 29);
ALYLAARLSWNQVDQ (peptide 20; SEQ ID NO: 30);
LAARLSWNQVDQVIR (peptide 21; SEQ ID NO: 31);
RLSWNQVDQVIRNAL (peptide 22; SEQ ID NO: 32);
WLQVDQVIRNALASP (peptide 23; SEQ ID NO: 33);

-continued

VDQVIRNALASPGSG (peptide 24; SEQ ID NO: 34);
VIRNALASPGSGGDL (peptide 25; SEQ ID NO: 35);
NALASPGSGGDLGEA (peptide 26; SEQ ID NO: 36);
ASPGSGGDLGEAIRE (peptide 27; SEQ ID NO: 37);
GSGGDLGEAIREQPE (peptide 28; SEQ ID NO: 38);
GDLGEAIREQPEQAR (peptide 29; SEQ ID NO: 39);
GEAIREQPEQARLAL (peptide 30; SEQ ID NO: 40);
IREQPEQARLALTLA (peptide 31; SEQ ID NO: 41);
QPEQARLALTLAAAE (peptide 32; SEQ ID NO: 42);
QARLALTLAAAESER (peptide 33; SEQ ID NO: 43);
LALTLAAAESERFVR (peptide 34; SEQ ID NO: 44);
TLAAAESERFVRQGT (peptide 35; SEQ ID NO: 45);
AAESERFVRQGTGND (peptide 36; SEQ ID NO: 46);
SERFVRQGTGNDEAG (peptide 37; SEQ ID NO: 47);
FVRQGTGNDEAGAAS (peptide 38; SEQ ID NO: 48);
QGTGNDEAGAASGPA (peptide 39; SEQ ID NO: 49);
GNDEAGAASGPADSG (peptide 40; SEQ ID NO: 50);
EAGAASGPADSGDAL (peptide 41; SEQ ID NO: 51);
AASGPADSGDALLER (peptide 42; SEQ ID NO: 52);
GPADSGDALLERNYP (peptide 43; SEQ ID NO: 53);
DSGDALLERNYPTGA (peptide 44; SEQ ID NO: 54);
DALLERNYPTGAEFL (peptide 45; SEQ ID NO: 55);
LERNYPTGAEFLGDG (peptide 46; SEQ ID NO: 56);
NYPTGAEFLGDGGDI (peptide 47; SEQ ID NO: 57);
TGAEFLGDGGDISFS (peptide 48; SEQ ID NO: 58);
EFLGDGGDISFSTRG (peptide 49; SEQ ID NO: 59);
GDISFSTRGTQNWTV (peptide 51; SEQ ID NO: 61);
TQNWTVERLLQAHRQ (peptide 54; SEQ ID NO: 64);
WTVERLLQAHRQLEE (peptide 55; SEQ ID NO: 65);
ERLLQAHRQLEERGY (peptide 56; SEQ ID NO: 66);
LQAHRQLEERGYVFV (peptide 57; SEQ ID NO: 67);
HRQLEERGYVFVGYH (peptide 58; SEQ ID NO: 68);
LEERGYVFVGYHGTF (peptide 59; SEQ ID NO: 69);
RGYVFVGYHGTFLEA (peptide 60; SEQ ID NO: 70);
GYHGTFLEAAQSIVF (peptide 62; SEQ ID NO: 72);
GTFLEAAQSIVFGGV (peptide 63; SEQ ID NO: 73);
LEAAQSIVFGGVRAR (peptide 64; SEQ ID NO: 74);
IVFGGVRARSQDLDA (peptide 66; SEQ ID NO: 76);
SQDLDAIWRGFYIAG (peptide 69; SEQ ID NO: 79);
LDAIWRGFYIAGDPA (peptide 70; SEQ ID NO: 80);

-continued

IWRGFYIAGDPALAY (peptide 71; SEQ ID NO: 81);

GFYIAGDPALAYGYA (peptide 72; SEQ ID NO: 82);

IAGDPALAYGYAQDQ (peptide 73; SEQ ID NO: 83);

DPALAYGYAQDQEPD (peptide 74; SEQ ID NO: 84);

LAYGYAQDQEPDARG (peptide 75; SEQ ID NO: 85);

GYAQDQEPDARGRIR (peptide 76; SEQ ID NO: 86);

QDQEPDARGRIRNGA (peptide 77; SEQ ID NO: 87);

EPDARGRIRNGALLR (peptide 78; SEQ ID NO: 88);

ARGRIRNGALLRVYV (peptide 79; SEQ ID NO: 89);

RIRNGALLRVYVPRS (peptide 80; SEQ ID NO: 90);

VYVPRSSLPGFYRTG (peptide 83; SEQ ID NO: 93);

PRSSLPGFYRTGLTL (peptide 84; SEQ ID NO: 94);

SLPGFYRTGLTLAAP (peptide 85; SEQ ID NO: 95);

GFYRTGLTLAAPEAA (peptide 86; SEQ ID NO: 96);

RTGLTLAAPEAAGEV (peptide 87; SEQ ID NO: 97);

LTLAAPEAAGEVERL (peptide 88; SEQ ID NO: 98);

AAPEAAGEVERLIGH (peptide 89; SEQ ID NO: 99);

EAAGEVERLIGHPLP (peptide 90; SEQ ID NO: 100);

GEVERLIGHPLPLRL (peptide 91; SEQ ID NO: 101);

ERLIGHPLPLRLDAI (peptide 92; SEQ ID NO: 102);

IGHPLPLRLDAITGP (peptide 93; SEQ ID NO: 103);

PLPLRLDAITGPEEE (peptide 94; SEQ ID NO: 104);

LRLDAITGPEEEGGR (peptide 95; SEQ ID NO: 105);

DAITGPEEEGGRLET (peptide 96; SEQ ID NO: 106);

TGPEEEGGRLETILG (peptide 97; SEQ ID NO: 107);

EEEGGRLETILGWPL (peptide 98; SEQ ID NO: 108);

GGRLETILGWPLAER (peptide 99; SEQ ID NO: 109);

LETILGWPLAERTVV (peptide 100; SEQ ID NO: 110);

ILGWPLAERTVVIPS (peptide 101; SEQ ID NO: 111);

WPLAERTVVIPSAIP (peptide 102; SEQ ID NO: 112);

AERTVVIPSAIPTDP (peptide 103; SEQ ID NO: 113);

TVVIPSAIPTDPRNV (peptide 104; SEQ ID NO: 114);

IPSAIPTDPRNVGGD (peptide 105; SEQ ID NO: 115);

AIPTDPRNVGGDLDP (peptide 106; SEQ ID NO: 116);

TDPRNVGGDLDPSSI (peptide 107; SEQ ID NO: 117);

RNVGGDLDPSSIPDK (peptide 108; SEQ ID NO: 118);

GGDLDPSSIPDKEQA (peptide 109; SEQ ID NO: 119);

PDKEQAISALPDYAS (peptide 112; SEQ ID NO: 122);

EQAISALPDYASQPG (peptide 113; SEQ ID NO: 123);

ISALPDYASQPGKPP (peptide 114; SEQ ID NO: 124);

LPDYASQPGKPPRED (peptide 115; SEQ ID NO: 125);

-continued

YASQPGKPPREDLK (peptide 116; SEQ ID NO: 126);

ITGPEEEGGRLDTIL (peptide 117; SEQ ID NO: 127);

PEEEGGRLDTILGWP (peptide 118; SEQ ID NO: 128);

EGGRLDTILGWPLAE (peptide 119; SEQ ID NO: 129); and

RLDTILGWPLAERTV (peptide 120; SEQ ID NO: 130).

Embodiments of the invention also comprise or consist of isolated polypeptides (proteins) and peptides comprising or consisting of the above-referenced amino acids sequences, except wherein one or more amino acids have been substituted with conservative amino acids substitutions. Embodiments of the invention also comprise or consist of isolated polypeptides (proteins) and peptides comprising or consisting of the above-referenced amino acids sequences, except wherein one or more amino acids have been substituted with amino acids which are naturally occurring, non-naturally occurring, non-standard amino acids, or amino acid analogs.

Embodiments of the invention include polypeptides comprising a PE-A Domain III (i.e., a cytotoxic domain; see e.g., FIG. 1). Examples of sequences comprising a cytotoxic portion of PE can be found in SEQ ID NO:1 and SEQ ID NO:4 spanning amino acid residues Phe-134 to Lys-347. Examples of sequences comprising a cytotoxic portion of PE can also be found in SEQ ID NO:133 and SEQ ID NO:134 spanning amino acid residues Phe-400 to Lys-613.

Embodiments of the invention include polypeptides comprising a PE-A Domain III (i.e., a cytotoxic domain) and one or more PE-A domains selected from the group consisting of:

(a) Domain II (i.e., a cytosolic translocation domain; e.g., amino acids corresponding to Gly-3 to Ser-114 in SEQ ID NO: 1 or amino acids corresponding to Gly-3 to Asn-114 in SEQ ID NO:4, see e.g., FIG. 1);

(b) Carboxy-terminal portion of Domain IB (e.g., amino acids corresponding to Gly-115 to Glu-133 in SEQ ID NO:1 or SEQ ID NO:4; and amino acids corresponding to Gly-381 to Glu-399 in SEQ ID NO:133 or SEQ ID NO:134; see e.g., FIG. 1);

(c) Amino-terminal portion of Domain IB (e.g., amino acids corresponding to Ala-365 to Ala-380 in SEQ ID NO:133 or SEQ ID NO:134; see e.g., FIG. 1);

(d) Domain IB (i.e., amino acid sequences intervening between Domains II and III; e.g., amino acids corresponding to Ala-365 to Glu-399 in SEQ ID NO:133 or SEQ ID NO:134; see e.g., FIG. 1);

(e) a carboxy-terminal tail selected from the group consisting of:

(i) Arg-Glu-Asp-Leu-Lys (SEQ ID NO: 135);

(ii) Arg-Glu-Asp-Leu (SEQ ID NO: 136); and (iii) Lys-Asp-Glu-Leu (SEQ ID NO: 137), wherein one or more of said domains has been modified with amino acid substitutions, as described herein, to reduce or eliminate immunogenicity.

Embodiments of the invention further comprise PE variants. For example, such variants include, without limitation, PE polypeptide examples as shown in SEQ ID Nos: 143 to 163 and SEQ ID No:175.

Embodiments of the invention comprise any one or more of the PE-A domains indicated in the preceding paragraphs, wherein said one or more domains are chemically linked, covalently coupled, or fused (i.e., as in-frame fusion proteins) with a heterologous polypeptide (for example, such as ligand or antigen-binding polypeptide).

Embodiments of the invention include polypeptides comprising PE wherein one or more amino acids are substituted with any combination of one or more conservative amino acid substitutions, non-conservative amino acid substitutions, non-naturally occurring amino acid substitutions, non-standard amino acids, and/or substitutions with amino acid analogs and further wherein said polypeptides are non-immunogenic or exhibit reduced immunogenicity as determined and assayed by comparison to immunogenicity of corresponding non-amino acid substituted forms of PE; as measured using in vitro or in vivo assays. In particular embodiments, amino acid substituted forms of PE are at least 25%, at least about 25%, at least 50%, at least about 50%, at least 75%, or at least about 75% less immunogenic compared to corresponding non-amino acid substituted forms of PE. In particular embodiments, amino acid substituted forms of PE are at least 2-fold, at least about 2-fold, at least 3-fold, at least about 3-fold, at least 4-fold, at least about 4-fold, at least 5-fold, at least about 5-fold, at least 10-fold, at least about 10-fold, at least 50-fold, at least about 50-fold, at least 100-fold, at least about 100-fold, at least 500-fold, at least about 500-fold, at least 1000-fold, or at least about 1000-fold less immunogenic compared to corresponding non-amino acid substituted forms of PE. In one embodiment, amino acid substituted forms of PE are non-immunogenic or exhibit undetectable immunogenicity compared to corresponding non-amino acid substituted forms of PE.

The immunogenicity of substituted peptides may be measured via assays routinely known and used by those of skill in the art. For example, immunogenicity may be assayed by methods including, but not limited to, the proliferation assays described in Example 1 herein.

Additionally, methods for predicting, and assays for assessing, immunogenicity include those methods and assays such as described or referenced in:

Baker M P and Jones T D. Identification and removal of immunogenicity in therapeutic proteins. *Curr. Opin. Drug. Disc. Dev.* 2007 10(2): 219-227.

Bryson C J, Jones T D, Baker M P. Prediction of immunogenicity of therapeutic proteins: validity of computational tools. *BioDrugs.* 2010; 24(1):1-8.

Chester, K, Baker, M P and Mayer A. Overcoming the immunologic response to foreign enzymes in cancer therapy. *Expert Rev. Clin. Immunol.* 2006 1(4): 549-559.

Hochuli E. Interferon immunogenicity: technical evaluation of interferon-alpha 2a. *J Interferon Cytokine Res.* 1997 17 Suppl 1:S15-21.

Jaber A and Baker M P. Assessment of the immunogenicity of different interferon beta-1a formulations using ex vivo T cell assays. *J Pharm Biomed Anal* 2007 43(4):1256-61.

Perry L C, Jones T D and Baker M P. New approaches to prediction of immune responses to therapeutic proteins during preclinical development. *Drugs R D.* 2008 9(6): 385-96.

Schellekens, H., Ryff, J. C., and Van Der Meide, P. H. Assays for antibodies to human interferon-alpha: the need for standardization. *J. Interferon Cytokine Res.* 1997 17(Suppl. 1), S5-S8.

Embodiments of the invention include polypeptides comprising PE wherein one or more amino acids are substituted with any combination of one or more conservative amino acid substitutions, non-conservative amino acid substitutions, non-naturally occurring amino acid substitutions, non-standard amino acids, and/or substitutions with amino acid analogs and further wherein said polypeptides retain biological activity as determined and assayed by comparison to biological activities of corresponding non-amino acid substituted forms of PE; such as, but not limited to, cell killing activity, cell cytotoxicity, inactivation of the translation elongation factor EF-2, ADP-ribosylation of EF-2, and inhibition of protein synthesis as measured using in vitro or in vivo assays. In particular embodiments, amino acid substituted forms of PE exhibit 100% or about 100% of biological activity compared to corresponding non-amino acid substituted forms of PE. In particular embodiments, amino acid substituted forms of PE exhibit at least 95%, or at least about 95% of biological activity compared to corresponding non-amino acid substituted forms of PE. In particular embodiments, amino acid substituted forms of PE exhibit at least 90%, at least about 90%, at least 85%, at least about 85%, at least 80%, at least about 80%, at least 75%, at least about 75%, at least 70%, at least about 70%, at least 60%, at least about 60%, at least 50%, or at least about 50% of biological activity compared to corresponding non-amino acid substituted forms of PE.

Embodiments of the invention further comprise fusion proteins, conjugates, covalently-linked, and non-covalently linked amino acid substituted forms of PE, or fragments thereof, as described herein. Amino acid substituted forms of PE may be fused, conjugated or otherwise linked with any artificial, recombinant, or naturally occurring molecule or polypeptide to modify PE activity and/or PE localization/targeting, such as by conferring to PE, via said fusion or conjugation, the tissue targeting, cell targeting, or subcellular localization properties of the molecule to which PE is fused, conjugated or otherwise linked. For example, but without limitation, amino acid substituted forms, or fragments thereof, of PE may be fused, conjugated, or otherwise linked with any type of antibody or antigen-binding fragments thereof, cell-surface receptor, secreted or cell-surface ligand, or fragments thereof.

In one embodiment, amino acid substituted forms of PE, including amino acid substituted forms of PE fused, conjugated or otherwise linked to another molecule or polypeptide are useful in the treatment of cancer; including, but not limited to, types of cancer described herein. In one embodiment, amino acid substituted forms of PE as described herein are useful for the preparation of a medicament for the treatment of cancer; including, but not limited to, types of cancer described herein.

In one embodiment, amino acid substituted forms of PE, or fragments thereof, may be fused, conjugated, or otherwise linked, without limitation, antigen-binding moieties such as antibodies, or fragments thereof, which specifically or preferentially bind to disease associated antigens. Such molecules include, for example, but without limitation, antibodies indicated in Table 1.

TABLE 1

Examples of Antibodies and Therapeutic Uses

| NAME | TRADE NAME | Putative Antigen Targets | Example(s) of Therapeutic Use |
|---|---|---|---|
| 3F8 | | GD2 | neuroblastoma |
| ABAGOVOMAB | | CA-125 (imitation) | ovarian cancer |
| ABCIXIMAB | REOPRO | CD41 (integrin alpha-IIb) | platelet aggregation inhibitor |
| ADALIMUMAB | HUMIRA | TNF-α | rheumatoid arthritis etc. |
| ADECATUMUMAB | | EpCAM | prostate and breast cancer |
| AFELIMOMAB | | TNF-α | sepsis |
| AFUTUZUMAB | | CD20 | lymphoma |
| ALACIZUMAB PEGOL | | VEGFR2 | cancer |
| ALD518 | | IL-6 | rheumatoid arthritis |
| ALEMTUZUMAB | CAMPATH, MABCAMPATH | CD52 | CLL, CTCL |
| ALTUMOMAB PENTETATE | HYBRI-CEAKER | CEA | colorectal cancer (diagnosis) |
| ANATUMOMAB MAFENATOX | | TAG-72 | non-small cell lung carcinoma |
| ANRUKINZUMAB | | IL-13 | antigen-induced pulmonary inflammation, asthma |
| APOLIZUMAB | | HLA-DR | hematological cancers |
| ARCITUMOMAB | CEA-SCAN | CEA | gastrointestinal cancers (diagnosis) |
| ASELIZUMAB | | L-selectin (CD62L) | severely injured patients |
| ATLIZUMAB | ACTEMRA, ROACTEMRA | IL-6 receptor | rheumatoid arthritis |
| ATOROLIMUMAB | | Rhesus factor | hemolytic disease of the newborn |
| BAPINEUZUMAB | | beta amyloid | Alzheimer's disease |
| BASILIXIMAB | SIMULECT | CD25 (α chain of IL-2 receptor) | prevention of organ transplant rejections |
| BAVITUXIMAB | | phosphatidylserine | cancer, viral infections |
| BECTUMOMAB | LYMPHOSCAN | CD22 | non-Hodgkin's lymphoma (detection) |
| BELIMUMAB | BENLYSTA, LYMPHOSTAT-B | BAFF | non-Hodgkin lymphoma etc. |
| BENRALIZUMAB | | CD125 | asthma |
| BERTILIMUMAB | | CCL11 (eotaxin-1) | severe allergic disorders |
| BESILESOMAB | SCINTIMUN | CEA-related antigen | inflammatory lesions and metastases (defection) |
| BEVACIZUMAB | AVASTIN | VEGF-A | metastatic cancer |
| BICIROMAB | FIBRISCINT | fibrin II, beta chain | thromboembolism (diagnosis) |
| BIVATUZUMAB MERTANSINE | | CD44 v6 | squamous cell carcinoma |
| BLINATUMOMAB | | CD19 | cancer |
| BRENTUXIMAB VEDOTIN | | CD30 (TNFRSF8) | hematologic cancers |
| BRIAKINUMAB | | IL-12, IL-23 | psoriasis, rheumatoid arthritis, inflammatory bowel diseases, multiple sclerosis |
| CANAKINUMAB | ILARIS | IL-1 | rheumatoid arthritis |
| CANTUZUMAB MERTANSINE | | mucin CanAg | colorectal cancer etc. |
| CAPROMAB PENDETIDE | PROSTASCINT | prostatic carcinoma cells | prostate cancer (detection) |
| CATUMAXOMAB | REMOVAB | EpCAM, CD3 | ovarian cancer, malignant ascites, gastric cancer |
| CC49 | | TAG-72 | tumor detection |
| CEDELIZUMAB | | CD4 | prevention of organ transplant rejections, treatment of autoimmune diseases |
| CERTOLIZUMAB PEGOL | CIMZIA | TNF-α | Crohn's disease |
| CETUXIMAB | ERBITUX | EGFR | metastatic colorectal cancer and head and neck cancer |
| CITATUZUMAB BOGATOX | | EpCAM | ovarian cancer and other solid tumors |
| CIXUTUMUMAB | | IGF-1 receptor | solid tumors |
| CLENOLIXIMAB | | CD4 | rheumatoid arthritis |
| CLIVATUZUMAB TETRAXETAN | | MUC1 | pancreatic cancer |

TABLE 1-continued

Examples of Antibodies and Therapeutic Uses

| NAME | TRADE NAME | Putative Antigen Targets | Example(s) of Therapeutic Use |
|---|---|---|---|
| CONATUMUMAB | | TRAIL-R2 | cancer |
| CR6261 | | Influenza A hemagglutinin | infectious disease/influenza A |
| DACETUZUMAB | | CD40 | hematologic cancers |
| DACLIZUMAB | ZENAPAX | CD25 (α chain of IL-2 receptor) | prevention of organ transplant rejections |
| DARATUMUMAB | | CD38 (cyclic ADP ribose hydrolase) | myleoma, CD38-positive multiple myeloma |
| DENOSUMAB | PROLIA | RANKL | osteoporosis, bone metastases etc. |
| DETUMOMAB | | B-lymphoma cell | lymphoma |
| DORLIMOMAB ARITOX | | auto immune associated antigen | auto immune disorders |
| DORLIXIZUMAB | | CD3 | type 1 diabetes, autoimmune diseases |
| ECROMEXIMAB | | GD3 ganglioside | malignant melanoma |
| ECULIZUMAB | SOLIRIS | C5 | paroxysmal nocturnal hemoglobinuria |
| EDOBACOMAB | | Endotoxin | sepsis caused by Gram-negative bacteria |
| EDRECOLOMAB | PANOREX | EpCAM | colorectal carcinoma |
| EFALIZUMAB | RAPTIVA | LFA-1 (CD11a) | psoriasis (blocks T-cell migration) |
| EFUNGUMAB | MYCOGRAB | Hsp90 | invasive *Candida* infection |
| ELOTUZUMAB | | SLAMF7 | multiple myeloma |
| ELSILIMOMAB | | IL-6 | Lymphoma, myeloma |
| ENLIMOMAB/ ENLIMOMAB PEGOL | | ICAM-1 (CD54) | stroke |
| EPITUMOMAB CITUXETAN | | Episialin | cancer |
| EPRATUZUMAB | | CD22 | cancer, SLE |
| ERLIZUMAB | | ITGB2 (CD18) | heart attack, stroke, traumatic shock |
| ERTUMAXOMAB | REXOMUN | HER2/neu, CD3 | breast cancer etc. |
| ETARACIZUMAB | ABEGRIN | integrin $\alpha v\beta 3$ | melanoma, prostate cancer, ovarian cancer etc. |
| EXBIVIRUMAB | | hepatitis B surface antigen | hepatitis B |
| FANOLESOMAB | NEUTROSPEC | CD15 | appendicitis (diagnosis) |
| FARALIMOMAB | | interferon receptor | autoimmune disorders |
| FARLETUZUMAB | | folate receptor 1 | ovarian cancer |
| FELVIZUMAB | | respiratory syncytial virus | respiratory syncytial virus infection |
| FEZAKINUMAB | | IL-22 | rheumatoid arthritis, psoriasis |
| FIGITUMUMAB | | IGF-1 receptor | adrenocortical carcinoma, non-small cell lung carcinoma etc. |
| FONTOLIZUMAB | HUZAF | IFN-γ | Crohn's disease etc. |
| FORAVIRUMAB | | rabies virus glycoprotein | rabies (prophylaxis) |
| FRESOLIMUMAB | | TGF-β | idiopathic pulmonary fibrosis, local segmental glomerulosclerosis, cancer |
| GALIXIMAB | | CD80 | B-cell lymphoma |
| GANTENERUMAB | | beta amyloid | Alzheimer's disease |
| GAVILIMOMAB | | CD147 (basigin) | graft versus host disease |
| GEMTUZUMAB OZOGAMICIN | MYLOTARG | CD33 | acute myelogenous leukemia |
| GIRENTUXIMAB | RENCAREX | carbonic anhydrase 9 (CA-IX) | clear cell renal cell carcinoma |
| GLEMBATUMUMAB VEDOTIN | | GPNMB | melanoma, breast cancer |
| GOLIMUMAB | SIMPONI | TNF-α | rheumatoid arthritis, psoriatic arthritis, ankylosing spondylitis |
| GOMILIXIMAB | | CD23 (IgE receptor) | allergic asthma |
| IBALIZUMAB | | CD4 | HIV infection |
| IBRITUMOMAB TIUXETAN | ZEVALIN | CD20 | non-Hodgkin's lymphoma |
| IGOVOMAB | INDIMACIS-125 | CA-125 | ovarian cancer (diagnosis) |

TABLE 1-continued

Examples of Antibodies and Therapeutic Uses

| NAME | TRADE NAME | Putative Antigen Targets | Example(s) of Therapeutic Use |
|---|---|---|---|
| IMCIROMAB | MYOSCINT | cardiac myosin | cardiac imaging |
| INFLIXIMAB | REMICADE | TNF-α | rheumatoid arthritis, ankylosing spondylitis, psoriatic arthritis, psoriasis, Crohn's disease, ulcerative colitis |
| INTETUMUMAB | | CD51 | solid tumors (prostate cancer, melanoma) |
| INOLIMOMAB | | CD25 (α chain of IL-2 receptor) | graft versus host disease |
| INOTUZUMAB OZOGAMICIN | | CD22 | cancer |
| IPILIMUMAB | YERVOY | CD152 | melanoma |
| IRATUMUMAB | | CD30 (TNFRSF8) | Hodgkin's lymphoma |
| KELIXIMAB | | CD4 | chronic asthma |
| LABETUZUMAB | CEA-CIDE | CEA | colorectal cancer |
| LEBRIKIZUMAB | | IL-13 | asthma |
| LEMALESOMAB | | NCA-90 (granulocyte antigen) | diagnostic agent |
| LERDELIMUMAB | | TGF beta 2 | reduction of scarring after glaucoma surgery |
| LEXATUMUMAB | | TRAIL-R2 | cancer |
| LIBIVIRUMAB | | hepatitis B surface antigen | hepatitis B |
| LINTUZUMAB | | CD33 | cancer |
| LORVOTUZUMAB MERTANSINE | | CD56 | cancer |
| LUCATUMUMAB | | CD40 | multiple myeloma, non-Hodgkin's lymphoma, Hodgkin's lymphoma |
| LUMILIXIMAB | | CD23 (IgE receptor) | chronic lymphocytic leukemia |
| MAPATUMUMAB | | TRAIL-R1 | cancer |
| MASLIMOMAB | | T-cell receptor | autoimmune disorders |
| MATUZUMAB | | EGFR | colorectal, lung and stomach cancer |
| MEPOLIZUMAB | BOSATRIA | IL-5 | asthma and white blood cell diseases |
| METELIMUMAB | | TGF beta 1 | systemic scleroderma |
| MILATUZUMAB | | CD74 | multiple myeloma and other hematological malignancies |
| MINRETUMOMAB | | TAG-72 | cancer |
| MITUMOMAB | | GD3 ganglioside | small cell lung carcinoma |
| MOROLIMUMAB | | Rhesus factor | disease antigen |
| MOTAVIZUMAB | NUMAX | respiratory syncytial virus | respiratory syncytial virus (prevention) |
| MUROMONAB-CD3 | ORTHOCLONE OKT3 | CD3 | prevention of organ transplant rejections |
| NACOLOMAB TAFENATOX | | C242 antigen | colorectal cancer |
| NAPTUMOMAB ESTAFENATOX | | 5T4 | non-small cell lung carcinoma, renal cell carcinoma |
| NATALIZUMAB | TYSABRI | integrin α4 | multiple sclerosis, Crohn's disease |
| NEBACUMAB | | Endotoxin | sepsis |
| NECITUMUMAB | | EGFR | non-small cell lung carcinoma |
| NERELIMOMAB | | TNF-α | auto immune disorders |
| NIMOTUZUMAB | THERACIM, THERALOC | EGFR | squamous cell carcinoma, head and neck cancer, nasopharyngeal cancer, glioma |
| NOFETUMOMAB MERPENTAN | VERLUMA | cancer-associated antigen | cancer (diagnosis) |
| OCRELIZUMAB | | CD20 | rheumatoid arthritis, lupus erythematosus etc. |
| ODULIMOMAB | | LFA-1 (CD11a) | prevention of organ transplant rejections, immunological diseases |
| OFATUMUMAB | ARZERRA | CD20 | chronic lymphocytic leukemia |
| OLARATUMAB | | PDGF-R α | cancer |

TABLE 1-continued

Examples of Antibodies and Therapeutic Uses

| NAME | TRADE NAME | Putative Antigen Targets | Example(s) of Therapeutic Use |
|---|---|---|---|
| OMALIZUMAB | XOLAIR | IgE Fc region | allergic asthma |
| OPORTUZUMAB MONATOX | | EpCAM | cancer |
| OREGOVOMAB | OVAREX | CA-125 | ovarian cancer |
| OTELIXIZUMAB | | CD3 | diabetes mellitus type 1 |
| PAGIBAXIMAB | | lipoteichoic acid | sepsis (*Staphylococcus*) |
| PALIVIZUMAB | SYNAGIS, ABBOSYNAGIS | respiratory syncytial virus | respiratory syncytial virus (prevention) |
| PANITUMUMAB | VECTIBIX | EGFR | colorectal cancer |
| PANOBACUMAB | | *Pseudomonas aeruginosa* | *Pseudomonas aeruginosa* infection |
| PASCOLIZUMAB | | IL-4 | asthma |
| PEMTUMOMAB | THERAGYN | MUC1 | cancer |
| PERTUZUMAB | OMNITARG | HER2/neu | cancer |
| PEXELIZUMAB | | C5 | reduction of side effects of cardiac surgery |
| PINTUMOMAB | | adenocarcinoma antigen | adenocarcinoa |
| PRILIXIMAB | | CD4 | Crohn's disease, multiple sclerosis |
| PRITUMUMAB | | vimentin | brain cancer |
| PRO 140 | | CCR5 | HIV infection |
| RAFIVIRUMAB | | rabies virus glycoprotein | rabies (prophylaxis) |
| RAMUCIRUMAB | | VEGFR2 | solid tumors |
| RANIBIZUMAB | LUCENTIS | VEGF-A | macular degeneration (wet form) |
| RAXIBACUMAB | | anthrax toxin, protective antigen | anthrax (prophylaxis and treatment) |
| REGAVIRUMAB | | cytomegalovirus glycoprotein B | cytomegalovirus infection |
| RESLIZUMAB | | IL-5 | inflammations of the airways, skin and gastrointestinal tract |
| RILOTUMUMAB | | HGF | solid tumors |
| RITUXIMAB | MABTHERA, RITUXAN | CD20 | lymphomas, leukemias, some autoimmune disorders |
| ROBATUMUMAB | | IGF-1 receptor | cancer |
| RONTALIZUMAB | | IFN-α | systemic lupus erythematosus |
| ROVELIZUMAB | LEUKARREST | CD11, CD18 | haemorrhagic shock |
| RUPLIZUMAB | ANTOVA | CD154 (CD40L) | rheumatic diseases |
| SATUMOMAB PENDETIDE | | TAG-72 | cancer |
| SEVIRUMAB | | cytomegalovirus | cytomegalovirus infection |
| SIBROTUZUMAB | | FAP | cancer |
| SIFALIMUMAB | | IFN-α | SLE, dermatomyositis, polymyositis |
| SILTUXIMAB | | IL-6 | cancer |
| SIPLIZUMAB | | CD2 | psoriasis, graft-versus-host disease (prevention) |
| SOLANEZUMAB | | beta amyloid | Alzheimer's disease |
| SONEPCIZUMAB | | sphiagosine-1-phosphate | choroidal and retinal neovascularization |
| SONTUZUMAB | | episialin | disease antigen |
| STAMULUMAB | | myostatin | muscular dystrophy |
| SULESOMA | LEUKOSCAN | NCA-90 (granulocyte antigen) | osteomyelitis (imaging) |
| TACATUZUMAB TETRAXETAN | AFP-CIDE | alpha-fetoprotein | cancer |
| TADOCIZUMAB | | integrin αIIbβ3 | percutaneous coronary intervention |
| TALIZUMAB | | IgE | allergic reaction |
| TANEZUMAB | | NGF | pain |
| TAPLITUMOMAB PAPTOX | | CD19 | cancer |
| TEFIBAZUMAB | AUREXIS | clumping factor A | *Staphylococcus aureus* infection |
| TELIMOMAB ARITOX | | autoimmune antigen | autoimmune disorders |
| TENATUMOMAB | | tenascin C | cancer |
| TENELIXIMAB | | CD40 | autoimmune disorders |
| TEPLIZUMAB | | CD3 | diabetes mellitus type 1 |

TABLE 1-continued

Examples of Antibodies and Therapeutic Uses

| NAME | TRADE NAME | Putative Antigen Targets | Example(s) of Therapeutic Use |
|---|---|---|---|
| TGN1412 | | CD2 | chronic lymphocytic leukemia, rheumatoid arthritis |
| TICILIMUMAB | | CTLA-4 | cancer |
| TIGATUZUMAB | | TRAIL-R2 | cancer |
| TNX-650 | | IL-13 | Hodgkin's lymphoma |
| TOCILIZUMAB | ACTEMRA, ROACTEMRA | IL-6 receptor | rheumatoid arthritis |
| TORALIZUMAB | | CD154 (CD40L) | rheumatoid arthritis, lupus nephritis |
| TOSITUMOMAB | BEXXAR | CD20 | follicular lymphoma |
| TRASTUZUMAB | HERCEPTIN | HER2/neu | breast cancer |
| TREMELIMUMAB | | CTLA-4 | cancer |
| TUCOTUZUMAB CELMOLEUKIN | | EpCAM | cancer |
| TUVIRUMAB | | hepatitis B virus | chronic hepatitis B |
| URTOXAZUMAB | | *Escherichia coli* | diarrhoea caused by *E. coli* |
| USTEKINUMAB | STELARA | IL-12, IL-23 | multiple sclerosis, psoriasis, psoriatic arthritis |
| VAPALIXIMAB | | AOC3 (VAP-1) | autoimmune disorders |
| VEDOLIZUMAB | | integrin α4β7 | Crohn's disease, ulcerative colitis |
| VELTUZUMAB | | CD20 | non-Hodgkin's lymphoma |
| VEPALIMOMAB | | AOC3 (VAP-1) | inflammation |
| VISILIZUMAB | NUVION | CD3 | Crohn's disease, ulcerative colitis |
| VOLOCIXIMAB | | integrin α5β1 | solid tumors |
| VOTUMUMAB | HUMASPECT | tumor antigen CTAA16.88 | colorectal tumors |
| ZALUTUMUMAB | HUMAX-EGFR | EGFR | squamous cell carcinoma of the head and neck |
| ZANOLIMUMAB | HUMAX-CD4 | CD4 | rheumatoid, arthritis, psoriasis, T-cell lymphoma |
| ZIRALIMUMAB | | CD147 (basigin) | autoimmune disorders |
| ZOLIMOMAB ARITOX | | CD5 | systemic lupus erythematosus, graft-versus-host disease |

In certain embodiments, amino acid substituted forms of PE, or fragments thereof, may be fused, conjugated, or otherwise linked, without limitation, to naturally occurring normal or disease related molecules such as secreted, extracellular, intracellular, transmembrane, or cell-surface-bound molecules or fragments thereof (or non-naturally occurring variants and fragments thereof), such as without limitation: ligands, receptors, receptor extracellular domains, cytokines, growth factors, cell signaling proteins, extracellular and intracellular enzymes, structural proteins, cell adhesion proteins and molecules, cluster of differentiation (CD) molecules, mitogens, cell division regulating molecules, cancer/tumor markers and antigens, et cetera. In certain embodiments, molecules which are normally transmembrane and cell-surface bound polypeptides may be fused or conjugated to amino acid substituted forms of PE as polypeptide fragments lacking at least their transmembrane domains or polypeptide regions responsible for cell-surface binding.

In certain embodiments, molecules may be fused or conjugated to amino acid substituted forms of PE wherein such molecules possess or retain the ability (even as fusion proteins or protein conjugates) to form multimeric complexes (such as hetero- and homopolymers including, but not limited to, dimers, trimers, tetramers, pentamers, hexamers, et cetera.)

In certain embodiments, amino acid substituted forms of PE, or fragments thereof, may be generated as in-frame polypeptide fusion proteins with molecules (such as, but not limited to, those referenced above) wherein the PE moiety is either an amino-terminal portion or a carboxyl-terminal portion of the fusion protein. Determination of which of these two configurations provides the desired results and/or biological activities may be determined by routine experimentation practiced by those skilled in the art.

In certain embodiments, amino acid substituted forms of PE, or fragments thereof, may be generated as fusion proteins wherein heterologous amino acid sequences (such as cell targeting sequences) are inserted within the amino acid substituted form of PE (i.e., heterologous amino acids are flanked at the amino terminus and at the carboxy terminus by PE amino acid sequences). An example of a non-amino acid substituted form of PE in such a configuration is demonstrated in U.S. Pat. No. 8,854,044 wherein a TGF-α polypeptide is incorporated at amino acid residues 607 to 604 within a "PE37" polypeptide sequence. See e.g., U.S. Pat. No. 8,854,044, FIG. 1.

Some examples of molecules which may be fused, conjugated, or otherwise linked to amino acid substituted forms of PE, include for example, but without limitation, those such as indicated in Table 2.

Table 2: Examples of Potential Compounds and Indications to which Amino Acid Substituted Forms of PE May Be Fused or Conjugated for Therapeutic Use Note: The potential indications and nucleic acid and amino acid sequences shown in Table 2 (as well as accession numbers listed) are presented for purposes of providing a few illustrative examples only. Thus, embodiments of the invention may or may not comprise these indications and sequences. Accordingly, it is envisioned that embodiments of the invention comprise other indication uses as well as other molecules and sequence variants (e.g., naturally occurring variants (such as allelic or polymorphic variants) and non-naturally occurring variants (such as genetically engineered or mutated variants)) of these sequences wherein one or multiple amino acids are changed and/or wherein only a fragment or fragments of such sequences are fused or conjugated to amino acid substituted forms of PE. Hence, the examples shown in Table 2 should in no manner be considered limiting with respect to potential therapeutic indications or protein fusions and conjugates of amino acid modified forms of PE.

| Example Molecule (Nucleotide Accession*) [Protein Accession**] | Potential Indications | Example Amino Acid Sequence |
|---|---|---|
| Mesothelin (NM_013404) [NP_037536] | Pancreatic cancer<br>Ovarian cancer | MALPTARPLLGSCGTPALGSLLFLLFSLGWVQPS RTLAGETGQEAAPLDGVLANPPNISSLSPRQLLG FPCAEVSGLSTERVRELAVALAQKNVKLSTEQLR CLAHRLSEPPEDLDALPLDLLLFLNPDAFSGPQA CTRFFSRITKANVDLLPRGAPERQRLLPAALACW GVRGSLLSEADVRALGGLACDLPGRFVAESAEVL LPRLVSCPGPLDQDQQEAARAALQGGGPPYGPPS TWSVSTMDALRGLLPVLGQPIIRSIPQGIVAAWR QRSSRDPSWRQPERTILRPRFRREVEKTACPSGK KAREIDESLIFYKKWELEACVDAALLATQMDRVN AIPFTYEQLDVLKHKLDELYPQGYPESVIQHLGY LFLKMSPEDIRKWNVTSLETLKALLEVNKGHEMS PQAPRRPLPQVATLIDRFVKGRGQLDKDTLDTLT AFYPGYLCSLSPEELSSVPPSSIWAVRPQDLDTC DPRQLDVLYPKARLAFQNMNGSEYFVKIQSFLGG APTEDLKALSQQNVSMDLATFMKLRTDAVLPLTV AEVQKLLGPHVEGLKAEERHRPVRDWILRQRQDD LDTLGLGLQGGIPNGYLVLDLSMQEALSGTPCLL GPGPVLTVLALLLASTLA (SEQ ID NO: 167) |
| CD24 (NM_013230) [AAH64619] | Liver cancer<br>Colorectal cancer<br>Pancreatic cancer | MGRAMVARLGLGLLLLALLLPTQIYSSETTTGTS SNSSQSTSNSGLAPNPTNATTKAAGGALQSTASL FVVSLSLLHLYS (SEQ ID NO: 168) |
| CD22 (AB013007) [BAA36576] | Hairy Cell Leukemia<br>Chronic Lymphocytic Leukemia<br>Non-Hodgkin's Lymphoma | VRRAPLSEGPHSLGCYNPMMEDGISYTTLRFPEM NIPRTG (SEQ ID NO: 169) |
| CD25 a.k.a., Interleukin 2 receptor, alpha chain (NM_000417) [NP_000408] | Hodgkin's Lymphoma<br>Hairy Cell Leukemia<br>Chronic Lymphocytic Leukemia<br>Cutaneous T-cell Lymphoma<br>Adult T-cell leukemia | MDSYLLMWGLLTFIMVPGCQAELCDDDPPEIPHA TFKAMAYKEGTMLNCECKRGFRRIKSGSLYMLCT GNSSHSSWDNQCQCTSSATRNTTKQVTPQPEEQK ERKTTEMQSPMQPVDQASLPGHCREPPPWENEAT ERIYHFVVGQMVYYQCVQGYRALHRGPAESVCKM THGKTRWTQPQLICTGEMETSQFPGEEKPQASPE GRPESETSCLVTTTDFQIQTEMAATMETSIFTTE YQVAVAGCVFLLISVLLLSGLTWQRRQRKSRRTI (SEQ ID NO: 170) |
| CD174 a.k.a., Lewis Y, galactoside 3 (4)-L-fucosyl-transferase (NM_000149) [NP_000140] | Bladder cancer<br>Breast cancer<br>Colorectal cancer<br>Esophageal cancer<br>Gastric cancer<br>Lung cancer<br>Pancreatic cancer | MDPLGAAKPQWPWRRCLAALLFQLLVAVCFFSYL RVSRDDATGSPRAPSGSSRQDTTPTRPTLLILLW TWPFHIPVALSRCSEMVPGTADCHITADRKVYPQ ADTVIVHHWDIMSNPKSRLPPSPRPQGQRWIWFN LEPPPNCQHLEALDRYFNLTMSYRSDSDIFTPYG WLEPWSGQPAHPPLNLSAKTELVAWAVSNWKPDS ARVRYYQSLQAHLKVDVYGRSHKPLPKGTMMETL SRYKFYLAFENSLHPDYITEKLWRNALEAWAVPV VLGPSRSNYERFLPPDAFIHVDDFQSPKDLARYL QELDKDHARYLSYFRWRETLRPRSFSWALDFCKA CWKLQQESRYQTVRSIAAWFT (SEQ ID NO: 171) |
| TPBG a.k.a., oncofetal | Non small cell lung cancer | MPGGCSRGPAAGDGRLRLARLALVLLGWVSSSSP TSSASSFSSSAPFLASAVSAQPPLPDQCPALCEC |

-continued

| Example Molecule (Nucleotide Accession*) [Protein Accession**] | Potential Indications | Example Amino Acid Sequence |
|---|---|---|
| antigen 5T4, 5T4 oncofetal trophoblast glycoprotein (NM_006670) [CAA09930] | Renal carcinoma<br>Pancreatic cancer | SEAARTVKCVNRNLTEVPTDLPAYVRNLFLTGNQ LAVLPAGAFARRPPLAELAALNLSGSRLDEVRAG AFEHLPSLRQLDLSHNPLADLSPFAFSGSNASVS APSPLVELILNHIVPPEDERQNRSFEGMVVAALL AGRALQGLRRLELASNHFLYLPRDVLAQLPSLRH LDLSNNSLVSLTYVSFRNLTHLESLHLEDNALKV LHNGTLAELQGLPHIRVFLDNNPWVCDCHMADMV TWLKETEVVQGKDRLTCAYPEKMRNRVLLELNSA DLDCDPILPPSLQTSYVFLGIVLALIGAIFLLVL YLNRKGIKKWMHNIRDACRDHMEGYHYRYEINAD PRLTNLSSNSDV (SEQ ID NO: 172) |
| CD56 a.k.a., NCAM1, neural cell adhesion molecule 1 isoform 1 precursor (NM_000615) [NP_000606] | Small cell lung cancer<br>Merkel cell carcinoma<br>Ovarian cancer<br>Neuroendocrine tumors<br>Multiple Myeloma | MLQTKDLIWTLFFLGTAVSLQVDIVPSQGEISVG ESKFFLCQVAGDAKDKDISWFSPNGEKLTPNQQR ISVVWNDDSSSTLTIYNANIDDAGIYKCVVTGED GSESEATVNVKIFQKLMFKNAPTPQEFREGEDAV IVCDVVSSLPPTIIWKHKGRDVILKKDVRFIVLS NNYLQIRGIKKTDEGTYRCEGRILARGEINFKDI QVIVNVPPTIQARQNIVNATANLGQSVTLVCDAE GFPEPTMSWTKDGEQIEQEEDDEKYIFSDDSSQL TIKKVDKNDEAEYICIAENKAGEQDATIHLKVFA KPKITYVENQTAMELEEQVTLTCEASGDPIPSIT WRTSTRNISSEEKTLDGHMVVRSHARVSSLTLKS IQYTDAGEYICTASNTIGQDSQSMYLEVQYAPKL QGPVAVYTWEGNQVNITCEVFAYPSATISWFRDG QLLPSSNYSNIKIYNTPSASYLEVTPDSENDFGN YNCTAVNRIGQESLEFILVQADTPSSPSIDQVEP YSSTAQVQFDEPEATGGVPILKYKAEWRAVGEEV WHSKWYDAKEASMEGIVTIVGLKPETTYAVRLAA LNGKGLGEISAASEFKTQPVQGEPSAPKLEGQMG EDGNSIKVNLIKQDDGGSPIRHYLVRYRALSSEW KPEIRLPSGSDHVMLKSLDWNAEYEVYVVAENQQ GKSKAAHFVFRTSAQPTAIPANGSPTSGLSTGAI VGILIVIFVLLLVVVDITCYFLNKCGLFMCIAVN LCGKAGPGAKGKDMEEGKAAFSKDESKEPIVEVR TEEERTPNHDGGKHTEPNETTPLTEPEKGPVEAK PECQETETKPAPAEVKTVPNDATQTKENESKA (SEQ ID NO: 173) |
| C-type lectin-like molecule-1 a.k.a., CLL-1 (AY547296) [AAT11783] | Acute myeloid leukemia | MWIDFFTYSSMSEEVTYADLQFQNSSEMEKIPEI GKFGEKAPPAPSHVWRPAALFLTLLCLLLLIGLG VLASMFHVTLKIEMKKMNKLQNISEELQRNISLQ LMSNMNISNKIRNLSTTLQTIATKLCRELYSKEQ EHKCKPCPRRWIWHKDSCYFLSDDVQTWQESKMA CAAQNASLLKINNKNALEFIKSQSRSYDYWLGLS PEEDSTRGMRVDNIINSSAWVIRNAPDLNNMYCG YINRLYVQYYHCTYKQRMICEKMANPVQLGSTYF REA (SEQ ID NO: 174) |

*"Nucleotide Accession" refers to the NCBI Reference Sequence accession number associated with the corresponding nucleic acid sequence as found in the "Nucleotide" database provided for public access and searching (via the Internet) through the National Center for Biotechnology Information, U.S. National Library of Medicine (8600 Rockville Pike, Bethesda MD, 20894 USA (www.ncbi.nlm.nih.gov)).
**"Protein Accession" refers to the NCBI Reference Sequence accession number associated with the corresponding amino acid sequence as found in the "Protein" database provided for public access and searching (via the Internet) through the National Center for Biotechnology Information, U.S. National Library of Medicine (8600 Rockville Pike, Bethesda MD, 20894
USA (www.ncbi.nlm.nih.gov)).

In one embodiment, the present invention includes isolated nucleic acids and methods of expressing nucleic acids encoding any of the herein-referenced modified forms of PE, including fusions, conjugates, and otherwise linked molecules; whether such forms are expressed from a single or one more separate polynucleotide sequences; whether such polynucleotide sequences are expressed from a single or one or more separate expression vectors.

Expression Vectors

In one embodiment, the present invention includes methods of making and using recombinant expression vectors to express nucleic acids encoding polypeptides comprising any of the herein-referenced modified forms of PE, including fusions, conjugates, and otherwise linked molecules. Use of a wide variety of expression vectors are well-known and routinely used by those skilled in the art. A few examples of the types of expression vectors which may be used include, but are not limited to: derivatives of human or animal viruses (such as retrovirus, adeno-associated virus, pox, baculovirus, vaccinia, herpes simplex, Epstein-Barr, adenovirus, geminivirus, and caulimovirus vectors) and insect viruses (such as baculovirus); yeast vectors; bacteriophage vectors (e.g., bacteriophage lambda); plasmids; cosmids; artificial chromosomes; liposomes; electrically charged lipids (cytofectins); DNA-protein complexes, and biopolymers.

Gene Delivery and Expression Systems

A wide variety of methods (i.e., gene delivery systems) are available and well-known to those of skill in the art; any of such methods may be used for introducing nucleic acids encoding modified forms of PE into a cell, tissue, or organism for in vitro, in vivo, in situ, or ex vivo expression. The methods referenced below represent examples of ways in which nucleic acid(s) encoding modified forms of PE may be introduced into a cell. These examples are in no way intended to limit the scope of that may be used for gene delivery and expression of modified forms of PE in cells, tissues, or organisms; these examples are presented to illustrate the many available methods.

—Viral-Based Delivery of Target Nucleic Acids—

Gene therapy based methods can be used to deliver (into a host cell, tissue or organism) target nucleic acids encoding modified forms of PE (and other polynucleotides, as needed, to allow expression of the same). As one example, polynucleotides operably encoding the target nucleic acid can be delivered to a tissue or organism either as "naked nucleic acid" or as part of an expression vector. The term vector includes for example, but is not limited to, vectors such as plasmid vectors, cosmid vectors, artificial chromosome vectors, and viral vectors. Some examples of viral vectors include adenovirus, herpes simplex virus (HSV), alphavirus, simian virus 40, picomavirus, vaccinia virus, retrovirus, lentivirus, and adeno-associated virus. Vectors encoding modified forms of PE may be capable of replication in a cell in which it is introduced, or it may be preferred that the vector is not capable of replication. Vectors encoding modified forms of PE may be capable of integration into the genomic DNA of a cell (and subsequent expression therefrom), or it may be preferred that the vector is not capable of integrating into the host genome. An example of a vector that can integrate into the genomic DNA of a cell is a retroviral vector, in which an integrase enzyme mediates integration of the retroviral vector sequences. A vector may also contain transposon sequences that facilitate integration of the coding region into the genomic DNA of a host cell. Liposomes represent another manner in which target DNA may be delivered to a subject.

Selection of a vector depends upon a variety of desired characteristics in the resulting construct, such as a selection marker, vector replication rate, type of target host cell, species of host organism, desired duration of protein expression. An expression vector optionally includes expression control sequences operably linked to the coding sequence such that the coding region is expressed in the cell. The invention is not limited by the use of any particular promoter, and a wide variety is known. Promoters act as regulatory signals that bind RNA polymerase in a cell to initiate transcription of a downstream (3' direction) operably linked coding sequence. The promoter used in the invention may be a constitutive or an inducible promoter. It can be, but need not be, heterologous with respect to the cell to which it is introduced.

In certain embodiments, adenovirus expression vectors can be used to deliver (into a host cell, tissue or organism) target nucleic acids encoding modified forms of PE (and other polynucleotides, as needed, to allow expression of the same). The terms "adenovirus expression vector" is meant to include those constructs containing nucleic acid sequences sufficient to (a) support packaging of the construct and (b) to ultimately express a recombinant gene construct that has been inserted therein. In contrast to retroviruses, use of adenovirus vectors does not result in chromosomal integration because adenovirus DNA replicates in an episomal manner. Moreover, adenoviruses are considered to be structurally stable with no genome rearrangement occurring even after extensive virus reproduction and amplification. Methods of constructing and using adenovirus vectors as gene delivery systems are well-known to those of skill in the art.

In certain embodiments, adeno-associated virus (AAV) expression vectors can be used to deliver (into a host cell, tissue or organism) target nucleic acids encoding modified forms of PE (and other polynucleotides, as needed, to allow expression of the same). AAV may be desirable for a number or reasons; for example, because AAV vectors exhibit a high frequency of integration, can infect nondividing cells, and have a broad host range. AAV is a dependent parvovirus in that it requires coinfection with another virus (either adenovirus or a member of the herpes virus family) to undergo a productive infection in cultured cells. In the absence of coinfection with helper virus, the wild-type AAV genome integrates through its ends into a human chromosome where it resides as a latent provirus. When a cell containing latent AAV provirus is superinfected with a helper virus, the AAV genome is "rescued" from the chromosome and a normal productive infection is established. Methods of constructing and using AAV vectors as gene delivery systems are well-known to those of skill in the art.

In certain embodiments, retrovirus expression vectors can be used to deliver (into a host cell, tissue or organism) target nucleic acids encoding modified forms of PE (and other polynucleotides, as needed, to allow expression of the same). Retroviruses are a group of single-stranded RNA viruses characterized by the ability to convert their genomic RNA to double-stranded DNA in infected cells through a reverse-transcription process. The resulting DNA stably integrates into cellular chromosomes as a provirus and directs synthesis of viral proteins. Retroviral integration results in the retention of viral gene sequences in the recipient cell and in its descendants. Retroviral vectors are able to infect a broad variety of cell types. Methods of constructing and using retroviruses as gene delivery systems are well-known to those of skill in the art.

Many other expression vectors can also be used to deliver (into a host cell, tissue or organism) target nucleic acids encoding modified forms of PE (and other polynucleotides, as needed, to allow expression of the same). For example, vectors derived from viruses such as vaccinia viruses, herpesviruses, equine encephalitis viruses, hepatitis viruses and lentiviruses can be used. Methods of constructing and using viral expression vectors as gene delivery systems are well-known to those of skill in the art. The examples of such vectors referenced herein are not intended to be limiting with respect to the means by which modified forms of PE may be delivered and expressed in various host cells, tissues, or organisms.

—Non-Viral Delivery of Modified Target Nucleic Acids—

In addition to viral delivery of modified target nucleic acid, the following are additional methods of recombinant gene delivery can be used to deliver (into a host cell, tissue or organism) target nucleic acids encoding modified forms of PE (and other polynucleotides, as needed, to allow expression of the same). Methods of constructing and using non-viral gene delivery systems are well-known to those of skill in the art. See, for example, Al-Dosari et al., "Nonviral gene delivery: principle, limitations, and recent progress," *AAPS Journal,* 11(4):671-681 (2009); and references cited therein.

In certain embodiments, electroporation can be used to deliver (into a host cell, tissue or organism) target nucleic acids encoding modified forms of PE (and other polynucleotides, as needed, to allow expression of the same). Methods of using electroporation are well-known to those of skill in the art. See, for example, Bodles-Brakhop et al., "Electroporation for the delivery of DNA-based vaccines and immunotherapeutics: current clinical developments," *Mol. Ther.,* 17(4):585-592 (2009); and references cited therein. See also, Golzio et al., "Observations of the mechanisms of electromediated DNA uptake-from vesicles to tissues," *Curr Gene Ther.,* 10(4):256-266 (2010); and references cited therein. See also, Andre et al., "Nucleic acids electrotransfer in vivo: mechanisms and practical aspects," *Curr Gene Ther.,* 10(4): 267-280 (2010); and references cited therein. See also, Wells, "Electroporation and ultrasound enhanced non-viral gene delivery in vitro and in vivo," *Cell Biol Toxicol.,* 26(1):21-28 (2010); and references cited therein.

In certain embodiments, particle bombardment can be used to deliver (into a host cell, tissue or organism) target nucleic acids encoding modified forms of PE (and other polynucleotides, as needed, to allow expression of the same). This method depends on the ability to accelerate nucleic acid-coated microprojectiles to a sufficient velocity to allow them to pierce cell membranes, thereby delivering nucleic acid "payloads," without killing them. Some typical microprojectiles consist of biologically inert substances such as tungsten, platinum, and gold beads. Methods of using particle bombardment are well-known to those of skill in the art.

See, for example, Klein et al., "Particle bombardment: a universal approach for gene transfer to cells and tissues," *Curr. Opin. Biotechnol.,* 4(5):583-590 (1993); and references cited therein.

In certain embodiments, a variety of methods incorporating calcium phosphate co-precipitation can be used to deliver (into a host cell, tissue or organism) target nucleic acids encoding modified forms of PE (and other polynucleotides, as needed, to allow expression of the same). Methods of using calcium phosphate co-precipitation are well-known to those of skill in the art. See, for example, Uskoković et al., "Nanosized hydroxyapatite and other calcium phosphates: chemistry of formation and application as drug and gene delivery agents," *J.* Biomed. Mater. Res. B Appl. Biomater, 96(1):152-191 (2011); and references cited therein. See also, Colosimo et al., "Transfer and expression of foreign genes in mammalian cells," *Biotechniques,* 29(2):314-8, 320-322 (2000); and references cited therein.

In certain embodiments, microinjection and sonication methods can be used to deliver (into a host cell, tissue or organism) target nucleic acids encoding modified forms of PE (and other polynucleotides, as needed, to allow expression of the same). Methods of using microinjection and sonication are well-known to those of skill in the art. See, for example, Rochlitz et al., "Gene therapy of cancer," *Swiss Med. Wkly.,* 131(1-2):4-9 (2001); and references cited therein. See also, Donnelly et al., "Microneedle-based drug delivery systems: microfabrication, drug delivery, and safety," *Drug Deliv.,* 17(4): 187-207 (2010); and references cited therein. See also, Miller et al., "Sonoporation: mechanical DNA delivery by ultrasonic cavitation", *Somat. Cell Mol. Genet.,* 27(1-6): 115-34 (2002); and references cited therein.

In certain embodiments, liposomes and lipid formulations can be used to deliver (into a host cell, tissue or organism) target nucleic acids encoding modified forms of PE (and other polynucleotides, as needed, to allow expression of the same). Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. An example of a commonly used, commercially available lipid formulation is Lipofectamine (Gibco BRL). Methods of using liposomes and lipid formulations to deliver nucleic acids to cells, tissues and organisms are well-known to those of skill in the art. See, for example, Xiong et al., "Cationic liposomes as gene delivery system: transfection efficiency and new application," *Pharmazie,* 66(3):158-64 (2011); and references cited therein. See also, Pichon et al., "Chemical vectors for gene delivery: uptake and intracellular trafficking," *Curr Opin Biotechnol.,* 21(5): 640-645 (2010); and references cited therein. See also, Pathak et al., "Recent trends in non-viral vector-mediated gene delivery," *Biotechnol J.,* 4(11): 1559-1572 (2009).

Expression of Modified Forms of PE Via Gene Switch Modulation Systems

Expression of modified forms of PE, including fusions, conjugates, and otherwise linked molecules, may be expressed in host cells, tissues, and organisms using gene switch expression systems. Some examples, without limitation, of such gene expression systems, and genetically engineered cells comprising gene switch expression systems, which can be used to express polynucleotides and polypeptides of the present invention, are described in the following publications; each of which are hereby incorporated by reference herein:

WO 2009/045370 (PCT/US2008/011270);

WO 2009/025866 (PCT/US2008/010040); WO 2002/066614 (PCT/US/2002/005706);

WO 2008/073154 (PCT/US2007/016747); WO 2002/066613 (PCT/US2002/005090);

WO 2005/108617 (PCT/US2005/015089); WO 2002/029075 (PCT/US2001/030608);

WO 2003/0/27289 (PCT/US2002/005026); WO 2001/070816 (PCT/US2001/090500);

WO 2002/066615 (PCT/US2002/005708); WO 2009/048560 (PCT/US2008/011563);

WO 2003/027266 (PCT/US/2002/05234); WO 2010/042189 (PCT/US2009/005510); and

WO 2002/066612 (PCT/US2002/005090); WO 2011/119773 (PCT/US2011/029682).

For purposes of expressing polynucleotides and polypeptides under control of a gene switch mechanism, the term "gene switch" refers to the combination of a response element associated with a promoter, and a ligand-dependent transcription factor-based system which, in the presence of one or more ligands, modulates the expression of a gene into which the response element and promoter are incorporated. Stated otherwise, a "gene switch" refers to a peptide, protein or polypeptide complex that functions to (a) bind an activating ligand, and (b) regulate the transcription of a gene of interest in a ligand-dependent fashion.

In one embodiment, the polynucleotide encoding a gene switch is a recombinant polynucleotide, i.e., a polynucleotide, that has been engineered, by molecular biological manipulation, to encode the gene switch. In another embodiment, the recombinant polynucleotide is a synthetic polynucleotide.

As used herein with respect to gene switch regulation systems, the term "dimerizes with the ligand binding domain that binds an activating ligand" refers to a selective protein-protein interaction that is induced by the presence of activating ligand.

As used herein, the term "ligand binding domain that binds an activating ligand" refers to an amino acid sequence that selectively binds an activating ligand. In the methods disclosed herein, an activating ligand binds to a ligand binding domain, e.g., an ecdysone receptor ligand binding domain, that is part of a ligand-dependent transcriptional activation complex that regulates the expression of a polynucleotide sequence that encodes a gene of interest. Hence, the expression of the gene of interest is regulated in a ligand-dependent fashion.

The term "ecdysone receptor-based," with respect to a gene switch, refers to a gene switch comprising at least a functional part of a naturally occurring or synthetic ecdysone receptor ligand binding domain and which regulates gene expression in response to a ligand that binds to the ecdysone receptor ligand binding domain.

As used herein, "selective binding" of an activating ligand to a ligand binding domain in a gene switch means that the ligand has an EC50 of about 700 nanomolar (nM), 650 nM, 600 nM, 550 nM, 500 nM, 450 nM, 400 nM, 350 nM, 300 nM, 250 nM, 225 nM, 200 nM, 175 nM, 150 nM, 125 nM, 100 nM, 95 nM, 90 nM, 85 nM, 80 nM, 75 nM 70 nM, 65 nM, 60 nM, 55 nM, 50 nM, 45 nM, 40 nM, 35 nM, 30 nM, 25 nM, 20 nM, 15 nM, 10 nM, 9 nM, 8 nM, 7 nM, 6 nM, 5 nM, 4 nM, 3 nM, 2 nM or 1 nM, or less, in a gene switch assay.

As used herein, "EC50" is the "half maximal effective concentration," which refers to the concentration of an activating ligand that induces a gene switch-regulated change in expression of a polynucleotide encoding an gene of interest (e.g., modified forms of PE, including fusions, conjugates, et cetera), that is halfway between the baseline level of expression and the maximum level of expression after a specified exposure time. Examples of cellular assays for measuring gene switch-regulated gene expression are well known to those of skill in the art. See, for example, Karzenowski et al., *BioTechniques* 39: 191-200 (2005).

In one embodiment, the ligand binding domain that binds an activating ligand, e.g., an ecdysone receptor ligand binding domain, dimerizes with another ligand binding domain, e.g., a retinoid X receptor ligand binding domain, to form a protein-protein complex.

In one embodiment, the expression of the gene of interest is regulated by an activating ligand in an on/off fashion that is independent of the concentration or dosage of an activating ligand. In another embodiment, the expression of the gene of interest is regulated by an activating ligand in a concentration (or dosage)-dependent fashion, i.e., there is a dose-response relationship between the concentration (or dosage) of an activating ligand and the level of gene expression of the gene of interest. See, e.g., US Patent Publication No. 2009/0123441 (see also, WO 2009/048560 (PCT/USUS2008/011563)).

The term "operably linked" refers to the association of polynucleotide sequences on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

In one embodiment, an activating ligand, or a composition thereof, is administered to a subject orally. In another embodiment, an activating ligand, or a composition thereof, is administered to a subject parenterally. In another embodiment, an activating ligand, or a composition thereof, is administered subcutaneously, intramuscularly, intravenously, intraperitoneally, transdermally, or intratumorally.

In one embodiment, the ligand binding domain in the gene switch is a Group H nuclear receptor ligand binding domain, or a mutant thereof that binds an activating ligand. In another embodiment, the Group H nuclear receptor ligand binding domain is selected from the group consisting of an ecdysone receptor ligand binding domain, a ubiquitous receptor ligand binding domain, an orphan receptor-1 ligand binding domain, an NER-1 ligand binding domain, a receptor-interacting protein-15 ligand binding domain, a liver X receptor-3 ligand binding domain, a steroid hormone receptor-like protein ligand binding domain, a liver X receptor ligand binding domain, a liver X receptor ligand binding domain, a farnesoid X receptor ligand binding domain, a receptor-interacting protein-14 ligand binding domain, and a farnesol receptor ligand binding domain ligand binding domain, or a mutant thereof that binds an activating ligand.

In another embodiment, the Group H nuclear receptor ligand binding domain is an ecdysone receptor ligand binding domain, or a mutant thereof that binds an activating ligand. In another embodiment, the ecdysone receptor ligand binding domain is selected from the group consisting of an Arthropod ecdysone receptor ligand binding domain a Lepidopteran ecdysone receptor ligand binding domain, a Dipteran ecdysone receptor ligand binding domain, an Orthopteran ecdysone receptor ligand binding domain, a Homopteran ecdysone receptor ligand binding domain and a Hemipteran ecdysone receptor ligand binding domain, a spruce budworm *Choristoneura fumiferana* ecdysone receptor ligand binding domain, a beetle *Tenebrio molitor* ecdysone receptor ligand binding domain, a *Manduca sexta* ecdysone receptor ligand binding domain, a *Heliothies virescens* ecdysone receptor ligand binding domain, a midge *Chironomus tentans* ecdysone receptor ligand binding domain, a silk moth *Bombyx mori* ecdysone receptor ligand binding domain, a squinting bush brown *Bicyclus anynana* ecdysone receptor ligand binding domain, a buckeye *Junonia coenia* ecdysone receptor ligand binding domain, a fruit fly *Drosophila melanogaster* ecdysone receptor ligand binding domain, a mosquito *Aedes aegypti* ecdysone receptor ligand binding domain, a blowfly *Lucilia capitata* ecdysone receptor ligand binding domain, a blowfly *Lucilia cuprina* ecdysone receptor ligand binding domain, a blowfly *Calliphora vicinia* ecdysone receptor ligand binding domain, a Mediterranean fruit fly *Ceratitis capitata* ecdysone receptor ligand binding domain, a locust *Locusta migratoria* ecdysone receptor ligand binding domain, an aphid *Myzus persicae* ecdysone receptor ligand binding domain, a fiddler crab *Celuca pugilator* ecdysone receptor ligand binding domain, an ixodid tick *Amblyomma americanum* ecdysone receptor ligand binding domain, a whitefly Bamecia argentifoli ecdysone receptor ligand binding domain, a leafhopper *Nephotetix cincticeps* ecdysone receptor ligand binding domain, or a mutant thereof that binds An activating ligand.

In another embodiment, the ecdysone receptor ligand binding domain is a spruce budworm *Choristoneura fumiferana* ecdysone receptor ligand binding domain, for which the amino acid sequence is:

(SEQ ID NO: 1)

```
Leu Thr Ala Asn Gln Gln Phe Leu Ile Ala Arg Leu

Ile Trp Tyr Gln Asp Gly Tyr Glu Gln Pro Ser Asp Glu Asp Leu Lys

Arg Ile Thr Gln Thr Trp Gln Gln Ala Asp Asp Glu Asn Glu Glu Ser

Asp Thr Pro Phe Arg GlnIle Thr Glu Met Thr Ile Leu Thr Val Gln

Leu Ile Val Glu Phe Ala Lys Gly Leu Pro Gly Phe Ala Lys Ile Ser

Gln Pro Asp Gln Ile Thr Leu Leu Lys Ala Cys Ser Ser Glu Val Met

Met Leu Arg Val Ala Arg Arg Tyr Asp Ala Ala Ser Asp Ser Val

(position 107) Leu Phe Ala Asn Asn Gln Ala Tyr Thr Arg Asp Asn

Tyr Arg Lys Ala Gly Met ala Tyr (position 127) Val Ile Glu Asp

Leu Leu His Phe Cys Arg Cys Met Tyr Ser Met ala Leu Asp Asn Ile

His Tyr Ala Leu Leu Thr Ala Val Val Ile Phe Ser Asp Arg Pro Gly

Leu Glu Gln Pro Gln Leu Val Glu Glu Ile Gln Arg Tyr Tyr Leu Asn

Thr Leu Arg Ile Tyr Ile Leu Asnw Gln Leu Ser Gly Ser Ala Arg Ser

Ser Val Ile Tyr Gly Lys Ile Leu Ser Ile Leu Ser Glu Leu Arg Thr

Leu Gly Met Gln Asn Ser Asn Met Cys Ile Ser Leu Lys Leu Lys Asn

Arg Lys Leu Pro Pro Phe Leu Glu Glu Ile Trp Asp Val,
```

which is also set forth as SEQ NO: 1 in U.S. Patent Publication No. 2006/0100416 A1 (see also, WO 2002/066612 (PCT/US2002/005090)).

Exemplary ecdysone receptor ligand binding domains include those disclosed, for example, in U.S. Pat. No. 7,935,510 (see also, WO 2003/0/27289 (PCT/US2002/005026)); U.S. Pat. No. 7,919,269 (see also, WO 2003/027266 (PCT/US/2002/05234)); U.S. Pat. No. 7,563,879 (see also, WO 2003/0/27289 (PCT/US2002/005026)); and in U.S. Patent Publication No. 2006/0100416 A1 (see also, WO 2002/066612 (PCT/US2002/005090)), each of which is hereby incorporated by reference in its entirety.

In one embodiment, the ecdysone receptor ligand binding domain is a mutant of an ecdysone receptor ligand binding domain that binds the activating compound. In another embodiment, the ecdysone receptor ligand binding domain is a mutant of the spruce budworm *Choristoneura fumiferana* ecdysone receptor ligand binding domain that binds the activating compound.

In one embodiment, the gene switch comprises a *Choristoneura fumiferana* ecdysone receptor ligand binding domain that is engineered to contain the mutations V107I and Y127E of the *Choristoneura fumiferana* ecdysone receptor sequence as set forth in SEQ ID NO:1 of U.S. Patent Publication No. 2006/0100416 (see also, WO 2002/066612 (PCT/US2002/005090)). The term "V107I" means that the valine amino acid residue at position 107 (a as set forth in SEQ ID NO:1 of U.S. Patent Publication No. 2006/0100416) is changed to isoleucine. The term "Y127E" means that the tyrosine amino acid residue at position 127 (as set forth in SEQ ID NO:1 of U.S. Patent Publication No. 2006/0100416) is changed to glutamate.

Exemplary mutant ecdysone receptor ligand binding domains are disclosed, for example, in US 2006/0100416 A1 (see also, WO 2002/066612 (PCT/US2002/005090)) and U.S. Pat. No. 7,935,510 (Pub. No. 2005/0266457) (see also, WO 2005/108617 (PCT/US2005/015089)) each of which is incorporated by reference in its entirety.

In one embodiment, the gene switch comprises a ligand binding domain that dimerizes with the ligand binding domain that binds an activating ligand. In one embodiment, the ligand binding domain that dimerizes with the ligand binding domain that binds an activating ligand is a Group B nuclear receptor ligand binding domain. In another embodiment, the Group B nuclear receptor ligand binding domain is selected from the group consisting of a retinoid X receptor ligand binding domain, an H-2 region II binding protein ligand binding domain, a nuclear receptor co-regulator-1 ligand binding domain, an ultraspiracle protein ligand binding domain, a 2Cl nuclear receptor ligand binding domain, and a chorion factor 1 ligand binding domain. In another embodiment, a ligand binding domain that dimerizes with the ligand binding domain that binds an activating ligand is not an ecdysone receptor ligand binding domain.

In one embodiment, the ligand binding domain that dimerizes with the ligand binding domain that binds an activating ligand is a retinoic X receptor ligand binding domain. In another embodiment, the retinoic X receptor ligand binding domain is a vertebrate retinoic X receptor ligand binding domain. In another embodiment, the retinoic X receptor ligand binding domain is a *Homo sapiens* retinoic X receptor ligand binding domain. In another embodiment, the retinoic X receptor ligand binding domain is a retinoic X receptor c isoform. In another embodiment, the retinoic X receptor ligand binding domain is a retinoic X receptor β isoform. In another embodiment, the retinoic X receptor ligand binding domain is a retinoic X receptor γ isoform.

In another embodiment, the retinoic X receptor ligand binding domain is an invertebrate retinoic X receptor ligand binding domain. In another embodiment, the invertebrate retinoic X receptor ligand binding domain is a *Locusta migratoria* retinoic X receptor ligand binding domain.

In another embodiment, the invertebrate retinoic X receptor ligand binding domain is a non-Lepidopteran, non-Dipteran retinoic X receptor ligand binding domain.

In one embodiment, the retinoid receptor ligand binding domain is a vertebrate retinoid X receptor ligand binding domain, an invertebrate retinoid X receptor ligand binding domain, an ultraspiracle protein ligand binding domain, or a chimeric retinoid X receptor ligand binding domain.

In one embodiment, the chimeric retinoid X receptor ligand binding domain comprises two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, a different invertebrate retinoid X receptor ligand binding domain, or a different ultraspiracle protein ligand binding domain.

In another embodiment, the chimeric retinoid X receptor ligand binding domain is one that is disclosed in U.S. Pat. No. 7,531,326, which is hereby incorporated by reference in its entirety.

In another embodiment, the first polypeptide fragment of the chimeric retinoid X receptor ligand binding domain comprises helices 1-6, helices 1-7, helices 1-8, helices 1-9, helices 1-10, helices 1-11, or helices 1-12 of a first species of retinoid X receptor, and the second polypeptide fragment of the chimeric retinoid X receptor ligand binding domain comprises helices 7-12, helices 8-12, helices 9-12, helices 10-12, helices 11-12, helix 12, or F domain of a second species of retinoid X receptor, respectively.

In another embodiment, the first polypeptide fragment of the chimeric retinoid X receptor ligand binding domain comprises helices 1-6 of a first species RXR according to the disclosure, and the second polypeptide fragment of the chimeric retinoid X receptor ligand binding domain comprises helices 7-12 of a second species of retinoid X receptor.

In another embodiment, the first polypeptide fragment of the chimeric retinoid X receptor ligand binding domain comprises helices 1-7 of a first species retinoid X receptor according to the disclosure, and the second polypeptide fragment of the chimeric retinoid X receptor ligand binding domain comprises helices 8-12 of a second species retinoid X receptor.

In another embodiment, the first polypeptide fragment of the chimeric retinoid X receptor ligand binding domain comprises helices 1-8 of a first species of retinoid X receptor, and the second polypeptide fragment of the chimeric retinoid X receptor ligand binding domain comprises helices 9-12 of a second species of retinoid X receptor.

In another embodiment, the first polypeptide fragment of the chimeric retinoid X receptor ligand binding domain comprises helices 1-9 of a first species of retinoid X receptor, and the second polypeptide fragment of the chimeric retinoid X receptor ligand binding domain comprises helices 10-12 of a second species of retinoid X receptor.

In another embodiment, the first polypeptide fragment of the chimeric retinoid X receptor ligand binding domain comprises helices 1-10 of a first species of retinoid X receptor, and the second polypeptide fragment of the chimeric retinoid X receptor ligand binding domain comprises helices 11-12 of a second species of retinoid X receptor.

In another embodiment, the first polypeptide fragment of the chimeric retinoid X receptor ligand binding domain comprises helices 1-11 of a first species of retinoid X receptor, and the second polypeptide fragment of the chimeric retinoid X receptor ligand binding domain comprises helix 12 of a second species of retinoid X receptor.

In another preferred embodiment, the first polypeptide fragment of the chimeric retinoid X receptor ligand binding domain comprises helices 1-12 of a first species of retinoid X receptor, and the second polypeptide fragment of the chimeric retinoid X receptor ligand binding domain comprises an F domain of a second species of retinoid X receptor.

In one embodiment, the first polypeptide fragment in the chimeric retinoid X receptor ligand binding domain is human retinoid X receptor sequence, and the second polypeptide fragment in the chimeric retinoid X receptor ligand binding domain is invertebrate retinoid X receptor sequence. In another embodiment, the invertebrate retinoid X receptor sequence is *Locusta migratoria* retinoid X receptor sequence.

In another embodiment, the first polypeptide fragment of the chimeric retinoid X receptor ligand binding domain comprises helices 1-8 of a human retinoid X receptor, and the second polypeptide fragment of the chimeric retinoid X receptor ligand binding domain comprises helices 9-12 of *Locusta migratoria* retinoid X receptor.

In one embodiment, the gene switch further comprises a DNA binding domain ("DBD"). In another embodiment, the DBD is selected from the group consisting of a GAL4 DBD, a LexA DBD, a transcription factor DBD, a steroid/thyroid hormone nuclear receptor superfamily member DBD, a bacterial LacZ DBD, and a yeast DBD.

In one embodiment, the gene switch further comprises a transactivation domain ("TD"). In another embodiment, the transactivation domain is selected from the group consisting of a VP16 TD, a GAL4 TD, an NF-κB TD, a BP64 TD, and a B42 acidic TD.

In one embodiment, a DNA binding domain, the ligand binding domain that binds an activating ligand, a ligand binding domain that dimerizes with the ligand binding domain that binds an activating ligand, and a transactivation domain are encoded by polynucleotide sequences that are contained in the same polynucleotide.

In another embodiment, a DNA binding domain, a ligand binding domain that binds an activating ligand, a ligand binding domain that dimerizes with the ligand binding domain that binds an activating ligand, and a transactivation domain are encoded by polynucleotide sequences that are contained in two or more separate polynucleotide sequences.

In another embodiment, a DNA binding domain, a ligand binding domain that binds an activating ligand, a ligand binding domain that dimerizes with the ligand binding domain that binds an activating ligand, and a transactivation domain are encoded by polynucleotide sequences that are contained in two separate polynucleotide sequences.

In another embodiment, a DNA binding domain and a ligand binding domain that binds an activating ligand are encoded by polynucleotide sequences that are contained in a first polynucleotide sequence, and a ligand binding domain that dimerizes with the ligand binding domain that binds an activating ligand and a transactivation domain are encoded by polynucleotide sequences that are contained in a second polynucleotide sequence.

In another embodiment, a DNA binding domain and a ligand binding domain that dimerizes with the ligand binding domain that binds an activating ligand are encoded by polynucleotide sequences that are contained in a first polynucleotide sequence, and a ligand binding domain that binds an activating ligand and a transactivation domain are encoded by polynucleotide sequences that are contained in a second polynucleotide sequence.

In embodiments in which one or more of the DNA binding domain, a ligand binding domain that binds an activating ligand, a ligand binding domain that dimerizes with the ligand binding domain that binds an activating ligand, and a transactivation domain are encoded by polynucleotide sequences that are contained in one or more separate polynucleotide sequences, then the one or more separate polynucleotide sequences are operably linked to one or more separate promoters. In another embodiment, the one or more separate polynucleotide sequences are operably linked to one or more separate enhancer elements. In another embodiment, the promoter(s) and/or the enhancer(s) are constitutively active. In another embodiment, the promoter(s) and/or the enhancer(s) are tissue specific promoters and/or enhancers.

In one embodiment, the gene switch comprises a DNA binding domain, an ecdysone receptor ligand binding domain, a ligand binding domain that dimerizes with the ecdysone receptor ligand binding domain, and a transactivation domain.

In another embodiment, the gene switch comprises a DNA binding domain, an ecdysone receptor ligand binding domain, a retinoid X receptor ligand binding domain, and a transactivation domain.

In another embodiment, the gene switch comprises a DNA binding domain, an ecdysone receptor ligand binding domain, a chimeric vertebrate/invertebrate retinoid X receptor ligand binding domain, and a transactivation domain.

In another embodiment, the gene switch comprises a GAL4 DNA binding domain, a *Choristoneura fumiferana* ecdysone receptor ligand binding domain that is engineered to contain the mutations V107I and Y127E of the *Choristoneura fumiferana* ecdysone receptor sequence set forth in SEQ ID NO:1, a chimeric *Homo sapiens/Locusta migratoria* retinoid X receptor ligand binding, and a VP16 transactivation domain.

In another embodiment, the host cell further comprises a polynucleotide encoding a peptide, protein or polypeptide whose expression is regulated by the gene switch. A promoter that binds the gene switch complex is operably linked to the polynucleotide encoding a peptide, protein or polypeptide whose expression is regulated by the gene switch.

In another embodiment, the polynucleotide encoding a peptide, protein or polypeptide whose expression is regulated by the gene switch is contained in the same polynucleotide as a polynucleotide that encodes one or more of a DNA binding domain, the ligand binding domain that binds an activating ligand, a ligand binding domain that dimerizes with the ligand binding domain that binds an activating ligand, and a transactivation domain. Such constructs are disclosed, for example, in U.S. Patent Publication No. 2009/0123441 (see also, WO 2009-048560 (PCT/USUS2008/011563)).

In another embodiment, the polynucleotide encoding a peptide, protein or polypeptide whose expression is regulated by the gene switch is contained in a different nucleic acid molecule than a nucleic acid molecule that encodes one or more of a DNA binding domain, the ligand binding domain that binds an activating ligand, a ligand binding domain that dimerizes with the ligand binding domain that binds an activating ligand, and a transactivation domain.

In one embodiment, the gene switch is more sensitive to an activating ligand than to a steroid hormone. In another embodiment, the gene switch is more sensitive to an activating ligand than to another diacylhydrazine compound.

The sensitivity of a gene switch to an activating ligand, relative to another ligand, can readily be determined in an in vitro assay, for example, an in vitro assay that employs a reporter gene, such as firefly luciferase. Examples of such in vitro assays are well known to those of ordinary skill in the art. See, for example, Karzenowski et al., *BioTechniques* 39: 191-200 (2005).

In one embodiment, the polynucleotide encoding the gene switch is contained in a vector. In one embodiment, the vector selected from the group consisting of a plasmid, an expression vector, a replicon, a phage vector, a cosmid, a viral vector, a liposome, an electrically charged lipid (e.g., a cytofectin), a DNA-protein complex, and a biopolymer.

In another embodiment, the vector is a retroviral vector. In another embodiment, the vector is selected from the group consisting of an adeno-associated viral vector, a pox viral vector, a baculoviral vector, a vaccinia viral vector, a herpes simplex viral vector, an Epstein-Barr viral vector, an adenoviral vector, a gemini viral vector, and a caulimo viral vector.

In one embodiment, a composition of the invention comprises one or more polynucleotides that encode two or more orthogonal gene switches. Two or more individually operable gene regulation systems are said to be "orthogonal" when (a) modulation of each of the given gene switches by its respective ligand results in a measurable change in the magnitude of expression of the gene that is regulated by that gene switch, and (b) the change is statistically significantly different than the change in expression of all other gene switches that are in the host cell. In one embodiment, regulation of each individually operable gene switch system effects a change in gene expression at least 2-fold, 3-fold, 4-fold, 5-fold, 10-fold, 20-fold, 50-fold, 70-fold, 100-fold, 200-fold, 300 fold, 400-fold or 500-fold greater than all of the other operable gene switches in the host cell. Non-limiting examples of orthogonal gene switch systems are set forth in U.S. Pat. No. 8,105,825 (Publication No. US 2002/0110861 A1).

As used herein, an "activating ligand" is a compound that binds selectively to the ligand binding domain of a gene switch.

In one embodiment, the activating ligand is administered to the subject within an hour of the time at which the priming dosage is administered to the subject. In another embodiment, the activating ligand is administered to the subject within about 24, 48, 96, 120, 144 or 168 hours of the time at which the priming dosage is administered to the subject. In another embodiment, the activating ligand is administered to the subject within about 1, 2, 3, 4 or 5 weeks of the time at which the priming dosage is administered to the subject.

In one embodiment, the activating ligand is administered to the subject within an hour of the time at which the first of the at least one boosting dosage is administered to the subject. In another embodiment, the activating ligand is administered to the subject within about 24, 48, 96, 120, 144 or 168 hours of the time at which the first of the at least one boosting dosage is administered to the subject. In another embodiment, the activating ligand is administered to the subject within about 1, 2, 3, 4 or 5 weeks of the time at which the first of the at least one boosting dosage is administered to the subject.

In another embodiment, a composition of the invention is contained within a container. In one embodiment, the container is a vial. In another embodiment the container is a multiple-use vial. In another embodiment, the container displays an expiration date for the composition. In another embodiment, the container contains instructions for using the composition.

In one embodiment, a composition of the invention is a unit dosage composition. In one embodiment, a unit dosage composition is a composition that is manufactured to supply a single dosage of the composition of the invention. In another embodiment, the unit dosage composition is manufactured to provide more than one measured dosages of the composition of the invention.

The present application also provides an article of manufacture comprising more than one of the unit dosage compositions of the invention. In one embodiment, the article of manufacture is a container. In another embodiment, the article of manufacture is a box. In another embodiment, the article of manufacture displays an expiration date for the unit dosage composition.

The present invention also provides a kit comprising more than one of the composition or unit dosage of the present invention. In one embodiment, the kit displays an expiration date for the composition or unit dosage. In another embodiment, the kit displays and/or or contains instructions for using the composition or unit dosage. In another embodiment, the kit also comprises an activating ligand that binds to the ligand binding domain of the gene switch encoded by the polynucleotide in the composition or unit dosage.

The present invention also provides a drug label for the composition or unit dosage of the present invention. In one embodiment, the drug label displays an expiration date for the composition or unit dosage. In another embodiment, the drug label displays instructions for using the composition or unit dosage. In another embodiment, the drug label displays the approved indication(s) for the composition or unit dosage. In another embodiment, the said label is in paper form. In another embodiment, the drug label is in digital or computer-readable form.

The term "activating ligand" as used herein refers to a compound that shows activity as an ecdysone receptor agonist, i.e., a compound that is able to mimic 20-hydroxyecdysone biological activity, and binds to a gene switch ligand binding domain. Activating ligands for use in the present invention include both ecdysteroids and non-steroidal compounds, e.g., tebufenozide and methoxyfenozide.

In one embodiment, the activating ligand is an ecdysone receptor agonist disclosed in U.S. Pat. No. 8,076,517 (Publication No. 2009/0163592), No. 2009/0298175, No. 2005/0228016 and in U.S. Pat. Nos. 6,258,603, 7,375,093, 7,456,315, 7,304,161, and 7,304,162; each of which are hereby incorporated by reference herein.

In certain embodiments, the activating ligand is a compound having Formula I:

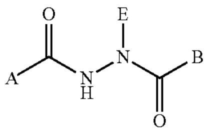

I wherein:

A is alkoxy, arylalkyloxy, aryloxy, arylalkyl, optionally substituted aryl or optionally substituted heteroaryl;

B is optionally substituted aryl or optionally substituted heteroaryl;

E is $CR^1R^2R^3$;

$R^1$ is optionally substituted alkyl, arylalkyl, hydroxyalkyl, haloalkyl, optionally substituted cycloalkyl, optionally substituted alkenyl, optionally substituted alkynyl, optionally substituted heterocycle, optionally substituted aryl or optionally substituted heteroaryl; and $R^2$ and $R^3$ are independently hydrogen, optionally substituted alkyl, arylalkyl, hydroxyalkyl, haloalkyl, optionally substituted cycloalkyl, optionally substituted alkenyl, optionally substituted alkynyl, optionally substituted heterocycle, optionally substituted aryl or optionally substituted heteroaryl; or $R^1$ and $R^2$ taken together form an optionally substituted alkenyl group.

In one embodiment, the activating ligand is a compound having Formula I:

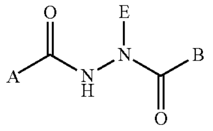

wherein:

A is selected from the group consisting of 2,3,6-tri-F-phenyl-; 2,3-di-$CH_3$-phenyl-; 2,6-di-F-phenyl-; 2-Br, 3,4-ethylenedioxy-phenyl-; 2-$CH{=}CH_2$, 3-$OCH_3$-phenyl-; 2-$CH_2CH_3$, 3,4-ethylenedioxy-phenyl-; 2-$CH_2CH_3$, 3-$OCH_3$-phenyl-; 2-$CH_2C1$, 3-$OCH_3$-phenyl-; 2-$CH_2F$, 3-$OCH_3$-phenyl-; 2-$CH_2NHCH_3$, 3-$OCH_3$-phenyl-; 2-$CH_2NMe_2$, 3-$OCH_3$-phenyl-; 2-$CH_2OAc$, 3-$OCH_3$-phenyl-; 2-$CH_2OCH_2CH{=}CH_2$, 3-$OCH_3$-phenyl-; 2-$CH_2OH$, 3-$OCH_3$-phenyl-; 2-$CH_2OMe$, 3-$OCH_3$-phenyl-; 2-$CH_2OMe$, 3-OMe-phenyl-; 2-$CH_2S(O)_2CH_3$, 3-$OCH_3$-phenyl-; 2-$CH_2S(O)CH_3$, 3-$OCH_3$-phenyl-; 2-$CH_2SCH_3$, 3-$OCH_3$-phenyl-; 2-$CH_3$, 3,4-ethylenedioxy-phenyl-; 2-$CH_3$, 3,4-$OCH_2O$-phenyl-; 2-$CH_3$, 3-Ac-phenyl-; 2-$CH_3$, 3-$CH_2CH_2CH_2O$-4-phenyl-; 2-$CH_3$, 3-$CH_3$-phenyl-; 2-$CH_3$, 3-Cl-phenyl-; 2-$CH_3$, 3-Et-phenyl-; 2-$CH_3$, 3-I-phenyl-; 2-$CH_3$, 3-$NMe_2$-phenyl-; 2-$CH_3$, 3-$NO_2$-phenyl-; 2-$CH_3$, 3-OAc-phenyl-; 2-$CH_3$, 3-$OCF_3$-phenyl-; 2-$CH_3$, 3-$OCH_2OCH_2$-4-phenyl-; 2-$CH_3$, 3-$OCH_3$-phenyl-; 2-$CH_3$, 3-OH-phenyl-; 2-$CH_3$, 3-Oi-Pr-phenyl-; 2-$CH_3$, 3-OMe-phenyl-; 2-$CH_3$, 4,5-methylenedioxy-phenyl-; 2-$CH_3$-3-$OCH_3$-phenyl-; 2-Cl 4,5-methylenedioxy-phenyl-; 2-Cl, 3-$CH_2OCH_2O$-4-phenyl-; 2-Cl, 3-$CH_2OCH_2O$-4-phenyl-; 2-Cl, 3-OMe-phenyl-; 2-Et, 3,4-ethylenedioxy-phenyl-; 2-Et, 3,4-$OCH(CH_3)O$-phenyl-; 2-Et, 3,4-$OCH_2O$-phenyl-; 2-Et, 3-$OCH_3$-phenyl-; 2-F, 3,4-$CH_2OCH_2O$-phenyl-; 2-F, 4-$CH_2CH_3$-phenyl-; 2-F, 4-Et-phenyl-; 2-I, 3-OMe-phenyl-; 2-$NH_2$, 3-OMe-phenyl-; 2-$NO_2$, 3-OMe-phenyl-; 2-Vinyl, 3-OMe-phenyl-; 3,4-$(CH_2)_4$-phenyl-; 3,4-di-Et-phenyl-; 3,4-ethylenedioxy-phenyl-; 3,4-$OCF_2O$-phenyl-; 3,4-$OCH(CH_3)O$-phenyl-; 3,4-$OCH_2O$-phenyl-; 3-Cl, 4-Et-phenyl-; 3-NH—C=C-4-phenyl-; 3-$OCH(CH_3)CH_2O$-4-phenyl-; 3-$OCH_3$, 4-$CH_3$-phenyl-; 3,4-S—C=N-phenyl-; 4-Br-phenyl-; 4-$C(O)CH_3$-phenyl-; 4-$CH(OH)CH_3$-phenyl-; 4-$CH_2CH_3$-phenyl-; 4-$CH_2CN$-phenyl-; 4-$CH_3$-phenyl-; 4-Cl-phenyl-; 4-Et-phenyl-; 4-$OCH_3$-phenyl-; phenyl-; and benzo[1,2,5]oxadiazole-5-yl;

B is selected from the group consisting of 1-trityl-5-benzimidazolyl-; 3-trityl-5-benzimidazolyl-; 1H-indazole-3-yl-; 1-methyl-1H-indole-2-yl-; 1-methyl-2-oxo-6-trifluoromethyl-3-pyridyl-; 1-trityl-1H-indazole-3-yl-; 2,3,4,5-phenyl-; 2,3,4,5-tetra-F-phenyl-; 2,3,4-F-phenyl-; 2,3-F-phenyl-; 2,3-$OCH_2O$-phenyl-; 2,4,5-F-phenyl-; 2,4-di-Cl-5-F-phenyl-; 2,5-di-$OCH_3$-phenyl-; 2,5-F-phenyl-; 2,6-di-Cl-4-pyridyl-; 2,6-dimethoxy-4- pyrimidinyl2,6-di-$OCH_3$-3-pyridyl2,6-F-phenyl-; 2-Cl, 5-$NO_2$-phenyl-; 2-Cl-3-pyridyl2-Cl-4-F-phenyl-; 2-Cl-5-$CH_3$-phenyl-; 2-Cl-6-$CH_3$-4-pyridyl-; 2-Et-phenyl-; 2-F, 4-Cl-phenyl-; 2-F, 5-$CH_3$-phenyl-; 2-methoxy-6-trifluoromethyl-3-pyridyl-; 2-$NO_2$-3,5-di-$OCH_3$, 4-$CH_3$-phenyl-; 2-$NO_2$-4-Cl-phenyl-; 2-$NO_2$-5-$CH_3$-phenyl-; 2-$NO_2$-5-Cl-phenyl-; 2-$NO_2$-5-F-phenyl-; 2-$NO_2$-phenyl-; 2-$OCH_2CF_3$, 5-$OCH_3$-phenyl-; 2-$OCH_3$-3-pyridyl2-$OCH_3$-4-CH3-phenyl-; 2-$OCH_3$-4-Cl-phenyl-; 2-$OCH_3$-4-F-phenyl-; 2-$OCH_3$-5-$CH_3$-phenyl-; 2-$OCH_3$-5-Cl-phenyl-; 2-$OCH_3$-phenyl-; 2-S(O)$CH_3$-phenyl-; 2-$SO_3H$-phenyl-; 3,4,5-F-phenyl-; 3,4,5-tri-$OCH_3$-phenyl-; 3,4-di-$CH_3$-5-Cl-phenyl-; 3,4-F-phenyl-; 3,4-methylenedioxy-phenyl-; 3,5-di($CH_2OH$)-phenyl-; 3,5-di-$CH_3$-4-Cl-phenyl-; 3,5-di-$CH_3$-phenyl-; 3,5-di-Cl-4-F-phenyl-; 3,5-di-Cl-phenyl-; 3,5-di-$CO_2H$-phenyl-; 3,5-di-F-phenyl-; 3,5-di-$OCH_3$, 4-$CH_3$-phenyl-; 3,5-di-$OCH_3$-4-OAc-phenyl-; 3,5-di-$OCH_3$-phenyl-; 3,6-dichloro-4-pyridazinyl-; 3,6-dimethoxy-4-pyridazinyl-; 3-Br-phenyl-; 3-$CF_3$, 5-F-phenyl-; 3-$CF_3$-4-F-phenyl-; 3-$CF_3$-4-F-phenyl3-$CF_3$-phenyl-; 3-CH═NNHCOCONH$_2$, 5-$CH_3$-phenyl-; 3-CH═NNHCONH$_2$, 5-$CH_3$-phenyl-; 3-CH═NOH, 5-$CH_3$-phenyl-; 3-$CH_2$OAc, 5-$CH_3$-phenyl-; 3-$CH_3$, 5-Br-phenyl-; 3-$CH_3$, 5-$CH_3$-phenyl-; 3-$CH_3$, 5-Cl-phenyl-; 3-$CH_3$-4-Br-phenyl-; 3-$CH_3$-phenyl-; 3-chloro-6-methylsulfanyl-pyrazine-2-yl-; 3-Cl, 5-Br-phenyl-; 3-Cl, 5-Cl-phenyl-; 3-Cl-5-$OCH_3$-4-pyridyl-; 3-Cl-phenyl-; 3-CN-phenyl-; 3-F, 5-F-phenyl-; 3-F-phenyl-; 3-$NO_2$-phenyl-; 3-$OCH_3$-4-$CH_3$-phenyl-; 3-$OCH_3$-4-pyridyl-; 3-$OCH_3$-phenyl-; 3-OMe, 5-$CH_3$-phenyl-; 3-OMe, 5-OMe-phenyl-; 3-oxo-6-methoxy-4-pyridazinyl-; 4,6-dimethyl-pyridyl-; 4-$CH_3$-phenyl-; 4-F-phenyl-; 4-pyridazinyl-; 5-benzimidazolyl-; 5-methoxycarbonyl-2-pyridyl-; 5-methyl-1-phenyl-1H-pyrazole-3-yl-; 5-methyl-pyrazine-2-yl-; 6-$CH_3$-2-pyridyl-; phenyl-; and pyrazine-2-yl; and E is selected from the group consisting of $C(CH_3)_2C(O)OEt$; $C(CH_3)_2CH{=}NCH_2CH_2OH$; $C(CH_3)_2CH{=}NNHC(O)C)C(O)NH_2$; $C(CH_3)_2CH{=}NNHC(O)NH_2$; $C(CH_3)_2CH{=}NOH$; $C(CH_3)_2CH_2OC(O)CH_3$; $C(CH_3)_2CH_2OCH_3$; $C(CH_3)_2CH_2OH$; $C(CH_3)_2CH_2OSi(CH_3)_2tBu$; $C(CH_3)_2CHO$; $C(CH_3)_2CN$; $C(CH_3)_2COOH$; $CH(CH_3)C(CH_3)_3$; CH(Et)(n-Bu); CH(Et)(t-Bu;) CH(n-Bu)(t-Bu); CH(n-Pr)(t-Bu); CH(Ph)(t-Bu); and t-Bu.

In another embodiment, the activating ligand is a compound having Formula I wherein A, B, and E are defined according to Table 3.

TABLE 3

| Ligand Components | | |
|---|---|---|
| A | B | E |
| 4-Cl—Ph | Ph | t-Bu |
| 4-Et—Ph | 2-$NO_2$—Ph | t-Bu |
| 4-$CH_3$—Ph | 3-$CH_3$, 5-$CH_3$—Ph | t-Bu |
| 4-Et—Ph | 3-$CH_3$, 5-$CH_3$—Ph | t-Bu |
| 2,6-di-F—Ph | 3-Cl, 5-Cl—Ph | t-Bu |
| 2-$CH_3$, 3-Cl—Ph | 3-Cl—Ph | t-Bu |
| 2-Cl, 3-OMe—Ph | 2-Cl-5-$CH_3$—Ph | t-Bu |
| 2-$CH_3$, 3-Cl—Ph | 3-$CH_3$-4-Br—Ph | t-Bu |
| 4-Et—Ph | 3,5-di-$CH_3$-4-Cl—Ph | t-Bu |
| 4-Et—Ph | 3,4-di-$CH_3$-5-Cl—Ph | t-Bu |
| 4-$OCH_3$—Ph | 2-Cl-4-F—Ph | t-Bu |
| 4-Et—Ph | 3-$CH_3$, 5-Cl—Ph | t-Bu |
| 4-Et—Ph | 2-Et—Ph | t-Bu |
| 4-$OCH_3$—Ph | 3-Cl, 5-Cl—Ph | t-Bu |
| 4-Et—Ph | 2-$NO_2$-5-$CH_3$—Ph | t-Bu |
| 4-$CH_2$CN—Ph | 3-$CH_3$, 5-$CH_3$—Ph | t-Bu |
| 2-$CH_3$, 3-OMe—Ph | 3-$CH_3$—Ph | t-Bu |
| 4-Br—Ph | 3-Cl, 5-Cl—Ph | t-Bu |
| 2-$CH_3$, 3-$NO_2$—Ph | 3-$CH_3$, 5-$CH_3$—Ph | t-Bu |
| 2-$CH_3$, 3-$CH_3$—Ph | 2,5-di-$OCH_3$—Ph | t-Bu |
| 2-$CH_3$, 3-$CH_3$—Ph | 2-$OCH_3$-5-Cl—Ph | t-Bu |
| 2-$NO_2$, 3-OMe—Ph | 3-$CH_3$, 5-$CH_3$—Ph | t-Bu |
| 2-$CH_3$, 3-$CH_3$—Ph | 3-OMe, 5-OMe—Ph | t-Bu |
| 3-Cl, 4-Et—Ph | 3-$CH_3$, 5-$CH_3$—Ph | t-Bu |
| 4-CH(OH)$CH_3$—Ph | 3-F, 5-F—Ph | t-Bu |
| 2-$CH_3$, 3-$NMe_2$—Ph | 3-Cl, 5-Cl—Ph | t-Bu |
| 2-$CH_3$, 3-Ac—Ph | 3-$CH_3$, 5-$CH_3$—Ph | t-Bu |
| 2-$CH_3$, 3-OAc—Ph | 3-$CH_3$, 5-$CH_3$—Ph | t-Bu |
| 2-$CH_3$, 3-I—Ph | 3-CH3, 5-$CH_3$—Ph | t-Bu |
| 2-$CH_3$, 3-OMe—Ph | 3-Cl, 5-Br—Ph | t-Bu |
| 2-$CH_3$, 3-Oi-Pr—Ph | 3-$CH_3$, 5-$CH_3$—Ph | t-Bu |
| 2-$CH_3$, 3-OCH3—Ph | 2-Cl-3-pyridyl | t-Bu |
| 2-$CH_3$, 3-OMe—Ph | 2-$OCH_3$-5-$CH_3$—Ph | t-Bu |
| 2-$CH_3$, 3-OMe—Ph | 2,5-F—Ph | t-Bu |
| 2-$CH_3$, 3-OMe—Ph | 2-Et—Ph | t-Bu |
| 2-$CH_3$, 3-OMe—Ph | 3-$CH_3$, 5-Br—Ph | t-Bu |
| 2-$CH_3$, 3-OMe—Ph | 3-OMe, 5-$CH_3$—Ph | t-Bu |
| 2-$CH_3$, 3-OMe—Ph | 2-$OCH_3$-4-Cl—Ph | t-Bu |
| 2-$CH_3$, 3-$OCF_3$—Ph | 3-$CH_3$, 5-$CH_3$—Ph | t-Bu |
| 2-$CH_3$, 3-OMe—Ph | 3-$OCH_3$-4-$CH_3$—Ph | t-Bu |
| 3-$OCH_3$, 4-CH3—Ph | 3-$CH_3$, 5-$CH_3$—Ph | t-Bu |
| 2-$CH_3$, 3-OMe—Ph | 2-$OCH_3$-4-$CH_3$—Ph | t-Bu |
| 2-$CH_3$, 3-$OCH_3$—Ph | 2,6-di-Cl-4-pyridyl | t-Bu |
| 2-$CH_3$, 3-OMe—Ph | 2-$NO_2$-5-$CH_3$—Ph | t-Bu |

TABLE 3-continued

| Ligand Components | | |
|---|---|---|
| A | B | E |
| 2-$CH_3$, 3-OMe—Ph | 2-F-4-Cl—Ph | t-Bu |
| 3,4-$OCH_2O$—Ph | 2-Cl-4-F—Ph | t-Bu |
| 2-Et, 3-OMe—Ph | 3-$CH_3$, 5-$CH_3$—Ph | t-Bu |
| 2-$CH_3$, 3-Et—Ph | 3-$CH_3$, 5-$CH_3$—Ph | t-Bu |
| 3-$CH_2CH_2O$-4-Ph | 3-$CH_3$, 5-$CH_3$—Ph | t-Bu |
| 2-$CH_3$, 3-OMe—Ph | 3,5-di-Cl-4-F—Ph | t-Bu |
| 2-$CH_3$, 3,4-$OCH_2O$—Ph | 4-F—Ph | t-Bu |
| 2-Et, 3,4-$OCH_2O$—Ph | 2-$OCH_3$—Ph | t-Bu |
| 3,4-di-Et—Ph | 3-$CH_3$, 5-$CH_3$—Ph | t-Bu |
| 2-Et, 3-OMe—Ph | 4-F—Ph | t-Bu |
| 2-Et, 3-OMe—Ph | 2-$OCH_3$—Ph | t-Bu |
| 2-$CH_3$, 3-OMe—Ph | 2-$OCH_3$-4-F—Ph | t-Bu |
| 2-Et, 3-$OCH_3$—Ph | 2-Cl-6-$CH_3$-4-pyridyl | t-Bu |
| 2-Et, 3-OMe—Ph | 3-OMe, 5-OMe—Ph | t-Bu |
| 2-I, 3-OMe—Ph | 3-$CH_3$, 5-$CH_3$—Ph | t-Bu |
| 3,4-ethylenedioxy-Ph | 2-$OCH_3$—Ph | t-Bu |
| 3,4-$(CH_2)_4$—Ph | 3-$CH_3$, 5-$CH_3$—Ph | t-Bu |
| 2-Et, 3-OMe—Ph | 2,3-$OCH_2O$—Ph | t-Bu |
| 2-F, 4-Et—Ph | 4-F—Ph | t-Bu |
| 2-Et, 3-OMe—Ph | 3,4-methylenedioxy-Ph | t-Bu |
| 2-$CH_3$, 3,4-ethylenedioxy-Ph | 4-F—Ph | t-Bu |
| 3,4-$OCH(CH_3)O$—Ph | 3-$CH_3$, 5-$CH_3$—Ph | t-Bu |
| 2-Et, 3,4-$OCH(CH_3)O$—Ph | 3-$CH_3$, 5-$CH_3$—Ph | t-Bu |
| 2-$CH_3$, 3,4-ethylenedioxy-Ph | 3-$OCH_3$—Ph | t-Bu |
| 3-$OCH(CH_3)CH_2O$-4-Ph | 3-$CH_3$, 5-$CH_3$—Ph | t-Bu |
| 2-Br, 3,4-ethylenedioxy-Ph | 3-$CH_3$, 5-$CH_3$—Ph | t-Bu |
| 2-Et, 3,4-ethylenedioxy-Ph | 3-$CH_3$, 5-Cl—Ph | t-Bu |
| 2-Et, 3,4-ethylenedioxy-Ph | 3-$CH_3$—Ph | t-Bu |
| 2-Et, 3,4-ethylenedioxy-Ph | 2-$OCH_3$—Ph | t-Bu |
| 2-Et, 3,4-ethylenedioxy-Ph | 3-$OCH_3$—Ph | t-Bu |
| 3-S—C═N-4-Ph | 3-$CH_3$, 5-$CH_3$—Ph | t-Bu |
| 2-Et, 3-OMe—Ph | 2-$OCH_3$-4-Cl—Ph | t-Bu |
| 2-Et, 3-OMe—Ph | 2,5-di-$OCH_3$—Ph | t-Bu |
| 2-$CH_3$, 4,5-methylenedioxy-Ph | 3-$CH_3$, 5-$CH_3$—Ph | t-Bu |
| 3-$CH_2OCH_2O$-4-Ph | 3-$CH_3$, 5-$CH_3$—Ph | t-Bu |
| 2-$CH_3$, 3-$OCH_2OCH_2$-4-Ph | 2-$OCH_3$—Ph | t-Bu |
| 2-Et, 3-$OCH_2OCH_2$-4-Ph | 4-F—Ph | t-Bu |
| 2-Cl 4,5-methylenedioxy-Ph | 3-$CH_3$, 5-$CH_3$—Ph | t-Bu |
| 2,3,6-tri-F—Ph | 2-Cl-4-F—Ph | t-Bu |
| 2-Et, 3-OMe—Ph | 2,6-F—Ph | t-Bu |
| 2-Et, 3-OMe—Ph | 3-F—Ph | t-Bu |
| 2-Et, 3-OMe—Ph | 3-Br—Ph | t-Bu |
| 2-Et, 3-OMe—Ph | 2-$NO_2$—Ph | t-Bu |
| 2-Et, 3-OMe—Ph | 2,3-F—Ph | t-Bu |
| 2-Et, 3-OMe—Ph | 3,4,5-tri-$OCH_3$—Ph | t-Bu |
| 2-Et, 3-OMe—Ph | 3-$CF_3$, 5-F—Ph | t-Bu |
| 2-Et, 3-OMe—Ph | 3-CN—Ph | t-Bu |
| 2-Vinyl, 3-OMe—Ph | 2,4-di-Cl-5-F—Ph | t-Bu |
| 2-Et, 3-$OCH_2OCH_2$-4-Ph | Ph | t-Bu |
| 2-Et, 3-OMe—Ph | 3-$CH_3$, 5-$CH_3$—Ph | —$C(CH_3)_2C(O)OEt$ |
| 2-Et, 3-OMe—Ph | 3-$CH_3$, 5-$CH_3$—Ph | —$C(CH_3)_2CH_2OH$ |
| 2-Et, 3-OMe—Ph | 3-$CH_3$, 5-$CH_3$—Ph | —$C(CH_3)_2CHO$ |
| 2-Et, 3-OMe—Ph | 3-$CH_3$, 5-$CH_3$—Ph | —$C(CH_3)_2CH_2OCH_3$ |
| 2-Et, 3-OMe—Ph | 3-$CH_3$, 5-$CH_3$—Ph | —$C(CH_3)_2CH$═NOH |
| 2-$NH_2$, 3-OMe—Ph | 3-$CH_3$, 5-$CH_3$—Ph | t-Bu |
| 2-Et, 3-OMe—Ph | 3-$CH_2OAc$, 5-$CH_3$—Ph | t-Bu |
| 2-Et, 3-OMe—Ph | 3-$CH_3$, 5-$CH_3$—Ph | —$C(CH_3)_2CH_2OC(O)CH_3$ |
| 2-$CH_3$, 3-OH—Ph | 2,3,4-F—Ph | t-Bu |
| 2-$CH_3$, 3-OH—Ph | 3-Cl-5-$OCH_3$-4-pyridyl | t-Bu |
| 2-$CH_3$, 3-OH—Ph | 2,6-di-Cl-4-pyridyl | t-Bu |
| 2-$CH_3$, 3-OH—Ph | 3-$OCH_3$-4-pyridyl | t-Bu |
| 2-$CH_3$, 3-OH—Ph | 3,5-di-$OCH_3$-4-$CH_3$—Ph | t-Bu |
| 2-$CH_3$, 3-$CH_2CH_2CH_2O$-4-Ph | 2-$OCH_3$—Ph | t-Bu |
| 2-Et, 3-OMe—Ph | 2,4-di-Cl-5-F—Ph | t-Bu |
| 2-$CH_3$, 3-$CH_2CH_2CH_2O$-4-Ph | 2,4-di-Cl-5-F—Ph | t-Bu |
| 2-$CH_3$, 3-$CH_2CH_2CH_2O$-4-Ph | 2-F, 5-$CH_3$—Ph | t-Bu |
| 2-$CH_3$, 3-$CH_2CH_2CH_2O$-4-Ph | 3,5-di-$OCH_3$-4-$CH_3$—Ph | t-Bu |
| 2-Et, 3,4-ethylenedioxy-Ph | 2,5-F—Ph | t-Bu |
| 2-Et, 3,4-ethylenedioxy-Ph | 2,3,4-F—Ph | t-Bu |
| 2-Et, 3,4-ethylenedioxy-Ph | 2,3,4,5--Ph | t-Bu |
| 2-Et, 3,4-ethylenedioxy-Ph | 3-$CF_3$-4-F—Ph | t-Bu |
| 2-Et, 3,4-ethylenedioxy-Ph | 2,6-di-Cl-4-pyridyl | t-Bu |
| 2-Et, 3,4-ethylenedioxy-Ph | 2-$OCH_3$—Ph | t-Bu |
| 2-Et, 3,4-ethylenedioxy-Ph | 2,4-di-Cl-5-F—Ph | t-Bu |
| 2-Et, 3,4-ethylenedioxy-Ph | 2-F, 4-Cl—Ph | t-Bu |
| 2-$CH_3$, 3-OAc—Ph | 3,5-di-$OCH_3$-4-$CH_3$—Ph | t-Bu |

TABLE 3-continued

| Ligand Components | | |
|---|---|---|
| A | B | E |
| 2-Et, 3-OMe—Ph | 2-$OCH_3$-5-Cl—Ph | t-Bu |
| 2-Et, 3,4-$OCH_2O$—Ph | 2-$OCH_3$-4-Cl—Ph | t-Bu |
| 2-$CH_3$, 3-$CH_2CH_2CH_2O$-4-Ph | 2-$OCH_3$-5-Cl—Ph | t-Bu |
| 2-Et, 3-OMe—Ph | 2-$NO_2$-5-$CH_3$—Ph | t-Bu |
| 2-Et, 3-OMe—Ph | 2-$NO_2$-4-Cl—Ph | t-Bu |
| 2-Et, 3-OMe—Ph | 2-$NO_2$-5-Cl—Ph | t-Bu |
| 2-$CH_3$, 3-$CH_2CH_2CH_2O$-4-Ph | 2-$NO_2$-5-$CH_3$—Ph | t-Bu |
| Benzo[1,2,5]oxadiazole-5-yl | 2-$OCH_3$-4-Cl—Ph | t-Bu |
| 2-Vinyl, 3-OMe—Ph | 2-Cl, 5-$NO_2$—Ph | t-Bu |
| 2-Vinyl, 3-OMe—Ph | 2-$OCH_3$-4-Cl—Ph | t-Bu |
| 2-Et, 3-$OCH_3$—Ph | 1-methyl-1H-indole-2-yl | t-Bu |
| 2-Et, 3,4-ethylenedioxy-Ph | 3,5-di-$OCH_3$-4-$CH_3$—Ph | t-Bu |
| 2-Cl, 3-$CH_2OCH_2O$-4-Ph | 3-$CH_3$, 5-$CH_3$—Ph | t-Bu |
| 2-F, 4-Et—Ph | 3-$NO_2$—Ph | t-Bu |
| 2-F, 4-Et—Ph | 3-$OCH_3$—Ph | t-Bu |
| 2-Cl, 3-$CH_2OCH_2O$-4-Ph | 3,5-di-$OCH_3$-4-$CH_3$—Ph | t-Bu |
| 2-F, 4-Et—Ph | 2,6-di-Cl-4-pyridyl | t-Bu |
| 2-F, 4-Et—Ph | 3,5-di-$OCH_3$-4-$CH_3$—Ph | t-Bu |
| 2-F, 4-Et—Ph | 3,4,5-F—Ph | t-Bu |
| 2-F, 4-Et—Ph | 3-$CH_3$—Ph | t-Bu |
| 2-F, 4-Et—Ph | 2-$OCH_3$—Ph | t-Bu |
| 2-F, 4-Et—Ph | 2-$NO_2$-5-F—Ph | t-Bu |
| 2-F, 4-Et—Ph | 2-$OCH_2CF_3$, 5-$OCH_3$—Ph | t-Bu |
| 2-F, 4-Et—Ph | 2-Cl-6-$CH_3$-4-pyridyl | t-Bu |
| 2-F, 4-Et—Ph | 2,6-di-$OCH_3$-3-pyridyl | t-Bu |
| 3-NH—C═C-4-Ph | 3-$CH_3$, 5-$CH_3$—Ph | t-Bu |
| 2-Et, 3-OMe—Ph | 2-S(O)$CH_3$—Ph | t-Bu |
| 3,4-$OCF_2O$—Ph | 2-$NO_2$—Ph | t-Bu |
| 3,4-$OCF_2O$—Ph | 3-$CH_3$, 5-$CH_3$—Ph | t-Bu |
| 3,4-$OCF_2O$—Ph | 3-$OCH_3$—Ph | t-Bu |
| 2-Et, 3-OMe—Ph | 3-Br—Ph | —$C(CH_3)_2CN$ |
| 2-$CH_2OMe$, 3-OMe—Ph | 3,5-di-Cl—Ph | t-Bu |
| 2-Et, 3-OMe—Ph | 3-CH═NOH, 5—$CH_3$—Ph | t-Bu |
| 2-Et, 3-OMe—Ph | 3-CH═$NNHCONH_2$, 5-$CH_3$—Ph | t-Bu |
| 2-Et, 3-OMe—Ph | 3-CH═$NNHCOCONH_2$, 5-$CH_3$—Ph | t-Bu |
| 2-Et, 3-OMe—Ph | 3-$CH_3$, 5-$CH_3$—Ph | —$C(CH_3)_2CN$ |
| 2-Et, 3-OMe—Ph | 3,5-di-$OCH_3$-4-$CH_3$—Ph | —$C(CH_3)_2CN$ |
| 2-Et, 3-$OCH_2OCH_2$-4-Ph | 2-$OCH_3$—Ph | t-Bu |
| 2-$CH_3$, 3-$CH_2CH_2CH_2O$-4-Ph | 2,4,5-F—Ph | t-Bu |
| 2-$CH_3$, 3-$CH_2CH_2CH_2O$-4-Ph | 3,4,5-F—Ph | t-Bu |
| 2-$CH_3$, 3-$CH_2CH_2CH_2O$-4-Ph | 3-F—Ph | t-Bu |
| 2-Et, 3,4-$OCH_2O$—Ph | 3-$CF_3$—Ph | t-Bu |
| 2-$CH_3$, 3-$CH_2CH_2CH_2O$-4-Ph | 4-F—Ph | t-Bu |
| 2-$CH_3$, 3-$CH_2CH_2CH_2O$-4-Ph | 3,4-F—Ph | t-Bu |
| 2-$CH_3$, 3-$CH_2CH_3CH_2O$-4-Ph | 3,5-di-F—Ph | t-Bu |
| 2-$CH_3$, 3-$CH_2CH_2CH_2O$-4-Ph | 2,3,4,5-tetra-F—Ph | t-Bu |
| 2-Et, 3-$OCH_2OCH_2$-4-Ph | 4-$CH_3$—Ph | t-Bu |
| 2-Et, 3-OMe—Ph | 3,5-di-$OCH_3$-4-OAc—Ph | t-Bu |
| 2-Et, 3-OMe—Ph | 3,5-di-$OCH_3$—OH—Ph | t-Bu |
| 2-$CH_3$, 3,4-ethylenedioxy-Ph | 3,5-di-$OCH_3$-4-$CH_3$—Ph | t-Bu |
| 2-$CH_3$, 3,4-ethylenedioxy-Ph | 2,6-di-$OCH_3$-3-pyridyl | t-Bu |
| 2-$CH_3$, 3,4-ethylenedioxy-Ph | 2,6-di-Cl-4-pyridyl | t-Bu |
| 2-$CH_3$, 3,4-ethylenedioxy-Ph | 3-F—Ph | t-Bu |
| 2-$CH_3$, 3,4-ethylenedioxy-Ph | 3-$CF_3$, 5-F—Ph | t-Bu |
| 2-$CH_3$, 3,4-ethylenedioxy-Ph | 2-$NO_2$-5-$CH_3$—Ph | t-Bu |
| 2-ethyl, 3-methoxy | 4,6-dimethyl-pyridyl | t-Bu |
| 2-$CH_3$, 3,4-ethylenedioxy-Ph | 3,5-di-$CH_3$—Ph | —CH(Et)$C(CH_3)_3$ |
| 2-$CH_3$, 3,4-ethylenedioxy-Ph | 3,5-di-$OCH_3$-4-$CH_3$—Ph | —CH(Et)$C(CH_3)_3$ |
| 2-$CH_3$, 3,4-ethylenedioxy-Ph | 3,5-di-$CH_3$—Ph | —CH(n-Pr)$C(CH_3)_3$ |
| 2-$CH_3$, 3,4-ethylenedioxy-Ph | 3,5-di-$OCH_3$-4-$CH_3$—Ph | —CH(n-Pr)$C(CH_3)_3$ |
| 2-$CH_2CH_3$, 3,4-ethylenedioxy-Ph | 3,5-di-$CH_3$—Ph | —CH(Et)$C(CH_3)_3$ |
| 2-$CH_2CH_3$, 3,4-ethylenedioxy-Ph | 3,5-di-OCH3-4-CH3—Ph | —CH(Et)$C(CH_3)_3$ |
| 2-$CH_2CH_3$, 3,4-ethylenedioxy-Ph | 3,5-di-$CH_3$—Ph | —CH(n-Pr)$C(CH_3)_3$ |
| 2-$CH_2CH_3$, 3,4-ethylenedioxy-Ph | 3,5-di-$OCH_3$-4-$CH_3$—Ph | —CH(n-Pr)$C(CH_3)_3$ |
| 2-$CH_3$, 3-$OCH_3$—Ph | 2-methoxy-6-trifluoromethyl-3-pyridyl | —$C(CH_3)_3$ |
| 2-$CH_3$, 3-$OCH_3$—Ph | 1-methyl-2-oxo-6-trifluoromethyl-3-pyridyl | —$C(CH_3)_3$ |
| 2-$CH_3$, 3-$OCH_3$—Ph | 2,6-dimethoxy-4-pyrimidinyl | —$C(CH_3)_3$ |
| 2-$CH_3$, 3-$OCH_3$—Ph | 3,6-dimethoxy-4-pyridazinyl | —$C(CH_3)_3$ |
| 2-$CH_3$, 3-$OCH_3$—Ph | 3,6-dichloro-4-pyridazinyl | —$C(CH_3)_3$ |
| 2-$CH_3$, 3-$OCH_3$—Ph | 4-pyridazinyl | —$C(CH_3)_3$ |
| 2-$CH_3$, 3-$OCH_3$—Ph | 3-oxo-6-methoxy-4-pyridazinyl | —$C(CH_3)_3$ |
| 2-$CH_3$, 3-$OCH_3$—Ph | 3,5-di-$CH_3$—Ph | —CH(Et)$C(CH_3)_3$ |
| 2-$CH_3$, 3-$OCH_3$—Ph | 3,5-di-$OCH_3$-4-$CH_3$—Ph | —CH(Et)$C(CH_3)_3$ |
| 2-$CH_3$, 3-$OCH_3$—Ph | 3,5-di-$CH_3$—Ph | —CH(n-Pr)$C(CH_3)_3$ |

TABLE 3-continued

| Ligand Components | | |
|---|---|---|
| A | B | E |
| 2-$CH_3$, 3-$OCH_3$—Ph | 3,5-di-$OCH_3$-4-$CH_3$—Ph | —CH(n-Pr)C$(CH_3)_3$ |
| 2-$CH_2CH_3$, 3-$OCH_3$—Ph | 3,5-di-$CH_3$—Ph | —CH(Et)C$(CH_3)_3$ |
| 2-$CH_2CH_3$, 3-$OCH_3$—Ph | 3,5-di-$OCH_3$-4-$CH_3$—Ph | —CH(Et)C$(CH_3)_3$ |
| 2-$CH_2CH_3$, 3-$OCH_3$—Ph | 3,5-di-$CH_3$—Ph | —CH(n-Pr)C$(CH_3)_3$ |
| 2-$CH_2CH_3$, 3-$OCH_3$—Ph | 3,5-di-$OCH_3$-4-$CH_3$—Ph | —CH(n-Pr)C$(CH_3)_3$ |
| 2-$CH_3$, 3-$OCH_3$—Ph | 3,5-di-$CH_3$—Ph | —CH(Et)C$(CH_3)_3$ |
| 2-$CH_3$, 3-OH—Ph | 3-$OCH_3$-4-pyridyl | —C$(CH_3)_3$ |
| 4-CH(OH)$CH_3$—Ph | 3,5-di($CH_2OH$)—Ph | —C$(CH_3)_3$ |
| 2-$CH_2CH_3$, 3-$OCH_3$—Ph | 2-S(O)$CH_3$—Ph | —C$(CH_3)_3$ |
| 4-C(O)$CH_3$—Ph | 3,5-di-$CO_2H$—Ph | —C$(CH_3)_3$ |
| 2-$CH_3$, 3,4-ethylenedioxy-Ph | 2,6-di-$OCH_3$-3-pyridyl | —C$(CH_3)_3$ |
| 2-$CH_2CH_3$, 3,4-ethylenedioxy-Ph | 3-$CF_3$-4-F-phenyl | —C$(CH_3)_3$ |
| 2-F, 4-$CH_2CH_3$—Ph | 3,5-di-$CH_3$—Ph | —C$(CH_3)_3$ |
| 2-$CH_2CH_3$, 3-$OCH_3$—Ph | 2-$SO_3H$—Ph | —C$(CH_3)_3$ |
| 2-$CH_3$, 3-$CH_2CH_2CH_2O$-4-Ph | 3,5-di-$CH_3$—Ph | —C$(CH_3)_3$ |
| 4-$CH_2CH_3$—Ph | 3,5-di-$CH_3$—Ph | —CH($CH_3$)C$(CH_3)_3$ |
| 2-$CH_2CH_3$, 3,4-ethylenedioxy-Ph | 3-$CH_3$—Ph | —C$(CH_3)_3$ |
| 2,3-di-$CH_3$—Ph | Ph | —CH(Et)(n-Bu) |
| 2,3-di-$CH_3$—Ph | 3-$CH_3$—Ph | —CH(Et)(t-Bu) |
| 2-$CH_3$, 3,4-ethylenedioxy-Ph | 3,5-di-$OCH_3$, 4-OH—Ph | —C$(CH_3)_3$ |
| 2-F, 3-$CH_2OCH_2O$-4-Ph | 3,5-di-$CH_3$—Ph | —C$(CH_3)_3$ |
| 2-$CH_3$, 3,4-ethylenedioxy-Ph | 2-S(O)$CH_3$—Ph | —C$(CH_3)_3$ |
| 2-$CH_3$, 3,4-ethylenedioxy-Ph | 3,5-di-$OCH_3$, 4-$CH_3$—Ph | —C$(CH_3)_2$CN |
| 2-$CH_2CH_3$-3-$OCH_3$—Ph | 6-$CH_3$-2-pyridyl- | —C$(CH_3)_3$ |
| 2-$CH_3$, 3,4-ethylenedioxy-Ph | 2-$NO_2$-3,5-di-$OCH_3$, 4-$CH_3$—Ph | —C$(CH_3)_3$ |
| 2-$CH_3$, 3,4-ethylenedioxy-Ph | 3,5-di-$CH_3$—Ph | —C$(CH_3)_3$ |
| 4-$CH_2CH_3$—Ph | 3,5-di-$CH_3$—Ph | —C$(CH_3)_3$ |
| 2-$CH_3$-3-$OCH_3$—Ph | 3,5-di-$CH_3$—Ph | —C$(CH_3)_3$ |
| 4-$CH_2CH_3$—Ph | 3,5-di-$CH_3$—Ph | —CH(Et)(t-Bu) |
| 4-$CH_2CH_3$—Ph | 2-$OCH_3$-3-pyridyl | —CH(Et)(t-Bu) |
| 4-$CH_2CH_3$—Ph | 3,5-di-$CH_3$—Ph | —CH(n-Bu)(t-Bu) |
| 4-$CH_2CH_3$—Ph | 3,5-di-$OCH_3$, 4-$CH_3$—Ph | —CH(n-Bu)(t-Bu) |
| 4-$CH_2CH_3$—Ph | 2-$OCH_3$-3-pyridyl | —CH(n-Bu)(t-Bu) |
| 4-$CH_2CH_3$—Ph | 3,5-di-$CH_3$—Ph | —CH(Ph)(t-Bu) |
| 4-$CH_2CH_3$—Ph | 3,5-di-$OCH_3$, 4-$CH_3$—Ph | —CH(Ph)(t-Bu) |
| 4-$CH_2CH_3$—Ph | 2-$OCH_3$-3-pyridyl | —CH(Ph)(t-Bu) |
| 2-$CH_2CH_3$, 3-$OCH_3$—Ph | 5-benzimidazolyl | —C$(CH_3)_3$ |
| 2-$CH_2CH_3$, 3-$OCH_3$—Ph | 1-(or 3-)trityl-5-benzimidazolyl | —C$(CH_3)_3$ |
| 2-$CH_2CH_3$, 3-$OCH_3$—Ph | 5-methyl-1-phenyl-1H-pyrazole-3-yl | —C$(CH_3)_3$ |
| 2-$CH_2CH_3$, 3-$OCH_3$—Ph | 3-chloro-6-methylsulfanyl-pyrazine-2-yl | —C$(CH_3)_3$ |
| 2-$CH_2CH_3$, 3-$OCH_3$—Ph | 1H-indazole-3-yl | —C$(CH_3)_3$ |
| 2-$CH_2CH_3$, 3-$OCH_3$—Ph | 1-trityl-1H-indazole-3-yl | —C$(CH_3)_3$ |
| 2-$CH_2CH_3$, 3-$OCH_3$—Ph | 5-methoxycarbonyl-2-pyridyl | —C$(CH_3)_3$ |
| 2-$CH_2CH_3$, 3-$OCH_3$—Ph | pyrazine-2-yl | —C$(CH_3)_3$ |
| 2-$CH_2CH_3$, 3-$OCH_3$—Ph | 3,5-di-$CH_3$—Ph | —C$(CH_3)_2CH_2$OSi$(CH_3)$2tBu |
| 2-$CH_2CH_3$, 3-$OCH_3$—Ph | 3,5-di-$CH_3$—Ph | —C$(CH_3)_2$CH═N$CH_2CH_2$OH |
| 2-$CH_2CH_3$, 3-$OCH_3$—Ph | 3,5-di-$CH_3$—Ph | —C$(CH_3)_2$CH═NNHC(O)$NH_2$ |
| 2-$CH_2CH_3$, 3-$OCH_3$—Ph | 3,5-di-$CH_3$—Ph | —C$(CH_3)_2$CH═NNHC(O)C(O)$NH_2$ |
| 2-$CH_2CH_3$, 3-$OCH_3$—Ph | 3,5-di-$CH_3$—Ph | —C$(CH_3)_2$COOH |
| 2-$CH_2$S(O)$CH_3$, 3-$OCH_3$—Ph | 3,5-di-$CH_3$—Ph | —C$(CH_3)_3$ |
| 2-$CH_3$S$(O)_2CH_3$, 3-OCH3—Ph | 3,5-di-$CH_3$—Ph | —C$(CH_3)_3$ |
| 2-$CH_2NMe_2$, 3-$OCH_3$—Ph | 3,5-di-$CH_3$—Ph | —C$(CH_3)_3$ |
| 2-$CH_2NHCH_3$, 3-$OCH_3$—Ph | 3,5-di-$CH_3$—Ph | —C$(CH_3)_3$ |
| 2-CH=$CH_2$, 3-$OCH_3$—Ph— | 3,5-di-$CH_3$—Ph | —C$(CH_3)_3$ |
| 2-$CH_2$OMe, 3-$OCH_3$—Ph— | 3,5-di-$CH_3$—Ph | —C$(CH_3)_3$ |
| 2-$CH_2SCH_3$, 3-$OCH_3$—Ph | 3,5-di-$CH_3$—Ph | —C$(CH_3)_3$ |
| 2-$CH_2OCH_2$CH=$CH_2$, 3-$OCH_3$—Ph | 3,5-di-$CH_3$—Ph | —C$(CH_3)_3$ |
| 2-$CH_2$Cl, 3-$OCH_3$—Ph— | 3,5-di-$CH_3$—Ph | —C$(CH_3)_3$ |
| 2-$CH_2$OH, 3-$OCH_3$—Ph— | 3,5-di-$CH_3$—Ph | —C$(CH_3)_3$ |
| 2-$CH_2$OAc, 3-$OCH_3$—Ph | 3,5-di-$CH_3$—Ph | —C$(CH_3)_3$ |
| 2-$CH_2$F, 3-$OCH_3$—Ph— | 3,5-di-$CH_3$—Ph | —C$(CH_3)_3$ |
| 2-$CH_3$, 3-$OCH_3$ | 3,5-di-$CH_3$ | —CH(n-Bu)(t-Bu) |
| 2-$CH_3$, 3-$OCH_3$ | 3,5-di-$OCH_3$, 4-$CH_3$ | —CH(n-Bu)(t-Bu) |
| 2-$CH_2CH_3$, 3-$OCH_3$—Ph | 5-Methyl-pyrazine-2-yl- | —C$(CH_3)_3$ |

In another embodiment, the activating ligand is a compound having Formula I selected from the group consisting of:

3,5-Dimethyl-benzoic acid N-tert-butyl-N'-(3-hydroxymethyl-5-methyl-2,3-dihydro-benzo[1,4]dioxine-6-carbonyl)-hydrazide;

3,5-Dimethyl-benzoic acid N-tert-butyl-N'-[3-(tert-butyl-dimethyl-silanyloxymethyl)-5-methyl-2,3-dihydro-benzo[1,4]dioxine-6-carbonyl]-hydrazide;

7-[N'-tert-Butyl-N'-(3,5-dimethyl-benzoyl)-hydrazinocarbonyl]-8-methyl-2,3-dihydro-benzo[1,4]dioxine-2-carboxylic acid;

7-[N'-tert-Butyl-N'-(3,5-dimethyl-benzoyl)-hydrazinocarbonyl]-8-methyl-2,3-dihydro-benzo[1,4]dioxine-2-carboxylic acid methyl ester;

3,5-Dimethyl-benzoic acid N-tert-butyl-N'-(3-semicarbazidomethyl-5-methyl-2,3-dihydro-benzo[1,4]dioxine-6-carbonyl)-hydrazide;

Phenyl-carbamic acid 7-[N'-tert-butyl-N'-(3,5-dimethyl-benzoyl)-hydrazinocarbonyl]-8-methyl-2,3-dihydro-benzo[1,4]dioxin-2-ylmethyl ester;

3,5-Dimethyl-benzoic acid N'-[3-(2-amino-ethyl)-5-methyl-2,3-dihydro-benzo[1,4]dioxine-6-carbonyl]-N-tert-butyl-hydrazide;

7-[N'-tert-Butyl-N'-(3,5-dimethyl-benzoyl)-hydrazinocarbonyl]-8-methyl-2,3-dihydro-benzo[1,4]dioxine-2-carboxylic acid pentafluorophenyl ester;

7-[N'-tert-Butyl-N'-(3,5-dimethyl-benzoyl)-hydrazinocarbonyl]-8-methyl-2,3-dihydro-benzo[1,4]dioxine-2-carboxylic acid methylamide;

3,5-Dimethyl-benzoic acid N-tert-butyl-N'-(3-formyl-5-methyl-2,3-dihydro-benzo[1,4]dioxine-6-carbonyl)-hydrazide;

Toluene-4-sulfonic acid 7-[N'-tert-butyl-N'-(3,5-dimethyl-benzoyl)-hydrazinocarbonyl]-8-methyl-2,3-dihydro-benzo[1,4]dioxin-2-ylmethyl ester;

3,5-Dimethyl-benzoic acid N-tert-butyl-N'-[3-(hydroxy-imino-methyl)-5-methyl-2,3-dihydro-benzo[1,4]dioxine-6-carbonyl]-hydrazide;

3,5-Dimethyl-benzoic acid N-tert-butyl-N'-(3-cyanomethyl-5-methyl-2,3-dihydro-benzo[1,4]dioxine-6-carbonyl)-hydrazide;

3,5-Dimethyl-benzoic acid N-tert-butyl-N'-(5-methyl-3-methylsulfanylmethyl-2,3-dihydro-benzo[1,4]dioxine-6-carbonyl)-hydrazide;

3,5-Dimethyl-benzoic acid N-tert-butyl-N'-(3-methanesulfonylmethyl-5-methyl-2,3-dihydro-benzo[1,4]dioxine-6-carbonyl)-hydrazide;

3,5-Dimethyl-benzoic acid N-tert-butyl-N'-(3-fluoromethyl-5-methyl-2,3-dihydro-benzo[1,4]dioxine-6-carbonyl)-hydrazide;

3,5-Dimethyl-benzoic acid N-(1-tert-butyl-heptyl)-N'-(3-methoxy-2-methyl-benzoyl)-hydrazide;

3,5-Dimethyl-benzoic acid N-(1-tert-butyl-heptyl)-N'-(4-ethyl-benzoyl)-hydrazide;

3,5-Dimethoxy-4-methyl-benzoic; acid-N-(1-tert-butyl-heptyl)-N'-(3-methoxy-2-methyl-benzoyl)-hydrazide;

3,5-Dimethoxy-4-methyl-benzoic acid-N-(1-tert-butyl-heptyl)-N'-(4-ethyl-benzoyl)-hydrazide;

2-Methoxy-nicotinic acid N-(1-tert-butyl-heptyl)-N'-(4-ethyl-benzoyl)-hydrazide;

3,5-Dimethyl-benzoic acid N-(1-tert-butyl-3,4,4-trimethyl-pent-2-enyl)-N'-(3-methoxy-2-methyl-benzoyl)-hydrazide;

3,5-Dimethyl-benzoic acid N-(1-tert-butyl-2-cyano-vinyl)-N'-(3-methoxy-2-methyl-benzoyl)-hydrazide;

3,5-Dimethyl-benzoic acid N-(1-butyl-2,2-dimethyl-pentyl)-N'-(3-methoxy-2-methyl-benzoyl)-hydrazide; and 3,5-Dimethyl-benzoic acid N-(1-butyl-2,2-dimethyl-pent-4-enyl)-N'-(3-methoxy-2-methyl-benzoyl)-hydrazide.

In another embodiment, the activating ligand is an enantiomerically enriched compound having Formula II:

II

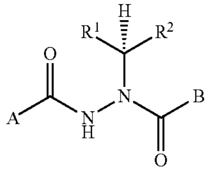

wherein:

A is alkoxy, arylalkyloxy, aryloxy, arylalkyl, optionally substituted aryl or optionally substituted heteroaryl;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocycle, optionally substituted aryl or optionally substituted heteroaryl;

with the proviso that $R^1$ does not equal $R^2$;

wherein the absolute configuration at the asymmetric carbon atom bearing $R^1$ and $R^2$ is predominantly S.

In another embodiment, the activating ligand is an enantiomerically enriched compound having Formula III:

III

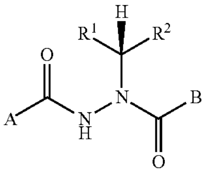

wherein:

A is alkoxy, arylalkyloxy, aryloxy, arylalkyl, optionally substituted aryl or optionally substituted heteroaryl;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocycle, optionally substituted aryl or optionally substituted heteroaryl;

with the proviso that $R^1$ does not equal $R^2$;

wherein the absolute configuration at the asymmetric carbon atom bearing $R^1$ and $R^2$ is predominantly R.

In another embodiment, the activating ligand is an enantiomerically enriched compound having Formula III, wherein:

A is:

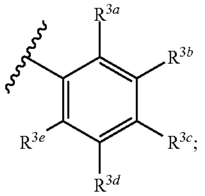

B is:

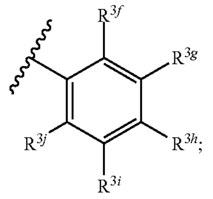

$R^{3a}$, $R^{3b}$, $R^{3c}$, $R^{3d}$, $R^{3e}$, $R^{3f}$, $R^{3g}$, $R^{3h}$, $R^{3i}$ and $R^{3j}$ are independently selected from hydrogen, halo, $(C_1-C_4)$alkyl, or $(C_1-C_4)$alkoxy;

$R^1$ is $(C_1-C_6)$alkyl, hydroxy$(C_1-C_4)$alkyl, or $(C_2-C_4)$alkenyl; and $R^2$ is optionally substituted $(C_1-C_6)$alkyl.

In another embodiment, the activating ligand is a compound having Formula III selected from the group consisting of:

(R)-N'-(1-tert-Butyl-butyl)-N'-(3,5-dimethyl-benzoyl)-hydrazinecarboxylic acid benzyl ester;

(R)-N'-(1-tert-Butyl-butyl)-N'-(3,5-dimethyl-benzoyl)-hydrazinecarboxylic acid tert-butyl ester;

(R)-N'-(1-tert-Butyl-4-hydroxy-butyl)-N'-(3,5-dimethyl-benzoyl)-hydrazine carboxylic acid benzyl ester;

(R)-3,5-Dimethyl-benzoic acid N-(1-tert-butyl-butyl)-N'-(2-ethyl-3-methoxy-benzoyl)-hydrazide;

(R)-3,5-Dimethyl-benzoic acid N'-benzoyl-N-(1-tert-butyl-butyl)-hydrazide;

(R)-3,5-Dimethyl-benzoic acid N-(1-tert-butyl-butyl)-N'-(2-methyl-benzoyl)-hydrazide;

(R)-3,5-Dimethyl-benzoic acid N-(1-tert-butyl-butyl)-N'-(2-methoxy-benzoyl)-hydrazide;

(R)-3,5-Dimethyl-benzoic acid N-(1-tert-butyl-butyl)-N'-(2-fluoro-benzoyl)-hydrazide;

(R)-3,5-Dimethyl-benzoic acid N-(1-tert-butyl-butyl)-N'-(2-chloro-benzoyl)-hydrazide;

(R)-3,5-Dimethyl-benzoic acid N'-(2-bromo-benzoyl)-N-(1-tert-butyl-butyl)-hydrazide;

(R)-3,5-Dimethyl-benzoic acid N-(1-tert-butyl-butyl)-N'-(3-methyl-benzoyl)-hydrazide;

(R)-3,5-Dimethyl-benzoic acid N-(1-tert-butyl-butyl)-N'-(3-methoxy-benzoyl)-hydrazide;

(R)-3,5-Dimethyl-benzoic acid N-(1-tert-butyl-butyl)-N'-(3-chloro-benzoyl)-hydrazide;

(R)-3,5-Dimethyl-benzoic acid N-(1-tert-butyl-butyl)-N'-(4-methyl-benzoyl)-hydrazide;

(R)-3,5-Dimethyl-benzoic acid N-(1-tert-butyl-butyl)-N'-(4-ethyl-benzoyl)-hydrazide;

(R)-3,5-Dimethyl-benzoic acid N-(1-tert-butyl-butyl)-N'-(4-methoxy-benzoyl)-hydrazide;

(R)-3,5-Dimethyl-benzoic acid N-(1-tert-butyl-butyl)-N'-(4-chloro-benzoyl)-hydrazide;

(R)-3,5-Dimethyl-benzoic acid N-(1-tert-butyl-butyl)-N'-(2,6-difluoro-benzoyl)-hydrazide;

(R)-3,5-Dimethyl-benzoic acid N-(1-tert-butyl-butyl)-N'-(2,6-dichloro-benzoyl)-hydrazide;

(R)-3,5-Dimethyl-benzoic acid N-(1-tert-butyl-butyl)-N'-(3,4-dimethoxy-benzoyl)-hydrazide;

(R)-3,5-Dimethyl-benzoic acid N-(1-tert-butyl-butyl)-N'-(3,5-difluoro-benzoyl)-hydrazide;

(R)-3,5-Dimethyl-benzoic acid N-(1-tert-butyl-butyl)-N'-(3,5-dimethoxy-4-methyl-benzoyl)-hydrazide;

(R)-3,5-Dimethyl-benzoic acid N-(1-tert-butyl-butyl)-N'-(4-methyl-benzo[1,3]dioxole-5-carbonyl)-hydrazide;

(R)-3,5-Dimethyl-benzoic acid N-(1-tert-butyl-butyl)-N'-(5-methyl-2,3-dihydro-benzo[1,4]dioxine-6-carbonyl)-hydrazide;

(R)-3,5-Dimethyl-benzoic acid N-(1-tert-butyl-butyl)-N'-(5-ethyl-2,3-dihydro-benzo[1,4]dioxine-6-carbonyl)-hydrazide;

(R)-3,5-Dimethyl-benzoic acid N-(1-tert-butyl-butyl)-N'-(naphthalene-1-carbonyl)-hydrazide;

(R)-3,5-Dimethyl-benzoic acid N-(1-tert-butyl-butyl)-N'-(naphthalene-2-carbonyl)-hydrazide;

(R)-3,5-Dimethyl-benzoic acid N-(1-tert-butyl-butyl)-N'-(thiophene-2-carbonyl)-hydrazide;

(R)-3,5-Dimethyl-benzoic acid N-(1-tert-butyl-butyl)-N'-(2,5-dimethyl-furan-3-carbonyl)-hydrazide;

(R)-3,5-Dimethyl-benzoic acid N-(1-tert-butyl-butyl)-N'-(2-chloro-pyridine-3-carbonyl)-hydrazide;

(R)-3,5-Dimethyl-benzoic acid N-(1-tert-butyl-butyl)-N'-(6-chloro-pyridine-3-carbonyl)-hydrazide;

(R)-3,5-Dimethyl-benzoic acid N-(1-tert-butyl-butyl)-N'-(3-methoxy-2-methyl-benzoyl)-hydrazide;

(R)-3,5-Dimethoxy-4-methyl-benzoic acid N-(1-tert-butyl-butyl)-N'-(3-methoxy-2-methyl-benzoyl)-hydrazide; and (R)-3,5-Dimethyl-benzoic acid N'-(4-ethyl-benzoyl)-N-(1-phenethyl-but-3-enyl)-hydrazide.

In another embodiment, the activating ligand is a compound having Formula IV:

IV

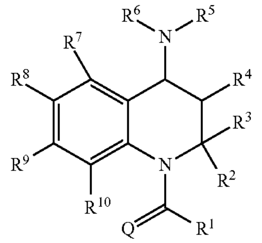

wherein:

Q is O or S;

$R^1$ is selected from the group consisting of hydrogen, $(C_1-C_{12})$alkyl, $(C_3-C_{12})$cycloalkyl, $(C_3-C_{12})$cycloalkyl$(C_1-C_3)$alkyl, $(C_1-C_{12})$haloalkyl, $(C_2-C_{12})$alkenyl, $(C_3-C_{12})$cycloalkenyl, $(C_2-C_{12})$haloalkenyl, $(C_2-C_{12})$alkynyl, $(C_1-C_6)$alkoxy$(C_1-C_6)$alkyl, $(C_1-C_6)$alkylthio$(C_1-C_6)$alkyl, $(C_1-C_6)$alkoxycarbonyl, succinimidylmethyl, benzosuccinimidylmethyl, optionally substituted phenyl, optionally substituted 1-naphthyl, optionally substituted 2-naphthyl, optionally substituted phenyl$(C_1-C_3)$alkyl, optionally substituted phenyl$(C_2-C_3)$alkenyl, optionally substituted naphthyl$(C_1-C_3)$alkyl, optionally substituted phenoxy$(C_1-C_3)$alkyl, optionally substituted phenylamino, and optionally substituted heterocycle;

$R^2$ and $R^3$ are each independently selected from hydrogen, $(C_1-C_6)$alkyl, and $(C_1-C_6)$haloalkyl;

$R^4$ is hydrogen, $(C_1-C_6)$alkyl, or $(C_1-C_6)$haloalkyl;

$R^5$ and $R^6$ are each independently selected from the group consisting of hydrogen, $(C_1-C_{12})$alkyl, $(C_3-C_{12})$cycloalkyl, $(C_1-C_{12})$haloalkyl, $(C_2-C_{12})$alkenyl, $(C_3-C_{12})$cycloalkenyl, $(C_2-C_{12})$haloalkenyl, $(C_2-C_{12})$alkynyl, $(C_1-C_6)$alkoxy$(C_1-C_6)$alkyl, $(C_1-C_6)$alkylthio$(C_1-C_6)$alkyl, aminocarbonyl, aminothiocarbonyl, formyl, $(C_1-C_6)$alkylsulfinyl, $(C_1-C_6)$alkylsulfonyl, $(C_1-C_6)$alkylcarbonyl, cyclo$(C_3-C_6)$alkylcarbonyl, halo$(C_1-C_6)$ alkylcarbonyl, ($C_1$-$C_6$)alkylaminocarbonyl, di($C_1$-$C_6$)alkylaminocarbonyl, ($C_1$-$C_6$)alkoxycarbonyl, ($C_1$-$C_6$)alkoxycarbonylcarbonyl, or phenyl($C_2$-$C_3$)alkenylcarbonyl, optionally substituted phenyl, optionally substituted 1-naphthyl, optionally substituted 2-naphthyl, optionally substituted phenyl($C_1$-$C_3$)alkyl, optionally substituted phenyl($C_2$-$C_3$)alkenyl, optionally substituted phenylcarbonyl, or optionally substituted heterocycle;

$R^7$, $R^8$, $R^9$, and $R^{10}$ are each independently selected from the group consisting of hydrogen, cyano, nitro, halogen, ($C_1$-$C_{12}$)alkyl, ($C_3$-$C_{12}$)cycloalkyl, ($C_1$-$C_{12}$)haloalkyl, ($C_2$-$C_{12}$)alkenyl, ($C_3$-$C_{12}$)cycloalkenyl, ($C_2$-$C_{12}$)haloalkenyl, ($C_2$-$C_{12}$)alkynyl, halo($C_2$-$C_6$)alkynyl, hydroxy, ($C_1$-$C_6$)alkoxy, halo($C_1$-$C_6$)alkoxy, ($C_2$-$C_6$)alkenyloxy, halo($C_2$-$C_6$)alkenyloxy, ($C_2$-$C_6$)alkynyloxy, halo($C_2$-$C_6$)alkynyloxy, aryloxy, ($C_1$-$C_6$)alkoxy($C_1$-$C_6$)alkyl, ($C_1$-$C_6$)alkylthio, halo($C_1$-$C_6$)alkylthio, ($C_2$-$C_6$)alkenylthio, halo($C_2$-$C_6$)alkenylthio, ($C_2$-$C_6$)alkynylthio, halo($C_2$-$C_6$)alkynylthio, ($C_1$-$C_6$)alkylsulfinyl, halo($C_1$-$C_6$)alkylsulfinyl, ($C_1$-$C_6$)alkylsulfonyl, halo($C_1$-$C_6$)alkylsulfonyl, ($C_1$-$C_6$)alkylamino, di($C_1$-$C_6$)alkylamino, ($C_1$-$C_3$)alkoxy($C_1$-$C_3$)alkyl, ($C_1$-$C_6$)alkylthio($C_1$-$C_6$)alkyl, ($C_1$-$C_3$)alkylsulfinyl($C_1$-$C_3$)alkyl, ($C_1$-$C_3$)alkylsulfonyl($C_1$-$C_3$)alkyl, ($C_1$-$C_3$)alkylamino($C_1$-$C_3$)alkyl, di($C_1$-$C_3$)alkylamino($C_1$-$C_3$)alkyl, ($C_1$-$C_6$)alkylcarbonyl, ($C_1$-$C_6$)alkylaminocarbonyl, di($C_1$-$C_6$)alkylaminocarbonyl, or ($C_1$-$C_6$)alkoxycarbonyl, optionally substituted phenyl, optionally substituted 1-naphthyl, optionally substituted 2-naphthyl, optionally substituted phenyl($C_1$-$C_3$)alkyl, optionally substituted phenyl($C_2$-$C_3$)alkenyl, or optionally substituted heterocycle.

In another embodiment, the activating ligand is a compound having Formula IV wherein:

Q is O;

$R^1$ is selected from the group consisting of 4-fluorophenyl, 3-fluorophenyl, 4-fluoro-3-methylphenyl, 4-fluoro-3-(trifluoromethyl)phenyl, 4-fluoro-3-iodophenyl, 3-fluoro-4-iodophenyl, 3,4-di-fluorophenyl, 4-ethylphenyl, 3-fluoro-4-methylphenyl, 3-fluoro-4-ethylphenyl, 3-chloro-4-fluorophenyl, 3-fluoro-4-chlorophenyl, 2-methyl-3-methoxyphenyl, 2-ethyl-3-methoxyphenyl, 2-ethyl-3,4-ethylenedioxyphenyl, 3-nitrophenyl, 4-iodophenyl, 3-fluoro-4-trifluoromethylphenyl, 3-methylphenyl, 4-methylphenyl, 4-chlorophenyl, 3-trifluoromethylphenyl, 3-methoxyphenyl, 3-chloro-6-pyridyl, 2-chloro-4-pyridyl, phenylamino, 3-chlorophenylamino, 3-methylphenylamino, 4-chlorophenylamino, and 4-methylphenylamino;

$R^2$ is hydrogen, methyl or $CF_3$;

$R^3$ is hydrogen, methyl or $CF_3$;

$R^4$ is hydrogen;

$R^5$ is optionally substituted phenyl, wherein the substituents are selected from the group consisting of cyano, nitro, halogen, ($C_1$-$C_3$)alkyl, halo($C_1$-$C_3$)alkyl, ($C_1$-$C_3$)alkoxy, halo($C_1$-$C_3$)alkoxy, ($C_3$)alkenyloxy, ($C_3$)alkynyloxy, ($C_1$-$C_3$)alkylthio, halo($C_1$-$C_3$)alkylthio, ($C_1$-$C_3$)alkylsulfinyl, halo($C_1$-$C_3$)alkylsulfinyl, ($C_1$-$C_3$)alkylsulfonyl, halo($C_1$-$C_3$)alkylsulfonyl, ($C_1$-$C_3$)alkoxy($C_1$-$C_3$)alkyl, ($C_1$-$C_2$)alkylthio($C_1$-$C_2$)alkyl, and ($C_1$-$C_3$)alkoxycarbonyl;

$R^6$ is selected from the group consisting of hydrogen, formyl, ($C_1$-$C_3$)alkylcarbonyl, and cyclo($C_3$-$C_6$)alkylcarbonyl; and $R^7$, $R^8$, $R^9$, $R^{10}$ are independently selected from the group consisting of hydrogen, cyano, nitro, chlorine, fluorine, methyl, trifluoromethyl, difluoromethyl, methoxy, trifluoromethoxy, difluoromethoxy, methylthio, trifluoromethylthio, difluoromethylthio, methylsulfinyl, trifluoromethylsulfinyl, difluoromethylsulfinyl, methylsulfonyl, trifluoromethylsulfonyl, difluoromethylsulfonyl, methoxymethyl, and methoxycarbonyl, or $R^7/R^8$, $R^8/R^9$, or $R^9/R^{10}$ form a 5- or 6-membered heterocyclic ring.

In another embodiment, the activating ligand is a compound having Formula IV wherein Q is O, $R^2$ is methyl, and $R^3$, $R^4$, $R^5$, $R^6$, $R^7$, $R^8$, $R^9$, and $R^{10}$ are defined according to Table 4.

TABLE 4

| Ligand Components | | | | | |
|---|---|---|---|---|---|
| $R^1$ | $R^3$, $R^4$, $R^7$, $R^9$, and $R^{10}$ | $R^5$ | $R^6$ | $R^8$ | Stereo.[1] |
| n-Hexyl | H | Ph | H | H | cis |
| n-Heptyl | H | Ph | H | H | cis |
| n-Bu | H | Ph | H | H | cis |
| 3-$CF_3$-4-F—Ph | H | 4-F—Ph | H | F | trans |
| 3-$CF_3$-4-F—Ph | H | 4-F—Ph | H | F | cis |
| 3-Cl-4-F—Ph | H | 4-F—Ph | H | F | trans |
| 3-Cl-4-F—Ph | H | 4-F—Ph | H | F | cis |
| 4-F—Ph | H | 4-F—Ph | H | F | trans |
| 4-F—Ph | H | 4-F—Ph | H | F | cis |
| Ph | H | 4-F—Ph | H | F | trans |
| Ph | H | 4-F—Ph | H | F | cis |
| 3-F-4-Me—Ph | H | 4-F—Ph | H | F | cis |
| 3-Me-4-F—Ph | H | 4-F—Ph | H | F | cis |
| 3-F-4-Me—Ph | H | 4-F—Ph | H | F | trans |
| 3,4-di-F—Ph | H | Ph | H | H | cis |
| 3-F-4-Me—Ph | H | Ph | H | H | cis |
| 3-F-4-$CF_3$—Ph | H | Ph | H | H | cis |
| 3,4-di-F—Ph | H | Ph | H | H | trans |
| 3-F-4-Me—Ph | H | Ph | H | H | trans |
| 3-F-4-$CF_3$—Ph | H | Ph | H | H | trans |
| 3,4-di-F—Ph | H | 4-Me—Ph | H | Me | cis |
| 3-F-4-Me—Ph | H | 4-Me—Ph | H | Me | cis |
| 3-F-4-$CF_3$—Ph | H | 4-Me—Ph | H | Me | cis |
| 3,4-di-F—Ph | H | 4-F—Ph | H | F | trans |
| 3-F-4-$CF_3$—Ph | H | 4-F—Ph | H | F | trans |

TABLE 4-continued

| Ligand Components | | | | | |
|---|---|---|---|---|---|
| $R^1$ | $R^3$, $R^4$, $R^7$, $R^9$, and $R^{10}$ | $R^5$ | $R^6$ | $R^8$ | Stereo.[1] |
| 3,4-di-F—Ph | H | 4-F—Ph | H | F | cis |
| 3-F-4-$CF_3$—Ph | H | 4-F—Ph | H | F | cis |
| 3-F-4-Me—Ph | H | 4-Me—Ph | H | Me | trans |
| 4-Cl—Ph | H | Ph | H | H | trans |
| 4-$CH_3OC(O)$—Ph | H | Ph | H | H | trans |
| 3,4-$OCH_2O$—Ph | H | Ph | H | H | trans |
| 4-Cl—Ph | H | 4-Me—Ph | H | Me | trans |
| 4-$CH_3OC(O)$—Ph | H | 4-Me—Ph | H | Me | trans |
| 3,4-$OCH_2O$—Ph | H | 4-Me—Ph | H | Me | trans |
| 4-Cl—Ph | H | 4-F—Ph | H | F | trans |
| 4-Et—Ph | H | 4-F—Ph | H | F | trans |
| 4-$CH_3OC(O)$—Ph | H | 4-F—Ph | H | F | trans |
| 3,4-$OCH_2O$—Ph | H | 4-F—Ph | H | F | trans |
| 4-Me—Ph | H | Ph | H | H | 80:20 cis:trans |
| 4-Me—Ph | H | 4-F—Ph | H | H | 75:25 cis:trans |
| 4-Me—Ph | H | 2-Cl—Ph | H | H | 80:20 cis:trans |
| 4-Me—Ph | H | 3-Cl—Ph | H | H | 50:50 cis:trans |
| 4-Me—Ph | H | 4-Cl—Ph | H | H | 80:20 cis:trans |
| 4-Me—Ph | H | 3-Me—Ph | H | H | 60:40 cis:trans |
| 4-Me—Ph | H | 4-Me—Ph | H | H | 70:30 cis:trans |
| 4-Me—Ph | H | 3-MeO—Ph | H | H | 60:40 cis:trans |
| 4-Me—Ph | H | 4-MeO—Ph | H | H | 80:20 cis:trans |
| 3-F-4-Me—Ph | H, ($R^9$ = Cl) | 4-F—Ph | H | H | 60:40 cis:trans |
| 3-F-4-$CF_3$—Ph | H | 4-Me—Ph | H | Me | trans |
| 2-Me-3-MeO—Ph | H | Ph | H | H | cis |
| 2-F—Ph | H | 4-Me—Ph | H | Me | cis |
| 2-Me—Ph | H | 4-Me—Ph | H | Me | cis |
| 2-MeO—Ph | H | 4-Me—Ph | H | Me | cis |
| 2-Me-3-MeO—Ph | H | 4-Me—Ph | H | Me | cis |
| 2-F—Ph | H | 4-F—Ph | H | F | cis |
| 2-Me—Ph | H | 4-F—Ph | H | F | cis |
| 2-MeO—Ph | H | 4-F—Ph | H | F | cis |
| 2-Me-3-MeO—Ph | H | 4-F—Ph | H | F | cis |
| 4-Et—Ph | H | Ph | H | H | trans |
| 4-Et—Ph | H | 4-Me—Ph | H | Me | trans |
| 4-Cl—Ph | H | Ph | H | H | cis |
| 4-Et—Ph | H | Ph | H | H | cis |
| 4-Cl—Ph | H | 4-Me—Ph | H | Me | cis |
| 4-Et—Ph | H | 4-Me—Ph | H | Me | cis |
| 4-Cl—Ph | H | 4-F—Ph | H | F | cis |
| 4-Et—Ph | H | 4-F—Ph | H | F | cis |
| Ph | H | Ph | H | H | cis |
| 3-F—Ph | H | Ph | H | H | cis |
| 2-$CF_3$—Ph | H | Ph | H | H | cis |
| 3-$CF_3$—Ph | H | Ph | H | H | cis |
| 4-$CF_3$—Ph | H | Ph | H | H | cis |
| Ph | H | 4-Me—Ph | H | Me | cis |
| 3-F—Ph | H | 4-Me—Ph | H | Me | cis |
| 2-$CF_3$—Ph | H | 4-Me—Ph | H | Me | cis |
| 3-$CF_3$—Ph | H | 4-Me—Ph | H | Me | cis |
| 4-$CF_3$—Ph | H | 4-Me—Ph | H | Me | cis |
| 3-F—Ph | H | 4-F—Ph | H | F | cis |
| 2-$CF_3$—Ph | H | 4-F—Ph | H | F | cis |
| 3-$CF_3$—Ph | H | 4-F—Ph | H | F | cis |
| 4-$CF_3$—Ph | H | 4-F—Ph | H | F | cis |
| 3-MeO—Ph | H | Ph | H | H | cis |
| 4-Me—Ph | H | Ph | H | H | cis |
| 4-MeO—Ph | H | Ph | H | H | cis |
| 4-$CH_3OC(O)$—Ph | H | Ph | H | H | cis |
| 3-Me—Ph | H | 4-Me—Ph | H | Me | cis |
| 3-MeO—Ph | H | 4-Me—Ph | H | Me | cis |
| 4-Me—Ph | H | 4-Me—Ph | H | Me | cis |
| 4-MeO—Ph | H | 4-Me—Ph | H | Me | cis |
| 4-$CH_3OC(O)$—Ph | H | 4-Me—Ph | H | Me | cis |
| 3-Me—Ph | H | 4-F—Ph | H | F | cis |

TABLE 4-continued

| Ligand Components | | | | | |
|---|---|---|---|---|---|
| $R^1$ | $R^3$, $R^4$, $R^7$, $R^9$, and $R^{10}$ | $R^5$ | $R^6$ | $R^8$ | Stereo.[1] |
| 3-MeO—Ph | H | 4-F—Ph | H | F | cis |
| 4-Me—Ph | H | 4-F—Ph | H | F | cis |
| 4-MeO—Ph | H | 4-F—Ph | H | F | cis |
| 4-$CH_3OC(O)$—Ph | H | 4-F—Ph | H | F | cis |
| 4-MeO—Ph | H | Ph | H | H | trans |
| 4-Me—Ph | H | Ph | H | H | trans |
| Ph | H | Ph | H | H | trans |
| 4-MeO—Ph | H | 4-Me—Ph | H | Me | trans |
| 4-Me—Ph | H | 4-Me—Ph | H | Me | trans |
| Ph | H | 4-Me—Ph | H | Me | trans |
| 4-MeO—Ph | H | 4-F—Ph | H | F | trans |
| 4-Me—Ph | H | 4-F—Ph | H | F | trans |
| 6-Cl-3-pyridyl | H | Ph | H | H | cis |
| 5-isoxazolyl | H | Ph | H | H | cis |
| 3-F-4-Cl—Ph | H | Ph | H | H | cis |
| 2-Cl-4-pyridyl | H | Ph | H | H | cis |
| 2-Et-3-MeO—Ph | H | Ph | H | H | cis |
| 3-Cl-6-pyridyl | H | 4-Me—Ph | H | Me | cis |
| 5-isoxazolyl | H | 4-Me—Ph | H | Me | cis |
| 3-F-4-Cl—Ph | H | 4-Me—Ph | H | Me | cis |
| 2-Cl-4-pyridyl | H | 4-Me—Ph | H | Me | cis |
| 2-Et-3-MeO—Ph | H | 4-Me—Ph | H | Me | cis |
| 3-Cl-6-pyridyl | H | 4-F—Ph | H | F | cis |
| 5-isoxazolyl | H | 4-F—Ph | H | F | cis |
| 3-F-4-Cl—Ph | H | 4-F—Ph | H | F | cis |
| 2-Cl-4-pyridyl | H | 4-F—Ph | H | F | cis |
| 2-Et-3-MeO—Ph | H | 4-F—Ph | H | F | cis |
| 2-Thienyl | H | Ph | Ac | H | |
| Styryl | H | Ph | Ac | H | |
| 4-Cl—Ph | H | Ph | 4-MeO—Ph—C(O) | H | |
| furan-2-ylvinyl | H | Ph | H | H | |
| 2-Thienyl | H | Ph | H | H | |
| 4-t-butyl—Ph | H | Ph | Ac | H | |
| 4-F—Ph | H | 4-Me—Ph | H | Me | |
| Benzosuccinimidyl-methyl | H | 4-Me—Ph | H | Me | |
| n-Pr | H | 4-F—Ph | benzoyl | H | |
| n-Octyl | H | Ph | H | H | cis |
| Me | H | Ph | 4-F—Ph—C(O) | H | |
| 2-Cl—$PhOCH_2$ | H | Ph | B | H | |
| Benzyl | H | Ph | H | H | |
| 4-MeO—Ph | H | Ph | 2-thiophenyl-C(O) | H | |
| Me | H | Ph | 4-Me—Ph—C(O) | H | |
| 3-MeO—Ph | H | Ph | n-hexanoyl | H | |
| 4-t-butyl—Ph | H | Ph | H | H | cis |
| 4-MeO—Ph | H, ($R^{10}$ = Me) | 2-Me—Ph | H | H | |
| 3-F—Ph | H | Ph | 3-F—Ph(CO) | H | |
| Ph | H | 3-MeO—Ph | H | H | |
| 4-n-pentyl—Ph | H | Ph | H | H | |
| 2-furanyl | H | Ph | H | H | |
| Ph | H | 3-MeO—Ph | Ac | H | |
| 4-Me—Ph | H | Ph | 3-MeO—PhC(O) | H | |
| Me | H | Ph | 3-MeO—PhC(O) | H | |
| 4-Me—Ph | H | Ph | 4-F—Ph—C(O) | H | |
| 4-Cl—Ph | H | 4-Me—Ph | H | Me | |
| $CO_2Et$ | H | Ph | EtOC(O)C(O) | H | |
| 3,4-di-MeO-styryl | H | Ph | H | H | cis |
| Styryl | H | Ph | styryl-C(O) | H | |
| 3-Br—Ph | H | Ph | H | H | |
| Ph | H | 4-Me—Ph | Ac | H | |
| 4-MeO-styryl | H | Ph | Ac | H | |
| Benxosuccinimidyl-methyl | H | Ph | H | H | |
| 4-MeO—Ph | H | 4-Me—Ph | H | Me | trans |
| 4-MeO—Ph | H | Ph | 4-MeO—Ph—C(O) | H | |
| 3-$NO_2$—Ph | H | 4-Me—Ph | H | Me | |
| cyclopropyl | H | Ph | cyclopropyl-C(O) | H | |
| Me | H | 3-MeO—Ph | benzoyl | H | |
| 4--n-propyl | H, ($R^{10}$ = Me) | 2-Me—Ph | H | H | |
| 3-$NO_2$—Ph | H | Ph | H | H | cis |
| 4-F—$PhOCH_2$ | H | Ph | H | H | |
| n-Pr | H | Ph | 3-MeO—PhC(O) | H | |
| 4-Cl—Ph | H | Ph | 4-Me—Ph—C(O) | H | |

TABLE 4-continued

| Ligand Components | | | | | |
|---|---|---|---|---|---|
| $R^1$ | $R^3$, $R^4$, $R^7$, $R^9$, and $R^{10}$ | $R^5$ | $R^6$ | $R^8$ | Stereo.[1] |
| 4-Et—Ph | H, ($R^{10}$ = Me) | 2-Me—Ph | styryl-C(O) | H | |
| Styryl | H | Ph | H | H | cis |
| 3-Me—Ph | H | Ph | 3-Me—Ph—C(O) | H | |
| 3,4-di-Cl—Ph | H | Ph | H | H | cis |
| 3-OH—Ph | H | Ph | 3-Br—Ph(CO) | H | |
| succinimidylmethyl | H | Ph | H | H | |
| 4-I—Ph | H | Ph | H | H | cis |
| 1-naphthylmethyl | H | Ph | H | H | |
| cyclohexylethyl | H | Ph | H | H | |
| $CO_2Et$ | H | Ph | H | H | |
| 4-F—Ph | H | Ph | 4-F—Ph—C(O) | H | |
| 4-n-propyl—Ph | H | Ph | H | H | |
| 3-F—Ph | H | 4-Me—Ph | H | Me | trans |
| 4-$CH_3S(O_2)NH$—Ph | H | Ph | H | H | |
| NHPh | H | Ph | H | H | |
| 4-MeO-styryl | H | Ph | H | H | cis |
| i-Pr | H | 4-$NO_2$—Ph | benzoyl | H | |
| 3-Cl-benzofuran-2-yl | H | Ph | 3-Cl-benzothiophen-2-yl | H | |
| 4-Cl—Ph$OCH_2$ | H | Ph | H | H | |
| 4-MeO—Ph | H | Ph | 4-MeO-styryl | H | |
| $CF_3$ | H | Ph | $CF_3C(O)$ | H | |
| Et | H | Ph | 4-$NO_2$—Ph—C(O) | H | |
| Ph | H, ($R^{10}$ = Me) | 2-Me—Ph | H | H | cis |
| Me | H | Ph | 2-F—Ph—C(O) | H | |
| n-pentyl | H | Ph | 2-F—Ph—C(O) | H | |
| 4-Me—Ph | H, ($R^{10}$ = Me) | 2-Me—Ph | H | H | cis |
| 3-F-4-Me—Ph | H | 4-Me—Ph | 3-F-4-Me—Ph(CO) | Me | trans |
| 3-F-4-$CF_3$—Ph | H | 4-Me—Ph | 3-F-4-$CF_3$—Ph—C(O) | Me | trans |
| 4-Cl—Ph | H | Ph | 4-Cl—Ph—C(O) | H | trans |
| 4-Et—Ph | H | Ph | 4-Et—Ph—C(O) | H | trans |
| 4-Cl—Ph | H | 4-Me—Ph | 4-Cl—Ph—C(O) | Me | trans |
| 4-Et—Ph | H | 4-Me—Ph | 4-Et—Ph—C(O) | Me | trans |
| 3,4-$OCH_2O$—Ph | H | 4-Me—Ph | 3,4-$OCH_2O$—Ph—C(O) | Me | trans |
| 3-F-4-Me—Ph | H | 4-F—Ph | Ac | F | trans |
| 3-F-4-Me—Ph | H | 4-F—Ph | 3-F-4-Me—Ph(CO) | F | trans |
| 3-F-4-Me—Ph | H | 4-F—Ph | 3-F-4-Me—Ph(CO) | F | cis |
| 3-Me—Ph | H | Ph | H | H | trans |
| 3-F—Ph | H | Ph | H | H | trans |
| 3-MeO—Ph | H | Ph | H | H | trans |
| 3-$CF_3$—Ph | H | Ph | H | H | trans |
| 3-Me—Ph | H | 4-Me—Ph | H | Me | trans |
| 3-F—Ph | H | 4-Me—Ph | H | Me | trans |
| 3-MeO—Ph | H | 4-Me—Ph | H | Me | trans |
| 3-$CF_3$—Ph | H | 4-Me—Ph | H | Me | trans |
| 3-Me—Ph | H | 4-F—Ph | H | F | trans |
| 3-F—Ph | H | 4-F—Ph | H | F | trans |
| 3-MeO—Ph | H | 4-F—Ph | H | F | trans |
| 3-$CF_3$—Ph | H | 4-F—Ph | H | F | trans |
| NHEt | H | Ph | H | H | cis |
| NHPh | H | Ph | H | H | cis |
| 4-Cl—Ph—NH | H | Ph | H | H | cis |
| 3-Cl—Ph—NH | H | Ph | H | H | cis |
| 4-Me—Ph—NH | H | Ph | H | H | cis |
| 3-Me—Ph—NH | H | Ph | H | H | cis |
| NHPh | H | 4-Me—Ph | H | Me | cis |
| 4-Cl—Ph—NH | H | 4-Me—Ph | H | Me | cis |
| 3-Cl—Ph—NH | H | 4-Me—Ph | H | Me | cis |
| 4-Me—Ph—NH | H | 4-Me—Ph | H | Me | cis |
| 3-Me—Ph—NH | H | 4-Me—Ph | H | Me | cis |
| NHPh | H | 4-F—Ph | H | F | cis |
| 4-Cl—Ph—NH | H | 4-F—Ph | H | F | cis |
| 3-Cl—Ph—NH | H | 4-F—Ph | H | F | cis |
| 4-Me—Ph—NH | H | 4-F—Ph | H | F | cis |
| 3-Me—Ph—NH | H | 4-F—Ph | H | F | cis |

[1]Relative stereochemistry at 2- and 4-positions

In another embodiment, the activating ligand is a compound having Formula V, VI, or VII:

V

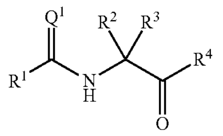

VI

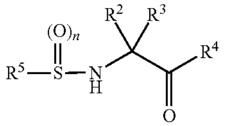

VII

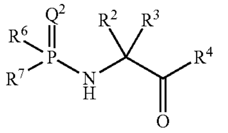

wherein $Q^1$ and $Q^2$ are independently selected from the group consisting of O and S;

n=1 or 2;

$R^1$ is selected from the group consisting of $(C_1\text{-}C_6)$alkyl, $(C_3\text{-}C_6)$cycloalkyl, $(C_1\text{-}C_6)$haloalkyl, $(C_3\text{-}C_6)$halocycloalkyl, $(C_2\text{-}C_6)$alkenyl, $(C_2\text{-}C_6)$haloalkenyl, $(C_2\text{-}C_6)$alkynyl, $(C_2\text{-}C_6)$haloalkynyl, $(C_1\text{-}C_6)$alkoxy, $(C_3\text{-}C_6)$cycloalkoxy, $(C_1\text{-}C_6)$haloalkoxy, $(C_3\text{-}C_6)$halocycloalkoxy, $(C_2\text{-}C_6)$alkenyloxy, $(C_2\text{-}C_6)$alkynyloxy, $(C_1\text{-}C_6)$alkylthio, $(C_3\text{-}C_6)$cycloalkylthio, $(C_1\text{-}C_6)$haloalkylthio, $(C_3\text{-}C_6)$halocycloalkylthio, $(C_1\text{-}C_6)$alkylamino, $(C_3\text{-}C_6)$cycloalkylamino, $(C_1\text{-}C_6)$haloalkylamino, $(C_3\text{-}C_6)$halocycloalkylamino, di$(C_1\text{-}C_6)$alkylamino, di$(C_3\text{-}C_6)$cycloalkylamino, di$(C_1\text{-}C_6)$haloalkylamino, di$(C_3\text{-}C_6)$halocycloalkylamino, $(C_1\text{-}C_6)$alkoxy$(C_1\text{-}C_6)$alkyl, $(C_1\text{-}C_6)$althylthio$(C_1\text{-}C_6)$alkyl, $(C_1\text{-}C_6)$alkylsulfinyl$(C_1\text{-}C_6)$alkyl, $(C_1\text{-}C_6)$alkylsulfonyl$(C_1\text{-}C_6)$alkyl, $(C_1\text{-}C_6)$alkylamino$(C_1\text{-}C_6)$alkyl, di$(C_1\text{-}C_6)$alkylamino$(C_1\text{-}C_6)$alkyl, $(C_1\text{-}C_6)$alkylcarbonyl$(C_1\text{-}C_6)$alkyl, cyano$(C_1\text{-}C_6)$alkyl, optionally substituted phenyl, optionally substituted 1-naphthyl, optionally substituted 2-naphthyl, optionally substituted phenyl$(C_1\text{-}C_3)$alkyl, optionally substituted phenyl$(C_2\text{-}C_3)$alkenyl, optionally substituted naphthyl$(C_1\text{-}C_3)$alkyl, optionally substituted phenoxy$(C_1\text{-}C_3)$alkyl, optionally substituted phenylamino, and optionally substituted heterocycle;

$R^2$ and $R^3$ are independently selected from the group consisting of hydrogen, cyano, aminocarbonyl, carboxy, $(C_1\text{-}C_6)$alkyl, $(C_3\text{-}C_6)$cycloalkyl, halo$(C_1\text{-}C_6)$alkyl, $(C_3\text{-}C_6)$halocycloalkyl, $(C_2\text{-}C_6)$alkenyl, $(C_3\text{-}C_6)$cycloalkenyl, $(C_2\text{-}C_6)$haloalkenyl, $(C_2\text{-}C_6)$alkynyl, $(C_1\text{-}C_6)$alkylsulfonyl, $(C_1\text{-}C_6)$alkoxy$(C_1\text{-}C_6)$alkyl, $(C_1\text{-}C_6)$althylthio$(C_1\text{-}C_6)$alkyl, $(C_1\text{-}C_6)$alkylsulfinyl$(C_1\text{-}C_6)$alkyl, $(C_1\text{-}C_6)$alkylsulfonyl$(C_1\text{-}C_6)$alkyl, $(C_1\text{-}C_6)$alkylamino$(C_1\text{-}C_6)$alkyl, di$(C_1\text{-}C_6)$alkylamino$(C_1\text{-}C_6)$alkyl, $(C_1\text{-}C_6)$alkylcarbonyl, $(C_1\text{-}C_6)$alkylcarbonyl$(C_1\text{-}C_6)$alkyl, $(C_1\text{-}C_6)$alkylaminocarbonyl, di$(C_1\text{-}C_6)$alkylaminocarbonyl, $(C_1\text{-}C_6)$alkylaminocarbonyl$(C_1\text{-}C_6)$alkyl, di$(C_1\text{-}C_6)$alkylaminocarbonyl$(C_1\text{-}C_6)$alkyl, $(C_1\text{-}C_6)$alkylcarbonylamino$(C_1\text{-}C_6)$alkyl, $(C_1\text{-}C_6)$alkoxycarbonyl, $(C_1\text{-}C_6)$alkoxycarbonyl$(C_1\text{-}C_6)$alkyl, cyano$(C_1\text{-}C_6)$alkyl, hydroxy$(C_1\text{-}C_6)$alkyl, carboxy$(C_1\text{-}C_6)$alkyl, optionally substituted phenyl, optionally substituted phenyl$(C_1\text{-}C_6)$alkyl, optionally substituted benzoyl, optionally substituted naphthyl, optionally substituted heterocycle, and optionally substituted heterocyclylcarbonyl, or $R^2$ and $R^3$ are joined together with the carbon to which they are attached to form an unsubstituted or substituted, partially unsaturated or saturated optionally substituted 3-, 4-, 5-, 6-, 7- or 8-membered carbocyclic or heterocyclic ring, wherein the heterocyclic ring contains from one to three heteroatoms selected from O, N, or S;

$R^4$ is selected from the group consisting of $(C_1\text{-}C_6)$alkyl, $(C_3\text{-}C_6)$cycloalkyl, $(C_1\text{-}C_6)$haloalkyl, $(C_3\text{-}C_6)$halocycloalkyl, $(C_2\text{-}C_6)$alkenyl, $(C_2\text{-}C_6)$haloalkenyl, $(C_2\text{-}C_6)$alkynyl, $(C_2\text{-}C_6)$haloalkynyl, $(C_1\text{-}C_6)$alkoxy, $(C_3\text{-}C_6)$cycloalkoxy, $(C_1\text{-}C_6)$haloalkoxy, $(C_3\text{-}C_6)$halocycloalkoxy, $(C_2\text{-}C_6)$alkenyloxy, $(C_2\text{-}C_6)$alkynyloxy, $(C_1\text{-}C_6)$alkylthio, $(C_3\text{-}C_6)$cycloalkylthio, $(C_1\text{-}C_6)$haloalkylthio, $(C_3\text{-}C_6)$halocycloalkylthio, $(C_1\text{-}C_6)$alkylamino, $(C_3\text{-}C_6)$cycloalkylamino, $(C_1\text{-}C_6)$haloalkylamino, $(C_3\text{-}C_6)$halocycloalkylamino, di$(C_1\text{-}C_6)$alkylamino, di$(C_3\text{-}C_6)$cycloalkylamino, di$(C_1\text{-}C_6)$haloalkylamino, di$(C_3\text{-}C_6)$halocycloalkylamino, $(C_1\text{-}C_6)$alkoxy$(C_1\text{-}C_6)$alkyl, $(C_1\text{-}C_6)$althylthio$(C_1\text{-}C_6)$alkyl, $(C_1\text{-}C_6)$alkylsulfinyl$(C_1\text{-}C_6)$alkyl, $(C_1\text{-}C_6)$alkylsulfonyl$(C_1\text{-}C_6)$alkyl, $(C_1\text{-}C_6)$alkylamino$(C_1\text{-}C_6)$alkyl, di$(C_1\text{-}C_6)$alkylamino$(C_1\text{-}C_6)$alkyl, $(C_1\text{-}C_6)$alkylcarbonyl$(C_1\text{-}C_6)$alkyl, cyano$(C_1\text{-}C_6)$alkyl, optionally substituted phenyl, optionally substituted 1-naphthyl, optionally substituted 2-naphthyl, optionally substituted phenyl$(C_1\text{-}C_3)$alkyl, optionally substituted phenyl$(C_2\text{-}C_3)$alkenyl, optionally substituted naphthyl$(C_1\text{-}C_3)$alkyl, optionally substituted phenoxy$(C_1\text{-}C_3)$alkyl, optionally substituted phenylamino, and optionally substituted heterocycle;

$R^5$ is selected from the group consisting of $(C_1\text{-}C_6)$alkyl, $(C_3\text{-}C_6)$cycloalkyl, $(C_1\text{-}C_6)$haloalkyl, $(C_3\text{-}C_6)$halocycloalkyl, $(C_2\text{-}C_6)$alkenyl, $(C_2\text{-}C_6)$haloalkenyl, $(C_2\text{-}C_6)$alkynyl, $(C_2\text{-}C_6)$haloalkynyl, $(C_1\text{-}C_6)$alkoxy$(C_1\text{-}C_6)$alkyl, $(C_1\text{-}C_6)$althylthio$(C_1\text{-}C_6)$alkyl, $(C_1\text{-}C_6)$alkylsulfinyl$(C_1\text{-}C_6)$alkyl, $(C_1\text{-}C_6)$alkylsulfonyl$(C_1\text{-}C_6)$alkyl, $(C_1\text{-}C_6)$alkylamino$(C_1\text{-}C_6)$alkyl, di$(C_1\text{-}C_6)$alkylamino$(C_1\text{-}C_6)$alkyl, $(C_1\text{-}C_6)$alkylcarbonyl$(C_1\text{-}C_6)$alkyl, cyano$(C_1\text{-}C_6)$alkyl, optionally substituted phenyl, optionally substituted 1-naphthyl, optionally substituted 2-naphthyl, optionally substituted phenyl $(C_1\text{-}C_3)$alkyl, optionally substituted phenyl$(C_2\text{-}C_3)$alkenyl, optionally substituted naphthyl$(C_1\text{-}C_3)$alkyl, optionally substituted phenoxy$(C_1\text{-}C_3)$alkyl, optionally substituted phenylamino, and optionally substituted heterocycle; and $R^6$ and $R^7$ are independently selected from the group consisting of $(C_1\text{-}C_6)$alkyl, $(C_3\text{-}C_6)$cycloalkyl, $(C_1\text{-}C_6)$haloalkyl, $(C_3\text{-}C_6)$halocycloalkyl, $(C_2\text{-}C_6)$alkenyl, $(C_2\text{-}C_6)$haloalkenyl, $(C_2\text{-}C_6)$alkynyl, $(C_2\text{-}C_6)$haloalkynyl, $(C_1\text{-}C_6)$alkoxy, $(C_3\text{-}C_6)$cycloalkoxy, $(C_1\text{-}C_6)$haloalkoxy, $(C_3\text{-}C_6)$halocycloalkoxy, $(C_2\text{-}C_6)$alkenyloxy, $(C_2\text{-}C_6)$alkynyloxy, $(C_1\text{-}C_6)$alkylthio, $(C_3\text{-}C_6)$cycloalkylthio, $(C_1\text{-}C_6)$haloalkylthio, $(C_3\text{-}C_6)$halocycloalkylthio, $(C_1\text{-}C_6)$alkylamino, $(C_3\text{-}C_6)$cycloalkylamino, $(C_1\text{-}C_6)$haloalkylamino, $(C_3\text{-}C_6)$halocycloalkylamino, di$(C_1\text{-}C_6)$alkylamino, di$(C_3\text{-}C_6)$cycloalkylamino, di$(C_1\text{-}C_6)$haloalkylamino, di$(C_3\text{-}C_6)$halocycloalkylamino, $(C_1\text{-}C_6)$alkoxy$(C_1\text{-}C_6)$alkyl, $(C_1\text{-}C_6)$althylthio$(C_1\text{-}C_6)$alkyl, $(C_1\text{-}C_6)$alkylsulfinyl$(C_1\text{-}C_6)$alkyl, $(C_1\text{-}C_6)$alkylsulfonyl$(C_1\text{-}C_6)$alkyl, $(C_1\text{-}C_6)$alkylamino$(C_1\text{-}C_6)$alkyl, di$(C_1\text{-}C_6)$alkylamino$(C_1\text{-}C_6)$ alkyl, $(C_1\text{-}C_6)$alkylcarbonyl$(C_1\text{-}C_6)$alkyl, cyano$(C_1\text{-}C_6)$alkyl, optionally substituted phenyl, optionally substituted phenyl$(C_1\text{-}C_6)$alkyl, optionally substituted heterocycle, optionally substituted phenoxy, optionally substituted heterocycloxy, optionally substituted phenylthio, optionally substituted heterocyclylthio, optionally substituted naphthyl, optionally substituted phenylamino, optionally substituted heterocyclylamino, optionally substituted N-phenyl-N—$(C_1\text{-}C_6)$alkylamino, and optionally substituted N-heterocyclyl-N—$(C_1\text{-}C_6)$alkylamino.

In another embodiment, the activating ligand is a compound having Formula V, wherein:

$Q^1$ is O;

$R^1$ is substituted phenyl wherein the substituents are independently selected from the group consisting of $(C_1\text{-}C_2)$alkyl and $(C_1\text{-}C_2)$alkoxy; or two adjacent positions are joined together with the atoms to which they are attached to form an unsubstituted or substituted, unsaturated, partially unsaturated, or saturated 5-, 6- or 7-membered carbocyclic or heterocyclic ring, wherein the heterocyclic ring contains from one to two oxygen atoms and one to four substituents are independently selected from the group consisting of: cyano, $(C_1\text{-}C_2)$alkyl, $(C_1\text{-}C_2)$alkylamino, di$(C_1\text{-}C_2)$alkylamino, $(C_1\text{-}C_2)$alkoxycarbonyl, $(C_1\text{-}C_2)$alkylaminocarbonyl, di$(C_1\text{-}C_2)$alkylaminocarbonyl, oxo, and methoxyimino;

$R^2$ and $R^3$ are independently selected from the group consisting of $(C_1\text{-}C_6)$alkyl, $(C_3\text{-}C_6)$cycloalkyl, halo$(C_1\text{-}C_6)$alkyl, $(C_1\text{-}C_3)$alkoxy$(C_1\text{-}C_3)$alkyl, $(C_1\text{-}C_3)$althylthio$(C_1\text{-}C_3)$alkyl, $(C_1\text{-}C_3)$alkylsulfinyl$(C_1\text{-}C_3)$alkyl, $(C_1\text{-}C_3)$alkylsulfonyl$(C_1\text{-}C_3)$alkyl, $(C_1\text{-}C_3)$alkylamino$(C_1\text{-}C_3)$alkyl, di$(C_1\text{-}C_3)$alkylamino$(C_1\text{-}C_3)$alkyl, $(C_1\text{-}C_6)$alkylcarbonyl, $(C_1\text{-}C_3)$alkylcarbonyl$(C_1\text{-}C_3)$alkyl, $(C_1\text{-}C_6)$alkylaminocarbonyl, di$(C_1\text{-}C_6)$alkylaminocarbonyl, $(C_1\text{-}C_3)$alkylaminocarbonyl$(C_1\text{-}C_3)$alkyl, di$(C_1\text{-}C_3)$alkylaminocarbonyl$(C_1\text{-}C_3)$alkyl, $(C_1\text{-}C_3)$alkylcarbonylamino$(C_1\text{-}C_3)$alkyl, $(C_1\text{-}C_6)$alkoxycarbonyl, and $C_1\text{-}C_3$)alkoxycarbonyl$(C_1\text{-}C_3)$alkyl; or $R^2$ and $R^3$ may be joined together with the carbon to which they are attached to form an unsubstituted or substituted, partially unsaturated or saturated 5-, 6- or 7-membered carbocyclic or heterocyclic ring, wherein the heterocyclic ring contains one heteroatom selected from O or S; and one to four substituents are independently selected from the group consisting of $(C_1\text{-}C_3)$alkyl, $(C_1\text{-}C_3)$alkylamino, di$(C_1\text{-}C_3)$alkylamino, $(C_1\text{-}C_4)$alkoxycarbonyl, $(C_1\text{-}C_3)$alkylaminocarbonyl, and di$(C_1\text{-}C_3)$alkylaminocarbonyl; and $R^4$ is selected from optionally substituted phenyl or pyridyl wherein the substituents are independently selected from the group consisting of $(C_1\text{-}C_3)$alkyl and $(C_1\text{-}C_3)$alkoxy;

In another embodiment, the activating ligand is a compound having Formula V, wherein Q is oxygen, and $R^1$, $R^2$, $R^3$, and $R^4$ are defined according to Table 5.

TABLE 5

| Ligand Components | | | |
|---|---|---|---|
| $R^1$ | $R^2$ | $R^3$ | $R^4$ |
| 2-Me-3-MeO—Ph | | —$(CH_2)_4$— | Ph |
| 2-Me-3-MeO—Ph | | —$(CH_2)_4$— | 3-Me—Ph |
| 4-Et—Ph | | —$(CH_2)_4$— | Ph |
| 2-Me-3-MeO—Ph | | —$(CH_2)_5$— | 3-MeO—Ph |
| 2-Me-3-MeO—Ph | | —$(CH_2)_4$— | 3-MeO—Ph |
| 2-Me-3-MeO—Ph | | —$(CH_2)_3$— | 3-Me—Ph |
| 2-Me-3-MeO—Ph | | —$(CH_2)_5$— | 3-Me—Ph |
| 2-Me-3-MeO—Ph | Bn | Me | 3-Me—Ph |
| 2-Me-3-MeO—Ph | | —$(CH_2)_2$— | 3-Me—Ph |
| 2-Me-3-MeO—Ph | | —$(CH_2)_4$— | 3,5-diMe—Ph |
| 2-Me-3-MeO—Ph | | —$(CH_2)_5$— | 3,5-diMe—Ph |
| 2-Me-3-MeO—Ph | Bn | Me | 3,5-diMe—Ph |
| 2-Me-3-MeO—Ph | | —$(CH_2)_2$— | 3,5-diMe—Ph |
| 2-Me-3-MeO—Ph | | —$(CH_2)_3$— | 3,5-diMe—Ph |
| 2-Me-3-MeO—Ph | | —$(CH_2)_5$— | 4-Me—Ph |
| 2-Me-3-MeO—Ph | Bn | Me | 4-Me—Ph |
| 2-Me-3-MeO—Ph | | —$(CH_2)_4$— | 3-Me-4-F—Ph |
| 2-Me-3-MeO—Ph | | —$(CH_2)_5$— | 3-Me-4-F—Ph |
| 2-Me-3-MeO—Ph | | —$(CH_2)_2$— | 3-Me-4-F—Ph |
| 2-Me-3-MeO—Ph | i-Pr | Me | 3,5-diMe—Ph |
| 2-Et-3-MeO—Ph | | —$(CH_2)_4$— | Ph |
| 2-Et-3,6-$OCH_2CH_2O$—Ph | | —$(CH_2)_4$— | Ph |
| 2-Me-3,4-$OCH_2O$—Ph | | —$(CH_2)_4$— | Ph |
| 2-Me-3-MeO—Ph | | —$(CH_2)_2$— | 4-Me—Ph |
| 2-Me-3-MeO—Ph | | —$CH_2CH_2OCH_2CH_2$— | 3-Me—Ph |
| 2-Me-3-MeO—Ph | | —$CH_2CH_2SCH_2CH_2$— | 3-Me—Ph |
| 2-Me-3-MeO—Ph | | —$CH_2CH_2OCH_2CH_2$— | 3,5-diMe—Ph |
| 2-Me-3-MeO—Ph | | —$CH_2CH_2SCH_2CH_2$— | 3,5-diMe—Ph |
| 2-Me-3-MeO—Ph | | —$CH_2CH_2C(OCH_2CH_2O)CH_2CH_2$— | 3,5-diMe—Ph |
| 2-Me-3-MeO—Ph | i-Pr | Me | 2-MeO—Ph |
| 2-Me-3-MeO—Ph | i-Pr | Me | 3-Me—Ph |
| 2-Me-3-MeO—Ph | i-Pr | Me | 3-MeO—Ph |
| 2-Me-3-MeO—Ph | i-Pr | Me | 4-Me—Ph |
| 2-Me-3-MeO—Ph | i-Pr | Me | Ph |
| 2-Me-3-MeO—Ph | | —$CH_2CH_2C(OCH_2CH_2O)CH_2CH_2$— | 3-Me—Ph |
| 2-Me-3-MeO—Ph | Et | Et | 2-Me—Ph |
| 2-Me-3-MeO—Ph | Et | Et | 2-MeO—Ph |
| 2-Me-3-MeO—Ph | Et | Et | 4-F—Ph |
| 2-Me-3-MeO—Ph | | —$(CH_2)_4$— | 2-Me—Ph |

TABLE 5-continued

| Ligand Components | | | |
|---|---|---|---|
| $R^1$ | $R^2$ | $R^3$ | $R^4$ |
| 2-Me-3-MeO—Ph | | —$(CH_2)_4$— | 2-MeO—Ph |
| 2-Me-3-MeO—Ph | | —$(CH_2)_4$— | 4-MeO—Ph |
| 2-Me-3-MeO—Ph | | —$(CH_2)_4$— | 4-F—Ph |
| 2-Me-3-MeO—Ph | | —$(CH_2)_4$— | 3,4-$OCH_2O$—Ph |
| 2-Me-3-MeO—Ph | | —$(CH_2)_5$— | 2-Me—Ph |
| 2-Me-3-MeO—Ph | | —$(CH_2)_5$— | 2-MeO—Ph |
| 2-Me-3-MeO—Ph | | —$(CH_2)_5$— | 4-MeO—Ph |
| 2-Me-3-MeO—Ph | | —$(CH_2)_5$— | 3,4-$OCH_2O$—Ph |
| 2-Me-3-MeO—Ph | Et | Et | 3-Me—Ph |
| 2-Me-3-MeO—Ph | Et | Et | 3-MeO—Ph |
| 2-Me-3-MeO—Ph | Et | Et | 3-Me-4-F—Ph |
| 2-Me-3-MeO—Ph | Et | Et | 3,5-diMe—Ph |
| 2-Me-3-MeO—Ph | i-Bu | Me | 3-Me—Ph |
| 2-Me-3-MeO—Ph | i-Bu | Me | 3-MeO—Ph |
| 2-Me-3-MeO—Ph | i-Bu | Me | 3-Me-4-F—Ph |
| 2-Me-3-MeO—Ph | i-Bu | Me | 3,5-diMe—Ph |
| 2-Me-3-MeO—Ph | i-Pr | Me | 3-Me-4-F—Ph |
| 2-Me-3-MeO—Ph | Ph | i-Pr | 3-Me—Ph |
| 2-Me-3-MeO—Ph | Et | Et | 4-MeO—Ph |
| 2-Me-3-MeO—Ph | Et | Et | 3,4-OCH2O—Ph |
| 2-Me-3-MeO—Ph | | —$(CH_2)_5$— | 4-F—Ph |
| 2-Me-3-MeO—Ph | | —$CH_2CH_2C(=O)CH_2CH_2$— | 3-Me—Ph |
| 2-Me-3-MeO—Ph | | —$CH_2CH_2S(=O)_2CH_2CH_2$— | 3,5-diMe—Ph |
| 2-Me-3-MeO—Ph | i-Pr | Me | 2-Me—Ph |
| 2-Me-3-MeO—Ph | | —$(CH_2)_5$— | 2,6-diMeO-3-pyridyl |
| 2-Me-3-MeO—Ph | | —$(CH_2)_4$— | 3,5-diMeO-4-Me—Ph |
| 2-Me-3-MeO—Ph | | —$(CH_2)_5$— | 3,5-diMeO-4-Me—Ph |
| 2-Me-3-MeO—Ph | | —$(CH_2)_4$— | 3-MeO-4,5-diF—Ph |
| 2-Me-3-MeO—Ph | | —$(CH_2)_5$— | 3-MeO-4,5-diF—Ph |
| 2-Me-3-MeO—Ph | | —$(CH_2)_5$— | Ph |
| 2-Me-3-MeO—Ph | | —$(CH_2)_6$— | 2-MeO—Ph |
| 2-Me-3-MeO—Ph | | —$(CH_2)_6$— | 3,5-diMe—Ph |
| 2-Me-3-MeO—Ph | 4-F—Ph | Me | 2-MeO—Ph |
| 2-Me-3-MeO—Ph | 4-F—Ph | Me | 3,5-diMe—Ph |
| 2-Me-3-MeO—Ph | Me | Me | 2-MeO—Ph |
| 2-Me-3-MeO—Ph | Me | Me | 3,5-diMe—Ph |
| 2-Me-3-MeO—Ph | Me | Me | Ph |
| 2-Me-3-MeO—Ph | Et | Et | 4-Me—Ph |
| 2-Me-3-MeO—Ph | Et | Et | Ph |
| 2-Me-3-MeO—Ph | | —$(CH_2)_4$— | 4-Me—Ph |
| 2-Et-3,4-$OCH_2CH_2O$—Ph | | —$(CH_2)_5$— | 3,5-di-Me—Ph |
| 2-Me-3,4-$OCH_2O$—Ph | | —$(CH_2)_5$— | 3,5-di-Me—Ph |
| 3,4-$OCH_2CH_2O$—Ph | | —$(CH_2)_5$— | 3,5-di-Me—Ph |
| 3,4-$CH_2OCH_2O$—Ph | | —$(CH_2)_5$— | 3,5-di-Me—Ph |
| 2-Et-3,4-$OCH_3CH_2O$—Ph | | —$(CH_2)_4$— | 3,5-di-Me—Ph |
| 2-Me-3,4-$OCH_2O$—Ph | | —$(CH_2)_4$— | 3,5-di-Me—Ph |
| 3,4-$OCH_2CH_2O$—Ph | | —$(CH_2)_4$— | 3,5-di-Me—Ph |
| 3,4-$CH_2OCH_2O$—Ph | | —$(CH_2)_4$— | 3,5-di-Me—Ph |
| 3,4-$OCH_2O$—Ph | | —$(CH_2)_4$— | 3,5-di-Me—Ph |
| 2-Me—Ph | | —$(CH_2)_4$— | 3,5-di-Me—Ph |
| Ph | t-Bu | H | 4-Cl—Ph |
| 4-Cl—Ph | | —$(CH_2)_4$— | Ph |
| Me | Ph | H | 4-Me—Ph |
| Me | 4-Me—Ph | H | Ph |
| Me | Ph | H | Ph |
| 4-Cl—Ph | Me | Me | Ph |
| 4-Me—Ph | t-Bu | H | Ph |
| 2,3-di-Me—Ph | t-Bu | H | Ph |
| 4-$NO_2$—Ph | t-Bu | H | Ph |
| 2-Me-3-MeO—Ph | | —$(CH_2)_2$— | 3-MeO—Ph |
| 2-Me-3-MeO—Ph | Benzyl | Me | 3-MeO—Ph |
| 2-Me-3-MeO—Ph | | —$(CH_2)_2$— | 2-Me—Ph |
| 3-Me-benzofuran-2-yl | | —$(CH_2)_4$— | Ph |
| Ph | Me | Me | Ph |
| 2-Me—Ph | Me | Me | Ph |
| 3,4-$OCH_2O$—Ph | Me | Me | Ph |
| 3-MeO—Ph | Me | Me | Ph |
| 4-Et—Ph | Me | Me | Ph |
| 2-Me-3-MeO—Ph | | —$CH_2CH_2N(C(O)OtBu)CH_2CH_2$— | 3-Me—Ph |
| 2-Me-3-MeO—Ph | | —$CH_2CH_2N(C(O)OtBu)CH_2CH_2$— | 3,5-di-Me—Ph |
| 2-Me-3-MeO—Ph | i-Pr | Me | 3,4-$OCH_2O$—Ph |
| 2-Me-3-MeO—Ph | i-Pr | Me | Me |
| 2-Me-3-MeO—Ph | t-Bu | H | 3-Me—Ph |

TABLE 5-continued

| Ligand Components | | | |
|---|---|---|---|
| $R^1$ | $R^2$ | $R^3$ | $R^4$ |
| 2-Me-3-MeO—Ph | t-Bu | H | 3-MeO—Ph |
| 2-Me-3-MeO—Ph | t-Bu | H | 3,5-di-Me—Ph |
| 2-MeO—Ph | Me | Me | 3-Me—Ph |
| 2-MeO—Ph | Me | Me | 3-MeO—Ph |
| 2-Me-3-MeO—Ph | i-Bu | Me | 4-MeO—Ph |
| 2-MeO—Ph | Me | Me | 3,5-di-Me—Ph |
| 2-Me-3-MeO—Ph | $(CH_2)_5$ | | n-Bu |
| Ph | Me | Me | Et |
| 3-MeO—Ph | Me | Me | Et |
| 3,4-$OCH_2O$—Ph | Me | Me | Et |
| 2-Me—Ph | Me | Me | El |
| 4-Et—Ph | Me | Me | Et |
| Ph | Me | Me | 3,5-di-Me—Ph |
| 2-Me—Ph | Me | Me | 3,5-di-Me—Ph |
| 3-MeO—Ph | Me | Me | 3,5-di-Me—Ph |
| 4-Et—Ph | Me | Me | 3,5-di-Me—Ph |
| 3,4-$OCH_2O$—Ph | Me | Me | 3,5-di-Me—Ph |
| Ph | $-(CH_2)_4-$ | | Et |
| 2-Me—Ph | $-(CH_2)_4-$ | | Et |
| 3-MeO—Ph | $-(CH_2)_4-$ | | Et |
| 4-Et—Ph | $-(CH_2)_4-$ | | Et |
| 3,4-$OCH_2O$—Ph | $-(CH_2)_4-$ | | Et |
| Ph | $-(CH_2)_4-$ | | 3,5-di-Me—Ph |
| 3-MeO—Ph | $-(CH_2)_4-$ | | 3,5-di-Me—Ph |
| 4-Et—Ph | $-(CH_2)_4-$ | | 3,5-di-Me—Ph |
| Ph | $-(CH_2)_4-$ | | Ph |
| 2-Me—Ph | $-(CH_2)_4-$ | | Ph |
| 3-MeO—Ph | $-(CH_2)_4-$ | | Ph |
| 3,4-$OCH_2O$—Ph | $-(CH_2)_4-$ | | Ph |
| 2-Et-3-MeO—Ph | $-(CH_2)_5-$ | | 3,5-di-Me—Ph |
| 2-Et-3-MeO—Ph | $-(CH_2)_4-$ | | 3,5-di-Me—Ph |
| $CF_3$ | $-(CH_2)_4-$ | | 3,5-di-Me—Ph |
| 2-Me-3-MeO—Ph | $-CH_2N[(C{=}O)Ot\text{-}Bu]CH_2CH_2CH_2-$ | | 3,5-di-Me—Ph |
| 2-Me-3-MeO—Ph | $-CH_2CH_2NHCH_2CH_2-$ | | 3,5-di-Me—Ph |
| 2-Me-3-MeO—Ph | $-CH_2NHCH_2CH_2CH_2-$ | | 3,5-di-Me—Ph |
| 2-Me-3-MeO—Ph | $-CH_2CH_2N[(C{=}O)CH_3]CH_2CH_2-$ | | 3,5-di-Me—Ph |
| 2-Me-3-MeO—Ph | $-CH_2CH_2N[(C{=}O)(C{=}O)OEt]CH_2CH_2-$ | | 3,5-di-Me—Ph |
| 2-Me-3-MeO—Ph | $-CH_2CH_2N[S(O)_2CH_3]CH_2CH_2-$ | | 3,5-di-Me—Ph |
| 2-Me-3-MeO—Ph | $-CH_2CH_2N[CH_2(C{=}O)OEt]CH_2CH_2-$ | | 3,5-di-Me—Ph |
| 2-Me-3-MeO—Ph | $-CH_2N[(C{=}O)CH_3]CH_2CH_2CH_2-$ | | 3,5-di-Me—Ph |
| 2-Me-3-MeO—Ph | $-CH_2N[(C{=}O)(C{=}O)OEt]CH_2CH_2CH_2-$ | | 3,5-di-Me—Ph |
| 2-Me-3-MeO—Ph | $-CH_2N[S(O)_2CH_3]CH_2CH_2CH_2-$ | | 3,5-di-Me—Ph |
| 2-Me-3-MeO—Ph | $-CH_2N[CH_2(C{=}O)OCH_3]CH_2CH_2CH_2-$ | | 3,5-di-Me—Ph |
| 2-Me-3-MeO—Ph | $-CH_2CH_2N[(C{=}O)NHEt]CH_2CH_2-$ | | 3,5-di-Me—Ph |
| 2-Me-3-MeO—Ph | $-CH_2CH_2N[(C{=}O)OiPr]CH_2CH_2-$ | | 3,5-di-Me—Ph |
| 2-Me-3-MeO—Ph | $-CH_2CH_2N[CH_2CN]CH_2CH_2-$ | | 3,5-di-Me—Ph |
| 2-Me-3-MeO—Ph | $-CH_2N[(C{=}O)NHEt]CH_2CH_2CH_2-$ | | 3,5-di-Me—Ph |
| 2-Me-3-MeO—Ph | $-CH_2CH_2CH_2N(CH_3)CH_2-$ | | 3,5-di-Me—Ph |
| 2-$NH_2$—Ph | Et | H | Ph |
| 4-Et—Ph | $-(CH_2)_5-$ | | 3,5-di-Cl—Ph |
| 2-Me-3-MeO—Ph | $-(CH_2)_5-$ | | 2-MeO-5-F—Ph |
| 2-Me-3-MeO—Ph | $-(CH_2)_5-$ | | 2-MeO-5-Me—Ph |
| 2-Me-3-MeO—Ph | $-(CH_2)_5-$ | | 2,5-di-MeO—Ph |
| 2-Me-3-MeO—Ph | $-(CH_2)_5-$ | | 4-Me-2-pyridyl |
| 2-Me-3-MeO—Ph | $-(CH_2)_5-$ | | 6-Me-2-pyridyl |
| 4-Et—Ph | $-(CH_2)_5-$ | | 2-MeO-5-F—Ph |
| 4-Et—Ph | $-(CH_2)_5-$ | | 2-MeO-5-Me—Ph |
| 4-Et—Ph | $-(CH_2)_5-$ | | 2,5-di-MeO—Ph |
| 4-Et—Ph | $-(CH_2)_5-$ | | 4-Me-2-pyridyl |
| 4-Et—Ph | $-(CH_2)_5-$ | | 6-Me-2-pyridyl |
| 4-Et—Ph | $-(CH_2)_5-$ | | 2-MeO—Ph |
| 4-Et—Ph | $-(CH_2)_5-$ | | 3,5-di-Me—Ph |
| 4-Et—Ph | $-(CH_2)_5-$ | | 3-Me—Ph |
| 2-Me-3-MeO—Ph | i-Pr | Et | 2-MeO—Ph |
| 2-Me-3-MeO—Ph | i-Pr | Et | 3,5-di-Me—Ph |

In another embodiment, the activating ligand is a compound having Formula VI, wherein n is 2, and $R^2$, $R^3$, $R^4$, and $R^5$ are defined according to Table 6.

TABLE 6

| Ligand Components | | |
|---|---|---|
| $R^2/R^3$ | $R^4$ | $R^5$ |
| $-(CH_2)_5-$ | 3,5-di-Me—Ph | 4H-benzo[1,3]dioxine-6-yl |
| $-(CH_2)_4-$ | 3,5-di-Me—Ph | 4-Me—Ph |
| $-(CH_2)_5-$ | 3,5-di-Cl—Ph | 4-Me—Ph |
| $-(CH_2)_5-$ | 3,5-di-Cl—Ph | 3-MeO—Ph |

In another embodiment, the activating ligand is a compound having Formula VIII:

VIII

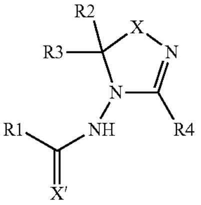

wherein:

X and X' are independently O or S;

$R^1$ is selected from the group consisting of hydrogen, $(C_1-C_6)$alkyl, $(C_1-C_6)$haloalkyl, $(C_1-C_6)$cyanoalkyl, $(C_1-C_6)$alkoxycarbonyl$(C_1-C_6)$alkyl, $(C_1-C_6)$alkoxy, benzyloxy, optionally substituted phenyl, optionally substituted naphthyl wherein the substituents are independently 1 to 3 halo, nitro, $(C_1-C_6)$ alkoxy, $(C_1-C_6)$ alkyl, or amino, optionally substituted benzothiophene-2-yl, benzothiophene-3-yl, benzofuran-2-yl, or benzofuran-3-yl wherein the substituents are independently 1 to 3 halo, nitro, hydroxy, $(C_1-C_6)$alkyl, $(C_1-C_6)$alkoxy, carboxy, or $(C_1-C_6)$alkoxycarbonyl ($-CO_2R^a$), optionally substituted 2-, 3-, or 4-pyridyl wherein the substituents are independently 1 to 3 halo, cyano, nitro, hydroxy, $(C_1-C_6)$alkyl, $(C_1-C_6)$alkoxy, or $(C_1-C_6)$haloalkoxy, optionally substituted 5-membered heterocycle selected from furyl, thiophenyl, triazolyl, pyrrolyl, isopyrrolyl, pyrazolyl, isoimidazolyl, thiazolyl, isothiazolyl, oxazolyl, or isooxazolyl wherein the substituents are independently 1 to 3 halo, nitro, hydroxy, $(C_1-C_6)$alkyl, $(C_1-C_6)$alkoxy, carboxy, $(C_1-C_6)$alkoxycarbonyl ($-CO_2R^a$), or unsubstituted or substituted phenyl wherein the substituents are independently 1 to 3 halo, nitro, $(C_1-C_6)$alkyl, $(C_1-C_6)$ haloalkyl, $(C_1-C_6)$alkoxy, $(C_1-C_6)$haloalkoxy, carboxy, $(C_1-C_4)$alkoxycarbonyl ($-CO_2R^a$), or amino ($-NR^aR^b$), aromatic substituted or unsubstituted phenyl$(C_1-C_6)$alkyl, phenyl$(C_1-C_6)$alkoxy$(C_1-C_6)$alkyl, or phenoxy$(C_1-C_6)$alkyl wherein the aromatic substituents are independently 1 to 3 halo, nitro, $(C_1-C_6)$ alkoxy, $(C_1-C_6)$alkyl, or amino, and aromatic substituted or unsubstituted phenylamino, phenyl$(C_1-C_6)$ alkylamino, or phenylcarbonylamino wherein the aromatic substituents are independently 1 to 3 halo, nitro, $(C_1-C_6)$alkoxy, $(C_1-C_6)$alkyl, or amino;

wherein $R^a$, $R^b$, and $R^c$ are independently H, $(C_1-C_6)$ alkyl, or phenyl;

$R^2$ and $R^3$ are independently H, $(C_1-C_6)$alkyl, $(C_1-C_6)$ haloalkyl, $(C_1-C_6)$cyanoalkyl, $(C_1-C_6)$hydroxyalkyl, $(C_1-C_6)$alkoxy$(C_1-C_6)$alkyl, phenyl, or together as an alkane linkage ($-(CH_2)_x-$), an alkyloxylalkyl linkage ($-(CH_2)_yO(CH_2)_z-$), an alkylaminoalkyl linkage ($-(CH_2)_yNR^a(CH_2)_z-$), or an alkylbenzoalkyl linkage ($-(CH_2)_y$-1-benzo-2-$(CH_2)_z-$) form a ring with the carbon atom to which they are attached, wherein x=3 to 7, y=1 to 3, z=1 to 3, and $R^a$ is H, $(C_1-C_6)$alkyl, or phenyl; and $R^4$ is optionally substituted phenyl, wherein the substituents are independently 1 to 5 H; halo; nitro; cyano; hydroxy; amino ($-NR^aR^b$); $(C_1-C_6)$alkyl; $(C_1-C_6)$haloalkyl; $(C_1-C_6)$cyanoalkyl; $(C_1-C_6)$hydroxyalkyl; $(C_1-C_6)$alkoxy; phenoxy; $(C_1-C_6)$haloalkoxy; $(C_1-C_6)$ alkoxy$(C_1-C_6)$alkyl; $(C_1-C_6)$alkoxy$(C_1-C_6)$alkoxy; $(C_1-C_6)$alkanoyloxy$(C_1-C_6)$alkyl; $(C_2-C_6)$alkenyl optionally substituted with halo, cyano, $(C_1-C_4)$ alkyl, or $(C_1-C_4)$alkoxy; $(C_2-C_6)$alkynyl optionally substituted with halo or $(C_1-C_4)$alkyl; formyl; carboxy; $(C_1-C_6)$alkylcarbonyl; $(C_1-C_6)$haloalkylcarbonyl; benzoyl; $(C_1-C_6)$alkoxycarbonyl; $(C_1-C_6)$haloalkoxycarbonyl; $(C_1-C_6)$alkanoyloxy ($-OCOR^a$); carboxamido ($-CONR^aR^b$); amido ($-NR^aCOR^b$); alkoxycarbonylamino ($-NR^aCO_2R^b$); alkylaminocarbonylamino ($-NR^aCONR^bR^c$); mercapto; $(C_1-C_6)$alkylthio; $(C_1-C_6)$ alkylsulfonyl; $(C_1-C_6)$alkylsulfoxido ($-S(O)R^a$); sulfamido ($-SO_2NR^aR^b$); or optionally substituted phenyl wherein the substituents are independently 1 to 3 halo, nitro, $(C_1-C_6)$ alkoxy, $(C_1-C_6)$alkyl, or amino; or when two adjacent positions on the phenyl ring are substituted with alkoxy groups, these groups, together with the carbon atoms to which they are attached, may be joined to form a 5- or 6-membered dioxolano ($-OCH_2O-$) or dioxano ($-OCH_2CH_2O-$) heterocyclic ring; wherein $R^a$, $R^b$, and $R^c$ are independently H, $(C_1-C_6)$alkyl, or phenyl.

In another embodiment, the activating ligand is a compound having Formula VIII, wherein:

X and X' are O;

$R^1$ is phenyl, 4-chlorophenyl-, 4-ethylphenyl-, 2-ethyl-3,4-ethylenedioxyphenyl, 3-fluorophenyl-, 2-fluoro-4-ethylphenyl-, 2-methyl-3-methoxyphenyl-, 2-ethyl-3-methoxyphenyl, 3-methylphenyl-, 2-methoxyphenyl-, 2-nitrophenyl-, 3-nitrophenyl-, 2-furanyl-, benzyl-, benzothiophene-2-yl-, phenylamino-, benzyloxymethyl, phenoxymethyl-, 3-toluoylamino-, benzylamino-, benzoylamino-, ethoxycarbonylethyl-, or 3-chloro-2,2,3,3-tetrafluoroethyl;

$R^2$ and $R^3$ are independently methyl, ethyl, or together as a tetramethylene ($-(CH2)_4-$), 4-pyrano ($-CH_2CH_2OCH_2CH_2-$), or methylenebenzoethylene ($-CH_2$-1-benzo-2-$CH_2CH_2-$) linkage form a ring with the carbon atom to which they are attached; and $R^4$ is phenyl, 4-biphenyl, 4-chlorophenyl, 2,4-dimethoxyphenyl, 3,5-dimethylphenyl, 2-methoxyphenyl, 3,4-methylenedioxyphenyl, 3-trifluoromethylphenyl, or 4-trifluromethoxyphenyl;

In another embodiment, the activating ligand is a compound having Formula VIII selected from the group consisting of:

1-[5,5-Dimethyl-3-(3-trifluoromethyl-phenyl)-[1,2,4]oxadiazol-4-yl]-3-phenyl-urea;

N-[3-(3,5-Dimethyl-phenyl)-5,5-dimethyl-[1,2,4]oxadiazol-4-yl]-3-fluoro-benzamide;

Furan-2-carboxylic acid [3-(3,5-dimethyl-phenyl)-1-oxa-2,4-diaza-spiro[4.4]non-2-en-4-yl]-amide;

3-Chloro-N-[3-(3,5-dimethyl-phenyl)-5-ethyl-5-methyl-[1,2,4]oxadiazol-4-yl]-2,2,3,3-tetrafluoro-propionamide;

N-[3-(3,5-Dimethyl-phenyl)-1,8-dioxa-2,4-diaza-spiro[4.5]dec-2-en-4-yl]-4-ethyl-benzamide;

2-Benzyloxy-N-[5,5-dimethyl-3-(3-trifluoromethyl-phenyl)-[1,2,4]oxadiazol-4-yl]-acetamide;

N-[3-(3,5-Dimethyl-phenyl)-1,8-dioxa-2,4-diaza-spiro[4.5]dec-2-en-4-yl]-2-ethyl-3-methoxy-benzamide;

2-Benzyloxy-N-[3-(3,5-dimethyl-phenyl)-1,8-dioxa-2,4-diaza-spiro[4.5]dec-2-en-4-yl]-acetamide;

N-[3-(3,5-Dimethyl-phenyl)-1-oxa-2,4-diaza-spiro[4.4]non-2-en-4-yl]-benzamide;

Furan-2-carboxylic acid [3-(2-methoxy-phenyl)-5,5-dimethyl-[1,2,4]oxadiazol-4-yl]-amide;

2-Phenoxy-N-(3-phenyl-1,8-dioxa-2,4-diaza-spiro[4.5]dec-2-en-4-yl)-acetamide;

N-(3-Phenyl-1-oxa-2,4-diaza-spiro[4.4]non-2-en-4-yl)-succinamic acid ethyl ester;

N-[5,5-Dimethyl-3-(3-trifluoromethyl-phenyl)-[1,2,4]oxadiazol-4-yl]-benzamide;

2-Ethyl-3-methoxy-N-[3-(2-methoxy-phenyl)-5,5-dimethyl-[1,2,4]oxadiazol-4-yl]-benzamide;

1-(3-Benzo[1,3]dioxol-5-yl-5,5-dimethyl-[1,2,4]oxadiazol-4-yl)-3-phenyl-urea;

2-Benzyloxy-N-[3-(2-methoxy-phenyl)-5,5-dimethyl-[1,2,4]oxadiazol-4-yl]-acetamide;

N-[3-(3,5-Dimethyl-phenyl)-1,8-dioxa-2,4-diaza-spiro[4.5]dec-2-en-4-yl]-benzamide;

N-(3-Biphenyl-4-yl-5,5-dimethyl-[1,2,4]oxadiazol-4-yl)-2-ethyl-3-methoxy-benzamide;

N-[5,5-Dimethyl-3-(3-trifluoromethyl-phenyl)-[1,2,4]oxadiazol-4-yl]-2-phenyl-acetamide;

N-[5,5-Dimethyl-3-(4-trifluoromethoxy-phenyl)-[1,2,4]oxadiazol-4-yl]-2-ethyl-3-methoxy-benzamide;

N-(3-Benzo[1,3]dioxol-5-yl-5,5-dimethyl-[1,2,4]oxadiazol-4-yl)-2-ethyl-3-methoxy-benzamide;

4-Chloro-N-[3-(3,5-dimethyl-phenyl)-5,5-dimethyl-[1,2,4]oxadiazol-4-yl]-benzamide;

1-[3-(2-Methoxy-phenyl)-5,5-dimethyl-[1,2,4]oxadiazol-4-yl]-3-phenyl-urea;

4-Ethyl-N-[3-(2-methoxy-phenyl)-5,5-dimethyl-[1,2,4]oxadiazol-4-yl]-benzamide;

1-Phenyl-3-(3-phenyl-1,8-dioxa-2,4-diaza-spiro[4.5]dec-2-en-4-yl)-urea;

N-[5,5-Dimethyl-3-(4-trifluoromethoxy-phenyl)-[1,2,4]oxadiazol-4-yl]-2-phenoxy-acetamide;

2-Phenyl-N-(3-phenyl-1-oxa-2,4-diaza-spiro[4.4]non-2-en-4-yl)-acetamide;

N-[3-(3,5-Dimethyl-phenyl)-1-oxa-2,4-diaza-spiro[4.4]non-2-en-4-yl]-succinamic acid ethyl ester;

N-[5,5-Dimethyl-3-(4-trifluoromethoxy-phenyl)-[1,2,4]oxadiazol-4-yl]-benzamide;

2-Benzyloxy-N-(3-phenyl-1,8-dioxa-2,4-diaza-spiro[4.5]dec-2-en-4-yl)-acetamide;

N-[3-(4-Chloro-phenyl)-5,5-dimethyl-[1,2,4]oxadiazol-4-yl]-4-ethyl-benzamide;

N-[3-(3,5-Dimethyl-phenyl)-1-oxa-2,4-diaza-spiro[4.5]-7,8-benzo-dec-2-en-4-yl]-3-methoxy-2-methyl-benzamide;

N-[3-(2,4-Dimethoxy-phenyl)-5,5-dimethyl-[1,2,4]oxadiazol-4-yl]-succinamic acid ethyl ester;

N-[3-(3,5-Dimethyl-phenyl)-5-ethyl-5-methyl-[1,2,4]oxadiazol-4-yl]-benzamide;

N-[3-(3,5-Dimethyl-phenyl)-1-oxa-2,4-diaza-spiro[4.4]non-2-en-4-yl]-4-ethyl-benzamide;

N-[3-(3,5-Dimethyl-phenyl)-1-oxa-2,4-diaza-spiro[4.4]non-2-en-4-yl]-2-phenoxy-acetamide;

N-(5,5-Dimethyl-3-phenyl-[1,2,4]oxadiazol-4-yl)-3-methoxy-2-methyl-benzamide;

N-(3-Phenyl-1,8-dioxa-2,4-diaza-spiro[4.5]dec-2-en-4-yl)-benzamide;

N-[3-(3,5-Dimethyl-phenyl)-5,5-dimethyl-[1,2,4]oxadiazol-4-yl]-3-methoxy-2-methyl-benzamide;

N-[3-(3,5-Dimethyl-phenyl)-1-oxa-2,4-diaza-spiro[4.4]non-2-en-4-yl]-2-phenyl-acetamide;

Benzo[b]thiophene-2-carboxylic acid [3-(2-methoxy-phenyl)-5,5-dimethyl-[1,2,4]oxadiazol-4-yl]-amide;

N-[3-(3,5-Dimethyl-phenyl)-1,8-dioxa-2,4-diaza-spiro[4.5]dec-2-en-4-yl]-2-phenoxy-acetamide;

N-[3-(3,5-Dimethyl-phenyl)-1-oxa-2,4-diaza-spiro[4.4]non-2-en-4-yl]-2-ethyl-3-methoxy-benzamide;

2-Benzyloxy-N-[3-(3,5-dimethyl-phenyl)-5-ethyl-5-methyl-[1,2,4]oxadiazol-4-yl]-acetamide;

1-[3-(3,5-Dimethyl-phenyl)-5-ethyl-5-methyl-[1,2,4]oxadiazol-4-yl]-3-phenyl-urea;

2-Benzyloxy-N-[3-(3,5-dimethyl-phenyl)-1-oxa-2,4-diaza-spiro[4.4]non-2-en-4-yl]-acetamide;

1-[3-(3,5-Dimethyl-phenyl)-1,8-dioxa-2,4-diaza-spiro[4.5]dec-2-en-4-yl]-3-phenyl-urea;

N-[5,5-Dimethyl-3-(4-trifluoromethoxy-phenyl)-[1,2,4]oxadiazol-4-yl]-4-ethyl-benzamide;

1-[3-(3,5-Dimethyl-phenyl)-5,5-dimethyl-[1,2,4]oxadiazol-4-yl]-3-m-tolyl-urea;

N-[3-(2-Methoxy-phenyl)-5,5-dimethyl-[1,2,4]oxadiazol-4-yl]-2-phenoxy-acetamide;

N-[3-(2,4-Dimethoxy-phenyl)-5,5-dimethyl-[1,2,4]oxadiazol-4-yl]-2-ethyl-3-methoxy-benzamide;

3-Chloro-N-[5,5-dimethyl-3-(3-trifluoromethyl-phenyl)-[1,2,4]oxadiazol-4-yl]-2,2,3,3-tetrafluoro-propionamide;

N-[3-(3,5-Dimethyl-phenyl)-5,5-dimethyl-[1,2,4]oxadiazol-4-yl]-4-ethyl-benzamide;

N-(3-Benzo[1,3]dioxol-5-yl-5,5-dimethyl-[1,2,4]oxadiazol-4-yl)-4-ethyl-benzamide;

3-Chloro-2,2,3,3-tetrafluoro-N-[3-(2-methoxy-phenyl)-5,5-dimethyl-[1,2,4]oxadiazol-4-yl]-propionamide;

3-Chloro-2,2,3,3-tetrafluoro-N-(3-phenyl-1-oxa-2,4-diaza-spiro[4.4]non-2-en-4-yl)-propionamide;

2-Benzyloxy-N-[5,5-dimethyl-3-(4-trifluoromethoxy-phenyl)-[1,2,4]oxadiazol-4-yl]-acetamide;

1-[3-(4-Chloro-phenyl)-5,5-dimethyl-[1,2,4]oxadiazol-4-yl]-3-phenyl-urea;

N-[3-(3,5-Dimethyl-phenyl)-5-ethyl-5-methyl-[1,2,4]oxadiazol-4-yl]-2-ethyl-3-methoxy-benzamide;

Furan-2-carboxylic acid [5,5-dimethyl-3-(3-trifluoromethyl-phenyl)-[1,2,4]oxadiazol-4-yl]-amide;

Furan-2-carboxylic acid (3-phenyl-1-oxa-2,4-diaza-spiro[4.4]non-2-en-4-yl)-amide;

1-[3-(3,5-Dimethyl-phenyl)-5,5-dimethyl-[1,2,4]oxadiazol-4-yl]-3-phenyl-urea;

3-Chloro-N-[3-(4-chloro-phenyl)-5,5-dimethyl-[1,2,4]oxadiazol-4-yl]-2,2,3,3-tetrafluoro-propionamide;

N-[3-(3,5-Dimethyl-phenyl)-5,5-dimethyl-[1,2,4]oxadiazol-4-yl]-2-methoxy-benzamide;

2-Ethyl-N-(5-ethyl-5-methyl-3-phenyl-[1,2,4]oxadiazol-4-yl)-3-methoxy-benzamide;

N-[3-(3,5-Dimethyl-phenyl)-5,5-dimethyl-[1,2,4]oxadiazol-4-yl]-3-methyl-benzamide;

N-[3-(2,4-Dimethoxy-phenyl)-5,5-dimethyl-[1,2,4]oxadiazol-4-yl]-2-phenyl-acetamide;

N-[3-(2,4-Dimethoxy-phenyl)-5,5-dimethyl-[1,2,4]oxadiazol-4-yl]-2-phenoxy-acetamide;

N-[3-(3,5-Dimethyl-phenyl)-5,5-dimethyl-[1,2,4]oxadiazol-4-yl]-2-ethyl-3-methoxy-benzamide;

N-(3-Benzo[1,3]dioxol-5-yl-5,5-dimethyl-[1,2,4]oxadiazol-4-yl)-2-phenyl-acetamide;

Furan-2-carboxylic acid [3-(4-chloro-phenyl)-5,5-dimethyl-[1,2,4]oxadiazol-4-yl]-amide;

N-(3-Benzo[1,3]dioxol-5-yl-5,5-dimethyl-[1,2,4]oxadiazol-4-yl)-succinamic acid ethyl ester;

N-[3-(3,5-Dimethyl-phenyl)-1,8-dioxa-2,4-diaza-spiro[4.5]dec-2-en-4-yl]-2-phenyl-acetamide;

N-[3-(3,5-Dimethyl-phenyl)-1,8-dioxa-2,4-diaza-spiro[4.5]dec-2-en-4-yl]-3-methoxy-2-methyl-benzamide;

Benzo[b]thiophene-2-carboxylic acid [3-(4-chloro-phenyl)-5,5-dimethyl-[1,2,4]oxadiazol-4-yl]-amide;

1-Benzyl-3-[3-(3,5-dimethyl-phenyl)-5,5-dimethyl-[1,2,4]oxadiazol-4-yl]-urea;

N-(3-Phenyl-1-oxa-2,4-diaza-spiro[4.4]non-2-en-4-yl)-benzamide;

3-Chloro-N-[3-(3,5-dimethyl-phenyl)-1-oxa-2,4-diaza-spiro[4.4]non-2-en-4-yl]-2,2,3,3-tetrafluoro-propionamide;

N-[3-(3,5-Dimethyl-phenyl)-5,5-dimethyl-[1,2,4]oxadiazol-4-yl]-3-nitro-benzamide;

2-Ethyl-3-methoxy-N-(3-phenyl-1-oxa-2,4-diaza-spiro[4.4]non-2-en-4-yl)-benzamide;

N-[5,5-Dimethyl-3-(3-trifluoromethyl-phenyl)-[1,2,4]oxadiazol-4-yl]-2-ethyl-3-methoxy-benzamide;

Furan-2-carboxylic acid [5,5-dimethyl-3-(4-trifluoromethoxy-phenyl)-[1,2,4]oxadiazol-4-yl]-amide;

1-(5-Ethyl-5-methyl-3-phenyl-[1,2,4]oxadiazol-4-yl)-3-phenyl-urea;

N-[3-(2,4-Dimethoxy-phenyl)-5,5-dimethyl-[1,2,4]oxadiazol-4-yl]-benzamide;

N-[3-(3,5-Dimethyl-phenyl)-5,5-dimethyl-[1,2,4]oxadiazol-4-yl]-2-nitro-benzamide;

N-[3-(4-Chloro-phenyl)-5,5-dimethyl-[1,2,4]oxadiazol-4-yl]-2-ethyl-3-methoxy-benzamide;

Furan-2-carboxylic acid (5-ethyl-5-methyl-3-phenyl-[1,2,4]oxadiazol-4-yl)-amide;

Furan-2-carboxylic acid [3-(2,4-dimethoxy-phenyl)-5,5-dimethyl-[1,2,4]oxadiazol-4-yl]-amide;

N-(5-Ethyl-5-methyl-3-phenyl-[1,2,4]oxadiazol-4-yl)-2-phenoxy-acetamide;

Furan-2-carboxylic acid [3-(3,5-dimethyl-phenyl)-5-ethyl-5-methyl-[1,2,4]oxadiazol-4-yl]-amide;

Benzo[b]thiophene-2-carboxylic acid [5,5-dimethyl-3-(3-trifluoromethyl-phenyl)-[1,2,4]oxadiazol-4-yl]-amide;

Benzo[b]thiophene-2-carboxylic acid [5,5-dimethyl-3-(4-trifluoromethoxy-phenyl)-[1,2,4]oxadiazol-4-yl]-amide;

2-Benzyloxy-N-[3-(2,4-dimethoxy-phenyl)-5,5-dimethyl-[1,2,4]oxadiazol-4-yl]-acetamide;

1-Benzoyl-3-[3-(3,5-dimethyl-phenyl)-5,5-dimethyl-[1,2,4]oxadiazol-4-yl]-urea;

1-[3-(3,5-Dimethyl-phenyl)-1-oxa-2,4-diaza-spiro[4.4]non-2-en-4-yl]-3-phenyl-urea;

1-[3-(2,4-Dimethoxy-phenyl)-5,5-dimethyl-[1,2,4]oxadiazol-4-yl]-3-phenyl-urea;

N-(5,5-Dimethyl-3-phenyl-[1,2,4]oxadiazol-4-yl)-4-ethyl-benzamide;

2-Benzyloxy-N-[3-(4-chloro-phenyl)-5,5-dimethyl-[1,2,4]oxadiazol-4-yl]-acetamide;

N-(5-Ethyl-5-methyl-3-phenyl-[1,2,4]oxadiazol-4-yl)-benzamide;

N-[3-(3,5-Dimethyl-phenyl)-5-ethyl-5-methyl-[1,2,4]oxadiazol-4-yl]-2-phenyl-acetamide;

N-[3-(4-Chloro-phenyl)-5,5-dimethyl-[1,2,4]oxadiazol-4-yl]-2-phenyl-acetamide;

1-[5,5-Dimethyl-3-(4-trifluoromethoxy-phenyl)-[1,2,4]oxadiazol-4-yl]-3-phenyl-urea;

4-Ethyl-N-(3-phenyl-1,8-dioxa-2,4-diaza-spiro[4.5]dec-2-en-4-yl)-benzamide;

4-Ethyl-N-(3-phenyl-1-oxa-2,4-diaza-spiro[4.4]non-2-en-4-yl)-benzamide;

N-[3-(3,5-Dimethyl-phenyl)-5-ethyl-5-methyl-[1,2,4]oxadiazol-4-yl]-succinamic acid ethyl ester;

N-(3-Benzo[1,3]dioxol-5-yl-5,5-dimethyl-[1,2,4]oxadiazol-4-yl)-2-phenoxy-acetamide;

N-[3-(3,5-Dimethyl-phenyl)-5-ethyl-5-methyl-[1,2,4]oxadiazol-4-yl]-4-ethyl-benzamide;

Benzo[b]thiophene-2-carboxylic acid [3-(2,4-dimethoxy-phenyl)-5,5-dimethyl-[1,2,4]oxadiazol-4-yl]-amide;

2-Phenyl-N-(3-phenyl-1,8-dioxa-2,4-diaza-spiro[4.5]dec-2-en-4-yl)-acetamide;

1-Phenyl-3-(3-phenyl-1-oxa-2,4-diaza-spiro[4.4]non-2-en-4-yl)-urea;

Benzo[b]thiophene-2-carboxylic acid (5-ethyl-5-methyl-3-phenyl-[1,2,4]oxadiazol-4-yl)-amide;

N-[3-(2,4-Dimethoxy-phenyl)-5,5-dimethyl-[1,2,4]oxadiazol-4-yl]-4-ethyl-benzamide;

4-Ethyl-N-(5-ethyl-5-methyl-3-phenyl-[1,2,4]oxadiazol-4-yl)-benzamide;

Furan-2-carboxylic acid [3-(3,5-dimethyl-phenyl)-1,8-dioxa-2,4-diaza-spiro[4.5]dec-2-en-4-yl]-amide;

Benzo[b]thiophene-2-carboxylic acid (3-benzo[1,3]dioxol-5-yl-5,5-dimethyl-[1,2,4]oxadiazol-4-yl)-amide;

N-[3-(3,5-Dimethyl-phenyl)-5-ethyl-5-methyl-[1,2,4]oxadiazol-4-yl]-2-phenoxy-acetamide;

N-(3-Biphenyl-4-yl-5,5-dimethyl-[1,2,4]oxadiazol-4-yl)-4-ethyl-benzamide;

N-[3-(2-Methoxy-phenyl)-5,5-dimethyl-[1,2,4]oxadiazol-4-yl]-succinamic acid ethyl ester;

N-(3-Benzo[1,3]dioxol-5-yl-5,5-dimethyl-[1,2,4]oxadiazol-4-yl)-2-benzyloxy-acetamide;

N-(5-Ethyl-5-methyl-3-phenyl-[1,2,4]oxadiazol-4-yl)-2-phenyl-acetamide;

N-[3-(2-Methoxy-phenyl)-5,5-dimethyl-[1,2,4]oxadiazol-4-yl]-benzamide;

N-[5,5-Dimethyl-3-(3-trifluoromethyl-phenyl)-[1,2,4]oxadiazol-4-yl]-4-ethyl-benzamide;

Furan-2-carboxylic acid (3-benzo[1,3]dioxol-5-yl-5,5-dimethyl-[1,2,4]oxadiazol-4-yl)-amide;

Benzo[b]thiophene-2-carboxylic acid (3-phenyl-1-oxa-2,4-diaza-spiro[4.4]non-2-en-4-yl)-amide;

N-[3-(4-Chloro-phenyl)-5,5-dimethyl-[1,2,4]oxadiazol-4-yl]-benzamide;

Benzo[b]thiophene-2-carboxylic acid [3-(3,5-dimethyl-phenyl)-1-oxa-2,4-diaza-spiro[4,4]non-2-en-4-yl]-amide;

N-[5,5-Dimethyl-3-(3-trifluoromethyl-phenyl)-[1,2,4]oxadiazol-4-yl]-succinamic acid ethyl ester;

2-Benzyloxy-N-(5-ethyl-5-methyl-3-phenyl-[1,2,4]oxadiazol-4-yl)-acetamide;

2-Benzyloxy-N-(3-phenyl-1-oxa-2,4-diaza-spiro[4.4]non-2-en-4-yl)-acetamide;

N-(3-Benzo[1,3]dioxol-5-yl-5,5-dimethyl-[1,2,4]oxadiazol-4-yl)-benzamide;

N-[3-(2-Methoxy-phenyl)-5,5-dimethyl-[1,2,4]oxadiazol-4-yl]-2-phenyl-acetamide;

2-Phenoxy-N-(3-phenyl-1-oxa-2,4-diaza-spiro[4.4]non-2-en-4-yl)-acetamide;

2-Ethyl-3-methoxy-N-(3-phenyl-1,8-dioxa-2,4-diaza-spiro[4.5]dec-2-en-4-yl)-benzamide;

N-[5,5-Dimethyl-3-(4-trifluoromethoxy-phenyl)-[1,2,4]oxadiazol-4-yl]-2-phenyl-acetamide;

Benzo[b]thiophene-2-carboxylic acid [3-(3,5-dimethyl-phenyl)-5-ethyl-5-methyl-[1,2,4]oxadiazol-4-yl]-amide;

N-[3-(4-Chloro-phenyl)-5,5-dimethyl-[1,2,4]oxadiazol-4-yl]-2-phenoxy-acetamide;

N-[5,5-Dimethyl-3-(3-trifluoromethyl-phenyl)-[1,2,4]oxadiazol-4-yl]-2-phenoxy-acetamide;

N-[3-(4-Chloro-phenyl)-5,5-dimethyl-[1,2,4]oxadiazol-4-yl]-succinamic acid ethyl ester;

N-[3-(3,5-Dimethyl-phenyl)-5-ethyl-5-methyl-[1,2,4]oxadiazol-4-yl]-4-ethyl-2-fluoro-benzamide;

4-Ethyl-2-fluoro-N-(3-phenyl-1-oxa-2,4-diaza-spiro[4.4]non-2-en-4-yl)-benzamide;

N-[3-(3,5-Dimethyl-phenyl)-1-oxa-2,4-diaza-spiro[4.4]non-2-en-4-yl]-4-ethyl-2-fluoro-benzamide;

N-(5,5-Dimethyl-3-phenyl-[1,2,4]oxadiazol-4-yl)-4-ethyl-2-fluoro-benzamide;

5-Ethyl-2,3-dihydro-benzo[1,4]dioxine-6-carboxylic acid (5,5-dimethyl-3-phenyl-[1,2,4]oxadiazol-4-yl)-amide; and 5-Ethyl-2,3-dihydro-benzo[1,4]dioxine-6-carboxylic acid [3-(3,5-dimethyl-phenyl)-5-ethyl-5-methyl-[1,2,4]oxadiazol-4-yl]-amide.

In another embodiment, the activating ligand is a compound having Formula IX or X:

IX

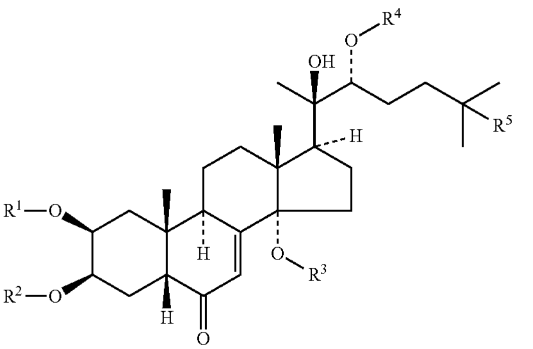

or

X

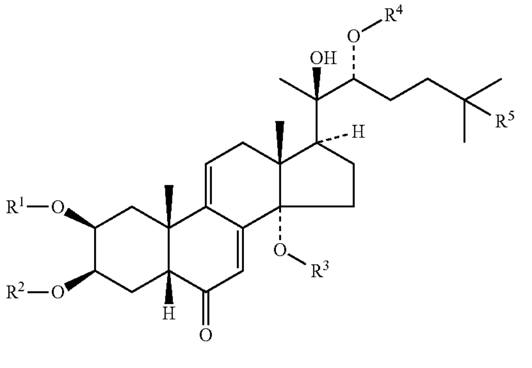

wherein $R^1$, $R^2$, $R^3$, and $R^4$ are each independently:

a) H, $(C_1$-$C_6)$alkyl; $(C_1$-$C_6)$haloalkyl; $(C_1$-$C_6)$cyanoalkyl; $(C_1$-$C_6)$hydroxyalkyl; $(C_1$-$C_4)$alkoxy$(C_1$-$C_6)$alkyl; $(C_2$-$C_6)$alkenyl optionally substituted with halo, cyano, hydroxyl, or $(C_1$-$C_4)$alkyl; $(C_2$-$C_6)$alkynyl optionally substituted with halo, cyano, hydroxyl, or $(C_1$-$C_4)$alkyl; $(C_3$-$C_5)$cycloalkyl optionally substituted with halo, cyano, hydroxyl, or $(C_1$-$C_4)$alkyl; oxiranyl optionally substituted with halo, cyano, or $(C_1$-$C_4)$alkyl; or b) unsubstituted or substituted benzyl wherein the substituents are independently 1 to 5 H, halo, nitro, cyano, hydroxyl, $(C_1$-$C_6)$alkyl, or $(C_1$-$C_6)$alkoxy; and $R^5$ is H; OH; F; Cl; or $(C_1$-$C_6)$alkoxy.

In another embodiment, the activating ligand is a compound selected from the group consisting of 20-hydroxyecdysone-2-methyl ether; 20-hydroxyecdysone-3-methyl ether; 20-hydroxyecdysone-14-methyl ether; 20-hydroxyecdysone-2,22-dimethyl ether; 20-hydroxyecdysone-3,22-dimethyl ether; 20-hydroxyecdysone-14,22-dimethyl ether; 20-hydroxyecdysone-22,25-dimethyl ether; 20-hydroxyecdysone-2,3,14,22-tetramethyl ether; 20-hydroxyecdysone-22-n-propyl ether; 20-hydroxyecdysone-22-n-butyl ether; 20-hydroxyecdysone-22-allyl ether; 20-hydroxyecdysone-22-benzyl ether; 20-hydroxyecdysone-22-(28R,S)-2'-ethyloxiranyl ether; ponasterone A-2-methyl ether; ponasterone A-14-methyl ether; ponasterone A-22-methyl ether; ponasterone A-2,22-dimethyl ether; ponasterone A-3,22-dimethyl ether; ponasterone A-14,22-dimethyl ether; dacryhainansterone-22-methyl ether; 25,26-didehydroponasterone A (isostachysterone C (Δ25(26))); shidasterone (stachysterone D); stachysterone C; 22-deoxy-20-hydroxyecdysone (taxisterone); ponasterone A; polyporusterone B; 22-dehydro-20-hydroxyecdysone; 20-hydroxyecdysone; pterosterone; (25R)-inokosterone; (25S)-inokosterone; pinnatasterone; 25-fluoroponasterone A; 24(28)-dehydromakisterone A; 24-epi-makisterone A; makisterone A; 20-hydroxyecdysone-22-methyl ether; 20-hydroxyecdysone-25-methyl ether; abutasterone; 22,23-di-epi-geradiasterone; 20,26-dihydroxyecdysone (podecdysone C); 24-epi-abutasterone; geradiasterone; 29-norcyasterone; ajugasterone B; 24(28)[Z]-dehydroamarasterone B; amarasterone A; makisterone C; rapisterone C; 20-hydroxyecdysone-22,25-dimethyl ether; 20-hydroxyecdysone-22-ethyl ether; carthamosterone; 24(25)-dehydroprecyasterone; leuzeasterone; cyasterone; 20-hydroxyecdysone-22-allyl ether; 24(28) [Z]-dehydro-29-hydroxymakisterone C; 20-hydroxyecdysone-22-acetate; viticosterone E (20-hydroxyecdysone 25-acetate); 20-hydroxyecdysone-22-n-propyl ether; 24-hydroxycyasterone; ponasterone A 22-hemisuccinate; 22-acetoacetyl-20-hydroxyecdysone; canescensterone; 20-hydroxyecdysone-22-hemisuccinate; inokosterone-26-hemisuccinate; 20-hydroxyecdysone-22-benzoate; 20-hydroxyecdysone-22-β-D-glucopyranoside; 20-hydroxyecdysone-25-β-D-glucopyranoside; sileneoside A (20-hydroxyecdysone-22α-galactoside); 3-deoxy-1β,20-dihydroxyecdysone (3-deoxyintegristerone A); 2-deoxyintegristerone A; 1-epi-integristerone A; integristerone A; sileneoside C (integristerone A 22α-galactoside); 2,22-dideoxy-20-hydroxyecdysone; 2-deoxy-20-hydroxyecdysone; 2-deoxy-20-hydroxyecdysone-3-acetate; 2-deoxy-20,26-dihydroxyecdysone; 2-deoxy-20-hydroxyecdysone-22-acetate; 2-deoxy-20-hydroxyecdysone-3,22-diacetate; 2-deoxy-20-hydroxyecdysone-22-benzoate; ponasterone A 2-hemisuccinate; 20-hydroxyecdysone-2-acetate; 20-hydroxyecdysone-2-hemisuccinate; 20-hydroxyecdysone-2-β-D-glucopyranoside; 2-dansyl-20-hydroxyecdysone; 20-hydroxyecdysone-2,22-dimethyl ether; ponasterone A 3β-D-xylopyranoside (limnantheoside B); 20-hydroxyecdysone-3-methyl ether; 20-hydroxyecdysone-3-acetate; 20-hydroxyecdysone-3β-D-xylopyranoside (limnantheoside A); 20-hydroxyecdysone-3-β-D-glucopyranoside; sileneoside D (20-hydroxyecdysone-3α-galactoside); 20-hydroxyecdysone 3-β-D-glucopyranosyl-[1-3]-β-D-xylopyranoside (limnantheoside C); cyasterone-3-acetate; 2-dehydro-3-epi-20-hydroxyecdysone; 3-epi-20-hydroxyecdysone (coronatasterone); rapisterone D; 3-dehydro-20-hydroxyecdysone; 5β-hydroxy-25,26-didehydroponasterone A; 5β-hydroxystachysterone C; 25-deoxypolypodine B; polypodine B; 25-fluoropolypodine B; 5β-hydroxyabutasterone; 26-hydroxypolypodine B; 29-norsengosterone, sengosterone; 6β-hydroxy-20-hydroxyecdysone; 6α-hydroxy-20-hydroxyecdysone; 20-hydroxyecdysone-6-oxime; ponasterone A 6-carboxymethyloxime; 20-hydroxyecdysone-6-carboxymethyloxime; ajugasterone C; rapisterone B; muristerone A; atrotosterone B; atrotosterone A; turkesterone-2-acetate; punisterone (rhapontisterone); turkesterone; atrotosterone C; 25-hydroxyatrotosterone B; 25-hydroxyatrotosterone A; paxillosterone; turkesterone-2,22-diacetate; turkesterone-22-acetate; turkesterone-11α-acetate; turkesterone-2,11α-diacetate; turkesterone-11α-propionate; turkesterone-11α-butanoate; turkesterone-11α-hexanoate; turkesterone-11α-decanoate; turkesterone-11α-laurate; turkesterone-11α-myristate; turkesterone-11α-arachidate, 22-dehydro-12β-hydroxynorsengosterone; 22-dehydro-12β-hydroxycyasterone; 22-dehydro-12β-hydroxysengosterone; 14-deoxy(14α-H)-20-hydroxyecdysone; 20-hydroxyecdysone-14-methyl ether; 14α-perhydroxy-20-hydroxyecdysone; 20-hydroxyecdysone-2,3,14,22-tetramethyl ether; (20S)-22-deoxy-20,21-dihydroxyecdysone; 22,25-dideoxyecdysone; (22S)-20-(2,2'-dimethylfuranyl)ecdysone; (22R)-20-(2,2'-dimethylfuranyl)ecdysone; 22-deoxyecdysone; 25-deoxyecdysone; 22-dehydroecdysone; ecdysone; 22-epi-ecdysone; 24-methylecdysone (20-deoxymakisterone A); ecdysone-22-hemisuccinate; 25-deoxyecdysone-22-β-D-glucopyranoside; ecdysone-22-myristate; 22-dehydro-20-iso-ecdysone; 20-iso-ecdysone; 20-iso-22-epi-ecdysone; 2-deoxyecdysone; sileneoside E (2-deoxyecdysone 3β-glucoside, blechnoside A); 2-deoxyecdysone-22-acetate; 2-deoxyecdysone-3,22-diacetate; 2-deoxyecdysone-22-β-D-glucopyranoside; 2-deoxyecdysone 25-β-D-glucopyranoside; 2-deoxy-21-hydroxyecdysone; 3-epi-22-iso-ecdysone; 3-dehydro-2-deoxyecdysone (silenosterone); 3-dehydroecdysone; 3-dehydro-2-deoxyecdysone-22-acetate; ecdysone-6-carboxymethyloxime; ecdysone-2,3-acetonide; 14-epi-20-hydroxyecdysone-2,3-acetonide; 20-hydroxyecdysone-2,3-acetonide; 20-hydroxyecdysone-20,22-acetonide; 14-epi-20-hydroxyecdysone-2,3,20,22-diacetonide; paxillosterone-20,22-p-hydroxybenzylidene acetal; poststerone; (20R)-dihydropoststerone; (20S)dihydropoststerone; poststerone-20-dansylhydrazine; (20S)-dihydropoststerone-2,3,20-tribenzoate; (20R)-dihydropoststerone-2,3,20-tribenzoate; (20R)dihydropoststerone-2,3-acetonide; (20S)dihydropoststerone-2,3-acetonide; (5α-H)-dihydrorubrosterone; 2,14,22,25-tetradeoxy-5α-ecdysone; 5α-keto-diol, bombycosterol; 2α,3α,22S,25-tetrahydroxy-5α-cholestan-6-one; (5α-H)-2-deoxy-21-hydroxyecdysone; castasterone; 24-epi-castasterone; (5α□-H)-2-deoxyintegristerone A; (5α-H)-22-deoxyintegristerone A; (5α-H)-20-hydroxyecdysone; 24,25-didehydrodacryhaninansterone; 25,26-didehydrodacryhainansterone; 5-deoxykaladasterone (dacryhainansterone); (14α-H)-14-deoxy-25-hydroxydacryhainansterone; 25-hydroxydacryhainansterone; rubrosterone; (5β-H)-dihydrorubrosterone; dihydrorubrosterone-17β-acetate; sidisterone; 20-hydroxyecdysone-2,3,22-triacetate; 14-deoxy(14β-H)-20-hydroxyecdysone; 14-epi-20-hydroxyecdysone; 9α,20-dihydroxyecdysone; malacosterone, 2-deoxypolypodine B-3-β-D-glucopyranoside; ajugalactone; cheilanthone B; 2β,3β,6α-trihydroxy-5β-cholestane; 2β,3β,6β-trihydroxy-5β-cholestane; 14-dehydroshidasterone; stachysterone B; 2β,3β,9α,20R,22R,25-hexahydroxy-5β-cholest-7,14-dien-6-one; kaladasterone; (14β-H)-14-deoxy-25-hydroxydacryhainansterone; 4-dehydro-20-hydroxyecdysone; 14-methyl-12-en-shidasterone; 14-methyl-12-en-15,20-dihydroxyecdysone; podecdysone B; 2β,3β,20R,22R-tetrahydroxy-25-fluoro-5β-cholest-8,14-dien-6-one (25-fluoropodecdysone B); calonysterone; 14-deoxy-14,18-cyclo-20-hydroxyecdysone; 9α,14α-epoxy-20-hydroxyecdysone; 9βα,14β-epoxy-20-hydroxyecdysone; 9α,14α-epoxy-20-hydroxyecdysone 2,3,20,22-diacetonide; 28-homobrassinolide; and iso-homobrassinolide.

The disclosure of all patents, patent applications, and publications cited herein are incorporated by reference in their entireties.

The following examples are illustrative, but not limiting, of the methods of the present invention. Other suitable modifications and adaptations of the variety of conditions and parameters normally encountered in medical treatment and gene expression systems and which are obvious to those skilled in the art are within the spirit and scope of the invention.

Pharmaceutical Compositions

In certain embodiments, polynucleotides and polypeptides of the invention can be administered as part of a medicament or pharmaceutical composition. Medicaments and pharmaceutical compositions of the invention comprise one or more pharmaceutically acceptable carriers, diluents, excipients or additives.

The term "excipient" as used herein is typically an inert substance added to a composition to facilitate processing, handling, administration, et cetera of a pharmaceutically acceptable composition. Useful excipients include, but are not limited to, adjuvants, anti-adherents, binders, carriers, disintegrants, fillers, flavors, colors, diluents, lubricants, glidants, preservatives, sorbents, solvents, surfactants, and sweeteners.

A few examples of pharmaceutically acceptable carriers, diluents, excipients and additives include, without limitation, water, saline, Ringer's solution, dextrose solution, buffers (such as phosphates (e.g., calcium phosphates such as tricalcium phosphate or calcium hydrogen phosphate)), citrate, succinate, acetic acid, and other organic acids or their salts), antioxidants, proteins and other high molecular weight molecules (such as serum albumin, gelatin, or immunoglobulins), hydrophilic polymers (such as polyvinylpyrrolidone), amino acids (such as glycine, glutamic acid, aspartic acid, and arginine), saccharides (for example monosaccharides, disaccharides, lactose, sucrose, mannitol, sorbitol, other carbohydrates and sugar-alcohols, cellulose or its derivatives, glucose, mannose, and dextrins), chelating agents (such as EDTA); sugar alcohols (such as mannitol or sorbitol), counterions (such as sodium), surfactants (such as polysorbates, poloxamers, or polyethylene glycol (PEG)), and binders (such as starch paste (e.g., maize starch, wheat starch, rice starch, potato starch)), gelatin, tragacanth, methyl cellulose, hydroxypropylmethylcellulose, sodium carboxymethylcellulose, and/or polyvinyl pyrrolidone).

Pharmaceutically acceptable carriers, diluents, excipients and additives may include: disintegrating agents such as the above-mentioned starches as well as compounds such as carboxymethyl-starch, cross-linked polyvinyl pyrrolidone, agar, or alginic acid or a salt thereof, such as sodium alginate; and, flow-regulating agents and lubricants, for example, silica, talc, stearic acid or salts thereof, such as magnesium stearate or calcium stearate, and/or polyethylene glycol. In one embodiment, dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules or nanoparticles which may optionally be mixed with fillers such as lactose, binders such as starches, and/or lubricants such as talc or magnesium stearate and, optionally, stabilizers. In one embodiment, the is dissolved or suspended in suitable liquids, such as fatty oils, or liquid paraffin, optionally with stabilizers.

Fatty oils may comprise mono-, di- or triglycerides. Mono-, di- and triglycerides include those that are derived from C6, C8, C10, C12, C14, C16, C18, C20 and C22 acids. Exemplary diglycerides include, in particular, diolein, dipalmitolein, and mixed caprylin-caprin diglycerides. Preferred triglycerides include vegetable oils, fish oils, animal fats, hydrogenated vegetable oils, partially hydrogenated vegetable oils, synthetic triglycerides, modified triglycerides, fractionated triglycerides, medium and long-chain triglycerides, structured triglycerides, and mixtures thereof. Exemplary triglycerides include: almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; partially soy and cottonseed oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; and glyceryl tricaprylate/caprate/stearate.

In one embodiment, the triglyceride is the medium chain triglyceride available under the trade name LABRAFAC CC. Other triglycerides include neutral oils, e.g., neutral plant oils, in particular fractionated coconut oils such as known and commercially available under the trade name MIGLYOL, including the products: MIGLYOL 810; MIGLYOL 812; MIGLYOL 818; and CAPTEX 355. Other triglycerides are caprylic-capric acid triglycerides such as known and commercially available under the trade name MYRITOL, including the product MYRITOL 813. Further triglycerides of this class are CAPMUL MCT, CAPTEX 200, CAPTEX 300, CAPTEX 800, NEOBEE M5 and MAZOL 1400.

Pharmaceutical compositions comprising triglycerides may further comprise lipophilic and/or hydrophilic surfactants which may form clear solutions upon dissolution with an aqueous solvent. One such surfactant is tocopheryl polyethylene glycol 1000 succinate (vitamin E TPGS). Examples of such compositions are described in U.S. Pat. No. 6,267,985.

In another embodiment, the pharmaceutically acceptable carrier comprises LABRASOL (Gattefosse SA), which is PEG-8 caprylic/capric glycerides. In another embodiment, the pharmaceutically acceptable carrier comprises PL90G, vitamin E TPGS, and Miglyol 812N.

Pharmaceutical compositions can be administered in any suitable manner as determined by those skilled in the art, such as, but without limitation, by oral, rectal, vaginal, topical (including dermal, buccal and sublingual), parenteral, intravenous, intraperitoneal, intramuscular, intratumoral, intraarticular, subcutaneous, intranasal, inhalation, intradermal, intrathecal, epidural, and by naso-gastric routes.

Methods and compositions for preparation, formulation, and delivery of pharmaceutically acceptable compositions and medicaments are well-known and routinely practiced by those skilled in the art. A few examples of textbooks and manuals providing information and instruction on such methods and compositions include: Rowe et al. (Editor), "*Handbook of Pharmaceutical Excipients*," Pharmaceutical Press, $6^{th}$ Ed. (August 2009); University of the Sciences in Philadelphia (Editor), "*Remington: The Science and Practice of Pharmacy*," Lippincott Williams & Wilkins, $21^{st}$ Ed. (2005); "*Physicians' Desk Reference* 2011," PDR Network (2010); "*Physicians' Desk Reference* 2012," PDR Network (2011); O'Neil, "*The Merck Index: An Encyclopedia of Chemicals, Drugs, and Biologicals,*" $14^{th}$ Ed. (2006); Allen et al. (Editor) "*Ansel's Pharmaceutical Dosage Forms and Drug Delivery Systems*," Lippincott Williams & Wilkins; $9^{th}$ Ed. (2011); and, Ash et al. (Editor), "*Handbook of Pharmaceutical Additives, Third Edition*," Synapse Information Resources, Inc.; $3^{rd}$ Ed. (2007).

Protocols for general molecular biology methods can be found in: *Methods in Molecular Biology*, series editor J M Walker, Humana Press, New York.

Embodiments of the invention comprise any amino acid substituted form of PE as indicated by, or represented in, Table 13. Embodiments of the invention further comprise any amino acid substituted form of PE which may comprise any combination of amino acid substitutions indicated by, or represented in, Table 13.

Embodiments of the invention also comprise variants, derivatives, or biologically active fragments of any amino acid substituted form of PE as indicated by, or represented in, Table 13, wherein said variant, derivative, or biologically active fragment of PE is at least 80% identical, at least 85% identical, at least 90% identical, at least 95% identical, at least 97% identical, at least 98% identical, at least 99% identical, or is at least 100% identical to an amino acid substituted form of PE, or a fragment thereof, as indicated by, or represented in, Table 13. For example, embodiments of the invention comprise variants, derivatives, or biologically active fragments of any amino acid substituted form of PE as indicated by, or represented in, Table 13, wherein said variant, derivative, or biologically active fragment of PE is at least 80% identical, at least 85% identical, at least 90% identical, at least 95% identical, at least 97% identical, at least 98% identical, at least 99% identical, or is at least 100% identical to PE constructs, or fragments thereof, as represented by pIEX02-003 through pIEX02-248 in Table 13 (such as, for example, as shown in SEQ ID NO:177 (pIEX02-228), SEQ ID NO:178 (pIEX02-244), and SEQ ID NO: 179 (pIEX02-246)).

Embodiments of the invention include methods of making, methods of using, methods of treatment using, medicaments comprising, pharmaceutically acceptable compositions comprising, therapeutically useful compositions comprising, and kits comprising any of the amino acid substituted forms of PE referenced, or otherwise described or provided for, herein.

Embodiments of the invention also include (where "E" indicates "embodiment"):

E1. An isolated polypeptide having *Pseudomonas* exotoxin A biological activity, wherein said polypeptide comprises an epitope selected from the group consisting of:

```
                                   (SEQ ID NO: 5)
a) ISFSTRGTQ;
                                   (SEQ ID NO: 6)
b) GTQNWTVER;
                                   (SEQ ID NO: 7)
c) IVFGGVRAR;
                                   (SEQ ID NO: 8)
d) ARSQDLDAI;
                                   (SEQ ID NO: 9)
e) LRVYVPRSS;
                                  (SEQ ID NO: 10)
f) IPDKEQAIS;
                                 (SEQ ID NO: 131)
g) ISFSTRGTQNWTVER;
and
                                 (SEQ ID NO: 132)
h) IVFGGVRARSQDLDAI
```

wherein one or more amino acid residues in any one or more of said epitopes in a) through h) are substituted with a different amino acid residue.

E2. An isolated polypeptide having *Pseudomonas* exotoxin A biological activity, wherein said polypeptide comprises an epitope selected from the group consisting of:

a) ISFSTRGTQ (SEQ ID NO:5), wherein amino acid residues at one or more of positions 1, 6 and 9 are substituted with a different amino acid residue;

b) GTQNWTVER (SEQ ID NO:6), wherein amino acid residues at one or more of positions 3, 4 and 6 are substituted with a different amino acid residue;

c) IVFGGVRAR (SEQ ID NO:7), wherein amino acid residues at one or more of positions 1 and 6 are substituted with a different amino acid residue;

d) ARSQDLDAI (SEQ ID NO:8), wherein amino acid residues at one or more of positions 4 and 7 are substituted with a different amino acid residue;

e) LRVYVPRSS (SEQ ID NO:9), wherein amino acid residues at one or more of positions 1, 2 and 9 are substituted with a different amino acid residue;

f) IPDKEQAIS (SEQ ID NO:10), wherein amino acid residues at one or more of positions 1, 4, 6 and 7 are substituted with a different amino acid residue;

g) ISFSTRGTQNWTVER (SEQ ID NO:131), wherein amino acid residues at one or more of positions 1, 6, 9, 10 and 12 are substituted with a different amino acid residue; and h) IVFGGVRARSQDLDAI (SEQ ID NO: 132), wherein amino acid residues at one or more of positions 1, 6, 11, and 14 are substituted with a different amino acid residue.

E3. The isolated polypeptide of embodiment E1 or E2, wherein said different amino acid residue is a conservative amino acid substitution.

E4. The isolated polypeptide of embodiment E3, wherein said conservative amino acid substitution is one or more substitutions selected from the group consisting of:

a) A is substituted with any one of G, I, L, S, T or V;

b) D is substituted with E;

c) I is substituted with any one of L, M or V;

d) K is substituted with any one of H or R;

e) L is substituted with any one of A, G, I, M or V;

f) N is substituted with any one of S, T or Q;

g) Q is substituted with any one of S, T or N;

h) R is substituted with any one of K or H;

i) S is substituted with any one of A, G, N, T or Q;

j) T is substituted with any one of A, G, N, Q or S; and k) V is substituted with any one of A, G, I, L or M.

E5. An isolated polypeptide having *Pseudomonas* exotoxin A biological activity, wherein said polypeptide comprises an epitope selected from the group consisting of:

a) ISFSTRGTQ (SEQ ID NO:5), wherein amino the acid residue at position 1 (I) is substituted with A, N, T, Q or H, or wherein the amino acid residue at position 6 (R) is substituted with Q, or wherein the amino acid residue at position 9 (Q) is substituted with N or T, or wherein the amino acid sequence ISFSTRGTQ (SEQ ID NO:5) comprises two or more of said substitutions in any combination;

b) GTQNWTVER (SEQ ID NO:6), wherein the amino acid residue at position 3 (Q) is substituted with N or T, wherein amino the acid residue at position 4 (N) is substituted with K or R, or wherein the amino acid residue at position 6 (T) is substituted with K or R, or wherein the amino acid sequence GTQNWTVER (SEQ ID NO:6) comprises two or more of said substitutions in any combination;

c) IVFGGVRAR (SEQ ID NO:7), wherein amino the acid residue at position 1 (I) is substituted with A or N, or wherein the amino acid residue at position 6 (V) is substituted with D, M, or N, or wherein the amino acid sequence IVFGGVRAR (SEQ ID NO:7) comprises substitutions at both positions in any combination of amino acid residues A or N at position 1 (I) and D, M, or N at position 6 (V);

d) ARSQDLDAI (SEQ ID NO:8), wherein amino the acid residue at position 4 (Q) is substituted with K or R, or wherein the amino acid residue at position 7 (D) is substituted with K or R, or wherein the amino acid sequence ARSQDLDAI (SEQ ID NO:8) comprises substitutions with K or R in any combination at both positions 4 (Q) and 7 (D);

e) LRVYVPRSS (SEQ ID NO:9), wherein amino the acid residue at position 1 (L) is substituted with A, or wherein the amino acid residue at position 2 (R) is substituted with D, S or A, or wherein the amino acid residue at position 9 (S) is substituted with D, E, N, K, P or T, or wherein the amino acid sequence LRVYVPRSS (SEQ ID NO:9) comprises two or more of said substitutions in any combination;

f) IPDKEQAIS (SEQ ID NO:10), wherein amino acid residues at one or more of positions 1, 4, 6 and 7 are substituted with a different amino acid residue. wherein amino the acid residue at position 1 (I) is substituted with A, N, T, Q or H, or wherein the amino acid residue at position 4 (K) is substituted with T, or wherein the amino acid residue at position 6 (Q) is substituted with D, or wherein the amino acid residue at position 7 (A) is substituted with D, or wherein the amino acid sequence IPDKEQAIS (SEQ ID NO:10) comprises two or more of said substitutions in any combination;

g) ISFSTRGTQNWTVER (SEQ ID NO:131), wherein amino acid residues at one or more of positions 1, 6, 9, 10 and 12 are substituted with a different amino acid residues wherein amino the acid residue at position 1 (I) is substituted with A, N, T, Q or H, or wherein the amino acid residue at position 6 (R) is substituted with Q, or wherein the amino acid residue at position 9 (Q) is substituted with N or T, or wherein amino the acid residue at position 10 (N) is substituted with K or R, or wherein the amino acid residue at position 12 (T) is substituted with K or R, or wherein the amino acid sequence ISFSTRGTQNWTVER (SEQ ID NO: 131) comprises two or more of said substitutions in any combination; and h) IVFGGVRARSQDLDAI (SEQ ID NO:132), wherein amino the acid residue at position 1 (I) is substituted with A or N, or wherein the amino acid residue at position 6 (V) is substituted with D, M, or N, wherein amino the acid residue at position 11 (Q) is substituted with K or R, or wherein the amino acid residue at position 14 (D) is substituted with K or R, or wherein the amino acid sequence IVFGGVRARSQDLDAI (SEQ ID NO:132) comprises two or more of said substitutions in any combination.

E6. An isolated polypeptide having *Pseudomonas* exotoxin A biological activity, wherein said polypeptide comprises an epitope selected from the group consisting of:

a) I at position 141 is a different amino acid;
b) R at position 146 is a different amino acid;
c) Q at position 149 is a different amino acid;
d) N at position 150 is a different amino acid;
e) T at position 152 is a different amino acid;
f) I at position 184 is a different amino acid;
g) V at position 189 is a different amino acid;
h) Q at position 194 is a different amino acid;
i) D at position 197 is a different amino acid;
j) L at position 233 is a different amino acid;
k) R at position 234 is a different amino acid;
l) S at position 241 is a different amino acid;
m) I at position 321 is a different amino acid;
n) K at position 324 is a different amino acid;
o) Q at position 326 is a different amino acid;
p) A at position 327 is a different amino acid;
q) any combination of one or more of a) through p), wherein the amino acid numbering corresponds to SEQ ID NO: 1.

E7. An isolated polypeptide comprising an amino acid sequence identical to SEQ ID NO:1, except for one or more amino acid substitutions selected from the group consisting of:

a) I at position 141 is substituted with a conservative amino acid substitution;
b) R at position 146 is substituted with a conservative amino acid substitution;
c) Q at position 149 is substituted with a conservative amino acid substitution;
d) N at position 150 is substituted with a conservative amino acid substitution;
e) T at position 152 is substituted with a conservative amino acid substitution;
f) I at position 184 is substituted with a conservative amino acid substitution;
g) V at position 189 is substituted with a conservative amino acid substitution;
h) Q at position 194 is substituted with a conservative amino acid substitution d;
i) D at position 197 is substituted with a conservative amino acid substitution;
j) L at position 233 is substituted with a conservative amino acid substitution;
k) R at position 234 is substituted with a conservative amino acid substitution;
l) S at position 241 is substituted with a conservative amino acid substitution;
m) I at position 321 is substituted with a conservative amino acid substitution;
n) K at position 324 is substituted with a conservative amino acid substitution;
o) Q at position 326 is substituted with a conservative amino acid substitution;
p) A at position 327 is substituted with a conservative amino acid substitution;
q) any combination of one or more of a) through p), wherein the amino acid numbering corresponds to SEQ ID NO: 1.

E8. The isolated polypeptide of embodiment E7, wherein said conservative amino acid substitution is one or more substitutions selected from the group consisting of:

a) A is substituted with any one of G, I, L, S, T or V;
b) D is substituted with E;
c) I is substituted with any one of L, M or V;
d) K is substituted with any one of H or R;
e) L is substituted with any one of A, G, I, M or V;
f) N is substituted with any one of S, T or Q;
g) Q is substituted with any one of S, T or N;
h) R is substituted with any one of K or H;
i) S is substituted with any one of A, G, N, T or Q;
j) T is substituted with any one of A, G, N, Q or S; and
k) V is substituted with any one of A, G, I, L or M.

E9. An isolated polypeptide comprising an amino acid sequence identical to SEQ ID NO:1, except for one or more amino acid substitutions selected from the group consisting of:

a) I at position 141 is A;
b) I at position 141 is N;
c) I at position 141 is T;
d) I at position 141 is Q;
e) I at position 141 is H;
f) R at position 146 is Q;
g) Q at position 149 is N;
h) Q at position 149 is T;
i) N at position 150 is R;
j) N at position 150 is K;
k) T at position 152 is R;
l) T at position 152 is K;
m) I at position 184 is A;
n) I at position 184 is N;
o) V at position 189 is D;
p) V at position 189 is M;
q) V at position 189 is N;
r) Q at position 194 is R;
s) Q at position 194 is K;
t) D at position 197 is R;
u) D at position 197 is K;
v) L at position 233 is A;
w) R at position 234 is D;
x) R at position 234 is S;
y) R at position 234 is A;
z) S at position 241 is D;
ab) S at position 241 is E;
ac) S at position 241 is N;
ad) S at position 241 is K;
ae) S at position 241 is P;
af) S at position 241 is T;
ag) I at position 321 is A;

-continued

| |
|---|
| ah) I at position 321 is N; |
| ai) I at position 321 is T; |
| ak) I at position 321 is Q; |
| al) I at position 321 is H; |
| am) K at position 324 is T; |
| an) Q at position 326 is D; |
| ao) A at position 327 is D; |
| ap) any combination of one or more of a) through ao), |

wherein the amino acid numbering corresponds to SEQ ID NO: 1.

E10. The polypeptide in any one of embodiments E1 to E9, comprising a number of amino acid substitutions selected from the group consisting of:

| |
|---|
| a) 1 amino acid substitution; |
| b) 2 amino acid substitutions; |
| c) 3 amino acid substitutions; |
| d) 4 amino acid substitutions; |
| e) 5 amino acid substitutions; |
| f) 6 amino acid substitutions; |
| g) 7 amino acid substitutions; |
| h) 8 amino acid substitutions; |
| i) 9 amino acid substitutions; |
| j) 10 amino acid substitutions; |
| k) 11 amino acid substitutions; |
| l) 12 amino acid substitutions; |
| m) 13 amino acid substitutions; |
| n) 14 amino acid substitutions; |
| o) 15 amino acid substitutions; and |
| p) 16 amino acid substitutions. |

E11. The polypeptide of embodiment E9, comprising amino acid substitutions present at each of amino acid positions 141, 146, 149, 150, 152, 184, 189, 194, 197, 233, 234, 241, 321, 324, 326 and 327.

E12. The polypeptide of any one of embodiments E1 to E11, wherein said polypeptide comprises the amino acid sequence in SEQ ID NO:1, except for amino acid substitutions indicated in embodiments E1 to E11.

E13. The polypeptide in any one of embodiments E1 to E11, wherein said polypeptide is a variant or fragment of a *Pseudomonas* exotoxin A polypeptide.

E14. The polypeptide of embodiment E13, wherein said variant or fragment comprises a number of epitopes selected from the group consisting of:

a) at least one epitope;
b) at least two epitopes;
c) at least three epitopes;
d) at least four epitopes;
e) at least five epitopes; and
f) at least six epitopes.

E15. The polypeptide of embodiment E14, wherein said polypeptide comprises a contiguous number of amino acids selected from the group consisting of:

a) at least 20 contiguous amino acids;
b) at least 30 contiguous amino acids;
c) at least 40 contiguous amino acids;
d) at least 50 contiguous amino acids;
e) at least 60 contiguous amino acids;
f) at least 70 contiguous amino acids.
g) at least 80 contiguous amino acids;
h) at least 90 contiguous amino acids;
i) at least 100 contiguous amino acids;
j) at least 125 contiguous amino acids;
k) at least 150 contiguous amino acids;
l) at least 175 contiguous amino acids.
m) at least 200 contiguous amino acids;
n) at least 225 contiguous amino acids;
o) at least 250 contiguous amino acids;
p) at least 275 contiguous amino acids;
q) at least 300 contiguous amino acids;
r) at least 325 contiguous amino acids; and
s) at least 350 contiguous amino acids.

E16. An isolated polypeptide comprising a *Pseudomonas* exotoxin A (PE-A) cytotoxic domain (Domain III), wherein the cytotoxic domain comprises one or more amino acid substitutions which prevent or reduce host immunogenic responses compared to the same polypeptide without said one or more amino acid substitutions.

E17. The polypeptide of embodiment E16, wherein said one or more amino acid substitutions are introduced into a cytotoxic domain sequence selected from the group consisting of:

(a) amino acid residues Phe-134 to Lys-347 of SEQ ID NO: 1;
(b) amino acid residues Phe-134 to Lys-347 of SEQ ID NO:4;
(c) amino acid residues Phe-400 to Lys-613 of SEQ ID NO: 133; and
(d) amino acid residues Phe-400 to Lys-613 of SEQ ID NO: 134.

E18. The polypeptide of embodiment E17, wherein the last five amino acids in said cytotoxic domain are replaced with an amino acid sequence selected from the group consisting of:

```
                              (SEQ ID NO: 136)
(i) Arg-Glu-Asp-Leu;
and
                              (SEQ ID NO: 137)
(ii) Lys-Asp-Glu-Leu.
```

E19. The polypeptide in any one of embodiments E16 to E18, wherein said polypeptide further comprises one or more PE-A domains selected from the group consisting of:

(a) a cytosolic translocation domain (Domain II);
(b) a carboxy-terminal portion of Domain IB;
(c) an amino-terminal portion of Domain IB; and
(d) a complete Domain IB.

wherein one or more of said domains has been modified with amino acid substitutions, as described herein, to reduce or eliminate immunogenicity.

E20. The polypeptide of embodiment E19, wherein said cytosolic translocation domain (Domain II) comprises an amino acid sequence selected from the group consisting of:

(a) amino acids Gly-3 to Ser-114 of SEQ ID NO:1; and
(b) amino acids Gly-3 to Asn-114 of SEQ ID NO:4.

E21. The polypeptide of embodiment E19, wherein said carboxy-terminal portion of Domain IB comprises the amino acid sequence of Gly-115 to Glu-133 of SEQ ID NO: 1 or wherein said amino-terminal portion of Domain IB comprises the amino acid sequence of Ala-365 to Ala-380 of SEQ ID NO:133.

E22. The polypeptide of embodiment E19, wherein said complete Domain IB comprises the amino acid sequence of Ala-365 to Glu-399 of SEQ ID NO: 133.

E23. The polypeptide in any one of embodiments E16 to E22, wherein said polypeptide is a variant or fragment of a *Pseudomonas* exotoxin A polypeptide.

E24. The polypeptide of any one of embodiments E1 to E23, wherein said polypeptide has one or more biological activities selected from the group consisting of:
  a) eukaryotic cell killing activity (cell cytotoxicity);
  b) inhibits translation elongation factor EF-2 biological activity;
  c) induces or catalyzes ADP-ribosylation of EF-2; and
  d) inhibits protein synthesis.

E25. The polypeptide of any one of embodiments E1 to E24, wherein said one or more amino acid substitutions prevent or reduce host immunogenic responses compared to the same polypeptide without the corresponding said one or more amino acid substitutions.

E26. The polypeptide of any one of embodiments E1 to E24, wherein said one or more amino acid substitutions prevent or reduce host immunogenic responses compared to a polypeptide comprising an amino acid sequence selected from the group consisting of:
  (a) SEQ ID NO: 1;
  (b) SEQ ID NO:4;
  (c) SEQ ID NO: 133; and
  (d) SEQ ID NO:134.

E27. The polypeptide of any one of embodiments E1 to E26, wherein said polypeptide is a fusion protein.

E28. The fusion protein of embodiment E27, wherein the amino-terminal end of said polypeptide in any one of embodiments E1 to E26 is fused to the carboxyl-terminal end of a different polypeptide.

E29. The fusion protein of embodiment E27, wherein the carboxyl-terminal end of said polypeptide in any one of embodiments E1 to E26 is fused to the amino-terminal end of a different polypeptide.

E30. The fusion protein in embodiment E28 or E29, wherein said different polypeptide comprises an antigen binding moiety.

E31. The fusion protein of embodiment E30, wherein said antigen binding moiety is an antibody or fragment thereof.

E32. The fusion protein of embodiment E31, wherein said antibody, or fragment thereof, is an antibody selected from the list in Table 1, or is a fragment thereof.

E33. The fusion protein of embodiment E31, wherein said antibody, or fragment thereof, specifically binds to a cancer-specific or tumor-specific antigen.

E34. The fusion protein of embodiment E33, wherein said cancer-specific or tumor-specific antigen is a breast cancer antigen.

E35. The fusion protein of embodiment E34, wherein said breast cancer antigen is HER2.

E36. The fusion protein of embodiment E31, wherein said antibody, or fragment thereof is selected from the group consisting of:
  a)

ERTUMAXOMAB (Rexomun);

b)

PERTUZUMAB (Omnitarg);

and c)

TRASTUZUMAB (Herceptin)

E37. The fusion protein of any one of embodiments E27 to E29, wherein said different polypeptide comprises a polypeptide selected from the group consisting of:
  a) Mesothelin;
  b) CD24;
  c) CD22;
  d) CD25;
  e) CD174;
  f) TPBG;
  g) CD56; and
  h) C-type lectin-like molecule-1.

E38. An isolated polynucleotide encoding the polypeptide or fusion protein in any one of embodiments E1 to E37.

E39. An expression vector comprising the polynucleotide of embodiment E38.

E40. A host cell comprising the expression vector of embodiment E39.

E41. A method of producing the polypeptide or fusion protein in any one of embodiments E1 to E37, wherein said method comprises:
  a) obtaining a host cell comprising a polynucleotide encoding said polypeptide or fusion protein;
  b) exposing said host cell to conditions wherein said polypeptide or fusion protein is produced.

E42. A method of producing the polypeptide or fusion protein in any one of embodiments E1 to E37, wherein said method comprises use of an expression system comprising:
  (A) a first polynucleotide encoding a first hybrid polypeptide comprising:
    (i) a first ligand binding domain; and
    (ii) a DNA-binding domain;
  (B) a second polynucleotide encoding a second hybrid polypeptide comprising:
    (i) a second ligand binding domain; and
    (ii) a transactivation domain;
  (C) a third polynucleotide encoding the polypeptide or fusion protein in any one of embodiments E1 to E37, wherein said third polynucleotide is operably associated with a response element capable of being bound by the DNA-binding domain of said first hybrid polypeptide;

wherein the first ligand binding domain and the second ligand binding domain are capable of ligand-induced dimerization, wherein expression of the polypeptide or fusion protein in any one of embodiments E1 to E37 is modulated by a ligand which induces dimerization of said first and said second ligand binding domains, wherein the polypeptide or fusion protein in any one of embodiments E1 to E37 is produced by allowing said ligand to contact said first and said second ligand binding domains.

E43. A single expression vector or two or more expression vectors comprising the first, second, and third polynucleotides of embodiment E42.

E44. The expression vector or expression vectors of embodiment E43, wherein one or more of the vectors is a viral expression vector.

E45. A host cell comprising the expression vector or expression vectors of embodiments E43 or E44.

E46. A method of treating a disease or disorder comprising administering to a subject in need thereof the polypeptide or fusion protein in any one of embodiments E1 to E37, the polynucleotide of embodiment E38, the vector of embodiment E39, the host cell of embodiment E40, or a polypeptide or fusion protein produced by the method of embodiment E41.

E47. A method of treating a disease or disorder comprising delivering to a subject in need thereof a polypeptide or fusion protein produced by the method of embodiment E42, wherein said method comprises administration of the ligand to said subject.

E48. The method of embodiment E47, wherein the polypeptide or fusion protein is delivered to the subject by first administering the first, second, and third polynucleotides.

E49. The method of embodiment E47, wherein the polypeptide or fusion protein is delivered to the subject by first administering the expression vector or expression vectors of embodiments E43 or E44.

E50. The method of embodiment E47, wherein said polypeptide or fusion protein is delivered to the subject by first administering the host cell of embodiment E45.

E51. A pharmaceutical composition comprising the polypeptide or fusion protein in any one of embodiments E1 to E37, comprising the polynucleotide of embodiment E38, comprising the expression vector or expression vectors in any one of embodiments E39, E43 or E44, or comprising the host cell of embodiments E40 or E45, and a pharmaceutically acceptable carrier, diluent or excipient.

E52. A medicament comprising the polypeptide or fusion protein in any one of embodiments E1 to E37, comprising the polynucleotide of embodiment E38, comprising the expression vector or expression vectors in any one of embodiments E39, E43 or E44, or comprising the host cell of embodiments E40 or E45.

E53. Use of the medicament of embodiment E52, wherein said use is for the treatment of a disease or disorder.

E54. Use of the medicament according to embodiment E53, wherein the disease or disorder is cancer.

E55. A polypeptide having at least one *Pseudomonas* exotoxin A (PE-A) biological activity, wherein said polypeptide comprises one or more amino acid substitutions compared to a wild-type PE-A polypeptide, wherein said one or more amino acid substitutions is a substitution of a different amino acid at one or more positions corresponding to amino acid residues in the polypeptide of SEQ ID NO:1, wherein said substitution positions are selected from the group consisting of:
- a) isoleucine (I) at position 141;
- b) arginine (R) at position 146;
- c) glycine (G) at position 147;
- d) glutamine (Q) at position 149;
- e) asparagine (N) at position 150;
- f) threonine (T) at position 152;
- g) valine (V) at position 189;
- h) arginine (R) at position 192;
- i) glutamine (Q) at position 194;
- j) aspartic acid (D) at position 197;
- k) serine (S) at position 241;
- l) isoleucine (I) at position 321; and
- m) glutamine (Q) at position 326.

E56. The polypeptide of embodiment E55, wherein said one or more amino acid substitutions is a conservative amino acid substitution.

E57. The polypeptide of embodiment E55, wherein said one or more amino acid substitutions is selected from the group consisting of:
- a) isoleucine (I) at position 141 is substituted with alanine (A), threonine (T), or histidine (H);
- b) arginine (R) at position 146 is substituted with glutamine (Q) or alanine (A);
- c) glycine (G) at position 147 is substituted with serine (S);
- d) glutamine (Q) at position 149 is substituted with threonine (T);
- e) asparagine (N) at position 150 is substituted with alanine (A);
- f) threonine (T) at position 152 is substituted with alanine (A) or arginine (R);
- g) valine (V) at 189 is substituted with alanine (A);
- h) arginine (R) at position 192 is substituted with alanine (A) or glutamine (Q);
- i) glutamine (Q) at position 194 is substituted with arginine (R);
- j) aspartic acid (D) at position 197 is substituted with lysine (K);
- k) serine (S) at position 241 is substituted with threonine (T), asparagine (N), lysine (K), or proline (P);
- l) isoleucine (I) at position 321 is substituted with alanine (A), asparagine (N), histidine (H), threonine (T), or glutamine (Q); and
- m) glutamine (Q) at position 326 is substituted with glutamic acid (E).

E58. The polypeptide of embodiment E55, wherein said polypeptide comprises a substitution for isoleucine (I) at position 141, a substitution for threonine (T) at position 152, a substitution for arginine (R) at position 192, a substitution for aspartic acid (D) at position 197, a substitution for serine (S) at position 241, and a substitution for glutamine (Q) at position 326.

E59. The polypeptide of embodiment E55, wherein said polypeptide comprises a substitution of threonine (T) or alanine (A) for isoleucine (I) at position 141, a substitution alanine (A) or arginine (R) for threonine (T) at position 152, a substitution of alanine (A) for arginine (R) at position 192, a substitution of lysine (K) for aspartic acid (D) at position 197, a substitution of threonine (T) for serine (S) at position 241, and a substitution of glutamic acid (E) for glutamine (Q) at position 326.

E60. The polypeptide of embodiment E55, wherein said polypeptide comprises a substitution of threonine (T) for isoleucine (I) at position 141, a substitution alanine (A) for threonine (T) at position 152, a substitution of alanine (A) for arginine (R) at position 192, a substitution of lysine (K) for aspartic acid (D) at position 197, a substitution of threonine (T) for serine (S) at position 241, and a substitution of glutamic acid (E) for glutamine (Q) at position 326.

E61. The polypeptide of embodiment E55, wherein said polypeptide comprises a substitution of alanine (A) for isoleucine (I) at position 141, a substitution alanine (A) for threonine (T) at position 152, a substitution of alanine (A) for arginine (R) at position 192, a substitution of lysine (K) for aspartic acid (D) at position 197, a substitution of threonine (T) for serine (S) at position 241, and a substitution of glutamic acid (E) for glutamine (Q) at position 326.

E62. The polypeptide of embodiment E55, wherein said polypeptide comprises a substitution for isoleucine (I) at position 141, a substitution for threonine (T) at position 152, a substitution for aspartic acid (D) at position 197, a substitution for serine (S) at position 241, and a substitution for glutamine (Q) at position 326.

E63. The polypeptide of embodiment E55, wherein said polypeptide comprises a substitution for isoleucine (I) at position 141, a substitution for threonine (T) at position 152, a substitution for arginine (R) at position 192, a substitution for aspartic acid (D) at position 197, and a substitution for serine (S) at position 241.

E64. The isolated polypeptide of embodiment E55, wherein said polypeptide comprises a substitution of alanine (A) or threonine (T) for isoleucine (I) at position 141, a substitution of arginine (R) or alanine (A) for threonine (T) at position 152, a substitution of lysine (K) for aspartic acid (D) at position 197, a substitution of threonine (T) for serine (S) at position 241, and a substitution of glutamic acid (E) for glutamine (Q) at position 326.

E65. The isolated polypeptide of embodiment E55, wherein said polypeptide comprises a substitution of alanine (A) for isoleucine (I) at position 141, a substitution of arginine (R) for threonine (T) at position 152, a substitution of lysine (K) for aspartic acid (D) at position 197, a substitution of threonine (T) for serine (S) at position 241, and a substitution of glutamic acid (E) for glutamine (Q) at position 326.

E66. The polypeptide of embodiment E55, wherein said polypeptide comprises a substitution of alanine (A) for isoleucine (I) at position 141, a substitution of alanine (A) for threonine (T) at position 152, a substitution of lysine (K) for aspartic acid (D) at position 197, a substitution of threonine (T) for serine (S) at position 241, and a substitution of glutamic acid (E) for glutamine (Q) at position 326.

E67. The polypeptide of embodiment E55, wherein said polypeptide comprises a substitution of threonine (T) for isoleucine (I) at position 141, a substitution of alanine (A) for threonine (T) at position 152, a substitution of lysine (K) for aspartic acid (D) at position 197, a substitution of threonine (T) for serine (S) at position 241, and a substitution of glutamic acid (E) for glutamine (Q) at position 326.

E68. The polypeptide in any one of embodiments E55 to E67, wherein the at least one *Pseudomonas* exotoxin A (PE-A) biological activity comprises the ability to inhibit in vitro transcription/translation compared to a corresponding wild-type or non-substituted PE-A polypeptide, wherein said ability to inhibit in vitro transcription/translation is in an amount selected from the group consisting of:

(a) at least 5% inhibition;
(b) at least 10% inhibition;
(c) at least 15% inhibition;
(d) at least 20% inhibition;
(e) at least 25% inhibition;
(f) at least 30% inhibition;
(g) at least 40% inhibition;
(h) at least 50% inhibition;
(i) at least 60% inhibition;
(j) at least 70% inhibition;
(k) at least 80% inhibition;
(l) at least 90% inhibition;
(m) at least 100% inhibition;
(n) about 100% inhibition; and
(o) 100% inhibition.

E69. The polypeptide in any one of embodiments E55 to E68, comprising a number of amino acid substitutions selected from the group consisting of:

a) 1 amino acid substitution;
b) 2 amino acid substitutions;
c) 3 amino acid substitutions;
d) 4 amino acid substitutions;
e) 5 amino acid substitutions; and
f) 6 amino acid substitutions.

E70. The polypeptide in any one of embodiments E55 to E69, wherein said polypeptide comprises one or more amino acid substitutions which prevent or reduce host immunogenic responses compared to the same polypeptide without said one or more amino acid substitutions.

E71. The polypeptide of embodiment E70, wherein host immunogenic responses are prevented or reduced in a human host.

E72. The polypeptide in any one of embodiments E55 to E71, wherein the last five or six amino acids in said polypeptide comprise one or more amino acid sequences selected from the group consisting of:

(i)

```
Arg-Glu-Asp-Leu-Lys;
```

(ii)

```
Arg-Glu-Asp-Leu;
```

(iii)

```
Lys-Asp-Glu-Leu;
```

(iv)

```
Glu-Asp-Leu-Lys;
```

and (v) a dimer, trimer, pentamer, hexamer, septamer, or octamer of (i), (ii), or (iii), or any combination thereof.

E73. The polypeptide of any one of embodiments E55 to E72, wherein said polypeptide has one or more biological activities selected from the group consisting of:

a) eukaryotic cell killing activity (cell cytotoxicity);
b) inhibits translation elongation factor EF-2 biological activity;
c) induces or catalyzes ADP-ribosylation of EF-2; and
d) inhibits protein synthesis.

E74. The polypeptide of any one of embodiments E55 to E72, wherein said one or more amino acid substitutions prevent or reduce host immunogenic responses compared to the same polypeptide without the corresponding said one or more amino acid substitutions.

E75. A polypeptide comprising a biologically active fragment of the polypeptide in any one of embodiments E55 to E74.

E76. A polypeptide comprising a variant or derivative of the polypeptide in any one of embodiments E55 to E75, wherein said variant or derivative shares amino acid sequence identity with the polypeptide in any one of embodiments E55 to E75, wherein said shared amino acid sequence identity is selected from the group consisting of:

a) at least 80% identity;
b) at least 85% identity;
c) at least 90% identity;
d) at least 95% identity;
e) at least 97% identity;

f) at least 98% identity; and g) at least 99% identity.

E77. The polypeptide of any one of embodiments E55 to E76, wherein said one or more amino acid substitutions prevent or reduce host immunogenic responses compared to a polypeptide comprising an amino acid sequence selected from the group consisting of:

(a) SEQ ID NO:1;

(b) SEQ ID NO:4;

(c) SEQ ID NO: 133; and (d) SEQ ID NO:134.

E78. The polypeptide of any one of embodiments E55 to E77, wherein said polypeptide is a fusion protein.

E79. The fusion protein of embodiment E78, wherein the amino-terminal end of said polypeptide in any one of embodiments E55 to E78 is fused to the carboxyl-terminal end of a different polypeptide.

E80. The fusion protein of embodiment E78, wherein the carboxyl-terminal end of said polypeptide in any one of embodiments E55 to E78 is fused to the amino-terminal end of a different polypeptide.

E81. The fusion protein in embodiment E79 or E80, wherein said different polypeptide comprises an antigen binding moiety.

E82. The fusion protein of embodiment E81, wherein said antigen binding moiety is an antibody or fragment thereof.

E83. The fusion protein of any one of embodiments E78 to E82, wherein said antibody, or fragment thereof, is an antibody selected from the list in Table 1, or is a fragment thereof.

E84. The fusion protein of embodiment E82, wherein said antibody, or fragment thereof, specifically binds to a cancer-specific or tumor-specific antigen.

E85. The fusion protein of embodiment E84, wherein said cancer-specific or tumor-specific antigen is a breast cancer antigen.

E86. The fusion protein of embodiment E85, wherein said breast cancer antigen is HER2.

E87. The fusion protein of embodiment E82, wherein said antibody, or fragment thereof is selected from the group consisting of:

a)

ERTUMAXOMAB (Rexomun);

b)

PERTUZUMAB (Omnitarg);

and c)

TRASTUZUMAB (Herceptin)

E88. The fusion protein of any one of embodiments E78 to E80, wherein said different polypeptide comprises a polypeptide selected from the group consisting of:

a) Mesothelin;

b) CD24;

c) CD22;

d) CD25;

e) CD174;

f) TPBG;

g) CD56; and h) C-type lectin-like molecule-1.

E89. A polynucleotide encoding the polypeptide or fusion protein in any one of embodiments E55 to E88.

E90. An expression vector comprising the polynucleotide of embodiment E89.

E91. A host cell comprising the expression vector of embodiment E90.

E92. A method of producing the polypeptide or fusion protein in any one of embodiments E55 to E88, wherein said method comprises:

a) obtaining a host cell comprising a polynucleotide encoding said polypeptide or fusion protein;

b) exposing said host cell to conditions wherein said polypeptide or fusion protein is produced.

E93. A method of producing the polypeptide or fusion protein in any one of embodiments E55 to E88, wherein said method comprises use of an expression system comprising:

(A) a first polynucleotide encoding a first hybrid polypeptide comprising:

(i) a first ligand binding domain; and (ii) a DNA-binding domain;

(B) a second polynucleotide encoding a second hybrid polypeptide comprising:

(i) a second ligand binding domain; and (ii) a transactivation domain;

(C) a third polynucleotide encoding the polypeptide or fusion protein in any one of embodiments E55 to E88, wherein said third polynucleotide is operably associated with a response element capable of being bound by the DNA-binding domain of said first hybrid polypeptide;

wherein the first ligand binding domain and the second ligand binding domain are capable of ligand-induced dimerization, wherein expression of the polypeptide or fusion protein in any one of embodiments E55 to E88 is modulated by a ligand which induces dimerization of said first and said second ligand binding domains, wherein the polypeptide or fusion protein in any one of embodiments E55 to E88 is produced by allowing said ligand to contact said first and said second ligand binding domains.

E94. A single expression vector or two or more expression vectors comprising the first, second, and third polynucleotides of embodiment E93.

E95. The expression vector or expression vectors of embodiment E94, wherein one or more of the vectors is a viral expression vector.

E96. A host cell comprising the expression vector or expression vectors of embodiments E94 or E95.

E97. A method of treating a disease or disorder comprising administering to a subject in need thereof the polypeptide or fusion protein in any one of embodiments E55 to E88, the polynucleotide of embodiment E89, the expression vector or expression vectors in any one of embodiments E90, E94 or E95, the host cell of embodiments E91 or E96, or a polypeptide or fusion protein produced by the method of embodiment E92.

E98. A method of treating a disease or disorder comprising delivering to a subject in need thereof a polypeptide or fusion protein produced by the method of embodiment E93, wherein said method comprises administration of the ligand to said subject.

E99. The method of embodiment E44, wherein the polypeptide or fusion protein is delivered to the subject by first administering the first, second, and third polynucleotides.

E100. The method of embodiment E98, wherein the polypeptide or fusion protein is delivered to the subject by first administering the expression vector or expression vectors of embodiments E94 or E95.

E101. The method of embodiment E98, wherein said polypeptide or fusion protein is delivered to the subject by first administering the host cell of embodiments E91 or E96.

E102. A pharmaceutical composition comprising the polypeptide or fusion protein in any one of embodiments E55 to E88, comprising the polynucleotide of embodiment E89, comprising the expression vector or expression vectors in any one of embodiments E90, E94 or E95, or comprising the host cell of embodiments E91 or E96, and a pharmaceutically acceptable carrier, diluent or excipient.

E103. A medicament comprising the polypeptide or fusion protein in any one of embodiments E55 to E88, comprising the polynucleotide of embodiment E89, comprising the expression vector or expression vectors in any one of embodiments E90, E94 or E95, or comprising the host cell of embodiments E91 or E96.

E104. Use of the pharmaceutical composition of embodiment E102 or the medicament of embodiment E103, wherein said use is for the treatment of a disease or disorder.

E105. Use of the pharmaceutical composition or the medicament according to embodiment E104, wherein the disease or disorder is cancer.

E106. An *Pseudomonas* exotoxin A (PE-A) polypeptide, wherein said polypeptide comprises a mutation at a position corresponding to amino acid position E184 in SEQ ID NO:1 (or position E196 in SEQ ID NO:2) wherein an isoleucine at position E184 (or position 196 in SEQ ID NO:2) is substituted with a different amino acid.

E107. The polypeptide of embodiment E106, wherein said polypeptide does not have PE-A biological activity.

E108. A method for assaying the immunogenicity of a mutated form of *Pseudomonas* exotoxin A (PE-A), wherein said method comprises:

(a) contacting immune cells with a mutated form of PE-A; and (b) assaying immune cell stimulation, wherein said mutated form of PE-A comprises a mutation at a position corresponding to amino acid position E184 in SEQ ID NO:1 (or position 196 in SEQ ID NO:2) wherein an isoleucine at position E184 (or position 196 in SEQ ID NO:2) is substituted with a different amino acid, and wherein said mutated form of PE-A also comprises one or more additional amino acid substitutions compared to a wild-type form of PE-A.

E109. The method of embodiment E108, wherein said immune cells are human immune cells.

E110. The method of embodiment E109, wherein said immune cells are human T-cells, cells of a human T-cell lineage, human B-cells, or cells of a human B-cell lineage.

E111. The method of embodiment E47, wherein the ligand is a compound having Formula I, or a pharmaceutically acceptable salt thereof.

E112. The method of embodiment E47, wherein the ligand is a compound having Formula II, or a pharmaceutically acceptable salt thereof.

E113. The method of embodiment E47, wherein the ligand is a compound having Formula III, or a pharmaceutically acceptable salt thereof.

E114. The method of embodiment E47, wherein the ligand is a compound of Table 3, or a pharmaceutically acceptable salt thereof.

E115. The method of embodiment E47, wherein the ligand is a compound having Formula III, wherein:

A is:

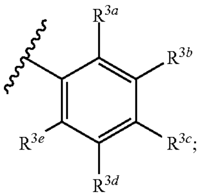

B is:

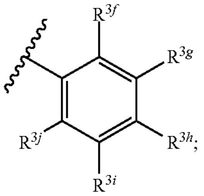

$R^{3a}$, $R^{3b}$, $R^{3c}$, $R^{3d}$, $R^{3e}$, $R^{3f}$, $R^{3g}$, $R^{3h}$, $R^{3i}$ and $R^{3j}$ are independently selected from hydrogen, halo, $(C_1\text{-}C_4)$alkyl, or $(C_1\text{-}C_4)$alkoxy;

$R^1$ is $(C_1\text{-}C_6)$alkyl, hydroxy$(C_1\text{-}C_4)$alkyl, or $(C_2\text{-}C_4)$alkenyl; and $R^2$ is optionally substituted $(C_1\text{-}C_6)$alkyl, or a pharmaceutically acceptable salt thereof.

E116. The method of embodiment E47, wherein the ligand is a compound selected from the group consisting of:

(R)-3,5-Dimethyl-benzoic acid N-(1-tert-butyl-butyl)-N'-(2-ethyl-3-methoxy-benzoyl)-hydrazide;

(R)-3,5-Dimethyl-benzoic acid N'-benzoyl-N-(1-tert-butyl-butyl)-hydrazide;

(R)-3,5-Dimethyl-benzoic acid N-(1-tert-butyl-butyl)-N'-(2-methyl-benzoyl)-hydrazide;

(R)-3,5-Dimethyl-benzoic acid N-(1-tert-butyl-butyl)-N'-(2-methoxy-benzoyl)-hydrazide;

(R)-3,5-Dimethyl-benzoic acid N-(1-tert-butyl-butyl)-N'-(2-fluoro-benzoyl)-hydrazide;

(R)-3,5-Dimethyl-benzoic acid N-(1-tert-butyl-butyl)-N'-(2-chloro-benzoyl)-hydrazide;

(R)-3,5-Dimethyl-benzoic acid N'-(2-bromo-benzoyl)-N-(1-tert-butyl-butyl)-hydrazide;

(R)-3,5-Dimethyl-benzoic acid N-(1-tert-butyl-butyl)-N'-(3-methyl-benzoyl)-hydrazide;

(R)-3,5-Dimethyl-benzoic acid N-(1-tert-butyl-butyl)-N'-(3-methoxy-benzoyl)-hydrazide;

(R)-3,5-Dimethyl-benzoic acid N-(1-tert-butyl-butyl)-N'-(3-chloro-benzoyl)-hydrazide;

(R)-3,5-Dimethyl-benzoic acid N-(1-tert-butyl-butyl)-N'-(4-methyl-benzoyl)-hydrazide;

(R)-3,5-Dimethyl-benzoic acid N-(1-tert-butyl-butyl)-N'-(4-ethyl-benzoyl)-hydrazide;

(R)-3,5-Dimethyl-benzoic acid N-(1-tert-butyl-butyl)-N'-(4-methoxy-benzoyl)-hydrazide;

(R)-3,5-Dimethyl-benzoic acid N-(1-tert-butyl-butyl)-N'-(4-chloro-benzoyl)-hydrazide;

(R)-3,5-Dimethyl-benzoic acid N-(1-tert-butyl-butyl)-N'-(2,6-difluoro-benzoyl)-hydrazide;

(R)-3,5-Dimethyl-benzoic acid N-(1-tert-butyl-butyl)-N'-(2,6-dichloro-benzoyl)-hydrazide;

(R)-3,5-Dimethyl-benzoic acid N-(1-tert-butyl-butyl)-N'-(3,4-dimethoxy-benzoyl)-hydrazide;

(R)-3,5-Dimethyl-benzoic acid N-(1-tert-butyl-butyl)-N'-(3,5-difluoro-benzoyl)-hydrazide;

(R)-3,5-Dimethyl-benzoic acid N-(1-tert-butyl-butyl)-N'-(3,5-dimethoxy-4-methyl-benzoyl)-hydrazide;

(R)-3,5-Dimethyl-benzoic acid N-(1-tert-butyl-butyl)-N'-(4-methyl-benzo[1,3]dioxole-5-carbonyl)-hydrazide;

(R)-3,5-Dimethyl-benzoic acid N-(1-tert-butyl-butyl)-N'-(5-methyl-2,3-dihydro-benzo[1,4]dioxine-6-carbonyl)-hydrazide;

(R)-3,5-Dimethyl-benzoic acid N-(1-tert-butyl-butyl)-N'-(5-ethyl-2,3-dihydro-benzo[1,4]dioxine-6-carbonyl)-hydrazide;

(R)-3,5-Dimethyl-benzoic acid N-(1-tert-butyl-butyl)-N'-(naphthalene-1-carbonyl)-hydrazide;

(R)-3,5-Dimethyl-benzoic acid N-(1-tert-butyl-butyl)-N'-(naphthalene-2-carbonyl)-hydrazide;

(R)-3,5-Dimethyl-benzoic acid N-(1-tert-butyl-butyl)-N'-(thiophene-2-carbonyl)-hydrazide;

(R)-3,5-Dimethyl-benzoic acid N-(1-tert-butyl-butyl)-N'-(2,5-dimethyl-furan-3-carbonyl)-hydrazide;

(R)-3,5-Dimethyl-benzoic acid N-(1-tert-butyl-butyl)-N'-(2-chloro-pyridine-3-carbonyl)-hydrazide;

(R)-3,5-Dimethyl-benzoic acid N-(1-tert-butyl-butyl)-N'-(6-chloro-pyridine-3-carbonyl)-hydrazide;

(R)-3,5-Dimethyl-benzoic acid N-(1-tert-butyl-butyl)-N'-(3-methoxy-2-methyl-benzoyl)-hydrazide;

(R)-3,5-Dimethoxy-4-methyl-benzoic acid N-(1-tert-butyl-butyl)-N'-(3-methoxy-2-methyl-benzoyl)-hydrazide; and (R)-3,5-Dimethyl-benzoic acid N'-(4-ethyl-benzoyl)-N-(1-phenethyl-but-3-enyl)-hydrazide, or a pharmaceutically acceptable salt thereof.

EXAMPLES

Example 1

T Cell Epitope Mapping of PE

Peptides spanning the sequence of an approximately 38 kD form of *Pseudomonas* exotoxin A protein ("PE38") were analyzed for the presence of immunogenic CD4+ T cell epitopes using EPISCREEN™ T cell epitope mapping analysis (Antitope Ltd, Cambridge, UK).

EPISCREEN™ is a proprietary technology commercially available through Antitope Ltd, Cambridge, UK, to map T cell epitopes within a protein sequence to determine potential for immunogenicity (based on the number and potency of T cell epitopes within a sequence). EPISCREEN™ T cell epitope mapping typically uses CD8+ T cell depleted PBMCs from a minimum of 50 HLA-typed donors (selected to represent the human population of interest). Typically, 15mer peptides with 12 amino acid overlaps spanning a protein sequence are analyzed in a large number of replicate cultures for in vitro CD4+ T cell stimulation by 3H TdR incorporation. CD4+ T cell stimulation is often detected in two or three adjacent and overlapping peptides since the core 9mer that binds the MHC class II binding groove will be present in more than one peptide sequence. Following identification of peptides that stimulate CD4+ T cells in vitro, in silico technology can be used to design epitope-depleted (deimmunized) variants by determining the precise location of core 9mer sequences and the location of key MHC class II anchor residues.

A total of 120 overlapping 15mer peptides spanning the entire PE38 sequence (SEQ ID NO:2), including 4 peptides covering a null mutation and 4 peptides spanning an N-terminal linker sequence (SEQ ID NO:3) were tested against a cohort of 52 healthy donors. CD4+ T cell responses against individual peptides were measured using proliferation assays (3H-thymidine incorporation). The proliferation assay data was used to compile a T cell epitope map of the PE38 sequence and six T cell epitopes were identified.

EPISCREEN™ Donor Selection

Peripheral blood mononuclear cells (PBMC) were isolated from healthy community donor buffy coats (from blood drawn within 24 hours) obtained from the UK National Blood Transfusion Service (Addenbrooke's Hospital, Cambridge, UK) and according to approval granted by Addenbrooke's Hospital Local Research Ethics Committee. PBMC were isolated from buffy coats by LYMPHOPREP™ (Axis-Shield UK, Dundee, Scotland) density centrifugation. (LYMPHOPREP™ is a ready-made, sterile and endotoxin tested solution for the isolation of human mononuclear cells from blood. See, Axis-Shield, package insert for LYMPHOPREP™ density gradient media No. 619. March 03. Div.—1114740.) CD8+ T cells were depleted using CD8+ ROSETTESEP™ (STEMCELL™ Technologies Inc, Manchester, UK) to remove CD8+ cells from the isolated mononuclear cells. See e.g., StemCell Technologies Inc., ROSETTESEP™ procedure for Human CD8+ T Cell Enrichment Cocktail (Catalog #15023/15063; Procedure version 1.3.0, "#28572 (May 2011)).

HLA allotypes of donors were characterized using the Biotest HLA SSP-PCR tissue-typing kit (Biotest, Solihull, UK, catalogue number 826215). T cell responses to a reproducibility control neo-antigen were also determined using Imject maricutlure keyhole limpet haemocyanin (KLH) (Pierce (Perbio Science UK, Ltd)), Cramlington, UK, catalogue number 77600) with the KLH diluted to a final concentration of 100 g/ml. PBMC were then frozen and stored in liquid nitrogen until required.

A cohort of 52 donors was selected to best represent the number and frequency of HLA-DR allotypes expressed in the world population. Analysis of the allotypes expressed in the cohort against those expressed in the world population revealed that coverage of >80% was achieved and that all major HLA-DR alleles (individual allotypes with a frequency >5% expressed in the world population) were well represented. Details of individual donor haplotypes and a comparison of the frequency of MHC class II haplotypes expressed in the world population and the sample population are shown in Table 7 and FIG. 2, respectively.

Table 7. Donor details and haplotypes. Donor responses (SI) to KLH are shown for two independent proliferation assays. Test 1 was performed using KLH on freshly isolated PBMC and IEX01 is the KLH re-test performed in the current study on PBMC recovered from liquid nitrogen storage as indicated above. Responses that did not produce the same result (i.e. positive including borderline SI>1.90 p<0.05 or negative) in both tests are highlighted in grey (i.e., donors 3, 7, 9, 33 and 44).

TABLE 7

Donor Haplotypes and Responses

| | | KLH | |
|---|---|---|---|
| Donor | Haplotype | Test 1 | IEX01 |
| 1 | DRB1*15, DRB1*16; DRB5* | **18.10** | **1.97** |
| 2 | DRB1*03, DRB1*07; DRB3*; DRB4* | **2.49** | **5.74** |
| 3 | DRB1*11, DRB1*13; DRB3*; DRB4* | 0.81 | **4.00** |
| 4 | DRB1*03; DRB3* | 1.73 | 1.78 |
| 5 | DRB1*01, DRB1*13; DRB3*; DRB4* | 0.99 | 1.05 |
| 6 | DRB1*03, DRB1*14; DRB3* | **2.91** | **2.01** |
| 7 | DRB1*13, DRB1*14; DRB3*; DRB4* | **3.13** | 1.20 |
| 8 | DRB1*01, DRB1*07; DRB4* | **2.49** | **5.74** |
| 9 | DRB1*03, DRB1*07; DRB3*; DRB4* | 0.81 | **4.00** |
| 10 | DRB1*03, DRB1*15; DRB5 | **6.16** | **6.16** |
| 11 | DRB1*01, DRB1*13; DRB3* | **7.15** | **17.34** |
| 12 | DRB1*13, DRB4*; DRB5* | **7.98** | **2.76** |
| 13 | DRB1*13, DRB1*14; DRB4* | 1.00 | 1.81 |
| 14 | DRB1*03, DRB1*13; DRB3* | **2.28** | **2.70** |
| 15 | DRB1*04, DRB1*11; DRB3*; DRB4* | **8.96** | **1.91** |
| 16 | DRB1*04, DRB1*14; DRB3*; DRB4* | **5.85** | **4.01** |
| 17 | DRB1*13, DRB1*15; DRB3*; DRB5* | **19.16** | **2.69** |
| 18 | DRB1*11, DRB1*13; DRB3* | **10.32** | **6.48** |
| 19 | DRB1*04, DRB1*15; DRB4* | **2.70** | **3.39** |
| 20 | DRB1*04, DRB1*07; DRB4* | 0.51 | 1.27 |
| 21 | DRB1*01, DRB1*04; DRB4* | 1.71 | 1.05 |
| 22 | DRB1*03; DRB3* | 1.05 | 1.59 |
| 23 | DRB1*04, DRB1*15; DRB4*; DRB5* | **2.83** | **2.34** |
| 24 | DRB1*01 | 1.63 | 1.09 |
| 25 | DRB1*04, DRB1*15; DRB4*; DRB5* | 1.12 | 1.44 |
| 26 | DRB1*03, DRB1*07; DRB3*; DRB4* | 1.18 | 0.84 |
| 27 | DRB1*11, DRB1*13; DRB3* | **8.80** | **14.30** |
| 28 | DRB1*01, DRB1*07; DRB4* | **3.68** | **4.53** |
| 29 | DRB1*12, DRB1*13; DRB3* | **3.68** | **2.40** |
| 30 | DRB1*11; DRB3* | **7.68** | **2.71** |
| 31 | DRB1*03, DRB1*11; DRB3* | **3.04** | **4.16** |
| 32 | DRB1*13; DRB3* | **1.96** | **2.22** |
| 33 | DRB1*15; DRB4* | 1.31 | **3.13** |
| 34 | DRB1*03, DRB1*04; DRB3*; DRB4* | 0.97 | 1.35 |
| 35 | DRB1*12; DRB3*; DRB4* | **3.51** | **2.55** |
| 36 | DRB1*07; DRB3*; DRB4* | **6.63** | **8.90** |
| 37 | DRB1*04, DRB1*04; DRB4* | **44.94** | **6.28** |
| 38 | DRB1*01, DRB1*15; DRB3*; DRB4* | 1.36 | 1.30 |
| 39 | DRB1*07, DRB1*13; DRB3*; DRB4* | **12.62** | **2.29** |
| 40 | DRB1*03, DRB1*04; DRB3*; DRB4* | 1.39 | 1.37 |
| 41 | DRB1*07, DRB1*08; DRB4* | **3.40** | **3.47** |
| 42 | DRB1*07, DRB1*13; DRB3*; DRB4* | **40.32** | **7.36** |
| 43 | DRB1*13, DRB1*15; DRB3*; DRB5* | **3.56** | **3.21** |
| 44 | DRB1*11, DRB1*14; DRB3* | 1.15 | **2.86** |
| 45 | DRB1*03, DRB1*13; DRB3* | **8.78** | **8.72** |
| 46 | DRB1*03, DRB1*13; DRB3* | **11.47** | **3.11** |
| 47 | DRB1*03, DRB1*04; DRB3*; DRB4* | **6.27** | **2.03** |
| 48 | DRB1*04, DRB1*15; DRB5* | **10.29** | **3.77** |
| 49 | DRB1*07, DRB1*15; DRB4*; DRB5* | **2.59** | **2.32** |
| 50 | DRB1*04, DRB1*15; DRB4*; DRB5* | **2.49** | **2.42** |
| 51 | DRB1*11; DRB3*; DRB4* | **8.30** | **2.09** |
| 52 | DRB1*03, DRB1*13; DRB3* | **3.99** | **6.22** |

EPISCREEN® Analysis: Proliferation Assay

PBMC from each donor were thawed, counted and viability was assessed. Cells were revived in room temperature AIM V® culture medium (Invitrogen, Paisley, UK) before adjusting the cell density to 2-3×10$^{6}$ PBMC/ml (proliferation cell stock). Peptides were synthesized on a 1-3 mg scale with free N-terminal amine and C-terminal carboxylic acid. Peptides were dissolved in DMSO to a concentration of 10 mM and peptide culture stocks prepared by diluting into AIM V® culture medium to a final concentration of 5 μM in the well. For each peptide and each donor, sextuplicate cultures were established in a flat bottomed 96 well plate. Both positive and negative control cultures were also tested in sextuplicate. For each donor, three control antigen/peptides (KLH protein and peptides derived from Influenza A and Epstein Barr viruses) were also included.

Cultures were incubated for a total of 6 days before adding 0.75 μCi 3[H]-thymidine (PERKIN ELMER®, Beaconsfield, UK) to each well. Cultures were incubated for a further 18 hours before harvesting onto filter mats using a TOMTEC MACH® III cell harvester (TOMTEC®, Hamden, Conn., USA). Counts per minute (cpm) for each well were determined by Meltilex™ (PERKIN ELMER®) scintillation counting on a Microplate Beta Counter (PERKIN ELMER®) in paralux, low background counting mode.

EPISCREEN™ Data Analysis

For proliferation assays, an empirical threshold of a stimulation index (SI) equal to or greater than 2 (SI≥2.00) has been previously established whereby samples inducing proliferative responses above this threshold are deemed positive (where included, borderline SI≥1.90 are highlighted). Extensive assay development and previous studies have shown that this is the minimum signal to noise threshold allowing maximum sensitivity without detecting large numbers of false positive responses. Positive responses are defined by the following statistical and empirical thresholds:

1. Significance (p<0.05) of the response by comparing cpm of test wells against medium control wells using unpaired two sample Student's t-test.
2. Stimulation index greater than 2.00 (SI≥2.00), where SI=mean cpm of test wells/mean cpm medium control wells. Data presented in this way is indicated as SI≥2.00, p<0.05.

In addition, intra-assay variation was assessed by calculating the coefficient of variance and standard deviation (SD) of the raw data from replicate cultures.

Proliferation assays were set up in sextuplicate cultures ("non-adjusted data"). To ensure that intra-assay variability was low, the data was also analyzed after removing the maximum and minimum cpm values ("adjusted data") and the SI of donor responses was compared using both data sets.

T cell epitopes were identified by calculating the average frequency of positive responses (defined above) to all peptides in the study plus standard deviation (SD) to give a background response threshold. Any peptide that induced a frequency of positive proliferation responses above this threshold in both the adjusted and non-adjusted data was considered to contain an immunogenic T cell epitope (and, thus, potentially represents an immunogenicity inducing epitope which could give rise to immunogenic responses in vivo).

In Silico Analysis of Peptides

The sequences of peptides that were positive in the proliferation assay were analyzed using Antitope's predictive iTOPE™ software (Perry et al. 2008). This software predicts favorable interactions between amino acid side chains of the peptide and specific binding pockets within the MHC class II binding groove. Analysis of the peptide sequences using iTOPE™ was performed with overlapping 9mers spanning the peptides which were tested against each of the 34 MHC class II alleles. Each 9mer was scored based on the potential 'fit' and interactions with the MHC class II molecules. 9mers that produced a high mean binding score were identified and, from the T cell proliferation data, 9mers which were considered as critical to T cell responses ("core 9mers") were highlighted. iTOPE™ analysis was then repeated with a range of amino acid changes in the core 9mers in order to determine preferred amino acid substitutions for use in deimmunization.

Results and Discussion

Figure 3A:
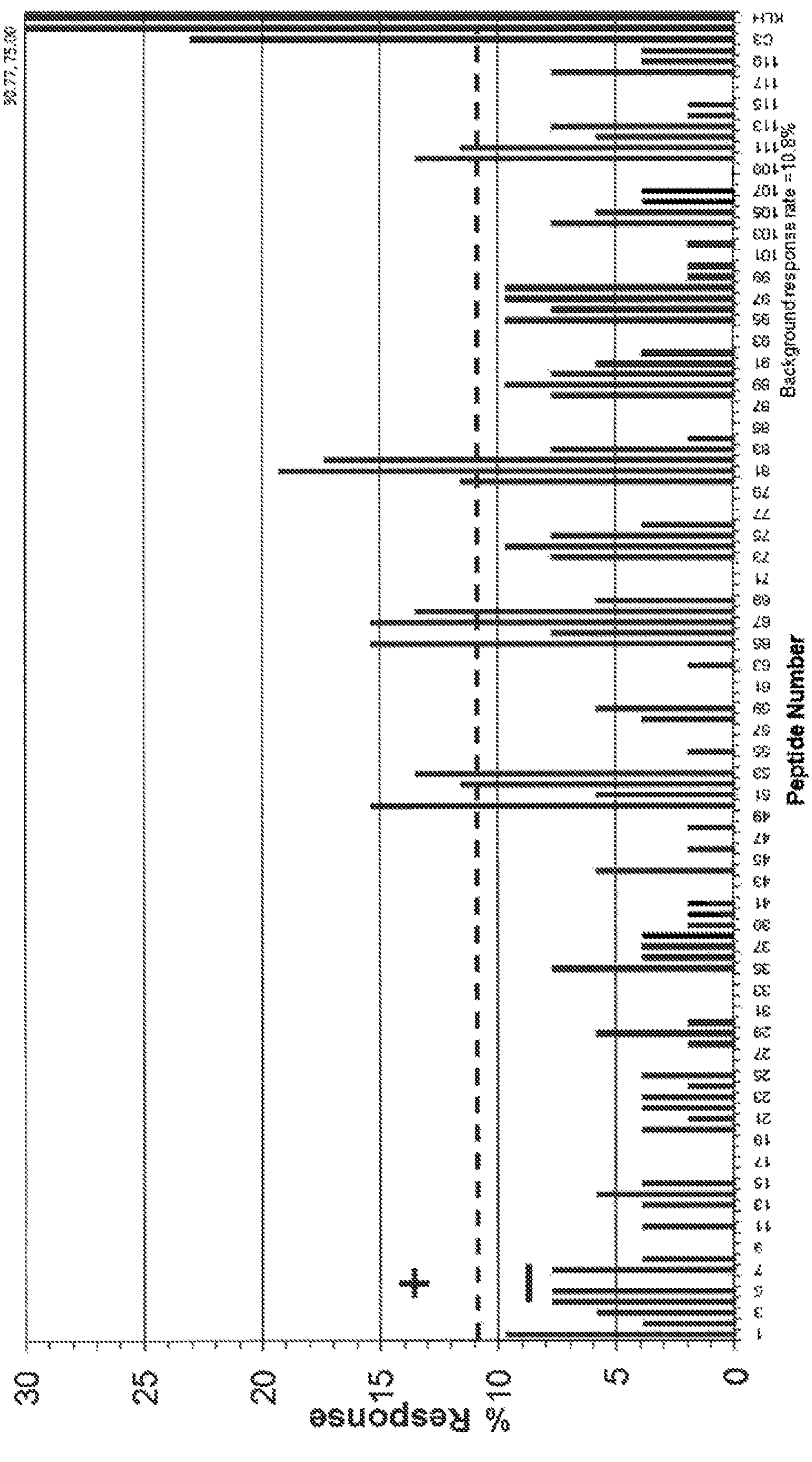
FIGS. 3A & 3B. CD4+ T cell epitope map of IEX01 PE38 sequence using overlapping 15mer peptides tested against 52 healthy donors. The non-adjusted (FIG. 3A) and adjusted (FIG. 3B) proliferation assay data for the PE38 sequence is shown. Peptides inducing positive (SI≥2.00, p<0.05, including borderline responses) T cell proliferation responses at a frequency above the background response rate (mean positive T cell responses plus SD) contain T cell epitopes (dotted line indicates the background response threshold). KLH induced positive responses in (SI≥2.00, p<0.05) 75% of (non-adjusted) donors.
Figure 3B:
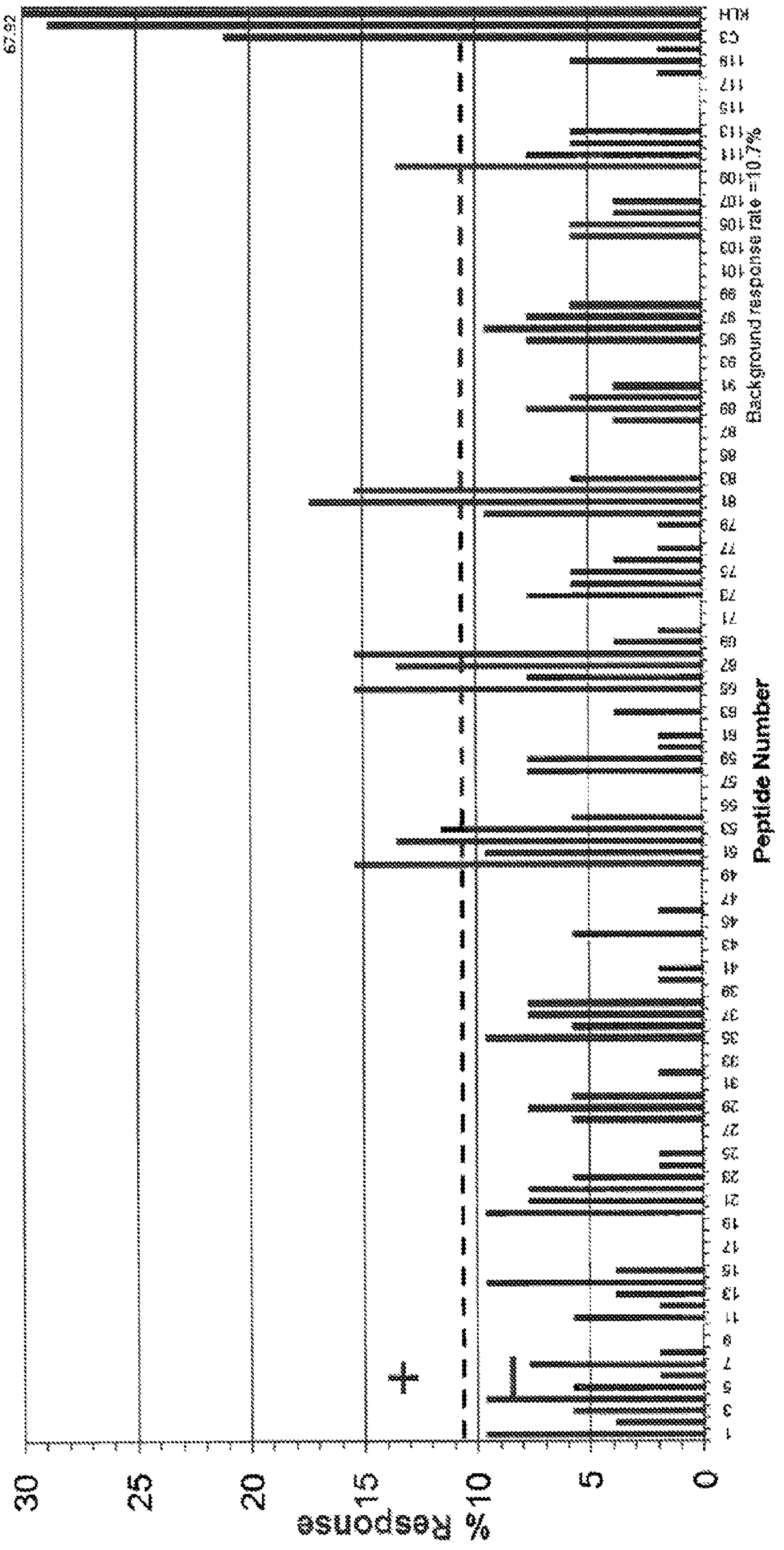
Figure 4:
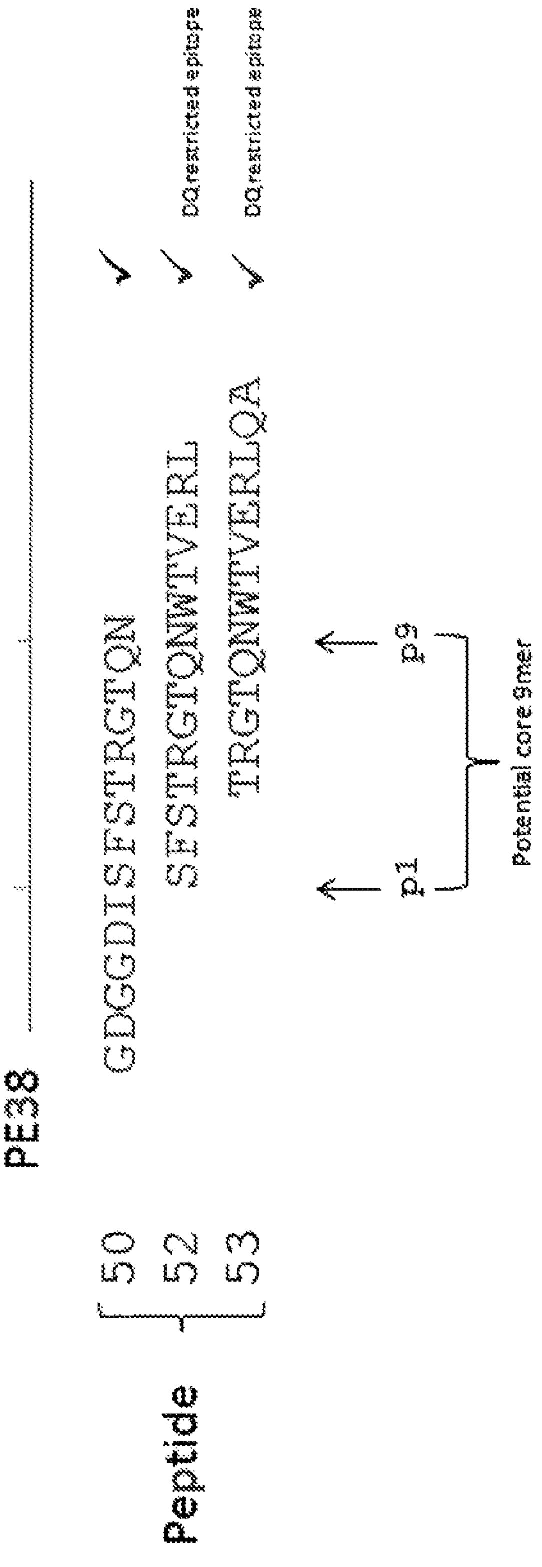
FIG. 4. Alignment of peptides 50, 52 and 53 showing the predicted HLA-DR core 9mer binding register. Predicted core 9mer sequences are bracketed by p1 and p9 anchor residues. Peptides that stimulated positive T cell responses in the adjusted data set are shown. Amino acid numbering (residues 153 and 161) correspond to SEQ ID NO:2 (PE38 of SEQ ID NO:1 plus amino-terminal linker GGGGGSGGGGGS (SEQ ID NO:3)).
Figure 5:
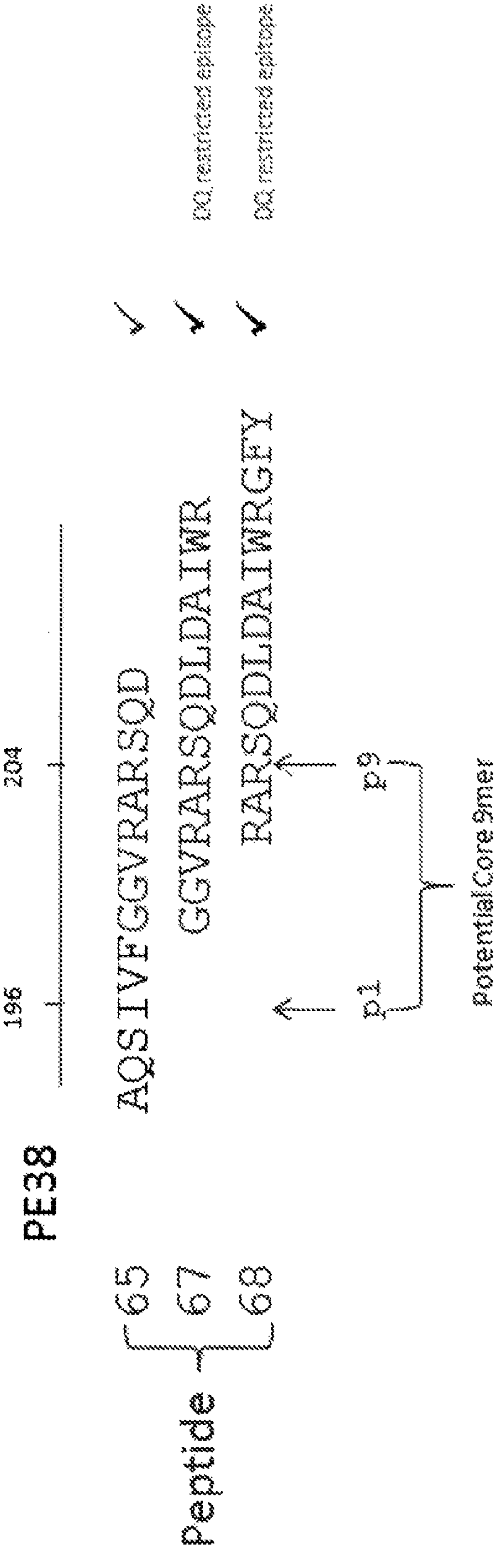
FIG. 5. Alignment of peptides 65, 67 and 68 showing one predicted HLA-DR core 9mer binding register. Predicted core 9mer sequences are bracketed by p1 and p9 anchor residues. Peptides that stimulated positive T cell responses in the adjusted data set are shown. Amino acid numbering (residues 196 and 204) correspond to SEQ ID NO:2 (PE38 of SEQ ID NO:1 plus amino-terminal linker GGGGGSGGGGGS (SEQ ID NO:3)).
Figure 6:
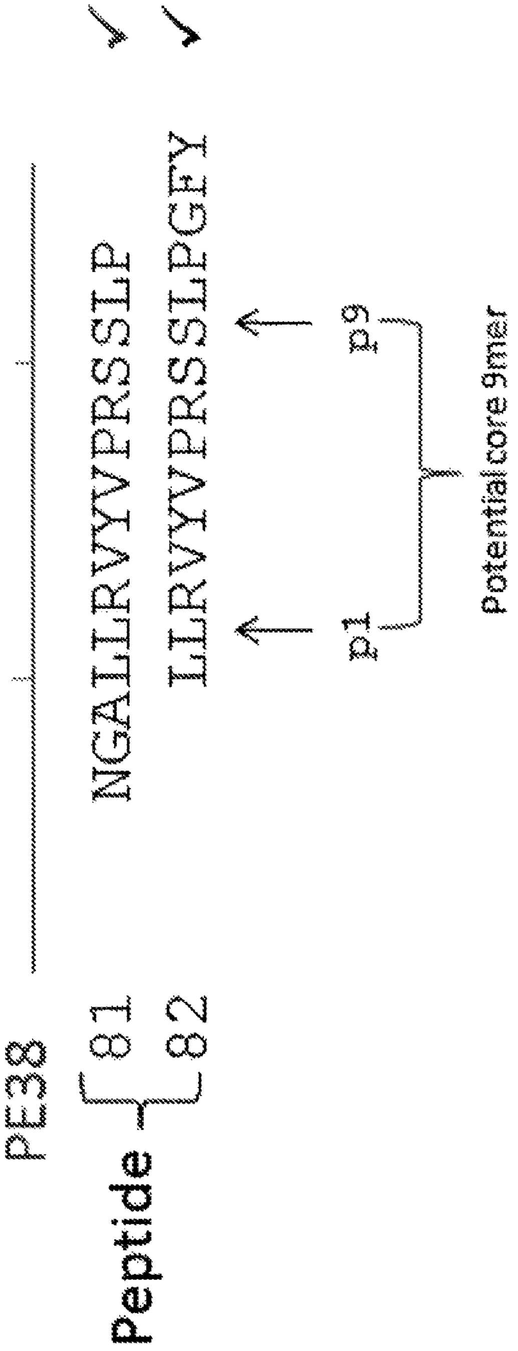
FIG. 6. Alignment of peptides 81 and 82 showing the potential HLA-DR core 9mer binding register. Predicted core 9mer sequences are bracketed by p1 and p9 anchor residues. Peptides that stimulated positive T cell responses in the adjusted data set are shown. Amino acid numbering (residues 244 and 252) correspond to SEQ ID NO:2 (PE38 of SEQ ID NO:1 plus amino-terminal linker GGGGGSGGGGGS (SEQ ID NO:3)).

A total of 120 peptides were synthesized spanning the entire PE38 sequence. The peptides were designed as 15mers to span the sequence in overlapping increments of 12 amino acids. These peptides were then tested for the presence of CD4+ T cell epitopes by EPISCREEN™ T cell epitope mapping analysis. Positive T cell responses were defined by donors that produced a significant ($p<0.05$) response with a SI≥2.00 to any given peptide (SI≥2.00, $p<0.05$). T cell epitopes were identified by calculating the average frequency of the positive responses to all peptides in the study plus SD (termed 'background response threshold'). This was calculated to be 10.8% in the raw 'non-adjusted' data and 10.7% in the adjusted data (where maximum and minimum values were removed and the mean cpm calculated on the remaining four wells). Thus, peptides containing a T cell epitope induced positive T cell proliferation responses (SI≥2.00, $p<0.05$) in ≥6 donors in the non-adjusted and adjusted data sets. Inter-assay variability was assessed using KLH as a reproducibility control where the frequency of positive T cell responses against KLH were compared in two separate EPISCREEN™ assays (Table 7). The results show that inter-assay variability is within the acceptable range and consistent with previous studies (≤10%). The frequency of T cell responses against the two control peptides C3 (EBNA derived epitope) and C32 (Influenza derived epitope) ranged between 23-31% (non-adjusted) and between 21-29% (adjusted) for the two peptides, respectively (FIG. 3). This is within the typical range observed for these two peptides in T cell epitope mapping studies.

The output from non-adjusted and adjusted data analysis was examined to ensure that intra-assay variability was low and that positive responses were not the result of spurious proliferation in individual wells. The results from each analysis showed, in most cases, only small differences between the methods and donor responses for both non-adjusted and adjusted analysis. Table 10 provides a summary of individual donor responses to each of the peptides. The proliferation assay data showing the frequency of positive donor responses to each peptide is shown in FIG. 3. For all peptides that induced a high frequency of positive (SI≥2.00, $p<0.05$, including borderline responses) T cell proliferation responses above the background response threshold, additional in silico analysis was performed to aid in the identification of the precise location of MHC class II core 9mer binding registers (using iTOPE™), and to identify peptides that are homologous to sequences containing T cell epitopes that have been tested in previous EPISCREEN™ T cell epitope mapping assays (using TCED™).

Table 8. Summary of individual donor responses to PE38 peptides. Positive responses (SI≥2.00, $p<0.05$, including borderline responses) are indicated by the donor number and individual SI are shown in parentheses next to the corresponding donor. The background response rate was 10.8% in the non-adjusted data and 10.7% in the adjusted data peptides inducing positive T cell proliferation above this frequency (positive response in ≥6 donors) contained T cell epitopes (indicated with bold text; i.e., peptides 50, 52, 53, 65, 67, 68, 81, 82 and 110 (also as indicated in FIGS. 3-6)).

TABLE 8

Donor Responses to PE38 Peptides

| Peptide # | Proliferation Non-Adjusted | Proliferation Adjusted | Peptide Sequence |
|---|---|---|---|
| 1 | 11(2.25), 19(2.42), 25(3.24), 35(2.77), 36(2.21) | 11(2.34), 19(2.72), 25(3.33), 35(2.76), 36(2.10) | GGGGGSGGGGGSPEG (SEQ ID NO: 11) |
| 2 | 19(2.44), 36(1.94) | 19(2.67), 48(2.06) | GGSGGGGGSPEGGSL (SEQ ID NO: 12) |
| 3 | 11(1.98), 16(1.92), 19(2.54) | 11(1.99), 19(2.78), 38(5.37) | GGGGGSPEGGSLAAL (SEQ ID NO: 13) |
| 4 | 16(2.33), 17(2.02), 19(2.29), 35(2.33) | 16(2.13), 17(2.02), 19(2.46), 35(2.35), 38(3.71) | GGSPEGGSLAALTAH (SEQ ID NO: 14) |

TABLE 8 -continued

| Donor Responses to PE38 Peptides | | | |
|---|---|---|---|
| Peptide # | Proliferation Non-Adjusted | Proliferation Adjusted | Peptide Sequence |
| 5 | 7(1.97), 10(2.24), 17(2.24), 24(1.90) | 7(2.05), 10(2.46), 17(2.20) | PEGGSLAALTAHQAC (SEQ ID NO: 15) |
| 6 | | 3(2.00) | GSLAALTAHQACHLP (SEQ ID NO: 16 |
| 7 | 3(2.11), 17(2.39), 24(2.20), 45(2.11) | 3(2.30), 17(2.22), 24(2.11), 45(1.90) | AALTAHQACHLPLET (SEQ ID NO: 17) |
| 8 | 17(2.23), 45(2.12) | 17(2.04) | TAHQACHLPLETFTR (SEQ ID NO: 18) |
| 9 | — | — | QACHLPLETFTRHRQ (SEQ ID NO: 19) |
| 10 | — | — | HLPLETFTRHRQPRG (SEQ ID NO: 20) |
| 11 | 10(2.48), 24(2.13) | 7(1.98), 10(2.90), 24(2.12) | LETFTRHRQPRGWEQ (SEQ ID NO: 21) |
| 12 | — | 7(1.95) | FTRHRQPRGWEQLEQ (SEQ ID NO: 22) |
| 13 | 10(3.20), 24(2.12) | 10(7.11), 24(2.12) | HRQPRGWEQLEQCGY (SEQ ID NO: 23) |
| 14 | 10(2.14), 17(2.47), 24(2.06) | 1(2.22), 10(2.04), 17(2.25), 24(2.17), 51(1.91) | PRGWEQLEQCGYPVQ (SEQ ID NO: 24) |
| 15 | 17(2.04), 24(2.24) | 17(2.05), 24(2.21) | WEQLEQCGYPVQRLV (SEQ ID NO: 25) |
| 16 | — | — | LEQCGYPVQRLVALY (SEQ ID NO: 26) |
| 17 | — | — | CGYPVQRLVALYLAA (SEQ ID NO: 27) |
| 18 | — | — | PVQRLVALYLAARLS (SEQ ID NO: 28) |
| 19 | — | — | RLVALYLAARLSWNQ (SEQ ID NO: 29) |
| 20 | 3(2.35), 40(1.96) | 3(9.55), 8(2.06), 9 (1.90), 19(1.94), 40(2.07) | ALYLAARLSWNQVDQ (SEQ ID NO: 30) |
| 21 | 11(1.90) | 3(4.22), 8(2.22), 11(2.17), 40(1.96) | LAARLSWNQVDQVIR (SEQ ID NO: 31) |
| 22 | 3(2.20), 40(2.10) | 3(4.32), 6(2.17), 19(2.00), 40(2.15) | RLSWNQVDQVIRNAL (SEQ ID NO: 32) |
| 23 | 6(2.24), 19(1.97) | 3(4.67), 6(2.40), 19(2.22), | WNQVDQVIRNALASP (SEQ ID NO: 33) |
| 24 | 3(3.08) | 3(3.99) | VDQVIRNALASPGSG (SEQ ID NO: 34) |
| 25 | 3(1.90), 6(1.92) | 6(2.36) | VIRNALASPGSGGDL (SEQ ID NO: 35) |
| 26 | — | — | NALASPGSGGDLGEA (SEQ ID NO: 36) |
| 27 | — | — | ASPGSGGDLGEAIRE (SEQ ID NO: 37) |
| 28 | 24(2.62) | 9(1.99), 11(1.92), 24(3.47), | GSGGDLGEAIREQPE (SEQ ID NO: 38) |

TABLE 8 -continued

Donor Responses to PE38 Peptides

| Peptide # | Proliferation Non-Adjusted | Proliferation Adjusted | Peptide Sequence |
|---|---|---|---|
| 29 | 4(2.05), 17(2.07), 45(2.18) | 4(1.91), 17(1.96), 24(2.29), 45(2.18) | GDLGEAIREQPEQAR (SEQ ID NO: 39) |
| 30 | 17(1.94) | 8(2.54), 17(2.18), 24(2.44) | GEAIREQPEQARLAL (SEQ ID NO: 40) |
| 31 | — | — | IREQPEQARLALTLA (SEQ ID NO: 41) |
| 32 | — | 31(1.96) | QPEQARLALTLAAAE (SEQ ID NO: 42) |
| 33 | — | — | QARLALTLAAAESER (SEQ ID NO: 43) |
| 34 | — | — | LALTLAAAESERFVR (SEQ ID NO: 44) |
| 35 | 4(1.91), 35(1.91), 37(2.18), 42(2.05) | 29(2.42), 35(1.98), 36(2.05), 37(2.27), 42(2.07) | TLAAAESERFVRQGT (SEQ ID NO: 45) |
| 36 | 3(2.14), 42(1.91) | 3(2.12), 29(3.71), 36(1.91) | AAESERFVRQGTGND (SEQ ID NO: 46) |
| 37 | 37(2.34), 42(1.96) | 13(1.91), 29(3.91), 35(2.06), 37(2.20) | SERFVRQGTGNDEAG (SEQ ID NO: 47) |
| 38 | 37(2.20), 42(2.12) | 29(2.28), 36(1.95), 37(2.20), 42(2.06) | FVRQGTGNDEAGAAS (SEQ ID NO: 48) |
| 39 | 42(1.90) | — | QGTGNDEAGAASGPA (SEQ ID NO: 49) |
| 40 | 1(2.21) | 1(2.08) | GNDEAGAASGPADSG (SEQ ID NO: 50) |
| 41 | 1(2.28) | 1(2.16) | EAGAASGPADSGDAL (SEQ ID NO: 51) |
| 42 | — | — | AASGPADSGDALLER (SEQ ID NO: 52) |
| 43 | — | — | GPADSGDALLERNYP (SEQ ID NO: 53) |
| 44 | 17(2.08), 22(1.95), 42(2.02) | 17(2.13), 22(2.00), 37(1.98) | DSGDALLERNYPTGA (SEQ ID NO: 54) |
| 45 | — | — | DALLERNYPTGAEFL (SEQ ID NO: 55) |
| 46 | 31(2.23) | 31(1.98) | LERNYPTGAEFLGDG (SEQ ID NO: 56) |
| 47 | — | — | NYPTGAEFLGDGGDI (SEQ ID NO: 57) |
| 48 | 2(2.63) | — | TGAEFLGDGGDISFS (SEQ ID NO: 58) |
| 49 | — | — | EFLGDGGDISFSTRG (SEQ ID NO: 59) |
| 50 | 10(2.54), 11(1.93), 19(2.29), 36(2.36), 37(1.92), 39(2.17), 42(2.66), 45(1.96) | 10(2.56), 11(2.33), 19(2.37), 36(2.37), 39(2.13), 42(2.63), 45(1.95), 46(1.93) | **GDGGDISFSTRGTQN** (SEQ ID NO: 60) |
| 51 | 19(2.03), 42(2.25), 45(1.93) | 2(2.57), 11(2.06), 19(1.97), 42(2.20), 45(1.90) | GDISFSTRGTQNWTV (SEQ ID NO: 61) |
| 52 | 3(7.10), 11(2.76), 16(2.41), 19(2.36), 42(1.97), 44(1.92) | 2(1.95), 3(6.19), 11(3.01), 16(2.58), | **SFSTRGTQNWTVERL** (SEQ ID NO: 62) |

TABLE 8 -continued

| Donor Responses to PE38 Peptides | | | |
|---|---|---|---|
| Peptide # | Proliferation Non-Adjusted | Proliferation Adjusted | Peptide Sequence |
| | | 19(2.45), 42(2.02), 44(2.05) | |
| 53 | 2(2.13), 3(5.19), 11(1.98), 16(2.12), 19(2.19), 27(2.09), 45(1.92) | 2(2.27), 3(4.50), 11(2.01), 16(1.94), 19(2.10), 27(2.46) | **TRGTQNWTVERLLQA** (SEQ ID NO: 63) |
| 54 | — | 3(1.90), 11(1.95), 16(1.92) | TQNWTVERLLQAHRQ (SEQ ID NO: 64) |
| 55 | 3(1.98) | — | WTVERLLQAHRQLEE (SEQ ID NO: 65) |
| 56 | — | — | ERLLQAHRQLEERGY (SEQ ID NO: 66) |
| 57 | — | — | LQAHRQLEERGYVFV (SEQ ID NO: 67) |
| 58 | 10(2.67), 11(2.90) | 9(1.99), 10(2.55), 11(3.46), 4(1.90) | HRQLEERGYVFVGYH (SEQ ID NO: 68) |
| 59 | 9(2.27), 37(2.56), 42(2.70) | 9(2.38), 11(2.15), 37(2.71), 42(3.01) | LEERGYVFVGYHGTF (SEQ ID NO: 69) |
| 60 | — | 16(2.09) | RGYVFVGYHGTFLEA (SEQ ID NO: 70) |
| 61 | — | 11(2.07) | VFVGYHGTFLEAAQS (SEQ ID NO: 71) |
| 62 | — | — | GYHGTFLEAAQSIVF (SEQ ID NO: 72) |
| 63 | 3(2.88) | 11(1.97), 16(2.02) | GTFLEAAQSIVFGGV (SEQ ID NO: 73) |
| 64 | — | — | LEAAQSIVFGGVRAR (SEQ ID NO: 74) |
| 65 | 2(2.17), 4(1.94), 14(3.63), 17(2.19), 18(2.46), 36(2.06), 39(1.97), 51(7.91) | 2(2.30), 4(1.93), 11(2.10), 14(3.65), 18(2.31), 36(2.09), 39(2.04), 51(6.71) | **AQSIVFGGVRARSQD** (SEQ ID NO: 75) |
| 66 | 18(1.95), 19(1.90), 36(1.94), 51(10.38) | 19(2.02), 36(1.98), 47(1.91), 51(9.41) | IVFGGVRARSQDLDA (SEQ ID NO: 76) |
| 67 | 6(2.07), 14(2.62), 16(2.21), 17(2.11), 18(2.60), 42(1.95), 47(1.93), 51(6.83) | 14(2.68), 16(2.55), 18(2.42), 19(2.06), 38(1.95), 47(1.95), 51(5.22) | **GGVRARSQDLDAIWR** (SEQ ID NO: 77) |
| 68 | 2(2.07), 14(2.24), 18(2.70), 38(1.94), 39(2.05), 42(2.10), 51(3.69) | 2(2.12), 11(2.11), 14(2.04), 16(2.00), 19(2.06), 38(2.15), 39(2.17), 51(3.62) | **RARSQDLDAIWRGFY** (SEQ ID NO: 78) |
| 69 | 31(1.95), 42(1.99), 51(2.47) | 31(1.93), 51(2.19) | SQDLDAIWRGFYIAG (SEQ ID NO: 79) |
| 70 | | 24(2.22) | LDAIWRGFYIAGDPA (SEQ ID NO: 80) |
| 71 | | — | IWRGFYIAGDPALAY (SEQ ID NO: 81) |
| 72 | — | — | GFYIAGDPALAYGYA (SEQ ID NO: 82) |
| 73 | 6(1.91), 14(2.70), 17(2.13), 39(1.98) | 11(2.02), 14(2.77), 17(1.94), 39(2.01) | IAGDPALAYGYAQDQ (SEQ ID NO: 83) |
| 74 | 6(1.99), 14(2.77), 38(1.99), 39(2.25), 42(1.90) | 14(2.89), 16(2.01), 39(2.27) | DPALAYGYAQDQEPD (SEQ ID NO: 84) |

TABLE 8 -continued

Donor Responses to PE38 Peptides

| Peptide # | Proliferation Non-Adjusted | Proliferation Adjusted | Peptide Sequence |
|---|---|---|---|
| 75 | 6(2.22), 14(2.27), 17(1.93), 39(2.05) | 14(2.24), 16(2.26), 39(2.07) | LAYGYAQDQEPDARG (SEQ ID NO: 85) |
| 76 | 14(2.20), 17(1.98) | 14(2.40), 39(1.94) | GYAQDQEPDARGRIR (SEQ ID NO: 86) |
| 77 | — | 38(1.90) | QDQEPDARGRIRNGA (SEQ ID NO: 87) |
| 78 | — | — | EPDARGRIRNGALLR (SEQ ID NO: 88) |
| 79 | — | 24(1.91) | ARGRIRNGALLRVYV (SEQ ID NO: 89) |
| 80 | 9(2.89), 11(2.85), 19(2.18), 36(2.63), 42(2.23), 45(2.23) | 9(2.84), 19(2.03), 36(2.59), 42(2.29), 45(2.20) | RIRNGALLRVYVPRS (SEQ ID NO: 90) |
| 81 | 1(2.08), 8(1.96), 9(2.05), 11 (3.22), 13(2.09), 19(2.09), 36(2.21), 42(2.31), 45(2.13), 49(2.07) | 1(2.13), 9(2.05), 13(2.10), 19(2.10), 36(2.21), 42(2.31), 45(1.94), 49(2.00), 51(2.25) | **NGALLRVYVPRSSLP** (SEQ ID NO: 91) |
| 82 | 9(1.93), 10(2.01), 11(2.41), 13(2.09), 16( 2.11), 19(2.01), 36(2.25), 45(1.97), 49(2.44) | 9(1.90), 10(2.00), 13(2.21), 16(2.23), 19(1.98), 36(2.28), 45(1.98), 49(2.37) | **LLRVYVPRSSLPGFY** (SEQ ID NO: 92) |
| 83 | 33(2.02), 42(2.14), 46(1.90), 49(1.92) | 33(1.97), 42(2.14), 49(1.95) | VYVPRSSLPGFYRTG (SEQ ID NO: 93) |
| 84 | 11(1.93) | — | PRSSLPGFYRTGLTL (SEQ ID NO: 94) |
| 85 | — | — | SLPGFYRTGLTLAAP (SEQ ID NO: 95) |
| 86 | — | — | GFYRTGLTLAAPEAA (SEQ ID NO: 96) |
| 87 | — | — | RTGLTLAAPEAAGEV (SEQ ID NO: 97) |
| 88 | 9(2.59), 11(3.03), 42(2.03), 51(2.30) | 9(2.47), 42(2.01) | LTLAAPEAAGEVERL (SEQ ID NO: 98) |
| 89 | 9(1.91), 11(4.31), 42(2.34), 49(2.09), 51(5.22) | 11(2.05), 13(2.28), 42(2.16), 51(6.48) | AAPEAAGEVERLIGH (SEQ ID NO: 99) |
| 90 | 11(2.59), 14(2.07), 49(2.12), 51(7.78) | 14(2.11), 49(2.11), 51(6.45) | EAAGEVERLIGHPLP (SEQ ID NO: 100) |
| 91 | 11(4.15), 42(1.99), 51(4.84) | 42(2.06), 51(4.07) | GEVERLIGHPLPLRL (SEQ ID NO: 101) |
| 92 | 11(2.19), 49(1.99) | — | ERLIGHPLPLRLDAI (SEQ ID NO: 102) |
| 93 | — | — | IGHPLPLRLDAITGP (SEQ ID NO: 103) |
| 94 | — | — | PLPLRLDAITGPEEE (SEQ ID NO: 104) |
| 95 | 3(2.10), 7(1.91), 18(1.90), 19(2.07), 35(2.17) | 3(2.00), 7(1.95), 19(2.04), 45(2.03) | LRLDAITGPEEEGGR (SEQ ID NO: 105) |
| 96 | 3(2.62), 13(2.19), 16(2.18), 39(1.96) | 3(2.34), 13(2.46), 16(2.24), 31(1.93), 39(2.10) | DAITGPEEEGGRLET (SEQ ID NO: 106) |

TABLE 8 -continued

Donor Responses to PE38 Peptides

| Peptide # | Proliferation Non-Adjusted | Proliferation Adjusted | Peptide Sequence |
|---|---|---|---|
| 97 | 13(2.29), 16(2.32), 19(2.20), 35(2.43), 45(2.13) | 13(2.48), 16(2.44), 19(2.31), 45(2.16) | TGPEEEGGRLETILG (SEQ ID NO: 107) |
| 98 | 11(1.92), 13(1.97), 16(2.26), 35(1.91), 50(1.98) | 11(2.26), 13(2.04), 16(2.33) | EEEGGRLETILGWPL (SEQ ID NO: 108) |
| 99 | 35(2.33) | — | GGRLETILGWPLAER (SEQ ID NO: 109) |
| 100 | 35(2.20) | — | LETILGWPLAERTVV (SEQ ID NO: 110) |
| 101 | — | — | ILGWPLAERTVVIPS (SEQ ID NO: 111) |
| 102 | 27(1.93) | — | WPLAERTVVIPSAIP (SEQ ID NO: 112) |
| 103 | | | AERTVVIPSAIPTDP (SEQ ID NO: 113) |
| 104 | 3(2.40), 16(2.20), 22(1.98), 49(1.91) | 3(2.17), 13(2.05), 16(2.15) | TVVIPSAIPTDPRNV (SEQ ID NO: 114) |
| 105 | 16(2.43), 22(1.96), 45(1.97) | 16(2.30), 45(1.95), 49(1.96) | IPSAIPTDPRNVGGD (SEQ ID NO: 115) |
| 106 | 16(2.02), 19(2.02) | 16(1.95), 19(1.90) | AIPTDPRNVGGDLDP (SEQ ID NO: 116) |
| 107 | 19(2.00), 27(2.06) | 19(1.93), 27(1.99) | TDPRNVGGDLDPSSI (SEQ ID NO: 117) |
| 108 | — | — | RNVGGDLDPSSIPDK (SEQ ID NO: 118) |
| 109 | — | — | GGDLDPSSIPDKEQA (SEQ ID NO: 119) |
| 110 | 8(2.07), 9(2.35), 11(2.27), 13(2.13), 16(1.91), 19(3.00), 35(1.90) | 9(2.46), 10(2.04), 13(2.11), 19(1.99), 35(1.94), 38(1.95), 50(2.01) | **LDPSSIPDKEQAISA** (SEQ ID NO: 120) |
| 111 | 3(2.29), 8(2.20), 9(1.93), 11 (2.08), 16(2.19), 19(2.60) | 3(2.33), 8(2.74), 9 (2.02), 13(1.98) | SSIPDKEQAISALPD (SEQ ID NO: 121) |
| 112 | 11(2.47), 16(3.07), 19(2.61) | 9(1.90), 16(2.11), 50(1.97) | PDKEQAISALPDYAS (SEQ ID NO: 122) |
| 113 | 3(2.07), 11(2.61), 16(2.44), 19(2.62) | 3(2.04), 11(1.93), 45(1.90) | EQAISALPDYASQPG (SEQ ID NO: 123) |
| 114 | 19(2.04) | — | ISALPDYASQPGKPP (SEQ ID NO: 124) |
| 115 | 16(1.99) | — | LPDYASQPGKPPRED (SEQ ID NO: 125) |
| 116 | — | — | YASQPGKPPREDLK (SEQ ID NO: 126) |
| 117 | — | — | ITGPEEEGGRLDTIL (SEQ ID NO: 127) |
| 118 | 9(2.04), 11(2.26), 16(2.12), 39(1.93), 5 | 9(2.27) | PEEEGGRLDTILGWP (SEQ ID NO: 128) |
| 119 | 16(2.11), 39(2.13) | 14(1.90), 38(1.96), 39(2.10) | EGGRLDTILGWPLAE (SEQ ID NO: 129) |
| 120 | 11(2.13), 39(2.05) | 39(2.07) | RLDTILGWPLAERTV (SEQ ID NO: 130) |

T Cell Epitope Map

Epitopes 1 and 2—

Peptides 50, 52 and 53 induced a high number of positive T cell proliferation responses in the study cohort (Table 8 and FIG. 3). Peptide 50 showed the highest number of positive responses with 15.38% donors responding in the non-adjusted dataset, and 15.38% in the adjusted data set, (SI≥2.00, p<0.05). From in silico analysis, the proposed core 9mer in this region is ISFSTRGTQ (SEQ ID NO:5). Peptides 52 and 53 induced lower frequencies of response with 11.54% and 13.46% positive donor responses in the non-adjusted dataset, and 13.46% and 11.54% in the adjusted datasets, respectively. A core 9mer was identified in peptide 50 but was only partially present in peptides 52 and 53 suggesting that these peptides must contain a different T cell epitope. In silico analysis of peptides 52 and 53 did not identify any core HLA-DR restricted 9mers so it is likely that the positive T cell responses seen are due to a HLA-DQ restricted T cell epitope.

The magnitude of T cell proliferation responses can provide an indication as to the T cell precursor frequency. In general, peptides that induce high frequency (of positive responses in the study cohort) and high magnitude T cell proliferation responses are a characteristic of 'recall-like' T cell responses in which the T cell pre-cursor frequency is high. In contrast, naive T cell responses are generally characterized by low magnitude T cell proliferation responses (with low T cell precursor frequencies). Peptides 52 and 53 induced moderately high magnitude T cell proliferation responses where the mean SI for positive (SI≥2.00, p<0.05) T cell responses in the non-adjusted and adjusted data sets were 3.09-2.89 (peptide 52) and 2.51-2.55 (peptide 53) (Table 9). Thus these peptides may induce T cell responses in clones that are present in high frequencies in healthy individuals and may be indicative of a memory T cell response. Peptide 50 induced lower magnitude T cell proliferation responses where the mean SI were 2.23 and 2.28 in the non-adjusted and adjusted datasets respectively suggesting that this peptide may induce a naive T cell response (Table 9).

Epitopes 3 and 4

A cluster of T cell responses were observed around peptides 65-68 and the subsequent analysis revealed the presence of two T cell epitopes in this region. Peptide 65 stimulated positive T cell proliferation responses in 15.38% of the study cohort for both non-adjusted and adjusted datasets (Table 8 and FIG. 3) (SI≥2.00, p<0.05). The positive responses were high magnitude (mean SI of positive responses ranged from 3.04-2.89 in the non-adjusted and adjusted data sets) suggesting that the T cell precursor frequency in healthy donors against this epitope is high (Table 9). In silico analysis revealed a potential core 9mer comprising IVFGGVRAR (FIG. 5; SEQ ID NO:7). Peptides 67 and 68 induced frequencies of response with 15.38% and 13.46% positive donor responses in the non-adjusted dataset, and 13.46% and 15.38% in the adjusted datasets, respectively. In silico analysis of these peptides did not identify any core HLA-DR 9mers so it is likely that the positive T cell responses seen are due to a HLA-DQ restricted T cell epitope.

Epitope 5

Peptides 81 and 82 stimulated a number of T cell responses in the study cohort (Table 8 and FIG. 3). Peptide 81 had the highest frequency of response of all the peptides tested with a frequency of positive responses of 19.23% in the non-adjusted and 17.31% in the adjusted data set. For peptide 82, the frequency of positive response was 17.31% and 15.38% in the non-adjusted and adjusted data sets respectively. The positive responses were relatively low in magnitude (mean SI of positive responses ranged from 2.12 to 2.22 in the non-adjusted and adjusted data sets) suggesting that the T cell precursor frequency in healthy donors against this epitope is relatively low (Table 9). Adjacent peptide 80 induced a sub-threshold response. In silico analysis of peptides 81 and 82 suggested a core 9mer of LRVYVPRSS (FIG. 6; SEQ ID NO:9).

Epitope 6

Figure 7:
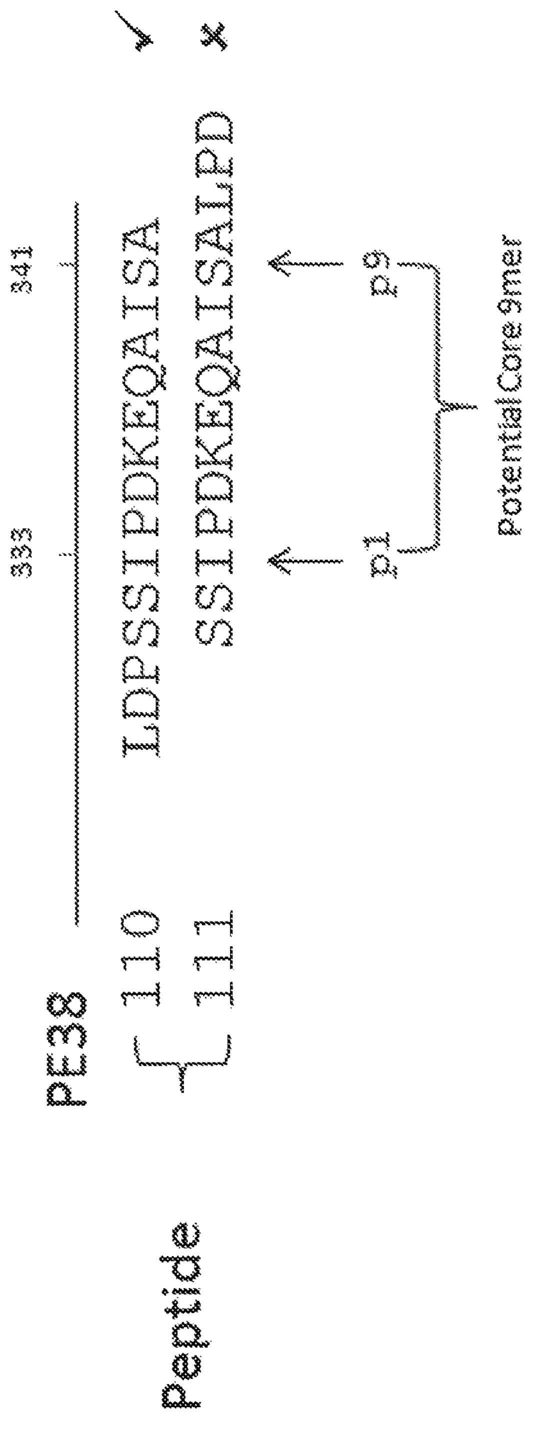
FIG. 7. Alignment of peptides 110 and 111 showing a predicted HLA-DR core 9mer binding register. Predicted core 9mer sequences are bracketed by p1 and p9 anchor residues. Peptides that stimulated positive T cell responses in the adjusted data set are shown. Amino acid numbering (residues 333 and 341) correspond to SEQ ID NO:2 (PE38 of SEQ ID NO:1 plus amino-terminal linker GGGGGSGGGGGS (SEQ ID NO:3)).

Peptide 110 induced positive T cell responses in 13.46% of the study cohort in non-adjusted and 13.46% in adjusted datasets (Table 8 and FIG. 3). The magnitude of positive proliferation responses was low with a mean SI of 2.23 for the non-adjusted dataset and 2.07 for the adjusted dataset (Table 9). There was also a sub-threshold response to peptide 111. In silico analysis of the peptides sequence revealed a core 9mer, IPDKEQAIS (FIG. 7; SEQ ID NO: 10) which, in addition to peptide 110, was also present in peptide 111.

Table 9. Summary of magnitude (mean SI and standard deviation) and frequency (% donor response) of positive T cell proliferation responses against peptides containing T cell epitopes for PE38. The position of p1 in potential core 9mers are shown as underlined/bolded text (as predicted by iTOPE™) in peptides 50, 65, 81, 82 and 110.

TABLE 9

Magnitude and Frequency of Donor Responses

| Peptide | Peptide Sequence | Response Frequency Non-Adjusted | Response Frequency Adjusted | Mean (±SD) Non-Adjusted Data | Mean (±SD) Adjusted Data |
|---|---|---|---|---|---|
| 50 | GDGGD**I**SFSTRGTQN (SEQ ID NO: 60) | 15.38% | 15.38% | 2.23 ± 0.28 | 2.28 ± 0.26 |
| 52 | SFSTRGTQNWTVERL (SEQ ID NO: 62) | 11.54% | 13.46% | 3.09 ± 1.99 | 2.89 ± 1.50 |
| 53 | TRGTQNWTVERLLQA (SEQ ID NO: 63) | 13.46% | 11.54% | 2.51 ± 1.18 | 2.55 ± 0.98 |
| 65 | AQS**I**VFGGVRARSQD (SEQ ID NO: 75) | 15.38% | 15.38% | 3.04 ± 2.04 | 2.89 ± 1.64 |

TABLE 9 -continued

Magnitude and Frequency of Donor Responses

| Peptide | Peptide Sequence | Response Frequency Non-Adjusted | Response Frequency Adjusted | Mean (±SD) Non-Adjusted Data | Mean (±SD) Adjusted Data |
|---|---|---|---|---|---|
| 67 | GGVRARSQDLDAIWR (SEQ ID NO: 77) | 15.38% | 13.46% | 2.79 ± 1.65 | 2.69 ± 1.15 |
| 68 | RARSQDLDAIWRGFY (SEQ ID NO: 78) | 13.46% | 15.38% | 2.40 ± 0.62 | 2.28 ± 0.54 |
| 81 | NGALLRVYVPRSSLP (SEQ ID NO: 91) | 19.23% | 17.31% | 2.22 ± 0.36 | 2.12 ± 0.12 |
| 82 | LLRVYVPRSSLPGFY (SEQ ID NO: 92) | 17.31% | 15.38% | 2.14 ± 0.19 | 2.12 ± 0.17 |
| 110 | LDPSSIPDKEQAISA (SEQ B5N0:120) | 13.46% | 13.46% | 2.23 ± 0.38 | 2.07 ± 0.18 |

HLA Analysis

Analysis of the responding donor haplotypes was performed whereby an association between MHC class II allotype and a response to a particular peptide was considered possible if the frequency of the allotype within the responding population was double the frequency observed in the study cohort. This analysis was only carried out for peptides that induced positive responses above the background response rate in the adjusted data in the study cohort and was also restricted to allotypes expressed at higher frequencies (>5%) in the study population.

Analysis of responding donor allotypes (Table 10 and FIG. 8) revealed that there was a possible association between T cell responses to peptides 81, and 82 and MHC class II allotype HLA DRB 1*07 which was expressed at twice the percentage of positively responding donors compared to the study population. Peptide 53 also had a possible association with DRB 1*11, and peptides 82 and 110 showed possible associations with DRB1*15. It should be noted that further studies (such as MHC class II binding analysis) would be required to show conclusively that responses to the T cell epitope are associated with these allotypes as the present analysis was performed on a small group of responding donors.

Table 10. Frequency (expressed as a percentage) of responding donor allotypes compared to the frequency of allotypes expressed in the IEX01 study cohort. An association between MHC class II allotype and a response to a particular epitope was considered if the frequency of the allotype within the responding population was double the frequency observed in the study population in the adjusted data set. Possible associations are indicated in heavily bordered boxes. The analysis has been restricted to allotypes expressed at higher frequencies (>5%) in the study population.

TABLE 10

Frequency of responding donor allotypes versus frequency of allotypes in the IEX01 study cohort.

| Frequency (%) of HLA alleles expressed within: | DRB1*03 | DRB1*04 | DRB1*07 | DRB1*11 | DRB1*15 | DRB3 | DRB4 | DRB5 |
|---|---|---|---|---|---|---|---|---|
| Study population | 8 | 8 | 7 | 5 | 7 | 20 | 18 | 6 |
| Peptide 50 | 8 | 8 | 12 | 0 | 8 | 23 | 15 | 4 |
| Peptide 52 | 4 | 8 | 8 | 8 | 4 | 24 | 20 | 0 |
| Peptide 53 | 5 | 10 | 5 | **10** | 5 | 24 | 19 | 0 |
| Peptide 65 | 12 | 0 | 12 | 8 | 0 | 32 | 16 | 0 |
| Peptide 67 | 8 | 13 | 0 | 8 | 8 | 25 | 21 | 0 |
| Peptide 68 | 7 | 7 | 7 | 4 | 7 | 25 | 21 | 0 |
| Peptide 81 | 7 | 0 | **14** | 7 | 7 | 21 | 21 | 7 |
| Peptide 82 | 8 | 8 | **15** | 0 | **15** | 15 | 23 | 8 |
| Peptide 110 | 4 | 13 | 4 | 0 | **17** | 13 | 25 | 8 |

Results

Figure 8:
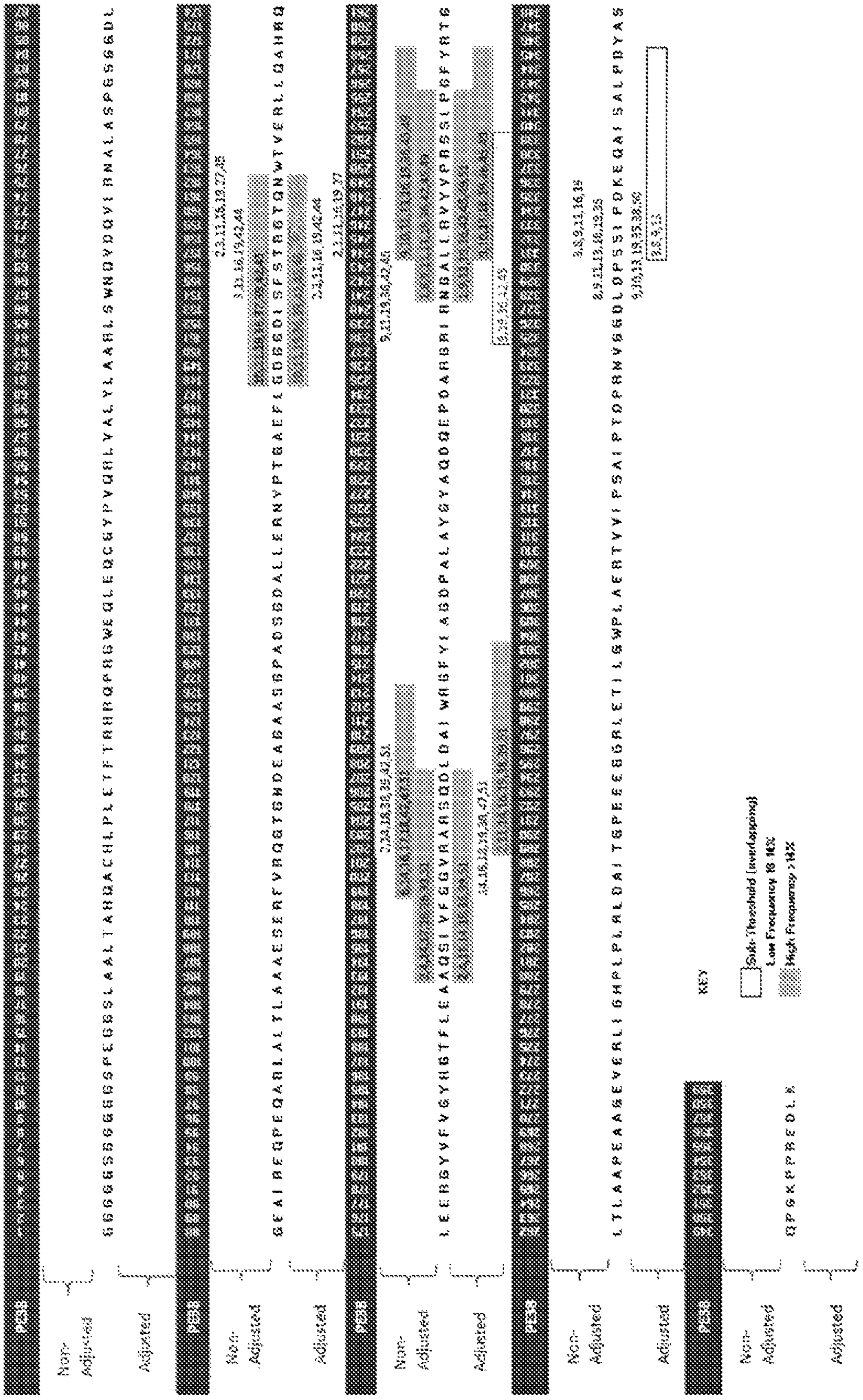
FIG. 8. Position of CD4+ T cell epitopes within the PE38 sequence. T cell epitopes identified by EPISCREEN™ T cell epitope mapping are shown as shaded bars above the sequence. The frequency of donors responding (SI≥2.00, p<0.05) to each epitope are indicated by the shading of the bars; light grey <10%, mid grey 10-14%; dark grey >=14%. Numbers assigned to each individual donor (that responded to a corresponding epitope) are included within each shaded bar.

The results show that six T cell epitopes were present in the PE38 sequence. Table 6 Table 11 and FIG. 8 summarize the location of the putative core 9mers in each sequence along with the frequency and magnitude of T cell responses against each epitope. The T cell epitopes identified in PE38 were prioritized according to their potency based on the frequency and magnitude (mean SI) of positive donor responses to each peptide. However since the responding donor magnitudes were similar (Table 4 Table 9) for most epitopes, the ranking was mainly based on frequency of positive donor responses (from highest to lowest):

Epitope 5>Epitope 4>Epitope 3>Epitope 1>Epitope 2>Epitope 6

Deimmunization Strategy

The six epitope core 9mer sequences were analyzed by proprietary software (iTOPE™) in order to identify mutations that remove the T cell epitopes by eliminating or significantly reducing binding to MHC class II (Table 11). As part of the strategy as to which residues to mutate, location within the structure was considered, especially whether the residue is buried, on the surface, or near active sites.

Table 11. Projected mutations to remove MHC class II binding (based upon iTOPE™ and crystal structure data).

TABLE 11

Location of Core 9-mers and Projected Mutations

| Epitope | Amino Acids in Sequence | Anchor Residues | Projected Mutations | Notes: |
|---|---|---|---|---|
| 1 | I | 1 | A, N, T, | P1 (Ile) is partially |
| | | | Q, H | surface exposed, therefore |
| | S | | | all alternatives should |
| | F | | | be possible. |
| | S | 4 | | P6 and P9 changes |
| | T | | | perform equally well, |
| | R | 6 | Q | but are less preferred |
| | G | 7 | | than P1 changes. |
| | T | | | |
| | Q | 9 | N, T | |
| 2 | G | 1 | | HLA-DQ epitopes have a |
| | T | | | strong negative preference |
| | Q | | | for positively charged |
| | N | 4 | K, R | residues in key anchor |
| | W | | | positions. All four |
| | T | 6 | K, R | mutations are equally |
| | V | 7 | | preferred. |
| | E | | | |
| | R | 9 | | |
| 3 | I | 1 | A, N | P1 is buried, therefore A |
| | V | | | is preferred. |
| | F | | | P6 V is partially exposed. |
| | G | 4 | | All mutations should be |
| | G | | | tolerated. Preference is |
| | V | 6 | D, M, N | D > M > N. |
| | R | 7 | | |
| | A | | | |
| | R | 9 | | |
| 4 | A | 1 | | HLA-DQ epitopes have a |
| | R | | | strong negative preference |
| | S | | | for positively charged |
| | Q | 4 | K, R | residues in key anchor |
| | D | | | positions. All four |
| | L | 6 | | mutations are equally |
| | D | 7 | K, R | preferred. |
| | A | | | |
| | I | 9 | | |
| 5 | L | 1 | A | P1 is buried and close in |
| | R | | D, S, A | the structure to epitope 3 |
| | V | | | P1, therefore changes are |
| | Y | 4 | | limited. For this epitope, |
| | V | | | changes at P2 affect |
| | P | 6 | | binding (D > S > A). |
| | R | 7 | | P9 is mostly surface |
| | S | | | exposed. Preferred |
| | S | 9 | D, E, N, | changes are D, E, N, then |
| | | | K, P, T | K > P > T. |
| 6 | I | 1 | A, N, T, | P1 I is partially surface |
| | | | Q, H | exposed, therefore all |
| | P | | | alternatives should be |
| | D | | | possible. |
| | K | 4 | T | P4, P6 and P9 changes are |
| | E | | | less preferred than P1 |
| | Q | 6 | D | changes. P6 D ≥ P7 D > |
| | A | 7 | D | P4 T. |
| | I | | | |
| | S | 9 | | |

TABLE 11-continued

Conclusions

EPISCREEN™ T cell epitope mapping of 120 overlapping 15mer peptides including 112 spanning the entire PE38 sequence suggested six novel T cell epitopes. In silico analysis was used to identify potential core 9mers for MHC binding and, together with structural analysis, was used as a basis for design of changes for re-engineering and deimmunizing PE38 in particular, and PE molecules in general.

Example 2

T Cell Epitope Mapping of Deimmunized/Amino Acid Substituted Forms of PE

The immunogenicity of amino acid substituted forms of PE can be assessed using the same procedures as described in Example 1. Accordingly, EPISCREEN™ T cell epitope mapping analysis (Antitope Ltd, Cambridge, UK) analysis permits identification of amino acid substituted epitopes in PE polypeptides, wherein the introduced amino acid changes result in reduced or undetectable immunogenicity (i.e., for generating deimmunized forms of PE) as compared to epitopes in corresponding forms of non-amino acid substituted PE polypeptides.

EPISCREEN™ is a proprietary technology commercially available through Antitope Ltd, Cambridge, UK, to map T cell epitopes within a protein sequence to determine potential for immunogenicity (based on the number and potency of T cell epitopes within a sequence). EPISCREEN™ T cell epitope mapping typically uses CD8+ T cell depleted PBMCs from a minimum of 50 HLA-typed donors (selected to represent the human population of interest). Typically, 15mer peptides with 12 amino acid overlaps spanning a protein sequence are analyzed in a large number of replicate cultures for in vitro CD4+ T cell stimulation by 3H TdR incorporation. CD4+ T cell stimulation is often detected in two or three adjacent and overlapping peptides since the core 9mer that binds the MHC class II binding groove will be present in more than one peptide sequence. Following identification of peptides that stimulate CD4+ T cells in vitro, in silico technology can be used to design epitope-depleted (deimmunized) variants by determining the precise location of core 9mer sequences and the location of key MHC class II anchor residues.

In this case, amino acid substituted PE peptides are analyzed for the presence of immunogenic CD4+ T cell epitopes using EPISCREEN™ T cell epitope mapping analysis. For example, amino acid substituted 15mer peptides (compared to non-substituted 15mer peptides corresponding to a non-amino acid substituted form of PE) are tested against a cohort of healthy donors. CD4+ T cell responses against individual peptides are measured using proliferation assays (3H-thymidine incorporation). Proliferation assay data is used to compile a T cell epitope map of varying responses to amino acid substituted forms of PE to determine those amino acid changes producing reduced or abrogated immunogenic responses.

EPISCREEN™ Donor Assessments

Peripheral blood mononuclear cells (PBMC) are isolated from healthy donor buffy coats (e.g., from blood drawn within 24 hours). For example, PBMC are isolated from buffy coats using density gradient centrifugation using LYMPHOPREP™ (Axis-Shield UK, Dundee, Scotland) or a similar density gradient centrifugation media for the isolation of human mononuclear cells from blood (such methods, media and products are well known and routinely used by those skilled in the art). See e.g., Axis-Shield, package insert for LYMPHOPREP™ density gradient media No. 619. March 03. Div.—1114740.) To remove CD8+ cells from the isolated mononuclear cells, CD8+ T cells are depleted using CD8+ ROSETTESEP™ kit (STEMCELL™ Technologies Inc, Manchester, UK) or similar CD8+ selection methods and techniques (such methods, media and products are well known and routinely used by those skilled in the art). See e.g., StemCell Technologies Inc., ROSETTESEP™ procedure for Human CD8+ T Cell Enrichment Cocktail (Catalog #15023/15063; Procedure version 1.3.0, "#28572 (May 2011)).

Donors HLA-DR haplotypes are determined using methods or kits well-known and routinely used by those skilled in the art. For example, Donors HLA-DR haplotypes are determined using a Biotest HLA SSP-PCR tissue-typing kit (Biotest, Solihull, UK, catalogue number 826215). T cell responses to a reproducibility control antigen are measured using, for example neo-antigen, using Imject maricutlure keyhole limpet haemocyanin (KLH) (Pierce (Perbio Science UK, Ltd), Cramlington, UK, catalogue number 77600), or other similar control antigen (such antigens and methods are well known and routinely used by those skilled in the art). PBMC are frozen and stored in liquid nitrogen until ready for use in to measuring immunogenicity of amino acid substituted forms of PE.

A cohort of donors are selected to best represent the number and frequency of HLA-DR allotypes expressed in the world population. It is desirable that allotypes expressed in the cohort represent a coverage of >80% of all major HLA-DR alleles in the world population (i.e., individual allotypes with a frequency >5% expressed in the world population are well represented). Records of individual donor haplotypes and comparison of the frequency of MHC class II haplotypes expressed in the world population and the sample population are recorded and assessed.

Donor responses (SI) to a control antigen (such as KLH) are assessed by comparing two independent proliferation assays. Test-1 is performed using the control antigen (such as KLH) on freshly isolated PBMC and Test-2 is the control antigen re-test performed on PBMC recovered from liquid nitrogen storage, the latter of which are used in assessing immunogenicity of amino acid substituted epitopes in PE. Responses that do not produce the same result in these two tests (i.e. positive including borderline SI>1.90 $p<0.05$ or negative) in both tests are disregarded.

EPISCREEN™ Analysis: Proliferation Assay

PBMC from each donor are thawed, counted and viability is assessed. Cells are revived in room temperature AIM V® Culture Medium (INVITROGEN™, Paisley, UK) before adjusting cell density to $2\text{-}3\times10^6$ PBMC/ml (proliferation cell stock). Peptides are synthesized on a 1-3 mg scale with free N-terminal amine and C-terminal carboxylic acid. Peptides are dissolved in DMSO to a concentration of 10 mM and peptide culture stocks are prepared by diluting into AIM V® Culture Medium to a final concentration of 5 μM per well. For each peptide and each donor, sextuplicate cultures are established in a flat bottomed 96 well plate. Both positive and negative control cultures are tested in sextuplicate. For each donor, three control antigen/peptides (KLH protein and peptides derived from Influenza A and Epstein Barr viruses) are also included.

Cultures are incubated for 6 days before adding 0.75 μCi 3[H]-thymidine (PERKIN ELMER®, Beaconsfield, UK) to each well. Cultures are incubated a further 18 hours before harvesting onto filter mats using a TOMTEC MACH® III cell harvester (TOMTEC®, Hamden, Conn., USA). Counts per minute (cpm) for each well are determined by MELTILEX™ (PERKIN ELMER®) scintillation counting on a Microplate Beta Counter (PERKIN ELMER®) in paralux, low background counting mode.

EPISCREEN™ Data Analysis

In proliferation assays, an empirical threshold of stimulation index (SI) equal to or greater than 2 (SI≥2.00) is considered to represent an induced proliferative response; samples registering values above this threshold are deemed positive (values of SI<2.00 but ≥1.90 are considered borderline). Extensive assay development and previous studies have shown that this is the minimum signal to noise threshold allowing maximum sensitivity without detecting large numbers of false positive responses. Positive responses are defined by the following statistical and empirical thresholds:

1. Significance ($p<0.05$) of the response by comparing cpm of test wells against medium control wells using unpaired two sample Student's t-test.
2. Stimulation index greater than 2.00 (SI≥2.00), where SI=mean cpm of test wells/mean cpm medium control wells. Thus, data presented is indicated as SI≥2.00, $p<0.05$.

In addition, intra-assay variation is assessed by calculating the coefficient of variance and standard deviation (SD) of raw data from replicate cultures.

Proliferation assays are set up in sextuplicate cultures from which "non-adjusted data" is gathered. To ensure intra-assay variability is low, data is also analyzed after removing maximum and minimum cpm values (to produce "adjusted data") and the SI of donor responses is compared using both data sets.

Reactive T cell epitopes are identified by calculating the average frequency of positive responses (defined above) to all peptides in the study plus standard deviation (SD) to give a background response threshold. Any peptide inducing a frequency of positive proliferation responses above the threshold in both adjusted and non-adjusted data is considered to contain an immunogenic T cell epitope (and, thus, potentially represents an immunogenicity inducing epitope which could give rise to immunogenic responses in vivo). Output from non-adjusted and adjusted data is examined to ensure that intra-assay variability is low and that positive responses are not the result of spurious proliferation in individual wells. An example of this type of analysis is provided in Example 1.

A comparison of corresponding forms of non-amino acid substituted PE immunogenic epitope responses versus responses obtained with amino acid substituted PE peptides is used to assess and predict the effects of various amino acid substitutions in reducing or eliminating the immunogenicity of PE polypeptides (i.e., for making deimmunized forms of PE).

Assays for measuring and testing the immunogenicity of amino acid substituted forms of PE may also be done as described and exemplified in Example 1 (i.e., via proliferation assays quantitating CD4+ T cell responses) wherein amino acid substituted forms of PE (i.e., "deimmunized PE" or "DI-PE"), and/or DI-PE conjugates and fusion proteins (e.g., fusions of DI-PE to antibodies or antigen-binding fragments thereof) are tested and measured for the presence and potency of immunogenic responses compared to responses induced by corresponding forms of non-amino acid substituted PE peptides, polypeptides, and fusion or conjugation constructs.

Assays for measuring immunogenicity of amino acid substituted forms of PE specifically (as indicated above), or PE molecules, generally, may also be done according to methods routinely used and well-known to those of skill in the art. For example, immunogenicity of amino acid substituted forms of PE, in particular, or PE molecules, in general, (as indicated above) may be measured in vivo in non-human primates and/or in transgenic mouse model systems.

Example 3

Measuring Biological Activity of Amino Acid Substituted Forms of PE

Assays for measuring the biological activity of amino acid substituted/deimmunized forms of PE, may be done according to methods routinely used and well-known to those of skill in the art. Measured biological activities of deimmunized ("DI") forms of PE ("DI-PE"), in particular, or PE molecules, in general, may include, for example, assays to measure:

a) general or specific inhibition of protein synthesis (i.e., measuring inhibition of synthesis of a specific protein (or specific proteins) or inhibition of overall (mass) protein synthesis;
b) inhibition of translation elongation factor EF-2 biological activity;
c) induction or catalysis of ADP-ribosylation of EF-2; and
d) eukaryotic cell killing activity (cell cytotoxicity).

Assays for Biological Activity: Inhibition of Protein Synthesis

In one example, measurement of inhibition of protein synthesis may be done via use of in vitro transcription/translation assays (which are routinely used and well-known to those of skill in the art). For example, a cell-free assay may be used to measure DI-PE induced inhibition of in vitro transcription/translation of a target plasmid (such as, but not limited to, T7-luc). In the case of using a T7-luc transcription/translation assay, the biological activity readout would be chemiluminescent measurement of luciferase activity wherein amino acid substituted forms of PE are compared to corresponding non-amino acid substituted forms of PE for ability/inability to inhibit translation of the luciferase enzyme in vitro. In such assays, the PE polypeptides being assayed can be introduced via expression from template DNA (e.g., a PCR product) encoding the toxin-conjugate gene, or by directly introducing quantified amounts of PE proteins. Such assays may be used to assess IC50 values* of the various forms of PE tested (*IC50=concentration at which 50% of protein synthesis is inhibited versus standardized control samples lacking PE).

Some examples of kits and reagents available for in vitro transcription/translation assays include, but are not limited to:

TNT® SP6 Coupled Reticulocyte Lysate System (e.g., PROMEGA® catalog #L4610 (PROMEGA® Corp., Madison, Wis., USA)) allows for eukaryotic cell-free protein expression in a single-tube, as a coupled transcription/translation process. More traditional rabbit reticulocyte lysate translations commonly use RNA synthesized in vitro from SP6, T3 or T7 RNA polymerase promoters and require three separate reactions with several steps between each reaction. The TNT® System bypasses many of these steps by incorporating transcription directly into the translation mix. See e.g., PROMEGA® Technical Bulletin #TB126 (Revised 12/2010) which is incorporated by reference herein. See also, Pelham et al., *Eur. J. Biochem.* 67, 247-56 (1976); Krieg et al., (1984) Nucl. Acids Res. 12, 7057-7070 (1984). See also, U.S. Pat. Nos. 5,324,637; 5,492,817; 5,641,641; and, 5,650,289.

TNT® T7 Quick Coupled Transcription/Translation System (e.g., PROMEGA® catalog #L1170 (PROMEGA® Corp., Madison, Wis., USA)) further simplifies in vitro transcription/translation reactions by combining RNA polymerase, nucleotides, salts and Recombinant RNasin® Ribonuclease Inhibitor with the reticulocyte lysate to form a single TnT® Quick Master Mix. The TnT® Quick Coupled Transcription/Translation System may be used with plasmids for transcription and translation of genes cloned downstream from either the T7 or SP6 RNA polymerase promoters. The TnT® Quick System includes a luciferase-encoding control plasmid and Luciferase Assay Reagent, which can be used in a non-radioactive assay for rapid (<30 seconds) detection of functionally active luciferase protein. Starting with either circular plasmid DNA or PCR-generated DNA, in vitro transcription/translation results may be obtained in 5-6 hours. See e.g., PROMEGA® Technical Bulletin #TM045 (Revised 05/2011) which is incorporated by reference herein.

STEADY-GLO® Luciferase Assay System (e.g., PROMEGA® catalog #E2510) (PROMEGA® Corp., Madison, Wis., USA)) allows for high-throughput quantitation of firefly (*Photinus pyralis*) luciferase expression in mammalian cells via batch processing of 96- and 384-well plates. The STEADY-GLO® Luciferase Assay System provides signal half-lives of over 5 hours in commonly used cell culture media without prior sample processing. Throughput rates of several thousand samples per hour may be achieved with high reproducibility under standard laboratory conditions. See e.g., PROMEGA® Technical Bulletin #TM051 (Revised 03/2009 & Revised 09/2011) which is incorporated by reference herein. See also, U.S. Pat. Nos. 5,641,641; 5,650,289; 5,583,024; 5,674,713; ands 5,700,673.

Full protocols for use of such kits are provided by the manufacturer with each kit. A brief example of a typical experimental procedure may include:

Assembling kit reagents (except target T7-luc plasmid), plus PE test samples (using an experimentally determined titration of PE test samples; e.g., in a range of 0-500 ng DNA per reaction for PCR templates or using a PE protein titre in a range to be determined experimentally), in a total volume of 12.5 ul RNAse-free water in PCR tubes or cell wells on plates.

For plasmid DNA: Pre-incubate for required time (e.g. 30-60 min, time to be determined experimentally) at 30° C. to allow pre-reaction transcription/translation to occur.

For purified protein: No pre-incubation step required.

Add target plasmid T7-luc (e.g. 250 ng/reaction, determined experimentally) and incubate further (e.g. 30-60 min, time to be determined experimentally) at 30° C.

Stop reaction by placing on ice. Increase sample volume to 50 ul with RNAse-free water.

Add luciferase reagent (e.g. SteadyGlo, 50 ul per well) to each well, incubate according to manufacturer's instructions, transfer to 96 well black/white plate and read chemiluminescent signal via chemiluminescence platereader.

Compare to 'zero toxin' control samples (i.e., no PE present) to determine the % inhibition of transcription/translation (i.e., as a function of inhibition of luciferase activity).

Compare inhibition of transcription/translation values of amino acid substituted/deimmunized forms of PE compared to corresponding forms of non-amino acid substituted PE.

Comparative protein synthesis inhibition values may show that various forms of DI-PE exhibit 100% or about 100% of biological activity (inhibition of protein synthesis) compared to corresponding forms of non-amino acid substituted PE. Comparative protein synthesis inhibition values may also show that various forms of DI-PE exhibit at least 95%, or at least about 95%, at least 90%, at least about 90%, at least 85%, at least about 85%, at least 80%, at least about 80%, at least 75%, at least about 75%, at least 70%, at least about 70%, at least 60%, at least about 60%, at least 50%, or at least about 50% of biological activity compared to corresponding forms of non-amino acid substituted PE.

Assays for Biological Activity: Cell Cytotoxic Activity

In one example, measurement of cell cytotoxic activity may be done via use of in vitro cell based assays wherein deimmunized PE (DI-PE)-antibody conjugates are assayed in comparison to non-amino acid substituted PE-antibody conjugates. The antibody portion of such conjugates would be antibodies, or antigen-binding fragments thereof, which specifically bind antigens expressed on the cell-surface of cell types used in such in vitro assays. Cell cytotoxicity may be quantitated, for example, by measuring cell lysis wherein the biological readout is represented by measurement of, for example, based on chemiluminescent (LUMI), fluorometric (FL), and colorimetric (COL) outputs; such as can be practiced using commercially available kits routinely used and well-known to those of skill in the art.

Some examples of kits available for measurement and comparison of DI-PE versus non-amino acid substituted PE cell cytotoxicity include, without limitation:

TOXILIGHT® BioAssay Kit (e.g., Catalog # #LT07-117 (Lonza Rockland, Inc., Rockland, Me., USA)) is a non-destructive bioluminescent cytotoxicity assay that quantitatively measures release of Adenylate Kinase (AK) from damaged mammalian cells and cell lines in vitro. The assay is based on the bioluminescent measurement of AK which is present in all cells. A loss of cell integrity, through damage to the plasma membrane, results in the leakage of a number of factors from cells cultured in vitro into the surrounding medium. The measurement of the release of AK from the cells allows the accurate and sensitive determination of cytotoxicity and cytolysis. The reaction involves two steps. The first involves the addition of ADP as a substrate for AK. In the presence of the enzyme, AK, the ADP is converted to ATP for assay by bioluminescence. The bioluminescent part of the assay utilizes the enzyme Luciferase, which catalyses the formation of light from ATP and luciferin. By combining these two reactions, the emitted light intensity is linearly related to the AK concentration and can be measured using a luminometer or beta counter. See, "TOXILIGHT® BioAssay Kit: Instructions for Use," ©2007 Lonza Rockland, Inc., which is incorporated by reference herein. See also, Crouch, et al., *J. Immunol. Methods,* 160(1):81-88 (1993); Olsson, T. et al., *J. Appl. Biochem* 5, 347-445 (1983); and, Squirrell et al., *A Practical Guide to Industrial Uses of ATP Luminescence in Rapid Microbiology*, p. 107-113 (1997).

CYTOTOX-GLO® (e.g., PROMEGA® catalog #G9290 (PROMEGA® Corp., Madison, Wis., USA)) is a luminescent cytotoxicity assay that measures the relative number of dead cells in cell populations. The assay measures extracellular activity of a distinct intracellular protease activity (dead-cell protease) when the protease is released from membrane-compromised cells. A luminogenic cell-impermeant peptide substrate (AAF-aminoluciferin) is used to measure dead-cell protease activity. The liberated aminoluciferin product is measured as "glow type" luminescence generated by ULTRA-GLO™ Recombinant Luciferase provided in the assay reagent. The AAF-aminoluciferin substrate cannot cross the intact membrane of viable cells and does not generate appreciable signal from the live-cell population. The amount of luminescence directly correlates with the percentage of cells undergoing cytotoxic stress. With the addition of a lysis reagent (provided with the kit), the CYTOTOX-GLO™ Assay provides a luminescent signal associated with the total number of cells in each assay well. Viability can be calculated by subtracting the luminescent dead-cell signal from the total luminescent value, thus allowing normalization of assay data to cell number and mitigation of assay interferences. The cytotoxicity protease biomarker is constitutive and conserved across cell lines. See e.g., PROMEGA® Technical Bulletin Nos. TB359 (Revised 05/2009 & Revised 10/2011) which is incorporated by reference herein. See also, Niles, A. et al. (2007) *Anal. Biochem.,* 366, 197-206 (2007) and U.S. Pat. Nos. 6,602,677 and 7,241,584.

CYTOTOX-ONE™ kit (e.g., PROMEGA® catalog #G7891 (PROMEGA® Corp., Madison, Wis., USA)) allows performance of homogeneous membrane integrity assays wherein a fluorometric method may be used to estimate the number of nonviable cells present in multiwell plates. This assay measures the release of lactate dehydrogenase (LDH) from cells with damaged membranes. LDH released into the culture medium is measured with a coupled enzymatic assay that results in the conversion of resazurin into a fluorescent resorufin product. The amount of fluorescence produced is proportional to the number of lysed cells (which may be monitored using a 96- or 384-well plate formats). The CYTOTOX-ONE™ Reagent does not damage normal healthy cells. Therefore, reactions to measure released quantities of LDH can be performed directly in a homogeneous format in assay wells containing a mixed population of viable and damaged cells. See e.g., PROMEGA® Technical Bulletin #TB306 (Revised 05/2009) which is incorporated by reference herein. See also, U.S. Pat. Nos. 6,982,152 and 7,282,348.

CELLTITER GLO® Luminescent Cell Viability Assay (e.g., PROMEGA® catalog #G7571 (PROMEGA® Corp., Madison, Wis., USA)) provides a homogeneous method for determining the number of viable cells in a culture based on quantitation of the amount of ATP present (an indicator of metabolically active cells). The CELLTITER GLO® Assay is particularly useful for automated high-throughput screening (HTS), cell proliferation and cytotoxicity assays. The homogeneous assay procedure involves adding the single reagent (CELLTITER GLO® Reagent) directly to cells cultured in serum-supplemented medium. The assay allows for detection of as few as 15 cells/well in a 384-well format in 10 minutes after adding reagent and mixing. The homogeneous "add-mix-measure" format results in cell lysis and generation of a luminescent signal proportional to the amount of ATP present (which is directly proportional to the number of cells present in culture). The CellTiter-Glo® Assay generates a "glow-type" luminescent signal, which has a half-life generally greater than five hours, depending on cell type and medium used. See e.g., PROMEGA® Technical Bulletin Nos. TB288 (Revised 06/2009 & Revised 08/2011) which are incorporated by reference herein. See also: U.S. Pat. Nos. 6,602,677; 7,241,584; 7,700,310; 7,083,911; 7,452,663; 7,732,128; 7,741,067; 5,583,024, 5,674,713; and 5,700,673.

VIALIGHT® Plus Kit (e.g., Catalog ##LT07-221 (Lonza Rockland, Inc., Rockland, Me., USA)) may be used for rapid detection of cytotoxicity in mammalian cells and cell lines in culture via determination of ATP levels. Any form of cell injury results in a rapid decrease in cytoplasmic ATP levels. Therefore, the VIALIGHT® Plus Kit may be used to measure a wide range of biological activities effecting cell viability. The kit is formulated for use with a microtitre plate reading luminometer for assay automation. The assay is based on bioluminescent measurement of ATP is present in all metabolically active cells. The bioluminescent method utilizes an enzyme, luciferase, which catalyses the formation of light from ATP and luciferin according to the following reaction:

$$ATP+Luciferin+O2\text{-}Luciferase/Mg^{2+}\text{->}Oxyluciferin+AMP+PPi+CO_2+LIGHT$$

The emitted light intensity is linearly related to the ATP concentration and can be measured using a luminometer or beta counter. The assay is conducted at ambient temperature (18° C.-22° C.), the optimal temperature for luciferase enzymes. See, "VIALIGHT® Plus Kit: Instructions for Use," ©2007 Lonza Rockland, Inc, which is incorporated by reference herein.

Full protocols for use of such kits are provided by the manufacturer with each kit. A brief example of a typical experimental procedure may include:

Plate cells to test plate (e.g., 96 well plates) in growth medium.

Incubate cells with titrations of amino acid substituted forms of PE-toxin conjugates (including zero toxin and non-amino acid substituted PE controls (up to a maximum toxicity point, e.g. 100% cell lysis) for required time (determined experimentally, e.g. 48-72 hr).

Add kit reagents for cytotoxicity measurements as per manufacturer's instructions.

Transfer test samples to 96 well black/white walled plate (as appropriate) and read reaction signal output.

Compare cell cytotoxicity values obtained for substituted/deimmunized forms of PE versus corresponding non-amino acid substituted forms of PE.

Comparative cell cytotoxicity values may show that various forms of DI-PE exhibit 100% or about 100% of biological activity (induction of cell cytotoxicity) compared to corresponding forms of non-amino acid substituted PE. Comparative cell cytotoxicity values may also show that various forms of DI-PE exhibit at least 95%, or at least about 95%, at least 90%, at least about 90%, at least 85%, at least about 85%, at least 80%, at least about 80%, at least 75%, at least about 75%, at least 70%, at least about 70%, at least 60%, at least about 60%, at least 50%, or at least about 50% of biological activity compared to corresponding forms of non-amino acid substituted PE.

Example 4

Measuring Ability of Deimmunized PE Variants to Inhibit Protein Synthesis

Quantitative in vitro transcription/translation (IVTT) assays to assess the biological activity of deimmunized variants of PE in inhibiting protein synthesis (i.e., possess wild-type PE biological activity) may be performed using the TNT® Quick Coupled Transcription/Translation Systems assay from PROMEGA® Corp. (Madison, Wis., USA). See, PROMEGA® Technical Bulletin #TB 126 (Revised 12/2010) which is incorporated by reference herein.

Example 5

Measuring Ability of a PE-IL2 Fusion Protein to Inhibit Protein Synthesis in an In Vitro Transcription/Translation (IVTT) Assay A preliminary experiment was performed to compare the ability of a PE-IL2 fusion protein to inhibit protein synthesis in an in vitro transcription/translation assay when a commercially available PE-IL fusion protein is translated in vitro following transcription from either a circular plasmid expression vector or a linearized plasmid expression vector. The PE-IL2 expression vector in this experiment is referred to as "VVN-52431." A few examples of IL2-PE fusion construct are shown in SEQ ID NO: 164, 165 and 166. The aim of this experiment was to determine if circular or linearized plasmids produced significantly different quantities of PE-IL protein in the PROMEGA® Corp. TNT® Quick Coupled Transcription/Translation Systems assay. A commercially available T7 Promoter/Luciferase expression vector (PROMEGA® Corp.; hereinafter "T7-Luc DNA") was used to measure the ability of PE-IL2 to inhibit protein synthesis in vitro.

Based on a pilot IVTT experiment, it was determined that 0.2 μg T7-Luc DNA provided optimal RLU (Relative Light Units) in a 90 minute IVTT reaction. In this experiment, VVN-52431 was linearized using the restriction enzyme Fsp-I. Linearized and circular VVN-52431 DNA were used as templates in the IVTT reactions. Reactions were done in triplicate, using 0.5, 1 and 2 μg of DNA. The T7 control reaction was performed using 1 μg DNA. Reactions were analyzed via SDS-PAGE and by Luciferase assay.

Materials:

| Item | Vendor | Lot # |
|---|---|---|
| Nuclease-free water (1000 ml) | Ambion | 1105062 |
| TNT T7 Quick Coupled T/T system | PROMEGA ® | 328577 |
| T7 luciferase plasmid DNA (From same kit) | PROMEGA ® | |
| Fsp I | NEB | 0571101 |
| Dual Glo ® Luciferase Assay System | PROMEGA ® | 322310 |
| Ultrapure Water | GIBCO | 896656 |
| Tris-Glycine SDS Sample Buffer, 2x | Invitrogen | 743995 |

-continued

| Item | Vendor | Lot # |
|---|---|---|
| 10x Reducing Agent | Invitrogen | 897034 |
| Criterion Tris HCl 4-15%, 1 mm, 12 + 2 well | Bio-Rad | 400059499 |
| Precision Plus Protein Standards, Kaleidoscope | Bio-Rad | 310009928 |
| 10x Tris/Glycine/SDS Buffer | Bio-Rad | 210007884 |
| Gelcode Blue Safe Protein Stain | ThermoFisher | LL152043 |

Equipment:

| Item | Vendor | ID # |
|---|---|---|
| P20, P200, P1,000 | Rainin | N/A |
| Water bath | | |
| Luminometer | | |
| Power Pac HC | Bio-Rad | N/A |
| Heat block | VWR | N/A |
| Microcentrifuge, refrigerated | Eppendorf | N/A |
| Platform Adjustable Tilt Rocker | Labnet | N/A |
| Thermal cycler | MJ Research | N/A |

Procedure:

Per manufacturer's instructions: Except for the actual transcription/translation incubation, all handling of the TNT® Quick Master Mix was performed at 4° C. Unused Master Mix was refrozen as soon as possible after thawing to minimize loss of translational activity.

Restriction Digest:

In PCR tubes, the following were combined:

VVN-52431 was linearized by combining the following:

| Rxn | NF $H_2O$ (μL) | VVN52431 (μL) | Fsp I dig. | final | Reaction Product |
|---|---|---|---|---|---|
| 1 | 5 | 5 (5 μg) | 0 | 0.5 μg/μl | Circular Vector - No Restriction enzyme added |
| 2 | 4 | 5 (5 μg) | 1 | 0.5 μg/μl | Linearized Vector |

Reactions were incubated at 37° C. for 60 min.

Reactions were heat inactivated at 65° C. for 20 min.

IVTT Reactions:

1. In nuclease-free 1.5 ml eppendorf tubes, the following were combined according to the chart below:
   Diluted T7-Luc DNA in NF (nuclease free) water at 1:5. Final DNA concentration=0.1 μg/μl.
   Serial diluted unlinearized and linearized VVN-52431 DNA (0.5 μg/μl) in NF water at 1:5. Final concentration=0.5 μg/μl, 0.1 μg/μl, 0.02 μg/μl.

| Rxn | NF $H_2O$ (μL) | T7 Luc DNA (μL) | VVN52431 (μL) | Fsp I dig. | Methionine (μL) | T7 TNT rex (μL) |
|---|---|---|---|---|---|---|
| 1 | 7 | 2 (0.2 μg) | | | 1 | 40 |
| 2 | 7 | | 2 (1 μg) | − | 1 | 40 |
| 3 | 7 | | 2 (1 μg) | + | 1 | 40 |
| 4 | 5 | 2 (0.2 μg) | 2 (1 μg) | − | 1 | 40 |
| 5 | 5 | 2 (0.2 μg) | 2 (0.2 μg) | − | 1 | 40 |
| 6 | 5 | 2 (0.2 μg) | 2 (0.04 μg) | − | 1 | 40 |
| 7 | 5 | 2 (0.2 μg) | 2 (1 μg) | + | 1 | 40 |
| 8 | 5 | 2 (0.2 μg) | 2 (0.2 μg) | + | 1 | 40 |
| 9 | 5 | 2 (0.2 μg) | 2 (0.04 μg) | + | 1 | 40 |
| 10 | 9 | | | | 1 | 40 |

2. Reactions were incubated at 30° C. for 90 minutes in a water bath.
3. Reactions were analyzed for the synthesis of functional Luciferase using a standard Luciferase assay.

Luciferase Assay:

1. Luciferase assay substrate was prepared according to manufacturer's instructions:
   Reagent Kit was thawed at room temperature.
   Dual-Glo® Luciferase Buffer was transferred into the Dual-Glo® Luciferase Substrate bottle and shaken slightly to ensure the substrate dissolved.
   Dual-Glo® Stop & Glo® substrate was transferred into the Dual-Glo® Stop & Glo® buffer and mixed well.
   Rehydrated reagent was aliquoted into 15 ml centrifuge tube (10 ml/tube) and wrapped with Aluminum foil.
   Rehydrated reagent was stored at −80° C. until ready for use (the reagent is good for 6 months).
2. 5 μl of reaction end products/well were transferred into a 96-well white plate
3. 100 μL of the Luciferase Assay Reagent was dispensed per well and mixed by pipetting 2-3×.
4. RLU's for each well on plate were read within 10 minutes.

Figure 9:
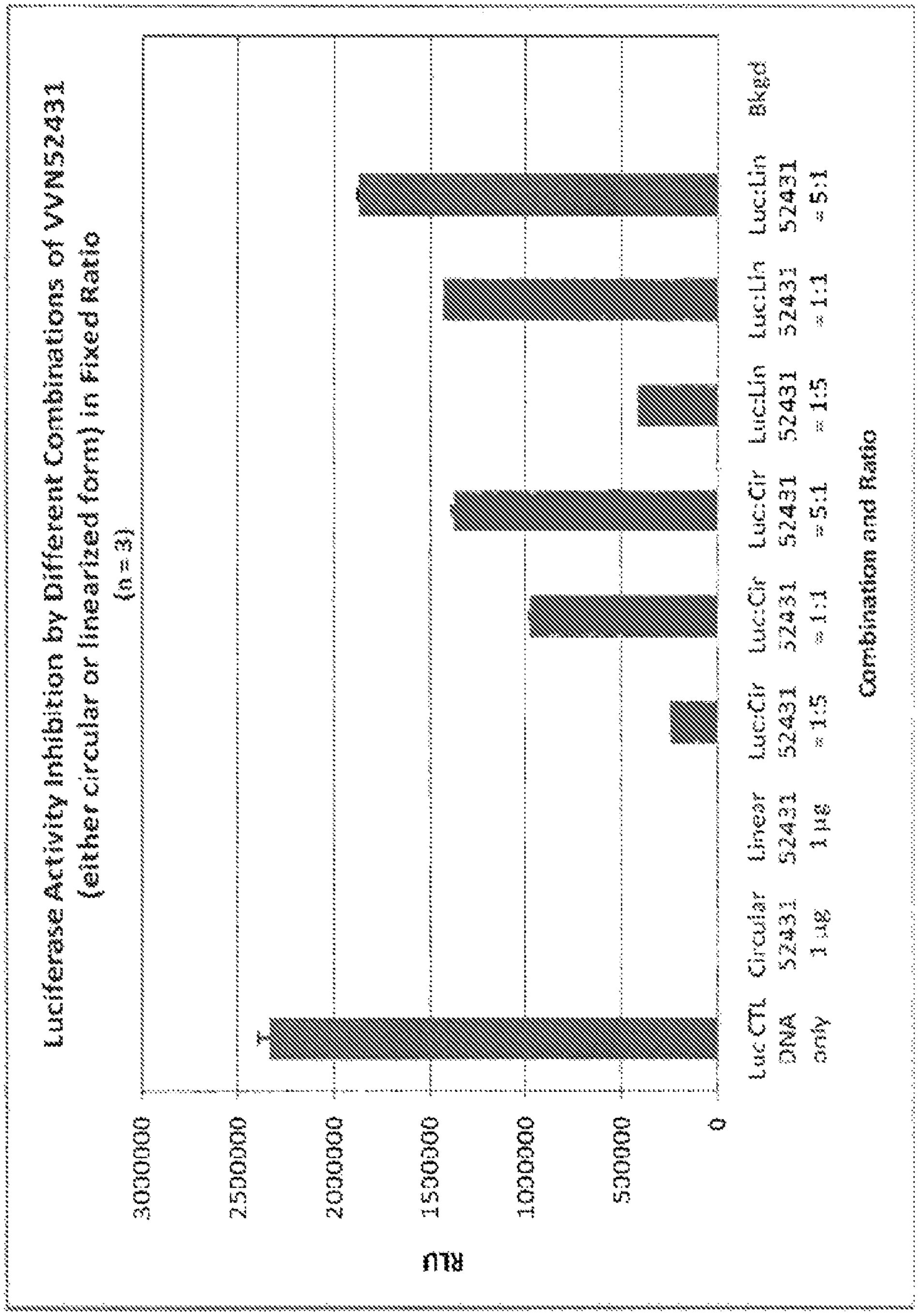
FIG. 9. In vivo Transcription/Translation (IVTT) shows that circular plasmid expression vector encoding PE38-IL2 fusion protein was slightly better at inhibiting Luciferase protein synthesis compared to linearized plasmid encoding the same PE38-IL2 fusion protein.

Results:

Results are shown in FIG. 9. Circular plasmid expression vector encoding PE-IL2 fusion protein was slightly better at inhibiting Luciferase protein synthesis compared to linearized plasmid encoding the same (at all Luciferase vector: VVN-52431 vector ratios). These results also demonstrate the ability of to test and compare the biological activity of PE-fusion proteins in inhibiting protein synthesis.

In addition to measuring inhibition of protein synthesis as a measure of light production catalyzed by Luciferase, quantitative analysis of inhibition of protein synthesis was also performed by separating polypeptide reaction products on SDS-PAGE gels, staining, and assessing amounts of polypeptide produced (data not shown).

Assays such as these may be used to compare the ability of amino acid substituted (e.g., deimmunized) forms of PE (alone or as fusion proteins) to retain biological activity (such as inhibition of protein synthesis) compared to corresponding non-amino acid substituted forms of PE (alone or as fusion proteins).

Example 6

In Vitro Transcription/Translation (IVTT) Assay to Measure and Compare Ribosylation Activity of Amino Acid Substituted Variants of PE Purpose: This protocol provides an example of they type of methods which may be used to measure and compare the ribosylation activity (i.e., inhibition of protein synthesis) of amino acid substituted forms of PE compared to corresponding non-amino acid substituted forms of PE.

Background: The IVTT assay measures PE mediated inhibition of in vitro transcription/translation of a target plasmid, T7-Luc. The level of inhibition (or lack thereof) is determined by chemiluminescent measurement of luciferase activity (i.e., the transcribed and translated protein). In this assay, a lowered level of transcription and translation (and thereby, lowered levels of chemiluminescent light output) corresponds to increased inhibition of protein synthesis. IVTT can be performed using template DNA encoding PE, or by directly using quantified protein. This assay may be used to rank different PE variants against each other and to compare their biological activities to corresponding non-amino acid substituted forms.

Materials: Test sample: Vectors comprising either circular plasmids with an SP6 promoter or linearized plasmids with a T7 promoter.

| Reagents and Materials | Vendor |
|---|---|
| Nuclease-free water (1000 ml) | Ambion |
| TNT SP6 Quick Coupled T/T system | PROMEGA ® |
| SP6 luciferase plasmid DNA (From same kit) | PROMEGA ® |
| RNase-free 1.5 ml microfuge tubes | Ambion |
| Dual Glo ® Luciferase Assay System | PROMEGA ® |

Equipment:

| Item | Vendor |
|---|---|
| P20, P200, P1,000 | Rainin |
| 96 well white plate | Costar |
| Water bath (circulation) | |
| Luminometer | |
| Microcentrifuge, refrigerated | Eppendorf |

Reagent Preparation:

Luciferase Preparation:

1. Thaw reagent Kit on ice or at 4 degrees C.
2. Transfer entire Dual-Glo® Luciferase Buffer into Dual-Glo® Luciferase Substrate bottle and shake bottle slightly to ensure substrate completely dissolved.
3. Transfer entire Dual-Glo® Stop & Glo® substrate into Dual-Glo® Stop & Glo® buffer and mix well.
4. Aliquot rehydrated reagent into 15 ml centrifuge tube (10 ml/tube) and wrap tube with Aluminum foil.
5. Store rehydrated reagent in −80° C. Freezer (reagent is good for 6 months)

Procedure:

Per manufacturer's recommendations: Except for the actual transcription/translation incubation, all handling of TNTR Quick Master Mix should be done at 4° C. Any unused Master Mix should be refrozen as soon as possible after thawing to minimize loss of translational activity. Do not freeze-thaw the Master Mix more than two times.

Plasmid DNA Dilution: Dilute plasmid DNA and Luc plasmid DNA in nuclease free water to final concentration of 0.1 μg/μl.

IVTT Reactions

1. In 1.5 ml NF (nuclease free) eppendorf tubes, the following are combined for each test sample:
   a. 5 μL of NF $H_2O$;
   b. 2 μl, 0.1 μg/μl test plasmid (for increased accuracy of results test a dilution series of samples);
   c. 1 μl, 1 mM Methionine;
   d. 40 μL TNT quick master mix;
   e. Negative control (reaction mix only. NF water 9 μl, methionine 1 μl, reaction mixture 40 μl;
2. Incubate reaction mixes at 30° C. for 15 minutes in water bath;
3. Add 2 μl, 0.1 μg/μl Luc plasmid to each reaction mix;
4. Incubate reactions at 30° C. for 90 minutes in water bath; and
5. Transfer all samples onto ice to stop reaction.

Luciferase Assay

6. Transfer 5 μl of end product/well into 96-well white plates in triplicate;
7. Dispense 100 μL of Luciferase Assay Reagent per well. Mix by pipetting 2-3×;
8. Read entire plate within 10 minutes.

Calculations

1. Calculate percent inhibition based on relative luminescence units (RFU) of the test sample divided by the RFU of the LUC plasmid with no test sample, then subtract the result from 100.
2. Calculate the percent of activity of non-amino acid substituted PE by percent inhibition of the test sample divided by the percent inhibition of non-amino acid substituted, then multiply the result by 100.
3. If a dilution series of samples is tested, calculate the IC50 (half maximal inhibition concentration) for each sample using the RFU of the test sample divided by the RFU of the LUC plasmid alone, then subtract the result from 100. Determine the concentration which results in 50% inhibition.
4. Calculate the percent of non-amino acid substituted PE inhibition by dividing the IC50 of the non-amino acid substituted PE by the IC50 of the test sample and multiplying the result by 100.

Example 7

Ex Vivo Assays to Assess Immunogenicity of Amino Acid Substituted Forms of PE (i.e. Deimmunized PE) Versus Corresponding Non-Amino Acid Substituted Forms The immunogenicity of amino acid substituted forms of PE (alone or as PE-fusion proteins) are assessed using methods well-known and routinely used by those skilled in the art. For example, ELISA assays are used wherein serum is assayed ex vivo (following extraction from organisms in which amino acid substituted forms of PE, or non-amino acid substituted PE, (alone or as fusion proteins) are administered) to determine whether or not antibodies that specifically bind the administered protein are produced. It is noted that in the case of PE-fusion proteins it is necessary to use, as the ELISA assay target antigen, not only intact PE-fusion proteins (i.e., amino acid substituted or non-amino acid substituted PE), but to also test the PE component and the polypeptide fusion component separately to determine whether or not antibodies produced specifically bind the PE portion or the fusion polypeptide portion (e.g., IL2 as used in a previous example of a PE-IL2 fusion protein). Accordingly, it is most desirable to identify amino acid substituted forms of PE which do not result in host production of antibodies that specifically bind modified forms of PE (i.e., deimmunized forms of PE).

Organisms in which amino acid substituted forms of PE may be administered (alone or as fusion proteins) include, for example, without limitation: mice (including transgenic mice expressing human immunoglobulin genes), rats, rabbits, dogs, goats, sheep, horses, cows (and other bovine species), non-human primates, and humans.

Example 8

In Vitro and In Vivo Assays to Assess Cytotoxicity of Amino Acid Substituted Forms of PE The cytotoxicity of amino acid substituted forms of PE (alone or as PE-fusion proteins) are assessed using methods well-known and routinely used by those skilled in the art. For example, the cytotoxic effects of amino acid substituted forms of PE (alone or as PE-fusion proteins) administered to cells in vitro or organisms in vivo, may be assessed with reference to cytotoxic (cell killing) effects on target cells, organs, tissues, or tumors against which PE or PE fusion proteins are expected to produce a cytotoxic effect. For example, the therapeutically beneficial cytotoxic effects of amino acid substituted PE-Mesothelin fusions may be assessed by monitoring and measuring reduction or elimination of tumor or cancer cells or tissues (in vitro or in vivo) in response to administration of amino acid substituted forms of PE-Mesothelin versus wild-type PE-Mesothelin fusion.

Organisms in which amino acid substituted forms of PE may be administered (alone or as fusion proteins) include, for example, without limitation: mice (including transgenic mice expressing human immunoglobulin genes), rats, rabbits, dogs, goats, sheep, horses, cows (and other bovine species), non-human primates, and humans.

Examples 9-13: Oligonucleotides Referenced in the Following Examples are Listed in Table 12.

Example 9

Generation of cDNAs Encoding Amino Acid Substituted Forms of PE

The Kozak sequence in vector pET14b (EMD Millipore catalog #69660, Darmstadt, Germany) was modified by introducing a linker made up of annealed oligonucleotides 5'-CATGGT <u>GGC</u>TCTCCTTCTTAAAGTTAAACAAAATTATTT-3' (SEQ ID NO:239)(OL2216 in Table 12) and 5'-CTAGAAATAATTTTGTTTAACTT-TAAGAAGGAGA<u>GCC</u>AC-3' (SEQ ID NO:240)(OL2217 in Table 12) (underlined letters indicate nucleotides changed in the Kozak sequence*) via NcoI and XbaI restriction sites into vector pET14b resulting in a modified Kozak sequence (SEQ ID NO:176) by mutation of three nucleotides at positions 587 to 589. The resulting vector was named pET14b-K.

*Kozak sequence=(gcc)gccRccAUGG (SEQ ID NO:286), where R is a purine (i.e., adenine or guanine) three bases upstream of the start codon (AUG), which is followed by another 'G'. See, Kozak, *Nucleic Acids Res.* 15 (20): 8125-8148 (1987).

Oligonucleotides for generation of genes encoding amino acid substituted forms of PE are listed as OL2164 to OL2194 and OL2281 to OL2366 in Table 12. A wild-type (WT) PE gene (SEQ ID NO:1) was made by gene synthesis and amplified using oligonucleotides: 5'-ATTGTCCATATGC-CAGAAGGCGGTAGCCTGGC-3' (SEQ ID NO:215) (OL2154 in Table 12) to introduce a NdeI site, and 5'-ATCCTCGAGTTACTTCAGGTCCTCACGCGGCG-3' (SEQ ID NO:222)(OL2167 in Table 12) to introduce a XhoI site. The resulting DNA fragment was subcloned into pGEMT®-T (PROMEGA® catalogue #A1360, PROMEGA®, Southampton, UK). Colonies were screened by PCR using M13 primers OL0001 and OL0002 (Table 12). Subsequently the wild-type (WT) PE gene was subcloned into pET14b-K using NdeI and XhoI restriction enzymes (Fermentas catalog #FD0583 and FD0695, respectively) and resulting in a gene encoding an N-terminal His6 tag fused to the WT PE sequence. The resulting vector was named pET14b-K-WT PE.

Oligonucleotides for generation of genes encoding amino acid substituted forms Genes encoding amino acid substituted forms of PE were generated using overlapping PCR with the WT PE gene in pET14b-K as template. Pairs of primers from the oligonucleotides of Table 12 (as noted in the "application" column of Table 12) were annealed to WT PE DNA and the amino acid substituted genes were PCR amplified using terminal oligonucleotides: 5'-ATCTC-CCTCTAGAAATAATTTTGTTTAACTTTAAGAAG-3' (SEQ ID NO:241)(OL2268 in Table 12) and 5'-ATCCTCGAGTTACTTCAGGTCCTCACGCGGCG-3' (SEQ ID NO:216)(OL2161 in Table 12). PCR fragments were and cloned into pET14b-K using XbaI and XhoI restriction sites.

TABLE 12

| Oligonucleotides | | | | |
|---|---|---|---|---|
| Name | | sequence | length | application |
| OL | 001 | CGCCAGGGTTTTCCCAGTCAC GAC (SEQ ID NO: 205) | 24 | M13 FOR |
| OL | 002 | AGCGGATAACAATTTCACACA GGA (SEQ ID NO: 206) | 24 | M13 REV |
| OL | 2043 | GAAGTGCAGCTGGTGGAG (SEQ ID NO: 207) | 18 | RFB4 VH5' PCR primer sequence |
| OL | 2044 | CAGAGCCACCTCCGCCTGAAC CGCCTCCACCTGAGGAGACA GTGACCAG (SEQ ID NO: 208) | 49 | RFB4 VH3' PCR primer sequence |
| OL | 2045 | CAGGCGGAGGTGGCTCTGGC GGTGGCGGATCGGATATCCA GATGACCCAG (SEQ ID NO: 209) | 50 | RFB4 VK 5' PCR Primer Sequence |
| OL | 2046 | TTTGATCTCCAGCTTGGTG (SEQ ID NO: 210) | 19 | RFB4 VK 3' PCR Primer sequence |

TABLE 12 -continued

Oligonucleotides

| Name | sequence | length | application |
|---|---|---|---|
| OL 2047 | CCCAGCCGGCCATGGCGGAA GTGCAGCTGGTGGAG (SEQ ID NO: 211) | 35 | RFB4 Pull through Primer (FOR)) |
| OL 2048 | GGTGCTCGAGTGCGGCCGCCC GTTTGATCTCCAGCTTGGTG (SEQ ID NO: 212) | 41 | RFB4 Pull through Primer (REV) |
| OL 2097 | AACCGCCCGGCCGTTCTTCTC CGTGTTGCCCGGAAAGCC (SEQ ID NO: 213) | 39 | IEX02 GroEL/ES REV |
| OL 2098 | GGGCCAAAGCTTGTTCTTGTT TGAGTCCACTCATGG (SEQ ID NO: 214) | 36 | IEX02 GroEL/ES FOR |
| OL 2154 | ATTGTCCATATGCCAGAAGGC GGTAGCCTGGC (SEQ ID NO: 215) | 32 | IEX02 PE38 FOR, introducing NdeI |
| OL 2161 | ATCCTCGAGTTACTTCAGGTC CTCACGCGGCG (SEQ ID NO: 216) | 32 | IEX02 PE38 REV, introducing XhoI |
| OL 2162 | GGGTGGTCGCCTGGACACTAT CCTGGGTTG (SEQ ID NO: 217) | 30 | IEX02 PE38 NM E229D FOR |
| OL 2163 | CAACCCAGGATAGTGTCCAG GCGACCACCC (SEQ ID NO: 218) | 30 | IEX02 PE38 NM E229D REV |
| OL 2164 | CAGTACGATAGAAACCCGGC AGATTGCTGCGCGGTACGTA (SEQ ID NO: 219) | 40 | IEX02 PE38 S253N |
| OL 2165 | CAGTACGATAGAAACCCGGC AGCTTGCTGCGCGGTACGTA (SEQ ID NO: 220) | 40 | IEX02 PE38 S253K |
| OL 2166 | CAGTACGATAGAAACCCGGC AGAGGGCTGCGCGGTACGTA (SEQ ID NO: 221) | 40 | IEX02 PE38 S253P |
| OL 2167 | CAGTACGATAGAAACCCGGC AGGGTGCTGCGCGGTACGTA (SEQ ID NO: 222) | 40 | IEX02 PE38 S253T |
| OL 2168 | GTACGTGCTCGTAGCAGAGAC CTGGATGCCATC (SEQ ID NO: 223) | 33 | IEX02 PE38 Q206R |
| OL 2169 | GATGGCATCCAGGTCTCTGCT ACGAGCACGTAC (SEQ ID NO: 224) | 33 | IEX02 PE38 Q206R |
| OL 2170 | CGTAGCCAGGACCTGAAGGC CATCTGGCGTGGC (SEQ ID NO: 225) | 33 | IEX02 PE38 D209K |
| OL 2171 | GCCACGCCAGATGGCCTTCAG GTCCTGGCTACG (SEQ ID NO: 226) | 33 | IEX02 PE38 D209K |
| OL 2183 | GAAGCTGCTCAGTCTGCCGTG TTCGGTGGCGT (SEQ ID NO: 227) | 32 | IEX02 PE38I196A FOR, to pair with OL2161 |
| OL 2184 | ACGCCACCGAACACGGCAGA CTGAGCAGCTTC (SEQ ID NO: 228) | 32 | IEX02 PE38I196A REV, to pair with OL2268 |
| OL 2185 | GAAGCTGCTCAGTCTAACGTG TTCGGTGGCGT (SEQ ID NO: 229) | 32 | IEX02 PE38I196N FOR, to pair with OL2161 |

TABLE 12 -continued

| Oligonucleotides | | | |
|---|---|---|---|
| Name | sequence | length | application |
| OL 2186 | ACGCCACCGAACACGTTAGA CTGAGCAGCTTC (SEQ ID NO: 230) | 32 | IEX02 PE38I196N REV, to pair with OL2268 |
| OL 2187 | GGTGATGGCGGCGATGCCTCT TTTTCTACCCGC (SEQ ID NO: 231) | 33 | IEX02 to introduce I153A FOR |
| OL 2188 | GCGGGTAGAAAAAGAGGCAT CGCCGCCATCACC (SEQ ID NO: 232) | 33 | IEX02 to introduce I153A REV |
| OL 2189 | GGTGATGGCGGCGATACCTCT TTTTCTACCCGC (SEQ ID NO: 233) | 33 | IEX02 to introduce I153T FOR |
| OL 2190 | GC GGGTAGAAAAAGAGGTAT CGCCGCCATCACC (SEQ ID NO: 234) | 33 | IEX02 to introduce I153T REV |
| OL 2191 | GGTGATGGCGGCGATCACTCT TTTTCTACCCGC (SEQ ID NO: 235) | 33 | IEX02 to introduce I153H FOR |
| OL 2192 | GCGGGTAGAAAAAGAGTGAT CGCCGCCATCACC (SEQ ID NO: 236) | 33 | IEX02 to introduce I153H REV |
| OL 2193 | GCACCCAGAACTGGAGAGTT GAACGTCTGCTG (SEQ ID NO: 237) | 32 | IEX02 to introduce T164R FOR |
| OL 2194 | CAGCAGACGTTCAACTCTCCA GTTCTGGGTGC (SEQ ID NO: 238) | 32 | IEX02 to introduce T164R REV |
| OL 2216 | CATGGTGGCTCTCCTTCTTAA AGTTAAACAAAATTATTT (SEQ ID NO: 239) | 39 | IEX02 Linker to optimize Kozak in pET14b, to anneal with OL2217 |
| OL 2217 | CTAGAAATAATTTTGTTTAAC TTTAAGAAGGAGAGCCAC (SEQ ID NO: 240) | 39 | IEX02 Linker to optimize Kozak in pET14b, to anneal with OL2216 |
| OL 2268 | ATCTCCCTCTAGAAATAATTT TGTTTAACTTTAAGAAG (SEQ ID NO: 241) | 38 | IEX02 outside FOR spanns over XbaIsite (pET14b)-to be paired with OL2161 |
| OL 2279 | GAAGCTGCTCAGTCTATCGTG TTCGGTGGCGT (SEQ ID NO: 242) | 32 | IEX02 FOR oligo to remove TM to be paired with OL2161 |
| OL 2280 | ACGCCACCGAACACGATAGA CTGAGCAGCTTC (SEQ ID NO: 243) | 32 | IEX02 REV oligo to remove TM to be paired with OL2268 |
| OL 2281 | CTCTGCTACGAGCACGGGCGC CACCGAACACG (SEQ ID NO: 244) | 32 | IEX02 A201 REV, ONLY for templates having Q206 |
| OL 2282 | CGTGTTCGGTGGCGCCCGTGC TCGTAGCAGAG (SEQ ID NO: 245) | 32 | IEX02 A201 FOR, ONLY for templates having Q206 |
| OL 2283 | CATCCAGGTCTCTGCTGGCAG CACGTACGCCAC (SEQ ID NO: 246) | 33 | IEX02 A204 REV, ONLY for templates having Q206 |
| OL 2284 | GTGGCGTACGTGCTGCCAGCA GAGACCTGGATG (SEQ ID NO: 247) | 33 | IEX02 A204 FOR, ONLY for templates having Q206 |
| OL 2285 | CATCCAGGTCTCTGCTCTGAG CACGTACGCCAC (SEQ ID NO: 248) | 33 | IEX02 Q204 REV, ONLY for templates having Q206 |

TABLE 12 -continued

| Oligonucleotides | | | | |
|---|---|---|---|---|
| Name | | sequence | length | application |
| OL | 2286 | GTGGCGTACGTGCTCAGAGCA GAGACCTGGATG (SEQ ID NO: 249) | 33 | IEX02 Q204 FOR, ONLY for templates having Q206 |
| OL | 2287 | CCAGTTCTGGGTGCCGGCGGT AGAAAAAGAG (SEQ ID NO: 250) | 31 | IEX02 A158 REV |
| OL | 2288 | CTCTTTTTCTACCGCCGGCAC CCAGAACTGG (SEQ ID NO: 251) | 31 | IEX02 A158 FOR |
| OL | 2289 | CCAGTTCTGGGTGCCCTGGGT AGAAAAAGAGATATC (SEQ ID NO: 252) | 36 | IEX02 Q158 REV |
| OL | 2290 | GATATCTCTTTTTCTACCCAG GGCACCCAGAACTGG (SEQ ID NO: 253) | 36 | IEX02 Q158 FOR |
| OL | 2291 | GTCCAGTTCTGGGTGGAGCGG GTAGAAAAAGAGATATC (SEQ ID NO: 254) | 38 | IEX02 5159 REV |
| OL | 2292 | GATATCTCTTTTTCTACCCGCT CCACCCAGAACTGGAC (SEQ ID NO: 255) | 38 | IEX02 5159 FOR |
| OL | 2293 | ACCACCCAGAACTGGACCGTT GAAC (SEQ ID NO: 256) | 25 | IEX02 T159 REV |
| OL | 2294 | CCAGTTCTGGGTGGTGCGGGT AGAAAAAGAG (SEQ ID NO: 257) | 31 | IEX02 T159 FOR |
| OL | 2295 | GAGCTTGGGTCCAGATCGCCA CC (SEQ ID NO: 258) | 23 | IEX02 generic REV oligo for mutations at 333 |
| OL | 2296 | CTGGACCCAAGCTCTGCCCCG GATAAAGAAC (SEQ ID NO: 259) | 31 | IEX02 A333 FOR |
| OL | 2297 | CTGGACCCAAGCTCTAACCCG GATAAAG (SEQ ID NO: 260) | 28 | IEX02 N333 FOR |
| OL | 2298 | CTGGACCCAAGCTCTACCCCG GATAAAG (SEQ ID NO: 261) | 28 | IEX02 T333 FOR |
| OL | 2299 | CTGGACCCAAGCTCTCAGCCG GATAAAGAAC (SEQ ID NO: 262) | 31 | IEX02 Q333 FOR |
| OL | 2300 | CTGGACCCAAGCTCTCACCCG GATAAAG (SEQ ID NO: 263) | 28 | IEX02 H333 FOR |
| OL | 2301 | CTGGACCCAAGCTCTATCCCG GATAAAGAAAACGCTATTTCT GCCCTG (SEQ ID NO: 264) | 48 | IEX02 N338 FOR |
| OL | 2302 | CTGGACCCAAGCTCTATCCCG GATAAAGAAGAGGCTATTTCT GCCC (SEQ ID NO: 265) | 46 | IEX02 E338 FOR |
| OL | 2303 | CTGGCTACGAGCACGGGCGC CACCGAAC (SEQ ID NO: 266) | 28 | IEX02 V201A REV |
| OL | 2304 | GTTCGGTGGCGCCCGTGCTCG TAGCCAG (SEQ ID NO: 267) | 28 | IEX02 V201A FOR |
| OL | 2305 | CTTCAGGTCCTGGCTGGCAGC ACGTACGCC (SEQ ID NO: 268) | 30 | IEX02 R204A REV, ONLY for templates having D209K |
| OL | 2306 | GGCGTACGTGCTGCCAGCCAG GACCTGAAG (SEQ ID NO: 269) | 30 | IEX02 R204A FOR, ONLY for templates having D209K |

TABLE 12 -continued

| Oligonucleotides | | | |
|---|---|---|---|
| Name | sequence | length | application |
| OL 2307 | CTTCAGGTCCTGGCTCTGAGC ACGTACGC (SEQ ID NO: 270) | 29 | IEX02 R204Q REV, ONLY for templates having D209K |
| OL 2308 | GCGTACGTGCTCAGAGCCAG GACCTGAAG (SEQ ID NO: 271) | 29 | IEX02 R204Q FOR, ONLY for templates having D209K |
| OL 2309 | GTTCAACGGTCCAGTTGTTGG TGCCGCGGGTAG (SEQ ID NO: 272) | 33 | IEX02 Q161N REV |
| OL 2310 | CTACCCGCGGCACCAACAACT GGACCGTTGAAC (SEQ ID NO: 273) | 33 | IEX02 Q161N FOR |
| OL 2311 | GTTCAACGGTCCAGTTGGTGG TGCCGCGGGTAG (SEQ ID NO: 274) | 33 | IEX02 Q161T REV |
| OL 2312 | CTACCCGCGGCACCACCAACT GGACCGTTGAAC (SEQ ID NO: 275) | 33 | IEX02 Q161T FOR |
| OL 2313 | CAGCAGACGTTCAACGGCCC AGTTCTGGGTG (SEQ ID NO: 276) | 31 | IEX02 T164A REV |
| OL 2314 | CACCCAGAACTGGGCCGTTGA ACGTCTGCTG (SEQ ID NO: 277) | 31 | IEX02 T164A FOR |
| OL 2315 | GACGTTCAACGGTCCAGGCCT GGGTGCCGCGGG (SEQ ID NO: 278) | 33 | IEX02 N162A REV |
| OL 2316 | CCCGCGGCACCCAGGCCTGG ACCGTTGAACGTC (SEQ ID NO: 279) | 33 | IEX02 N162A FOR |
| OL 2318 | ATTGCCACCATGGCGGAAGTG C (SEQ ID NO: 280) | 22 | IEX02 FOR RFB4 (NcoI) |
| OL 2320 | CACCAGGCCGCTGCTTTTGAT CTCCAGCTTG (SEQ ID NO: 281) | 31 | IEX02 REV to create RBF4 for RFB4-PE38-8xHis to pair with OL2318 |
| OL 2321 | CAAGCTGGAGATCAAAAGCA GCGGCCTGGTG (SEQ ID NO: 282) | 31 | IEX02 FOR to create RFB4-PE38-8xHis to pair with OL2322 |
| OL 2322 | CGATTCTCGAGTTACTTCAGG TCC TC GTGGTGGTGGTGATGA TGATGATGACGCGGCGGTTTA CCC (SEQ ID NO: 283) | 66 | IEX02 REV introducing 8xHis C-terminus of PE, introducing XhoI |
| OL 2323 | CAAGCTGGAGATCAAAGCTC ATGGGGGCAGCCATCATCATC ATC (SEQ ID NO: 284) | 44 | IEX02 FOR to create RFB4-6xHis PE38 fusions (pIEX02-302 and pIEX02-304) to pair with OL2161 |
| OL 2324 | GATGATGATGATGGCTGCCCC CATGAGCTTTGATCTCCAGCT TG (SEQ ID NO: 285) | 44 | IEX02 REV to create RFB4-6xHis PE38 fusions (pIEX02-302 and pIEX02-304) to pair with OL2318 |

Example 10

Analysis of Genes Encoding Amino Acid Substituted Forms of PE by an In Vitro Transcription/Translation (IVTT) Assay The cell-free in vitro transcription/translation (IVTT) assay was performed with a TnT® T7 Coupled Reticulocyte Lysate System (PROMEGA® catalog #L4610) following the procedure described in the User's Manual provided in the kit. See, PROMEGA®, Technical Bulletin #TB 126, Revised 12/10, pp. 1-28 (2010) which is incorporated by reference herein.

WT PE in plasmid pET14b-K was used as standard on every plate and tested at concentrations ranging from 0.08 ng to 10 ng in a 12.5 microliter final volume reaction. All test samples were run in triplicate. DNAs encoding WT or amino acid substituted PE in plasmid pET14b-K were added to the IVTT reaction mix supplemented with NAD+ (final concentration 0.15 mM; Fisher Scientific catalog #BPE9746-212) and incubated at 30° C. for 15 min. Following a subsequent cooling step at 4° C. for 5 min, 250 ng of T7 Luciferase plasmid (Luciferase T7 control DNA supplied in the TnT® T7 Coupled Reticulocyte Lysate System) was added to each reaction and incubated at 30° C. for 90 min. The reaction was stopped by placing the samples on ice. Samples were analyzed using the STEADY-GLO® Luciferase Assay (PROMEGA® catalog #E2510) according to the protocol provided by the manufacturer. See, PROMEGA®, Technical Bulletin #TM051, revised 9/11, pp. 1-23 (2011) which is incorporated by reference herein. Luminescence was measured in a FLUOstar OPTIMA plate reader (BMG Labtech Ltd., Aylesbury, UK)

Figure 10:
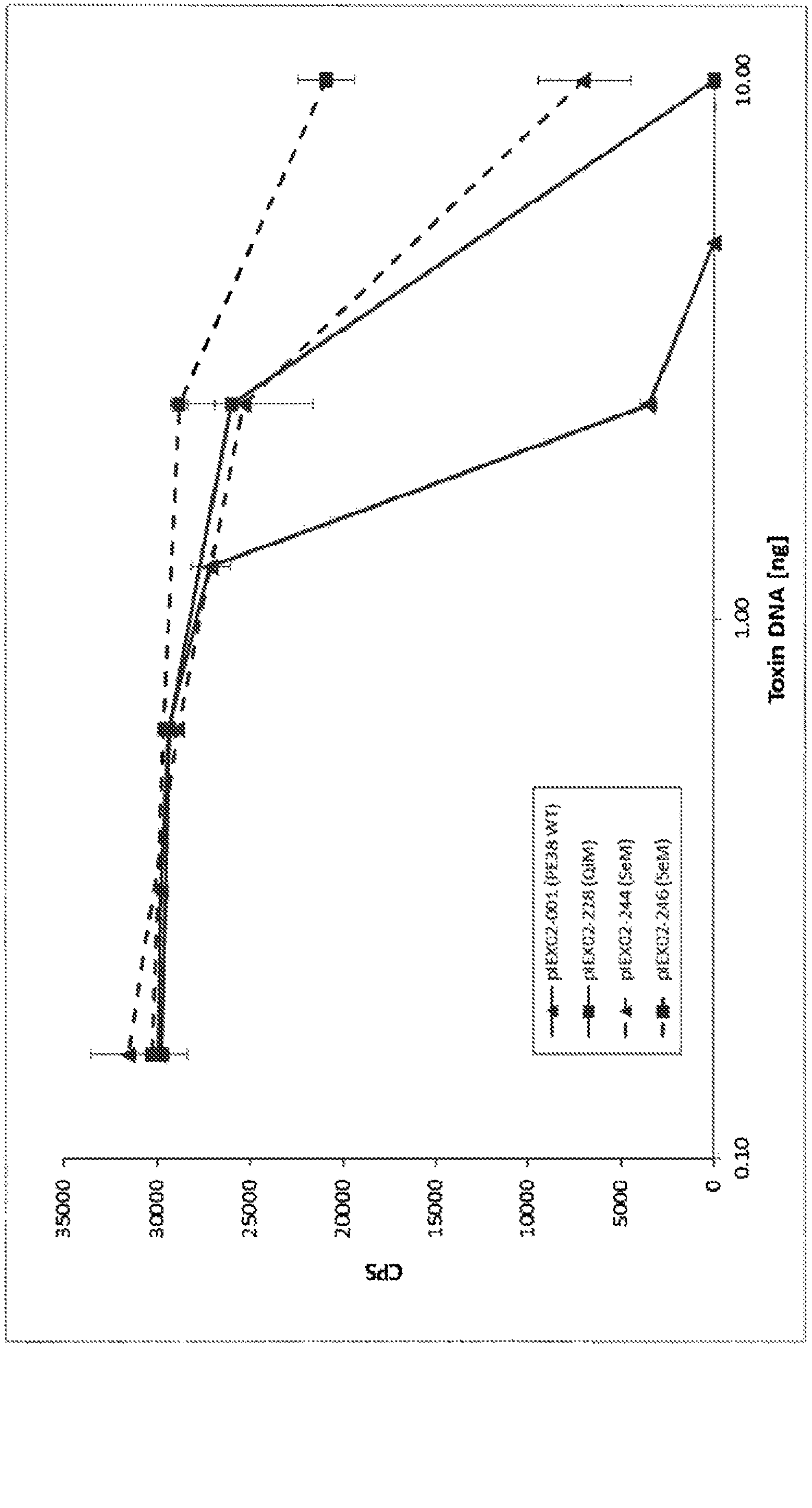
FIG. 10. Luciferase activity measure in counts per second (CPS) in In vitro Transcription/Translation (IVTT) assays of genes encoding either Wild-Type (WT) PE or encoding amino acid substituted PE.

A representative result is shown in FIG. 10 which shows the results expressed in CPS (counts per second as read from the FLUOstar OPTIMA fluorescence plate reader) for luciferase activity from IVTT assays of genes encoding either WT PE (pIEX02-001 (SEQ ID NO:1)) or encoding amino acid substituted PE (pIEX02-228 (SEQ ID NO:177), pIEX02-244 (SEQ ID NO:178), pIEX02-246 (SEQ ID NO:179)); which were expressed as fusion proteins comprising a histidine polymer and a linker sequence preceding a sequence of WT PE or amino acid substituted PE; see, pIEX02-001 PE WT (SEQ ID NO:189 (DNA) and SEQ ID NO:190 (AA)), pIEX02-228 amino acid substituted PE (SEQ ID NO:193 (DNA) and SEQ ID NO:194 (AA)), pIEX02-244 amino acid substituted PE (SEQ ID NO:197 (DNA) and SEQ ID NO:198 (AA)), pIEX02-246 amino acid substituted PE (SEQ ID NO:201 (DNA) and SEQ ID NO:202 (AA)). See also, Table 13.

For the analysis of various amino acid substituted PEs, the potency of each mutated PE in inhibiting IVTT was expressed as relative inhibition exhibited via expression from 2.5 nanograms of DNA encoding amino acid substituted PE compared to expression from 2.5 nanograms WT PE DNA as shown in Table 13 (data expressed as % inhibition of IVTT for the DNA encoding amino acid substituted PE compared to wild-type PE). In order to identify “inhibitory” amino acid substituted PE polypeptides (i.e., genes encoding amino acid substituted forms of PE which inhibit IVTT), selected mutations in each T cell epitope as identified in Table 11 were initially tested using various combinations of epitope 5 mutations (e.g., corresponding to S241N, S241K, S241P and S241T in SEQ ID NO:1) along with mutations in either: epitope 4; epitopes 4 and 3; epitopes 4 and 1; epitopes 4 and 2; or, epitopes 4 and 6 (see, Table 13). For all combinations except those including amino acid substitutions in epitope 3 at I184 (SEQ ID NO:1; or, I196 in SEQ ID NO:2) (which produced 0% inhibition), one or more inhibitory PE polypeptides were identified (Table 13). (Note: “Inhibitory PE polypeptides” indicates amino acid substituted forms of PE which exhibit PE biological activity in the inhibition of IVTT). From structural analysis of PE, it was noted that residue I184 (SEQ ID NO:1; or, I196 in SEQ ID NO:2) (anchor residue 1, Table 11) was located within the active enzymatic site of PE. In view of this result, alternative mutations distal to the active site were sought at anchor residues 6 and 9 (V189 and R192 in SEQ ID NO:1; or, V201 and R204 in SEQ ID NO:2). Alternative epitope 3 mutations at V189 and R192 in SEQ ID NO:1 were tested in combination with other epitope mutations. These mutations confirmed that inhibitory PE polypeptides with epitope 3 mutations could also be generated (Table 13, pIEX02-173 to -248). A range of combinations of DNAs encoding multiple amino acid substituted forms of PE were tested progressively leading to a final analysis of mutations in four of six, five of six, and six of six identified immunogenic epitopes. See, Table 13, “Quadruplicates”, “Quintuplicates” and “Sextuplicates”. In this regard, quadruplicate epitope mutations were identified which exhibited IVTT inhibitory activity ranging from 0% to about 70%. Quintuplicate mutations were identified that exhibited IVTT inhibitory activity ranging from about 5% to about 35%. Sextuplicate mutations were identified that exhibited IVTT inhibitory activity ranging from about 5% to about 20%. It is also noted that multiple single, double, and triple epitope mutations also resulted in amino acid substituted forms of PE exhibiting PE biological activity in the inhibition of IVTT such that the percent (%) inhibitory activity ranged from 0% to 100% (or about 100%); see Table 13.

Three different “candidates” (i.e., amino acid substituted forms of PE or DNA constructs encoding the same) were selected for use as examples in performing subsequent experiments described further herein. In particular, additional experiments were performed using the sextuplicate AA substituted candidate pIEX02-244 (SEQ ID NO:178; see also, Table 13); which retained approximately 20% of the WT PE inhibitory activity. Likewise, additional experiments were also performed using the sextuplicate AA substituted candidate pIEX02-246 (SEQ ID NO: 179; see also, Table 13) which retained approximately 8% of the WT PE inhibitory activity; and using the quintuplicate AA substituted candidate pIEX02-228 (SEQ ID NO: 177; see also, Table 13) which retained approximately 36% of the WT PE inhibitory activity. These were expressed as fusion proteins comprising a histidine polymer and a linker sequence preceding a sequence of WT PE or amino acid substituted PE; see, pIEX02-001 PE WT (SEQ ID NO:189 (DNA) and SEQ ID NO:190 (AA)), pIEX02-228 amino acid substituted PE (SEQ ID NO:193 (DNA) and SEQ ID NO:194 (AA)), pIEX02-244 amino acid substituted PE (SEQ ID NO:197 (DNA) and SEQ ID NO:198 (AA)), pIEX02-246 amino acid substituted PE (SEQ ID NO:201 (DNA) and SEQ ID NO:202 (AA)). These AA substituted PE polypeptides, and DNA constructs encoding, them may be referenced herein as “228”, “244” or “246” using simply these three numbers, or using these numbers and a prefix or suffix included therewith.

Moreover, it is noted that in view of the highly cytotoxic nature of wild-type PE, IVTT inhibition activity (i.e., cytotoxicity) as low as about 5% (or higher) of WT (e.g., 8%, 20%, and 36%) in amino acid substituted forms of PE may provide a therapeutically effective polypeptide. See, for example, Thomas et al., “Abrogation of Head and Neck Squamous Cell Carcinoma Growth by Epidermal Growth Factor Receptor Ligand Fused to *Pseudomonas* Exotoxin Transforming Growth Factor α-PE38,” *Clin. Cancer Res.* 10:7079-7087 (2004); Siegall et al., “Cell-specific toxicity of a chimeric protein composed of interleukin-6 and *Pseudomonas* exotoxin (IL6-PE40) on tumor cells”, Mol. Cell. Biol. 10(6); 2443-2447 (1990); and, Weldon & Pastan, “A Guide to Taming a Toxin—Recombinant Immunotoxins Constructed From *Pseudomonas* Exotoxin A for the Treatment of Cancer”, FEBS Journal 278(23):4683-4700 (2011).

TABLE 13

Examples of Amino Acid Substituted Forms of PE and Associated Cell Cytotoxic Activity.

| Epitopes changed | pIEX02 - ### | Epitope 5 | Epitope 4 | Epitope 3 | Epitope 1 | Epitope 2 | Epitope 6 | % Inhibition of IVTT |
|---|---|---|---|---|---|---|---|---|
| Wild-Type (WT) | | | | | | | | |
| | 001 (WT) | | | | | | | 100.00 |
| Single Substitutions | | | | | | | | |
| 5 | 003 | S241N [S253N] | | | | | | 100.00 |
| 5 | 004 | S241K [S253K] | | | | | | 100.00 |
| 5 | 005 | S241P [S253P] | | | | | | 99.71 |
| 5 | 006 | S241T [S253T] | | | | | | 99.99 |
| Double Substitutions | | | | | | | | |
| 4, 5 | 007 | S241N [S253N] | Q194R [Q206R] | | | | | 41.63 |
| 4, 5 | 008 | S241K [S253K] | Q194R [Q206R] | | | | | 69.51 |
| 4, 5 | 009 | S241P [S253P] | Q194R [Q206R] | | | | | 20.58 |
| 4, 5 | 010 | S241T [S253T] | Q194R [Q206R] | | | | | 21.44 |
| 4, 5 | 011 | S241N [S253N] | D197K [D209K] | | | | | 99.88 |
| 4, 5 | 012 | S241K [S253K] | D197K [D209K] | | | | | 42.49 |
| 4, 5 | 013 | S241P [S253P] | D197K [D209K] | | | | | 74.87 |
| 4, 5 | 014 | S241T [S253T] | D197K [D209K] | | | | | 98.84 |
| Triple Substitutions | | | | | | | | |
| 3, 4, 5 | 015 | S241N [S253N] | Q194R [Q206R] | I184A [I196A] | | | | 0.00 |
| 3, 4, 5 | 016 | S241K [S253K] | Q194R [Q206R] | I184A [I196A] | | | | 0.00 |
| 3, 4, 5 | 017 | S241P [S253P] | Q194R [Q206R] | I184A [I196A] | | | | 0.00 |
| 3, 4, 5 | 018 | S241T [S253T] | Q194R [Q206R] | I184A [I196A] | | | | 0.00 |
| 3, 4, 5 | 019 | S241N [S253N] | Q194R [Q206R] | I184N [I196N] | | | | 0.00 |
| 3, 4, 5 | 020 | S241K [S253K] | Q194R [Q206R] | I184N [I196N] | | | | 0.00 |
| 3, 4, 5 | 021 | S241P [S253P] | Q194R [Q206R] | I184N [I196N] | | | | 0.00 |
| 3, 4, 5 | 022 | S241T [S253T] | Q194R [Q206R] | I184N [I196N] | | | | 0.00 |
| 3, 4, 5 | 024 | S241K [S253K] | D197K [D209K] | I184A [I196A] | | | | 0.00 |
| 3, 4, 5 | 027 | S241N [S253N] | D197K [D209K] | I184N [I196N] | | | | 0.00 |
| 3, 4, 5 | 028 | S241K [S253K] | D197K [D209K] | I184N [I196N] | | | | 0.00 |
| 3, 4, 5 | 029 | S241P [S253P] | D197K [D209K] | I184N [I196N] | | | | 0.00 |
| 3, 4, 5 | 030 | S241T [S253T] | D197K [D209K] | I184N [I196N] | | | | 0.00 |
| 1, 4, 5 | 127 | S241T [S253T] | Q194R [Q206R] | | I141A [I153A] | | | 15.58 |
| 1, 4, 5 | 128 | S241T [S253T] | Q194R [Q206R] | | I141T [I153T] | | | 14.16 |
| 1, 4, 5 | 129 | S241T [S253T] | Q194R [Q206R] | | I141H [I153H] | | | 56.73 |
| 1, 4, 5 | 130 | S241T [S253T] | D197K [D209K] | | I141H [I153H] | | | 20.46 |
| 1, 4, 5 | 131 | S241T [S253T] | D197K [D209K] | | I141T [I153T] | | | 86.84 |
| 1, 4, 5 | 132 | S241T [S253T] | D197K [D209K] | | I141A [I153A] | | | 88.15 |
| 1, 4, 5 | 139 | S241T [S253T] | D197K [D209K] | | R146Q [R158Q] | | | 21.81 |

TABLE 13-continued

Examples of Amino Acid Substituted Forms of PE and Associated Cell Cytotoxic Activity.

| Epitopes changed | pIEX02 - ### | Epitope 5 | Epitope 4 | Epitope 3 | Epitope 1 | Epitope 2 | Epitope 6 | % Inhibition of IVTT |
|---|---|---|---|---|---|---|---|---|
| 1, 4, 5 | 140 | S241T | D197K | | G147S | | | 42.81 |
| | | [S253T] | [D209K] | | [G159S] | | | |
| 1, 4, 5 | 143 | S241T | D197K | | Q149T | | | 49.33 |
| | | [S253T] | [D209K] | | [Q161T] | | | |
| 1, 4, 5 | 170 | S241T | Q194R | | R146A | | | 39.74 |
| | | [S253T] | [Q206R] | | [R158A] | | | |
| 1, 4, 5 | 171 | S241T | Q194R | | R146Q | | | 6.01 |
| | | [S253T] | [Q206R] | | [R158Q] | | | |
| 1, 4, 5 | 172 | S241T | Q194R | | G147S | | | 1.49 |
| | | [S253T] | [Q206R] | | [G159S] | | | |
| 2, 4, 5 | 144 | S241T | D197K | | | T152A | | 100.67 |
| | | [S253T] | [D209K] | | | [T164A] | | |
| 2, 4, 5 | 145 | S241T | D197K | | | N150A | | 70.69 |
| | | [S253T] | [D209K] | | | [N162A] | | |
| 2, 4, 5 | 133 | S241T | Q194R | | | T152R | | 17.46 |
| | | [S253T] | [Q206R] | | | [T164R] | | |
| 2, 4, 5 | 134 | S241T | D107K | | | T152R | | 23.78 |
| | | [S253T] | [D209K] | | | [T164R] | | |
| 6, 4, 5 | 146 | S241T | D197K | | | | I321A | 104.47 |
| | | [S253T] | [D209K] | | | | [I333A] | |
| 6, 4, 5 | 147 | S241T | D197K | | | | I321N | 99.97 |
| | | [S253T] | [D209K] | | | | [I333N] | |
| 6, 4, 5 | 148 | S241T | D197K | | | | I321T | 53.19 |
| | | [S253T] | [D209K] | | | | [I333T] | |
| 6, 4, 5 | 149 | S241T | D197K | | | | I321Q | 99.91 |
| | | [S253T] | [D209K] | | | | [I333Q] | |
| 6, 4, 5 | 150 | S241T | D197K | | | | I321H | 89.43 |
| | | [S253T] | [D209K | | | | [I333H] | |
| 6, 4, 5 | 152 | S241T | D197K | | | | Q326E | 99.97 |
| | | [S253T] | [D209K] | | | | [Q338E] | |
| 3, 4, 5 | 173 | S241T | Q194R | R192A | | | | 23.15 |
| | | [S253T] | [Q206R] | [R204A] | | | | |
| 3, 4, 5 | 174 | S241T | Q194R | R192Q | | | | 16.37 |
| | | [S253T] | [Q206R] | [R204Q] | | | | |
| 3, 4, 5 | 175 | S241T | Q194R | V189A | | | | 6.50 |
| | | [S253T] | [Q206R] | [V201A] | | | | |
| Quadruplicate Substitutions | | | | | | | | |
| 1, 2, 4, 5 | 156 | S241N | Q194R | | I141T | T152R | | 6.16 |
| | | [S253N] | [Q206R] | | [I153T] | [T164R] | | |
| 1, 2, 4, 5 | 166 | S241N | D197K | | I141A | T152R | | 7.90 |
| | | [S253N] | [D209K] | | [I153A] | [T164R] | | |
| 1, 3, 4, 5 | 105 | S241N | D197K | I184A | I141A | | | 0.00 |
| | | [S253N] | [D209K] | [I196A] | [I153A] | | | |
| 1, 3, 4, 5 | 106 | S241K | D197K | I184A | I141A | | | 0.00 |
| | | [S253K] | [D209K] | [I196A] | [I153A] | | | |
| 1, 3, 4, 5 | 110 | S241K | D197K | I184A | I141T | | | 0.00 |
| | | [S253K] | [D209K] | [I196A] | [I153T] | | | |
| 1, 3, 4, 5 | 111 | S241P | D197K | I184A | I141T | | | 0.00 |
| | | [S253P] | [D209K] | [I196A] | [I153T] | | | |
| 1, 3, 4, 5 | 112 | S241T | D197K | I184A | I141T | | | 0.00 |
| | | [S253T] | [D209K] | [I196A) | [I153T] | | | |
| 1, 3, 4, 5 | 114 | S241K | D197K | I184A | I141H | | | 0.00 |
| | | [S253K] | [D209K] | [I196A] | [I153H] | | | |
| 1, 3, 4, 5 | 115 | S241P | D197K | I184A | I141H | | | 0.00 |
| | | [S253P] | [D209K] | [I196A] | [I153H] | | | |
| 1, 3, 4, 5 | 117 | S241N | D197K | I184N | I141A | | | 0.00 |
| | | [S253N] | [D209K | [I196N] | [I153A] | | | |
| 1, 3, 4, 5 | 118 | S241K | D197K | I184N | I141A | | | 0.00 |
| | | [S253K] | [D209K] | [I196N] | [I153A] | | | |
| 1, 3, 4, 5 | 120 | S241T | D197K | I184N | I141A | | | 0.00 |
| | | [S253T] | [D209K] | [I196N] | [I153A] | | | |
| 1, 3, 4, 5 | 121 | S241N | D197K | I184N | I141T | | | 0.00 |
| | | [S253N] | [D209K] | [I196N] | [I153T] | | | |
| 1, 3, 4, 5 | 122 | S241K | D197K | I184N | I141T | | | 0.00 |
| | | [S253K] | [D209K] | [I196N] | [I153T] | | | |
| 1, 3, 4, 5 | 123 | S241P | D197K | I184N | I141T | | | 0.00 |
| | | [S253P] | [D209K] | [I196N] | [I153T] | | | |
| 1, 3, 4, 5 | 124 | S241T | D197K | I184N | I141T | | | 0.00 |
| | | [S253T] | [D209K] | [I196N] | [I153T] | | | |
| 1, 3, 4, 5 | 125 | S241N | D197K | I184N | I141H | | | 0.00 |
| | | [S253N] | [D209K] | [I196N] | [I153H] | | | |
| 2, 3, 4, 5 | 179 | S241T | Q194R | V189A | | T152R | | 13.37 |
| | | [S253T] | [Q206R] | [V201A] | | [T164R] | | |

TABLE 13-continued

Examples of Amino Acid Substituted Forms of PE and Associated Cell Cytotoxic Activity.

| Epitopes changed | pIEX02 - ### | Epitope 5 | Epitope 4 | Epitope 3 | Epitope 1 | Epitope 2 | Epitope 6 | % Inhibition of IVTT |
|---|---|---|---|---|---|---|---|---|
| 2, 3, 4, 5 | 180 | S241T [S253T] | Q194R [Q206R] | R192A [R204A] | | T152R [T164R] | | 58.9 |
| 2, 3, 4, 5 | 181 | S241T [S253T] | Q194R [Q206R] | R192Q [R204Q] | | T152R [T164R] | | 13.70 |
| 1, 3, 4, 5 | 183 | S241T [S253T] | D197K [D209K] | R192A [R204A] | I141A [I153A] | | | 36.87 |
| 1, 3, 4, 5 | 188 | S241T [S253T] | D197K [D209K] | R192A [R204A] | I141T [I153T] | | | 20.75 |
| 1, 2, 4, 5 | 195 | S241T [S253T] | D197K [D209K] | | I141T [I153T] | T152A [T164A] | | 42.90 |
| 1, 4, 5, 6 | 200 | S241T [S253T] | D197K [D209K] | | I141T [I153T] | | I321A [I333A] | 22.04 |
| 1, 4, 5, 6 | 201 | S241T [S253T] | D197K [D209K] | | I141T [I153T] | | I321N [I333N] | 58.30 |
| 1, 4, 5, 6 | 204 | S241T [S253T | D197K (D209K | | I141T [I153T] | | I321H [I333H] | 12.76 |
| 1, 2, 4, 5 | 208 | S241T [S253T] | D197K [D209K] | | I141A [I153A] | T152A [T164A] | | 49.49 |
| 1, 4, 5, 6 | 213 | S241T [S253T] | D197K [D209K] | | I141A [I153A] | | I321A [I333A] | 18.03 |
| 1, 4, 5, 6 | 214 | S241T [S253T] | D197K [D209K] | | I141A [I153A] | | I321N [I333N] | 0.18 |
| 1, 4, 5, 6 | 215 | S241T [S253T] | D197K [D209K] | | I141A [I153A] | | I321T [I333T] | 5.87 |
| 1, 4, 5, 6 | 216 | S241T [S253T] | D197K [D209K] | | I141A [I153A] | | I321Q [I333Q] | 20.21 |
| 1, 4, 5, 6 | 217 | S241T [S253T] | D197K [D209K] | | I141A [I153A] | | I321H [I333H] | 11.22 |
| 1, 4, 5, 6 | 219 | S241T [S253T] | D197K [D209K] | | I141A [I153A] | | Q326E [Q338E] | 70.65 |
| Quintuplicate Substitutions | | | | | | | | |
| | 222 | S241T [S253T] | D197K [D209K] | | G147S [G159S] | T152A [T164A] | Q326E [Q338E] | 4.87 |
| | 224 | S241T [S253T] | D197K [D209K] | | Q149T [Q161T] | T152A [T164A] | Q326E [Q338E] | 3.69 |
| | 226 | S241T [S253T] | D197K [D209K] | | I141A [I153A] | N150A [N162A] | Q326E [Q338E] | 11.23 |
| 1, 2, 4, 5, 6 | 228 | S241T [S253T] | D197K [D209K] | | I141A [I153A] | T152R [T164R] | Q326E [Q338E] | 36.27 |
| 1, 2, 4, 5, 6 | 229 | S241T [S253T] | D197K [D209K] | | I141A [I153A] | T152A [T164A] | Q326E [Q338E] | 18.11 |
| 1, 2, 3, 4, 5 | 221 | S241T [S253T] | Q194R [Q206R] | R192A [R204A] | I141A [I153A] | T152R [T164R] | | 4.79 |
| 1, 2, 4, 5, 6 | 242 | S241T [S253T] | D197K [D209K] | | I141T [I153T] | T152A [T164A] | Q326E [Q338E] | 21.64 |
| Sextuplicate Substitutions | | | | | | | | |
| 1-6 | 244 | S241T [S253T] | D197K [D209K] | R192A [R204A] | I141T [I153T] | T152A [T164A] | Q326E [Q338E] | 20.53 |
| 1-6 | 246 | S241T [S253T] | D197K [D209K] | R192A [R204A] | I141A [I153A] | T152A [T164A] | Q326E [Q338E] | 7.95 |
| 1-6 | 248 | S241T [S253T] | D197K [D209K] | R192A [R204A] | I141A [I153A] | T152R [T164R] | Q326E [Q338E] | 4.45 |

Note:
Non-bracketed amino acid substitution positions correspond to the PE polypeptide sequence in SEQ ID NO: 1. Bracketed [amino acid substitution positions] correspond to the PE polypeptide sequence in SEQ ID NO: 2 (comprising an N-terminal 12-amino acid linker).

Example 11

Ex Vivo Human T Cell Assay to Assess Immunogenicity of Wild-Type (WT) and Amino Acid Substituted PE Ex vivo human T cell assays (EPISCREEN™; see e.g., preceding Examples) were performed to assess the immunogenicity of whole proteins corresponding to pIEX02-244 (SEQ ID NO:178) pIEX02-246 (SEQ ID NO:179) and pIEX02-228 (SEQ ID NO:177) (Example 10). In order to avoid direct cytotoxicity to cells used in the assay, "null mutants" were generated for the three candidates and WT PE by overlapping PCR as in Example 9 using primers OL2162 and 2163 (Table 12) to introduce an amino acid substitution of E287D in the three candidates and WT PE (to give SEQ ID NOs: 180 to 183). (Note: "Null mutants" is intended to indicate mutated forms of PE which lack cell cytotoxic biological activity; the amino acid substitution used to generate null mutants corresponds to a change of E287D in SEQ ID NO:1 or E299 in SEQ ID NO:2.) The E287D (SEQ ID NOs: 180 to 183) encoding genes were cloned into pET14b-K as in Example 9. WT PE sequence is shown in SEQ ID NO:180; pIEX02-228 sequence is shown in SEQ ID NO:181; pIEX02-244 sequence is shown in SEQ ID NO:182; and, pIEX02-246 sequence is shown in SEQ ID NO:183. These were expressed as fusion proteins comprising a histidine polymer and a linker sequence preceding a "null mutant" sequence of WT PE or amino acid substituted PE; see, pIEX02-001 PE WT null mutant (SEQ ID NO:191 (DNA) and SEQ ID NO:192 (AA)), pIEX02-228 null mutant (SEQ ID NO: 195 (DNA) and SEQ ID NO:196 (AA)), pIEX02-244 null mutant (SEQ ID NO:199 (DNA) and SEQ ID NO:200 (AA)), pIEX02-246 null mutant (SEQ ID NO:203 (DNA) and SEQ ID NO:204 (AA)).

The host cell for expression of the PE E287D genes was an *Escherichia coli* BL21 derivative strain called SHuffle™ T7 Express (NEB catalog #C3029H, New England Biolabs UK Ltd., Knowl Piece, UK) which was altered to overexpress the chaperonins GroEL/ES by amplification of the GroEL/ES operon, including its promoter/regulatory sites, from *E. coli* DH5alpha™ (Invitrogen catalog #18265-017, Life Technologies Ltd., Paisley, UK) using OL2097 (introducing EagI site) and OL2098, introducing HindIII site (Table 12). The resulting PCR fragment was subcloned into pACYC184 (NEB catalog #E4152S) which was then transformed into SHuffle™ T7 with selection for chloramphenicol resistance. The PE E287D (SEQ ID NOs: 180 to 183) genes in pET14b-K were transformed into the SHuffle™ T7/GroEL/ES strain with selection for ampicillin resistance. Single colonies were grown in 2×YT medium (Sigma-Aldrich catalog #Y2627-1KG) and protein expression was induced at $OD_{600nm}$ 1.0 by adding isopropyl-β-D-thio-galactoside (IPTG) to a final concentration of 0.4 mM. Cultures were then grown at 16 degrees C. for 17 h before harvesting by centrifugation. Cell pellets were resuspended in 35 ml of binding buffer (50 mM Tris pH 8.0, 500 mM NaCl and 10 mM imidazole) supplemented with protease inhibitors (cOmplete protease inhibitor tablets, Roche catalog #11873580001, Roche Diagnostics Ltd., Burgess Hill, UK (mixture of several protease inhibitors for inhibition of serine and cysteine proteases)). Cells were lysed by sonication (SONICATOR®, Misonix catalog #XL2020, Misonix Inc., Farmingdale, N.Y.), and cell debris and insoluble material removed by centrifugation. Proteins were purified from the soluble fraction by nickel chelate affinity chromatography using HISTRAP® FF Crude columns (GE Healthcare catalog #11-004-58, GE Healthcare Life Sciences, Little Chalfont, UK). After loading, the columns were washed with 50 mM Tris (pH 8.0) containing 500 mM NaCl and 20 mM imidazole and bound protein was eluted with 50 mM Tris (pH 8.0) containing 500 mM NaCl and 500 mM imidazole. Following buffer exchange to 20 mM Tris (pH 8.0) using Zeba Spin desalting columns (7K MWCO, Pierce catalog #89893), a negative purification step was employed using anion exchange chromatography on Q-Sepharose (1 ml, HISTRAP® Q FF column (GE Healthcare catalog #17-5053-01) with 20 mM Tris pH 8.0 and an NaCl gradient form 0 M to 1.5 M. For each protein, the column flow through was concentrated using an AMICON® Ultra centrifugal filter (EMD Millipore catalog #UFC 800 396, EMD Millipore, Feltham, UK) and further purified by size-exclusion chromatography (120 ml, HiLoad 16/60 SUPERDEX® 75 pg (GE Healthcare catalog #28-9893-33)) using 1×PBS pH 7.4 (PAA catalog #H15-002, PAA Laboratories Ltd, Yeovil, UK). For each protein, the protein peak was collected and concentrated.

Endotoxin levels were determined using an ENDOSAFE®-PTS™ Portable Test System reader (Charles River Laboratories Inc., Wilmington, Mass.) with ENDOSAFE® Licensed PTS Endotoxin cartridges (Charles River catalog #PTS20F). Endotoxins were reduced to a value below 5 endotoxin units (EU)/mg by repeatedly performing a phase separation using TritonX-114, (Aida Y. and Pabst M. J., *Journal of Immunological Methods,* 132 (1990) 191-195). Triton X-114 was removed using PIERCE® Detergent Removal Spin Columns according to the manufacturer's provided protocol (PIERCE® catalog #87779; Thermo Fisher Scientific/PIERCE® Biotechnology, Rockford, Ill.; see, Thermo Scientific Instructions manual #2164.3). Protein concentration was quantified by absorbance at 280 nm using a BIOMATE™ 3 UV-Visible spectrophotometer (Thermo Fisher Scientific) and a conversion factor of $OD_{280}$ 1.0=1.15 mg/ml derived from the calculated molar extinction coefficient of 6×His PE (Pace C. N. et al. Protein Science 1995 4:2411-2423).

Ex vivo human T cell assays (EPISCREEN®) were performed using PBMC isolated from healthy community donor buffy coats as in Example 2. A cohort of 20 donors was selected to best represent the number and frequency of HLA-DR allotypes expressed in the world population. The haplotypes of the 20 donors in the assay is shown in Table 14. PBMCs from each donor were thawed, counted and viability assessed. Cells were revived in room temperature AIM-V® culture medium (INVITROGEN®, Paisley, UK), washed and resuspended in AIM-V® to 4-6×$10^6$ PBMC/ml. For each donor, 1 ml of cells were dispensed into multiple wells of a 24 well plate. 0.5 ml of proteins were added at 50 micrograms/ml per sample together with 0.5 ml of AIM-V® culture medium. For each donor, a reproducibility control (cells incubated with 100 micrograms/ml keyhole limpet hemocyanin (KLH), an "intermediate" positive control (expected to give 20-30% T cell responses) of humanized A33 antibody (Welt et al. Clinical Cancer Research, 9 (2003) p1338-1343)(cells were incubated with 50 micrograms/ml humanized A33), and a culture medium only control well were also included. Cultures were incubated for a total of 8 days at 37° C. with 5% $CO_2$.

TABLE 14

Donor Haplotypes

| Donor No | Haplotype | KLH Test 1 | KLH IEX02 |
|---|---|---|---|
| 1 | DRB1*01, DRB1*11; DRB3* | 1.95 | 5.41 |
| 2 | DRB1*11, DRB1*15; DRB3*; DRB5* | N/D | 8.39 |
| 3 | DRB1*04, DRB1*11; DRB3*; DRB4* | 6.04 | 4.58 |
| 4 | DRB1*08, DRB1*14; DRB3* | 1.78 | 1.35 |
| 5 | DRB1*07, DRB1*13; DRB3*; DRB4* | 5.57 | 6.77 |
| 6 | DRB1*04; DRB4* | 12.36 | 11.25 |
| 7 | DRB1*03, DRB1*04; DRB3*; DRB4* | 1.48 | 1.12 |
| 8 | DRB1*03, DRB1*13; DRB3* | 2.73 | 1.63 |
| 9 | DRB1*03, DRB1*07; DRB3*; DRB4* | 3.59 | 3.07 |
| 10 | DRB1*04, DRB1*12; DRB3*; DRB4* | 3.35 | 3.26 |
| 11 | DRB1*01, DRB1*07 | 13.67 | 15.34 |
| 12 | DRB1*01, DRB1*14; DRB3* | 6.05 | 50.13 |
| 13 | DRB1*07, DRB1*09; DRB4* | 9.17 | 19.32 |
| 14 | DRB1*15; DRB5* | 2.83 | 3.97 |
| 15 | DRB1*03, DRB1*15; DRB3*; DRB5* | 3.36 | 3.09 |
| 16 | DRB1*07, DRB1*13; DRB3*; DRB4* | 2.18 | 6.76 |
| 17 | DRB1*15, DRB1*13, DRB3*; DRB5* | 1.93 | 7.04 |
| 18 | DRB1*01, DRB1*04; DRB4* | 2.49 | 28.59 |
| 19 | DRB1*01, DRB1*11; DRB3* | 0.83 | 4.50 |
| 20 | DRB1*01 | 2.03 | 3.18 |

For the T cell proliferation assay, on days 5, 6, 7 and 8, the cells in each well were gently resuspended and triplicate 100 microliter aliquots were transferred to each well of a round bottomed 96 well plate. The cultures were pulsed with 0.75 microCi [3H]-Thymidine (PERKIN ELMER®, Beaconsfield, UK) in 100 microliters AIM-V® culture medium and incubated for a further 18 hours before harvesting onto filter mats (Perkin Elmer®) using a TOMTEC® HARVESTER 96™ Mach III cell harvester (TOMTEC® Inc., Hamden, Conn., USA). Counts per minute (cpm) for each well were determined using MELTILEX® solid scintillator (PERKIN ELMER® Life and Analytical Sciences, Shelton, Conn., USA) via scintillation counting on a Wallac 1450 Microbeta Trilux Microplate Scintillation and Luminescence Counter (Perkin Elmer®) in paralux, low background counting.

For proliferation assays, an empirical Stimulation Index (S) threshold of equal to, or greater than, 2 (SI≥2.0) was used whereby samples inducing proliferative responses above this threshold at any day after addition of protein were deemed positive. (The Stimulation Index is a ratio of stimulated proliferative response compared to a background index; an SI of 1=background or "noise".) For the triplicate proliferation data for each time point with each protein, the significance ($p<0.05$) of positive responses was defined by statistical and empirical thresholds by comparing CPM of test protein wells against medium-only control wells using unpaired two sample Student's T-Test.

The results of the proliferation assay are shown in Table 15. The results demonstrate a significantly reduced level of T cell responses from the amino acid substituted PE molecules: pIEX02-228 (SEQ ID NO:181) 5% donor responses; pIEX02-244 (SEQ ID NO:182) 10% donor responses; and, pIEX02-246 (SEQ ID NO:183) 20% donor responses, compared to WT PE (SEQ ID NO:180) which induced T cell responses in 70% of donors.

TABLE 15

Relative T-cell Stimullated Proliferative Responses to Amino Acid Substituted variants of PE compared to Wild-Type (WT) PE.

| | WT PE | pIEX02-228 | pIEX02-244 | pIEX02-246 | Hu A33 |
|---|---|---|---|---|---|
| Donor 1 | P | | | | |
| Donor 2 | P* | | | | P |
| Donor 3 | P* | | P | P | P |
| Donor 4 | | | | | |
| Donor 5 | | | | | |
| Donor 6 | P | | | | |
| Donor 7 | | | | | |
| Donor 8 | P | | | | |
| Donor 9 | P | | | | |
| Donor 10 | P | | | | |
| Donor 11 | P | | | P | P |
| Donor 12 | P | | | | P |
| Donor 13 | P | | | | |
| Donor 14 | P | P | | P | |
| Donor 15 | P | | | | |
| Donor 16 | P | | | | P |
| Donor 17 | P | | | | |
| Donor 18 | | | | | |
| Donor 19 | | | P | P | P |
| Donor 20 | | | | | |
| % Donor Proliferation | 70 | 5 | 10 | 20 | 30 |

*Positive T cell responses for proliferation (SI ≥ 2.00, significant $p < 0.05$) during the entire time course days 5-8 ("P") are shown.
**Borderline responses (significant $p < 0.05$ with SI ≥ 1.90) are shown (*).

In addition to the proliferation assay, additional analysis of the cytokines IL-2 and IL-6 was performed using aliquots of culture supernatant taken on day 6. The analysis was performed using the BD Cytometric Bead Array (CBA) Enhanced Sensitivity Flex Set Systems for IL-2 and IL-6 (BD Bioscience, Oxford, UK) according to the manufacturer's instructions. The enhanced sensitivity standards from the CBA kit were reconstituted and serially diluted before adding 50 microliters of supernatant or standard to 20 microliters of mixed capture beads in 96 well filter plates (Millipore, Watford, UK) and incubating for 2 hours. Mixed human detection reagent (20 microliters) was then added to each well and incubated for a further 2 hours. Plates were washed twice and enhanced detection (100 microliters) reagent added to each well for a final 1 hour incubation. Plates were washed before reading on an Accuri C6 instrument (BD Biosciences).

Data was analysed using FCAP v3.0 software (BD Biosciences). For each individual donor, data was expressed as pg/ml of cytokine for each donor and plotted on a log scale with a median of cytokine levels depicted as a line. The results are shown in FIG. 11 which shows a significantly reduced level of the cytokines IL-2 and IL-6 from the amino acid substituted PE molecules pIEX02-228 (SEQ ID NO:181), pIEX02-244 (SEQ ID NO:182) and pIEX02-246 (SEQ ID NO:183) compared to WT PE (SEQ ID NO:180).

The proliferation and cytokine results both independently demonstrate that the amino acid substitutions in PE result in greatly reduced level of T cell responses when using amino acid substituted forms of PE. These results considered and expected to correlate with low or reduced PE immunogenicity in human subjects.

Example 12

Cytotoxicity Analysis of Amino Acid Substituted PE in Dendritic Cells

Amino acid substituted forms of PE and WT PE may be generated as in Example 11. For a dendritic cell cytotoxicity assay, PBMC are isolated from healthy community donor buffy coats (preferably from blood drawn within 24 hours), for example, by Lymphoprep (Axis-shield, Dundee, UK) density centrifugation. To prepare monocyte-derived dendritic cells (DC), CD14+ cells (monocytes) may be isolated from donor PBMC preparations using Miltenyi Monocyte Isolation Kit II (human) and LS columns (Miltenyi Biotech GmbH, Bergisch Gladbach, Germany; catalog #130-091-153). Monocytes are resuspended in an appropriate culture medium, such as AIM-V® cell culture medium supplemented with 1000 IU/ml IL-4 and 1000 IU/ml GM-CSF ("DC culture medium") to 4-6×$10^6$ cells/ml and then distributed in 24 well plates (e.g., 2 ml final culture volume). Cells are fed on day 2 by half volume DC culture medium change. On day 3, amino acid substituted PE and WT PE proteins are added to semi-mature DC to selected final concentrations, such as 1 micrograms/ml or 10 micrograms/ml. Semi-mature DC are incubated for a period of time, such as 24-72 hours, after which cells are assessed for cytotoxicity by viability, such as via use of Trypan Blue (Sigma, Dorset, UK) dye exclusion and by propidium iodide (PI) and Annexin V staining (Invitrogen, Paisley UK) followed by FACS analysis.

Example 13

Cytotoxicity Analysis of Anti-CD22 scFv Fused to Amino Acid Substituted PE in RAJI Cells WT PE and amino acid substituted PE encoded by pIEX02-244 (SEQ ID NO: 178) are fused to an anti-CD22 single-chain Fv (scFv). The VH and VL ($V_{kappa}$) regions of RFB4 (Campana D. et al., *J. Immunol.,* 134:1524-1530 (1985); Mansfield, E., et al., Blood, 90:2020-2026 (1997) are synthesized. RFB4 VH is amplified using oligonucleotides: OL2043 and OL2044 (Table 12). RFB4 and VL (Vk) is amplified using oligonucleotides OL2045 and OL2046

(Table 12). The RFB4 scFv is obtained using a pull-through PCR reaction using oligonucleotides OL2047 introducing a NcoI site and OL2048 introducing a XhoI site. The resultant PCR product is subcloned into pET14b-K via NcoI and XhoI restriction enzymes (Fermentas catalog #FD0573 and FD0695, respectively).

The gene encoding RFB4 scFv is fused to genes encoding either WT PE or amino acid substituted PE encoded by pIEX02-244 (SEQ ID NO: 178) having a C-terminal 8×His-tag followed by the sorting signal EDLK to give fusion sequences SEQ ID NO:184 and SEQ ID NO:186, respectively, which are cloned into the expression vector pET14b-K by fusion PCR. To create these RFB4-PE fusions a fusion PCR is carried out. The RFB4 scFv gene is amplified from pET14b-RFB4 using oligonucleotides OL2318 introducing a NcoI site and OL2320 (Table 12). The WT PE or the lead amino acid substituted PE genes are amplified from pET14b-K-WT PE or pET14b-K-244 PE, respectively, using oligonucleotides OL2321 and OL2322 introducing a N-terminal 8×His-EDLK and a XhoI site (Table 12). Both scFv and PE genes are fused by performing a PCR with oligonucleotides OL2318 and OL2322 (Table 12). The resulting full-length fragments are subcloned into pET14b-K using NcoI and XhoI restriction enzymes. Plasmids are transformed into BL21(DE3) *E. coli* (EMD Millipore, Feltham, UK) and clones are inoculated into 2TY+Amp and grown overnight at 37° C. Two ml of overnight culture is inoculated into 350 ml 2TY+Amp media in a 1 L flask and grown to $OD_{600nm}$=1 before addition of IPTG (Sigma) to 1 mM (final concentration). Cultures are grown overnight at 30 degrees C. overnight and centrifuged at 10000 rpm. Bacterial pellets are frozen at −80 until ready to use.

Pellets are defrosted on ice, extracted with 10 ml B-PER® Bacterial Protein Extraction Reagent (PIERCE® Biotechnology, Rockford, Ill.; Thermo Scientific, Hemel Hempstead, UK) containing Lysozyme and DNaseI (both Thermo Scientific), and rotated for 1 hour at room temperature. Samples are then centrifuged at 10000 rpm and supernatants are discarded. Each pellet is resuspended in 5 ml B-PER containing Lysozyme and DNaseI as above and extracted for an additional 30 min at room temperature. After centrifugation, pellets are pooled and washed successively with Wash Buffer A (50 mM Tris-HCl pH 8.0, 100 mM NaCl, 1 mM EDTA, 0.5 M urea and 1.0% Triton X-100), Wash Buffer B (Buffer A but without urea), and twice with Wash Buffer C (Buffer A but without urea or Triton X-100). After final wash, insoluble pellets are stored at −80° C. cOmplete® mini-EDTA protease inhibitors (Roche Diagnostics Ltd.) are included at each step.

Pellets are resuspended in 10 ml Solubilisation Buffer (50 mM Tris-HCl pH 8.0, 100 mM NaCl, 8 M Urea and 1 mM DTT). $OD_{280nm}$ is determined and the samples are diluted to approximately 1 mg/ml in Solubilisation Buffer. Protein samples are allowed to denature for 4 hours at room temperature and centrifuged at 10000 rpm to remove insoluble debris. 10 ml of each solubilised protein samples is injected into a pre-soaked 12 ml, 3K MWCO cut-off SLIDE-A-LYSER® Dialysis Cassette dialysis device (Thermo Scientific; PIERCE® Biotechnology, Inc., IL, USA), and dialyzed by placement overnight in a beaker containing 2.5 L Refolding Buffer A (50 mM Tris HCl pH 8.0, 100 mM NaCl, 5 mM reduced glutathione, 1 mM oxidised glutathione, 0.1 M arginine, 4 M urea). Dialysis buffer is replaced with, in order, 2.5 L Refolding Buffer B (Buffer A with 2 M urea), 2.5 L Refolding Buffer C (Buffer A with 1 M urea) and 5 L Refolding Buffer D (Buffer A without urea or arginine) for a minimum of 4 hours at each step.

Each sample is recovered from the dialysis cassette, buffer exchanged into 50 mM 2-N-morpholino)ethanesulfonic acid (MES) pH 6.2 using PD10 desalting columns (GE Healthcare, Little Chalfont, UK) and loaded onto a 1 ml SP FF Anion Exchange column (GE Healthcare). Each column is washed with 50 mM MES pH 6.2 before eluting using a linear 0M to 1M NaCl gradient in 50 mM MES pH6.2. Protein-containing fractions are pooled and run through a pre-equilibrated 16/60 Size Exclusion column (GE Healthcare) using 1×PBS as running buffer. Fractions containing the main protein peaks are collected, pooled and concentrated to approximately 1 ml, filter sterilized and quantified.

For cytotoxicity analysis, Raji cells (ATCC, CCL-86) are propagated in growth medium (RPMI-1640, 10% FBS, 1% Pen/Strep) and harvested during mid-log growth phase. Cells are diluted to $1\times10^5$ cells/ml in growth medium and 50 microliter aliquots are dispensed per well in white walled, clear bottom 96 well plates (CORNING® catalogue #3610, FISHER SCIENTIFIC®, Loughborough, UK). Each protein concentration (8×4-fold dilutions from 500 nanograms/ml) is tested in triplicate wells, and controls containing cells or growth medium only are also included. Test protein is diluted to 2× desired concentration in growth medium. 50 microliters of the test protein dilutions or controls are added to the Raji cells and plates are incubated 72 hrs in a humidified cell culture incubator (37° C., 5% $CO_2$). After incubation, plates are equilibrated at room temperature for 10 min. CELLTITER-GLO® (PROMEGA® catalogue #G7571) is prepared according to manufacturer's instructions and 100 microliters is added per well. Plates are incubated for 10 min before reading via a FLUOstar OPTIMA fluorescence plate reader (BMG Labtech Ltd., Aylesbury, UK)(also known as a fluorometer).

REFERENCES

Aida Y. & Pabst M. J., *Journal of Immunological Methods,* 132:191-195 (1990)

Al-Dosari et al., *AAPS Journal,* 11(4):671-681 (2009).

Allen et al. (Editor), *Ansel's Pharmaceutical Dosage Forms and Drug Delivery Systems*, Lippincott Williams & Wilkins; 9th Ed. (2011).

Andre et al., *Curr Gene Ther.,* 10(4):267-280 (2010).

Antoniewski et al., Mol. Cell Biol. 14:4465 (1994).

Ash et al. (Editor), *Handbook of Pharmaceutical Additives, Third Edition*, Synapse Information Resources, Inc.; 3rd Ed. (2007).

Baker & Carr, *Current Drug Safety*, 5(4):1-6 (2010).

Baker & Jones, *Curr. Opin. Drug. Disc. Dev.,* 10(2):219-227 (2007).

Bodles-Brakhop et al., *Mol. Ther.,* 17(4):585-592 (2009).

Brent et al., *Cell,* 43:729-736 (1985).

Bryson et al., *BioDrugs.,* 24(1): 1-8 (2010).

Campana D. et al., *J Immunol.,* 134:1524-1530 (1985).

Canadian Patent No. 2,012,311.

Chaudhary et al., *Proc. Natl. Acad. Sci. USA*, 87:308-312 (1990).

Cherbas et. al., *Genes Dev.* 5:120-131 (1991).

Chester et. al., *Expert Rev. Clin. Immunol.,* 1(4): 549-559 (2006).

Colosimo et al., *Biotechniques,* 29(2):314-8, 320-322 (2000).

Crouch, et al., *J. Immunol. Methods,* 160(1):81-88 (1993).

Curiel et al., *Hum. Gene Ther.* 3:147 (1992).

D'Avino et al., *Mol. Cell. Endocrinol.* 113:1 (1995).

Donnelly et al., *Drug Deliv.* 17(4):187-207 (2010).
European Patent No. 234,994B1.
European Patent No. 461,809B1.
Feigner et al., *Proc. Natl. Acad. Sci* USA. 84:7413 (1987).
Feigner et al., *Science* 337:387 (1989).
Golzio et al., *Curr Gene Ther.* 10(4):256-266 (2010).
Hansen et al., *J. Immunother.* 33(3):297-304 (2011).
Harlow & Lane, Antibodies: *A Laboratory Manual*, Cold Spring Harbor Laboratory Press, 2nd ed., ISBN 978-087969314-5 (1988).
Harlow & Lane, Using Antibodies: *A Laboratory Manual*, Cold Spring Harbor Laboratory Press, ISBN 0879695447 (1999).
Hausman & Cooper, *The Cell: A Molecular Approach*, Washington, D.C.: ASM Press. p. 51 (2004).
Higuchi, *Using PCR to Engineer DNA*, PCR Technology: Principles and Applications for DNA Amplification, H. Erlich, ed., Stockton Press, Chapter 6, pp. 61-70 (1989).
Hochuli et al., *J Interferon Cytokine Res.* 17 Suppl 1:S15-21 (1997).
Holgate & Baker, *Idrugs*, 12(4):233-237 (2009).
Hu et al., *Int. J. Cancer,* 127(9):2222-2229 (2010).
Hutchinson et al., *J. Biol. Chem.* 255:6551 (1978).
Hutchinson et al., *Proc. Natl. Acad. Sci. USA* 83:710 (1986).
Hwang et al., *Cell* 48:129-136 (1987).
Itoi et al. *J. Neurosci.* 31(16):6132-6139 (2011).
Jaber & Baker, *J. Pharm. Biomed. Anal.* 43(4):1256-61 (2007).
Karzenowski et al., *BioTechniques* 39: 191-200 (2005).
Klein et al., *Curr. Opin. Biotechnol.* 4(5):583-590 (1993).
Kreitman et al., *Leuk. Lymphoma* Suppl. 2:82-86 (2011).
Krieg et al., *Nucl. Acids Res.* 12, 7057-7070 (1984).
Kuan et al., *Int. J. Cancer* 129(1):111-21 (2011).
Kyte & Doolittle, *J. Mol. Biol.* 157(1):105-132 (1982).
Lim, et al., *Hematology* 10(3):255-9 (2005).
Mackey et al., *Proc. Natl. Acad. Sci* USA 85:8027 (1988).
Mansfield, E., et al., *Blood,* 90:2020-2026 (1997).
Mareeva et al., *J. Immunol. Methods* 353(1-2):78-86 (2010).
Miller et al., *Somat. Cell Mol. Genet.* 27(1-6): 115-34 (2002).
Nagata et al., *Adv. Drug Deliv. Rev.* 61(11):977-985 (2009).
Namaka, et al., *Curr MedRes Opin.* 22(2):223-39 (2006).
Niles, et al., *Anal. Biochem.,* 366, 197-206 (2007).
O'Neil, "*The Merck Index: An Encyclopedia of Chemicals, Drugs, and Biologicals,*" 14$^{th}$ Ed. (2006).
Oliphant et al., *Gene* 44:177 (1986).
Olsson et al., *J. Appl. Biochem* 5, 347-445 (1983).
Onda et al., *Proc. Natl. Acad. Sci. USA* 105(32):11311-11316 (2008).
Onda et al., *Proc. Natl. Acad. Sci. USA* 108(14):5742-5747 (2011).
Pastan et al., *Leukemia and Lymphoma* 52(S2):87-90 (2011).
Pastan et al., *Science* 254:1173-1177 (1991).
Pathak et al., *Biotechnol J.* 4(11): 1559-1572 (2009).
PDR Network, *Physicians' Desk Reference* 2011," PDR Network (2010).
PDR Network, *Physicians' Desk Reference* 2012," PDR Network (2011).
Pelham et al., *Eur. J Biochem.* 67, 247-56 (1976).
Perry et al., *Drugs R D.* 9(6):385-96 (2008).
Pichon et al., *Curr Opin Biotechnol.* 21(5):640-645 (2010).
PROMEGA® Technical Bulletin #TB 126 (Revised 12/2010).
PROMEGA® Technical Bulletin #TB288 (Revised 06/2009).
PROMEGA® Technical Bulletin #TB288 (Revised 08/2011).
PROMEGA® Technical Bulletin #TB306 (Revised 05/2009).
PROMEGA® Technical Bulletin #TB359 (Revised 05/2009).
PROMEGA® Technical Bulletin #TB359 (Revised 10/2011).
PROMEGA® Technical Bulletin #TM045 (Revised 05/2011).
PROMEGA® Technical Bulletin #TM051 (Revised 03/2009).
PROMEGA® Technical Bulletin #TM051 (Revised 09/2011).
Rochlitz et al., "Gene therapy of cancer," *Swiss Med. Wkly.,* 131(1-2):4-9 (2001).
Rowe et al. (Editor), "*Handbook of Pharmaceutical Excipients*," Pharmaceutical Press, 6$^{th}$ Ed. (2009).
Sadowski et al., *Nature* 335:563 (1988).
Schellekens et al., *J. Interferon Cytokine Res.* 17(Suppl. 1), S5-S8 (1997).
Seetharam et al., *Jour. Biol. Chem.* 266:17376-17381 (1991).
Shapira et al., *Gastroenterology* 140(3):935-946 (2011).
Siegall et al., *Mol. Cell. Biol.* 10(6); 2443-2447 (1990).
Siegall et al., *Biochemistry* 30:7154-7159 (1991).
Squirrell et al., *A Practical Guide to Industrial Uses of ATP Luminescence in Rapid Microbiology*, Cara Technology Ltd., Lingfield, pp. 107-113 (1997).
Stish et al., *Br. J. Cancer* 101(7):1114-1123 (2009).
Theuer et al., *J. Biol. Chem.*, 267(24): 16872-16877 (1992).
Thomas et al., *Clin. Cancer Res.* 10:7079-7087 (2004).
U.S. Patent Application Publication No. 2005/0228016.
U.S. Patent Application Publication No. 2006/0100416.
U.S. Patent Application Publication No. 2009/0123441.
U.S. Patent Application Publication No. 2009/0142341.
U.S. Patent Application Publication No. 2009/0298175.
U.S. Pat. No. 4,892,827.
U.S. Pat. No. 4,985,461.
U.S. Pat. No. 5,117,057.
U.S. Pat. No. 5,225,443.
U.S. Pat. No. 5,324,637.
U.S. Pat. No. 5,378,726.
U.S. Pat. No. 5,459,127.
U.S. Pat. No. 5,492,817.
U.S. Pat. No. 5,530,028.
U.S. Pat. No. 5,580,859.
U.S. Pat. No. 5,583,024.
U.S. Pat. No. 5,589,466.
U.S. Pat. No. 5,641,641.
U.S. Pat. No. 5,650,289.
U.S. Pat. No. 5,674,713.
U.S. Pat. No. 5,693,622;
U.S. Pat. No. 5,700,673.
U.S. Pat. No. 5,821,238.
U.S. Pat. No. 6,013,836.
U.S. Pat. No. 6,258,603.
U.S. Pat. No. 6,602,677.
U.S. Pat. No. 6,982,152.
U.S. Pat. No. 7,083,911.
U.S. Pat. No. 7,241,584.
U.S. Pat. No. 7,282,348.
U.S. Pat. No. 7,304,161.
U.S. Pat. No. 7,304,162.
U.S. Pat. No. 7,375,093
U.S. Pat. No. 7,452,663.
U.S. Pat. No. 7,456,315.
U.S. Pat. No. 7,531,326.
U.S. Pat. No. 7,563,879.

U.S. Pat. No. 7,700,310.
U.S. Pat. No. 7,732,128.
U.S. Pat. No. 7,741,067.
U.S. Pat. No. 7,750,136
U.S. Pat. No. 7,919,269.
U.S. Pat. No. 7,935,510.
U.S. Pat. No. 8,076,517.
U.S. Pat. No. 8,105,825.
U.S. Pat. No. 8,854,044.
Ulmer et al., *Science* 259:1745 (1993).
University of the Sciences in Philadelphia (Editor), "*Remington: The Science and Practice of Pharmacy*," Lippincott Williams & Wilkins, 21st Ed. (2005).
Uskoković et al., *J. Biomed. Mater. Res. B Appl. Biomater* 96(1):152-191 (2011).
Wells, *Cell Biol Toxicol.* 26(1):21-28 (2010).
Weldon & Pastan, *FEBS Journal* 278(23):4683-4700 (2011)
WO 1995/018863 (PCT/FR1995/000022).
WO 1995/021931 (PCT/FR1995/000098).
WO 1996/017823 (PCT/FR1995/001595).
WO 1996/025508 (PCT/FR1996/000248).
WO 2001/070816 (PCT/US2001/090500).
WO 2002/029075 (PCT/US2001/030608).
WO 2002/066612 (PCT/US2002/005090).
WO 2002/066613 (PCT/US2002/005090).
WO 2002/066614 (PCT/US/2002/005706).
WO 2002/066615 (PCT/US2002/005708).
WO 2003/027266 (PCT/US/2002/05234).
WO 2003/027289 (PCT/US2002/005026).
WO 2005/108617 (PCT/US2005/015089).
WO 2008/073154 (PCT/US2007/016747).
WO 2008/153801 (PCT/US2008/006757).
WO 2009/025866 (PCT/US2008/010040).
WO 2009/045370 (PCT/US2008/011270).
WO 2009/048560 (PCT/US2008/011563).
WO 2010/042189 (PCT/US2009/005510).
WO 2011/119773 (PCT/US2011/029682).
Wu et al., *J. Biol. Chem.* 263:14621 (1988).
Wu et al., *J. Biol. Chem.* 267:963 (1992).
Wu et al., *J. Biol. Chem.* 262:4429 (1987).
Xiong et al., *Pharmazie* 66(3):158-64 (2011).
Yao et al., *Cell* 71:63 (1992).
Yao et al., *Nature* 366:476 (1993).
Zielinski et al., *J. Immunother.* 32(8):817-825 (October-2009).
Zoller et al., *DNA* 3:479 (1984).

The invention claimed is:

1. A polypeptide having at least one *Pseudomonas* exotoxin A (PE-A) biological activity, wherein said polypeptide comprises one or more amino acid substitutions compared to a wild-type PE-A polypeptide, wherein said one or more amino acid substitutions is a substitution of a different amino acid at one or more positions corresponding to amino acid residues in the polypeptide of SEQ ID NO:1, wherein one of said substitutions is selected from the group consisting of:

a) arginine (R) at position 146 is substituted with a different basic amino acid;

b) arginine (R) at position 146 is substituted with a different polar amino acid residue wherein the substitution at position 146 is not lysine (K) or histidine (H).

2. The polypeptide of claim 1, wherein the different polar amino acid substitution for arginine (R) at position 146 is asparagine (N), aspartic acid (D), cysteine (C), glutamic acid (E), glutamine (Q), serine (S), threonine (T) or tyrosine (Y).

3. The polypeptide of claim 1, wherein the at least one *Pseudomonas* exotoxin A (PE-A) biological activity comprises the ability to inhibit in vitro transcription/translation compared to a corresponding wild-type or non-substituted PE-A polypeptide, wherein said ability to inhibit in vitro transcription/translation is in an amount selected from the group consisting of:

(a) at least 5% inhibition;
(b) at least 10% inhibition;
(c) at least 15% inhibition;
(d) at least 20% inhibition;
(e) at least 25% inhibition;
(f) at least 30% inhibition;
(g) at least 40% inhibition;
(h) at least 50% inhibition;
(i) at least 60% inhibition;
(j) at least 70% inhibition;
(k) at least 80% inhibition;
(l) at least 90% inhibition;
(m) at least 100% inhibition;
(n) about 100% inhibition; and
(o) 100% inhibition.

4. The polypeptide of claim 1, wherein said polypeptide comprises one or more amino acid substitutions which prevent or reduce host immunogenic responses compared to the same polypeptide without said one or more amino acid substitutions.

5. The polypeptide of claim 1, wherein the last five or six amino acids in said polypeptide comprise one or more amino acid sequences selected from the group consisting of:

(i) Arg-Glu-Asp-Leu-Lys;
(ii) Arg-Glu-Asp-Leu;
(iii) Lys-Asp-Glu-Leu;
(iv) Glu-Asp-Leu-Lys; and
(v) a dimer, trimer, pentamer, hexamer, septamer, or octamer of (i), (ii), or (iii), or any combination thereof.

6. The polypeptide of claim 1, wherein said polypeptide has one or more biological activities selected from the group consisting of:

a) eukaryotic cell killing activity (cell cytotoxicity);
b) inhibits translation elongation factor EF-2 biological activity;
c) induces or catalyzes ADP-ribosylation of EF-2; and
d) inhibits protein synthesis.

7. The polypeptide of claim 1, wherein said one or more amino acid substitutions reduce host immunogenic responses compared to a polypeptide comprising an amino acid sequence selected from the group consisting of:

(a) SEQ ID NO:1;
(b) SEQ ID NO:4;
(c) SEQ ID NO:133; and
(d) SEQ ID NO:134.

8. The polypeptide of claim 1, wherein said polypeptide is a fusion protein.

9. A polynucleotide encoding the polypeptide of claim 1.

10. An expression vector comprising the polynucleotide of claim 9.

11. A host cell comprising the expression vector of claim 10.

12. A polynucleotide encoding the fusion protein of claim 8.

13. The polypeptide of claim 1, wherein said polypeptide is a fusion protein.

14. The polypeptide of claim 2, wherein said polypeptide is a fusion protein.

15. A polynucleotide encoding the polypeptide of claim 1.

16. A polynucleotide encoding the polypeptide of claim 2.

17. A polynucleotide encoding the fusion protein of claim 13.

18. A polynucleotide encoding the fusion protein of claim 14.

19. An expression vector comprising the polynucleotide of claim 15.

20. An expression vector comprising the polynucleotide of claim 16.

21. A host cell comprising the expression vector of claim 19.

22. A host cell comprising the expression vector of claim 20.

* * * * *